United States Patent
Shelton, IV et al.

(10) Patent No.: US 11,141,160 B2
(45) Date of Patent: Oct. 12, 2021

(54) CLIP APPLIER COMPRISING A MOTOR CONTROLLER

(71) Applicant: Ethicon LLC, Guaynabo, PR (US)

(72) Inventors: Frederick E. Shelton, IV, Hillsboro, OH (US); Chester O. Baxter, III, Loveland, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 228 days.

(21) Appl. No.: 16/172,168

(22) Filed: Oct. 26, 2018

(65) Prior Publication Data
US 2019/0125360 A1   May 2, 2019

Related U.S. Application Data

(60) Provisional application No. 62/750,555, filed on Oct. 25, 2018, provisional application No. 62/659,900, (Continued)

(51) Int. Cl.
*A61B 17/068* (2006.01)
*A61B 17/072* (2006.01)
(Continued)

(52) U.S. Cl.
CPC ........ *A61B 17/105* (2013.01); *A61B 17/0682* (2013.01); *A61B 17/083* (2013.01); (Continued)

(58) Field of Classification Search
CPC .. A61B 17/122; A61B 17/1285; A61B 17/072
See application file for complete search history.

(56) References Cited

U.S. PATENT DOCUMENTS 1,853,416 A   4/1932   Hall
3,082,426 A   3/1963   Miles
(Continued)

FOREIGN PATENT DOCUMENTS

AU   2015201140 A1   3/2015
CA   2795323 A1   5/2014
(Continued)

OTHER PUBLICATIONS

US 10,504,709 B2, 12/2019, Karancsi et al. (withdrawn)
(Continued)

*Primary Examiner* — Nathaniel C Chukwurah

(57) ABSTRACT

A surgical device for clipping tissue is disclosed. The surgical device comprises a clip magazine comprising a plurality of clips, an end effector movable between an open position and a closed position, and a jaw actuator operably responsive to a first rotatable input. The jaw actuator is configured to move the end effector between the open position and the closed position. The surgical device further comprises a reciprocating feeder drive and a controller. The reciprocating feeder drive is operably responsive to a second rotatable input. The controller is configured to advance a clip from the clip magazine into the end effector by way of the feeder drive when the end effector is in the open configuration. The controller is further configured to actuate the jaw actuator to move the first jaw and the second jaw toward the closed position without advancing a clip into the end effector.

22 Claims, 131 Drawing Sheets

Related U.S. Application Data filed on Apr. 19, 2018, provisional application No. 62/665,128, filed on May 1, 2018, provisional application No. 62/665,129, filed on May 1, 2018, provisional application No. 62/665,134, filed on May 1, 2018, provisional application No. 62/665,139, filed on May 1, 2018, provisional application No. 62/665,177, filed on May 1, 2018, provisional application No. 62/665,192, filed on May 1, 2018, provisional application No. 62/649,291, filed on Mar. 28, 2018, provisional application No. 62/649,294, filed on Mar. 28, 2018, provisional application No. 62/649,296, filed on Mar. 28, 2018, provisional application No. 62/649,300, filed on Mar. 28, 2018, provisional application No. 62/649,302, filed on Mar. 28, 2018, provisional application No. 62/649,307, filed on Mar. 28, 2018, provisional application No. 62/649,309, filed on Mar. 28, 2018, provisional application No. 62/649,310, filed on Mar. 28, 2018, provisional application No. 62/649,313, filed on Mar. 28, 2018, provisional application No. 62/649,315, filed on Mar. 28, 2018, provisional application No. 62/649,320, filed on Mar. 28, 2018, provisional application No. 62/649,323, filed on Mar. 28, 2018, provisional application No. 62/649,327, filed on Mar. 28, 2018, provisional application No. 62/649,333, filed on Mar. 28, 2018, provisional application No. 62/611,339, filed on Dec. 28, 2017, provisional application No. 62/611,340, filed on Dec. 28, 2017, provisional application No. 62/611,341, filed on Dec. 28, 2017, provisional application No. 62/578,793, filed on Oct. 30, 2017, provisional application No. 62/578,804, filed on Oct. 30, 2017, provisional application No. 62/578,817, filed on Oct. 30, 2017, provisional application No. 62/578,835, filed on Oct. 30, 2017, provisional application No. 62/578,844, filed on Oct. 30, 2017, provisional application No. 62/578,855, filed on Oct. 30, 2017.

(51) Int. Cl.

| | |
|---|---|
| *A61B 17/10* | (2006.01) |
| *A61B 34/30* | (2016.01) |
| *A61B 90/98* | (2016.01) |
| *G16H 40/60* | (2018.01) |
| *A61B 17/08* | (2006.01) |
| *A61B 17/122* | (2006.01) |
| *A61B 17/128* | (2006.01) |
| *A61B 17/34* | (2006.01) |
| *A61B 90/00* | (2016.01) |
| *A61B 17/00* | (2006.01) |
| *A61B 17/29* | (2006.01) |

(52) U.S. Cl.
CPC ............ *A61B 17/10* (2013.01); *A61B 17/122* (2013.01); *A61B 17/128* (2013.01); *A61B 17/1222* (2013.01); *A61B 17/1227* (2013.01); *A61B 17/1285* (2013.01); *A61B 17/3421* (2013.01); *A61B 34/30* (2016.02); *A61B 90/98* (2016.02); *G16H 40/60* (2018.01); *A61B 17/00234* (2013.01); *A61B 17/072* (2013.01); *A61B 17/29* (2013.01); *A61B 17/2909* (2013.01); *A61B 2017/00017* (2013.01); *A61B 2017/00026* (2013.01); *A61B 2017/0039* (2013.01); *A61B 2017/0046* (2013.01); *A61B 2017/00057* (2013.01); *A61B 2017/00119* (2013.01); *A61B 2017/00123* (2013.01); *A61B 2017/00128* (2013.01); *A61B 2017/00221* (2013.01); *A61B 2017/00327* (2013.01); *A61B 2017/00367* (2013.01); *A61B 2017/00393* (2013.01); *A61B 2017/00398* (2013.01); *A61B 2017/00424* (2013.01); *A61B 2017/00464* (2013.01); *A61B 2017/00473* (2013.01); *A61B 2017/00477* (2013.01); *A61B 2017/00734* (2013.01); *A61B 2017/07214* (2013.01); *A61B 2017/2903* (2013.01); *A61B 2017/2927* (2013.01); *A61B 2017/2929* (2013.01); *A61B 2017/2931* (2013.01); *A61B 2017/2936* (2013.01); *A61B 2017/2943* (2013.01); *A61B 2017/2944* (2013.01); *A61B 2034/305* (2016.02); *A61B 2090/032* (2016.02); *A61B 2090/035* (2016.02); *A61B 2090/065* (2016.02); *A61B 2090/0808* (2016.02); *A61B 2090/0811* (2016.02); *A61B 2090/0814* (2016.02)

(56) References Cited

U.S. PATENT DOCUMENTS

| | | | |
|---|---|---|---|
| 3,503,396 | A | 3/1970 | Pierie et al. |
| 3,584,628 | A | 6/1971 | Green |
| 3,626,457 | A | 12/1971 | Duerr et al. |
| 3,633,584 | A | 1/1972 | Farrell |
| 3,759,017 | A | 9/1973 | Young |
| 3,863,118 | A | 1/1975 | Lander et al. |
| 3,898,545 | A | 8/1975 | Coppa et al. |
| 3,912,121 | A | 10/1975 | Steffen |
| 3,915,271 | A | 10/1975 | Harper |
| 3,932,812 | A | 1/1976 | Milligan |
| 4,041,362 | A | 8/1977 | Ichiyanagi |
| 4,052,649 | A | 10/1977 | Greenwell et al. |
| 4,087,730 | A | 5/1978 | Goles |
| 4,157,859 | A | 6/1979 | Terry |
| 4,412,539 | A | 11/1983 | Jarvik |
| 4,448,193 | A | 5/1984 | Ivanov |
| 4,523,695 | A | 6/1985 | Braun et al. |
| 4,608,160 | A | 8/1986 | Zoch |
| 4,614,366 | A | 9/1986 | North et al. |
| 4,701,193 | A | 10/1987 | Robertson et al. |
| 4,735,603 | A | 4/1988 | Goodson et al. |
| 4,788,977 | A | 12/1988 | Farin et al. |
| 4,892,244 | A | 1/1990 | Fox et al. |
| 5,010,341 | A | 4/1991 | Huntley et al. |
| 5,035,692 | A | 7/1991 | Lyon et al. |
| 5,042,460 | A | 8/1991 | Sakurai et al. |
| 5,084,057 | A | 1/1992 | Green et al. |
| 5,100,402 | A | 3/1992 | Fan |
| 5,129,570 | A | 7/1992 | Schulze et al. |
| 5,151,102 | A | 9/1992 | Kamiyama et al. |
| 5,156,315 | A | 10/1992 | Green et al. |
| 5,158,585 | A | 10/1992 | Saho et al. |
| 5,197,962 | A | 3/1993 | Sansom et al. |
| 5,242,474 | A | 9/1993 | Herbst et al. |
| 5,253,793 | A | 10/1993 | Green et al. |
| 5,271,543 | A | 12/1993 | Grant et al. |
| RE34,519 | E | 1/1994 | Fox et al. |
| 5,318,516 | A | 6/1994 | Cosmescu |
| 5,322,055 | A | 6/1994 | Davison et al. |
| 5,342,349 | A | 8/1994 | Kaufman |
| 5,383,880 | A | 1/1995 | Hooven |
| 5,396,900 | A | 3/1995 | Slater et al. |
| 5,397,046 | A | 3/1995 | Savage et al. |
| 5,403,312 | A | 4/1995 | Yates et al. |
| 5,403,327 | A | 4/1995 | Thornton et al. |
| 5,413,267 | A | 5/1995 | Solyntjes et al. |
| 5,415,335 | A | 5/1995 | Knodell, Jr. |
| 5,417,699 | A | 5/1995 | Klein et al. |
| 5,439,468 | A | 8/1995 | Schulze et al. |
| 5,445,304 | A | 8/1995 | Plyley et al. |
| 5,465,895 | A | 11/1995 | Knodel et al. |
| 5,467,911 | A | 11/1995 | Tsuruta et al. |
| 5,474,566 | A | 12/1995 | Alesi et al. |

(56) References Cited

U.S. PATENT DOCUMENTS

| | | |
|---|---|---|
| 5,485,947 A | 1/1996 | Olson et al. |
| 5,496,315 A | 3/1996 | Weaver et al. |
| 5,503,320 A | 4/1996 | Webster et al. |
| 5,531,743 A | 7/1996 | Nettekoven et al. |
| 5,545,148 A | 8/1996 | Wurster |
| 5,552,685 A | 9/1996 | Young et al. |
| 5,584,425 A | 12/1996 | Savage et al. |
| 5,610,379 A | 3/1997 | Muz et al. |
| 5,613,966 A | 3/1997 | Makower et al. |
| 5,624,452 A | 4/1997 | Yates |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,766,186 A | 6/1998 | Faraz et al. |
| 5,769,791 A | 6/1998 | Benaron et al. |
| 5,797,537 A | 8/1998 | Oberlin et al. |
| D399,561 S | 10/1998 | Ellingson |
| 5,817,093 A | 10/1998 | Wlliamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,997,528 A | 12/1999 | Bisch et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,109,500 A | 8/2000 | Alli et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,273,887 B1 | 8/2001 | Yamauchi et al. |
| 6,301,495 B1 | 10/2001 | Gueziec et al. |
| 6,302,881 B1 | 10/2001 | Farin |
| 6,308,089 B1 | 10/2001 | Ruhr et al. |
| 6,325,808 B1 | 12/2001 | Bernard et al. |
| 6,325,811 B1 | 12/2001 | Messerly |
| 6,341,164 B1 | 1/2002 | Dilkie et al. |
| 6,391,102 B1 | 5/2002 | Bodden et al. |
| 6,434,416 B1 | 8/2002 | Mizoguchi et al. |
| 6,443,973 B1 | 9/2002 | Whitman |
| 6,454,781 B1 | 9/2002 | Witt et al. |
| 6,457,625 B1 | 10/2002 | Tormala et al. |
| 6,461,352 B2 | 10/2002 | Morgan et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,585,791 B1 | 7/2003 | Garito et al. |
| 6,618,626 B2 | 9/2003 | West, Jr. et al. |
| 6,648,223 B2 | 11/2003 | Boukhny et al. |
| 6,679,899 B2 | 1/2004 | Wiener et al. |
| 6,685,704 B2 | 2/2004 | Greep |
| 6,699,187 B2 | 3/2004 | Webb et al. |
| 6,742,895 B2 | 6/2004 | Robin |
| 6,752,816 B2 | 6/2004 | Culp et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,663 B2 | 9/2004 | Kneifel et al. |
| 6,846,308 B2 | 1/2005 | Whitman et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | Guillebon et al. |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,097,640 B2 | 8/2006 | Wang et al. |
| 7,103,688 B2 | 9/2006 | Strong |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,169,145 B2 | 1/2007 | Isaacson et al. |
| 7,177,533 B2 | 2/2007 | McFarlin et al. |
| 7,182,775 B2 | 2/2007 | Guillebon et al. |
| 7,208,005 B2 | 4/2007 | Frecker et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |

(56) References Cited

U.S. PATENT DOCUMENTS

| | | |
|---|---|---|
| 7,422,139 B2 | 9/2008 | Shelton, IV et al. |
| 7,423,972 B2 | 9/2008 | Shaham et al. |
| 7,457,804 B2 | 11/2008 | Uber, III et al. |
| 7,464,847 B2 | 12/2008 | Viola et al. |
| 7,464,849 B2 | 12/2008 | Shelton, IV et al. |
| 7,515,961 B2 | 4/2009 | Germanson et al. |
| 7,568,604 B2 | 8/2009 | Ehrenfels et al. |
| 7,575,144 B2 | 8/2009 | Ortiz et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,641,092 B2 | 1/2010 | Kruszynski et al. |
| 7,644,848 B2 | 1/2010 | Swayze et al. |
| 7,667,839 B2 | 2/2010 | Bates |
| 7,670,334 B2 | 3/2010 | Hueil et al. |
| 7,694,865 B2 | 4/2010 | Scirica |
| 7,699,860 B2 | 4/2010 | Huitema et al. |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,736,357 B2 | 6/2010 | Lee, Jr. et al. |
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| 7,862,560 B2 | 1/2011 | Marlon |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,942,300 B2 | 5/2011 | Rethy et al. |
| 7,954,682 B2 | 6/2011 | Giordano et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,075,571 B2 | 12/2011 | Vitali et al. |
| 8,096,459 B2 | 1/2012 | Ortiz et al. |
| 8,118,206 B2 | 2/2012 | Zand et al. |
| 8,120,301 B2 | 2/2012 | Goldberg et al. |
| 8,123,764 B2 | 2/2012 | Meade et al. |
| 8,131,565 B2 | 3/2012 | Dicks et al. |
| 8,136,712 B2 | 3/2012 | Zingman |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,160,098 B1 | 4/2012 | Yan et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,328,065 B2 | 12/2012 | Shah |
| 8,335,590 B2 | 12/2012 | Costa et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| 8,365,975 B1 | 2/2013 | Manoux et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,439,910 B2 | 5/2013 | Greep et al. |
| 8,444,663 B2 | 5/2013 | Houser et al. |
| 8,452,615 B2 | 5/2013 | Abri |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,476,227 B2 | 7/2013 | Kaplan et al. |
| 8,489,235 B2 | 7/2013 | Moll et al. |
| 8,499,992 B2 | 8/2013 | Whitman et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |

(56) References Cited

U.S. PATENT DOCUMENTS

| | | |
|---|---|---|
| 8,512,365 B2 | 8/2013 | Wiener et al. |
| 8,521,331 B2 | 8/2013 | Itkowitz |
| 8,523,043 B2 | 9/2013 | Ullrich et al. |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,571,598 B2 | 10/2013 | Valavi |
| 8,573,459 B2 | 11/2013 | Smith et al. |
| 8,573,465 B2 | 11/2013 | Shelton, IV |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,620,055 B2 | 12/2013 | Barratt et al. |
| 8,620,473 B2 | 12/2013 | Diolaiti et al. |
| 8,623,027 B2 | 1/2014 | Price et al. |
| 8,627,483 B2 | 1/2014 | Rachlin et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,666,544 B2 | 3/2014 | Moll et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,701,962 B2 | 4/2014 | Kostrzewski |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Man |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,820,603 B2 | 9/2014 | Shelton, IV et al. |
| 8,820,608 B2 | 9/2014 | Miyamoto |
| 8,827,134 B2 | 9/2014 | Viola et al. |
| 8,840,003 B2 | 9/2014 | Morgan et al. |
| 8,851,354 B2 | 10/2014 | Swensgard et al. |
| 8,852,174 B2 | 10/2014 | Burbank |
| 8,875,973 B2 | 11/2014 | Whitman |
| 8,882,662 B2 | 11/2014 | Charles |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,918,207 B2 | 12/2014 | Prisco |
| 8,920,414 B2 | 12/2014 | Stone et al. |
| 8,920,433 B2 | 12/2014 | Barrier et al. |
| 8,930,203 B2 | 1/2015 | Klaie et al. |
| 8,930,214 B2 | 1/2015 | Woolford |
| 8,931,679 B2 | 1/2015 | Kostrzewski |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,309 B2 | 3/2015 | Roy et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,302 B2 | 3/2015 | Aldridge et al. |
| 8,989,903 B2 | 3/2015 | Weir et al. |
| 8,991,678 B2 | 3/2015 | Wellman et al. |
| 8,992,565 B2 | 3/2015 | Brisson et al. |
| 8,998,797 B2 | 4/2015 | Omori |
| 9,002,518 B2 | 4/2015 | Manzo et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |

(56) References Cited

U.S. PATENT DOCUMENTS

| | | |
|---|---|---|
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,161,803 B2 | 10/2015 | Yates et al. |
| 9,168,054 B2 | 10/2015 | Turner et al. |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,202,078 B2 | 12/2015 | Abuelsaad et al. |
| 9,204,879 B2 | 12/2015 | Shelton, IV |
| 9,204,995 B2 | 12/2015 | Scheller et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,265,585 B2 | 2/2016 | Wingardner et al. |
| 9,272,406 B2 | 3/2016 | Aronhalt et al. |
| 9,277,956 B2 | 3/2016 | Zhang |
| 9,280,884 B1 | 3/2016 | Schultz et al. |
| 9,282,974 B2 | 3/2016 | Shelton, IV |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,325,732 B1 | 4/2016 | Stickle et al. |
| 9,326,767 B2 | 5/2016 | Koch et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,546 B2 | 5/2016 | Toth et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,468,438 B2 | 10/2016 | Baber et al. |
| 9,480,492 B2 | 11/2016 | Aranyi et al. |
| 9,485,475 B2 | 11/2016 | Speier et al. |
| 9,492,146 B2 | 11/2016 | Kostrzewski et al. |
| 9,492,237 B2 | 11/2016 | Kang et al. |
| 9,498,215 B2 | 11/2016 | Duque et al. |
| 9,498,231 B2 | 11/2016 | Haider et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,587 B2 | 12/2016 | Zhao et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 * | 2/2017 | Shelton, IV ............ A61B 34/30 |
| 9,561,045 B2 | 2/2017 | Hinman et al. |
| 9,566,708 B2 | 2/2017 | Kumianto |
| 9,572,592 B2 | 2/2017 | Price et al. |
| 9,579,503 B2 | 2/2017 | McKinney et al. |
| 9,585,657 B2 | 3/2017 | Shelton, IV et al. |
| 9,592,095 B2 | 3/2017 | Panescu et al. |
| 9,597,081 B2 | 3/2017 | Swayze et al. |
| 9,600,138 B2 | 3/2017 | Thomas et al. |
| 9,603,024 B2 | 3/2017 | Wang et al. |
| 9,610,114 B2 | 4/2017 | Baxter, III et al. |
| 9,622,808 B2 | 4/2017 | Beller et al. |
| 9,628,501 B2 | 4/2017 | Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,188 B2 | 5/2017 | Gattani et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,649,110 B2 | 5/2017 | Parihar et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |

(56) References Cited

U.S. PATENT DOCUMENTS

| | | |
|---|---|---|
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Schelb et al. |
| 9,750,523 B2 | 9/2017 | Tsubuku |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |
| 9,764,164 B2 | 9/2017 | Wener et al. |
| 9,770,541 B2 | 9/2017 | Carr et al. |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,470 B2 | 12/2017 | Gilbert et al. |
| 9,839,487 B2 | 12/2017 | Dachs, II |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,867,612 B2 | 1/2018 | Parihar et al. |
| 9,867,651 B2 | 1/2018 | Wham |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,914 B2 | 2/2018 | Martin et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,949,785 B2 | 4/2018 | Price et al. |
| 9,962,157 B2 | 5/2018 | Sapre |
| 9,968,355 B2 | 5/2018 | Shelton, IV et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |

(56) References Cited

U.S. PATENT DOCUMENTS

| | | |
|---|---|---|
| 10,016,199 B2 | 7/2018 | Baber et al. |
| 10,021,318 B2 | 7/2018 | Hugosson et al. |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,564 B2 | 8/2018 | Hibner et al. |
| 10,039,565 B2 | 8/2018 | Vezzu |
| 10,041,822 B2 | 8/2018 | Zemlok |
| 10,044,791 B2 | 8/2018 | Kamen et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,069,633 B2 | 9/2018 | Gulati et al. |
| 10,076,326 B2 | 9/2018 | Yates et al. |
| 10,080,618 B2 | 9/2018 | Marshall et al. |
| D831,209 S | 10/2018 | Huitema et al. |
| 10,085,748 B2 | 10/2018 | Morgan et al. |
| 10,085,749 B2 | 10/2018 | Cappola et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,105,140 B2 | 10/2018 | Malinouskas et al. |
| 10,105,142 B2 | 10/2018 | Baxter, III et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappoketai. |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,133,248 B2 | 11/2018 | Fitzsimmons et al. |
| 10,135,242 B2 | 11/2018 | Baber et al. |
| 10,136,887 B2 | 11/2018 | Shelton, IV et al. |
| 10,136,949 B2 | 11/2018 | Felder et al. |
| 10,143,526 B2 | 12/2018 | Walker et al. |
| 10,143,948 B2 | 12/2018 | Bonifas et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,169,862 B2 | 1/2019 | Andre et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,194,907 B2 | 2/2019 | Marczyk et al. |
| 10,194,913 B2 | 2/2019 | Nalagatla et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,035 B2 | 4/2019 | Fehre et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,870 B2 | 5/2019 | Connolly et al. |
| 10,305,926 B2 | 5/2019 | Mihan et al. |
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |

(56) References Cited

U.S. PATENT DOCUMENTS

| | | |
|---|---|---|
| 10,335,149 B2 | 7/2019 | Baxter, III et al. |
| 10,335,180 B2 | 7/2019 | Johnson et al. |
| 10,335,227 B2 | 7/2019 | Heard |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,941 B2 | 7/2019 | Marczyk et al. |
| 10,350,016 B2 | 7/2019 | Burbank et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,863 B2 | 9/2019 | Wse et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,512,461 B2 | 12/2019 | Gupta et al. |
| 10,512,499 B2 | 12/2019 | McHenry et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,422 B2 | 2/2020 | Schellin et al. |
| 10,561,471 B2 | 2/2020 | Nichogi |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,586,074 B2 | 3/2020 | Rose et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,691 B2 | 4/2020 | Wener et al. |
| 10,631,423 B2 | 4/2020 | Collins et al. |
| 10,631,858 B2 | 4/2020 | Burbank |

(56) References Cited

U.S. PATENT DOCUMENTS

| | | |
|---|---|---|
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,453 B2 | 10/2020 | Chen et al. |
| 10,806,454 B2 | 10/2020 | Kopp |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sharifi Sedeh et al. |
| 10,828,028 B2 | 11/2020 | Harris et al. |
| 10,828,030 B2 | 11/2020 | Weir et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| 10,849,697 B2 | 12/2020 | Yates et al. |
| 10,849,700 B2 | 12/2020 | Kopp et al. |
| 10,856,867 B2 | 12/2020 | Shelton, IV et al. |
| 10,856,868 B2 | 12/2020 | Shelton, IV et al. |
| 10,856,870 B2 | 12/2020 | Harris et al. |
| 10,864,050 B2 | 12/2020 | Tabandeh et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,881,464 B2 | 1/2021 | Odermatt et al. |
| 10,888,321 B2 | 1/2021 | Shelton, IV et al. |
| 10,888,322 B2 | 1/2021 | Morgan et al. |
| 10,892,899 B2 | 1/2021 | Shelton, IV et al. |
| 10,892,995 B2 | 1/2021 | Shelton, IV et al. |
| 10,893,863 B2 | 1/2021 | Shelton, IV et al. |
| 10,893,864 B2 | 1/2021 | Harris et al. |
| 10,893,884 B2 | 1/2021 | Stoddard et al. |
| 10,898,183 B2 | 1/2021 | Shelton, IV et al. |
| 10,898,186 B2 | 1/2021 | Bakos et al. |
| 10,898,189 B2 | 1/2021 | McDonald, II |
| 10,898,280 B2 | 1/2021 | Kopp |
| 10,898,622 B2 | 1/2021 | Shelton, IV et al. |
| 10,903,685 B2 | 1/2021 | Yates et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,912,559 B2 | 2/2021 | Harris et al. |
| 10,912,580 B2 | 2/2021 | Green et al. |
| 10,912,619 B2 | 2/2021 | Jarc et al. |
| 10,918,385 B2 | 2/2021 | Overmyer et al. |
| 10,930,400 B2 | 2/2021 | Robbins et al. |
| 10,932,705 B2 | 3/2021 | Muhsin et al. |
| 10,932,772 B2 | 3/2021 | Shelton, IV et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,939,313 B2 | 3/2021 | Eom et al. |
| 10,943,454 B2 | 3/2021 | Shelton, IV et al. |
| 10,944,728 B2 | 3/2021 | Wiener et al. |
| 10,945,727 B2 | 3/2021 | Shelton, IV et al. |
| 10,952,708 B2 | 3/2021 | Scheib et al. |
| 10,954,935 B2 | 3/2021 | O'Shea et al. |

(56) References Cited

U.S. PATENT DOCUMENTS

| | | |
|---|---|---|
| 10,959,727 B2 | 3/2021 | Hunter et al. |
| 10,959,729 B2 | 3/2021 | Ehrenfels et al. |
| 10,959,744 B2 | 3/2021 | Shelton, IV et al. |
| 10,959,788 B2 | 3/2021 | Grover et al. |
| 10,960,150 B2 | 3/2021 | Zergiebel et al. |
| 2002/0049551 A1 | 4/2002 | Friedman et al. |
| 2003/0093503 A1 | 5/2003 | Yamaki et al. |
| 2003/0114851 A1 | 6/2003 | Truckai et al. |
| 2003/0210812 A1 | 11/2003 | Khamene et al. |
| 2003/0223877 A1 | 12/2003 | Anstine et al. |
| 2004/0078236 A1 | 4/2004 | Stoodley et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0243148 A1 | 12/2004 | Wasielewski |
| 2004/0243435 A1 | 12/2004 | Williams |
| 2005/0020909 A1 | 1/2005 | Barrera et al. |
| 2005/0063575 A1 | 3/2005 | Ma et al. |
| 2005/0065438 A1 | 3/2005 | Miller |
| 2005/0131390 A1 | 6/2005 | Heinrich et al. |
| 2005/0143759 A1 | 6/2005 | Kelly |
| 2005/0149001 A1 | 7/2005 | Uchikubo et al. |
| 2005/0149356 A1 | 7/2005 | Cyr et al. |
| 2005/0192633 A1 | 9/2005 | Montpetit |
| 2005/0222631 A1 | 10/2005 | Dalal et al. |
| 2005/0236474 A1 | 10/2005 | Onuma et al. |
| 2005/0277913 A1 | 12/2005 | McCary |
| 2006/0020272 A1 | 1/2006 | Gildenberg |
| 2006/0059018 A1 | 3/2006 | Shiobara et al. |
| 2006/0079874 A1 | 4/2006 | Faller et al. |
| 2006/0116908 A1 | 6/2006 | Dew et al. |
| 2006/0241399 A1 | 10/2006 | Fabian |
| 2007/0010838 A1 | 1/2007 | Shelton et al. |
| 2007/0016235 A1 | 1/2007 | Tanaka et al. |
| 2007/0027459 A1 | 2/2007 | Horvath et al. |
| 2007/0049947 A1 | 3/2007 | Menn et al. |
| 2007/0078678 A1 | 4/2007 | DiSilvestro et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175955 A1 | 8/2007 | Shelton et al. |
| 2007/0191713 A1 | 8/2007 | Eichmann et al. |
| 2007/0225556 A1 | 9/2007 | Ortiz et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282333 A1 | 12/2007 | Fortson et al. |
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0033404 A1 | 2/2008 | Romoda et al. |
| 2008/0040151 A1 | 2/2008 | Moore |
| 2008/0059658 A1 | 3/2008 | Williams |
| 2008/0077158 A1 | 3/2008 | Haider et al. |
| 2008/0083414 A1 | 4/2008 | Messerges |
| 2008/0177362 A1 | 7/2008 | Phillips et al. |
| 2008/0200940 A1 | 8/2008 | Eichmann et al. |
| 2008/0255413 A1 | 10/2008 | Zemlok et al. |
| 2008/0262654 A1 | 10/2008 | Omori et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0182577 A1 | 7/2009 | Squilla et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0065604 A1 | 3/2010 | Weng |
| 2010/0069942 A1 | 3/2010 | Shelton, IV |
| 2010/0070417 A1 | 3/2010 | Flynn et al. |
| 2010/0132334 A1 | 6/2010 | Duclos et al. |
| 2010/0137845 A1 | 6/2010 | Ramstein et al. |
| 2010/0179831 A1 | 7/2010 | Brown et al. |
| 2010/0191100 A1 | 7/2010 | Anderson et al. |
| 2010/0198248 A1 | 8/2010 | Vakharia |
| 2010/0217991 A1 | 8/2010 | Choi |
| 2010/0235689 A1 | 9/2010 | Tian et al. |
| 2010/0250571 A1 | 9/2010 | Pierce et al. |
| 2010/0292535 A1 | 11/2010 | Paskar |
| 2011/0022032 A1 | 1/2011 | Zemlok et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0105895 A1 | 5/2011 | Kornblau et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0237883 A1 | 9/2011 | Chun |
| 2011/0306840 A1 | 12/2011 | Allen et al. |
| 2012/0022519 A1 | 1/2012 | Huang et al. |
| 2012/0059684 A1 | 3/2012 | Hampapur et al. |
| 2012/0116265 A1 | 5/2012 | Houser et al. |
| 2012/0116381 A1 | 5/2012 | Houser et al. |
| 2012/0130217 A1 | 5/2012 | Kauphusman et al. |
| 2012/0172696 A1 | 7/2012 | Kallback et al. |
| 2012/0191091 A1 | 7/2012 | Allen |
| 2012/0203785 A1 | 8/2012 | Awada |
| 2012/0211542 A1 | 8/2012 | Racenet |
| 2012/0245958 A1 | 9/2012 | Lawrence et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0024213 A1 | 1/2013 | Poon |
| 2013/0046182 A1 | 2/2013 | Hegg et al. |
| 2013/0046279 A1 | 2/2013 | Niklewski et al. |
| 2013/0066647 A1 | 3/2013 | Andrie et al. |
| 2013/0090526 A1 | 4/2013 | Suzuki et al. |
| 2013/0093829 A1 | 4/2013 | Rosenblatt et al. |
| 2013/0116218 A1 | 5/2013 | Kaplan et al. |
| 2013/0165776 A1 | 6/2013 | Blomqvist |
| 2013/0178853 A1 | 7/2013 | Hyink et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005694 A1* | 1/2014 | Shelton, IV ......... A61B 17/105 606/143 |
| 2014/0006132 A1 | 1/2014 | Barker |
| 2014/0029411 A1 | 1/2014 | Nayak et al. |
| 2014/0035762 A1 | 2/2014 | Shelton, IV et al. |
| 2014/0066700 A1 | 3/2014 | Wilson et al. |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patanl et al. |
| 2014/0108035 A1 | 4/2014 | Akbay et al. |
| 2014/0108983 A1 | 4/2014 | William et al. |
| 2014/0148729 A1 | 5/2014 | Schmitz et al. |
| 2014/0166724 A1 | 6/2014 | Schellln et al. |
| 2014/0187856 A1 | 7/2014 | Holoien et al. |

(56) References Cited

U.S. PATENT DOCUMENTS

| | | |
|---|---|---|
| 2014/0204190 A1 | 7/2014 | Rosenblatt, III et al. |
| 2014/0243799 A1 | 8/2014 | Parihar |
| 2014/0243809 A1 | 8/2014 | Gelfand et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0303660 A1 | 10/2014 | Boyden et al. |
| 2015/0006201 A1 | 1/2015 | Fait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051617 A1 | 2/2015 | Takemura et al. |
| 2015/0053737 A1 | 2/2015 | Leimbach et al. |
| 2015/0066000 A1 | 3/2015 | An et al. |
| 2015/0070187 A1 | 3/2015 | Wiesner et al. |
| 2015/0108198 A1 | 4/2015 | Estrella |
| 2015/0133945 A1 | 5/2015 | Dushyant et al. |
| 2015/0196295 A1 | 7/2015 | Shelton, IV et al. |
| 2015/0199109 A1 | 7/2015 | Lee |
| 2015/0238355 A1 | 8/2015 | Vezzu et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297233 A1 | 10/2015 | Huitema et al. |
| 2015/0297311 A1 | 10/2015 | Tesar |
| 2015/0302157 A1 | 10/2015 | Collar et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0332003 A1 | 11/2015 | Stamm et al. |
| 2015/0332196 A1 | 11/2015 | Stiller et al. |
| 2016/0000437 A1 | 1/2016 | Giordano et al. |
| 2016/0015471 A1 | 1/2016 | Piron et al. |
| 2016/0034648 A1 | 2/2016 | Mohlenbrock et al. |
| 2016/0038253 A1 | 2/2016 | Piron et al. |
| 2016/0066913 A1 | 3/2016 | Swayze et al. |
| 2016/0078190 A1 | 3/2016 | Greene et al. |
| 2016/0106516 A1 | 4/2016 | Mesallum |
| 2016/0106934 A1 | 4/2016 | Hiraga et al. |
| 2016/0180045 A1 | 6/2016 | Syed |
| 2016/0192960 A1 | 7/2016 | Bueno et al. |
| 2016/0206202 A1 | 7/2016 | Frangioni |
| 2016/0235303 A1 | 8/2016 | Fleming et al. |
| 2016/0249910 A1 | 9/2016 | Shelton, IV et al. |
| 2016/0287912 A1 | 10/2016 | Warnking |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0321400 A1 | 11/2016 | Durrant et al. |
| 2016/0323283 A1 | 11/2016 | Kang et al. |
| 2016/0342916 A1 | 11/2016 | Arceneaux et al. |
| 2016/0345857 A1 | 12/2016 | Jensrud et al. |
| 2016/0345976 A1 | 12/2016 | Gonzalez et al. |
| 2016/0350490 A1 | 12/2016 | Martinez et al. |
| 2016/0361070 A1 | 12/2016 | Ardel et al. |
| 2016/0374723 A1 | 12/2016 | Frankhouser et al. |
| 2016/0374762 A1 | 12/2016 | Case et al. |
| 2017/0000516 A1 | 1/2017 | Stolen et al. |
| 2017/0000553 A1 | 1/2017 | Wiener et al. |
| 2017/0027603 A1 | 2/2017 | Pandey |
| 2017/0068792 A1 | 3/2017 | Reiner |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0116873 A1 | 4/2017 | Lendvay et al. |
| 2017/0132374 A1 | 5/2017 | Lee et al. |
| 2017/0132785 A1 | 5/2017 | Wshah et al. |
| 2017/0143284 A1 | 5/2017 | Sehnert et al. |
| 2017/0143442 A1 | 5/2017 | Tesar et al. |
| 2017/0164997 A1 | 6/2017 | Johnson et al. |
| 2017/0165012 A1 | 6/2017 | Chaplin et al. |
| 2017/0172565 A1 | 6/2017 | Heneveld |
| 2017/0172614 A1 | 6/2017 | Scheib et al. |
| 2017/0177807 A1 | 6/2017 | Fabian |
| 2017/0196637 A1 | 7/2017 | Shelton, IV et al. |
| 2017/0202591 A1 | 7/2017 | Shelton, IV et al. |
| 2017/0202607 A1 | 7/2017 | Shelton, IV et al. |
| 2017/0224332 A1 | 8/2017 | Hunter et al. |
| 2017/0224334 A1 | 8/2017 | Worthington et al. |
| 2017/0224428 A1 | 8/2017 | Kopp |
| 2017/0231627 A1 | 8/2017 | Shelton, IV et al. |
| 2017/0231628 A1 | 8/2017 | Shelton, IV et al. |
| 2017/0245809 A1 | 8/2017 | Ma et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0273715 A1 | 9/2017 | Piron et al. |
| 2017/0281171 A1 | 10/2017 | Shelton, IV et al. |
| 2017/0281173 A1 | 10/2017 | Shelton, IV et al. |
| 2017/0281186 A1 | 10/2017 | Shelton, IV et al. |
| 2017/0281189 A1 | 10/2017 | Nalagatla et al. |
| 2017/0290585 A1 | 10/2017 | Shelton, IV et al. |
| 2017/0296169 A1 | 10/2017 | Yates et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304020 A1 | 10/2017 | Ng et al. |
| 2017/0312456 A1 | 11/2017 | Phillips |
| 2017/0325876 A1 | 11/2017 | Nakadate et al. |
| 2017/0325878 A1 | 11/2017 | Messerly et al. |
| 2017/0360499 A1 | 12/2017 | Greep et al. |
| 2017/0367695 A1 | 12/2017 | Shelton, IV et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0050196 A1 | 2/2018 | Pawsey et al. |
| 2018/0055529 A1 | 3/2018 | Messerly et al. |
| 2018/0065248 A1 | 3/2018 | Barral et al. |
| 2018/0098816 A1 | 4/2018 | Govari et al. |
| 2018/0110523 A1 | 4/2018 | Shelton, IV |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0125590 A1 | 5/2018 | Giordano et al. |
| 2018/0132895 A1 | 5/2018 | Silver |
| 2018/0153574 A1 | 6/2018 | Faller et al. |
| 2018/0153632 A1 | 6/2018 | Tokarchuk et al. |
| 2018/0154297 A1 | 6/2018 | Maletich et al. |
| 2018/0161716 A1 | 6/2018 | Li et al. |
| 2018/0168575 A1 | 6/2018 | Simms et al. |
| 2018/0168577 A1 | 6/2018 | Aronhalt et al. |
| 2018/0168578 A1 | 6/2018 | Aronhalt et al. |
| 2018/0168579 A1 | 6/2018 | Aronhalt et al. |
| 2018/0168584 A1 | 6/2018 | Harris et al. |
| 2018/0168590 A1 | 6/2018 | Overmyer et al. |
| 2018/0168592 A1 | 6/2018 | Overmyer et al. |
| 2018/0168597 A1 | 6/2018 | Fanelli et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168614 A1 | 6/2018 | Shelton, IV et al. |
| 2018/0168615 A1 | 6/2018 | Shelton, IV et al. |
| 2018/0168617 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168627 A1 | 6/2018 | Weaner et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168649 A1 | 6/2018 | Shelton, IV et al. |

(56) References Cited

U.S. PATENT DOCUMENTS

| | | |
|---|---|---|
| 2018/0168650 A1 | 6/2018 | Shelton, IV et al. |
| 2018/0168651 A1 | 6/2018 | Shelton, IV et al. |
| 2018/0206884 A1 | 7/2018 | Beaupre |
| 2018/0214025 A1 | 8/2018 | Homyk et al. |
| 2018/0221598 A1 | 8/2018 | Silver |
| 2018/0228557 A1 | 8/2018 | Darisse et al. |
| 2018/0235719 A1 | 8/2018 | Jarc |
| 2018/0242967 A1 | 8/2018 | Meade |
| 2018/0263710 A1 | 9/2018 | Sakaguchi et al. |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0296286 A1 | 10/2018 | Peine et al. |
| 2018/0304471 A1 | 10/2018 | Tokuchi |
| 2018/0310935 A1 | 11/2018 | Wixey |
| 2018/0310986 A1 | 11/2018 | Batchelor et al. |
| 2018/0351987 A1 | 12/2018 | Patel et al. |
| 2018/0360454 A1 | 12/2018 | Shelton, IV et al. |
| 2018/0360456 A1 | 12/2018 | Shelton, IV et al. |
| 2018/0368930 A1 | 12/2018 | Esterberg et al. |
| 2019/0000478 A1 | 1/2019 | Messerly et al. |
| 2019/0000565 A1 | 1/2019 | Shelton, IV et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0053801 A1 | 2/2019 | Wixey et al. |
| 2019/0053866 A1 | 2/2019 | Seow et al. |
| 2019/0069949 A1 | 3/2019 | Vrba et al. |
| 2019/0069964 A1 | 3/2019 | Hagn |
| 2019/0070550 A1 | 3/2019 | Lalomia et al. |
| 2019/0070731 A1 | 3/2019 | Bowling et al. |
| 2019/0087544 A1 | 3/2019 | Peterson |
| 2019/0104919 A1 | 4/2019 | Shelton, IV et al. |
| 2019/0125320 A1 | 5/2019 | Shelton, IV et al. |
| 2019/0125321 A1 | 5/2019 | Shelton, IV et al. |
| 2019/0125324 A1 | 5/2019 | Scheib et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125339 A1 | 5/2019 | Shelton, IV et al. |
| 2019/0125347 A1 | 5/2019 | Stokes et al. |
| 2019/0125348 A1 | 5/2019 | Shelton, IV et al. |
| 2019/0125352 A1 | 5/2019 | Shelton, IV et al. |
| 2019/0125353 A1 | 5/2019 | Shelton, IV et al. |
| 2019/0125354 A1 | 5/2019 | Deck et al. |
| 2019/0125355 A1 | 5/2019 | Shelton, IV et al. |
| 2019/0125356 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125359 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125379 A1 | 5/2019 | Shelton, IV et al. |
| 2019/0125380 A1 | 5/2019 | Hunter et al. |
| 2019/0125384 A1 | 5/2019 | Scheib et al. |
| 2019/0125387 A1 | 5/2019 | Parihar et al. |
| 2019/0125388 A1 | 5/2019 | Shelton, IV et al. |
| 2019/0125389 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125456 A1 | 5/2019 | Shelton, IV et al. |
| 2019/0125457 A1 | 5/2019 | Parihar et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142449 A1 | 5/2019 | Shelton, IV et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0192157 A1 | 6/2019 | Scott et al. |
| 2019/0192236 A1 | 6/2019 | Shelton, IV et al. |
| 2019/0200844 A1 | 7/2019 | Shelton, IV et al. |
| 2019/0200863 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200996 A1 | 7/2019 | Shelton, IV et al. |
| 2019/0200997 A1 | 7/2019 | Shelton, IV et al. |
| 2019/0200998 A1 | 7/2019 | Shelton, IV et al. |
| 2019/0201020 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201037 A1 | 7/2019 | Houser et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201041 A1 | 7/2019 | Kimball et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201074 A1 | 7/2019 | Yates et al. |
| 2019/0201075 A1 | 7/2019 | Shelton, IV et al. |
| 2019/0201077 A1 | 7/2019 | Yates et al. |
| 2019/0201079 A1 | 7/2019 | Shelton, IV et al. |
| 2019/0201080 A1 | 7/2019 | Messerly et al. |
| 2019/0201081 A1 | 7/2019 | Shelton, IV et al. |
| 2019/0201082 A1 | 7/2019 | Shelton, IV et al. |
| 2019/0201083 A1 | 7/2019 | Shelton, IV et al. |
| 2019/0201084 A1 | 7/2019 | Shelton, IV et al. |
| 2019/0201085 A1 | 7/2019 | Shelton, IV et al. |
| 2019/0201086 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201092 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201105 A1 | 7/2019 | Shelton, IV et al. |
| 2019/0201111 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201114 A1 | 7/2019 | Shelton, IV et al. |
| 2019/0201115 A1 | 7/2019 | Shelton, IV et al. |
| 2019/0201116 A1 | 7/2019 | Shelton, IV et al. |
| 2019/0201118 A1 | 7/2019 | Shelton, IV et al. |
| 2019/0201119 A1 | 7/2019 | Harris et al. |
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201125 A1 | 7/2019 | Shelton, IV et al. |
| 2019/0201126 A1 | 7/2019 | Shelton, IV et al. |
| 2019/0201127 A1 | 7/2019 | Shelton, IV et al. |

(56) References Cited

U.S. PATENT DOCUMENTS

| | | |
|---|---|---|
| 2019/0201128 A1 | 7/2019 | Yates et al. |
| 2019/0201129 A1 | 7/2019 | Shelton, IV et al. |
| 2019/0201130 A1 | 7/2019 | Shelton, IV et al. |
| 2019/0201135 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201138 A1 | 7/2019 | Yates et al. |
| 2019/0201139 A1 | 7/2019 | Shelton, IV et al. |
| 2019/0201140 A1 | 7/2019 | Yates et al. |
| 2019/0201141 A1 | 7/2019 | Shelton, IV et al. |
| 2019/0201142 A1 | 7/2019 | Shelton, IV et al. |
| 2019/0201143 A1 | 7/2019 | Shelton, IV et al. |
| 2019/0201145 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201159 A1 | 7/2019 | Shelton, IV et al. |
| 2019/0201594 A1 | 7/2019 | Shelton, IV et al. |
| 2019/0201597 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205441 A1 | 7/2019 | Shelton, IV et al. |
| 2019/0205566 A1 | 7/2019 | Shelton, IV et al. |
| 2019/0205567 A1 | 7/2019 | Shelton, IV et al. |
| 2019/0206003 A1 | 7/2019 | Harris et al. |
| 2019/0206004 A1 | 7/2019 | Shelton, IV et al. |
| 2019/0206050 A1 | 7/2019 | Yates et al. |
| 2019/0206542 A1 | 7/2019 | Shelton, IV et al. |
| 2019/0206551 A1 | 7/2019 | Yates et al. |
| 2019/0206555 A1 | 7/2019 | Morgan et al. |
| 2019/0206556 A1 | 7/2019 | Shelton, IV et al. |
| 2019/0206561 A1 | 7/2019 | Shelton, IV et al. |
| 2019/0206562 A1 | 7/2019 | Shelton, IV et al. |
| 2019/0206563 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0206576 A1 | 7/2019 | Shelton, IV et al. |
| 2019/0208641 A1 | 7/2019 | Yates et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cutl et al. |
| 2019/0274716 A1 | 9/2019 | Nott et al. |
| 2019/0274717 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274750 A1 | 9/2019 | Jayme et al. |
| 2019/0274752 A1 | 9/2019 | Denzinger et al. |
| 2019/0290389 A1 | 9/2019 | Kopp |
| 2019/0298340 A1 | 10/2019 | Shelton, IV et al. |
| 2019/0298341 A1 | 10/2019 | Shelton, IV et al. |
| 2019/0298342 A1 | 10/2019 | Shelton, IV et al. |
| 2019/0298343 A1 | 10/2019 | Shelton, IV et al. |
| 2019/0298346 A1 | 10/2019 | Shelton, IV et al. |
| 2019/0298347 A1 | 10/2019 | Shelton, IV et al. |
| 2019/0298350 A1 | 10/2019 | Shelton, IV et al. |
| 2019/0298351 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298354 A1 | 10/2019 | Shelton, IV et al. |
| 2019/0298355 A1 | 10/2019 | Shelton, IV et al. |
| 2019/0298356 A1 | 10/2019 | Shelton, IV et al. |
| 2019/0298357 A1 | 10/2019 | Shelton, IV et al. |
| 2019/0298464 A1 | 10/2019 | Abbott |
| 2019/0298481 A1 | 10/2019 | Rosenberg et al. |
| 2019/0307520 A1 | 10/2019 | Peine et al. |
| 2019/0314015 A1 | 10/2019 | Shelton, IV et al. |
| 2019/0314016 A1 | 10/2019 | Huitema et al. |
| 2019/0321117 A1 | 10/2019 | Itkowitz et al. |
| 2019/0333626 A1 | 10/2019 | Mansi et al. |
| 2019/0343594 A1 | 11/2019 | Kilroy et al. |
| 2019/0374140 A1 | 12/2019 | Tucker et al. |
| 2020/0054317 A1 | 2/2020 | Pisarnwongs et al. |
| 2020/0054320 A1 | 2/2020 | Harris et al. |
| 2020/0054321 A1 | 2/2020 | Harris et al. |
| 2020/0054322 A1 | 2/2020 | Harris et al. |
| 2020/0054323 A1 | 2/2020 | Harris et al. |
| 2020/0054326 A1 | 2/2020 | Harris et al. |
| 2020/0054328 A1 | 2/2020 | Harris et al. |
| 2020/0054330 A1 | 2/2020 | Harris et al. |
| 2020/0078096 A1 | 3/2020 | Barbagli et al. |
| 2020/0100830 A1 | 4/2020 | Henderson et al. |
| 2020/0162896 A1 | 5/2020 | Su et al. |
| 2020/0178971 A1 | 6/2020 | Harris et al. |
| 2020/0261075 A1 | 8/2020 | Boudreaux et al. |
| 2020/0261076 A1 | 8/2020 | Boudreaux et al. |
| 2020/0261077 A1 | 8/2020 | Shelton, IV et al. |
| 2020/0261078 A1 | 8/2020 | Bakos et al. |
| 2020/0261080 A1 | 8/2020 | Bakos et al. |
| 2020/0261081 A1 | 8/2020 | Boudreaux et al. |
| 2020/0261082 A1 | 8/2020 | Boudreaux et al. |
| 2020/0261083 A1 | 8/2020 | Bakos et al. |
| 2020/0261084 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0261089 A1 | 8/2020 | Shelton, IV et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0405375 A1 | 12/2020 | Shelton, IV et al. |
| 2021/0000555 A1 | 1/2021 | Shelton, IV et al. |
| 2021/0015568 A1 | 1/2021 | Liao et al. |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 108652695 A | 10/2018 |
| DE | 2037167 A1 | 7/1980 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| GB | 2509523 A | 7/2014 |
| JP | S5373315 A | 6/1978 |
| JP | 2017513561 A | 6/2017 |
| KR | 20140104587 A | 8/2014 |
| KR | 101587721 B1 | 1/2016 |
| WO | WO-9734533 A1 | 9/1997 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2007137304 A2 | 11/2007 |
| WO | WO-2008056618 A2 | 5/2008 |
| WO | WO-2008069816 A1 | 6/2008 |

(56) References Cited

FOREIGN PATENT DOCUMENTS

| | | |
|---|---|---|
| WO | WO-2008147555 A2 | 12/2008 |
| WO | WO-2011112931 A1 | 9/2011 |
| WO | WO-2013143573 A1 | 10/2013 |
| WO | WO-2014134196 A1 | 9/2014 |
| WO | WO-2015129395 A1 | 9/2015 |
| WO | WO-2016100719 A1 | 6/2016 |
| WO | WO-2016206015 A1 | 12/2016 |
| WO | WO-201 7011382 A1 | 1/2017 |
| WO | WO-2017011646 A1 | 1/2017 |
| WO | WO-2017058695 A1 | 4/2017 |
| WO | WO-2017151996 A1 | 9/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |
| WO | WO-2018152141 A1 | 8/2018 |
| WO | WO-2018176414 A1 | 10/2018 |

OTHER PUBLICATIONS

Flores et al., "Large-scale Offloading in the Internet of Things," 2017 IEEE International Conference on Pervasive Computing and Communications Workshops (Percom Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trendbased methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.

Phumzile Malindi, "5. QoS in Telemedicine," "Telemedicine," Jun. 20, 2011, IntechOpen, pp. 119-138.

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Octobers, 2015, pp. 553-568.

Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.

Altenberg et al., "Genes of Glycolysis are Ubiquitously Overexpressed in 24 Cancer Classes," Genomics, vol. 84, pp. 1014-1020 (2004).

Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%200fc/o20Electrosurgical%20Smoke.pdf> (Year: 1997).

Marshall Brain, How Microcontrollers Work, 2006, retrieved from the internet <https://web.archive.org/web/20060221235221/http://electronics.howstuffworks.com/microcontroller.htm/printable> (Year: 2006).

CRC Press, "The Measurement, Instrumentation and Sensors Handbook," 1999, Section VII, Chapter 41, Peter O'Shea, "Phase Measurement," pp. 1303-1321, Isbn 0-8493-2145-X.

Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.

Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.

Salamon, "AI Detects Polyps Better Than Colonoscopists" Online Article, Jun. 3, 2018, Medscape Medical News, Digestive Disease Week (DDW) 2018: Presentation 133.

Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.

Dottorato, "Analysis and Design of the Rectangular Microstrip Patch Antennas for TMOn0 operating mode,"Article, Oct. 8, 2010, pp. 1-9, Microwave Journal.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

Hsiao-Wei Tang, "ARCM", Video, Sep. 2012. YouTube, 5 screenshots. Retrieved from Internet: <https://www.youtube.com/watch?v=UldQaxb3fRw&feature=youtu.be>.

Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.

(56) References Cited

OTHER PUBLICATIONS

Vander Heiden, et al., "Understanding the Warburg effect: the metabolic requirements of cell proliferation," Article, May 22, 2009, pp. 1-12, vol. 324, Issue 5930, Science.
Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.
Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.
Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.
"ATM-MPLS Network Interworking Version 2.0, af-aic-0178.001" ATM Standard, The ATM Forum Technical Committee, published Aug. 2003.
IEEE Std 802.Mar. 2012 (Revision of IEEE Std 802.3-2008, published Dec. 28, 2012.
IEEE Std No. 177, "Standard Definitions and Methods of Measurement for Piezoelectric Vibrators," published May 1966, The Institute of Electrical and Electronics Engineers, Inc., New York, N.Y.
Shi et al., An intuitive control console for robotic syrgery system, 2014, IEEE, p. 404-407 (Year: 2014).
Choi et al., A haptic augmented reality surgeon console for a laparoscopic surgery robot system, 2013, IEEE, p. 355-357 (Year: 2013).
Xie et al., Development of stereo vision and master-slave controller for a compact surgical robot system, 2015, IEEE, p. 403-407 (Year: 2015).
Sun et al., Innovative effector design for simulation training in robotic surgery, 2010, IEEE, p. 1735-1759 (Year: 2010).
Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgical_devices.pdf.
Draijer, Matthijs et al., "Review of laser speckle contrast techniques for visualizing tissue perfusion," Lasers in Medical Science, Springer-Verlag, LO, vol. 2 4, No. 4, Dec. 3, 2008, pp. 639-651.
Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand col. paragraph 3.
"Surgical instrumentation: the true cost of instrument trays and a potential strategy for optimization"; Mhlaba et al.; Sep. 23, 2015 (Year: 2015).
Nabil Simaan et al., "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863,.
Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.

\* cited by examiner

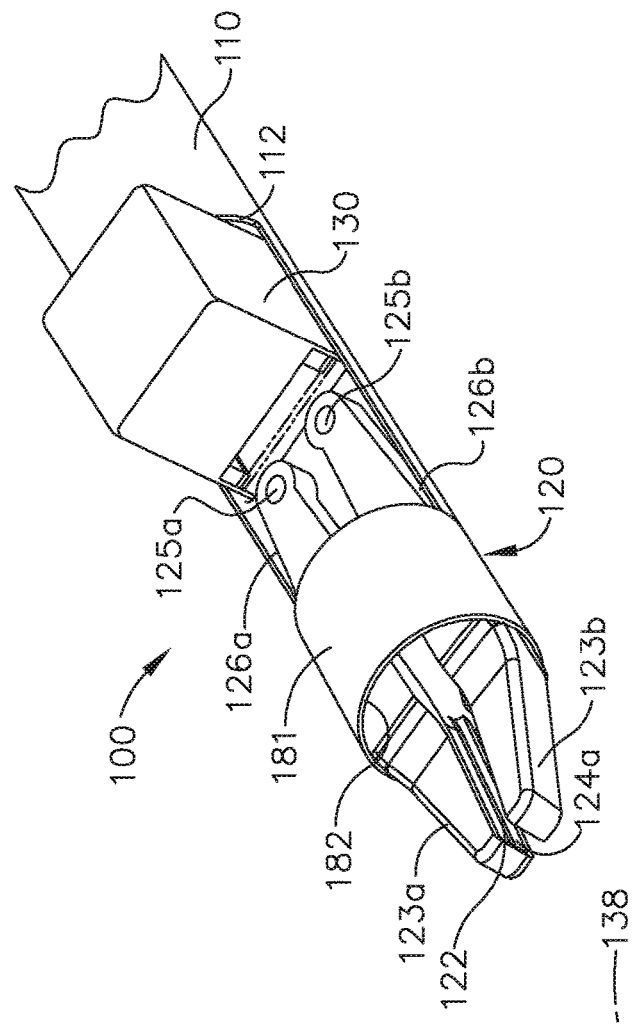
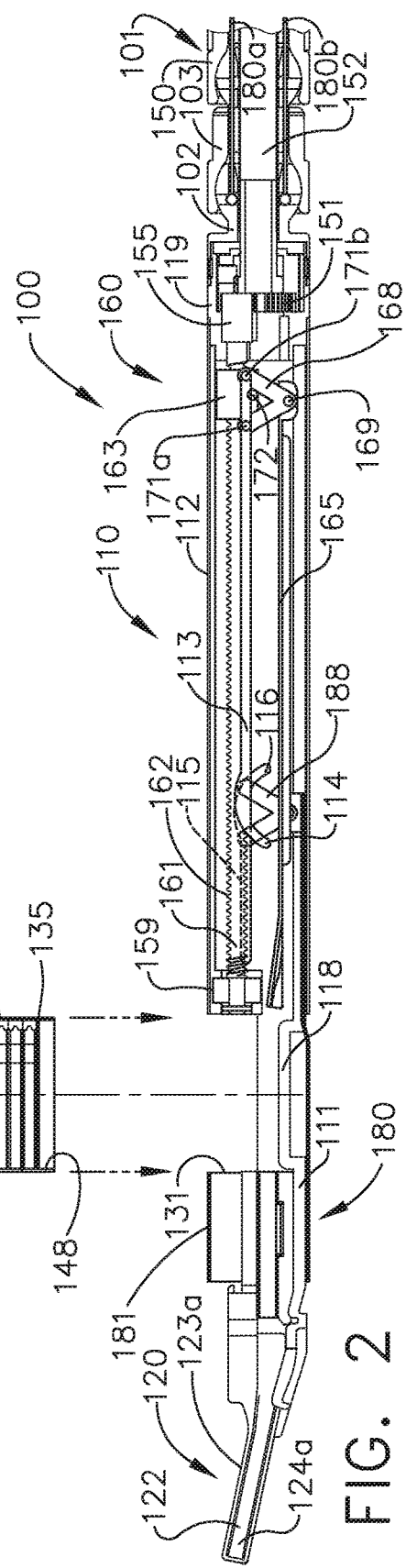
FIG. 1
FIG. 2

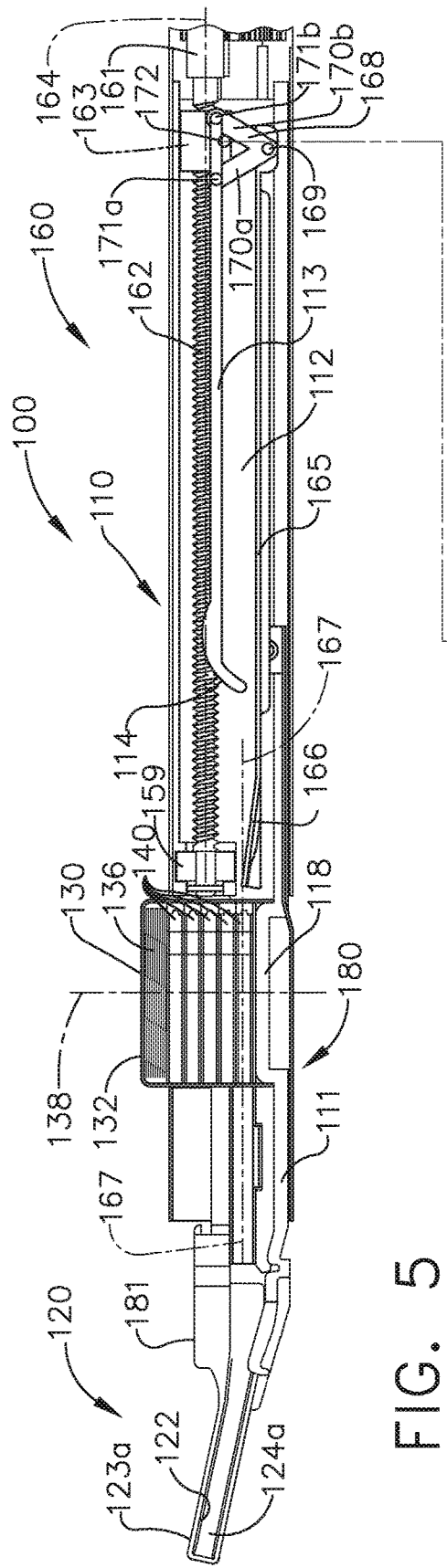
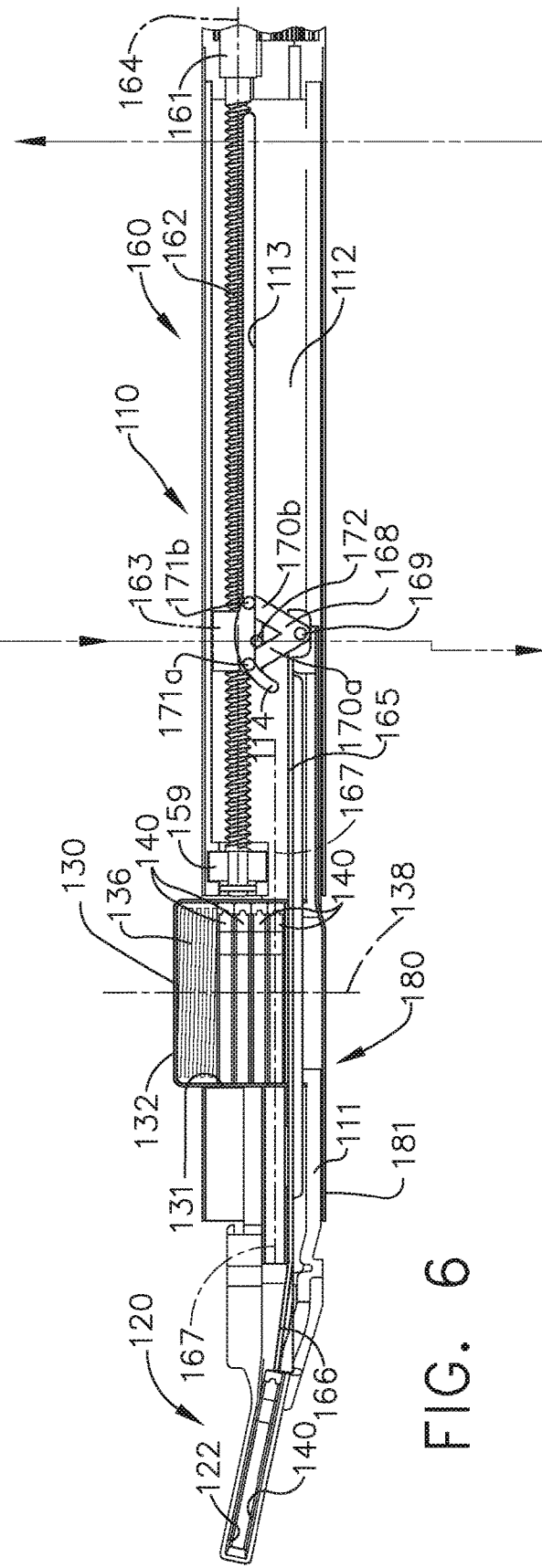
FIG. 5
FIG. 6

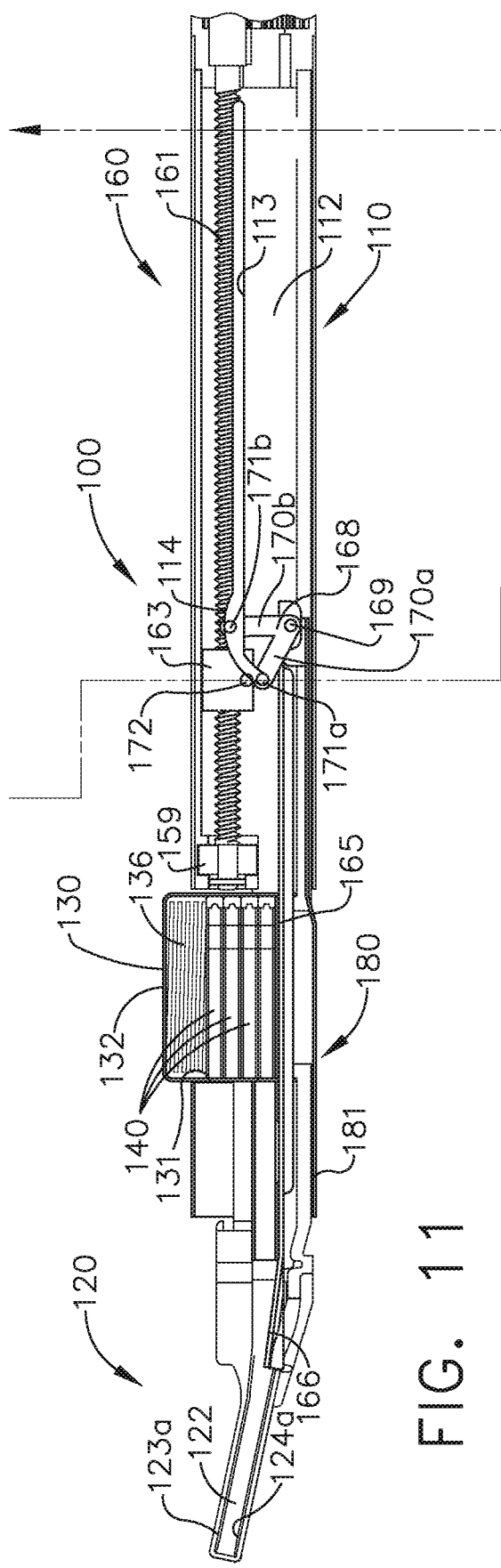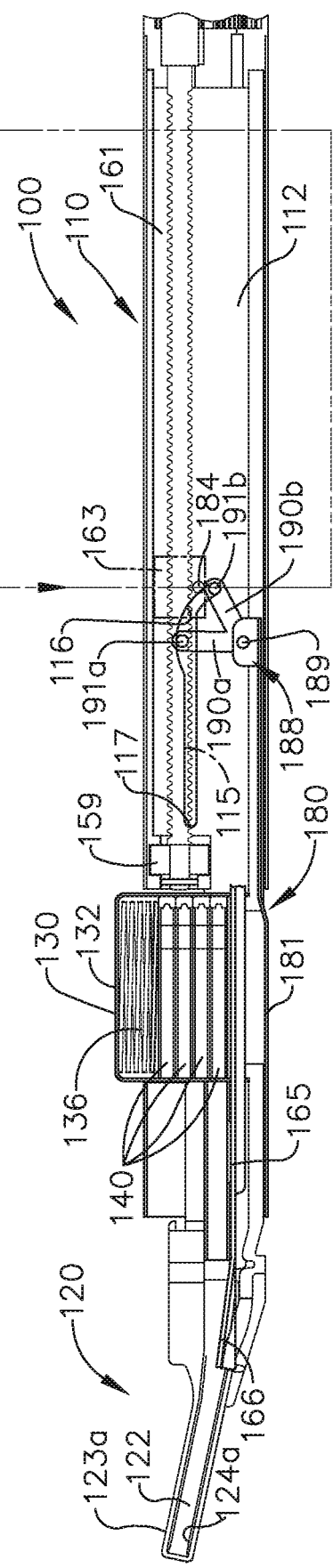
FIG. 11
FIG. 12

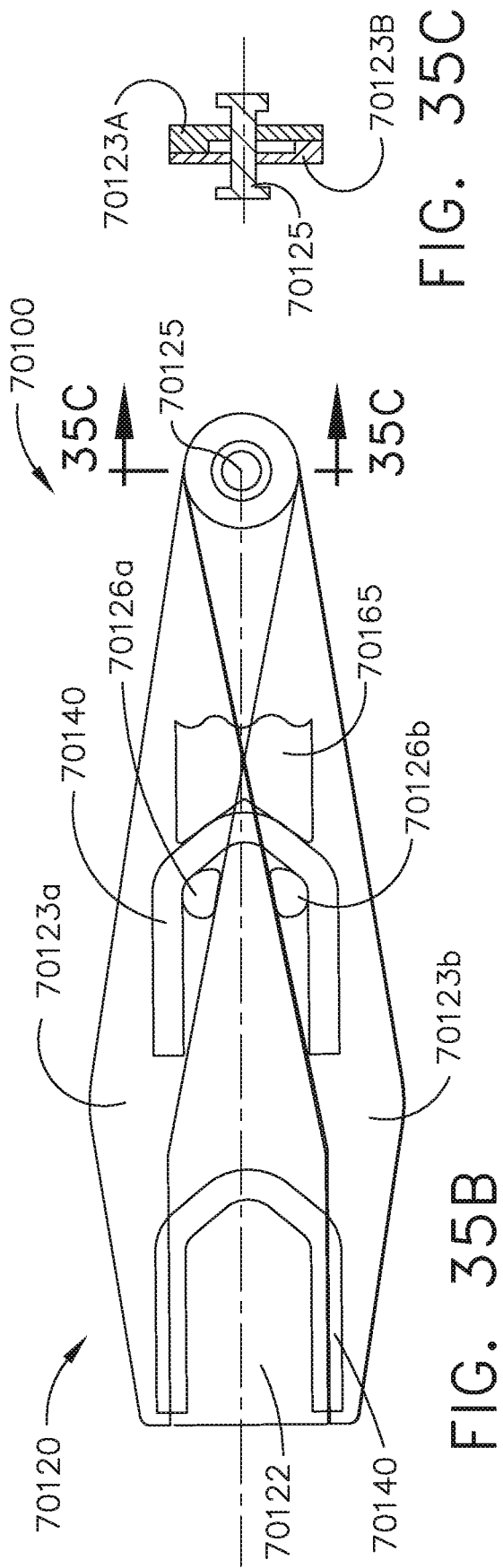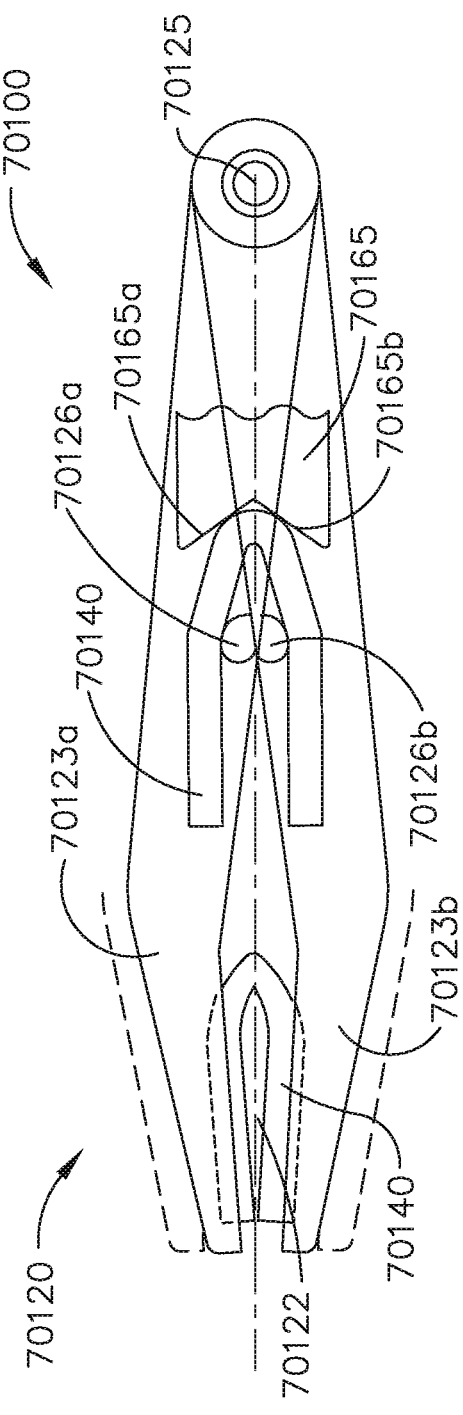

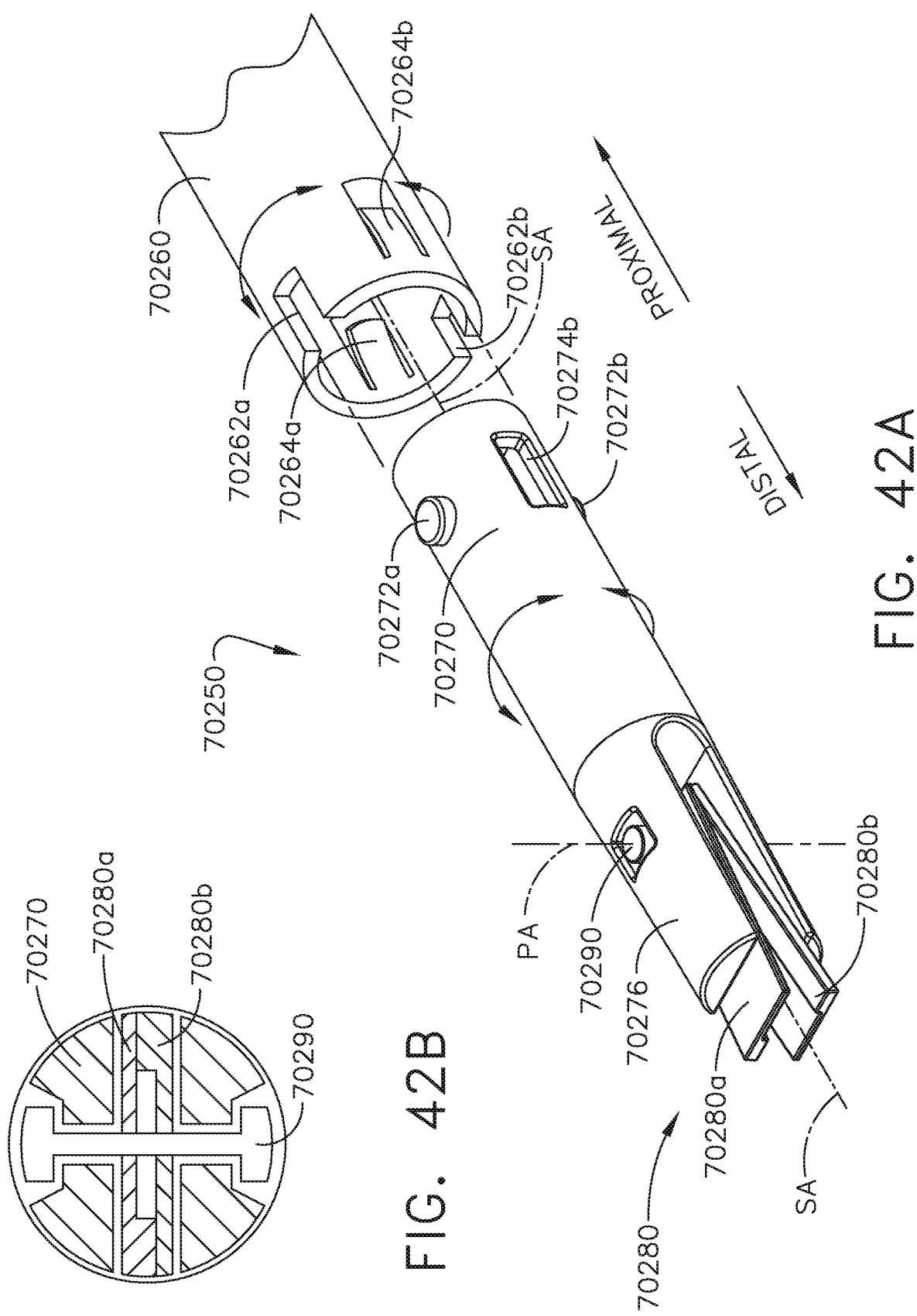

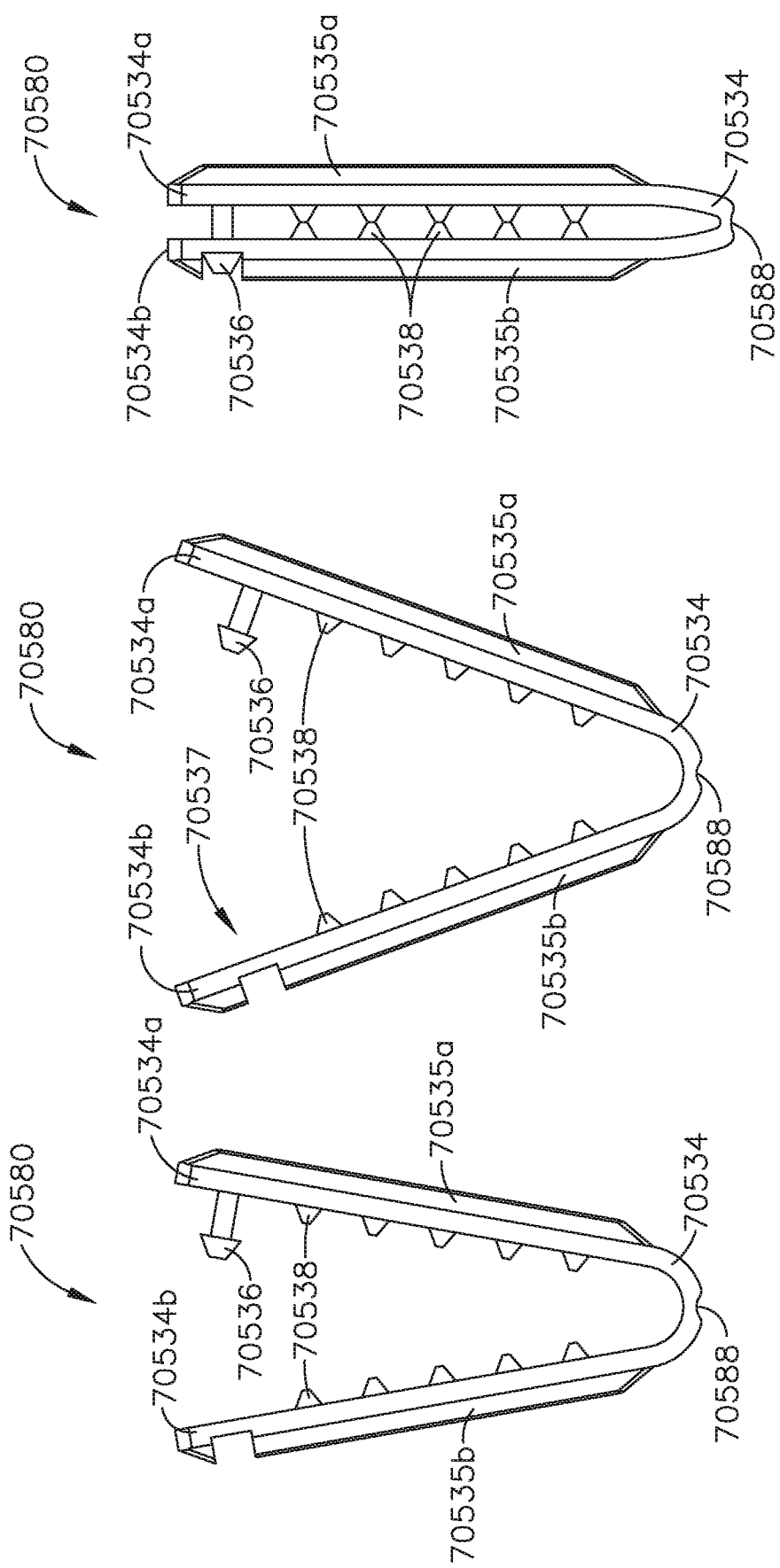

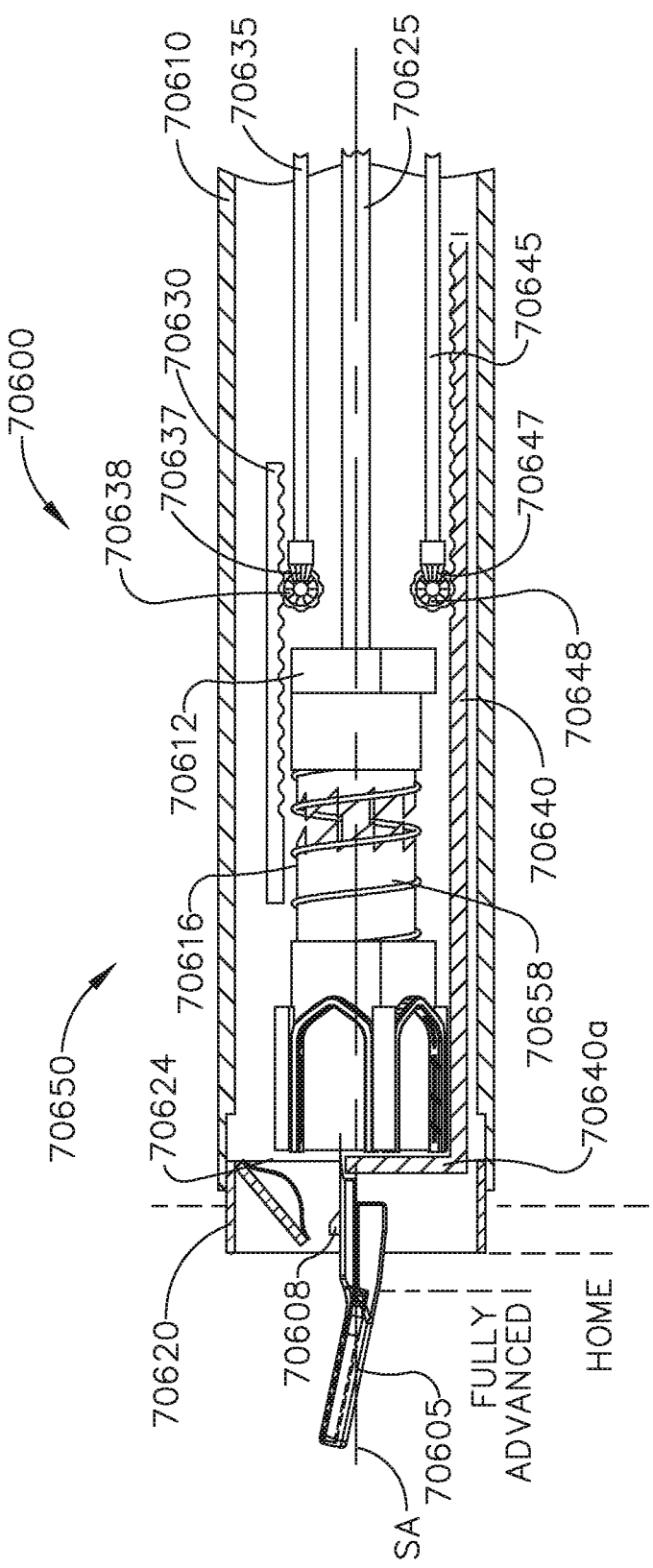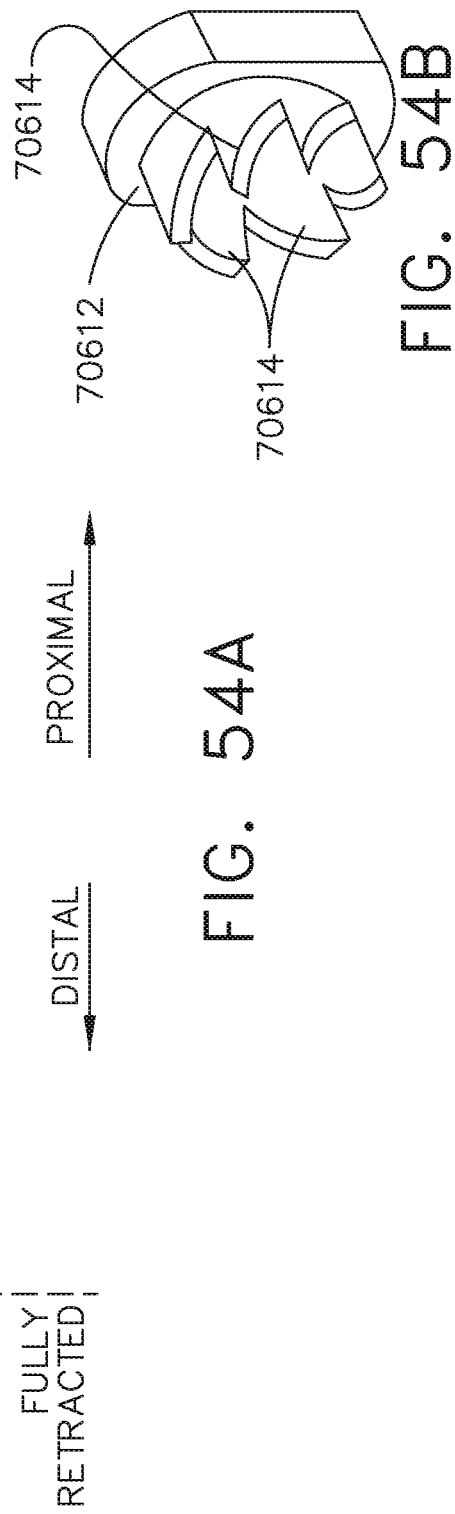
FIG. 54A
FIG. 54B

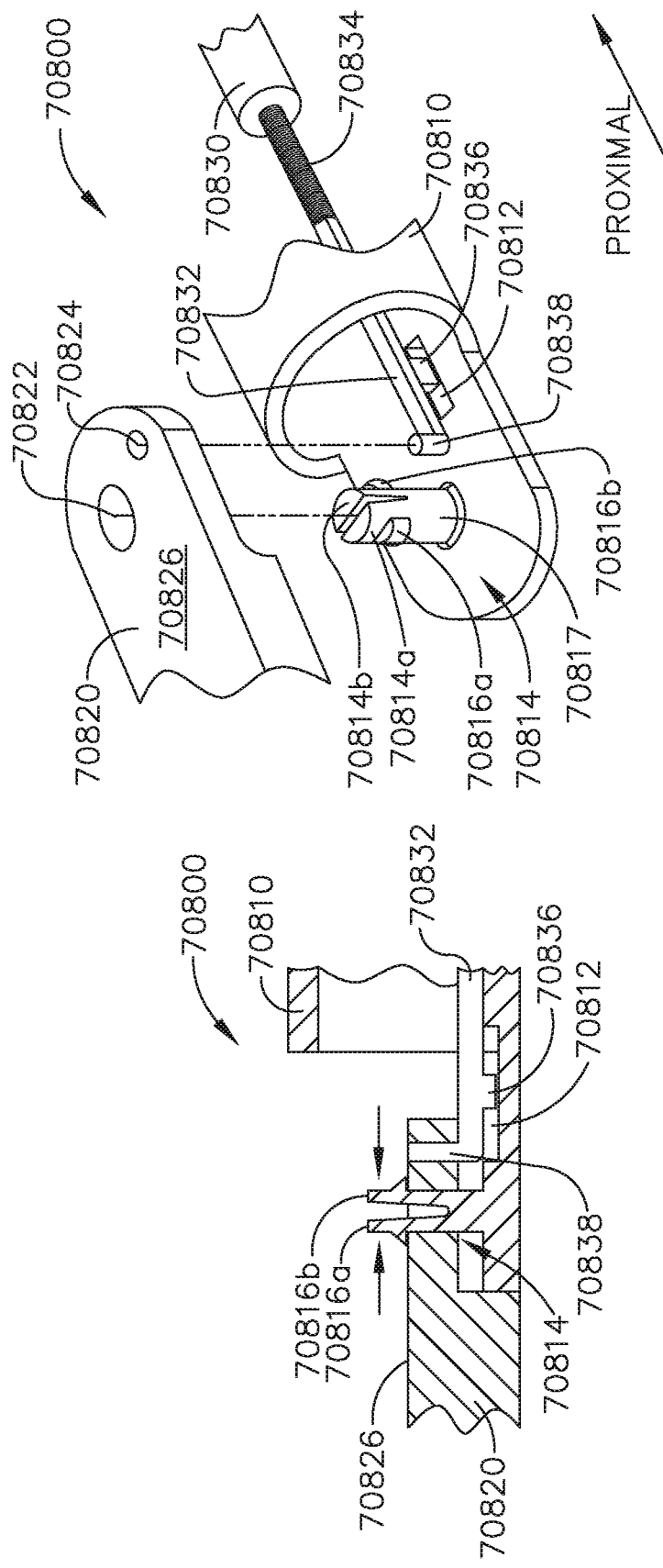

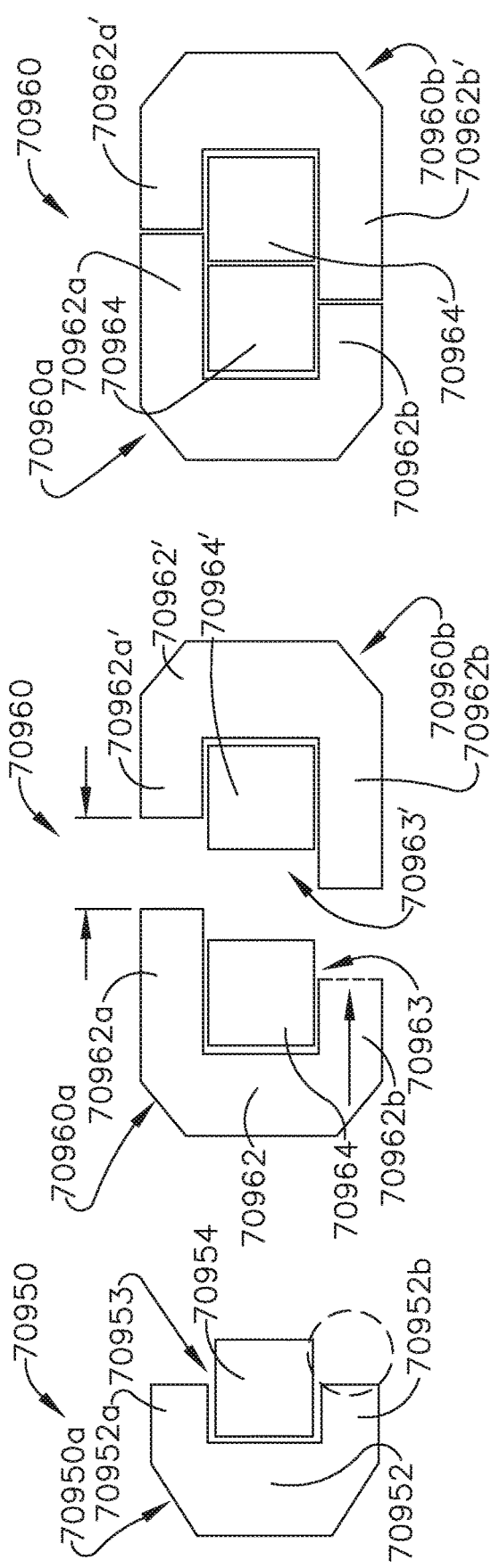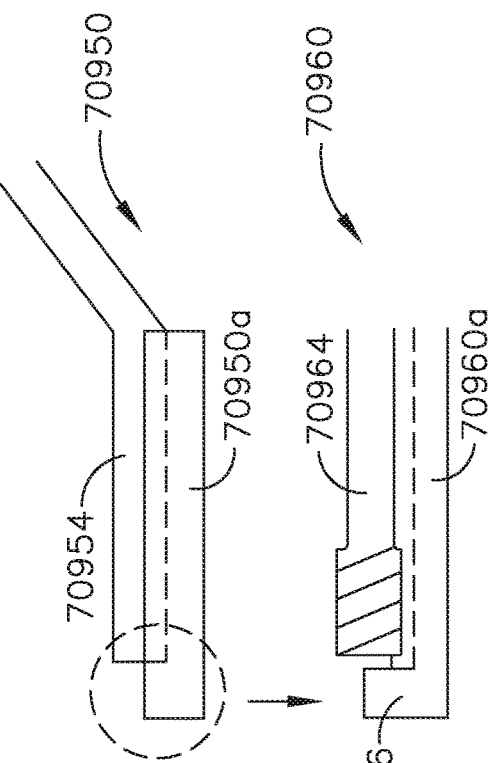

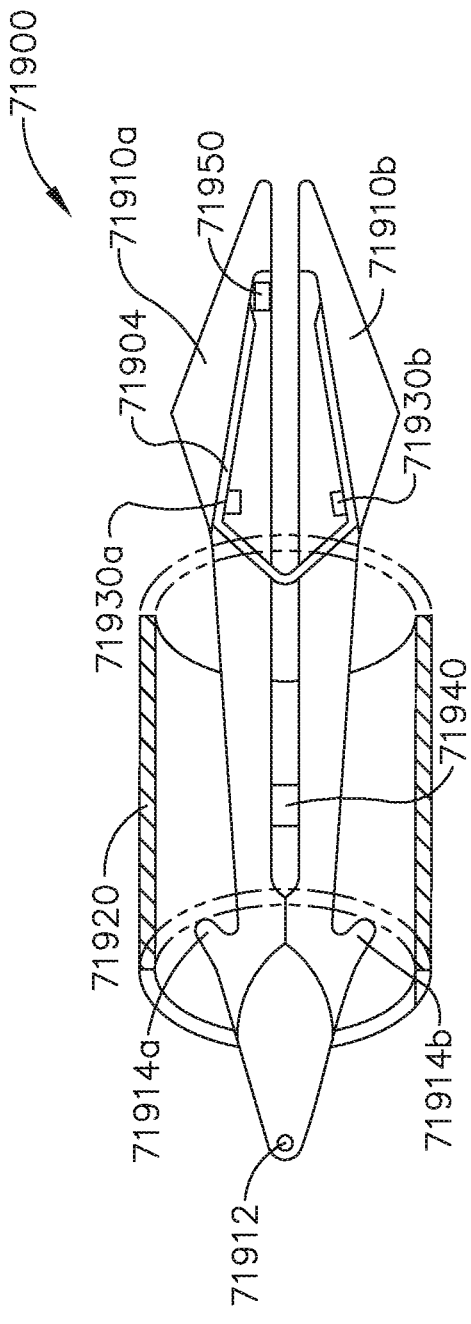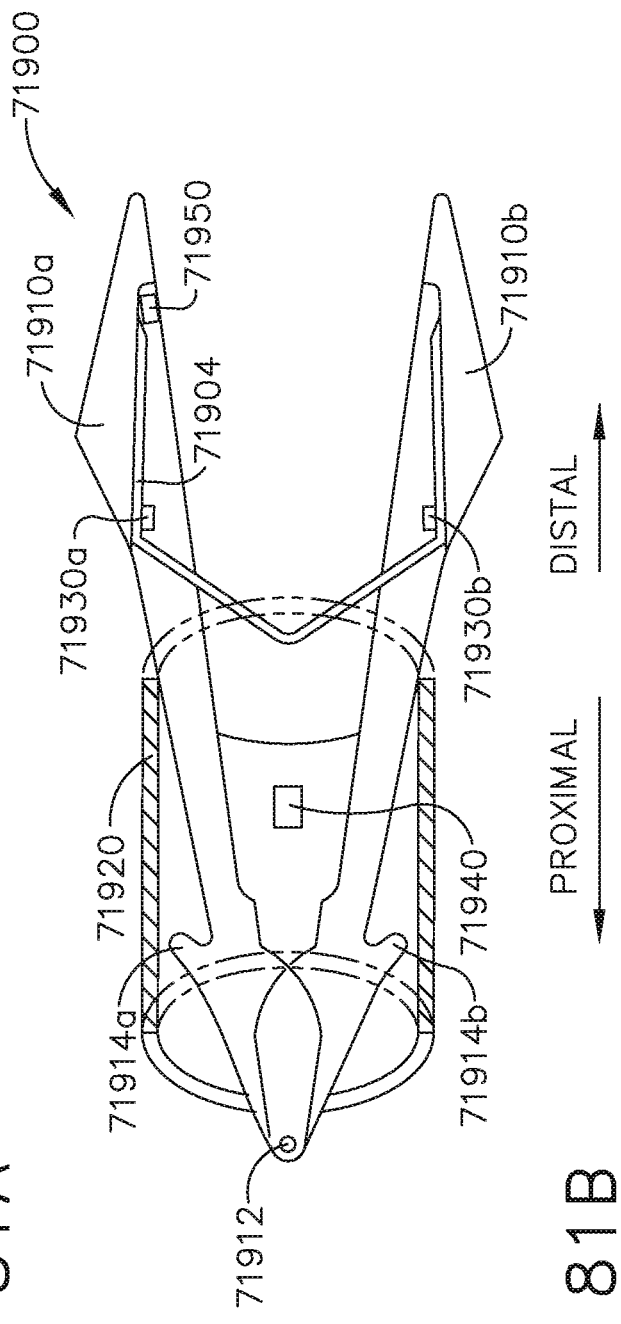
FIG. 81A
FIG. 81B

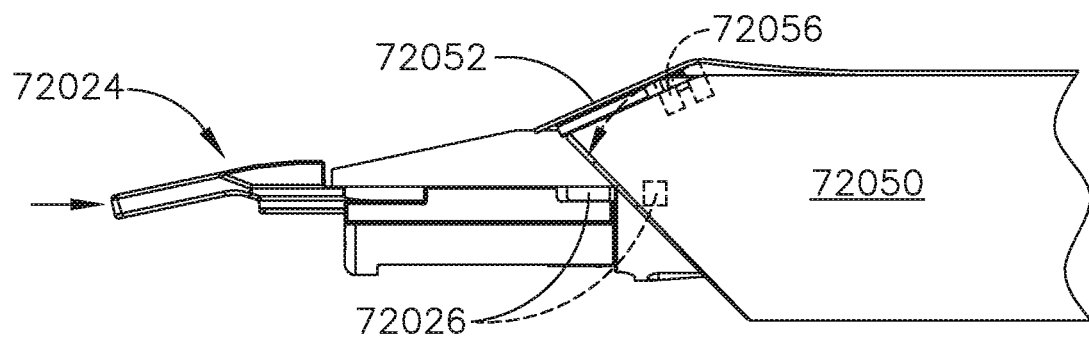
FIG. 84A    DISTAL ← → PROXIMAL
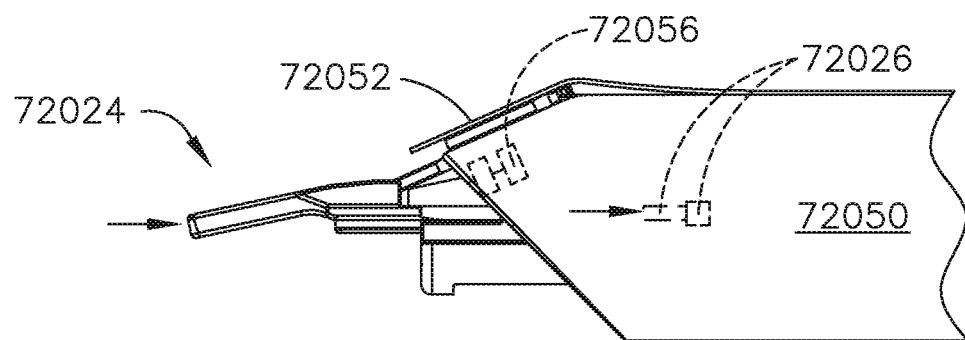
FIG. 84B    DISTAL ← → PROXIMAL
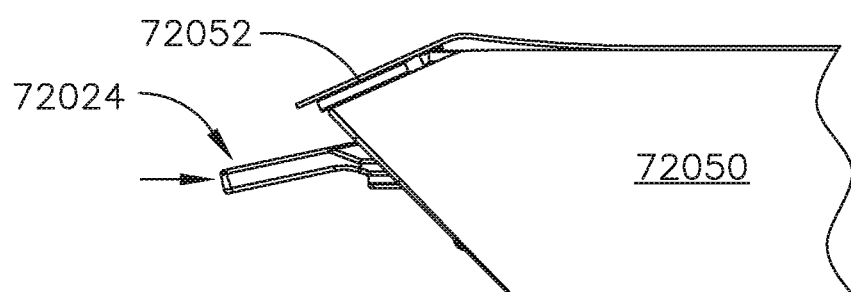
FIG. 84C    DISTAL ← → PROXIMAL

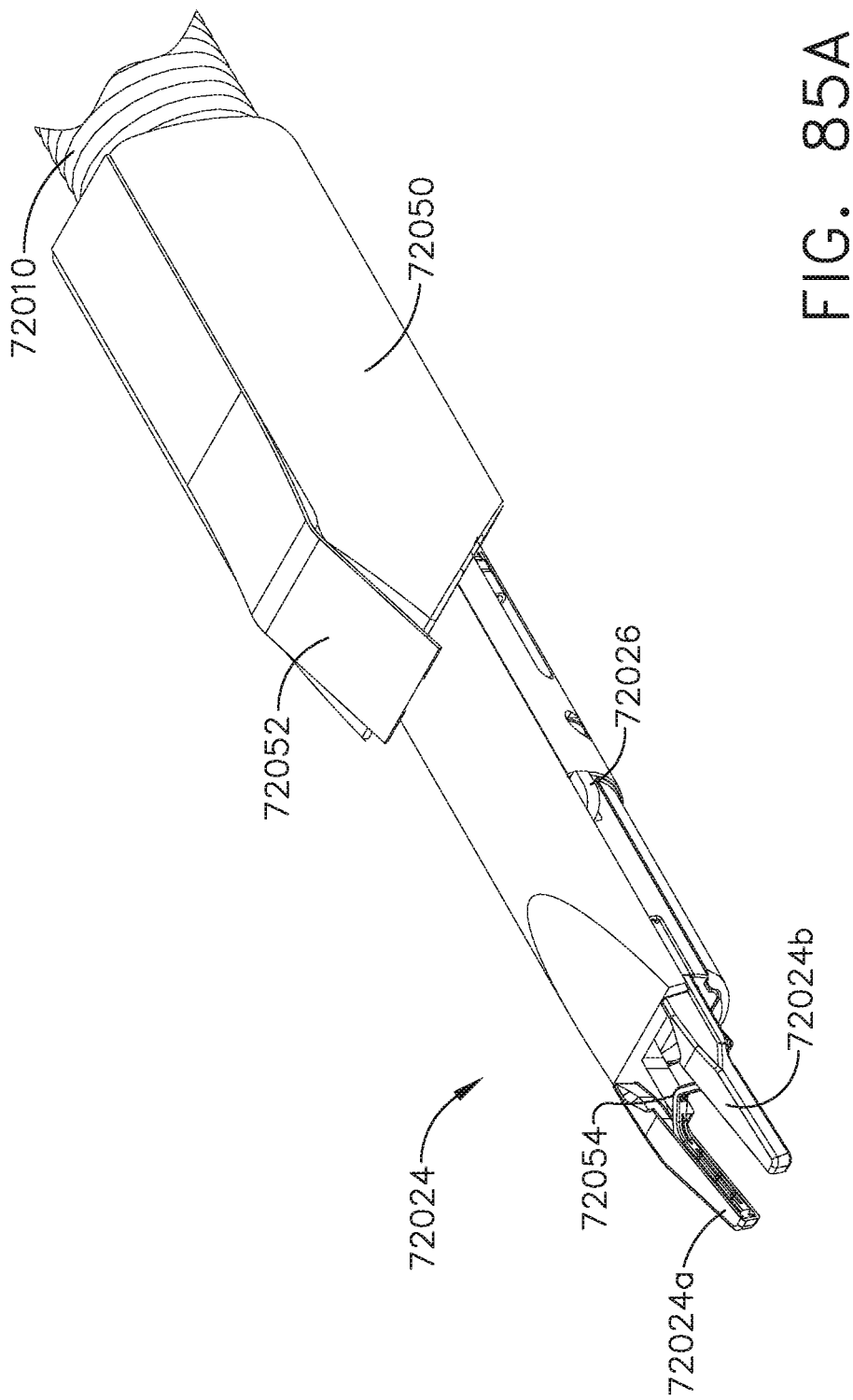

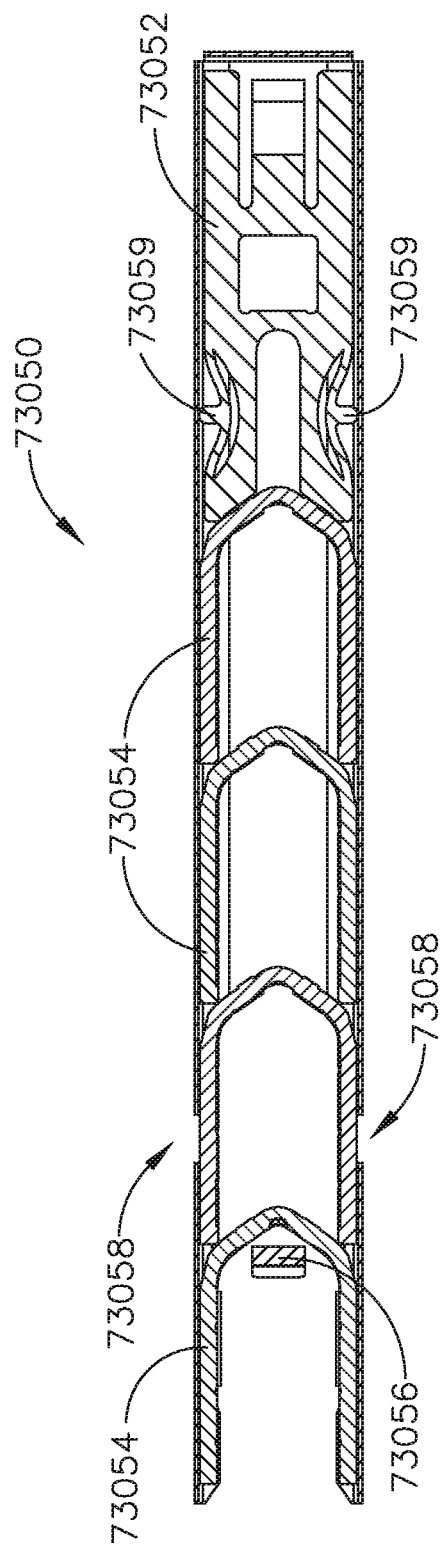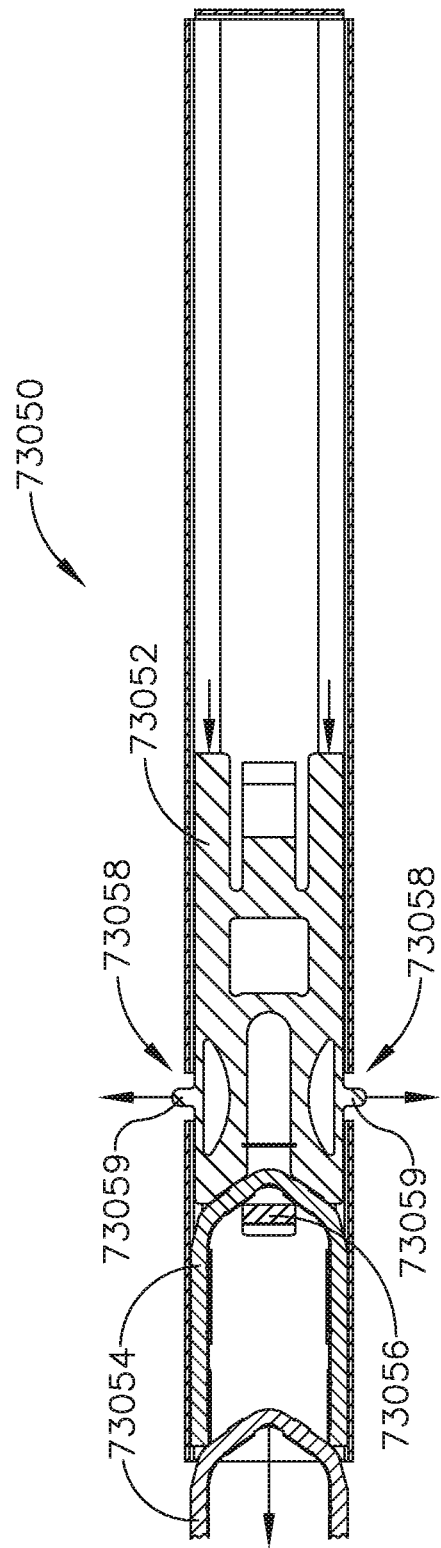

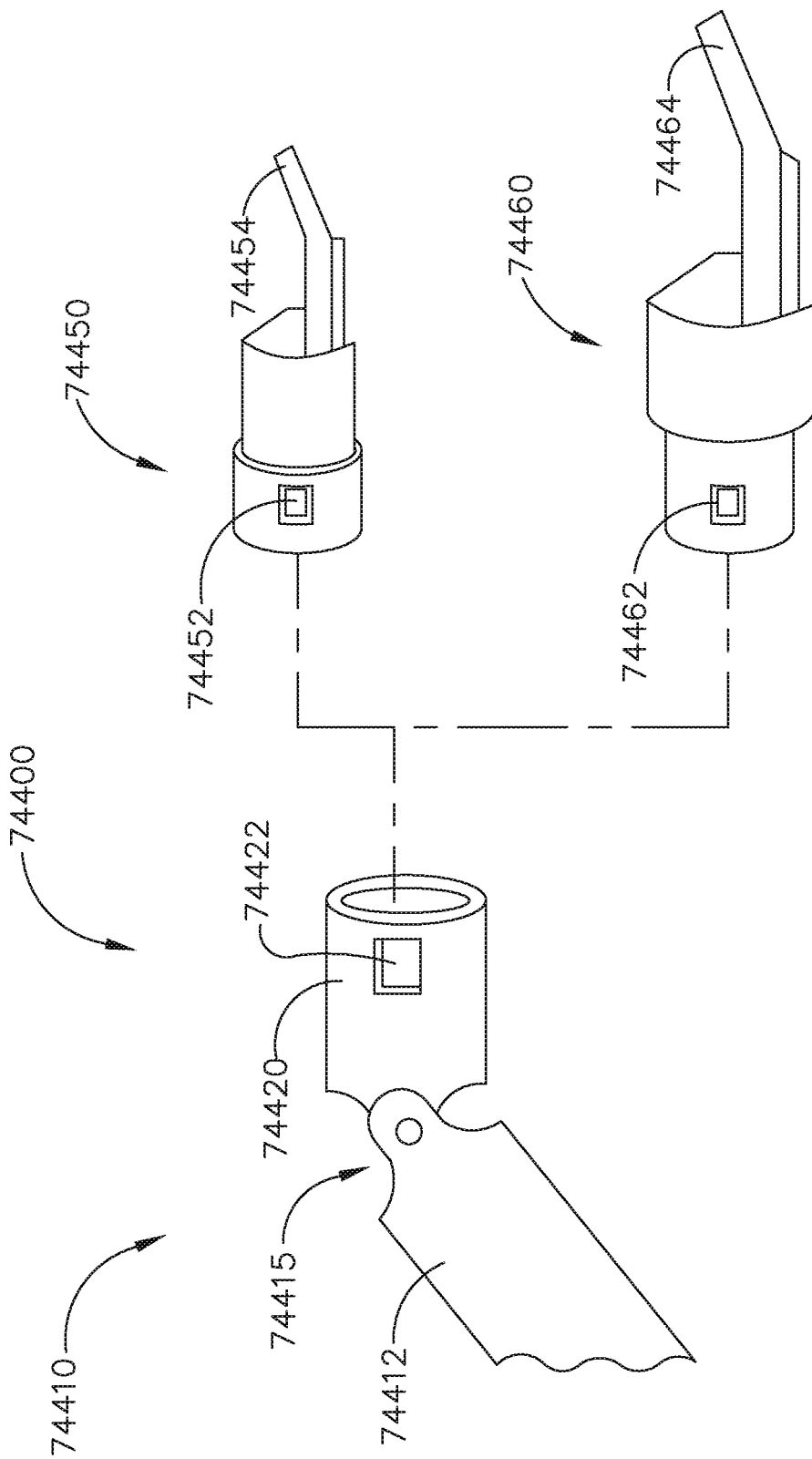

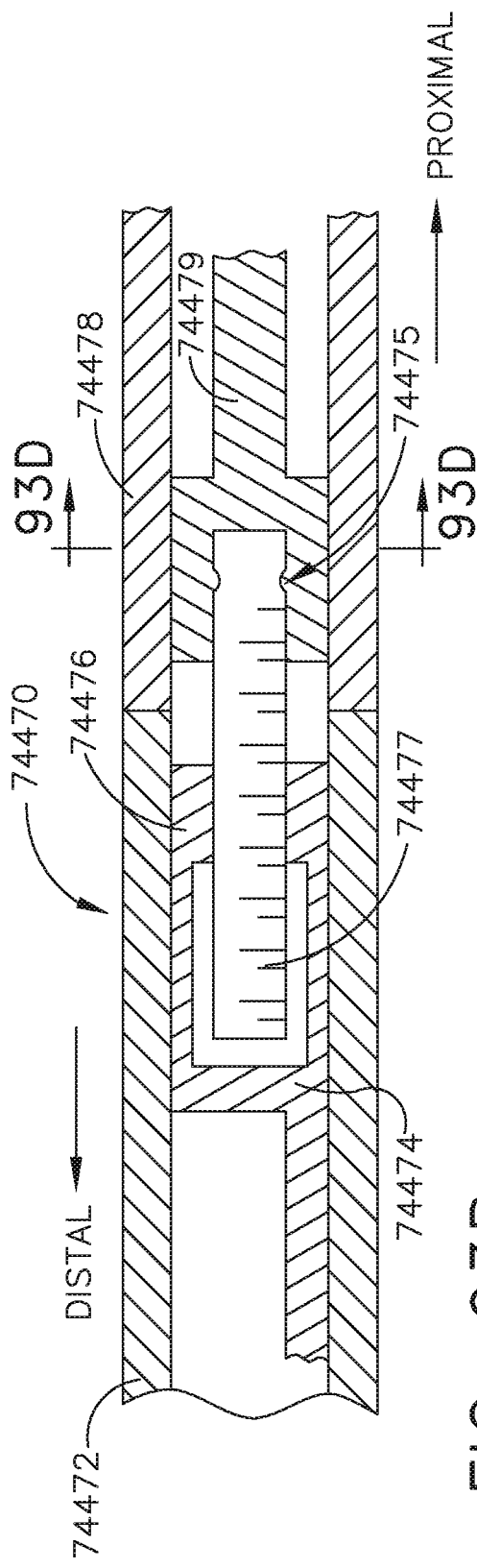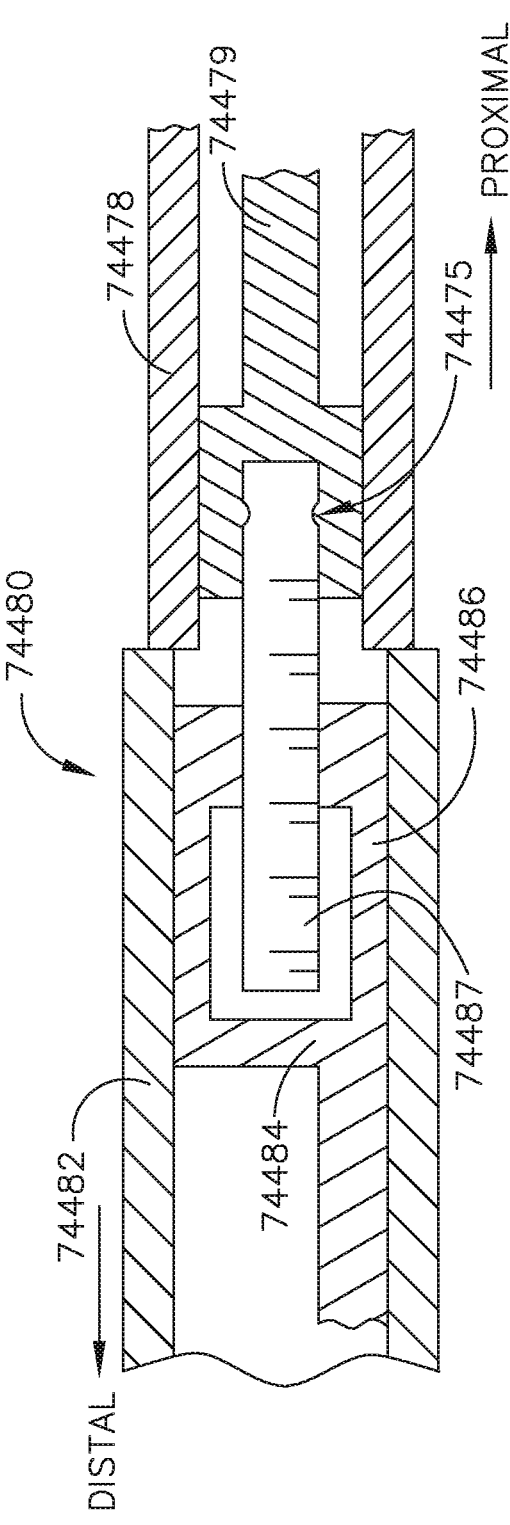

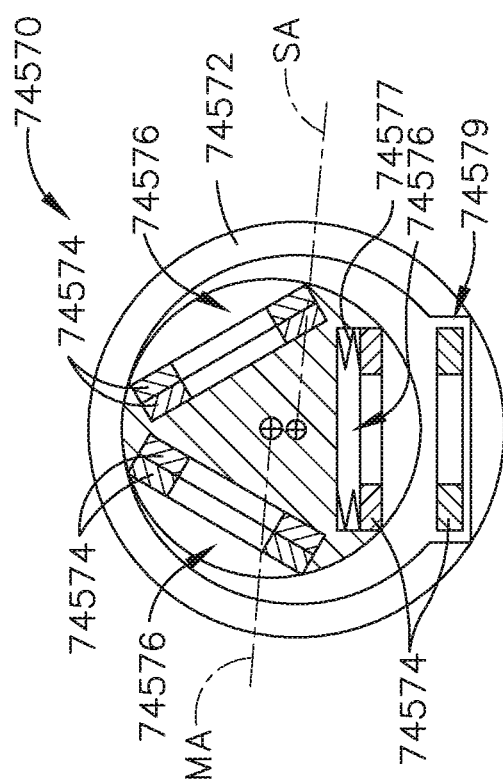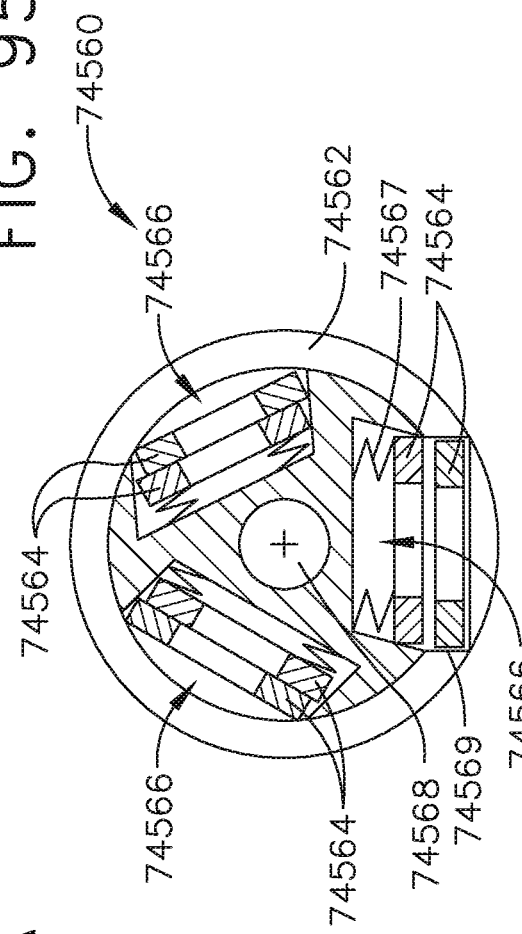
FIG. 95A
FIG. 95B
FIG. 95C

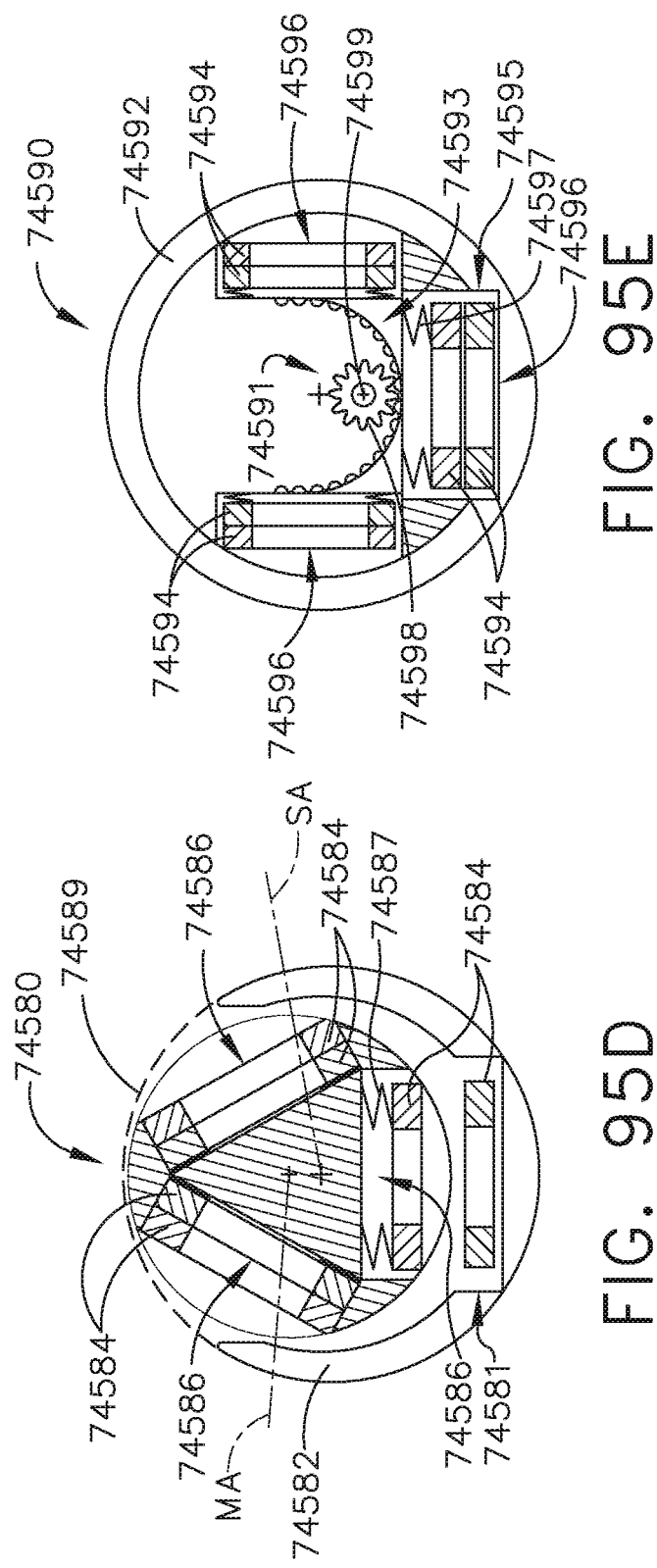

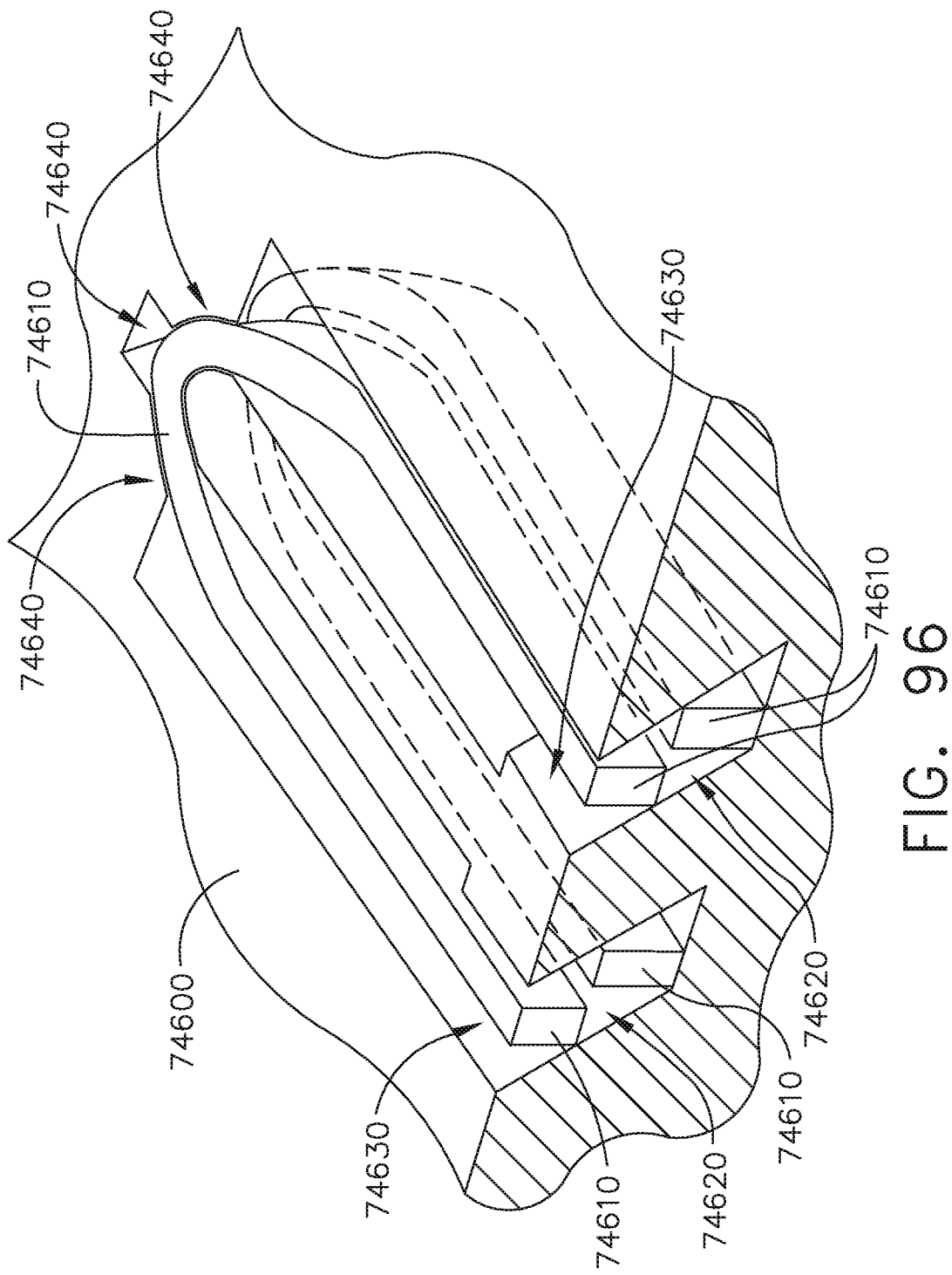

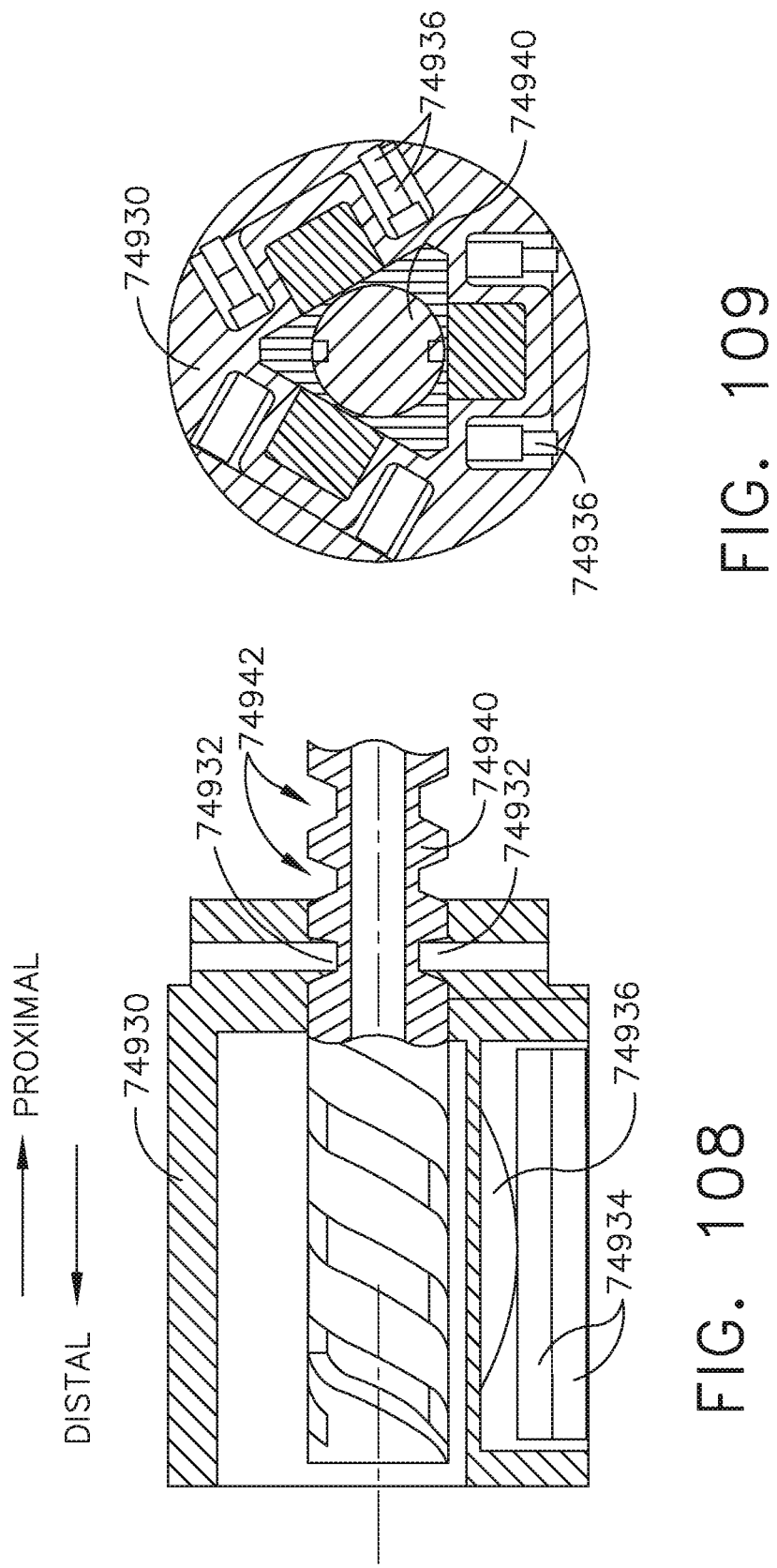

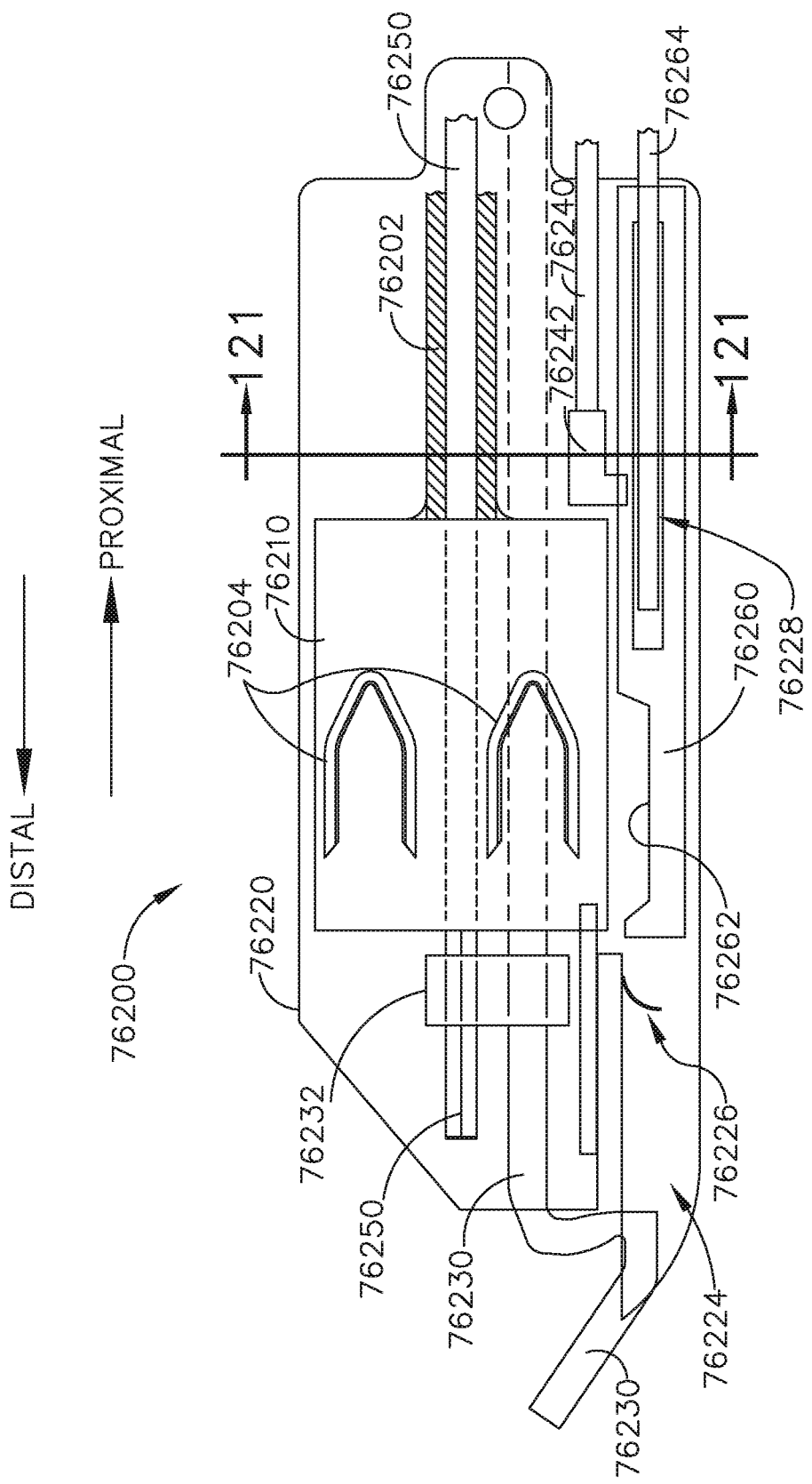

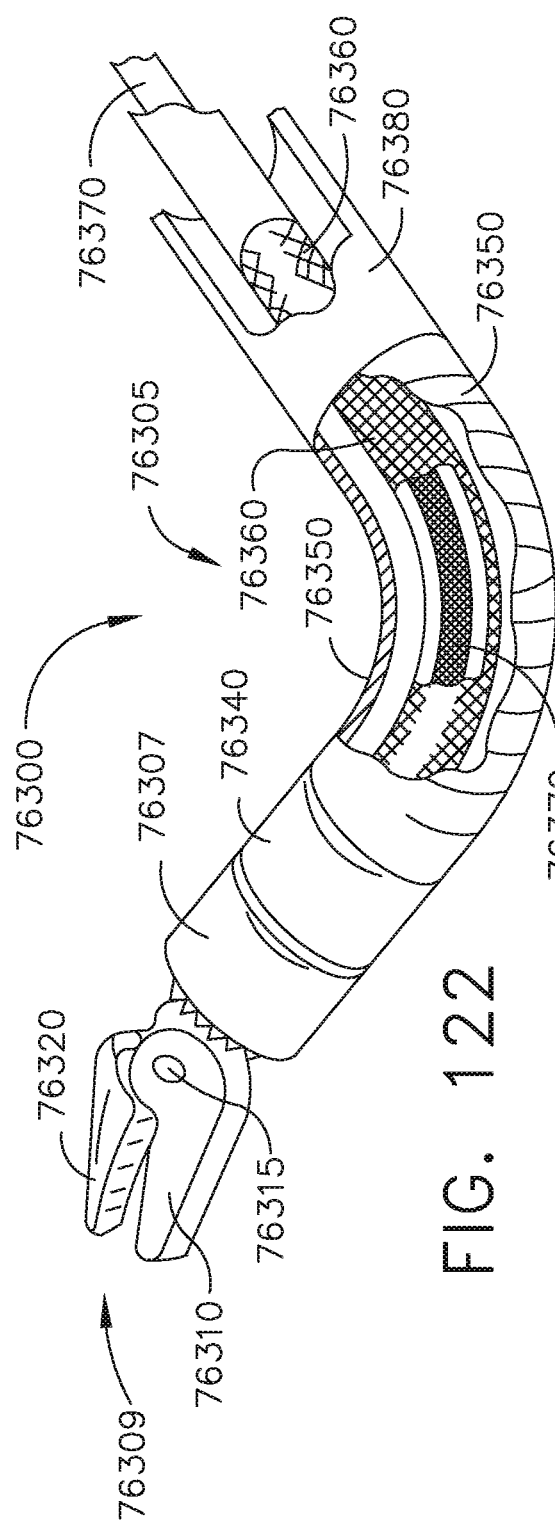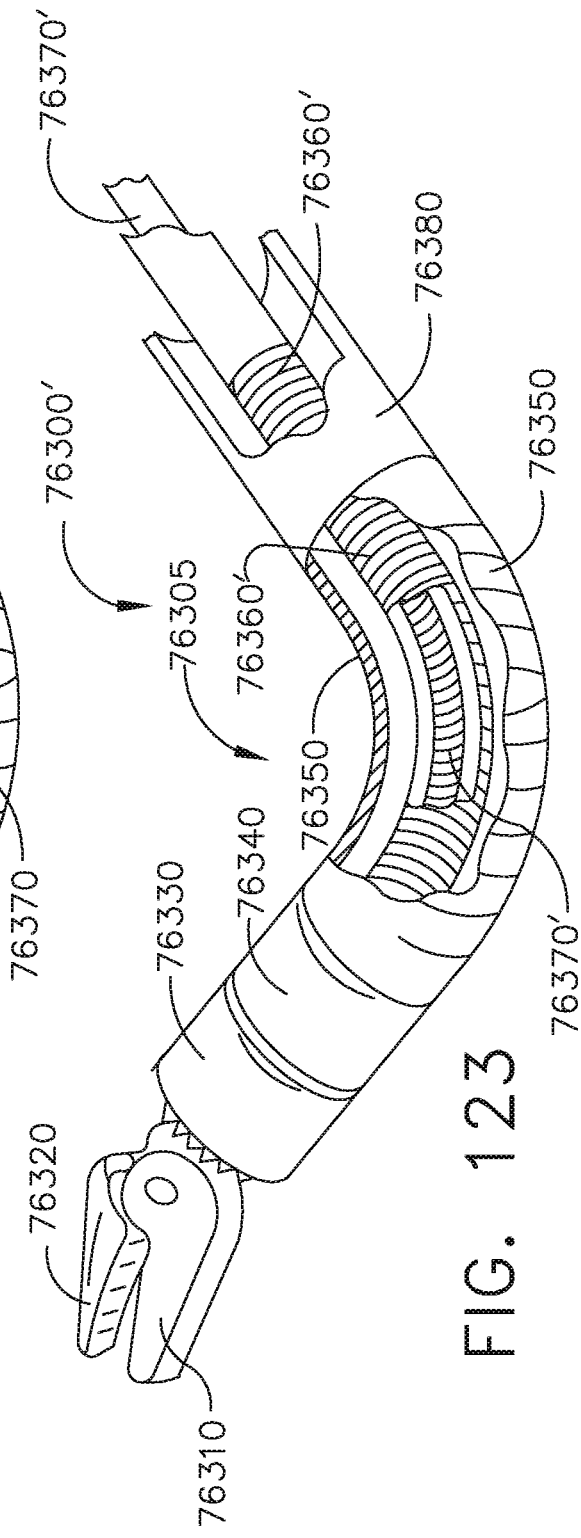

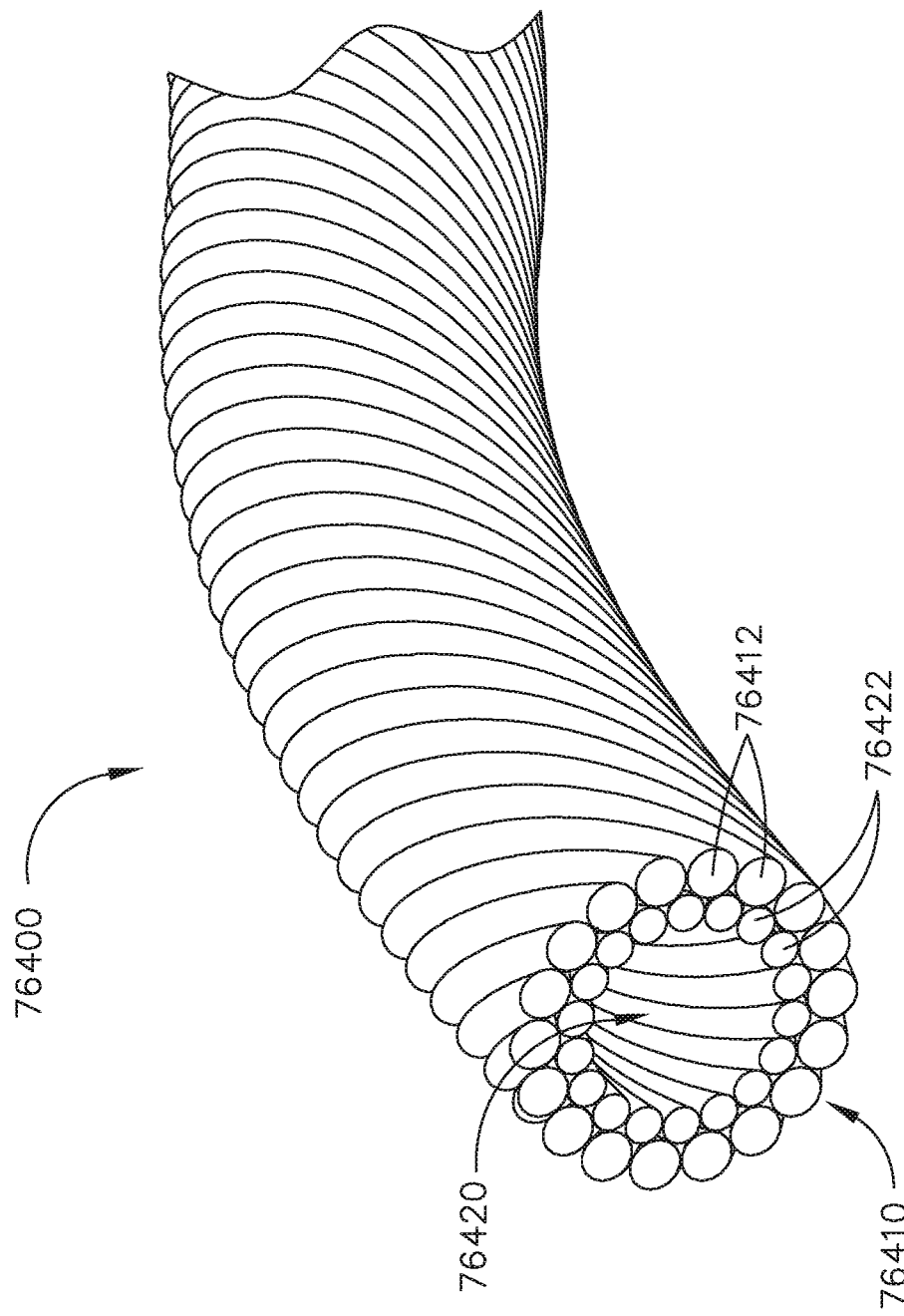

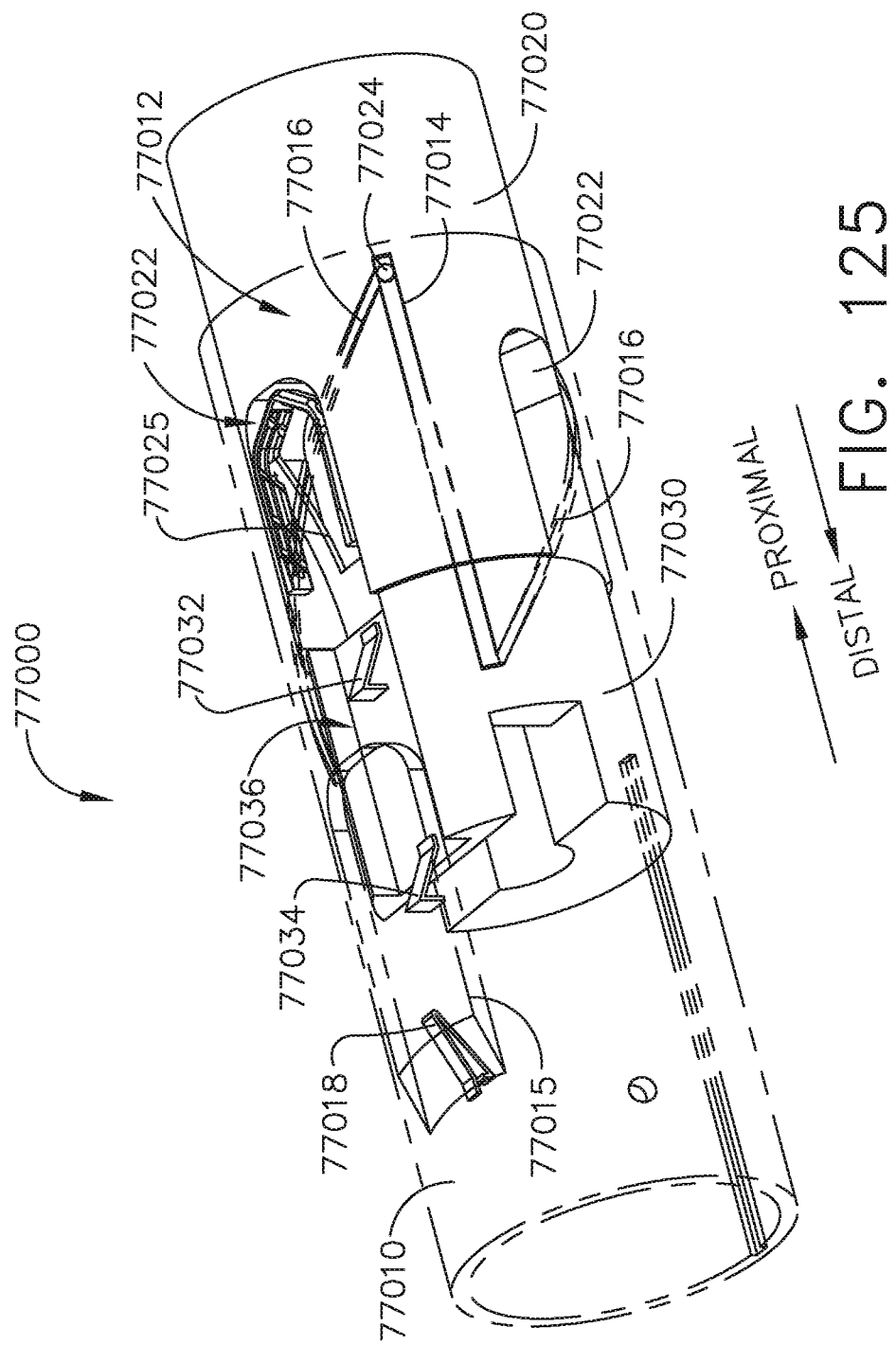

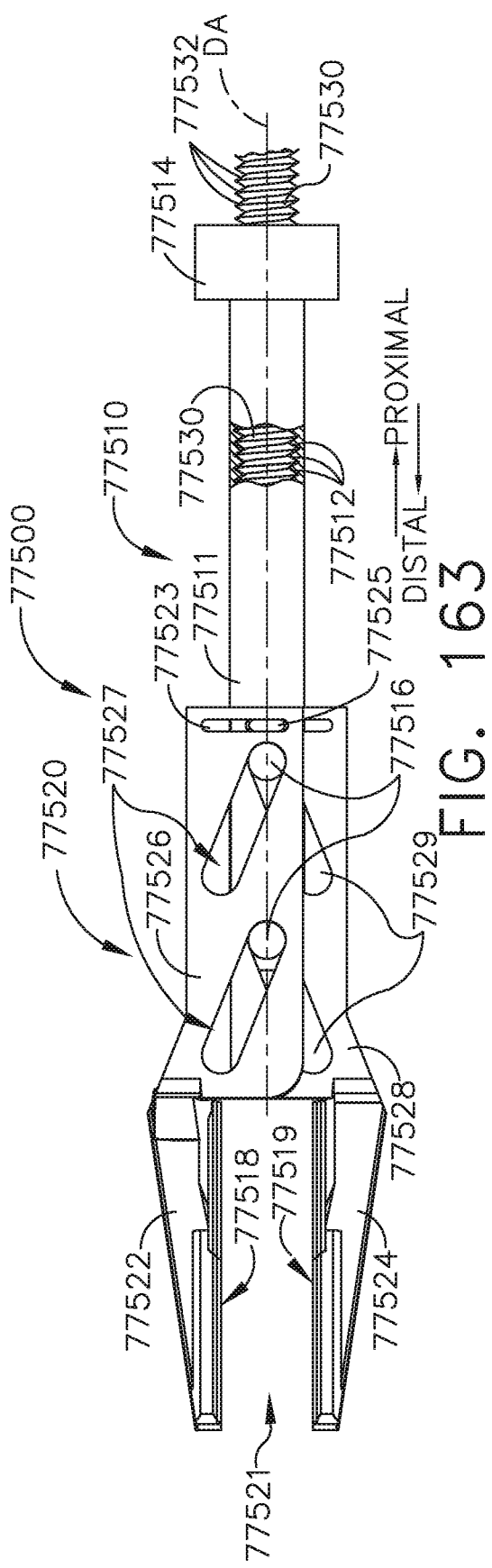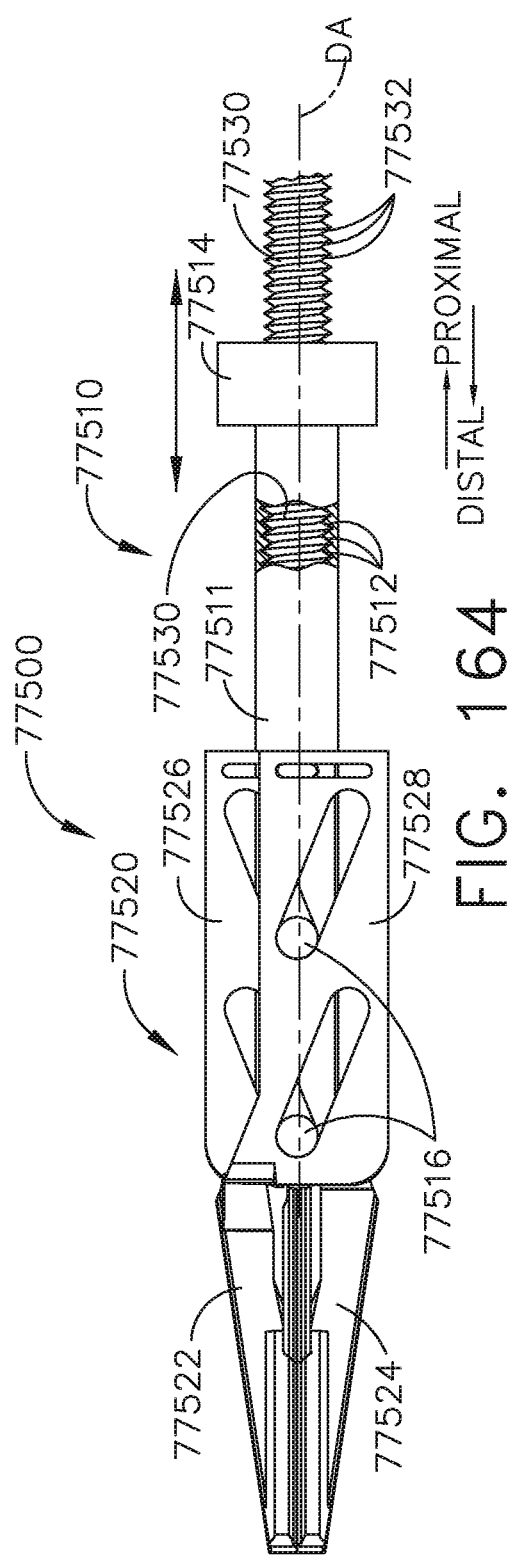

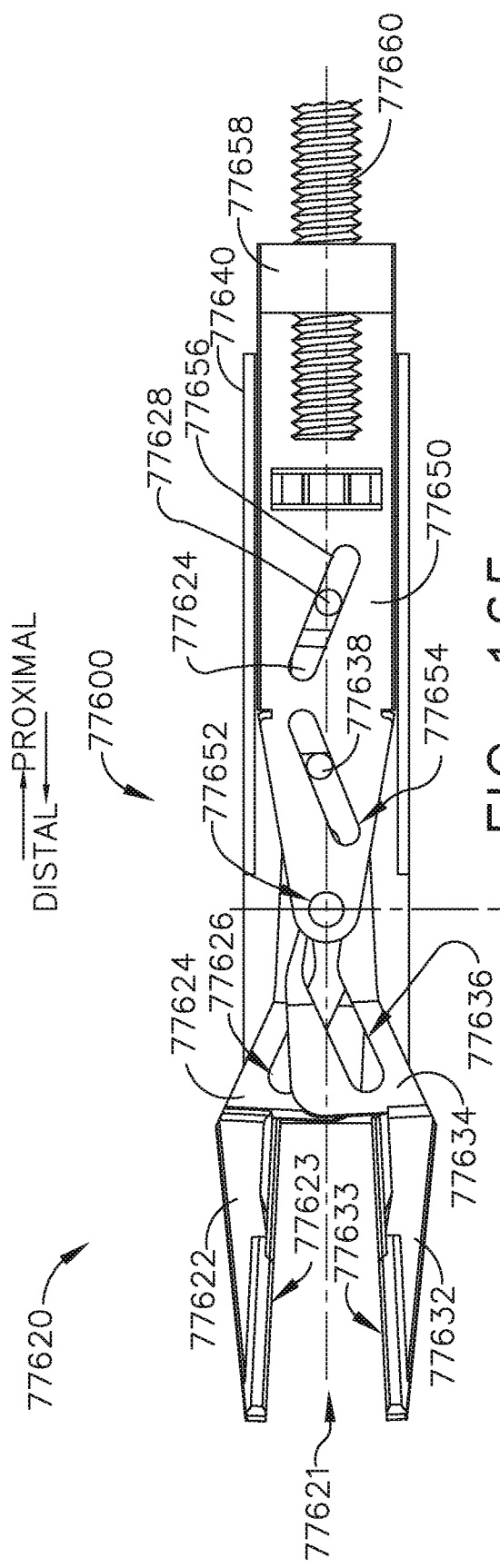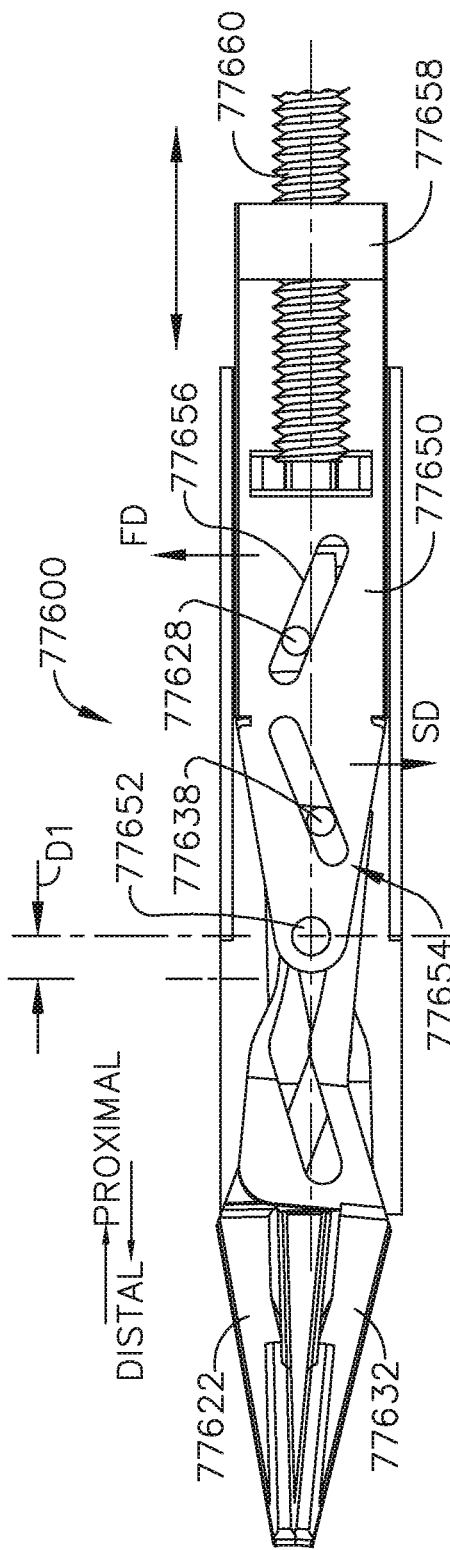

CLIP APPLIER COMPRISING A MOTOR CONTROLLER

CROSS-REFERENCE TO RELATED APPLICATIONS

This application claims the benefit of U.S. Provisional Patent Application Ser. No. 62/750,555, entitled SURGICAL CLIP APPLIER, filed Oct. 25, 2018, the disclosure of which is incorporated by reference herein in its entirety. This application claims the benefit of U.S. Provisional Patent Application Ser. No. 62/659,900, entitled METHOD OF HUB COMMUNICATION, filed Apr. 19, 2018, the disclosure of which is incorporated by reference herein in its entirety. This application claims the benefit of U.S. Provisional Patent Application Ser. No. 62/665,128, entitled MODULAR SURGICAL INSTRUMENTS, filed May 1, 2018, of U.S. Provisional Patent Application Ser. No. 62/665,129, entitled SURGICAL SUTURING SYSTEMS, filed May 1, 2018, of U.S. Provisional Patent Application Ser. No. 62/665,134, entitled SURGICAL CLIP APPLIER, filed May 1, 2018, of U.S. Provisional Patent Application Ser. No. 62/665,139, entitled SURGICAL INSTRUMENTS COMPRISING CONTROL SYSTEMS, filed May 1, 2018, of U.S. Provisional Patent Application Ser. No. 62/665,177, entitled SURGICAL INSTRUMENTS COMPRISING HANDLE ARRANGEMENTS, filed May 1, 2018, and of U.S. Provisional Patent Application Ser. No. 62/665,192, entitled SURGICAL DISSECTORS, filed May 1, 2018, the disclosures of which are incorporated by reference herein in their entireties. This application claims the benefit of U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT, filed Mar. 28, 2018, of U.S. Provisional Patent Application Ser. No. 62/649,294, entitled DATA STRIPPING METHOD TO INTERROGATE PATIENT RECORDS AND CREATE ANONYMIZED RECORD, filed Mar. 28, 2018, of U.S. Provisional Patent Application Ser. No. 62/649,296, entitled ADAPTIVE CONTROL PROGRAM UPDATES FOR SURGICAL DEVICES, filed Mar. 28, 2018, of U.S. Provisional Patent Application Ser. No. 62/649,300, entitled SURGICAL HUB SITUATIONAL AWARENESS, filed Mar. 28, 2018, of U.S. Provisional Patent Application Ser. No. 62/649,302, entitled INTERACTIVE SURGICAL SYSTEMS WITH ENCRYPTED COMMUNICATION CAPABILITIES, filed Mar. 28, 2018, of U.S. Provisional Patent Application Ser. No. 62/649,307, entitled AUTOMATIC TOOL ADJUSTMENTS FOR ROBOT-ASSISTED SURGICAL PLATFORMS, filed Mar. 28, 2018, of U.S. Provisional Patent Application Ser. No. 62/649,309, entitled SURGICAL HUB SPATIAL AWARENESS TO DETERMINE DEVICES IN OPERATING THEATER, filed Mar. 28, 2018, of U.S. Provisional Patent Application Ser. No. 62/649,310, entitled COMPUTER IMPLEMENTED INTERACTIVE SURGICAL SYSTEMS, filed Mar. 28, 2018, of U.S. Provisional Patent Application Ser. No. 62/649,313, entitled CLOUD INTERFACE FOR COUPLED SURGICAL DEVICES, filed Mar. 28, 2018, of U.S. Provisional Patent Application Ser. No. 62/649,315, entitled DATA HANDLING AND PRIORITIZATION IN A CLOUD ANALYTICS NETWORK, filed Mar. 28, 2018, of U.S. Provisional Patent Application Ser. No. 62/649,320, entitled DRIVE ARRANGEMENTS FOR ROBOT-ASSISTED SURGICAL PLATFORMS, filed Mar. 28, 2018, of U.S. Provisional Patent Application Ser. No. 62/649,323, entitled SENSING ARRANGEMENTS FOR ROBOT-ASSISTED SURGICAL PLATFORMS, filed Mar. 28, 2018, of U.S. Provisional Patent Application Ser. No. 62/649,327, entitled CLOUD-BASED MEDICAL ANALYTICS FOR SECURITY AND AUTHENTICATION TRENDS AND REACTIVE MEASURES, filed Mar. 28, 2018, and of U.S. Provisional Patent Application Ser. No. 62/649,333, entitled CLOUD-BASED MEDICAL ANALYTICS FOR CUSTOMIZATION AND RECOMMENDATIONS TO A USER, filed Mar. 28, 2018, the disclosures of which are incorporated by reference herein in their entireties. This application claims the benefit of U.S. Provisional Patent Application Ser. No. 62/611,339, entitled ROBOT ASSISTED SURGICAL PLATFORM, filed Dec. 28, 2017, of U.S. Provisional Patent Application Ser. No. 62/611,340, entitled CLOUD-BASED MEDICAL ANALYTICS, filed Dec. 28, 2017, and of U.S. Provisional Patent Application Ser. No. 62/611,341, entitled INTERACTIVE SURGICAL PLATFORM, filed Dec. 28, 2017, the disclosures of which are incorporated by reference herein in their entireties. This application claims the benefit of U.S. Provisional Patent Application Ser. No. 62/578,793, entitled SURGICAL INSTRUMENT WITH REMOTE RELEASE, filed Oct. 30, 2017, of U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT, filed Oct. 30, 2017, of U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS, filed Oct. 30, 2017, of U.S. Provisional Patent Application Ser. No. 62/578,844, entitled SURGICAL INSTRUMENT WITH MODULAR POWER SOURCES, filed Oct. 30, 2017, and of U.S. Provisional Patent Application Ser. No. 62/578,855, entitled SURGICAL INSTRUMENT WITH SENSOR AND/OR CONTROL SYSTEMS, filed Oct. 30, 2017, the disclosures of which are incorporated by reference herein in their entireties.

BACKGROUND

A variety of fasteners can be utilized to treat, clamp, fasten, secure, and/or hold tissue. Clips can be positioned relative to tissue located within a surgical site in a patient and then deformed to apply a clamping force, for example, to the tissue.

BRIEF DESCRIPTION OF THE DRAWINGS

The features and advantages of this invention, and the manner of attaining them, will become more apparent and the invention itself will be better understood by reference to the following description of exemplary embodiments of the invention taken in conjunction with the accompanying drawings, wherein:

FIG. 1 is a partial perspective view of a clip applier;

FIG. 2 is a cross-sectional view of an end effector of the clip applier of FIG. 1 comprising a removable clip cartridge, a reciprocating firing drive for sequentially advancing the clips, a receiver for receiving the clips, and a crimping drive for deforming the clips;

FIG. 5 is a cross-sectional view of the end effector of FIG. 2 in an unfired condition;

FIG. 6 is a cross-sectional view of the end effector of FIG. 2 illustrating the firing drive in a partially fired condition in which a firing member of the firing drive has advanced a clip into the receiver;

FIG. 11 is a cross-sectional view of the firing drive of the end effector of FIG. 2 in a partially retracted position in which the firing drive is being re-engaged with the firing member;

FIG. 12 is a cross-sectional view of the firing drive of the end effector of FIG. 2 being disengaged from the crimping drive;

FIG. 35A is a partial cross-sectional view of an end effector of a clip applier in a closed configuration;

FIG. 35B is a partial cross-sectional view of the end effector of FIG. 35A in an open configuration;

FIG. 35C is a cross-sectional view of the end effector of FIG. 35A in an open configuration;

FIG. 42A is a perspective view of a clip applier comprising an attachment mechanism;

FIG. 42B is a cross-sectional view of the clip applier of FIG. 42A;

FIG. 51D is a side view of the clip of FIG. 51C in a storage configuration;

FIG. 51E is a side view of the clip of FIG. 51C in a pre-firing configuration;

FIG. 51F is a side view of the clip of FIG. 51C in a post-firing configuration;

FIG. 54A is a partial cross-sectional view of the clip applier of FIG. 52 illustrating the closure tube in a home position;

FIG. 54B is a perspective view of a ground portion including a clocking portion of the clip applier of FIG. 52;

FIG. 63A is a perspective view of a releasable clip cartridge including an articulation joint;

FIG. 63B is a partial cross-sectional view of the releasable clip cartridge and articulation joint of FIG. 63A;

FIG. 65 is a partial cross-sectional view of a clip applier jaw assembly;

FIG. 66A is a partial cross-sectional view of clip applier jaw assembly including offset support legs;

FIG. 66B is a partial cross-sectional view of the clip applier jaw assembly of FIG. 66A;

FIG. 67 is a partial cross sectional plan view of the clip applier jaw assembly of FIG. 65;

FIG. 68 is a partial cross sectional plan view of the clip applier jaw assembly of FIG. 66A;

FIG. 81A is a partial cross-sectional view of a clip applier including a sensor array and a magnet;

FIG. 81B is a partial cross-sectional view of the clip applier of FIG. 81A;

FIG. 84A is a partial side elevational view of the clip applier system of FIG. 82 depicting a jaw wing of a clip applier of the clip applier system positioned distal to a loading arm of a clip magazine of the clip applier system;

FIG. 84B is a partial side elevational view of the clip applier system of FIG. 82 depicting the jaw wing of the clip applier positioned proximal to the loading arm of the clip magazine;

FIG. 84C is a partial side elevational view of the clip applier system of FIG. 82 depicting the jaw wing of the clip applier positioned proximal to the loading arm of the clip magazine;

FIG. 85A is a partial perspective view of the clip applier system of FIG. 82;

FIG. 88C is a cross-sectional plan view of the clip applier and the clip magazine of FIG. 87A;

FIG. 88D is a cross-sectional plan view of the clip applier and the clip magazine of FIG. 87A in a nearly spent configuration.

FIG. 92B is a front elevational view of the distal head and shaft of FIG. 92A;

FIG. 93A is an exploded perspective view of a clip applier system comprising interchangeable distal heads that are releasably attachable to a clip applier;

FIG. 93B is a cross-sectional view of a quick disconnect configured for use between a shaft and a distal head of a clip applier;

FIG. 93C is a cross-sectional view of the quick disconnect of FIG. 93B;

FIG. 93D is a cross-sectional front view of the quick disconnect of FIG. 93B;

FIG. 94 is a cross-sectional view of a clip magazine including clips that are stacked in an offset manner;

FIG. 95A is a cross-sectional view of a clip magazine including an opening for an internal drive of a clip applier;

FIG. 95B is a cross-sectional view of a clip magazine comprising slanted clip channels and an opening for an internal drive of a clip applier;

FIG. 95C is a cross-sectional view of a clip magazine for use with a clip applier;

FIG. 95D is a cross-sectional view of a clip magazine for use with a clip applier;

FIG. 95E is a cross-sectional view of a clip magazine comprising clips stacked in a non-concentric radial array;

FIG. 96 is a perspective view of a clip magazine comprising an angled clip storage channel;

Figure 97A:
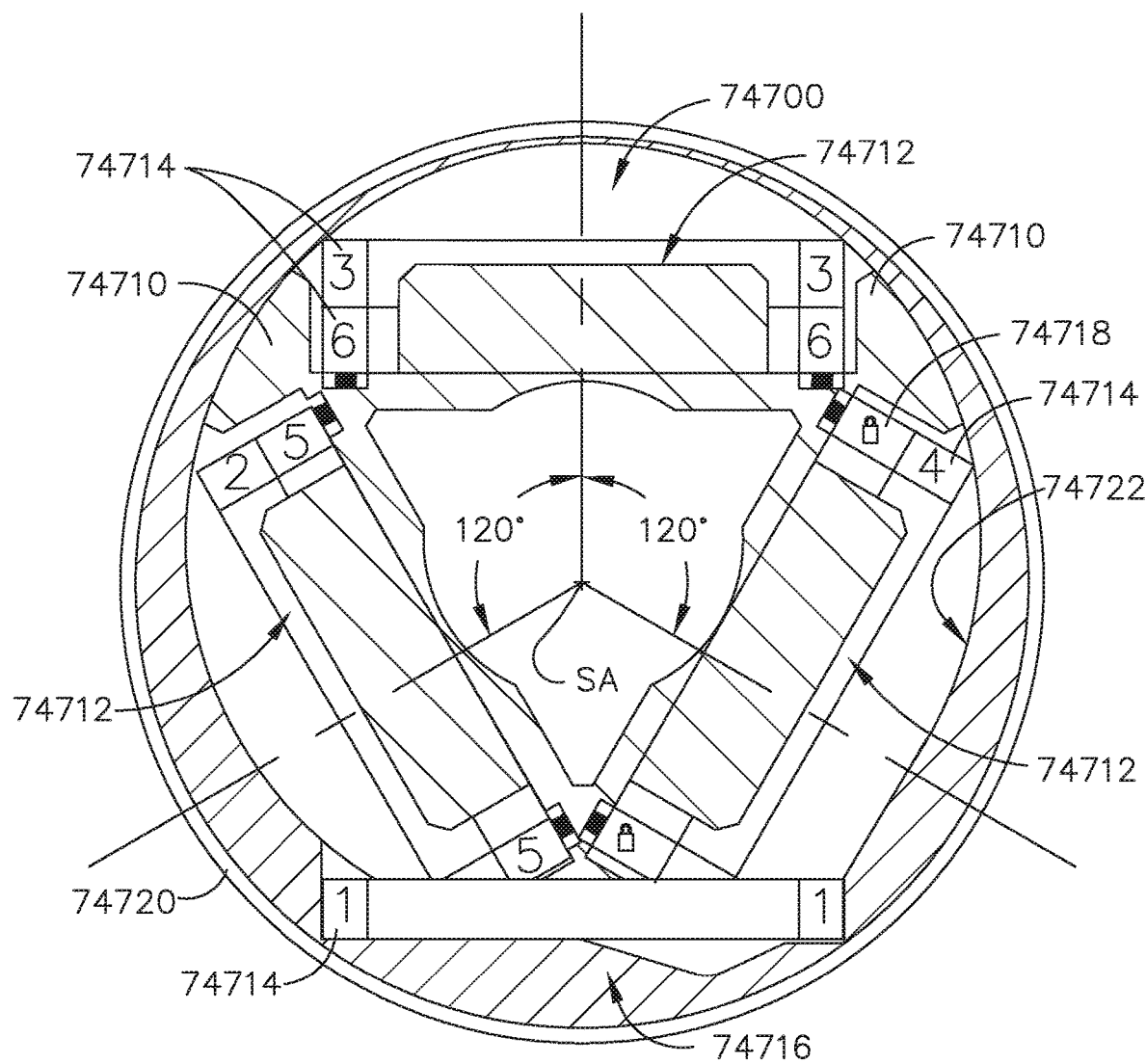
Figure 97B:
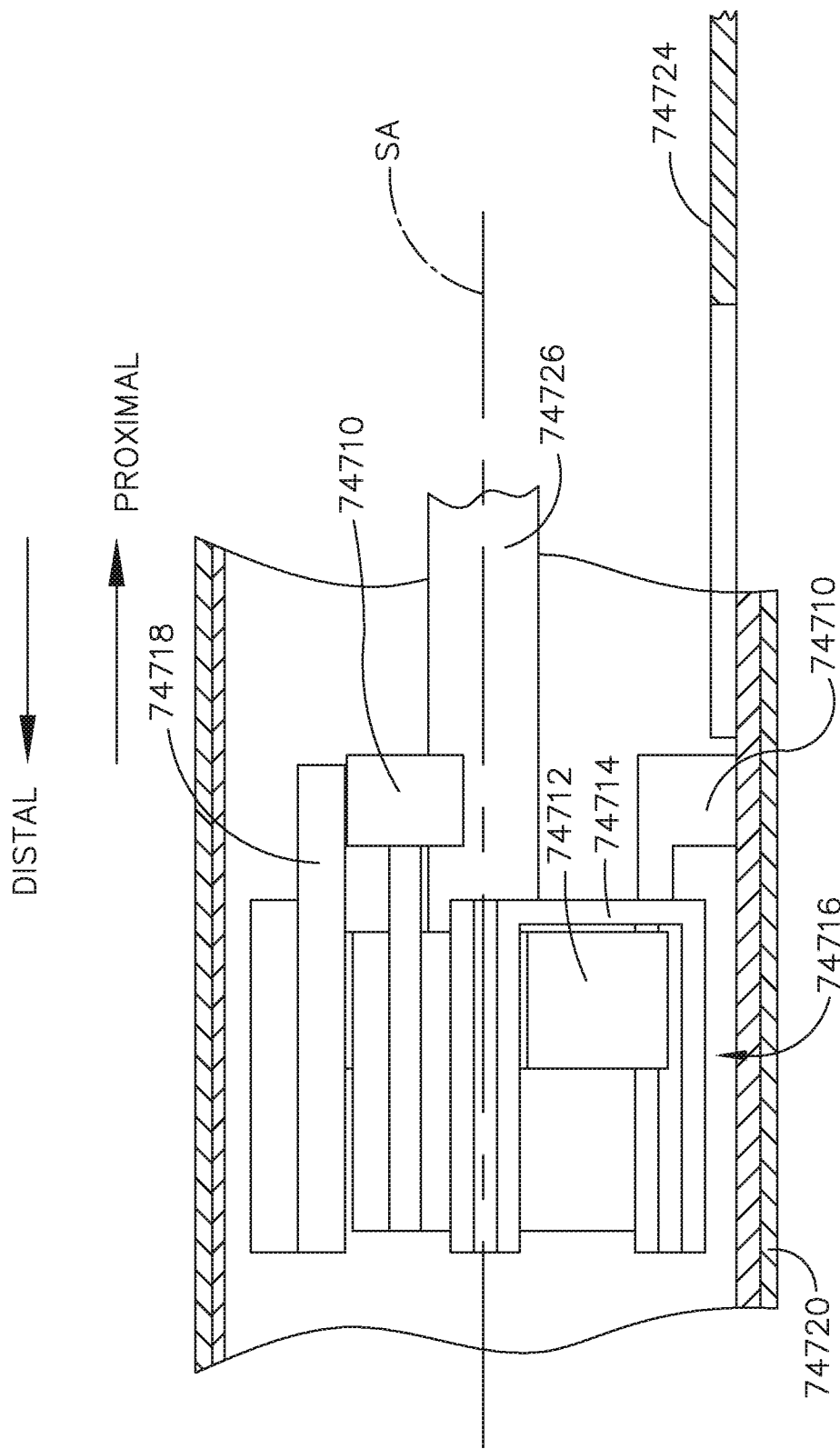
Figure 98:
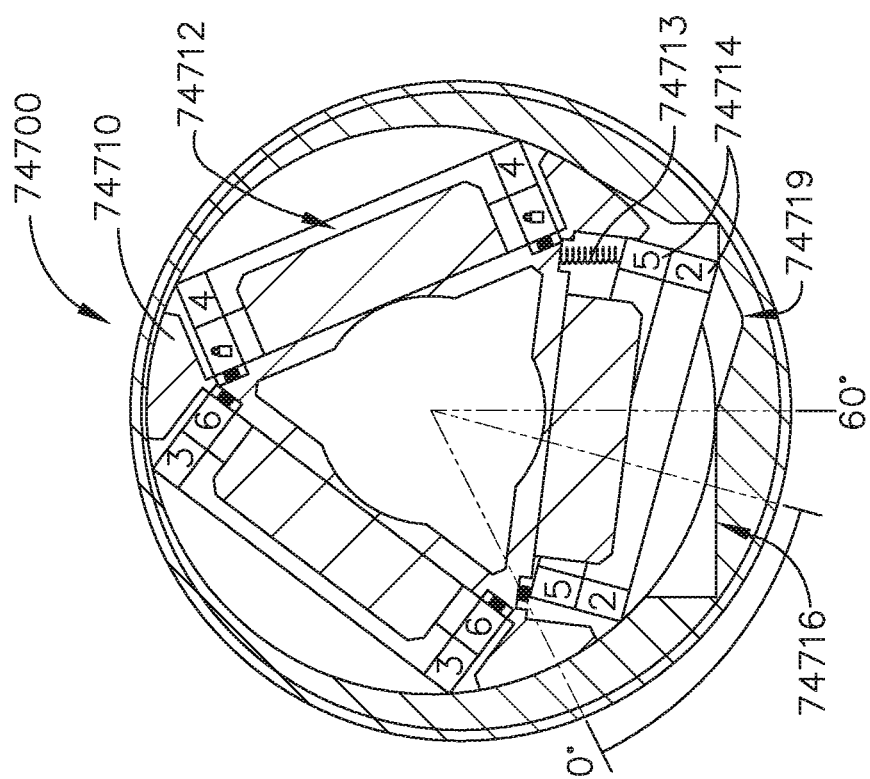
Figure 99:
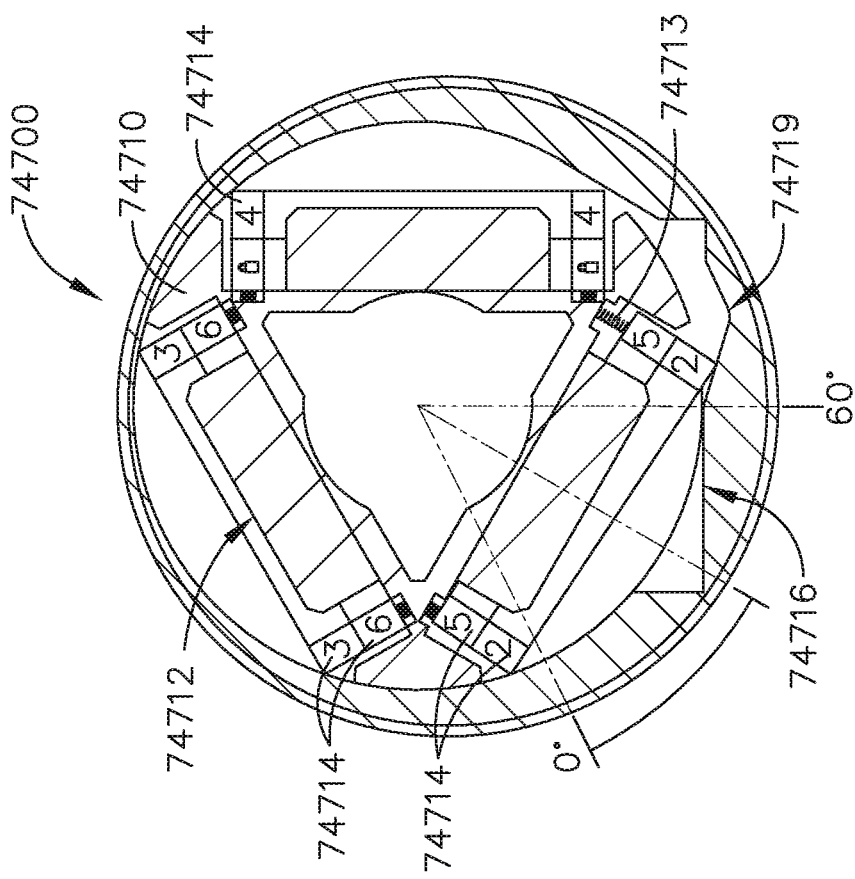
Figure 101:
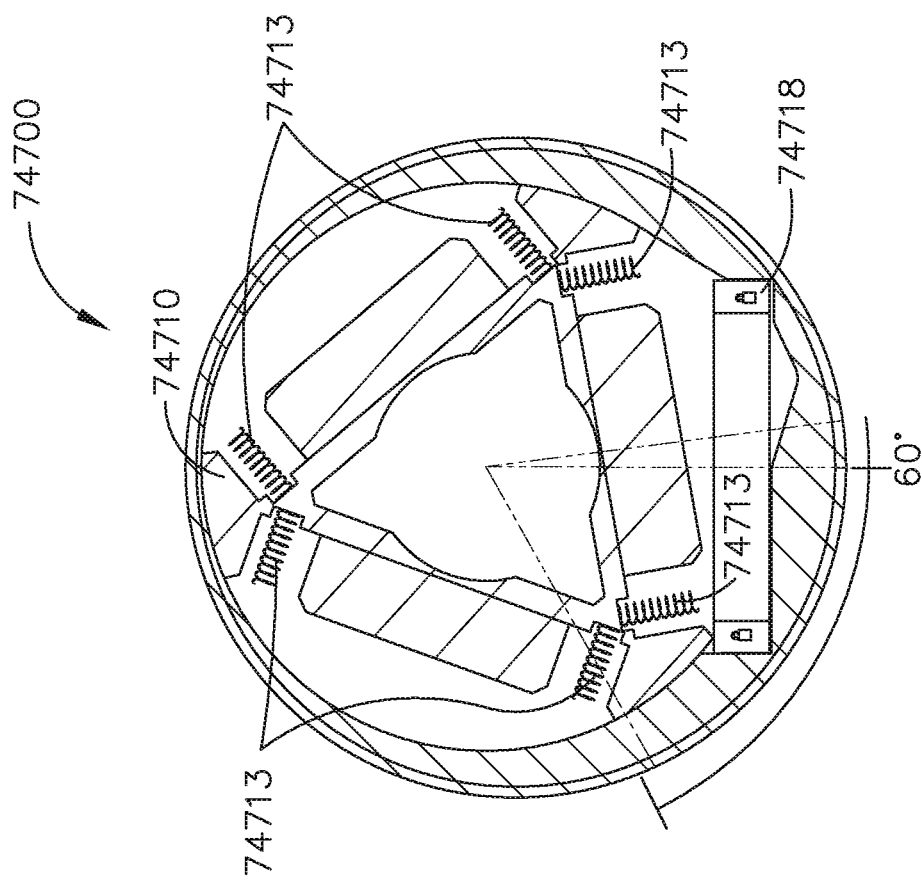
Figure 100:
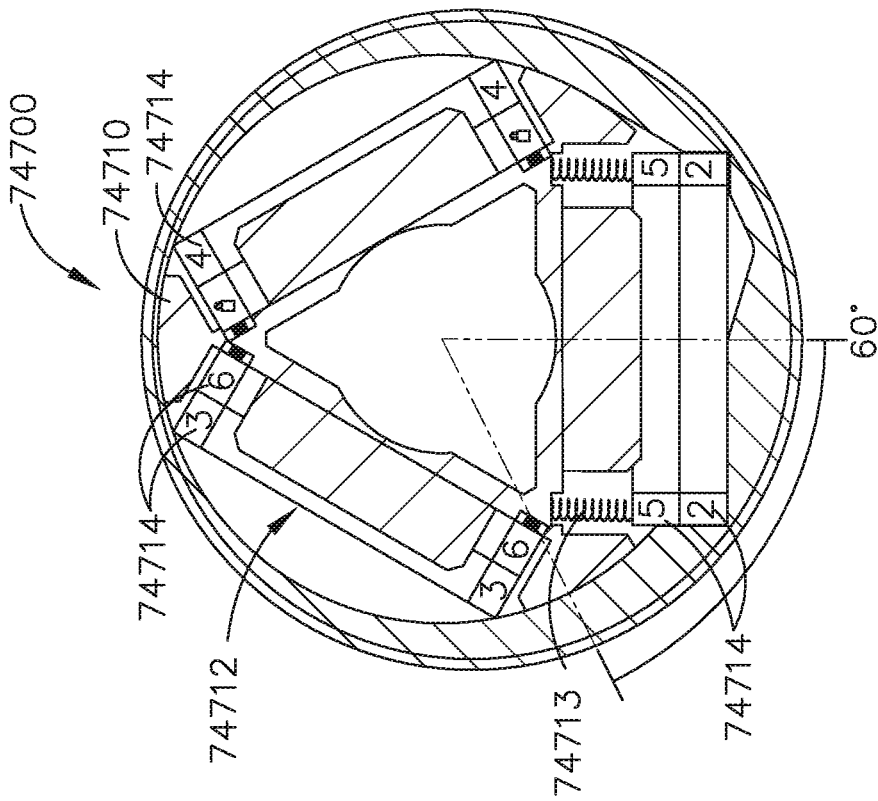
Figure 102:
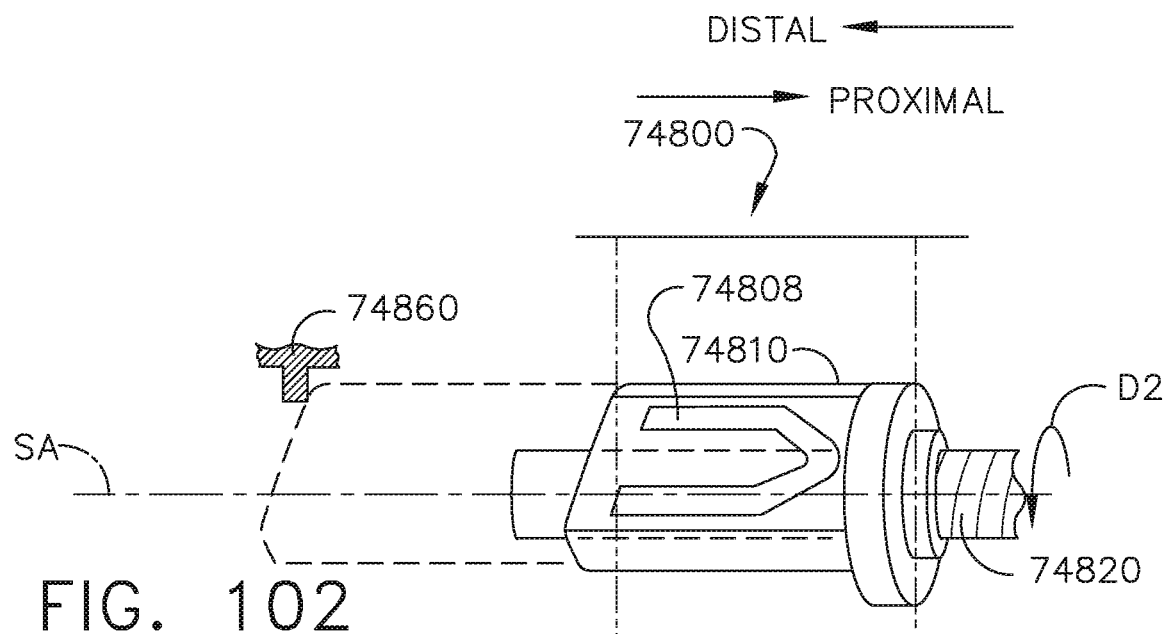
Figure 103:
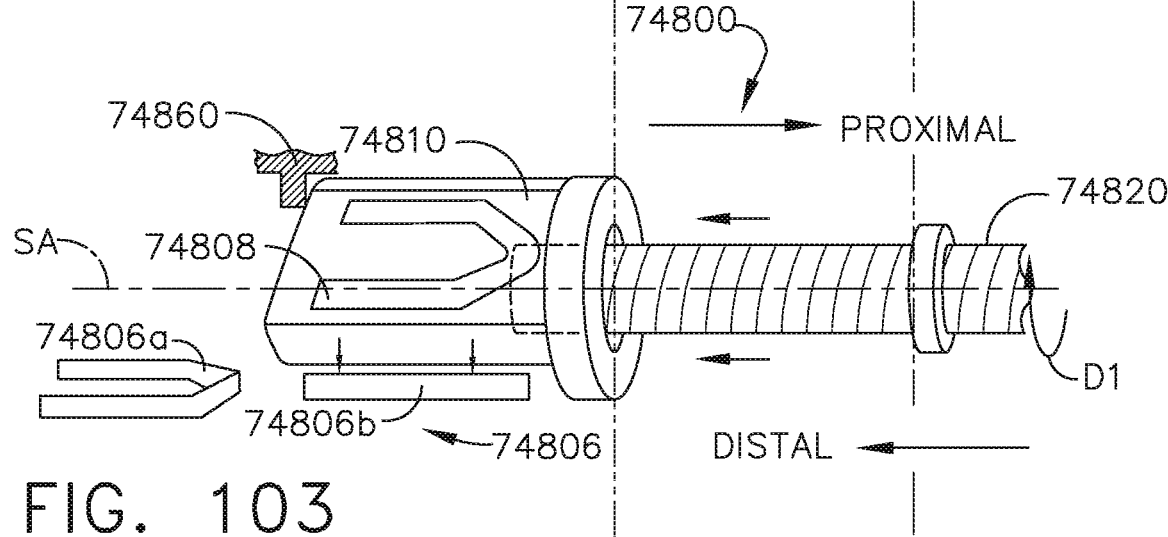
Figure 104:
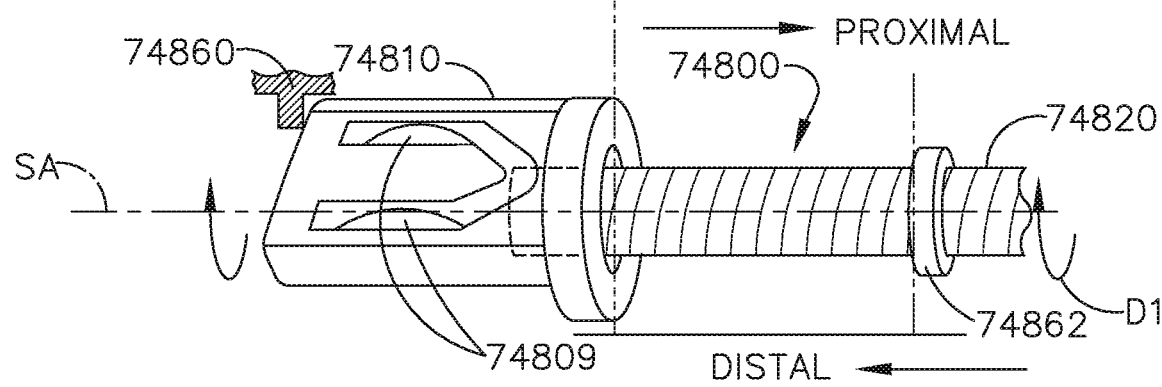
Figure 105:
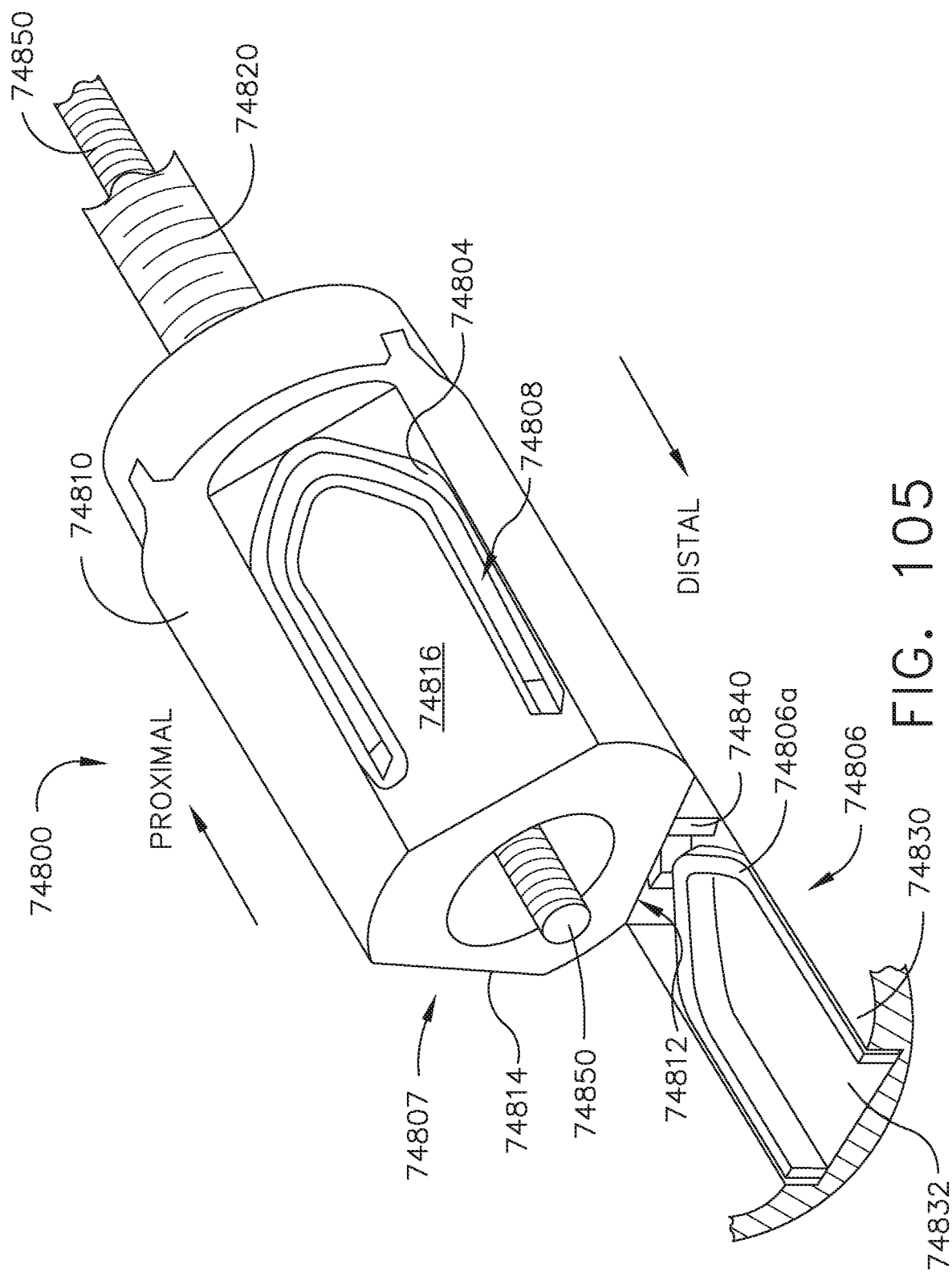
Figure 106:
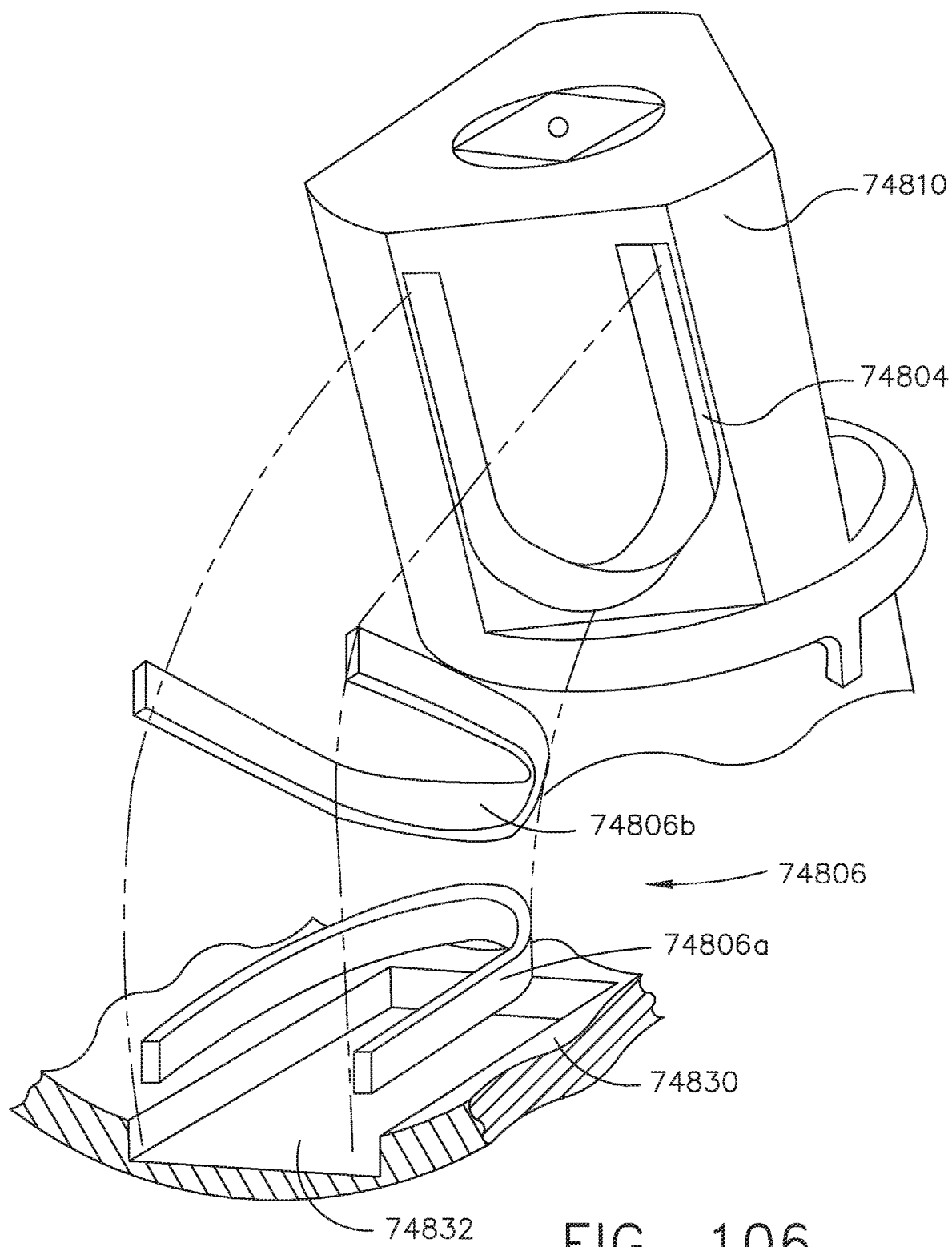
Figure 107:
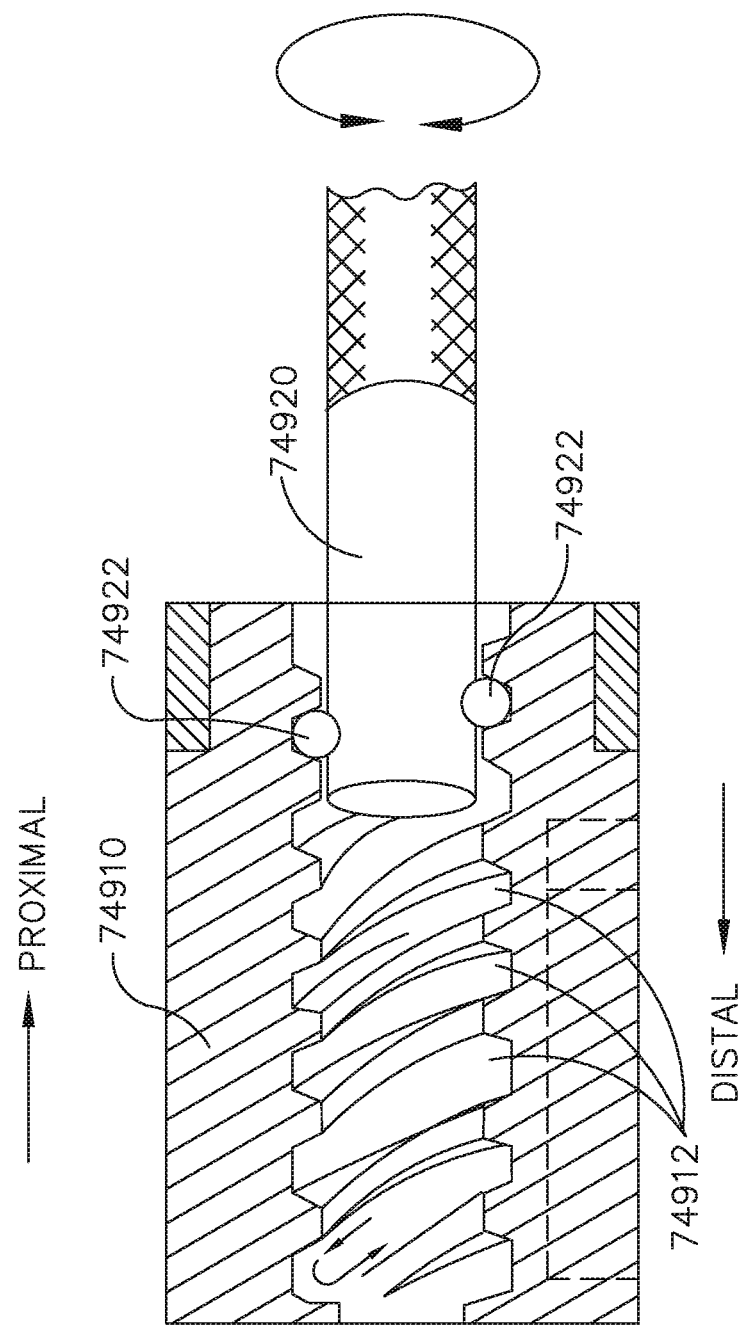
Figure 110:
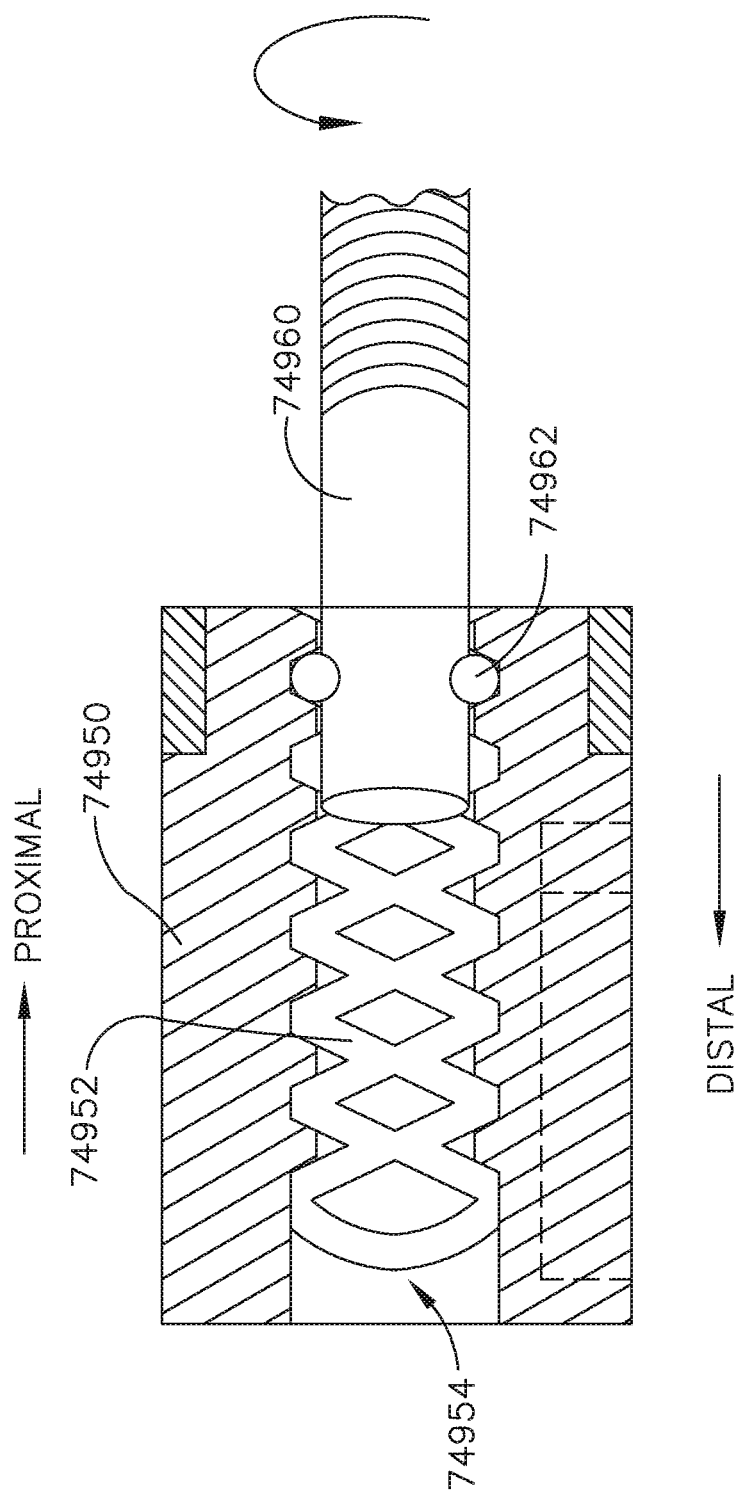
Figure 111:
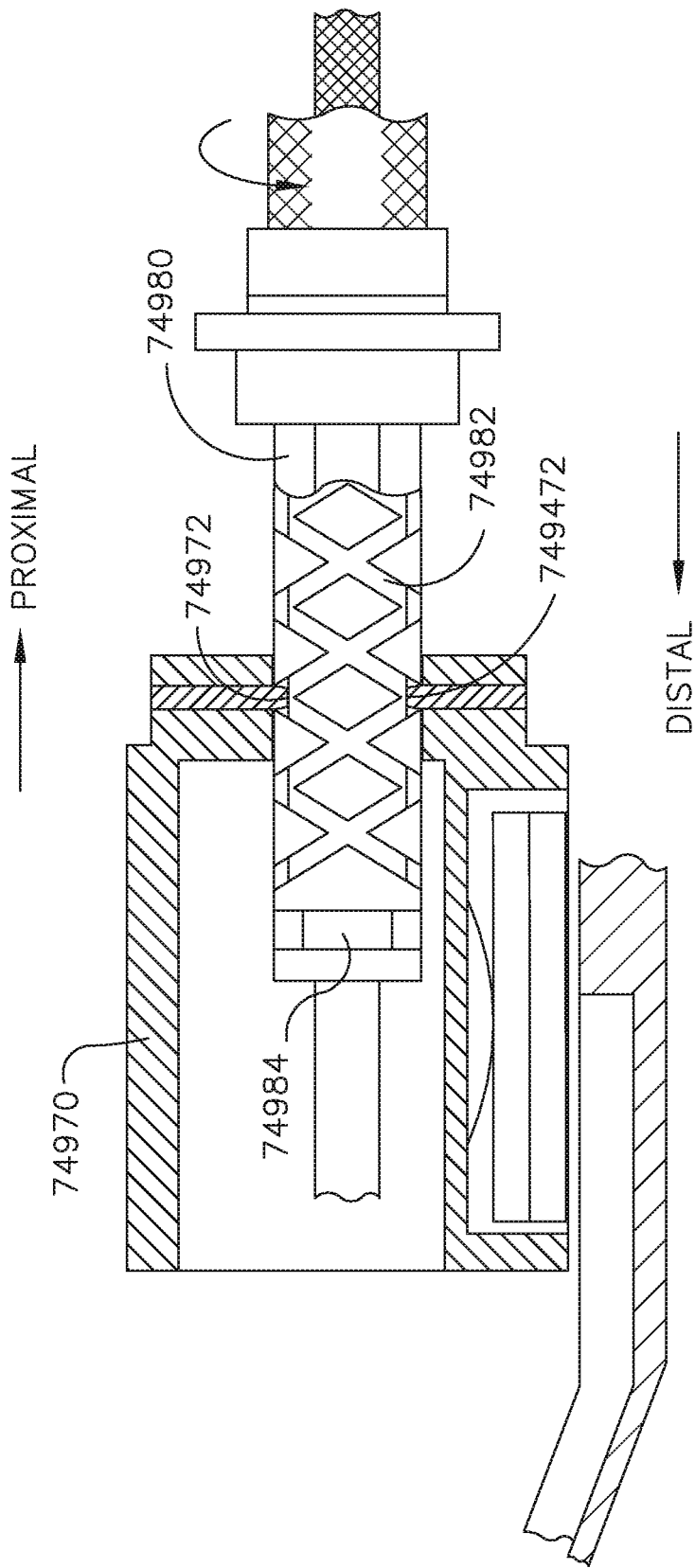
Figure 112:
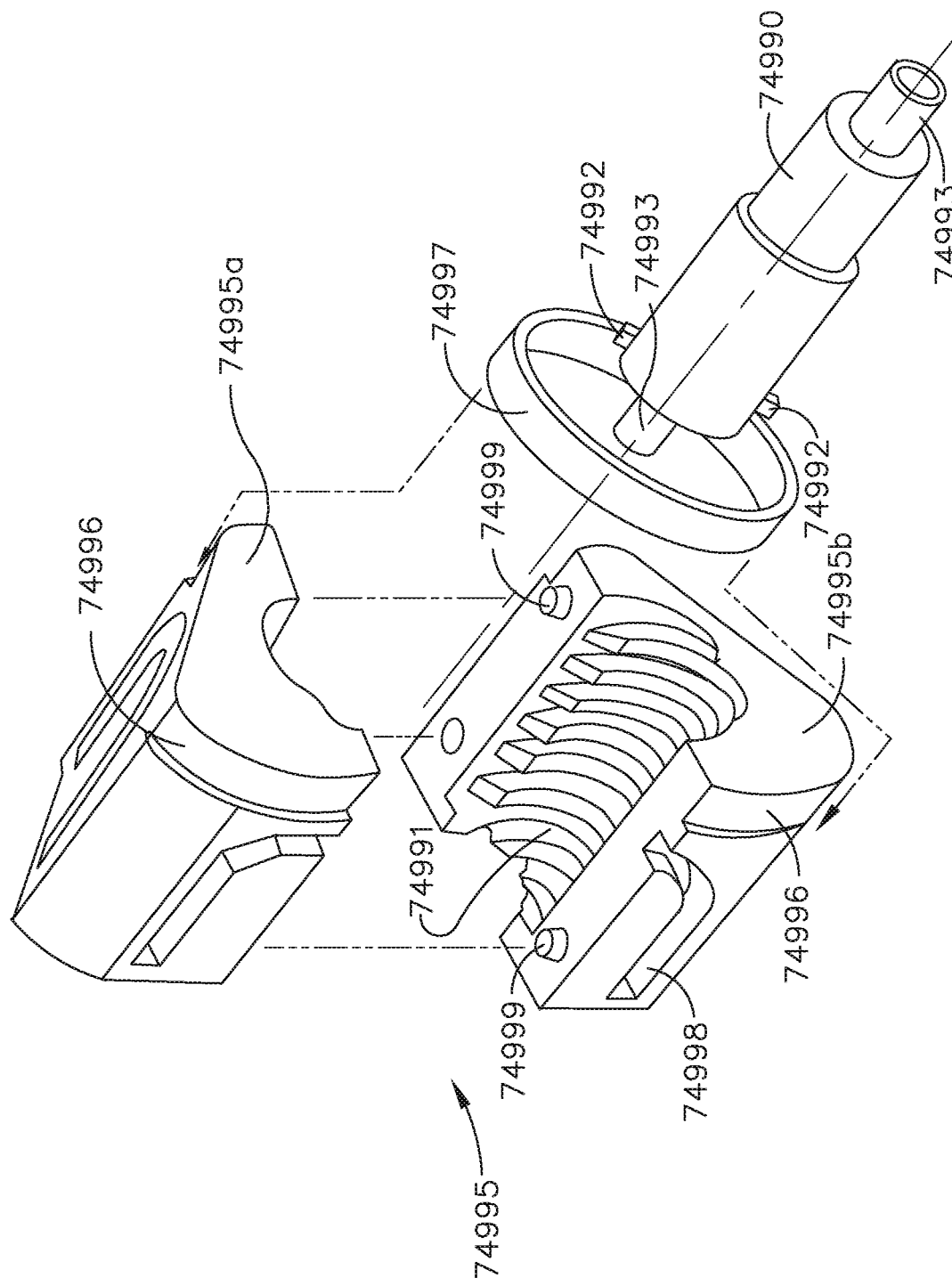
Figure 113:
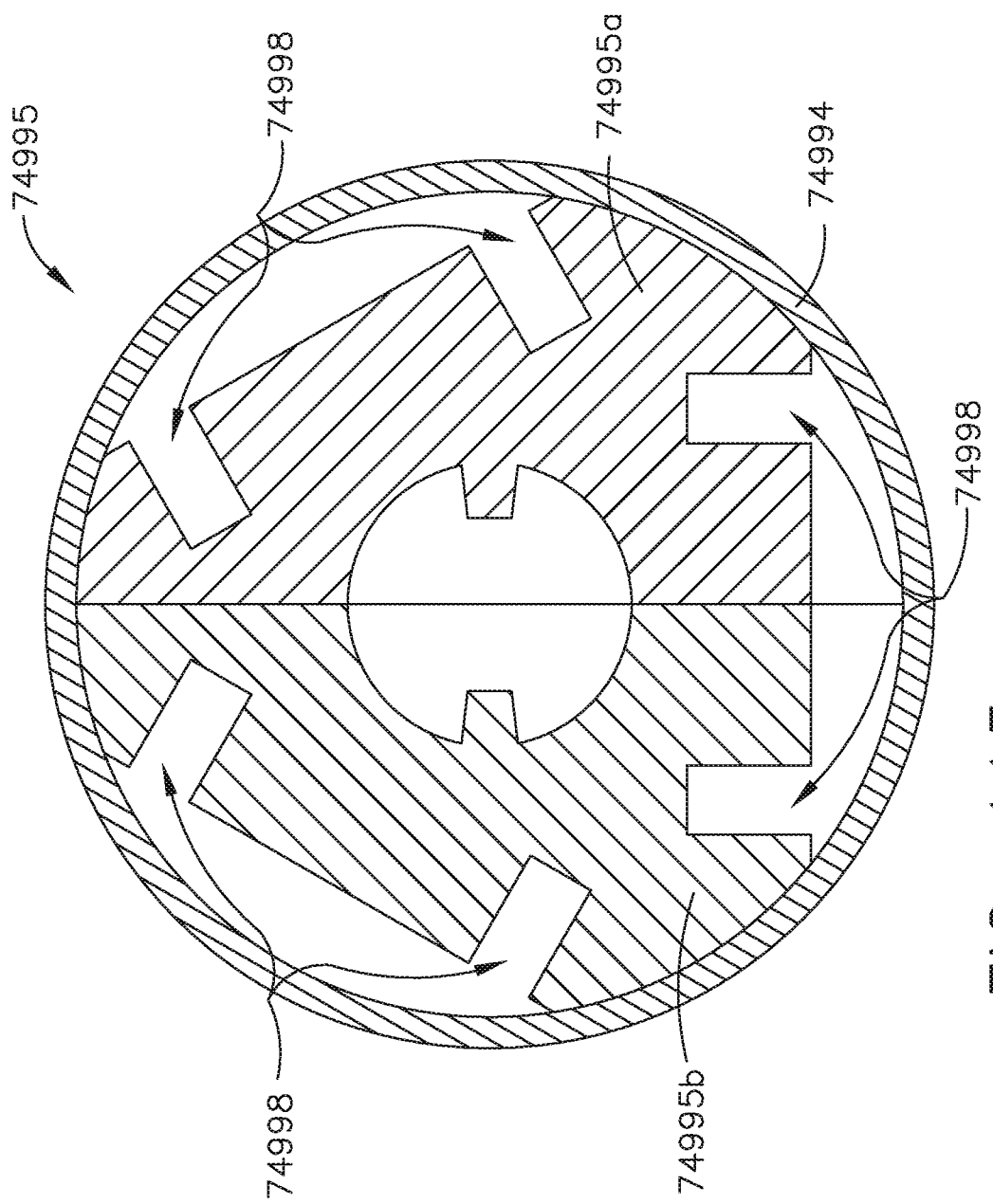
Figure 114:
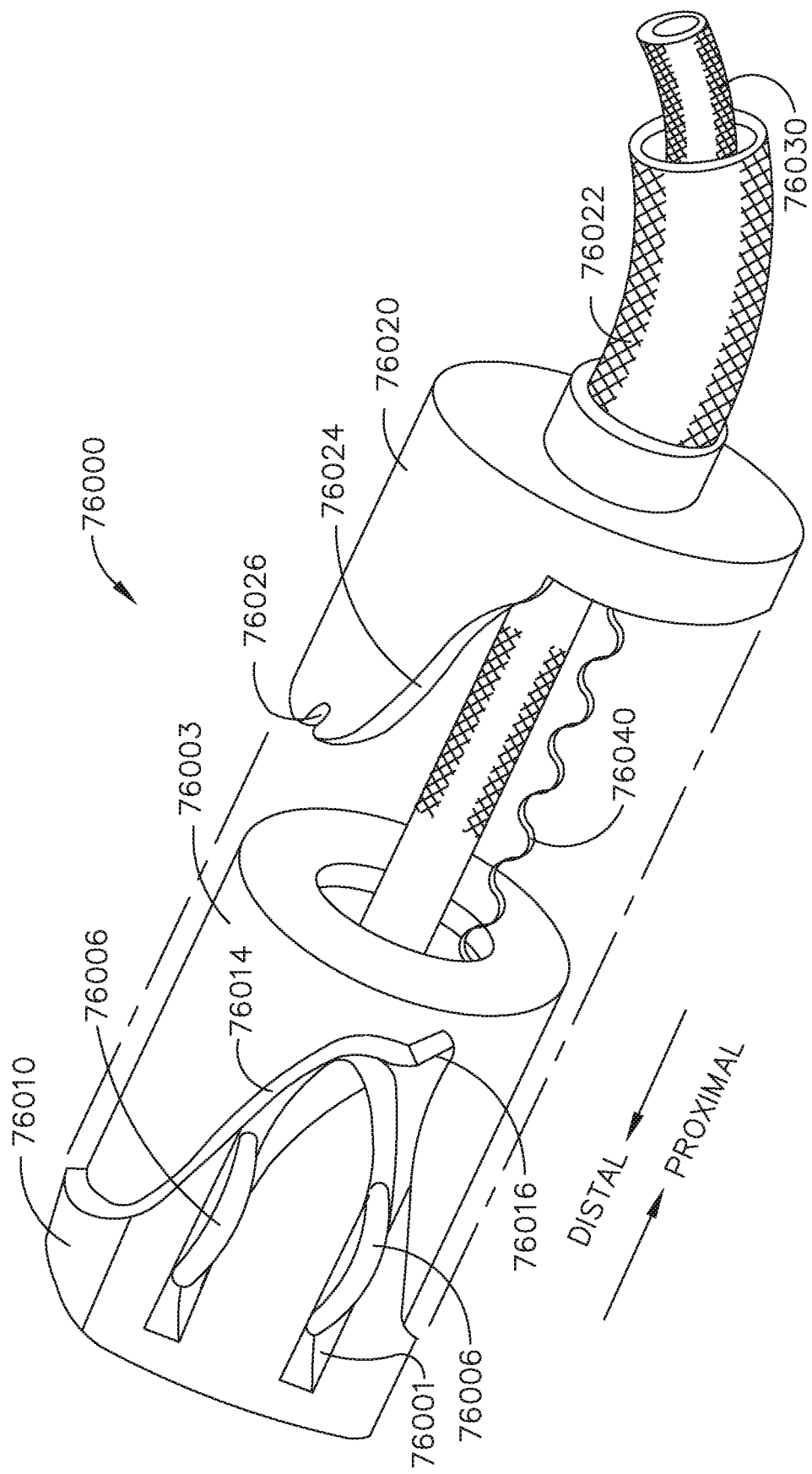
Figure 115A:
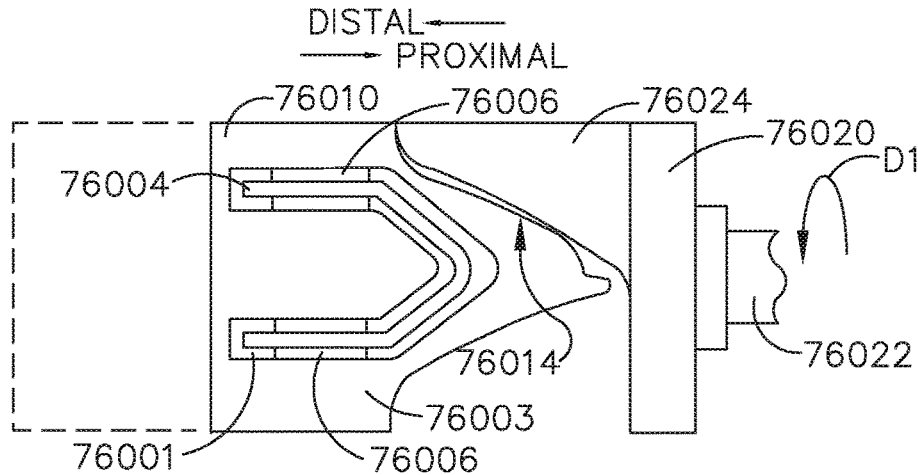
Figure 115B:
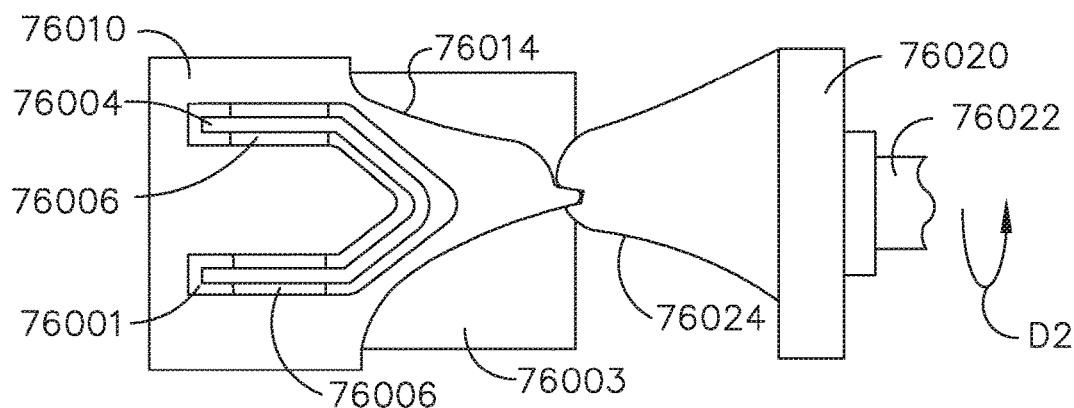
Figure 115C:
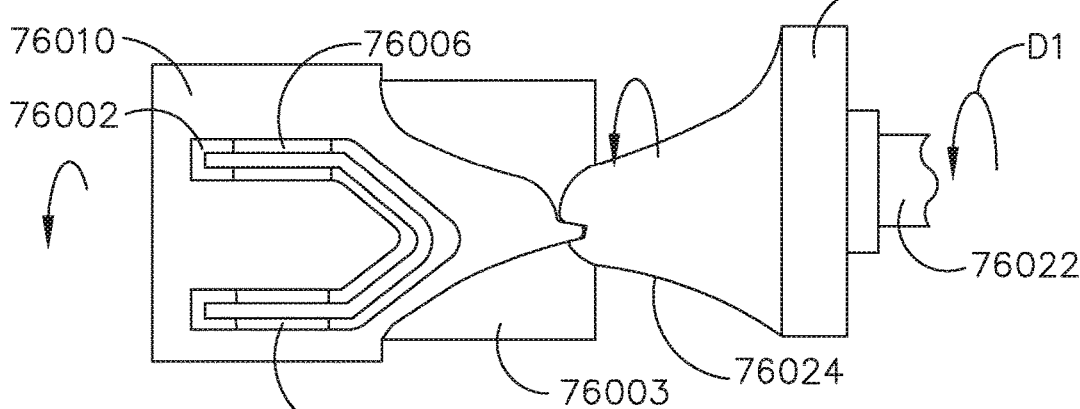
Figure 116:
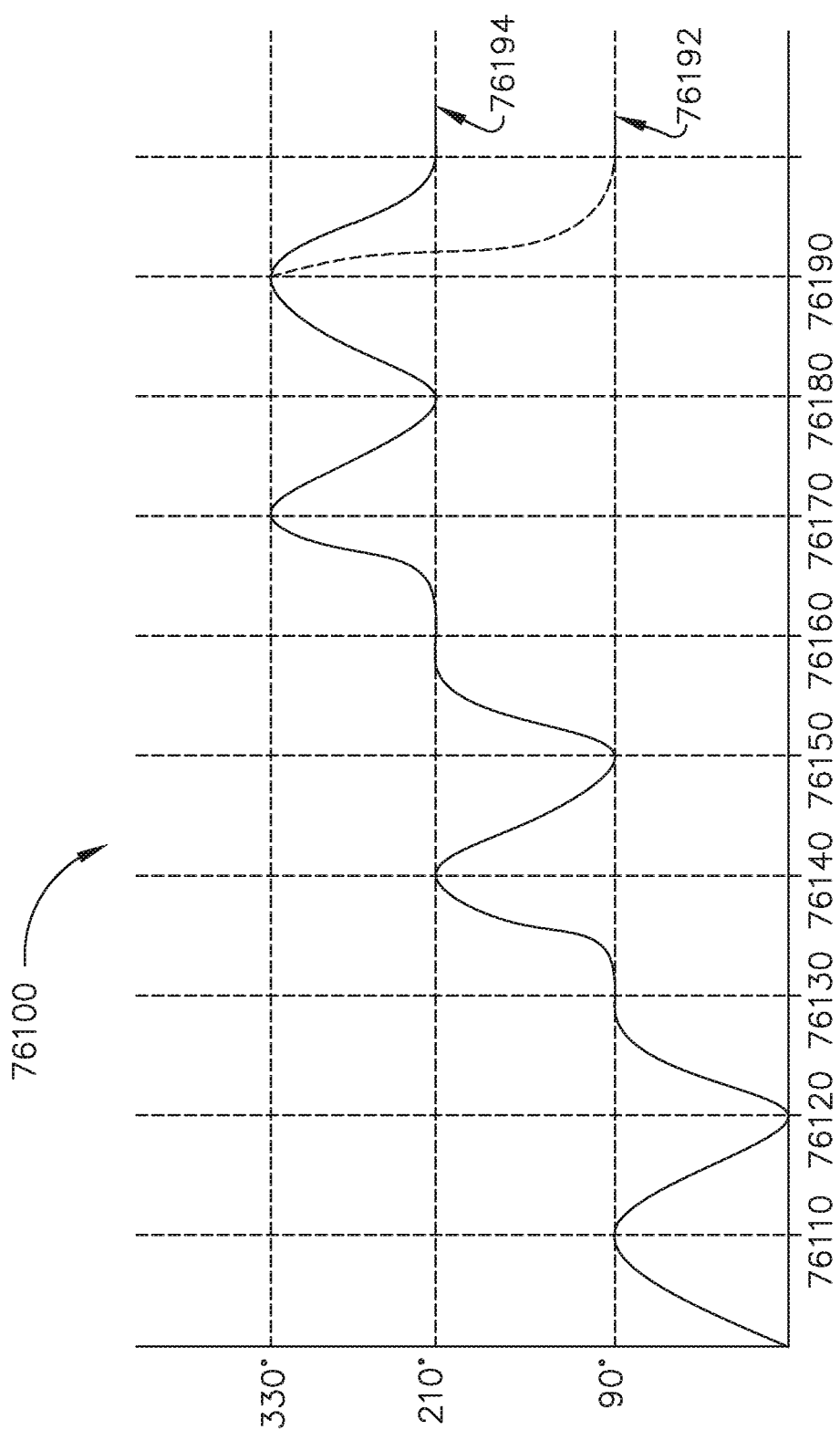
Figure 118A:
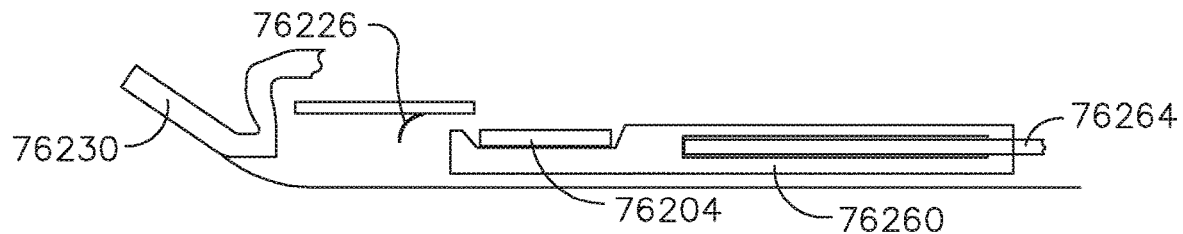
Figure 118B:
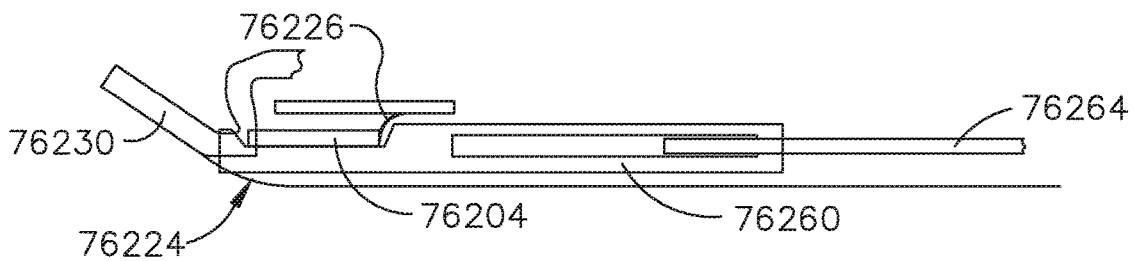
Figure 118C:
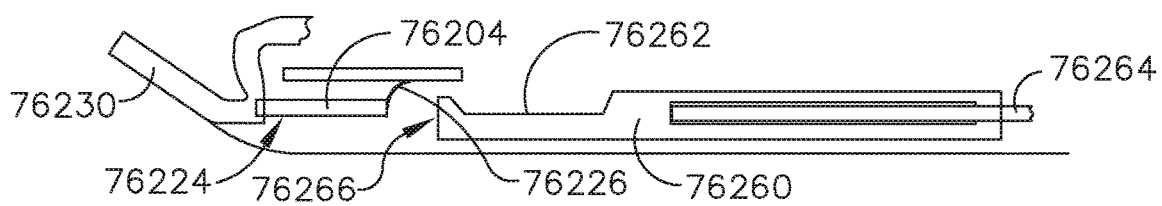
Figure 118D:
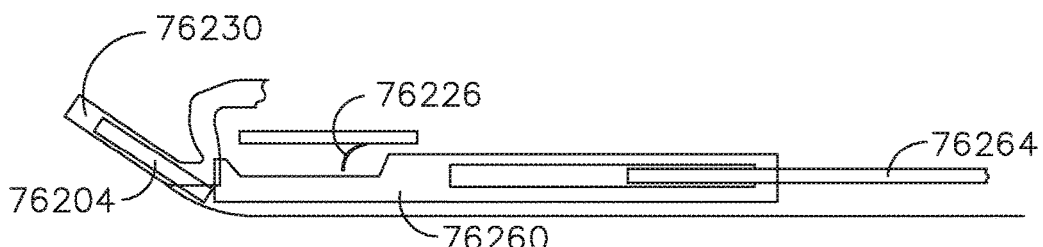
Figure 119A:
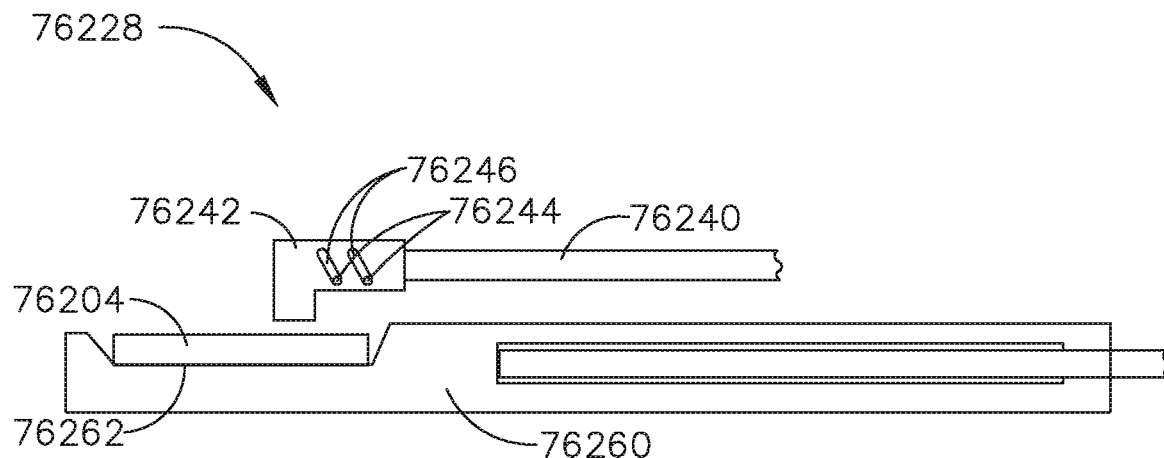
Figure 119B:
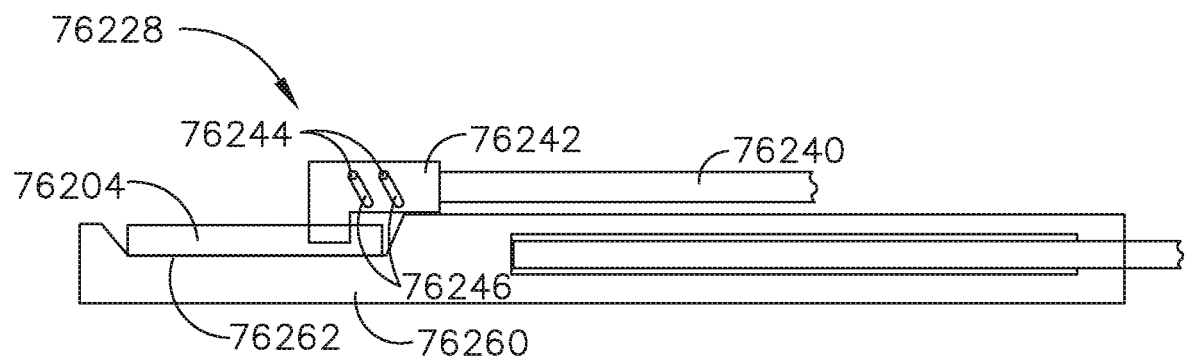
Figure 120A:
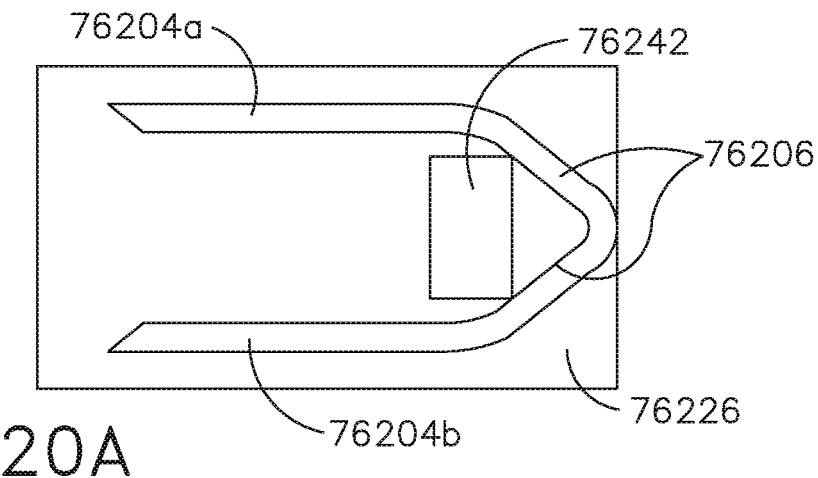
Figure 120B:
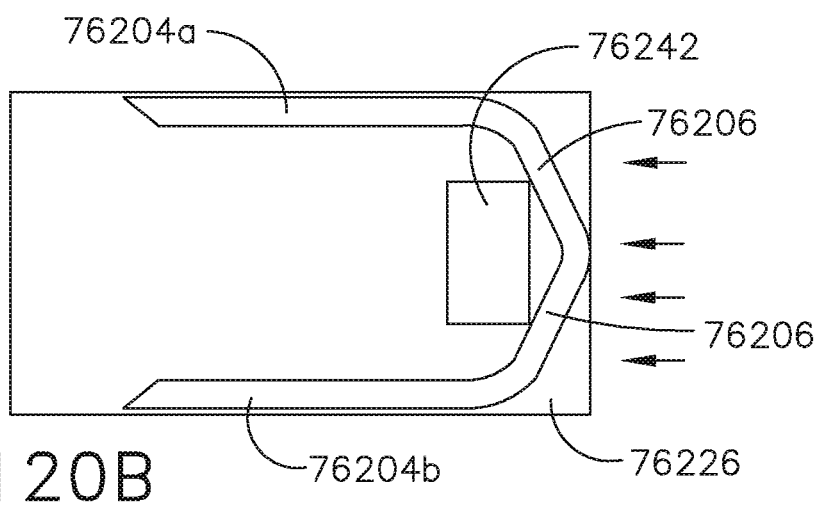
Figure 121:
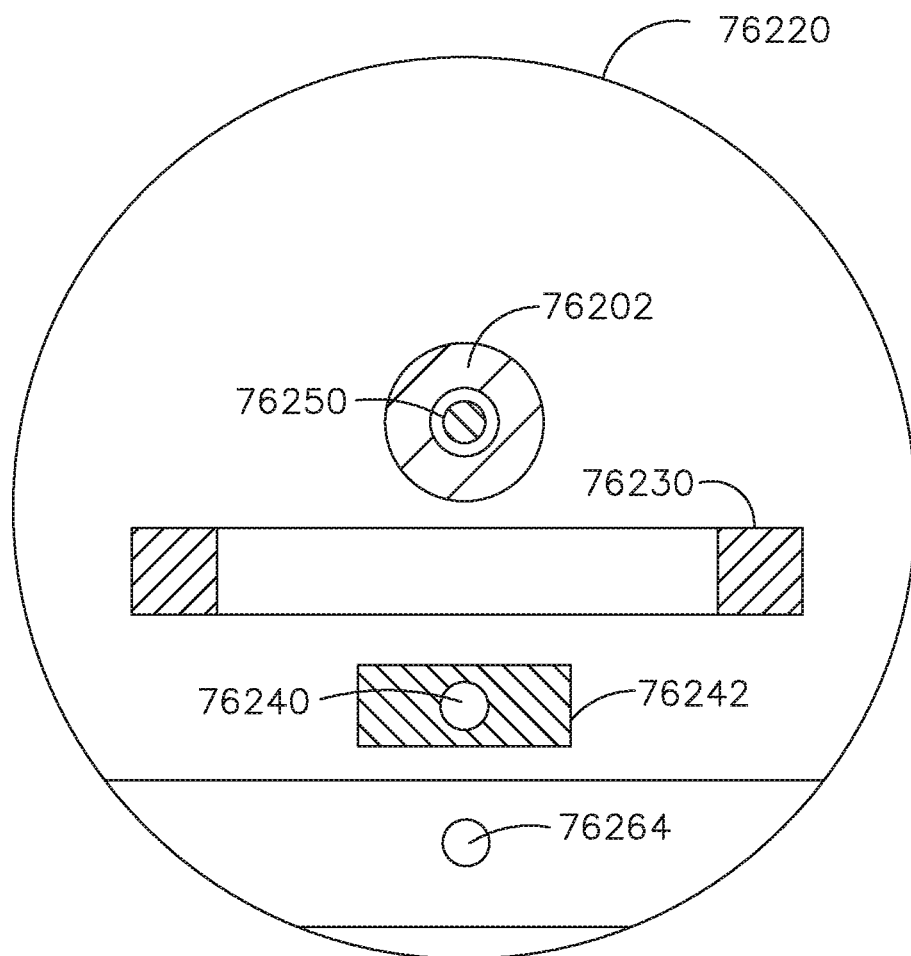
Figure 126:
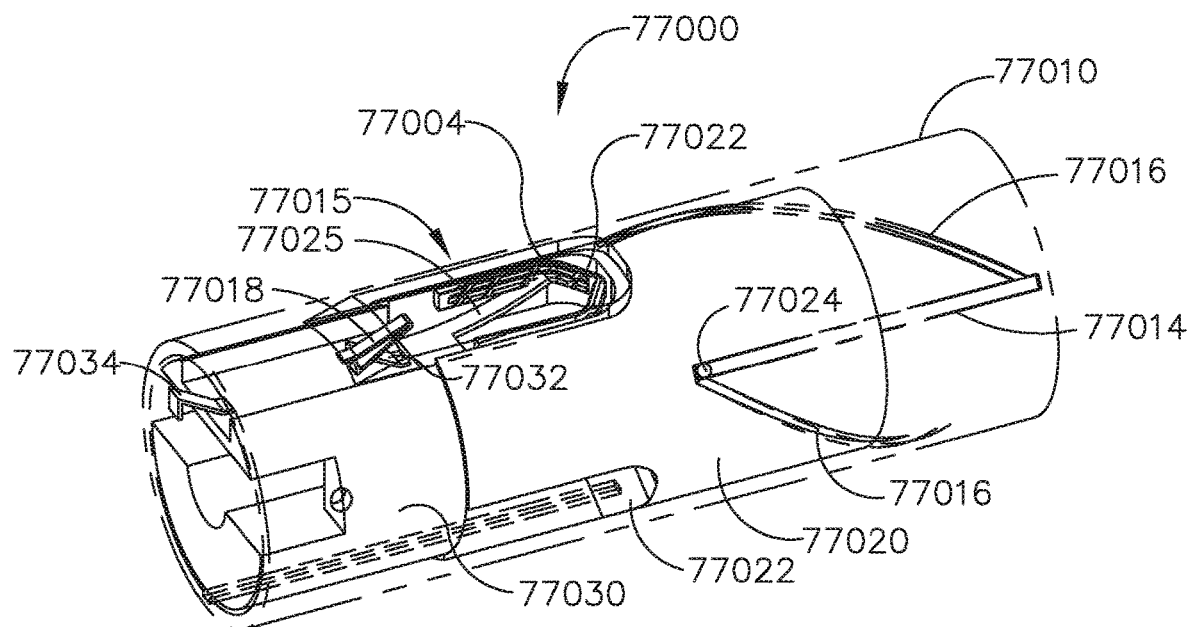
Figure 127:
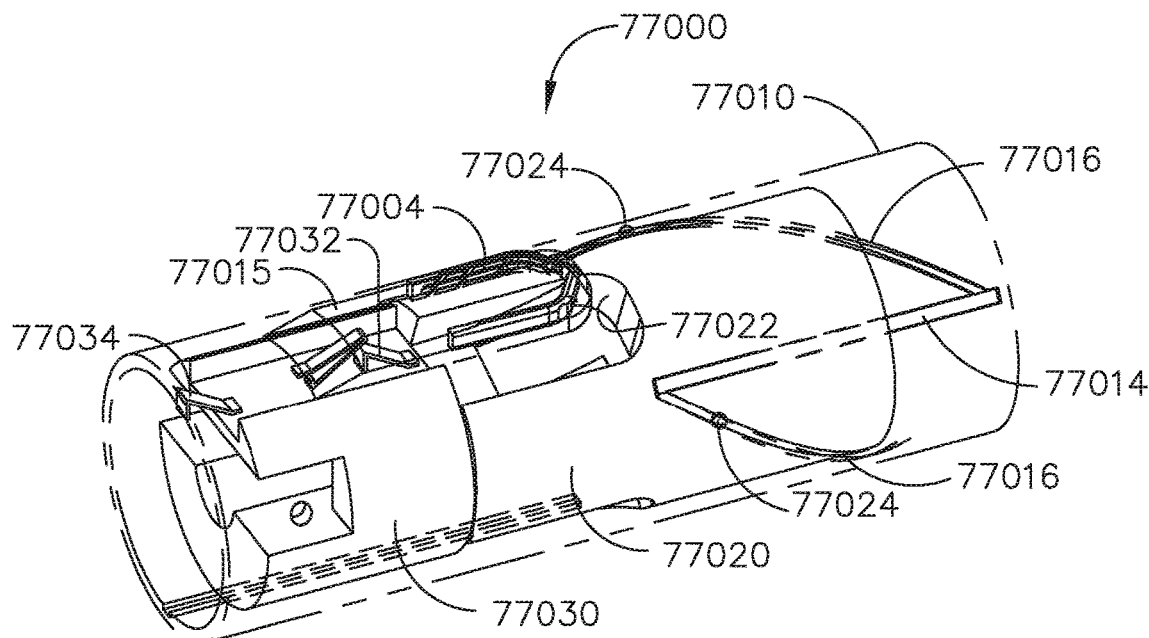
Figure 128:
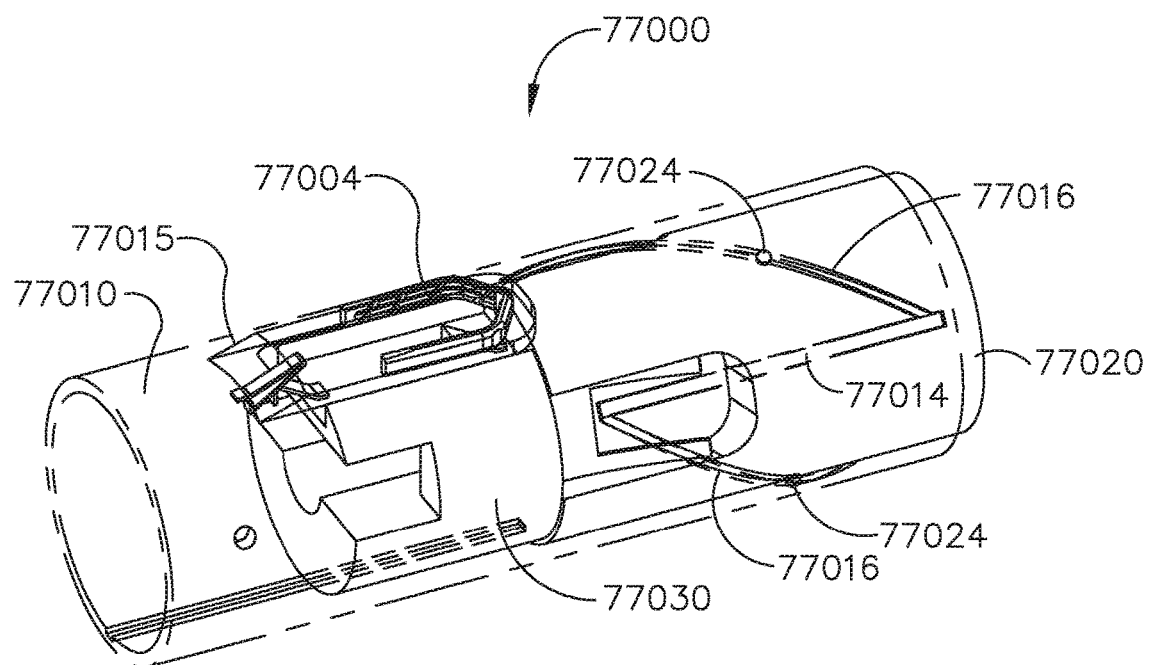
Figure 129:
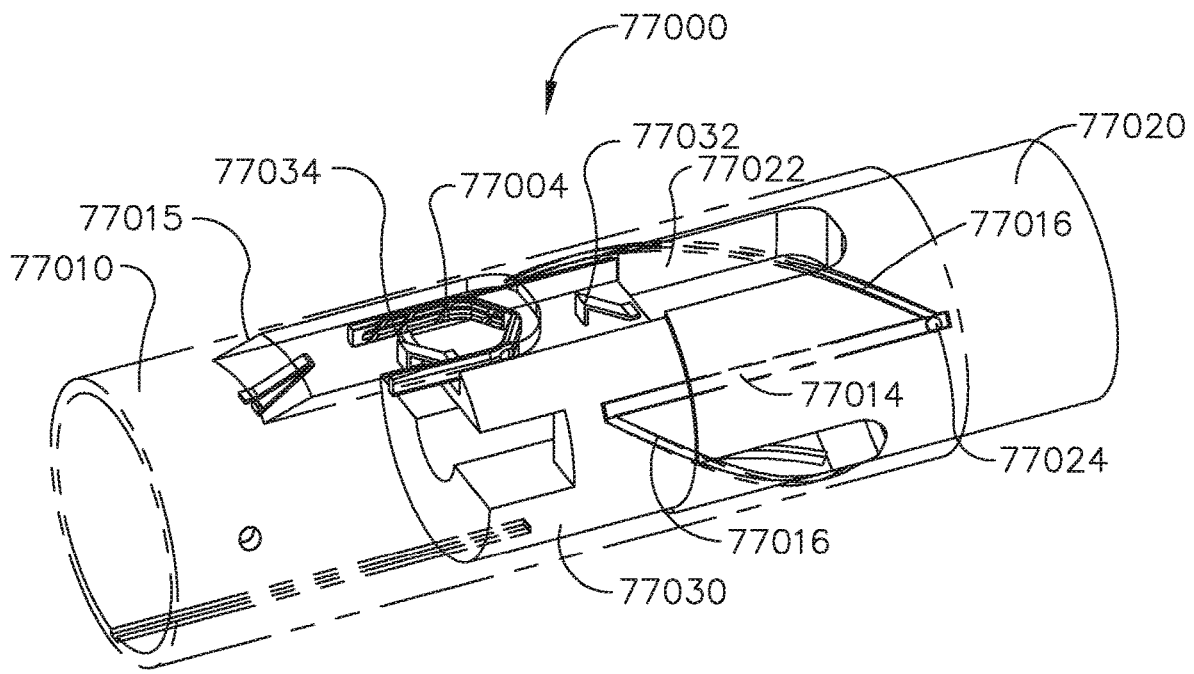
Figure 130:
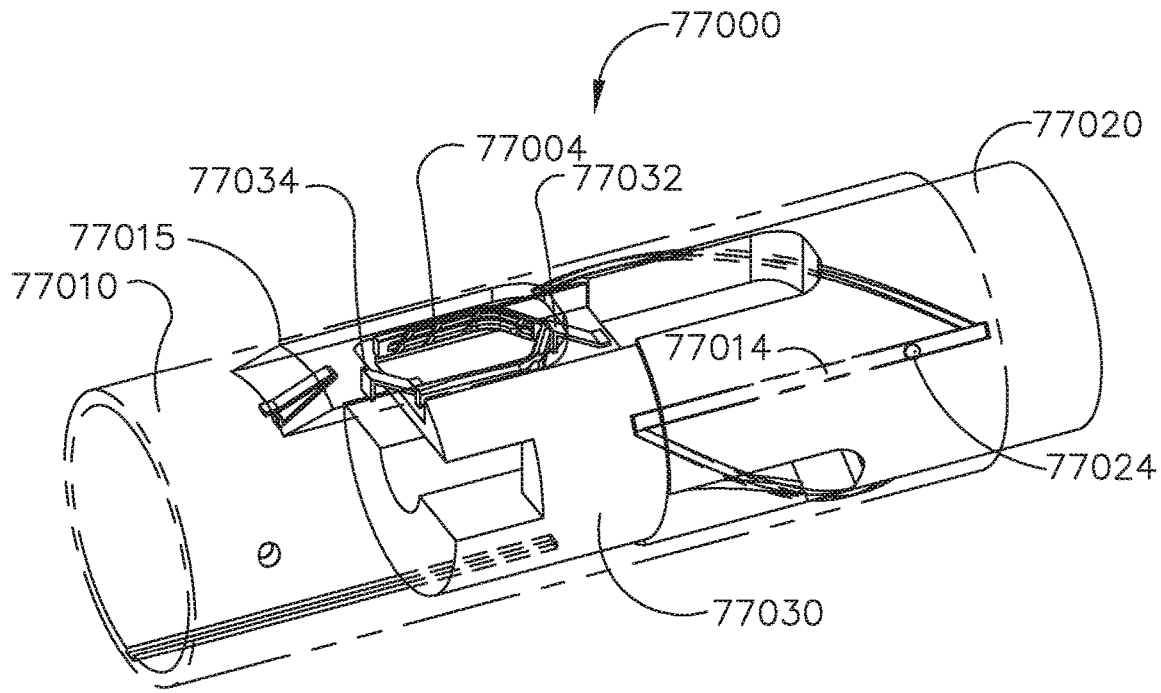
Figure 131:
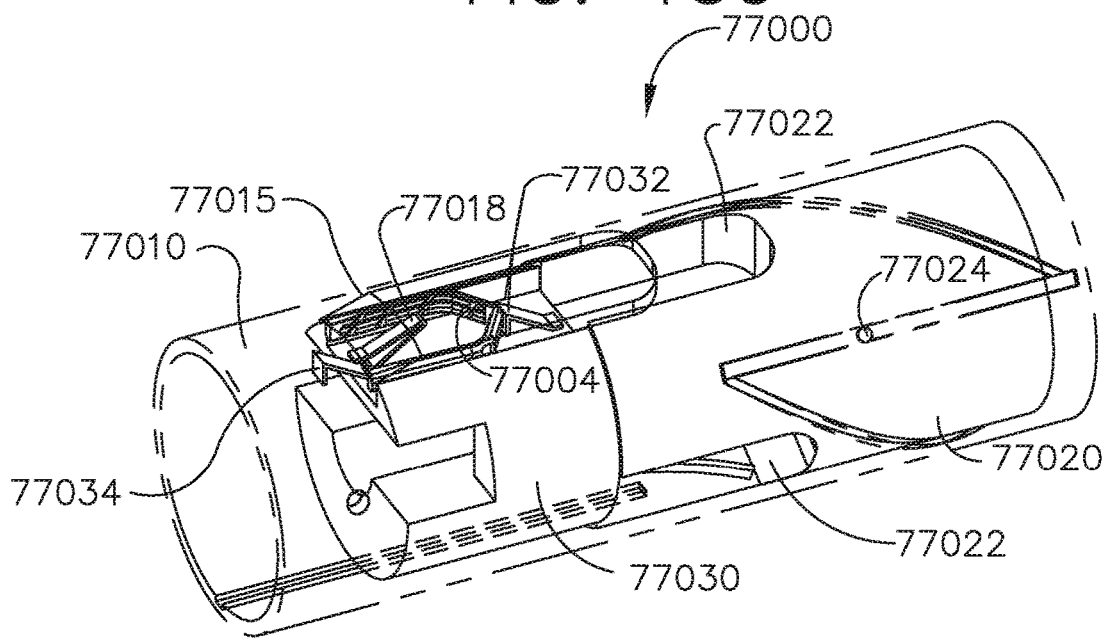
Figure 132:
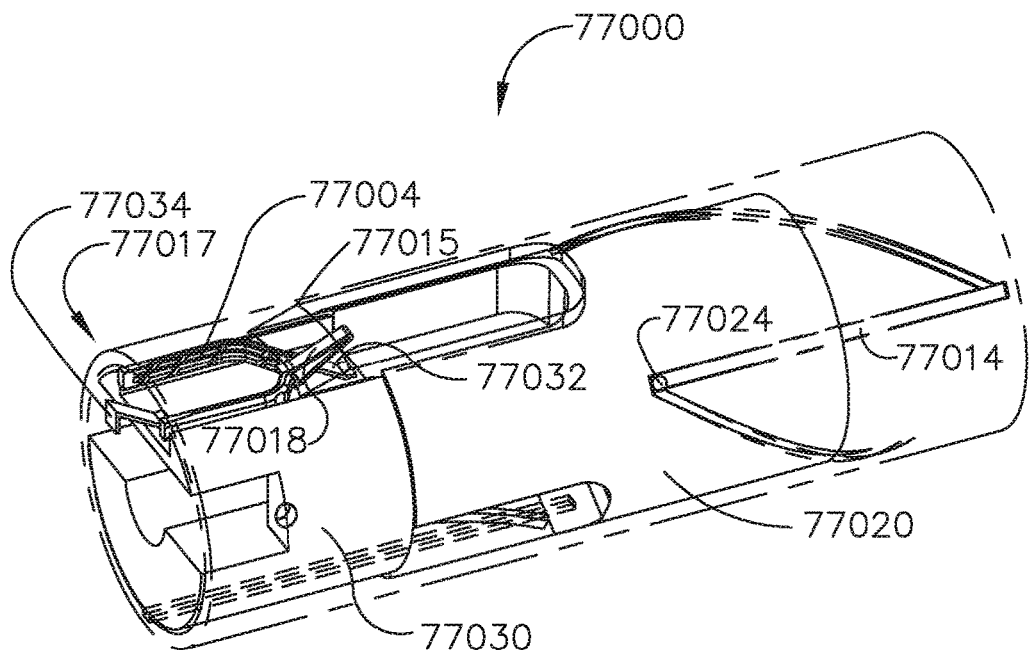
Figure 133:
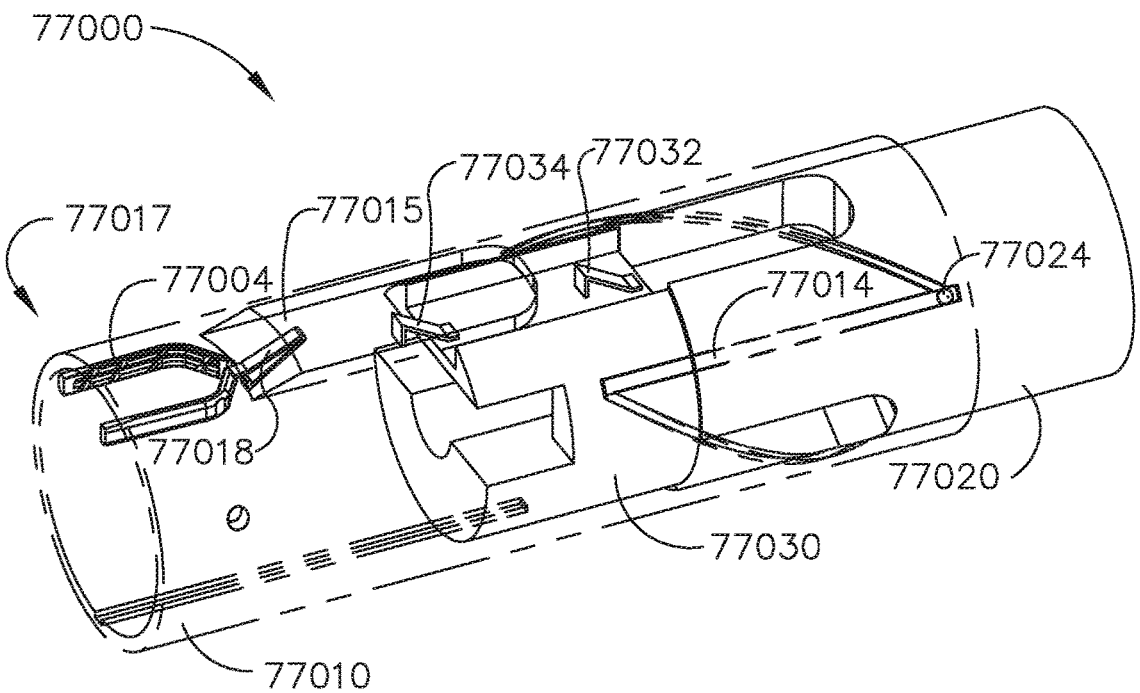
Figure 134:
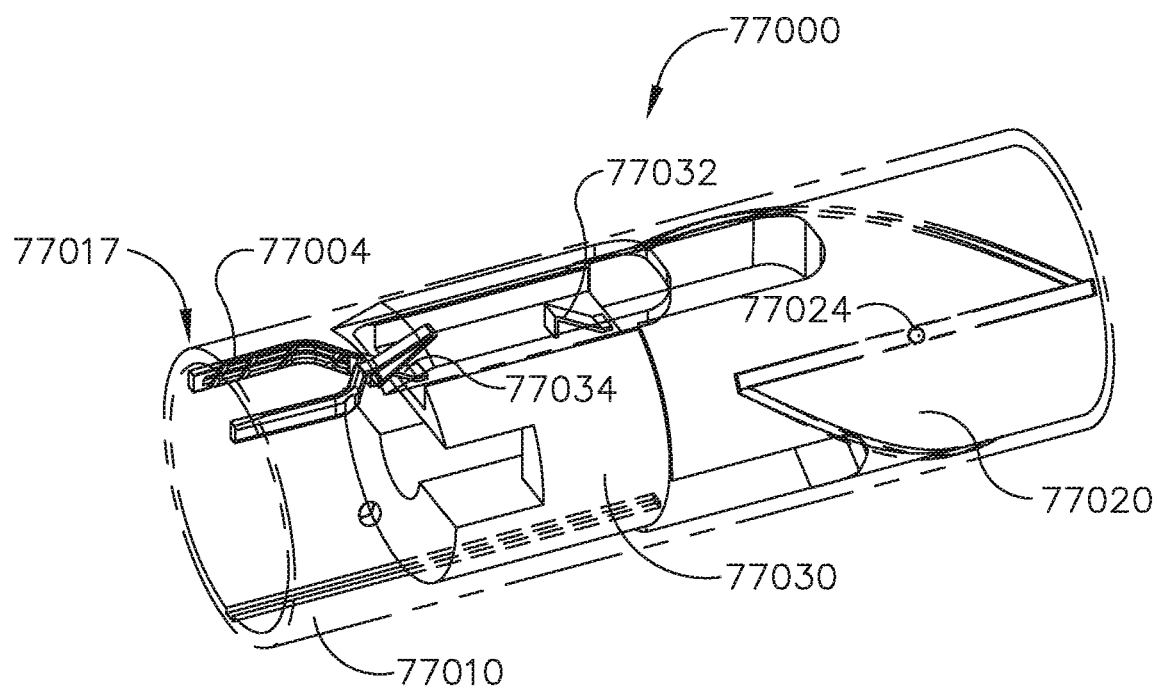
Figure 135:
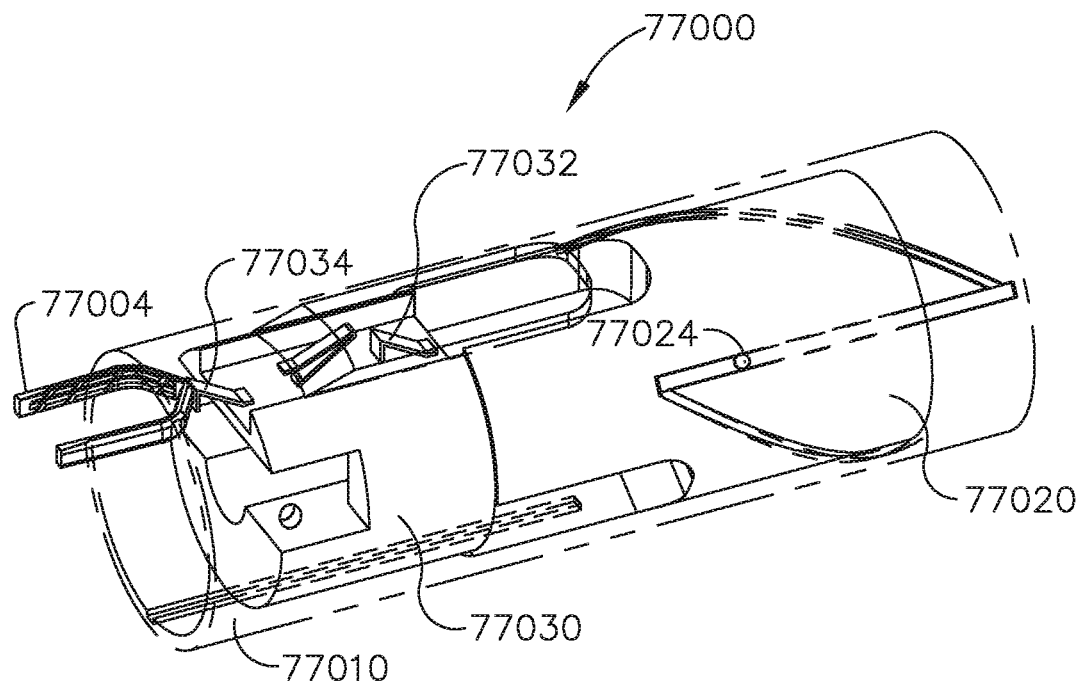
Figure 136:
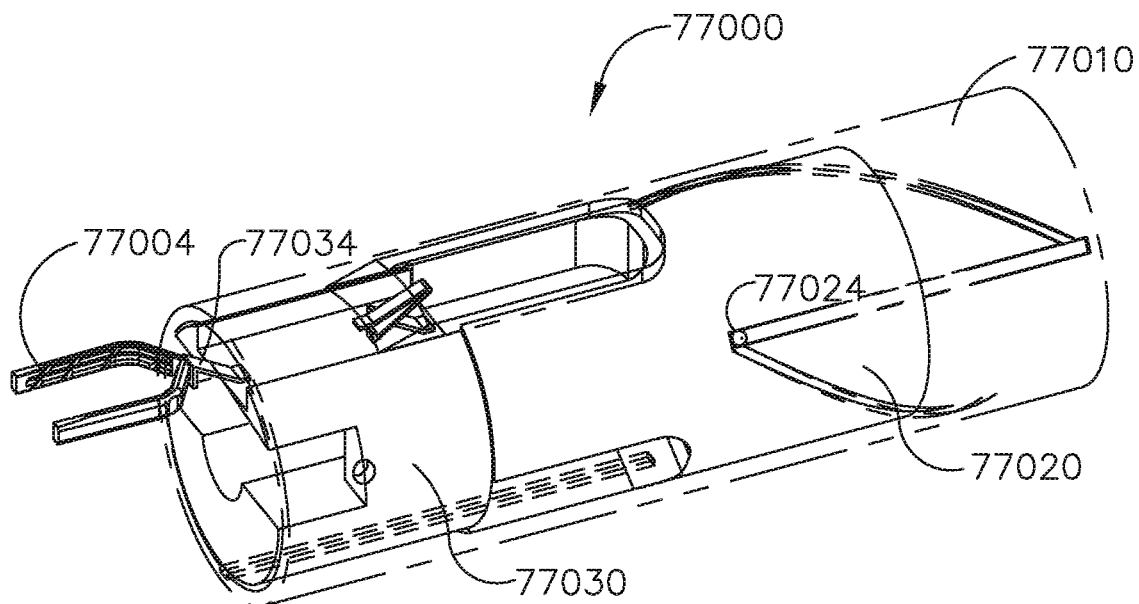
Figure 137:
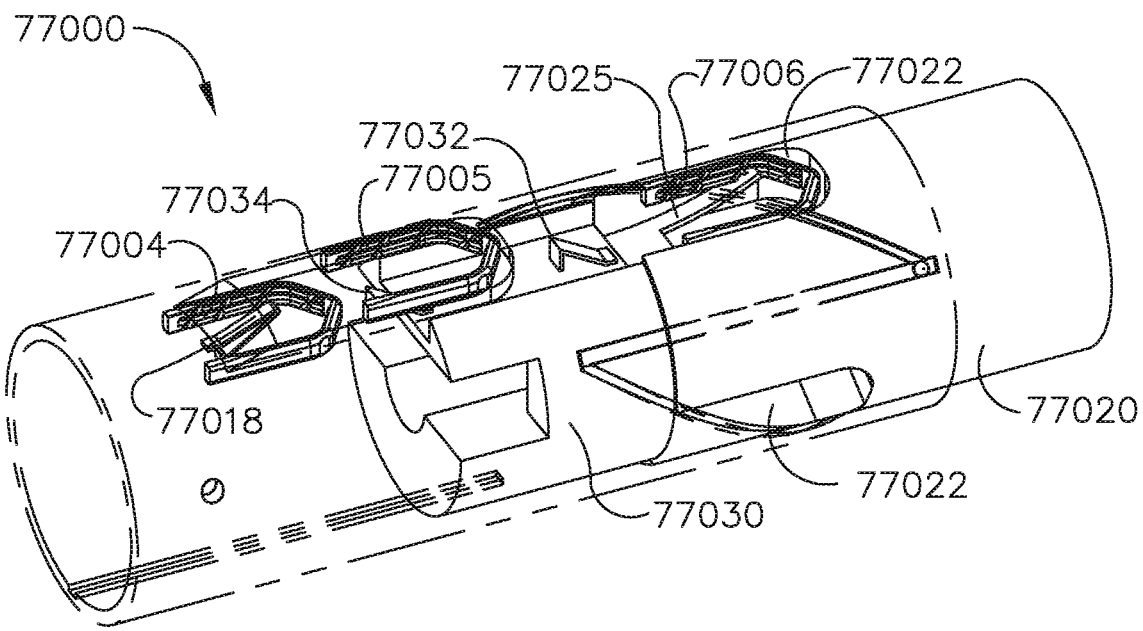
Figure 138:
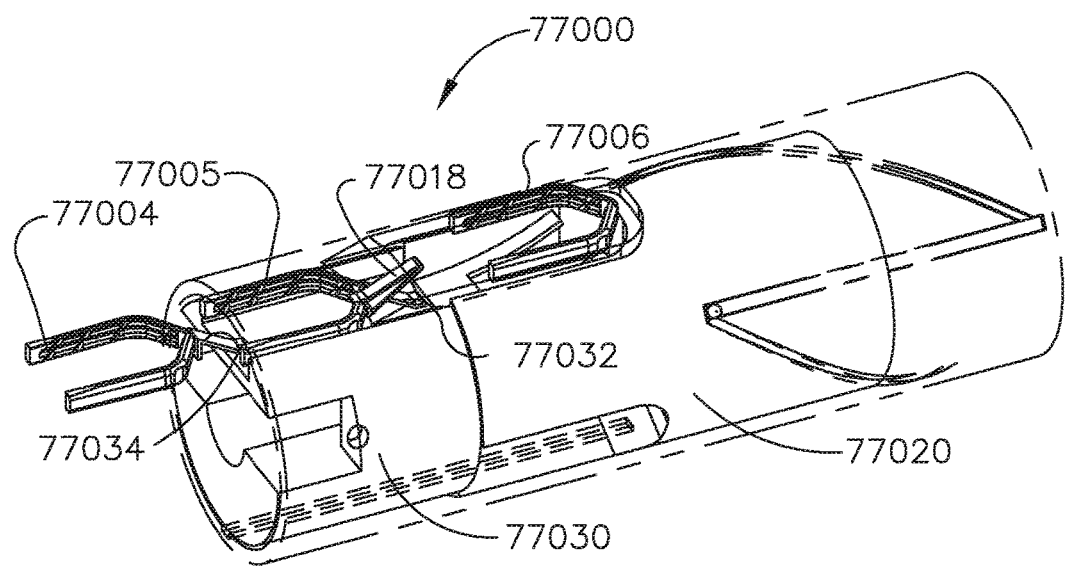
Figure 139:
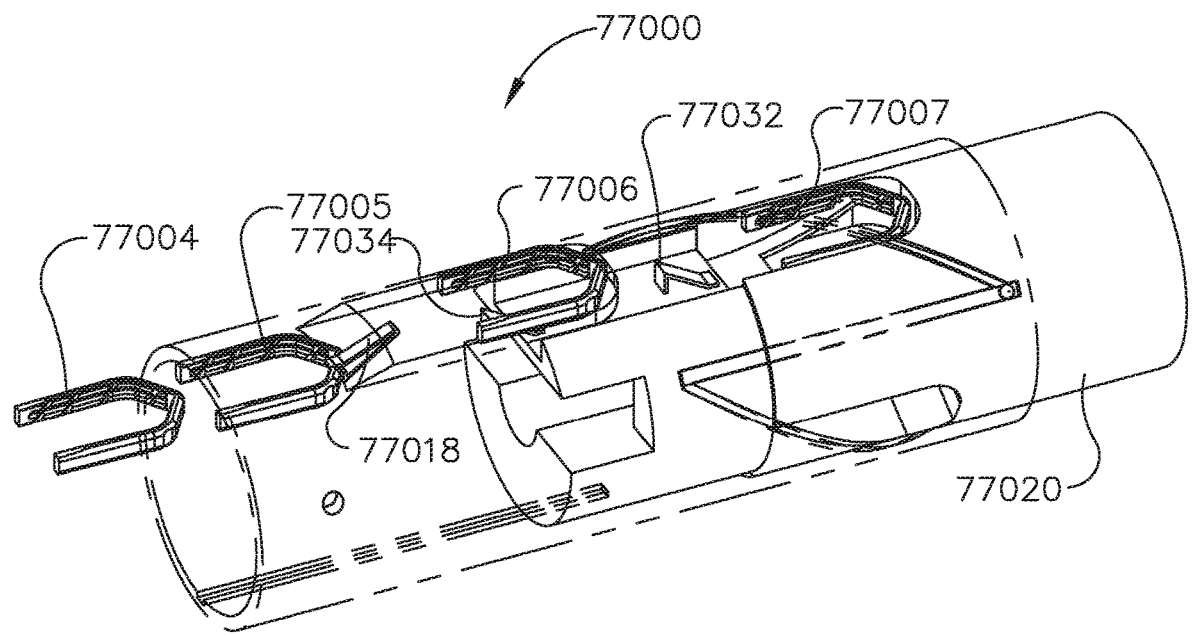
Figure 140:
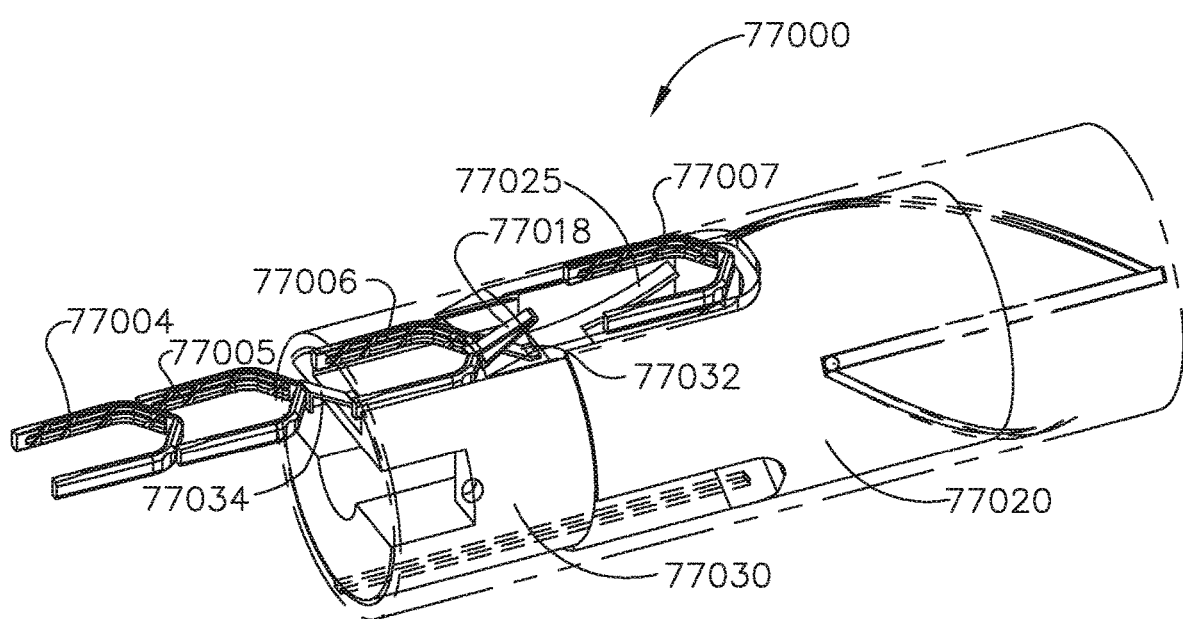
Figure 141A:
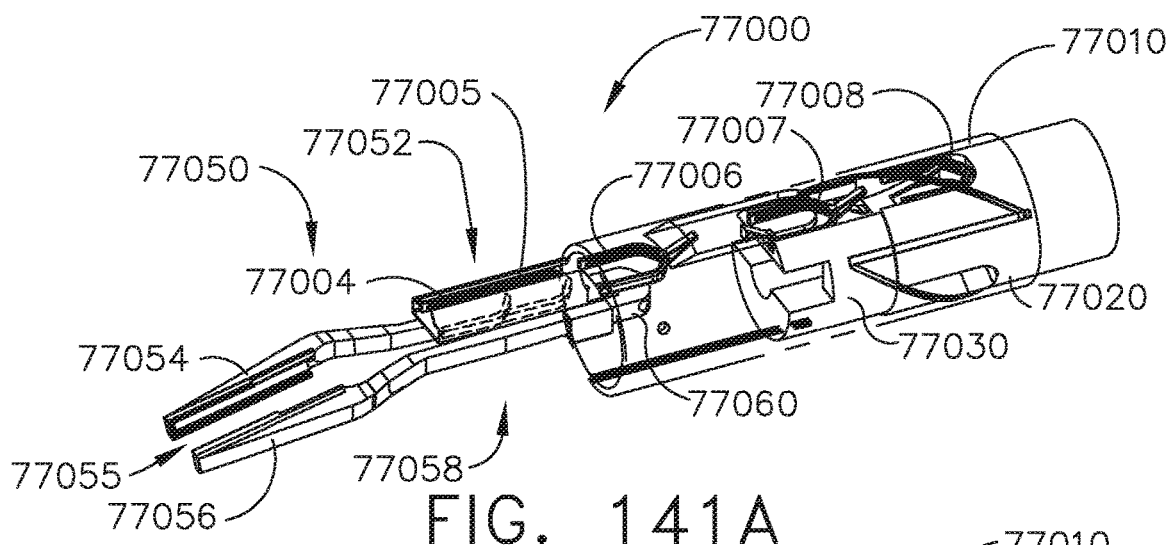

FIG. 97A is a cross-sectional view of a clip magazine including a plurality of clips and a lockout, illustrated with the clip magazine in a firing position;

FIG. 97B is a cross-sectional side elevation view of the clip magazine of FIG. 97A;

FIG. 98 is a cross-sectional view of the clip magazine of FIG. 97A which has been rotated counter clock-wise approximately 30 degrees from the firing position of FIG. 97A toward a clip loading position;

FIG. 99 is a cross-sectional view of the clip magazine of FIG. 97A which has been rotated counter clock-wise approximately 60 degrees from the firing position of FIG. 97A toward the clip loading position;

FIG. 100 is a cross-sectional view of the clip magazine of FIG. 97A in the clip loading position, wherein a clip is positioned in a loading slot;

FIG. 101 is a cross-section view of the clip magazine of FIG. 97A in the clip loading position, wherein a lockout clip is positioned in the loading slot;

FIG. 102 is a perspective view of a clip applier comprising a clip magazine and a rotary input, illustrated with the clip magazine is in a proximal position;

FIG. 103 is a perspective view of the clip applier of FIG. 102, illustrated with the clip magazine is in a distal position;

FIG. 104 is a perspective view of the clip applier of FIG. 102, illustrated with the clip magazine is in the distal position and has rotated approximately 120 degrees;

FIG. 105 is a perspective view of the clip applier of FIG. 102 including a feeder shoe, a crimping drive, and a shaft comprising a loading slot, wherein the loading slot has a clip from the clip magazine stored therein;

FIG. 106 is a perspective exploded view of the clip applier of FIG. 105;

FIG. 107 is a cross-sectional view of a rotary input and a clip magazine for use with a clip applier, wherein the rotary input is a multi-directional rotary input;

FIG. 108 is a cross-sectional side view of a rotary input and a clip magazine for use with a clip applier, wherein the rotary input is a multi-directional rotary input;

FIG. 109 is a cross-sectional front view of the rotary input and clip magazine of FIG. 108;

FIG. 110 is a cross-sectional view of a rotary input and a clip magazine for use with a clip applier, wherein the rotary input is a single-direction rotary input;

FIG. 111 is a cross-sectional view of a rotary input, a clip magazine, and a loading slot for use with a clip applier, wherein the rotary input is a single-direction rotary input;

FIG. 112 is a perspective view of a rotary input and a clip magazine for use with a clip applier, wherein the clip magazine includes a clam-shell construction;

FIG. 113 is a cross-sectional front view of the clip magazine of FIG. 112;

FIG. 114 is an exploded perspective view of a clip applier comprising a clip magazine and a magazine driver, wherein the clip magazine and magazine driver comprise camming surfaces;

FIG. 115A is a side elevational view of the clip applier of FIG. 114, illustrated with the clip magazine in a proximal position;

FIG. 115B is a side elevational view of the rotatable clip magazine of FIG. 114 wherein the cam advancer has advanced the rotatable clip magazine from the proximal position to a distal position;

FIG. 115C is a side elevational view of the rotatable clip magazine of FIG. 114 in a ready to clock position relative to the cam advancer of FIG. 114;

FIG. 116 is a graphical depiction of the absolute rotary position of the magazine driver of the clip applier of FIG. 114 during an operation sequence;

FIG. 117 is a cross-sectional view of a clip applier comprising an end effector, a clip magazine, a clip carriage, and a clip former configured to form a clip from the clip magazine;

FIG. 118A is a cross-sectional view of the clip applier of FIG. 117 depicting the clip carriage holding a clip with portions of the clip applier removed for the purpose of illustration;

FIG. 118B is a cross-sectional view of the clip applier of FIG. 117 depicting the clip carriage advancing a clip into a staging position with portions of the clip applier removed for the purpose of illustration;

FIG. 118C is a cross-sectional view of the clip applier of FIG. 117 depicting the clip carriage retracted and a clip in the staging position with portions of the clip applier removed for the purpose of illustration;

FIG. 118D is a cross-sectional view of the clip applier of FIG. 117 depicting the clip carriage advancing a clip in the staging position into the end effector with portions of the clip applier removed for the purpose of illustration;

FIG. 119A is a cross-sectional view of the clip applier of FIG. 117 depicting the clip carriage retracted a clip to a forming position, wherein the an anvil is positioned above the clip;

FIG. 119B is a cross-sectional view of the clip applier of FIG. 117 depicting the clip carriage retracted a clip to the forming position, wherein the an anvil is positioned in between a first leg and a second leg of the clip;

FIG. 120A is a plan view of the clip carriage and anvil of the clip applier of FIG. 117, wherein a clip has been positioned around the anvil, and wherein the clip is in an unformed state;

FIG. 120B is a plan view of the clip carriage and anvil of the clip applier of FIG. 117, wherein a clip has been positioned around the anvil, and wherein the clip is in a formed state;

FIG. 121 is a cross-sectional view of the clip applier of FIG. 117;

FIG. 122 is a perspective view of a clip applier comprising an end effector, a clip magazine, and co-axial rotary inputs comprised of dual-woven cables;

FIG. 123 is a perspective view of a clip applier comprising an end effector, a clip magazine, and co-axial rotary inputs comprises of wire tubing;

FIG. 124 is a perspective view of rotary input for use with a clip applier, wherein the rotary input comprises layers of coiled springs wound in opposite directions;

FIG. 125 is a perspective view of a clip applier comprising a shaft, a clip magazine, and a clip advancer configured to advance clips from the clip magazine into a loading slot, then into a staging position, and then into a clip track of the clip applier, wherein a first clip is shown in the clip magazine;

FIG. 126 is a perspective view of the clip applier of FIG. 125 depicting the first clip being advanced into the loading slot of the clip applier as the clip magazine moves distally;

FIG. 127 is a perspective view of the clip applier of FIG. 125 depicting the first clip being stripped from the clip magazine by the loading slot of the clip applier as the clip magazine is rotated and retracted;

FIG. 128 is a perspective view of the clip applier of FIG. 125 depicting the first clip in the loading slot as the clip magazine is further rotated and retracted;

FIG. 129 is a perspective view of the clip applier of FIG. 125 depicting the first clip in the loading slot as the clip magazine is fully retracted placing the first clip in a position to be advanced through the loading slot;

FIG. 130 is a perspective view of the clip applier of FIG. 125 depicting the first clip in the loading slot as the clip magazine is advanced to engage the clip advancer with the backside of the first clip;

FIG. 131 is a perspective view of the clip applier of FIG. 125 depicting the first clip after it has been advanced through the loading slot by the clip advancer;

FIG. 132 is a perspective view of the clip applier of FIG. 125 depicting the first clip after it has been advanced out of the loading slot into the staging position by the clip advancer;

FIG. 133 is a perspective view of the clip applier of FIG. 125 depicting the first clip positioned in the staging position and the clip advancer and clip magazine retracted;

FIG. 134 is a perspective view of the clip applier of FIG. 125 depicting the clip magazine and the clip advancer advanced and abutted against the first clip in the staging position;

FIG. 135 is a perspective view of the clip applier of FIG. 125 depicting the first clip after it has been advanced from the staging position into the clip track by the clip advancer;

FIG. 136 is a perspective view of the clip applier of FIG. 125 depicting the first clip after it has been completely advanced into the clip track by the clip advancer;

FIG. 137 is a perspective view of the clip applier of FIG. 125 depicting the first clip after it has been advanced through the loading slot, with a second clip positioned in the loading slot and a third clip positioned in the clip magazine;

FIG. 138 is a perspective view of the clip applier of FIG. 125 depicting the first clip in the clip track, the second clip in the staging position, and the third clip in the loading slot;

FIG. 139 is a perspective view of the clip applier of FIG. 125 depicting the first clip in the clip track, the second clip in the staging position, the third clip in the loading slot, and a fourth clip in the clip magazine;

FIG. 140 is a perspective view of the clip applier of FIG. 125 depicting the first clip in the clip track, the second clip in the clip track, the third clip in the staging position, and a fourth clip in the loading slot;

FIG. 141A is a perspective view of the clip applier of FIG. 125 depicting an end effector extending from the shaft of the clip applier, wherein the first clip is in the clip track, the second clip is in the clip track, the third clip is in the staging position, a fourth clip is in the loading slot, and a fifth clip is in the clip magazine.

Figure 141B:
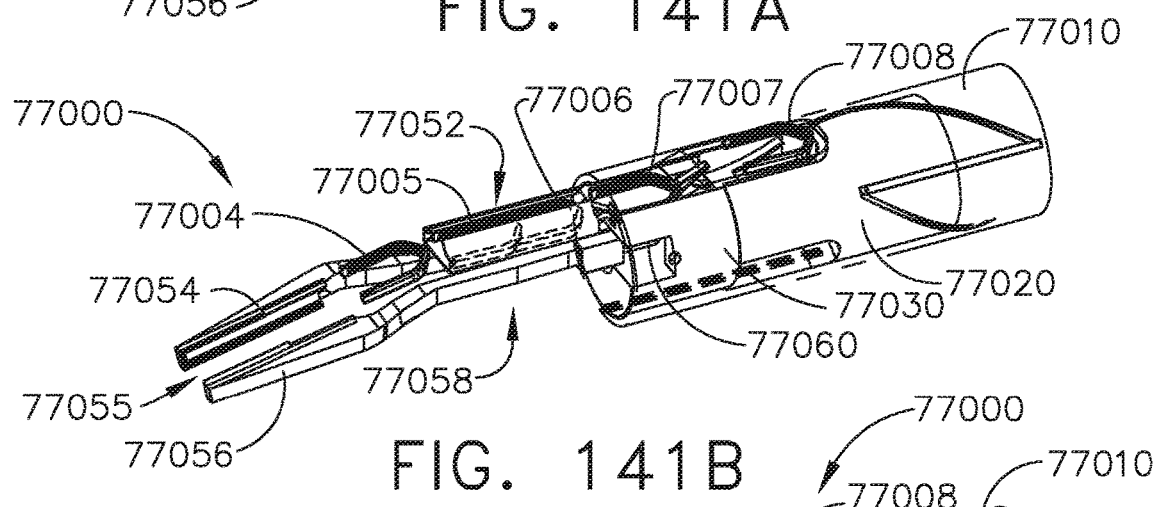

FIG. 141B is a perspective view of the clip applier of FIG. 125, wherein the first, second, third, fourth, and fifth clips have been advanced toward the end effector.

Figure 141C:
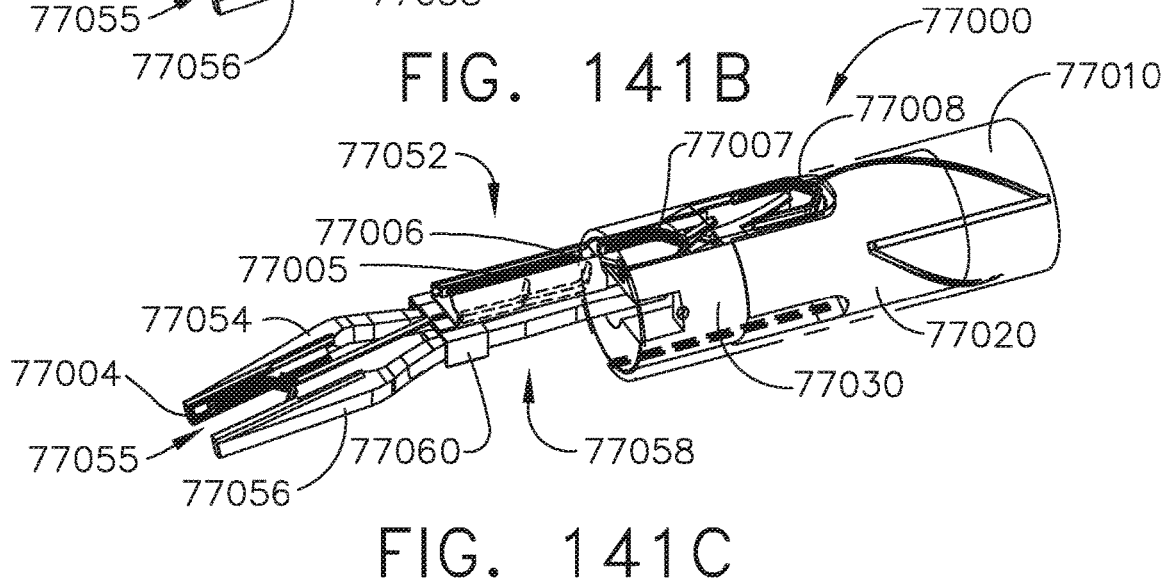

FIG. 141C is a perspective view of the clip applier of FIG. 125, wherein the first clip has been advanced into the end effector.

Figure 142:
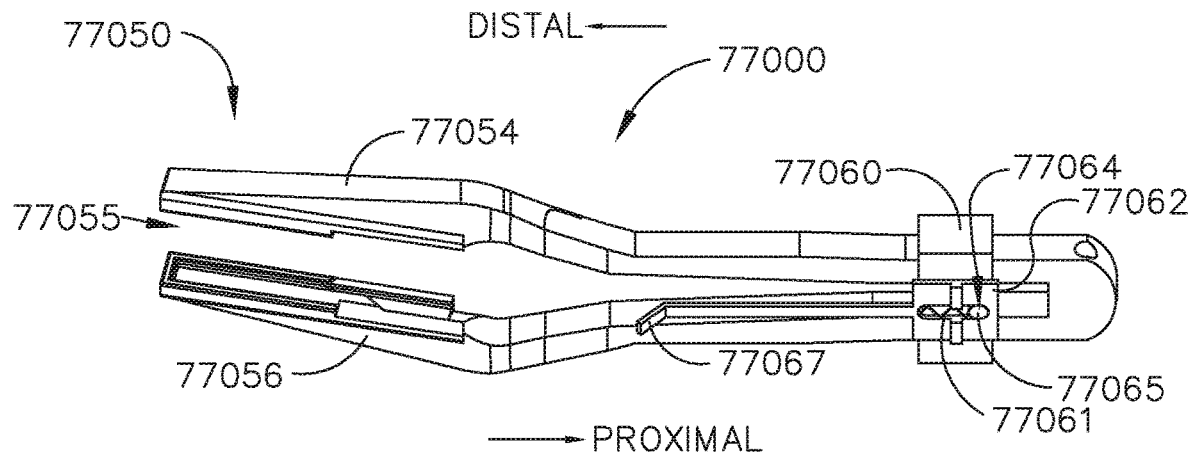

FIG. 142 is a perspective view of the clip applier of FIG. 125 depicting a jaw cam and feeder shoe mounted to the end effector.

Figure 143:
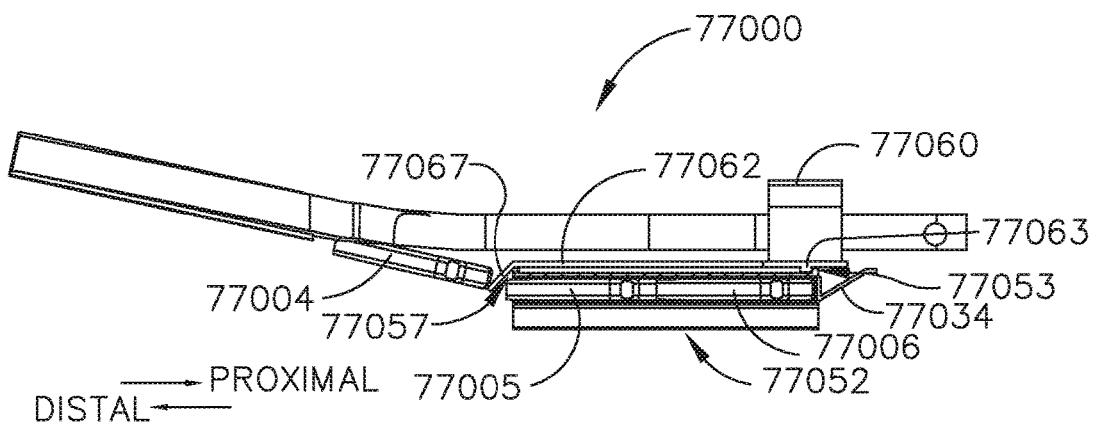

FIG. 143 is a perspective view of the clip applier of FIG. 125 depicting the feeder shoe engaged with the backside of the first clip and the jaw cam in a proximal position.

Figure 144A:
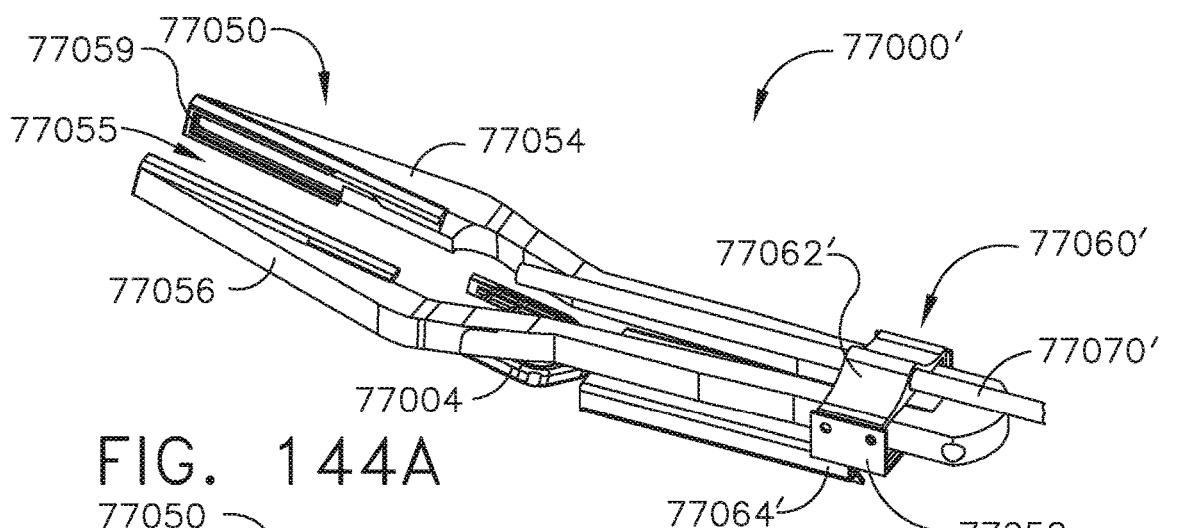
Figure 144B:
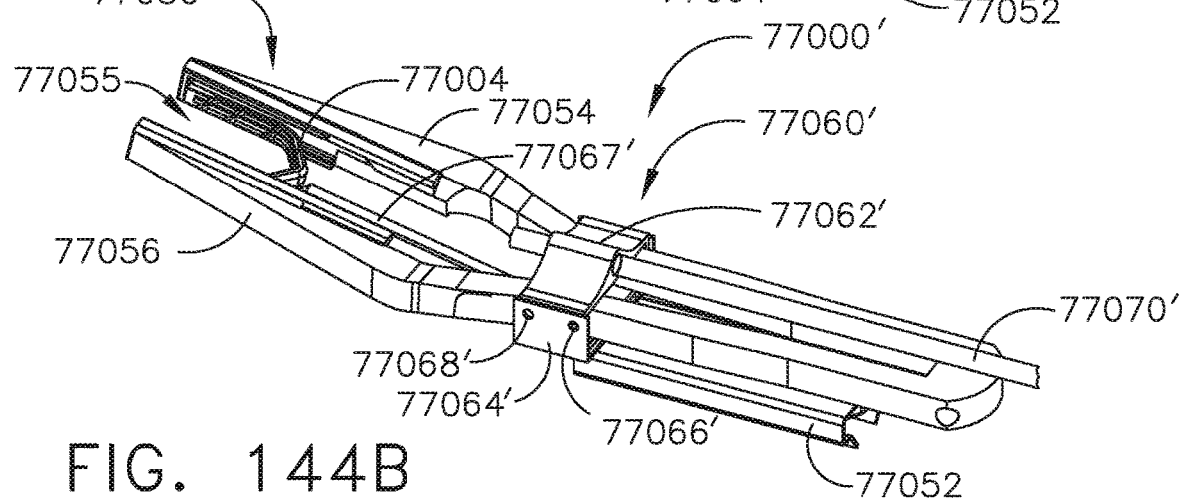

FIG. 144A is a perspective view of an alternative embodiment of a jaw cam for use with the end effector of the clip applier of FIG. 125, illustrated with the jaw cam in a proximal position;

FIG. 144B is a perspective view of the alternative embodiment of FIG. 144A, illustrated with the jaw cam in a distal position.

Figure 144C:
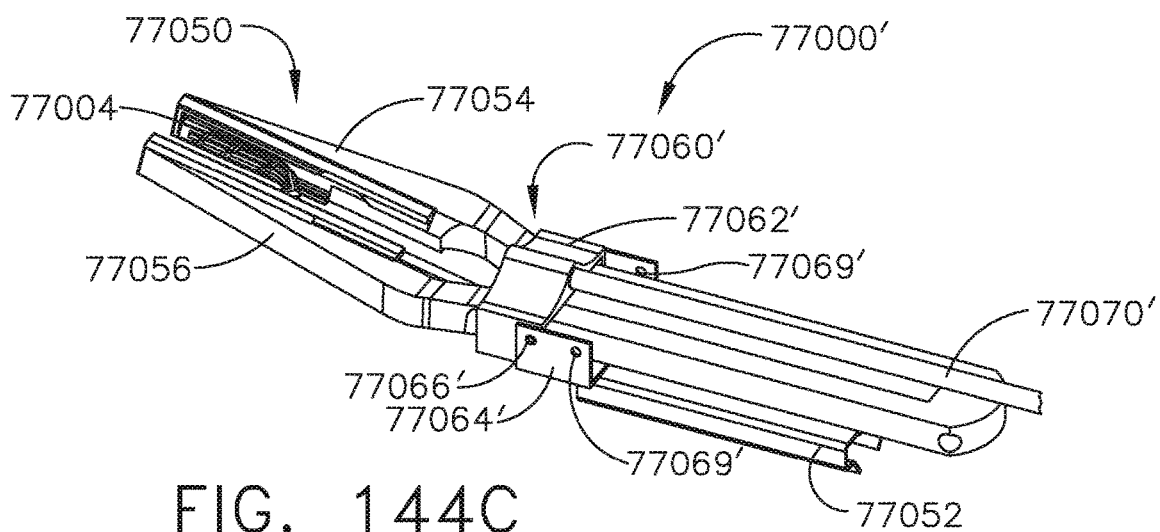
Figure 145:
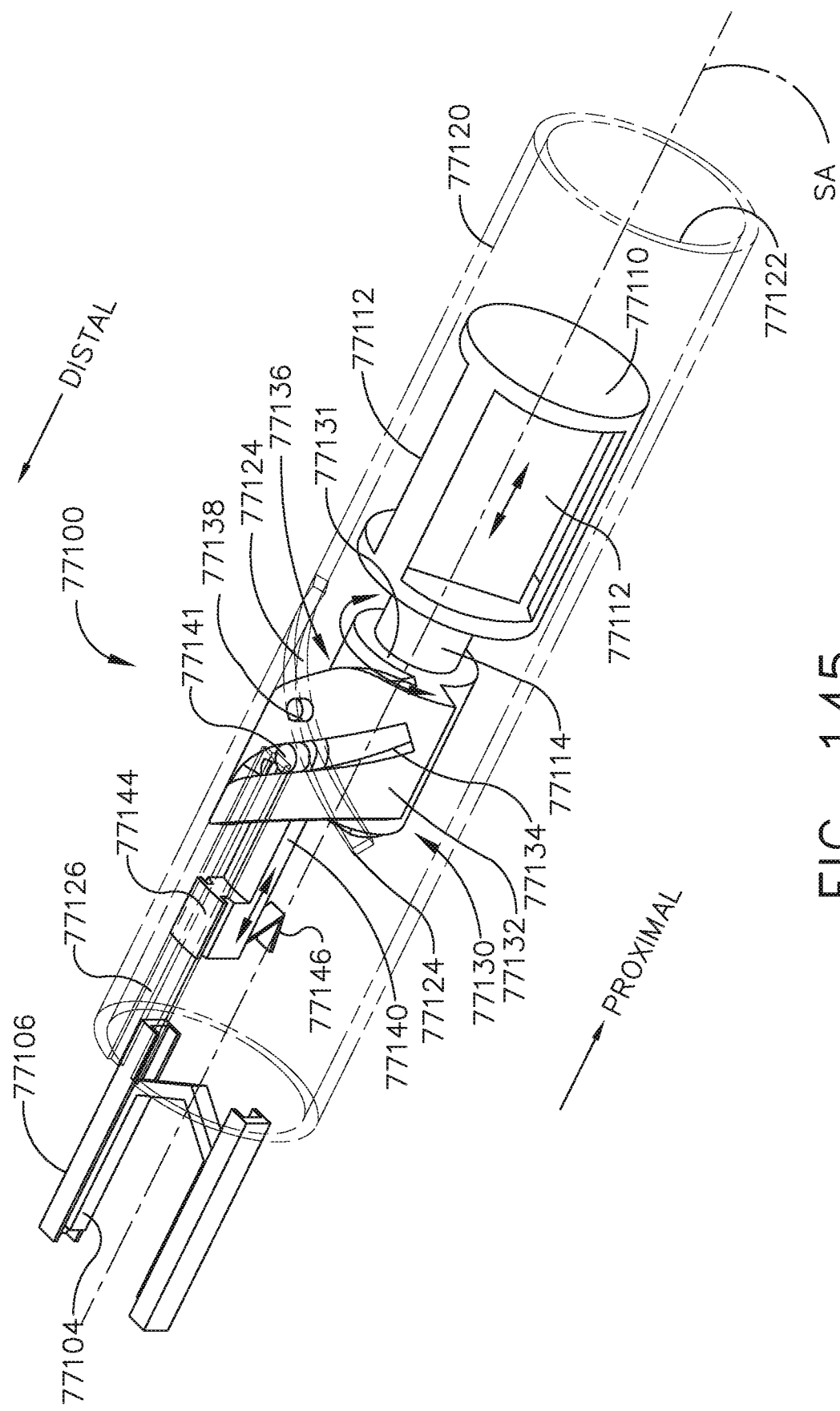
Figure 146:
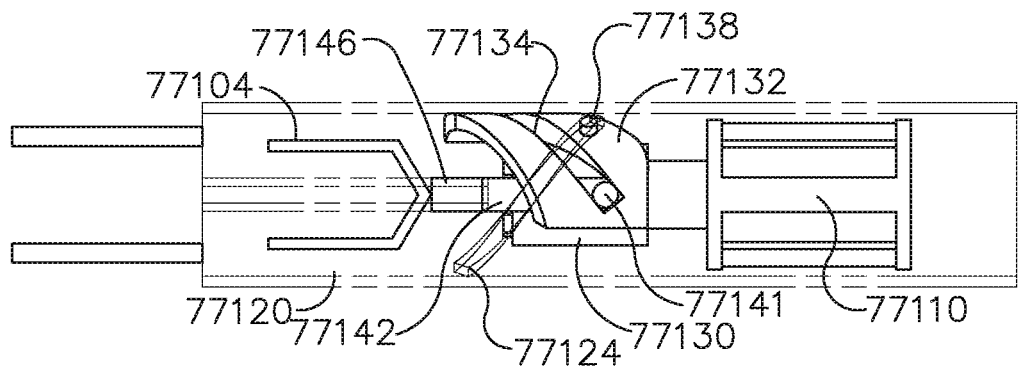
Figure 147:
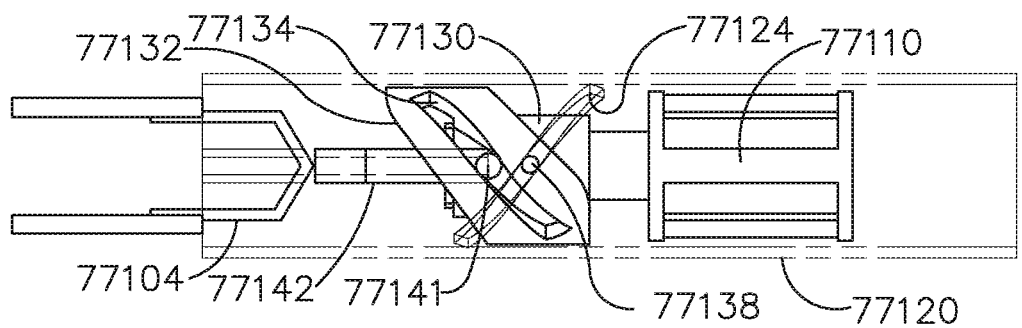
Figure 148:
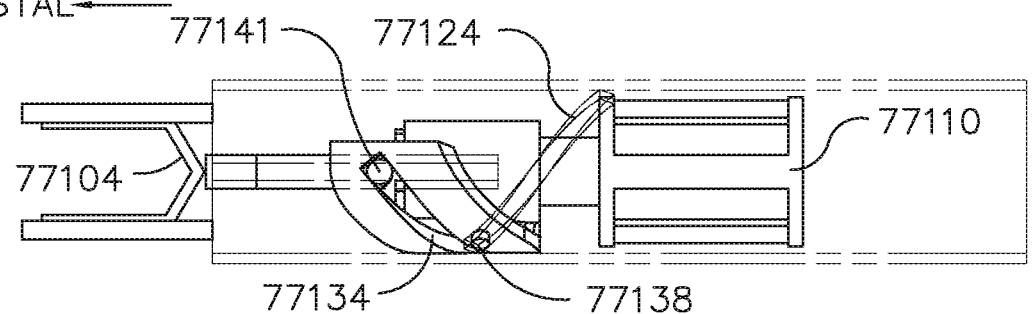
Figure 149:
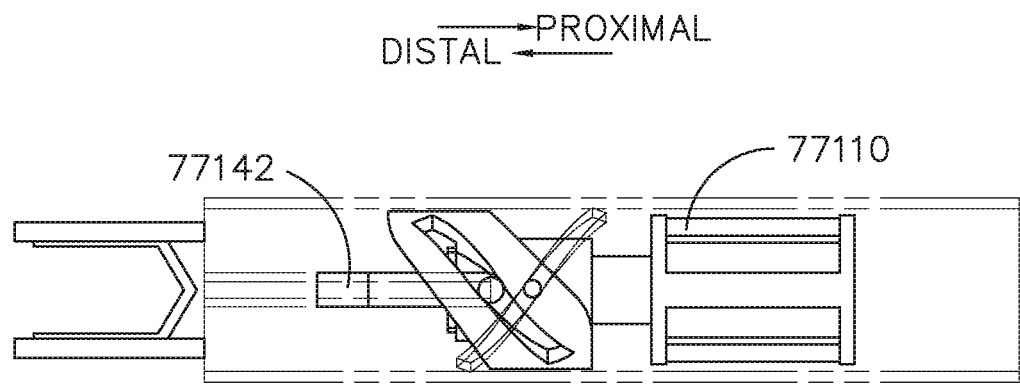
Figure 150:
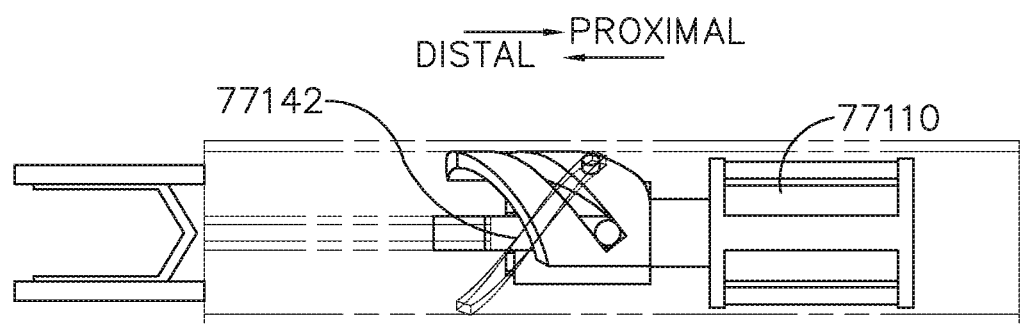
Figure 151:
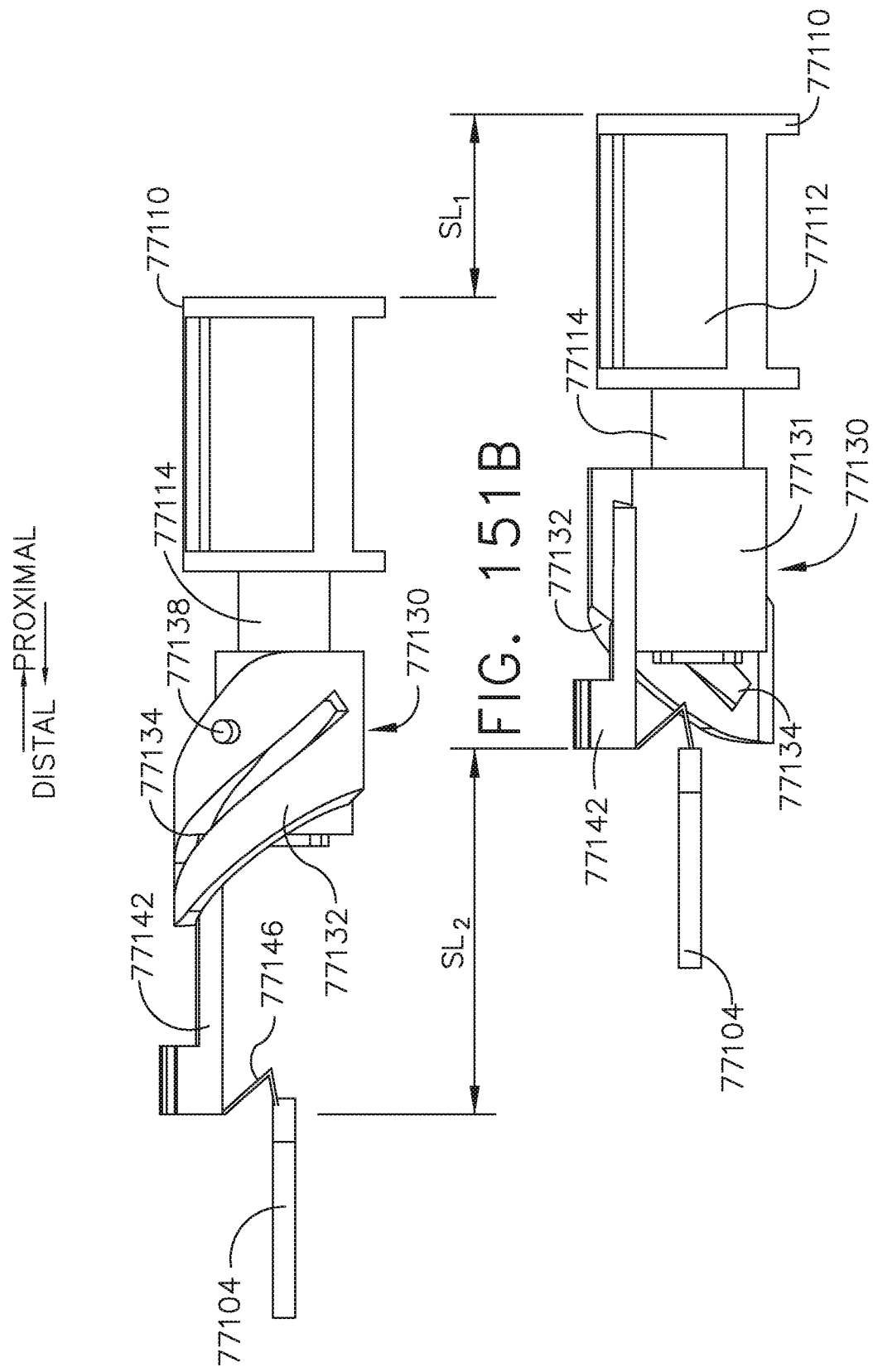
Figure 152:
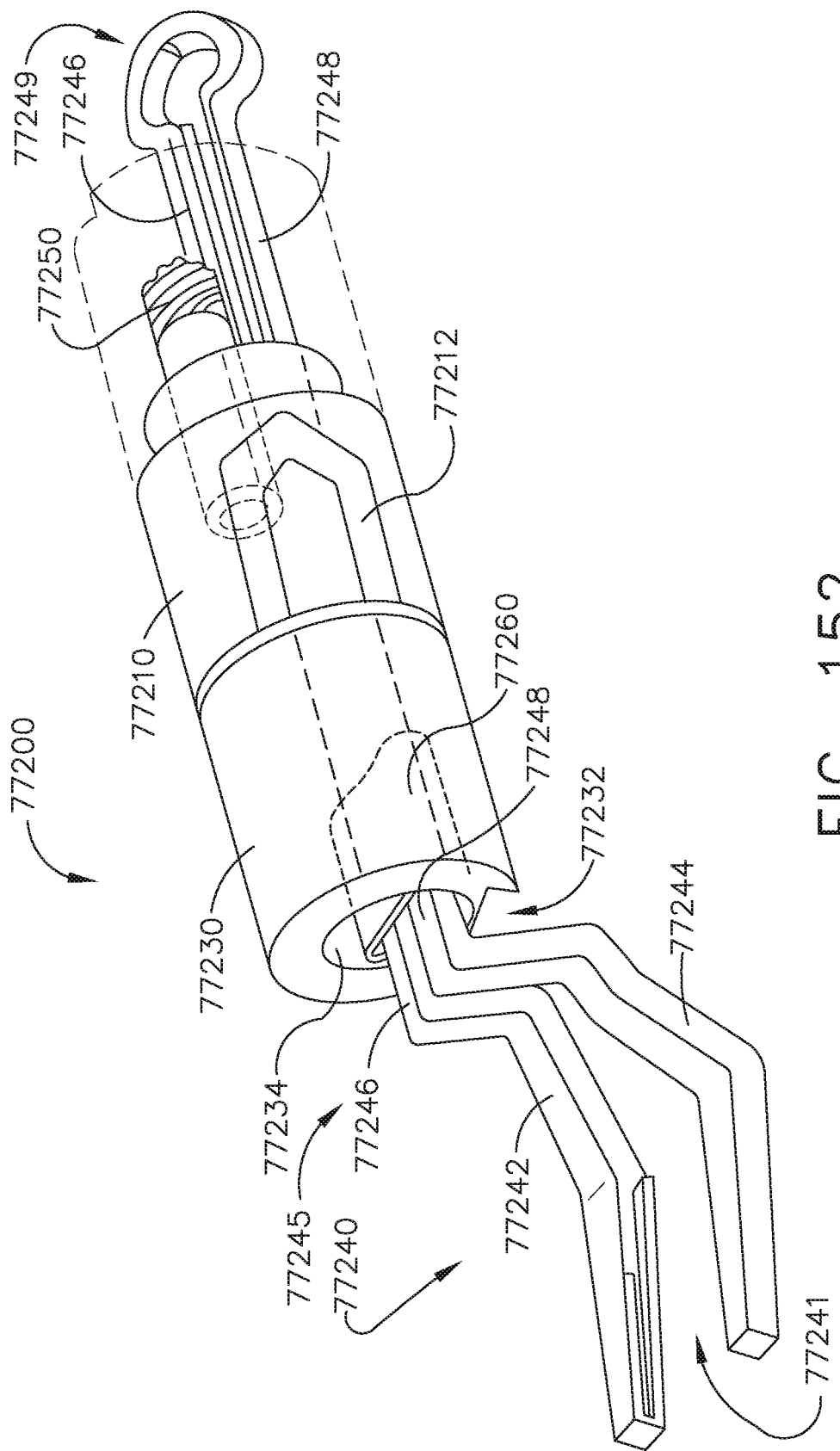
Figure 153:
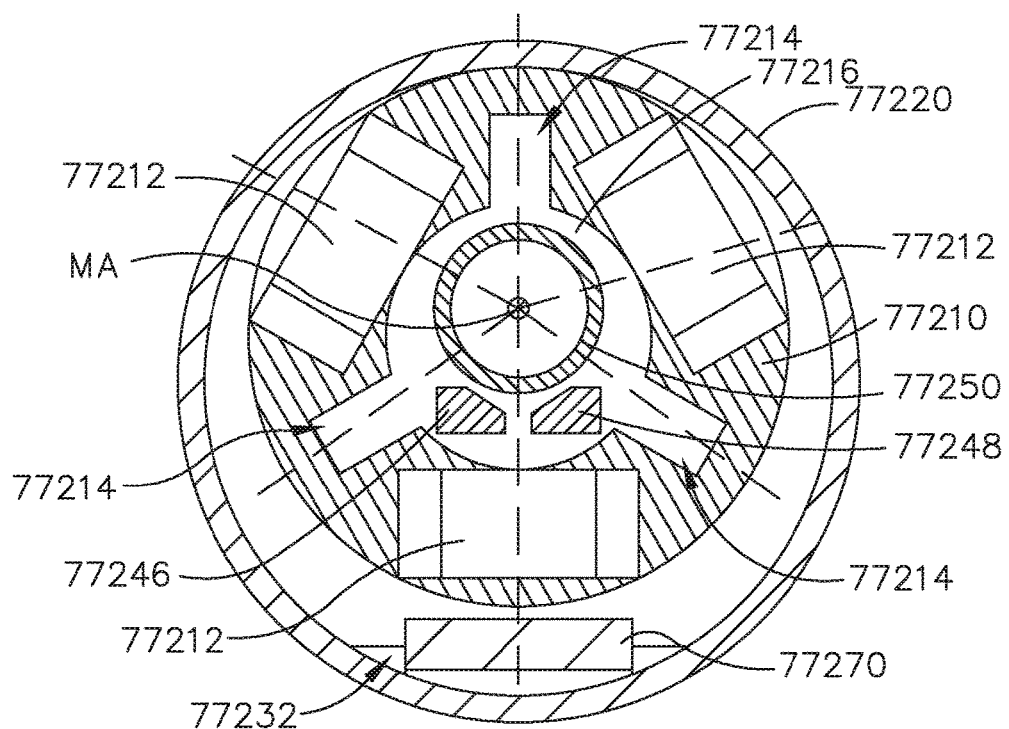
Figures 154, 155:
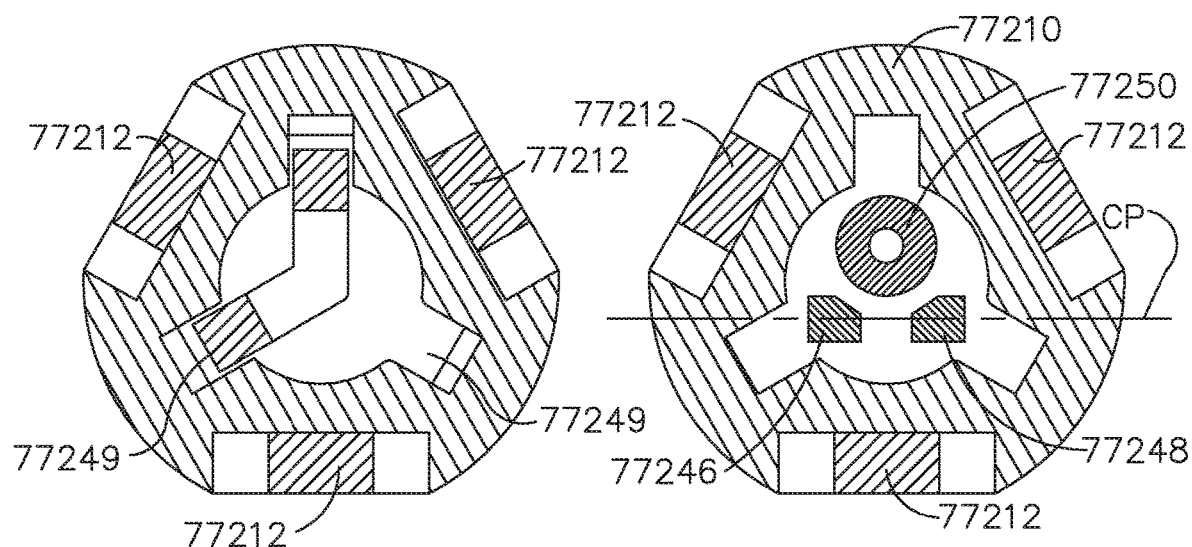
Figure 156:
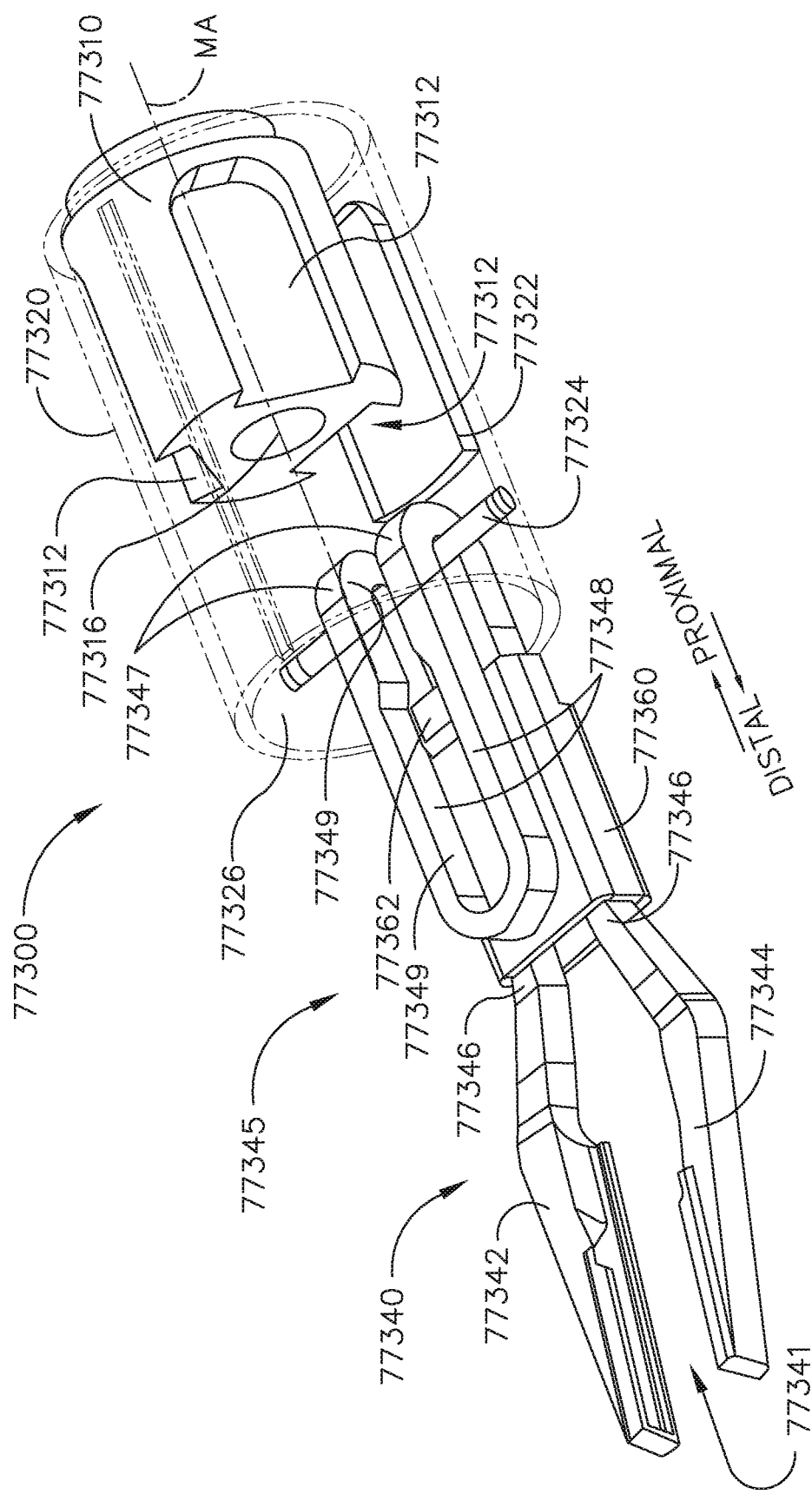
Figure 157:
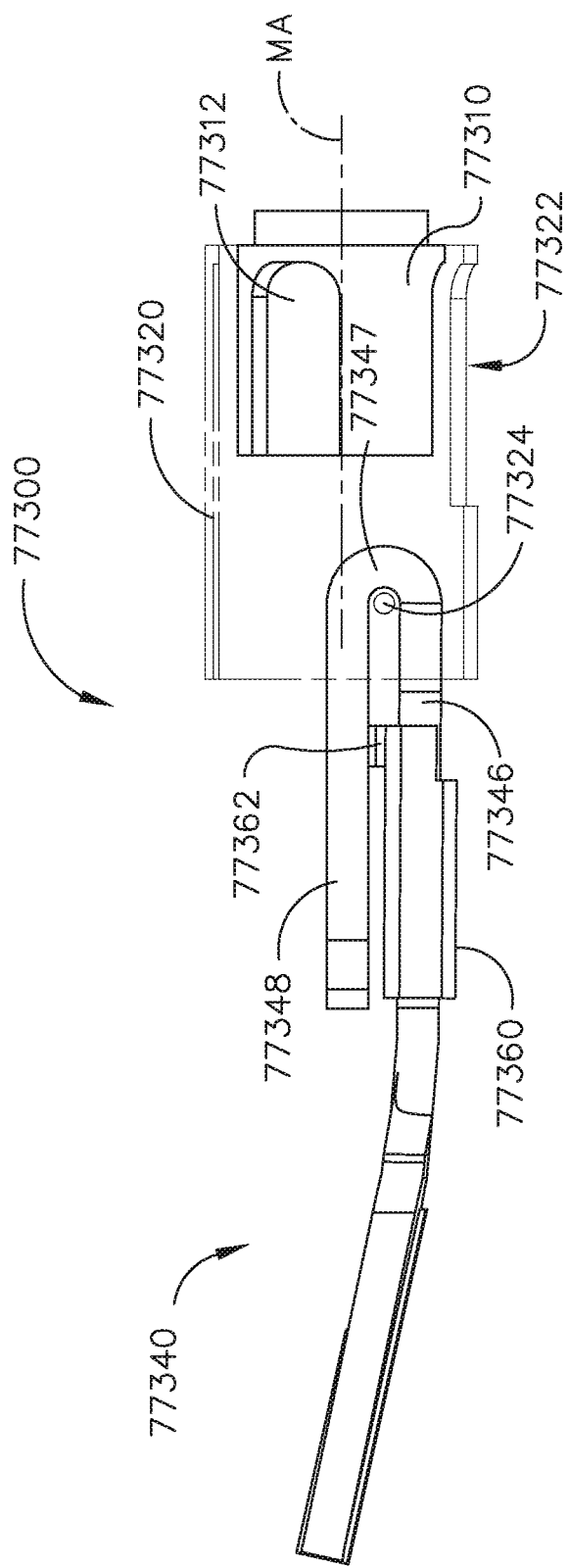
Figure 158:
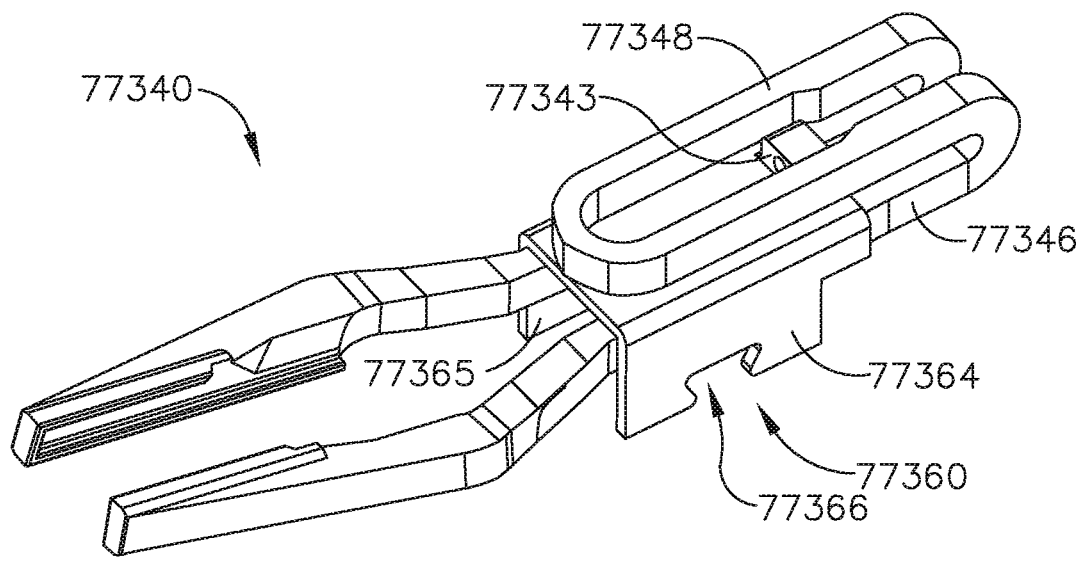
Figure 159:
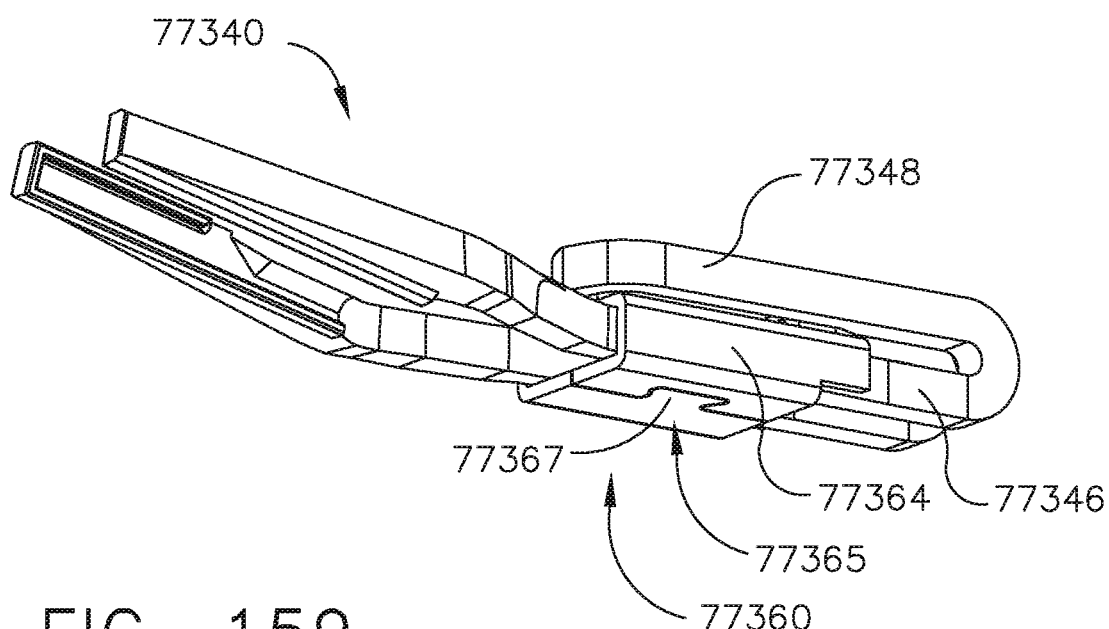
Figure 160:
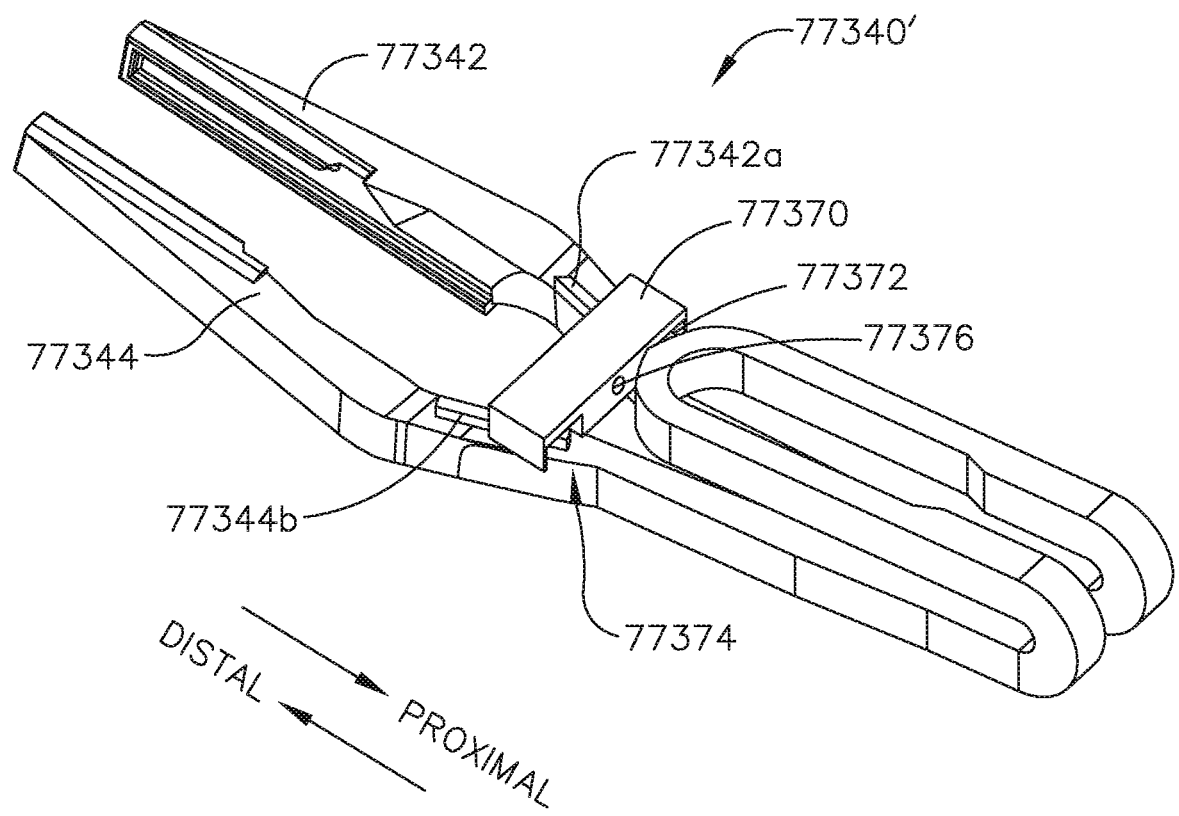

FIG. 144C is a perspective view of the alternative embodiment of FIG. 144B, illustrated with the jaw cam in a closing position;

FIG. 145 is a perspective view of a clip applier comprising a translatable clip magazine and a translatable and rotatable clip advancer configured to advance a clip;

FIG. 146 is a plan view of the clip applier of FIG. 145, illustrating the clip magazine and clip advancer in proximal positions;

FIG. 147 is a plan view of the clip applier of FIG. 145, illustrating the clip magazine and clip advancer moved distally from their proximal positions to advance the clip;

FIG. 148 is a plan view of the clip applier of FIG. 145, illustrating the clip magazine and clip advancer moved to their distal-most positions to completely advance the clip;

FIG. 149 is a plan view of the clip applier of FIG. 145, illustrating the clip magazine and clip advancer partially retracted from their distal-most positions toward their proximal position;

FIG. 150 is a plan view of the clip applier of FIG. 145, illustrating the clip magazine and clip advancer in their proximal positions;

FIG. 151A is a side view of the clip applier of FIG. 145, illustrating the clip magazine and clip advancer in their proximal positions with the clip ready to be advanced;

FIG. 151B is a side view of the clip applier of FIG. 145, illustrating the clip magazine and clip advancer in their distal-most positions after advancing the clip;

FIG. 152 is a perspective view of a clip applier comprising an end effector spanning two different planes, a clip magazine, and a rotary input extending through the clip magazine;

FIG. 153 is a cross-sectional view of the clip applier of FIG. 152 depicting a portion of the end effector and the rotary input extending through the clip magazine;

FIG. 154 is a cross-sectional view of the clip applier of FIG. 152 depicting an anchor portion of the end effector extending through the clip magazine;

FIG. 155 is a cross-sectional view of the clip applier of FIG. 152 depicting a portion of the end effector and the rotary input extending through the clip magazine including clip holders;

FIG. 156 is a perspective view of a clip applier comprising an end effector extending from a shaft, and a clip magazine, wherein the end effector spans two different planes;

FIG. 157 is a side view of the clip applier of FIG. 156;

FIG. 158 is a perspective view of the clip applier of FIG. 156 depicting a collar of the clip applier being installed onto the end effector;

FIG. 159 is a perspective view of the clip applier of FIG. 156 depicting the collar of the clip applier installed onto the end effector;

FIG. 160 is a perspective view of an end effector of an alternative embodiment.

Figure 161:
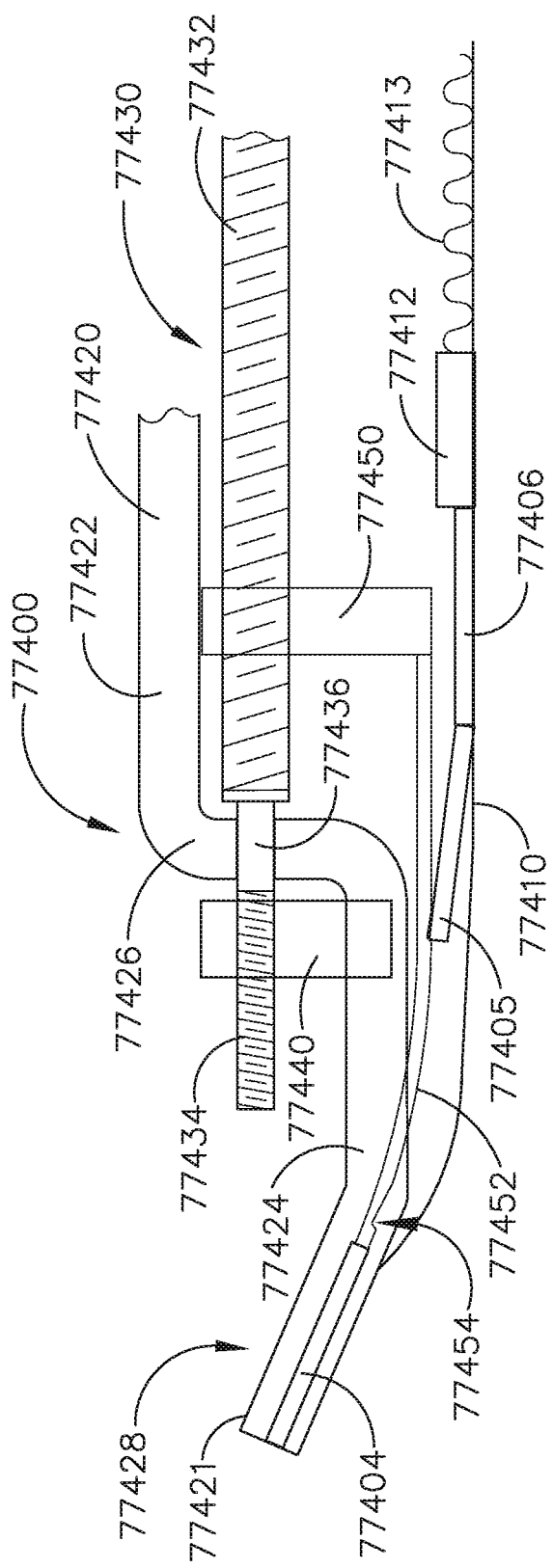
Figure 162:
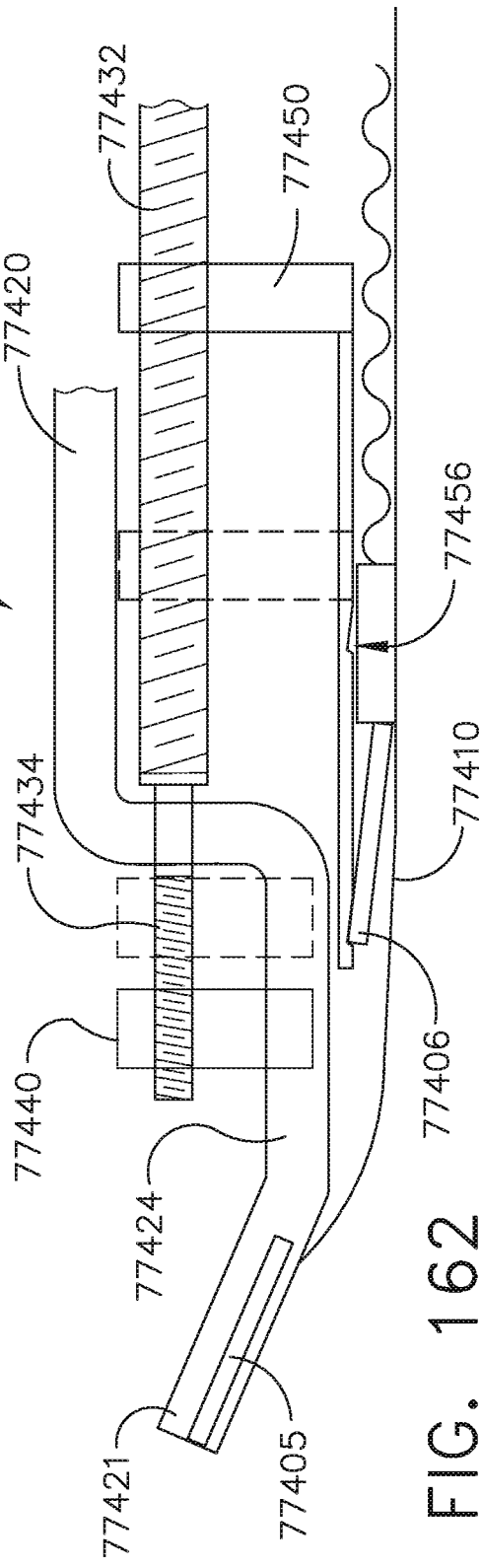
Figure 167A:
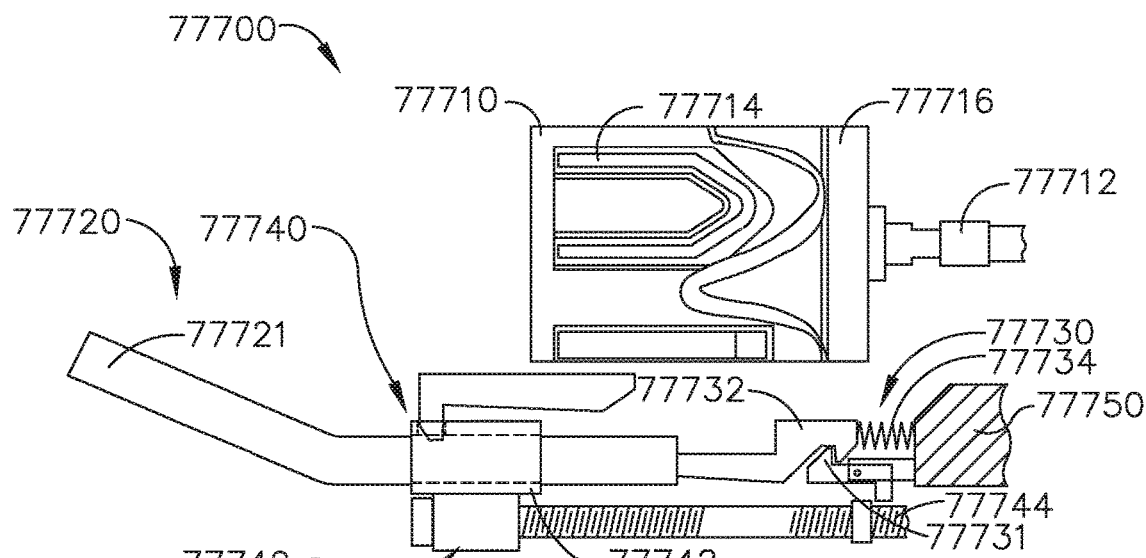
Figure 167B:
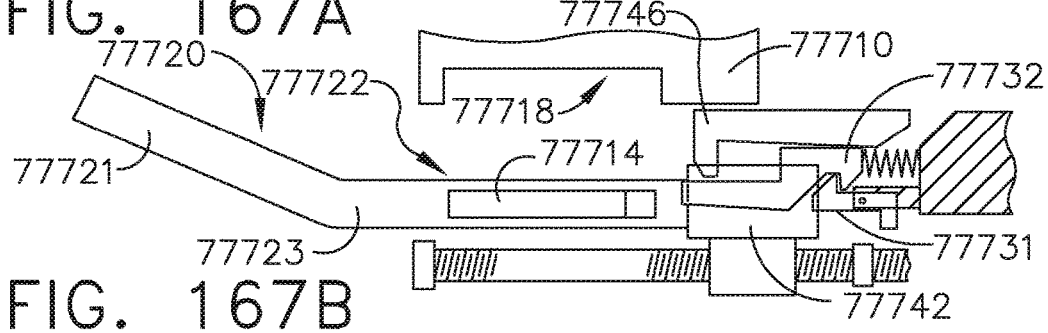
Figure 167C:
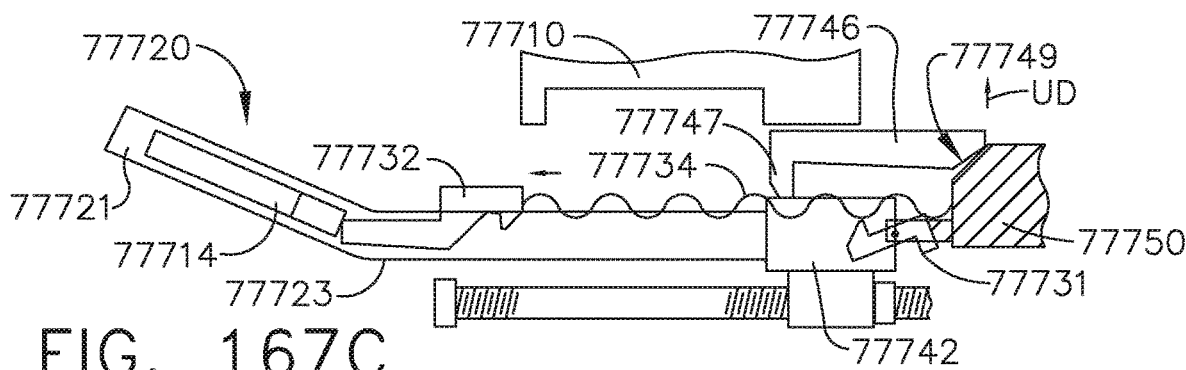
Figure 167D:
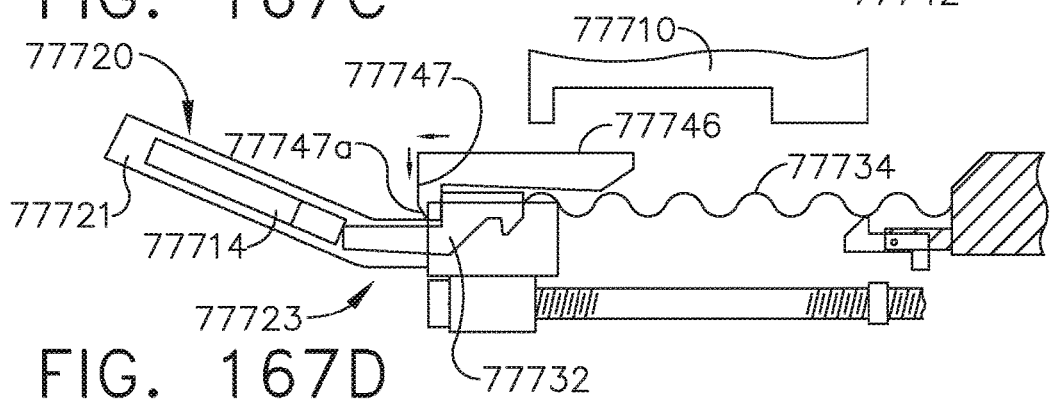
Figure 168:
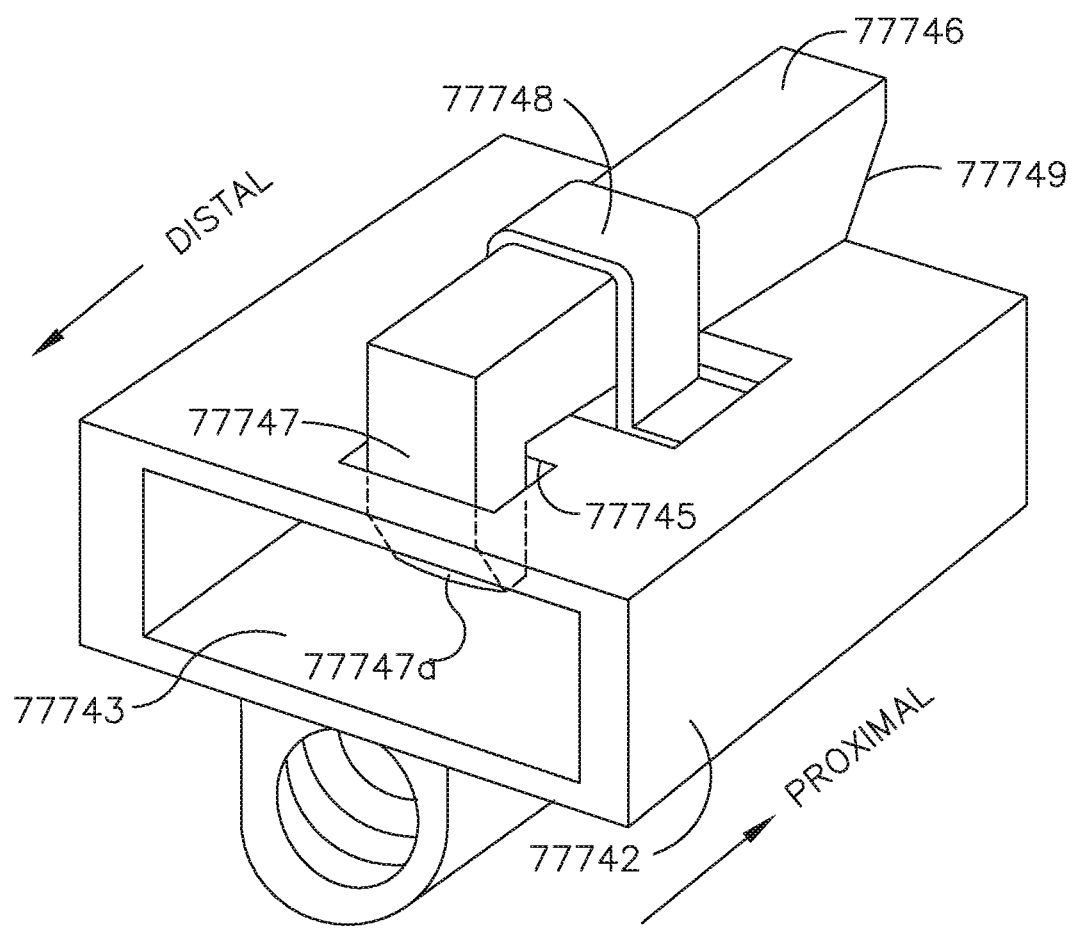
Figure 169:
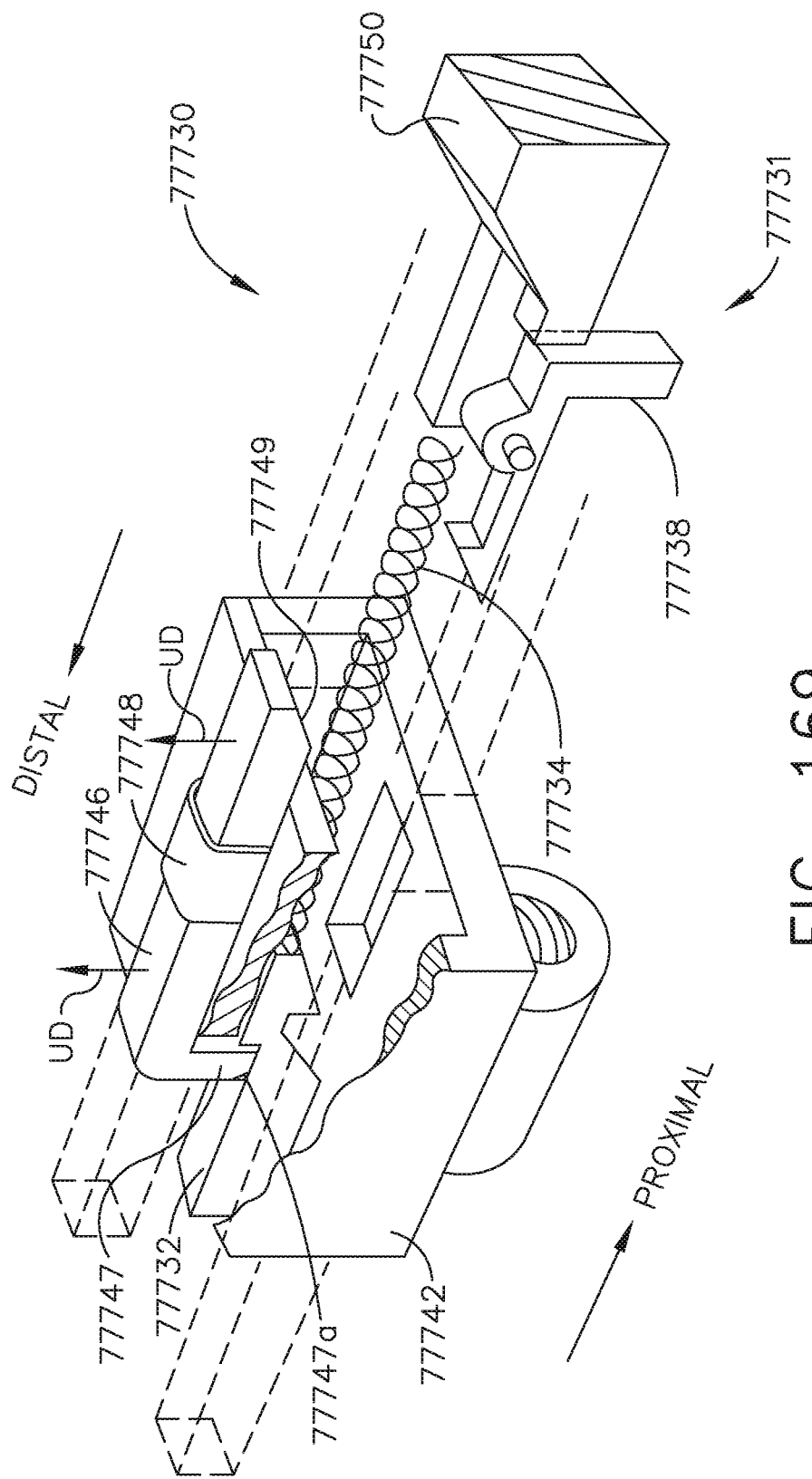
Figure 170:
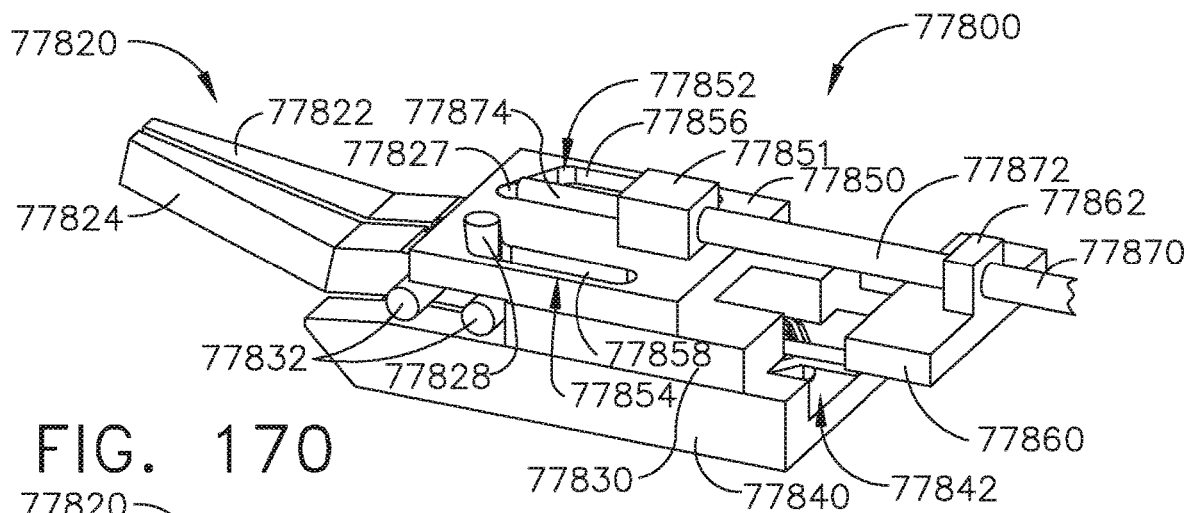
Figure 171:
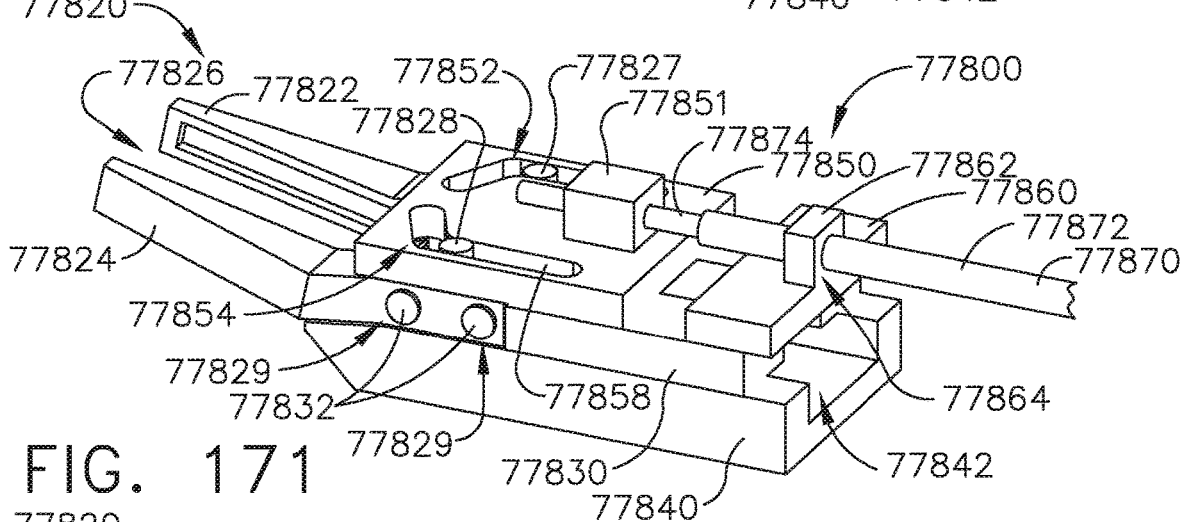
Figure 172:
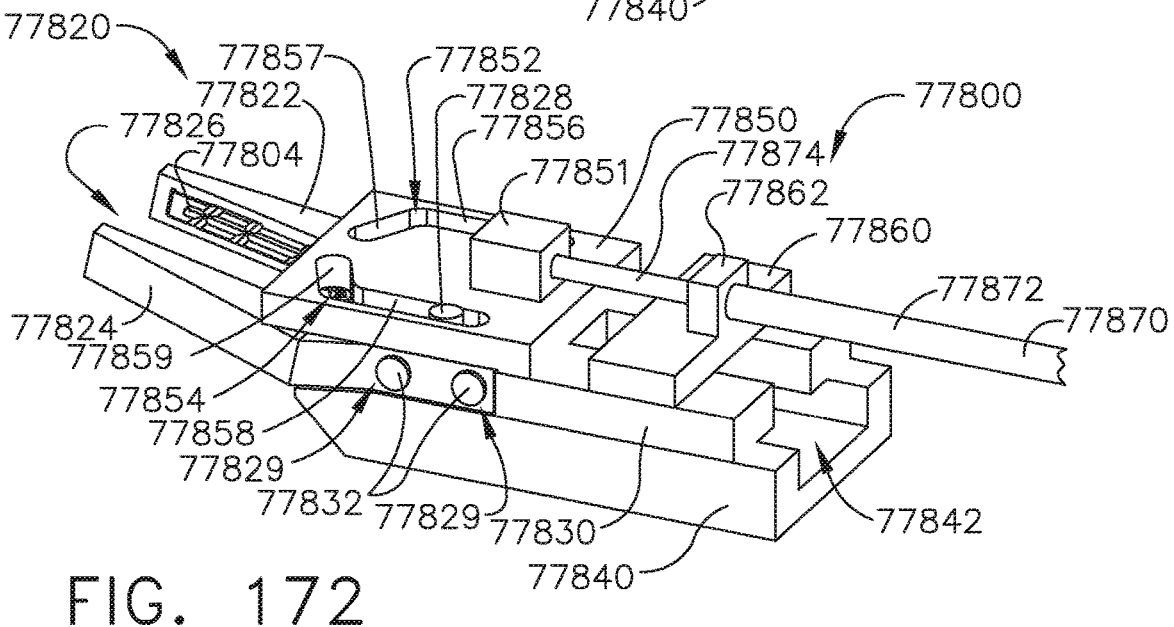
Figure 173:
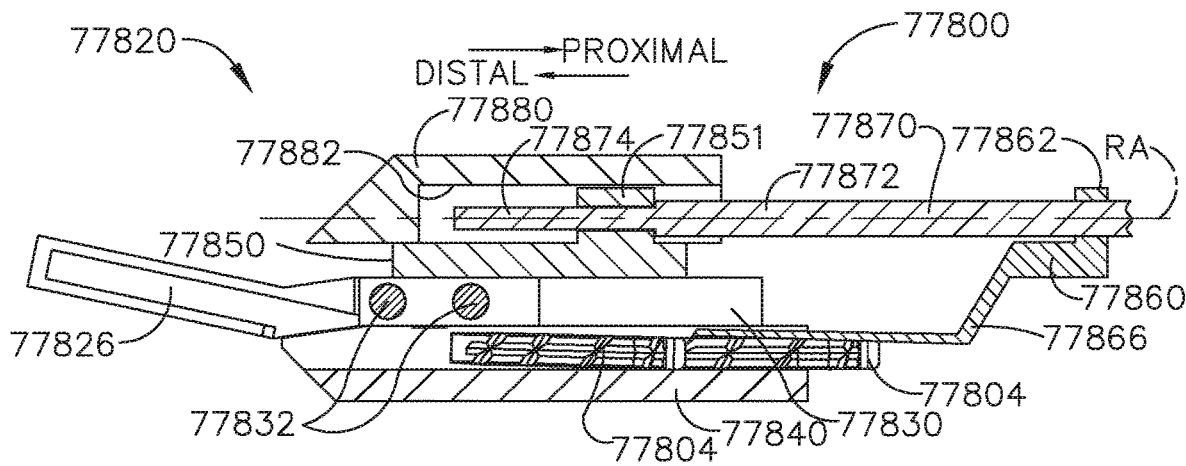
Figure 174:
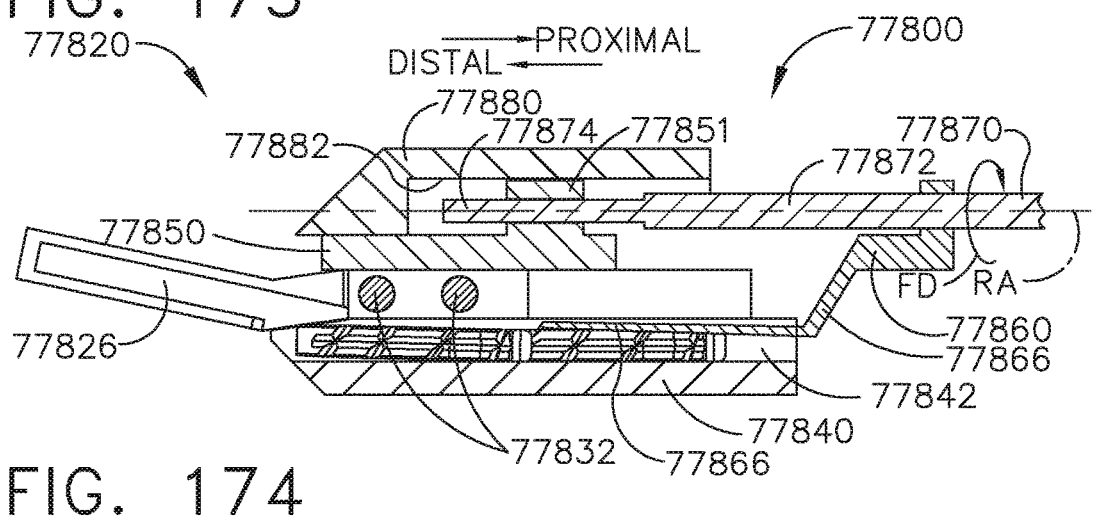
Figure 175:
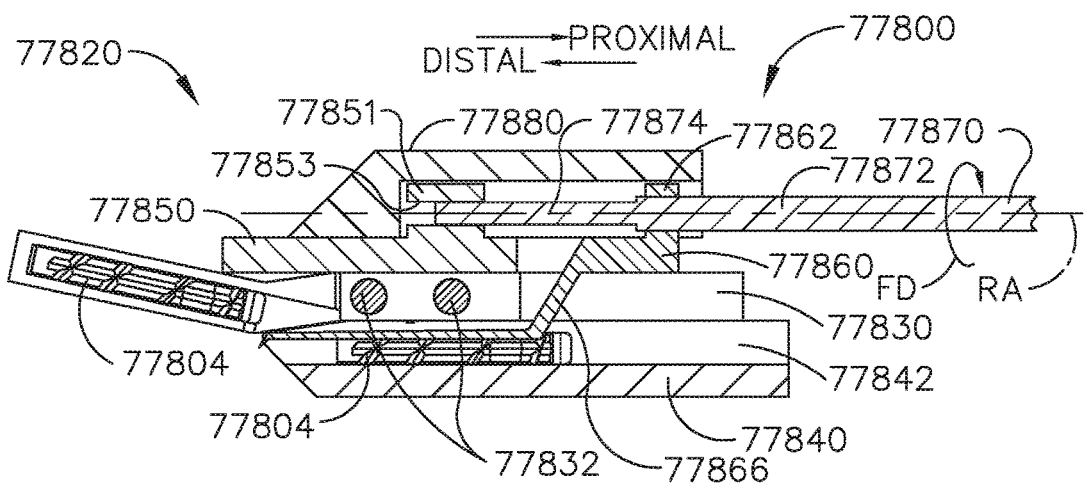
Figure 176:
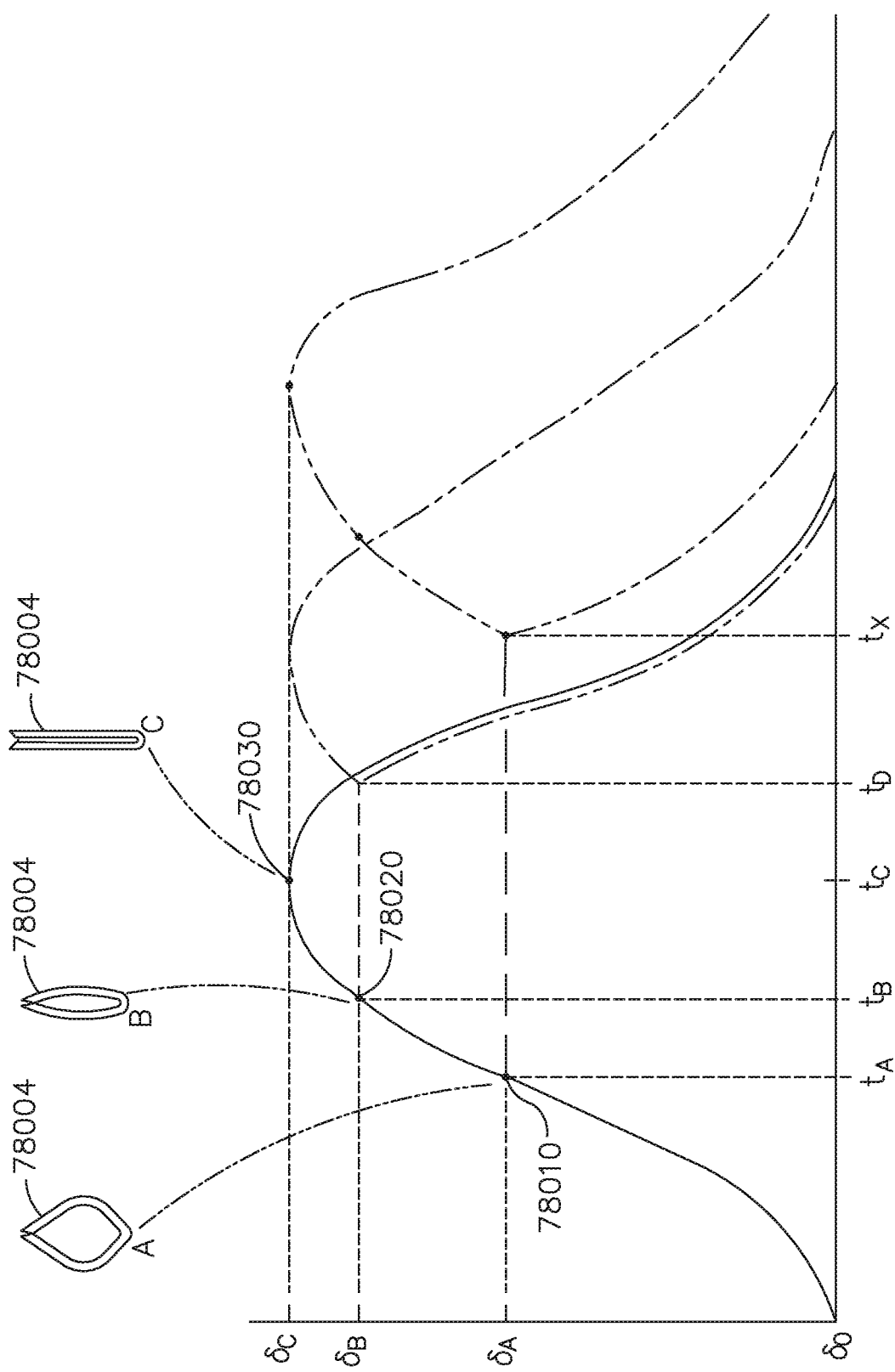
Figure 177:
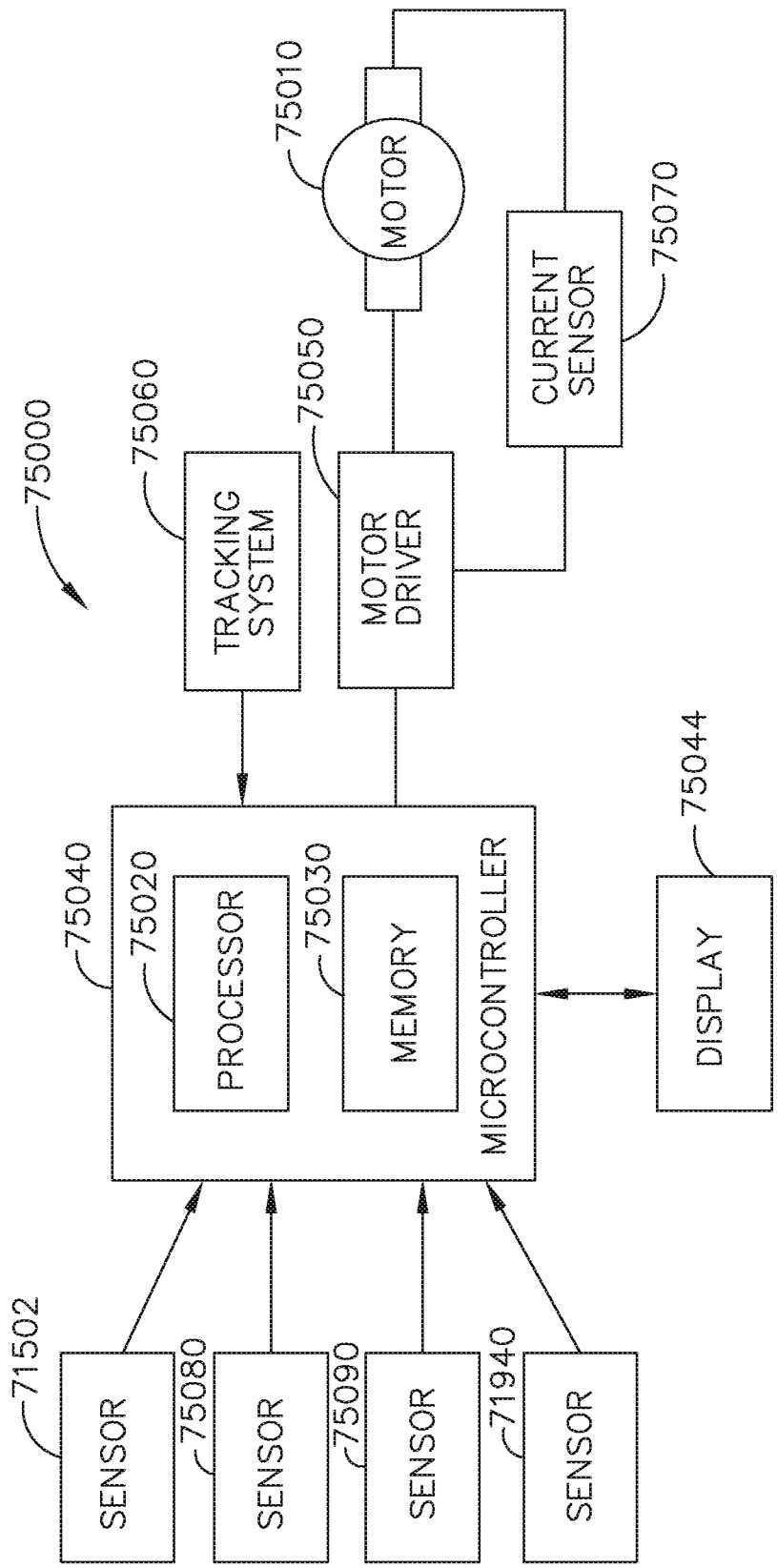

FIG. 161 is a side view of a clip applier comprising a drive screw with two different thread pitches configured to move a camming member and a feeder shoe in opposite directions to advance and crimp a clip, illustrating the camming member in a proximal position and the feeder shoe in a distal position;

FIG. 162 is a side view of the clip applier of FIG. 161, illustrating the camming member in a distal position and the feeder shoe in a proximal position;

FIG. 163 is a plan view of a clip applier comprising an end effector including jaws configured to close parallel to one another in response to a rotation of a drive screw, illustrating the jaws in an open position;

FIG. 164 is a plan view of the clip applier of FIG. 163, illustrating the jaws in a closed position;

FIG. 165 is a plan view of a clip applier comprising an end effector including jaws configured to provide tip first closure in response to a rotation of a drive screw, illustrating the jaws in an open position;

FIG. 166 is a plan view of the clip applier of FIG. 165, illustrating the jaws in a closed position;

FIG. 167A is a side elevational view of a clip applier comprising a jaw cam and a clip advancer, wherein the clip applier is configured to advance a clip and approximate a pair of jaws in response to the same rotary input, illustrating the jaw cam in a distal position and the jaws in a closed configuration;

FIG. 167B is a side elevational view of the clip applier of FIG. 167A, illustrating the pair of jaws in an open configuration and the jaw cam retracted to a proximal position;

FIG. 167C is a side elevational view of the clip applier of FIG. 167A, illustrating the pair of jaws in the open configuration and the jaw cam retracted to a fully-retracted position to release the clip advancer and to advance a clip into the pair of jaws;

FIG. 167D is a side elevational view of the clip applier of FIG. 167A, wherein a shoe retrieval latch of the jaw cam is operably engaged with the clip advancer when the jaw cam is advanced again to the distal position;

FIG. 168 is a perspective view of the jaw cam and the shoe retrieval latch of the clip applier of FIG. 167A;

FIG. 169 is a perspective view of the jaw cam and the shoe retrieval latch of the clip applier of FIG. 167A engaging a feeder shoe of the clip advancer;

FIG. 170 is a perspective view of a clip applier comprising a cam member and a clip advancer threadably engaged with a rotary input and configured to advance a clip and approximate a pair of opposing jaws, wherein the cam member and clip advancer are in a proximal position and the pair of jaws are closed;

FIG. 171 is a perspective view of the clip applier of FIG. 170, wherein the cam member and clip advancer are in an intermediate position and the pair of jaws are open;

FIG. 172 is a perspective view of the clip applier of FIG. 170, wherein the cam member and clip advancer are in a distal position, the pair of jaws are open, and a clip has been advanced into the pair of jaws;

FIG. 173 is a cross-sectional side view of the clip applier of FIG. 170, wherein the cam member and clip advancer are in the proximal position and the pair of jaws are closed;

FIG. 174 is a cross-sectional side view of the clip applier of FIG. 170, wherein the cam member and clip advancer are in the intermediate position and the pair of jaws are open;

FIG. 175 is a cross-sectional side view of the clip applier of FIG. 170, wherein the cam member and clip advancer are in the distal position, the pair of jaws are open, and the clip has been advanced into the pair of jaws;

FIG. 176 is a graphical depiction of a clip applier illustrating position of a crimping drive of the clip applier over time and including set points indicative of clip formation; and FIG. 177 is a schematic of a control system for use with any of the surgical instruments disclosed herein.

Corresponding reference characters indicate corresponding parts throughout the several views. The exemplifications set out herein illustrate various embodiments of the invention, in one form, and such exemplifications are not to be construed as limiting the scope of the invention in any manner.

DETAILED DESCRIPTION

Applicant of the present application owns the following U.S. Patent Applications that were filed on Oct. 26, 2018 and which are each herein incorporated by reference in their respective entireties:

U.S. patent application Ser. No. 16/172,130, entitled CLIP APPLIER COMPRISING INTERCHANGEABLE CLIP RELOADS, now U.S. Patent Application Publication No. 2019/0125358;

U.S. patent application Ser. No. 16/172,066, entitled CLIP APPLIER COMPRISING A MOVABLE CLIP MAGAZINE, now U.S. Patent Application Publication No. 2019/0125355;

U.S. patent application Ser. No. 16/172,078, entitled CLIP APPLIER COMPRISING A ROTATABLE CLIP MAGAZINE, now U.S. Patent Application Publication No. 2019/0125356;

U.S. patent application Ser. No. 16/172,087, entitled CLIP APPLIER COMPRISING CLIP ADVANCING SYSTEMS, now U.S. Patent Application Publication No. 2019/0125339;

U.S. patent application Ser. No. 16/172,094, entitled CLIP APPLIER COMPRISING A CLIP CRIMPING SYSTEM, now U.S. Patent Application Publication No. 2019/0125357;

U.S. patent application Ser. No. 16/172,128, entitled CLIP APPLIER COMPRISING A RECIPROCATING CLIP ADVANCING MEMBER, now U.S. Patent Application Publication No. 2019/0159778; and U.S. patent application Ser. No. 16/172,164, entitled SURGICAL SYSTEM COMPRISING A SURGICAL TOOL AND A SURGICAL HUB, now U.S. Patent Application Publication No. 2019/0125359.

Applicant of the present application owns the following U.S. Patent Applications that were filed on Aug. 24, 2018, which are each herein incorporated by reference in their respective entireties:

U.S. patent application Ser. No. 16/112,129, entitled SURGICAL SUTURING INSTRUMENT CONFIGURED TO MANIPULATE TISSUE USING MECHANICAL AND ELECTRICAL POWER;

U.S. patent application Ser. No. 16/112,155, entitled SURGICAL SUTURING INSTRUMENT COMPRISING A CAPTURE WIDTH WHICH IS LARGER THAN TROCAR DIAMETER;

U.S. patent application Ser. No. 16/112,168, entitled SURGICAL SUTURING INSTRUMENT COMPRISING A NON-CIRCULAR NEEDLE;

U.S. patent application Ser. No. 16/112,180, entitled ELECTRICAL POWER OUTPUT CONTROL BASED ON MECHANICAL FORCES;

U.S. patent application Ser. No. 16/112,193, entitled REACTIVE ALGORITHM FOR SURGICAL SYSTEM;

U.S. patent application Ser. No. 16/112,099, entitled SURGICAL INSTRUMENT COMPRISING AN ADAPTIVE ELECTRICAL SYSTEM;

U.S. patent application Ser. No. 16/112,112, entitled CONTROL SYSTEM ARRANGEMENTS FOR A MODULAR SURGICAL INSTRUMENT;

U.S. patent application Ser. No. 16/112,119, entitled ADAPTIVE CONTROL PROGRAMS FOR A SURGICAL SYSTEM COMPRISING MORE THAN ONE TYPE OF CARTRIDGE;

U.S. patent application Ser. No. 16/112,097, entitled SURGICAL INSTRUMENT SYSTEMS COMPRISING BATTERY ARRANGEMENTS;

U.S. patent application Ser. No. 16/112,109, entitled SURGICAL INSTRUMENT SYSTEMS COMPRISING HANDLE ARRANGEMENTS;

U.S. patent application Ser. No. 16/112,114, entitled SURGICAL INSTRUMENT SYSTEMS COMPRISING FEEDBACK MECHANISMS;

U.S. patent application Ser. No. 16/112,117, entitled SURGICAL INSTRUMENT SYSTEMS COMPRISING LOCKOUT MECHANISMS;

U.S. patent application Ser. No. 16/112,095, entitled SURGICAL INSTRUMENTS COMPRISING A LOCKABLE END EFFECTOR SOCKET;

U.S. patent application Ser. No. 16/112,121, entitled SURGICAL INSTRUMENTS COMPRISING A SHIFTING MECHANISM;

U.S. patent application Ser. No. 16/112,151, entitled SURGICAL INSTRUMENTS COMPRISING A SYSTEM FOR ARTICULATION AND ROTATION COMPENSATION;

U.S. patent application Ser. No. 16/112,154, entitled SURGICAL INSTRUMENTS COMPRISING A BIASED SHIFTING MECHANISM;

U.S. patent application Ser. No. 16/112,226, entitled SURGICAL INSTRUMENTS COMPRISING AN ARTICULATION DRIVE THAT PROVIDES FOR HIGH ARTICULATION ANGLES;

U.S. patent application Ser. No. 16/112,062, entitled SURGICAL DISSECTORS AND MANUFACTURING TECHNIQUES;

U.S. patent application Ser. No. 16/112,098, entitled SURGICAL DISSECTORS CONFIGURED TO APPLY MECHANICAL AND ELECTRICAL ENERGY;

U.S. patent application Ser. No. 16/112,237, entitled SURGICAL CLIP APPLIER CONFIGURED TO STORE CLIPS IN A STORED STATE;

U.S. patent application Ser. No. 16/112,245, entitled SURGICAL CLIP APPLIER COMPRISING AN EMPTY CLIP CARTRIDGE LOCKOUT;

U.S. patent application Ser. No. 16/112,249, entitled SURGICAL CLIP APPLIER COMPRISING AN AUTOMATIC CLIP FEEDING SYSTEM;

U.S. patent application Ser. No. 16/112,253, entitled SURGICAL CLIP APPLIER COMPRISING ADAPTIVE FIRING CONTROL; and U.S. patent application Ser. No. 16/112,257, entitled SURGICAL CLIP APPLIER COMPRISING ADAPTIVE CONTROL IN RESPONSE TO A STRAIN GAUGE CIRCUIT.

Applicant of the present application owns the following U.S. patent applications that were filed on May 1, 2018 and which are each herein incorporated by reference in their respective entireties:

U.S. Provisional Patent Application Ser. No. 62/665,129, entitled SURGICAL SUTURING SYSTEMS;

U.S. Provisional Patent Application Ser. No. 62/665,139, entitled SURGICAL INSTRUMENTS COMPRISING CONTROL SYSTEMS;

U.S. Provisional Patent Application Ser. No. 62/665,177, entitled SURGICAL INSTRUMENTS COMPRISING HANDLE ARRANGEMENTS;

U.S. Provisional Patent Application Ser. No. 62/665,128, entitled MODULAR SURGICAL INSTRUMENTS;

U.S. Provisional Patent Application Ser. No. 62/665,192, entitled SURGICAL DISSECTORS; and U.S. Provisional Patent Application Ser. No. 62/665,134, entitled SURGICAL CLIP APPLIER.

Applicant of the present application owns the following U.S. patent applications that were filed on Feb. 28, 2018 and which are each herein incorporated by reference in their respective entireties:

U.S. patent application Ser. No. 15/908,021, entitled SURGICAL INSTRUMENT WITH REMOTE RELEASE;

U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT;

U.S. patent application Ser. No. 15/908,040, entitled SURGICAL INSTRUMENT WITH ROTARY DRIVE SELECTIVELY ACTUATING MULTIPLE END EFFECTOR FUNCTIONS;

U.S. patent application Ser. No. 15/908,057, entitled SURGICAL INSTRUMENT WITH ROTARY DRIVE SELECTIVELY ACTUATING MULTIPLE END EFFECTOR FUNCTIONS;

U.S. patent application Ser. No. 15/908,058, entitled SURGICAL INSTRUMENT WITH MODULAR POWER SOURCES; and U.S. patent application Ser. No. 15/908,143, entitled SURGICAL INSTRUMENT WITH SENSOR AND/OR CONTROL SYSTEMS.

Applicant of the present application owns the following U.S. patent applications that were filed on Oct. 30, 2017 and which are each herein incorporated by reference in their respective entireties:

U.S. Provisional Patent Application Ser. No. 62/578,793, entitled SURGICAL INSTRUMENT WITH REMOTE RELEASE;

U.S. Provisional Patent Application Ser. No. 62/578,804, entitled SURGICAL INSTRUMENT HAVING DUAL ROTATABLE MEMBERS TO EFFECT DIFFERENT TYPES OF END EFFECTOR MOVEMENT;

U.S. Provisional Patent Application Ser. No. 62/578,817, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,835, entitled SURGICAL INSTRUMENT WITH ROTARY DRIVE SELECTIVELY ACTUATING MULTIPLE END EFFECTOR FUNCTIONS;

U.S. Provisional Patent Application Ser. No. 62/578,844, entitled SURGICAL INSTRUMENT WITH MODULAR POWER SOURCES; and U.S. Provisional Patent Application Ser. No. 62/578,855, entitled SURGICAL INSTRUMENT WITH SENSOR AND/OR CONTROL SYSTEMS.

Applicant of the present application owns the following U.S. Provisional patent applications, filed on Dec. 28, 2017, the disclosure of each of which is herein incorporated by reference in its entirety:

U.S. Provisional Patent Application Ser. No. 62/611,341, entitled INTERACTIVE SURGICAL PLATFORM;

U.S. Provisional Patent Application Ser. No. 62/611,340, entitled CLOUD-BASED MEDICAL ANALYTICS; and U.S. Provisional Patent Application Ser. No. 62/611,339, entitled ROBOT ASSISTED SURGICAL PLATFORM.

Applicant of the present application owns the following U.S. Provisional patent applications, filed on Mar. 28, 2018, each of which is herein incorporated by reference in its entirety:

U.S. Provisional Patent Application Ser. No. 62/649,302, entitled INTERACTIVE SURGICAL SYSTEMS WITH ENCRYPTED COMMUNICATION CAPABILITIES;

U.S. Provisional Patent Application Ser. No. 62/649,294, entitled DATA STRIPPING METHOD TO INTERROGATE PATIENT RECORDS AND CREATE ANONYMIZED RECORD;

U.S. Provisional Patent Application Ser. No. 62/649,300, entitled SURGICAL HUB SITUATIONAL AWARENESS;

U.S. Provisional Patent Application Ser. No. 62/649,309, entitled SURGICAL HUB SPATIAL AWARENESS TO DETERMINE DEVICES IN OPERATING THEATER;

U.S. Provisional Patent Application Ser. No. 62/649,310, entitled COMPUTER IMPLEMENTED INTERACTIVE SURGICAL SYSTEMS;

U.S. Provisional Patent Application Ser. No. 62/649,291, entitled USE OF LASER LIGHT AND RED-GREEN-BLUE COLORATION TO DETERMINE PROPERTIES OF BACK SCATTERED LIGHT;

U.S. Provisional Patent Application Ser. No. 62/649,296, entitled ADAPTIVE CONTROL PROGRAM UPDATES FOR SURGICAL DEVICES;

U.S. Provisional Patent Application Ser. No. 62/649,333, entitled CLOUD-BASED MEDICAL ANALYTICS FOR CUSTOMIZATION AND RECOMMENDATIONS TO A USER;

U.S. Provisional Patent Application Ser. No. 62/649,327, entitled CLOUD-BASED MEDICAL ANALYTICS FOR SECURITY AND AUTHENTICATION TRENDS AND REACTIVE MEASURES;

U.S. Provisional Patent Application Ser. No. 62/649,315, entitled DATA HANDLING AND PRIORITIZATION IN A CLOUD ANALYTICS NETWORK;

U.S. Provisional Patent Application Ser. No. 62/649,313, entitled CLOUD INTERFACE FOR COUPLED SURGICAL DEVICES;

U.S. Provisional Patent Application Ser. No. 62/649,320, entitled DRIVE ARRANGEMENTS FOR ROBOT-ASSISTED SURGICAL PLATFORMS;

U.S. Provisional Patent Application Ser. No. 62/649,307, entitled AUTOMATIC TOOL ADJUSTMENTS FOR ROBOT-ASSISTED SURGICAL PLATFORMS; and U.S. Provisional Patent Application Ser. No. 62/649,323, entitled SENSING ARRANGEMENTS FOR ROBOT-ASSISTED SURGICAL PLATFORMS.

Applicant of the present application owns the following U.S. patent applications, filed on Mar. 29, 2018, each of which is herein incorporated by reference in its entirety:

U.S. patent application Ser. No. 15/940,641, entitled INTERACTIVE SURGICAL SYSTEMS WITH ENCRYPTED COMMUNICATION CAPABILITIES;

U.S. patent application Ser. No. 15/940,648, entitled INTERACTIVE SURGICAL SYSTEMS WITH CONDITION HANDLING OF DEVICES AND DATA CAPABILITIES;

U.S. patent application Ser. No. 15/940,656, entitled SURGICAL HUB COORDINATION OF CONTROL AND COMMUNICATION OF OPERATING ROOM DEVICES;

U.S. patent application Ser. No. 15/940,666, entitled SPATIAL AWARENESS OF SURGICAL HUBS IN OPERATING ROOMS;

U.S. patent application Ser. No. 15/940,670, entitled COOPERATIVE UTILIZATION OF DATA DERIVED FROM SECONDARY SOURCES BY INTELLIGENT SURGICAL HUBS;

U.S. patent application Ser. No. 15/940,677, entitled SURGICAL HUB CONTROL ARRANGEMENTS;

U.S. patent application Ser. No. 15/940,632, entitled DATA STRIPPING METHOD TO INTERROGATE PATIENT RECORDS AND CREATE ANONYMIZED RECORD;

U.S. patent application Ser. No. 15/940,640, entitled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;

U.S. patent application Ser. No. 15/940,645, entitled SELF DESCRIBING DATA PACKETS GENERATED AT AN ISSUING INSTRUMENT;

U.S. patent application Ser. No. 15/940,649, entitled DATA PAIRING TO INTERCONNECT A DEVICE MEASURED PARAMETER WITH AN OUTCOME;

U.S. patent application Ser. No. 15/940,654, entitled SURGICAL HUB SITUATIONAL AWARENESS;

U.S. patent application Ser. No. 15/940,663, entitled SURGICAL SYSTEM DISTRIBUTED PROCESSING;

U.S. patent application Ser. No. 15/940,668, entitled AGGREGATION AND REPORTING OF SURGICAL HUB DATA;

U.S. patent application Ser. No. 15/940,671, entitled SURGICAL HUB SPATIAL AWARENESS TO DETERMINE DEVICES IN OPERATING THEATER;

U.S. patent application Ser. No. 15/940,686, entitled DISPLAY OF ALIGNMENT OF STAPLE CARTRIDGE TO PRIOR LINEAR STAPLE LINE;

U.S. patent application Ser. No. 15/940,700, entitled STERILE FIELD INTERACTIVE CONTROL DISPLAYS;

U.S. patent application Ser. No. 15/940,629, entitled COMPUTER IMPLEMENTED INTERACTIVE SURGICAL SYSTEMS;

U.S. patent application Ser. No. 15/940,704, entitled USE OF LASER LIGHT AND RED-GREEN-BLUE COLORATION TO DETERMINE PROPERTIES OF BACK SCATTERED LIGHT;

U.S. patent application Ser. No. 15/940,722, entitled CHARACTERIZATION OF TISSUE IRREGULARITIES THROUGH THE USE OF MONO-CHROMATIC LIGHT REFRACTIVITY; and U.S. patent application Ser. No. 15/940,742, entitled DUAL CMOS ARRAY IMAGING.

Applicant of the present application owns the following U.S. patent applications, filed on Mar. 29, 2018, each of which is herein incorporated by reference in its entirety:

U.S. patent application Ser. No. 15/940,636, entitled ADAPTIVE CONTROL PROGRAM UPDATES FOR SURGICAL DEVICES;

U.S. patent application Ser. No. 15/940,653, entitled ADAPTIVE CONTROL PROGRAM UPDATES FOR SURGICAL HUBS;

U.S. patent application Ser. No. 15/940,660, entitled CLOUD-BASED MEDICAL ANALYTICS FOR CUSTOMIZATION AND RECOMMENDATIONS TO A USER;

U.S. patent application Ser. No. 15/940,679, entitled CLOUD-BASED MEDICAL ANALYTICS FOR LINKING OF LOCAL USAGE TRENDS WITH THE RESOURCE ACQUISITION BEHAVIORS OF LARGER DATA SET;

U.S. patent application Ser. No. 15/940,694, entitled CLOUD-BASED MEDICAL ANALYTICS FOR MEDICAL FACILITY SEGMENTED INDIVIDUALIZATION OF INSTRUMENT FUNCTION;

U.S. patent application Ser. No. 15/940,634, entitled CLOUD-BASED MEDICAL ANALYTICS FOR SECURITY AND AUTHENTICATION TRENDS AND REACTIVE MEASURES;

U.S. patent application Ser. No. 15/940,706, entitled DATA HANDLING AND PRIORITIZATION IN A CLOUD ANALYTICS NETWORK; and U.S. patent application Ser. No. 15/940,675, entitled CLOUD INTERFACE FOR COUPLED SURGICAL DEVICES.

Applicant of the present application owns the following U.S. patent applications, filed on Mar. 29, 2018, each of which is herein incorporated by reference in its entirety:

U.S. patent application Ser. No. 15/940,627, entitled DRIVE ARRANGEMENTS FOR ROBOT-ASSISTED SURGICAL PLATFORMS;

U.S. patent application Ser. No. 15/940,637, entitled COMMUNICATION ARRANGEMENTS FOR ROBOT-ASSISTED SURGICAL PLATFORMS;

U.S. patent application Ser. No. 15/940,642, entitled CONTROLS FOR ROBOT-ASSISTED SURGICAL PLATFORMS;

U.S. patent application Ser. No. 15/940,676, entitled AUTOMATIC TOOL ADJUSTMENTS FOR ROBOT-ASSISTED SURGICAL PLATFORMS;

U.S. patent application Ser. No. 15/940,680, entitled CONTROLLERS FOR ROBOT-ASSISTED SURGICAL PLATFORMS;

U.S. patent application Ser. No. 15/940,683, entitled COOPERATIVE SURGICAL ACTIONS FOR ROBOT-ASSISTED SURGICAL PLATFORMS;

U.S. patent application Ser. No. 15/940,690, entitled DISPLAY ARRANGEMENTS FOR ROBOT-ASSISTED SURGICAL PLATFORMS; and U.S. patent application Ser. No. 15/940,711, entitled SENSING ARRANGEMENTS FOR ROBOT-ASSISTED SURGICAL PLATFORMS.

Applicant of the present application owns the following U.S. Provisional patent applications, filed on Mar. 30, 2018, each of which is herein incorporated by reference in its entirety:

U.S. Provisional Patent Application Ser. No. 62/650,887, entitled SURGICAL SYSTEMS WITH OPTIMIZED SENSING CAPABILITIES;

U.S. Provisional Patent Application Ser. No. 62/650,877, entitled SURGICAL SMOKE EVACUATION SENSING AND CONTROLS;

U.S. Provisional Patent Application Ser. No. 62/650,882, entitled SMOKE EVACUATION MODULE FOR INTERACTIVE SURGICAL PLATFORM; and U.S. Provisional Patent Application Ser. No. 62/650,898, entitled CAPACITIVE COUPLED RETURN PATH PAD WITH SEPARABLE ARRAY ELEMENTS.

Applicant of the present application owns the following U.S. Provisional patent application, filed on Apr. 19, 2018, which is herein incorporated by reference in its entirety:

U.S. Provisional Patent Application Ser. No. 62/659,900, entitled METHOD OF HUB COMMUNICATION.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including"), and "contain" (and any form of contain, such as "contains" and "containing") are open-ended linking verbs. As a result, a surgical system, device, or apparatus that "comprises," "has," "includes", or "contains" one or more elements possesses those one or more elements, but is not limited to possessing only those one or more elements. Likewise, an element of a system, device, or apparatus that "comprises," "has," "includes", or "contains" one or more features possesses those one or more features, but is not limited to possessing only those one or more features.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

Figure 3:
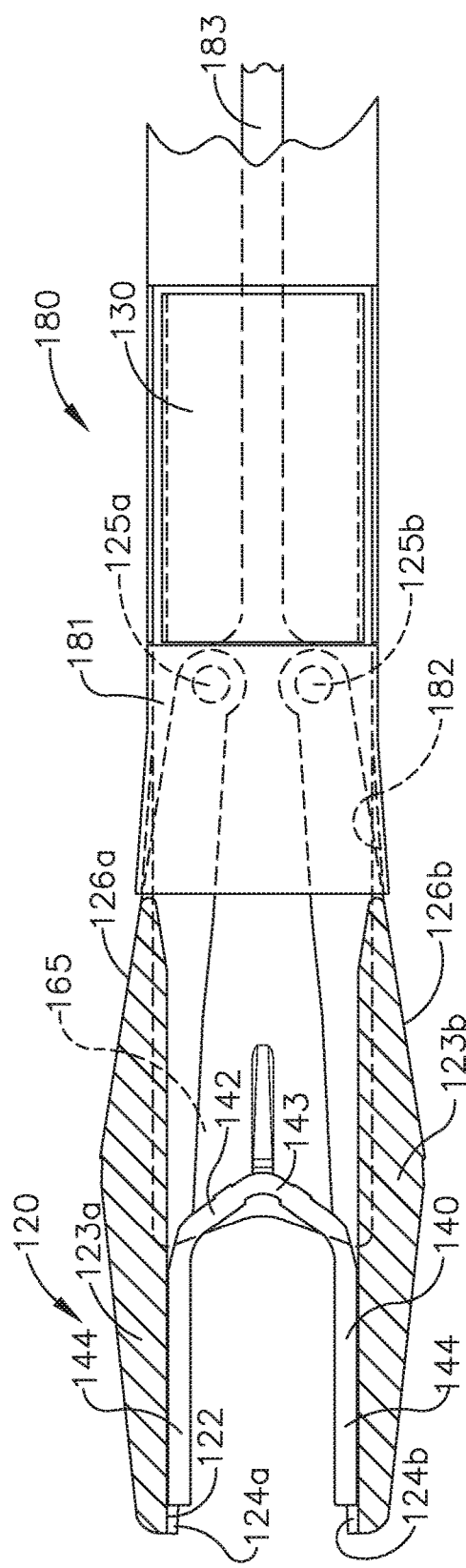
FIG. 3 is a partial cross-sectional view of the clip applier of FIG. 1 in an open configuration.
Figure 4:
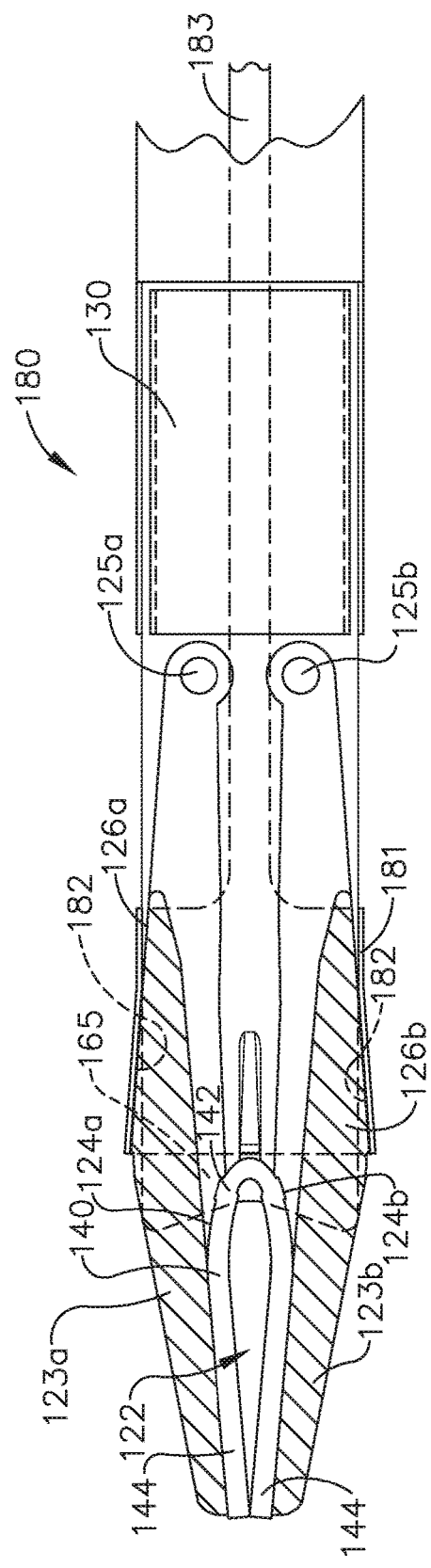
FIG. 4 is a partial cross-sectional view of the clip applier of FIG. 1 in a closed configuration.
Figure 13:
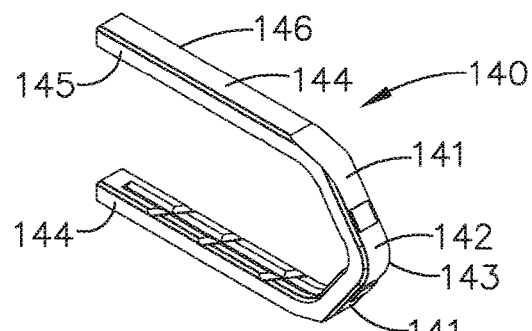
FIG. 13 is a perspective view of a clip illustrated in FIGS. 2-12.

During various surgical procedures, a surgeon, or other clinician, may apply a clip to a patient's tissue in order to achieve various effects and/or therapeutic results. Referring to FIG. 1, a surgical instrument, such as a clip applier 100, for example, can be configured to apply one or more clips to tissue located within a surgical site in the patient. Generally, referring now to FIG. 13, the clip applier 100 can be structured and arranged to position a clip 140 relative to the tissue in order to compress the tissue within the clip 140. The clip applier 100 can be configured to deform the clip 140 as illustrated in FIGS. 3 and 4, for example, and as described in greater detail further below. Each clip 140 can comprise a base 142 and opposing legs 144 extending from the base 142. The base 142 and the legs 144 can comprise any suitable shape and can define a substantially U-shaped configuration and/or a substantially V-shaped configuration, for example. The base 142 can comprise angled portions 141 which are connected together by a joint 143. In use, the legs 144 of the clip 140 can be positioned on opposite sides of the tissue wherein the legs 144 can be pushed toward one another to compress the tissue positioned between the legs 144. The joint 143 can be configured to permit the angled portions 141 of the base 142, and the legs 144 extending therefrom, to deform inwardly. In various circumstances, the clip 140 can be configured to yield, or deform plastically, when the clip 140 is sufficiently compressed, although some amount of elastic deformation, or spring-back, may occur within the deformed clip 140.

Figure 14:
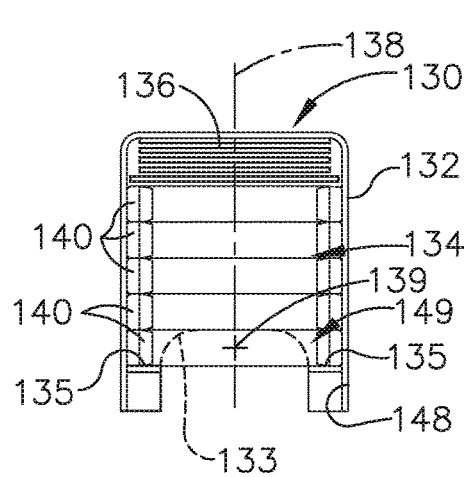
FIG. 14 is a front view of a cartridge illustrated in FIGS. 1-12 comprising a plurality of clips with portions of the cartridge removed to illustrate the clips stored in the cartridge.
Figure 15:
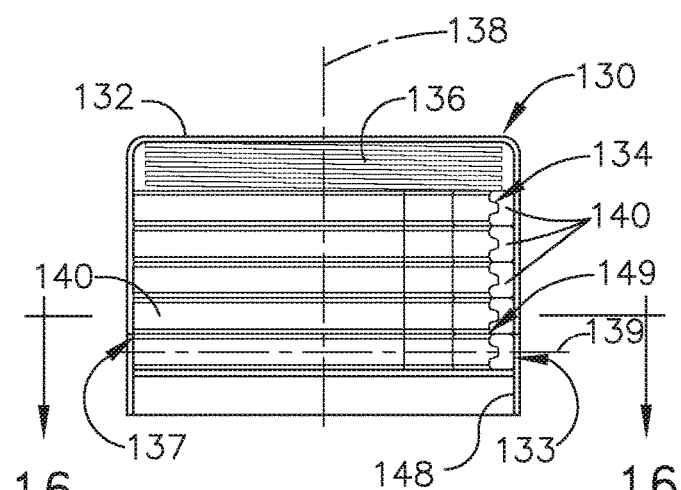
FIG. 15 is a side view of the cartridge of FIG. 14 illustrated with portions removed to illustrate the clips stored in the cartridge.
Figure 16:
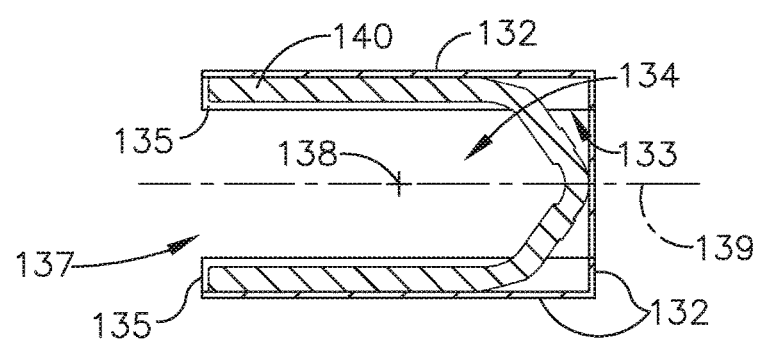
FIG. 16 is a cross-sectional plan view of the cartridge of FIG. 14 taken along line 16-16 in FIG. 15.

Referring now to FIGS. 1 and 2, the clip applier 100 can include a shaft 110, an end effector 120, and a replaceable clip cartridge, or magazine, 130. Referring to FIGS. 14-16, the clip cartridge 130 can comprise a housing 132 and a plurality of clips 140 positioned within the housing 132. The housing 132 can define a storage chamber 134 in which the clips 140 can be stacked. The storage chamber 134 can comprise sidewalls which extend around, or at least substantially around, the perimeter of the clips 140. Referring again to FIG. 13, each clip 140 can comprise opposing faces, such as a top face 145 and a bottom face 146 on opposite sides of the clip 140 wherein, when the clips 140 are stacked in the housing 132, the top face 145 of a clip 140 can be positioned against the bottom face 146 of an adjacent clip 140 and wherein the bottom face 146 of the clip 140 can be positioned against the top face 145 of another adjacent clip 140. In various circumstances, the bottom faces 146 of the clips 140 can face downwardly toward one or more support shelves, or platforms, 135 defined in the housing 132 while the top faces 145 of the clips 140 can face upwardly away from the support shelves 135. The top faces 145 and the bottom faces 146 of the clips 140 may be identical, or at least substantially identical, in some cases, while, in other cases, the top faces 145 and the bottom faces 146 may be different. The stack of clips 140 depicted in FIGS. 14-16 comprises five clips 140, for example; however, other embodiments are envisioned in which the stack of clips 140 can include more than five clips 140 or less than five clips 140. In any event, the clip cartridge 130 can further comprise at least one biasing member, such as biasing member 136, for example, positioned intermediate the housing 132 and the top clip 140 in the stack of clips 140. As described in greater detail below, the biasing member 136 can be configured to bias the bottom clip 140 in the stack of clips 140 or, more particularly, the bottom face 146 of the bottom clip 140, against the support shelves 135 defined in the housing 132. The biasing member 136 can comprise a spring, and/or any suitable compressed elastic element, for example, which can be configured to apply a biasing force to the clips 140, or at least apply a biasing force to the top clip 140 which is transmitted downwardly through the stack of clips 140.

When a clip 140 is positioned against the support shelves 135 as described above, the clip 140 can be supported in a firing position in which the clip 140 can be advanced and ejected from the cartridge 130. In various circumstances, the support shelves 135 can define at least a portion of a firing chamber 149 in which the clips 140 can be sequentially positioned in the firing position. In some cases, the firing chamber 149 can be entirely defined within the cartridge 130 or, in other cases, the firing chamber 149 can be defined within and/or between the shaft 110 and the cartridge 130. In any event, as described in greater detail further below, the clip applier 100 can comprise a firing drive which can advance a firing member into the cartridge 130 and push the clip 140 from its firing position positioned against the support shelves 135 to a fired position in which it is received within the end effector 120 of the clip applier 100. Referring primarily to FIGS. 14-16, the housing 132 of the cartridge 130 can comprise a proximal opening, or window, 133 which can be aligned, or at least substantially aligned, with the support shelves 135 such that the firing member can enter into the cartridge 130 through the proximal opening 133 and advance a clip 140 distally out of the cartridge 130. In at least one such embodiment, the housing 132 can further comprise a distal, or discharge, opening, or window, 137 which is also aligned with the support shelves 135 such that the clip 140 can be advanced, or fired, distally along a firing axis 139 extending through the proximal opening 133, the firing chamber 149, and the distal opening 137, for example.

In order to advance a clip 140 out of the cartridge 130, further to the above, the firing member of the firing drive can be advanced into to the cartridge housing 132 and, in various circumstances, into the firing chamber 149. As disclosed in greater detail further below, the firing member can pass entirely through the cartridge 130 in order to advance the clip 140 into its fired position within the end effector 120. After the clip 140 positioned in the firing chamber 149 has been advanced distally by the firing member, as outlined above, the firing member can be retracted sufficiently such that the biasing member 136 can position another clip 140 against the support shelves 135. In various circumstances, the biasing member 136 can bias a clip 140 against the firing member while the firing member is positioned within the housing 132. Such a clip 140 can be referred to as a queued clip. After the firing member has been sufficiently retracted and slid out from underneath the queued clip 140, the biasing member 136 can then bias the clip 140 against the support shelves 135 where it is staged for the next stroke of the reciprocating firing member. Referring primarily to FIGS. 2 and 14-16, the cartridge 130 can be configured to supply the clips 140 to the firing chamber 149 along a predetermined path, such as supply axis 138, for example. The supply axis 138 can be transverse to the firing axis 139 such that the clips 140 are fed into the firing chamber 149 in a direction which is different than the direction in which the firing member passes through the firing chamber 149. In at least one such embodiment, the supply axis 138 can be perpendicular, or at least substantially perpendicular, to the firing axis 139, for example.

Referring again to FIG. 2, the shaft 110 can comprise a cartridge, or magazine, aperture 131 which can be sized and configured to receive a clip cartridge 130, for example, therein. The cartridge aperture 131 can be sized and configured such that the housing 132 of the cartridge 130 is closely received within the cartridge aperture 131. The sidewalls which define the cartridge aperture 131 can limit, or at least substantially limit, the lateral movement of the cartridge 130 relative to the shaft 110. The shaft 110 and/or the cartridge 130 can further comprise one or more locks which can be configured to releasably hold the cartridge 130 in the cartridge aperture 131. As illustrated in FIG. 2, the cartridge 130 can be loaded into the cartridge aperture 131 along an axis which is, in at least one embodiment, parallel to or collinear with the supply axis 138. As also illustrated in FIG. 2, the shaft 110 can further comprise a pad or seat 118 extending from the sidewall 111 of the shaft 110 wherein the pad 118 can be configured to be received within and/or engaged with the housing 132 of the cartridge 130. The pad 118 can be sized and configured to be closely received within a recess 148 defined in the cartridge housing such that the pad 118 can limit, or at least substantially limit, the lateral movement of the cartridge 130 relative to the shaft 110. The pad 118 can be sized and configured to align the cartridge 130 within the shaft 110 and/or support the cartridge housing 132.

Once the clip cartridge 130 has been positioned and seated within the shaft aperture 131, referring now to FIGS. 5 and 6, a firing drive 160 of the clip applier 100 can be actuated to advance the clips 140 from the clip cartridge 130 as described above. The firing drive 160 can comprise a rotary drive input such as a drive screw 161, for example, and a displaceable firing nut 163 operably engaged with the drive screw 161. The drive screw 161 can comprise at least one drive thread 162 which can be threadably engaged with a threaded aperture extending through the firing nut 163. In various embodiments, the clip applier 100 can further include an electric motor, for example, operably coupled with the drive screw 161. In various instances, the drive screw 161 can be operably coupled with the motor of a surgical instrument system comprising a hand-held instrument or a robotic arm, for example. In any event, the movement of the firing nut 163 within the shaft 110 can be constrained such that the firing nut 163 moves along a longitudinal axis 164 when the drive screw 161 is rotated about the longitudinal axis 164 by the motor. For instance, when the drive screw 161 is rotated in a first direction by the motor, the drive screw 161 can advance the firing nut 163 distally toward the end effector 120, as illustrated in FIG. 6. When the drive screw 161 is rotated in a direction opposite the first direction by the motor, the drive screw 161 can retract the firing nut 163 proximally away from the end effector 120. The shaft 110 can comprise one or more bearings which can be configured to rotatably support the drive screw 161. For instance, a bearing 159 can be configured to rotatably support the distal end of the drive screw 161, for example, as illustrated in FIGS. 5 and 6.

The firing drive 160 can further comprise a firing member 165 extending from the firing nut 163 which can be advanced distally and retracted proximally with the firing nut 163, as described in greater detail further below. Upon comparing FIGS. 5 and 6, the reader will note that the firing nut 163 and the firing member 165 have been advanced from a proximal, unfired position, illustrated in FIG. 5, to a distal, fired position, illustrated in FIG. 6, in which the firing member 165 has advanced a clip 140 from the clip cartridge 130 into the end effector 120. Referring primarily to FIG. 5, the clip cartridge 130 is illustrated as comprising a plurality of clips 140 stored therein wherein one of the clips 140 is positioned in a firing position, as described above. As illustrated in FIGS. 5 and 6, the firing member 165 can include a distal portion 166 which can be advanced into the staple cartridge 130 along a firing axis 167 and engage the clip 140 positioned in the firing position when the firing member 165 and the firing nut 163 are advanced distally. In some cases, the firing member 165 can comprise a linear member while, in other cases, the distal end 166 of the firing member 165 can extend upwardly from the firing member 165, for example. Further to the above, the firing member 165 can advance the clip 140 distally out of the clip cartridge 130 along the firing axis 167 and into a receiving cavity 122 defined in the end effector 120.

In various cases, the firing member 165 can be attached to and extend distally from the firing nut 163 while, in other cases, the firing member 165 and the firing nut 163 can be operably connected to one another by a firing actuator 168. The firing actuator 168 can be pivotably mounted to the firing member 165 at a pivot 169 and can include a distal arm 170a and a proximal arm 170b which can be engaged with a longitudinal slot 113 defined in the housing 112 of the shaft 110. In at least one such embodiment, each of the arms 170a, 170b can include a projection, such as projections 171a and 171b, respectively, extending therefrom which can be configured to slide within the longitudinal slot 113. Further to the above, the firing nut 163 can further include a firing pin 172 extending therefrom which can be configured to engage the distal arm 170a in order to advance the actuator 168 and the firing member 165 distally, as described above. In use, referring again to the progression illustrated in FIGS. 5 and 6, the firing nut 163 can be advanced distally by the drive screw 161 wherein the firing pin 172, which is positioned intermediate the distal arm 170a and the proximal arm 170b, can contact the distal arm 170a and drive the actuator 168 and the firing member 165 distally. As the actuator 168 is advanced distally, the actuator 168 may be prevented from rotating about the pivot pin 169 as one or both of the projections 171a and 171b sliding in the shaft slot 113 can be prevented from being moved laterally relative to the longitudinal shaft slot 113 until the actuator 168 reaches the position illustrated in FIG. 6.

Figure 9:
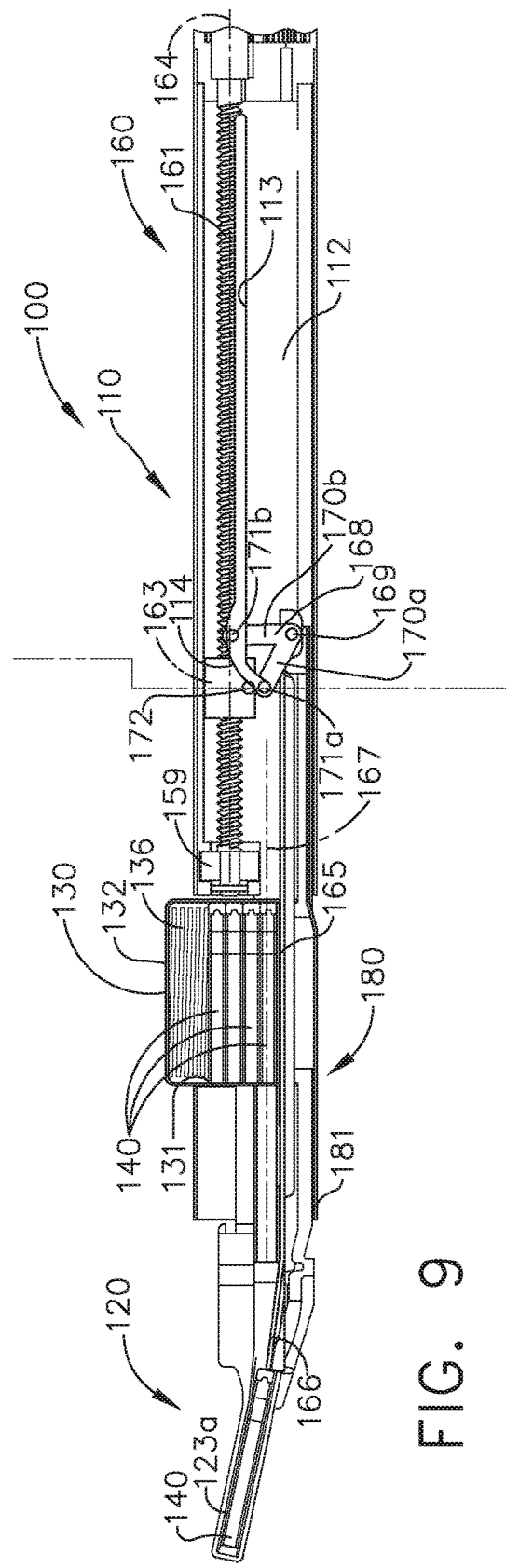
FIG. 9 is a cross-sectional view of the end effector of FIG. 2 illustrating the firing drive becoming disengaged from the firing member.

When the actuator 168 has reached the position illustrated in FIG. 6, the distal projection 171a can enter into a distal slot portion 114 of the longitudinal slot 113 which can be configured to pivot the actuator 168 downwardly, or permit the actuator 168 to be pivoted downwardly, as illustrated in FIG. 9. In at least one such embodiment, the distal projection 171a can come into contact with the sidewall of the distal slot portion 114 which can guide the distal projection 171a downwardly and pivot the actuator 168 about the pivot 169 as the actuator 168 is advanced forward by the firing nut 163. In such a pivoted position, the firing pin 172 extending from the firing nut 163 may no longer be engaged with the distal arm 170a of the actuator 168 wherein, subsequently, the firing nut 163 may move distally independently of the actuator 168 thereby leaving behind the actuator 168 and the firing member 165. Stated another way, the distal end 114 of the longitudinal shaft slot 113 may deactivate the firing member 165 wherein, at such point, the position of the firing member 165 may represent the fully-fired or distal-most position of the firing member 165. In such a position, the clip 140 has been fully advanced into the receiving cavity, or receiver, 122. Furthermore, in such a position, the next clip 140 to be advanced into the receiving cavity 122 may be biased against the top surface of the firing member 165, further to the above.

Once a clip 140 has been positioned within the receiving cavity 122, further to the above, the clip 140 can be deformed by a crimping drive 180, for example. Referring now to FIGS. 3 and 4, the end effector 120 of the clip applier 100 can further comprise a first jaw 123a and a second jaw 123b wherein the first jaw 123a and the second jaw 123b can at least partially define the receiving chamber 122. As illustrated in FIGS. 3 and 4, the first jaw 123a can comprise a first channel 124a and the second jaw 123b can comprise a second channel 124b which can each be configured to receive and support at least a portion of a clip 140 therein. The first jaw 123a can be pivotably coupled to a frame 111 of the shaft 110 by a pin 125a and the second jaw 123b can be pivotably coupled to the frame 111 by a pin 125b. In use, the crimping drive 180 can be configured to rotate the first jaw 123a toward the second jaw 123b and/or rotate the second jaw 123b toward the first jaw 123a in order to compress the clip 140 positioned therebetween. In at least one such embodiment, the crimping drive 180 can comprise a cam actuator 181 which can be configured to engage a first cam surface 126a defined on the first jaw 123a and a second cam surface 126b on the second jaw 123b in order to pivot the first jaw 123a and the second jaw 123b toward one another. The cam actuator 181 can comprise a collar which at least partially surrounds the first jaw 123a and the second jaw 123b. In at least one such embodiment, the collar can comprise an inner cam surface 182 which can be contoured to contact the cam surfaces 126a, 126b of the jaws 123a, 123b and drive them inwardly toward one another. In various circumstances, the clip 140 positioned within the receiving chamber 122 defined in the end effector 120 can be positioned relative to tissue before the crimping drive 180 is actuated. In some circumstances, the crimping drive 180 can be at least partially actuated prior to positioning the clip 140 relative to the tissue in order to at least partially compress the clip 140. In certain instances, the clip 140 and the receiving chamber 122 can be sized and configured such that the clip 140 can be biased or flexed inwardly when the end effector 120 is in its unactuated state, as illustrated in FIG. 3. In various instances, the crimping first jaw 123a and the second jaw 123b can be actuated to elastically crimp and/or permanently crimp the clip 140 positioned therebetween.

Figure 7:
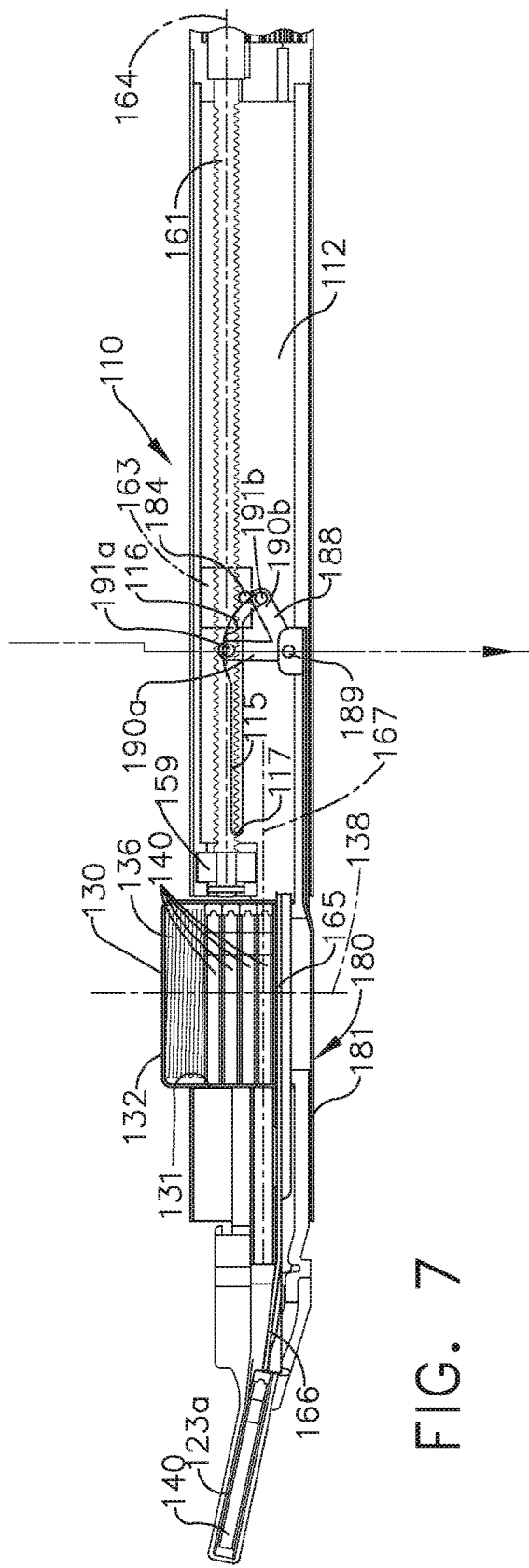
FIG. 7 is a cross-sectional view of the end effector of FIG. 2 illustrating the firing drive coming into engagement with the crimping drive.
Figure 8:
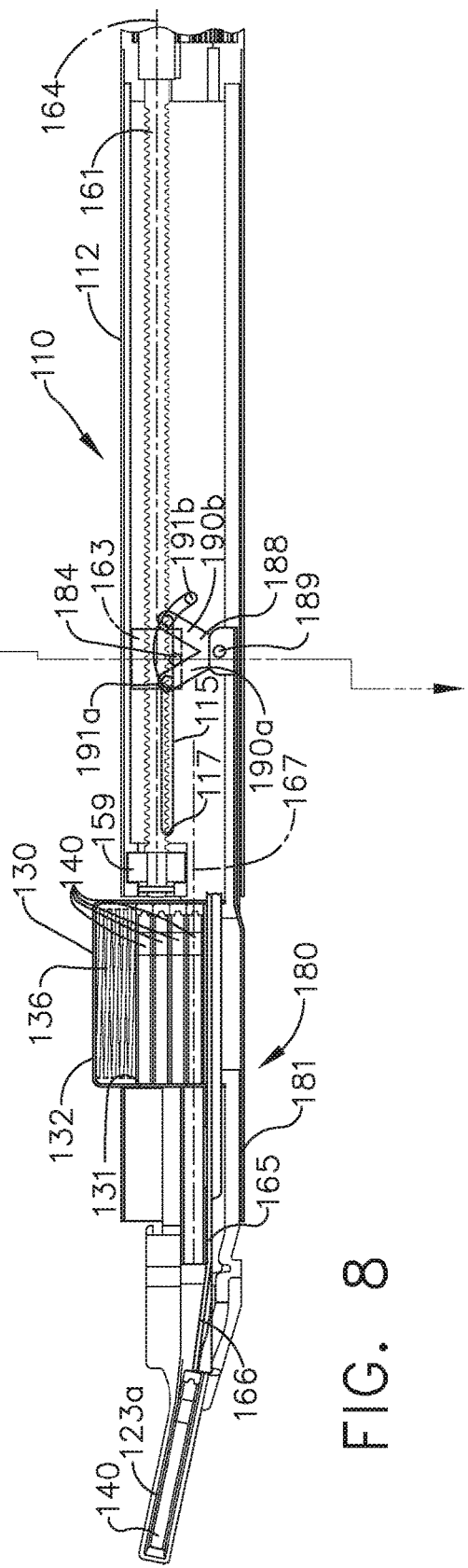
FIG. 8 is a cross-sectional view of the end effector of FIG. 2 illustrating the crimping drive in an at least partially fired condition.

Further to the above, the firing nut 163 can be configured to actuate the crimping drive 180. More particularly, referring now to FIG. 7, the crimping drive 180 can comprise a crimping actuator 188 operably coupled with the cam actuator 181 wherein the crimping actuator 188 can be selectively engaged by the firing nut 163 as the firing nut 163 is advanced distally as described above. In at least one such embodiment, the firing nut 163 can further comprise a second firing pin, such as firing pin 184, for example, extending therefrom which can be configured to engage the crimping actuator 188 as the firing nut 163 is advancing the firing actuator 168. Referring again to FIG. 7, the crimping actuator 188 is positioned in an unactuated position and, when the firing nut 163 is advanced sufficiently to engage a distal arm 190a of the crimping actuator 188, the firing nut 163 can rotate the crimping actuator 188 upwardly into an actuated position as illustrated in FIG. 8. As also illustrated in FIG. 8, the distal arm 190a and a proximal arm 190b can each comprise a projection, such as projections 191a and 191b, respectively, extending therefrom which can be positioned within a second longitudinal slot defined in shaft 110, such as slot 115, for example. As the crimping actuator 188 is rotated upwardly from its unactuated position about a pivot 189, the projections 191a and 191b can move from the proximal curved end 116 of the longitudinal slot 115 into a portion of the longitudinal slot 115 which is substantially linear. Similar to the above, the sidewalls of the longitudinal slot 115 can be configured to confine the movement of the crimping actuator 188 along a longitudinal path and can be configured to limit or prevent the rotation of the crimping actuator 188 once the crimping actuator 188 has been rotated upwardly into an at least partially actuated position, as discussed above. As the reader will understand, the firing pin 172 of the firing drive 160 and the firing pin 184 of the crimping drive 180 both extend from the firing nut 163. For the sake of expediency and demonstration, the firing pins 172 and 184 are illustrated as extending from the same side of the firing nut 163; however, it is envisioned that the firing pin 172 can extend from a first lateral side of the firing nut 163 while the firing pin 184 can extend from the other lateral side of the firing nut 163. In such circumstances, the firing actuator 168 can be positioned alongside the first lateral side of the drive screw 161 and the crimping actuator 188 can be positioned alongside the opposite lateral side of the drive screw 161. Correspondingly, the longitudinal slot 113 can be defined in a first lateral side of the shaft housing 112 while the longitudinal slot 115 can be defined in the opposite lateral side of the shaft housing 112.

Figure 10:
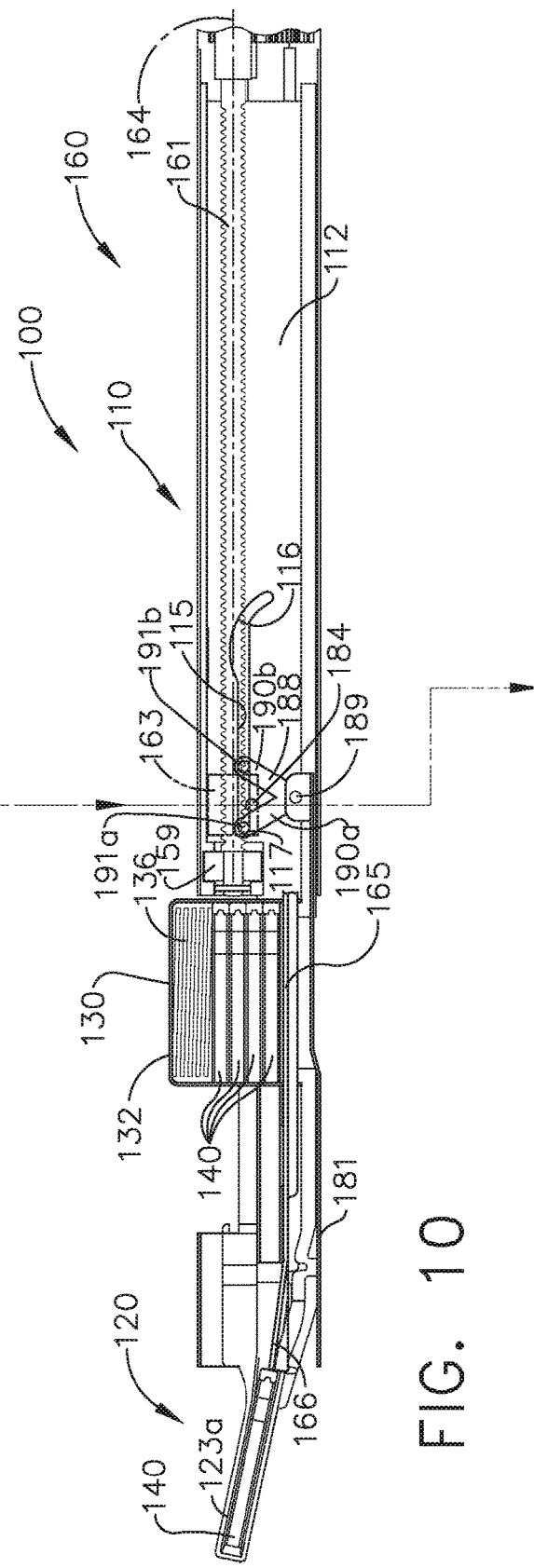
FIG. 10 is a cross-sectional view of the end effector of FIG. 2 illustrating the crimping drive in its fully fired condition.

Further to the above, the cam actuator 181 can be operably coupled with crimping actuator 188 such that, when the crimping actuator 188 is advanced distally by the firing nut 163, the cam actuator 181 can be advanced distally, as illustrated in FIGS. 8 and 10, until the distal projection 191a extending from the distal arm 190a reaches the distal end 117 of the longitudinal slot 115. In such a distal position, the cam actuator 181 may be in a fully advanced position and the clip 140 positioned within the receiving chamber 122 can be in a fully deformed or crimped configuration. Thereafter, the cam actuator 181 can be retracted and the end effector 120 can be reopened. More particularly, the drive screw 161 can be rotated in an opposite direction in order to move the firing nut 163 proximally and retract the cam actuator 181 wherein, in certain instances, the end effector 120 can further include a biasing member which can be configured to bias the first jaw 123 and the second jaw 123b from the closed, or fired, position illustrated in FIG. 4 into the open, or unfired, position illustrated in FIG. 3. As the firing nut 163 is retracted from its position illustrated in FIG. 10, the firing pin 184 extending from the firing nut 163 can engage the proximal arm 190b of the crimping actuator 188 and move the crimping actuator 188, and the cam actuator 181 extending therefrom, proximally as illustrated in FIG. 12. Similar to the above, the proximal projection 191b extending from the proximal arm 190b of the crimping actuator 188 can be configured to contact the sidewall of the curved proximal end 116 wherein the sidewall can guide the crimping actuator 188 downwardly and rotate the crimping actuator 188 about the pivot 189. At such point, the firing pin 184 may no longer be engaged with the crimping actuator 188, the cam actuator 181 may be fully retracted, and the firing nut 163 may continue to be retracted proximally relative to the crimping actuator 188.

Further to the above, referring now to FIG. 11, the firing nut 163 can be configured to re-engage the firing actuator 168 as the firing nut 163 is being retracted proximally. As discussed above, the firing actuator 168 is rotated downwardly when the firing actuator 168 reaches the distal end 114 of the longitudinal slot 113 and, as a result, the firing actuator 168 may still be in its downwardly rotated position when the firing nut 163 is retracted proximally to re-engage the firing actuator 168. As illustrated in FIG. 11, the firing pin 172 extending from the firing nut 163 can engage the proximal arm 170b of the firing actuator 168 and, as the firing nut 163 is further retracted, the firing nut 163 can rotate the firing actuator 168 upwardly such that the projections 171a and 171b extending from the arms 170a and 170b, respectively, can re-enter the longitudinal portion of the longitudinal slot 113. Thereafter, the firing nut 163 and can be retracted until the firing actuator 168 and the firing member 165 extending therefrom have been returned to their starting, or unfired, positions illustrated in FIG. 5. In such circumstances, the firing member 165 can be withdrawn from the clip cartridge 130 as the firing member 165 is retracted proximally by the firing nut 163 such that a new clip 140 can be biased into the firing chamber of the clip cartridge 130 by the biasing member 136. Once the firing member 165 and the firing actuator 168 have been retracted to their starting positions and the next clip 140 has been positioned within the firing chamber, the firing drive 160 can be actuated once again in order to move the firing nut 163 and the firing member 165 distally to advance the next clip 140 into the end effector 120. Likewise, the firing nut 163 can re-actuate the crimping drive 180 as the firing nut 163 is moved distally once again in order to deform the next clip 140. Thereafter, the firing nut 163 can retracted in order to re-set the crimping drive 180 and the firing drive 160 once again. This process can be repeated until a sufficient number of clips 140 have been applied to the targeted tissue and/or until the clips 140 contained within the clip cartridge 130 have been depleted. In the event that additional clips 140 are needed, the expended clip cartridge 130 can be removed from the shaft 110 and a replacement clip cartridge 130 containing additional clips 140 can be inserted into the shaft 110. In some circumstances, an at least partially depleted clip cartridge 130 can be replaced with an identical, or at least nearly identical, replacement clip cartridge 130 while, in other circumstances, the clip cartridge 130 can be replaced with a clip cartridge having more than or less than five clips 140 contained therein and/or a clip cartridge having clips other than clips 140 contained therein, for example.

Referring again to FIGS. 6-9, the firing nut 163 of the illustrated embodiment can be configured to become disengaged from the firing actuator 168 at the same time that the firing nut 163 becomes engaged with the crimping actuator 188. Stated another way, the firing drive 160 can be deactivated at the same time that the crimping drive 180 is activated. In various circumstances, such timing can be achieved when the distal end 114 of the longitudinal slot 113 is aligned, or at least substantially aligned, with the proximal end 116 of the second longitudinal slot 115, for example. In the illustrated embodiment and/or any other suitable embodiment, a lag can exist between the deactivation of the firing drive 160 and the activation of the crimping drive 180. Such a lag between the end of the firing stroke of the firing member 165 and the beginning of the firing stroke of the cam actuator 181 can be created, in some circumstances, to assure that the clip 140 has been positioned in its fully-seated position within the receiving chamber 122 before the clip 140 is deformed by the cam actuator 181. In various circumstances, such a lag can be created when the distal end 114 of the longitudinal slot 113 is positioned proximally with respect to the proximal end 116 of the second longitudinal slot 115, for example. In the illustrated embodiment and/or any other suitable embodiment, the deactivation of the firing drive 160 may occur after the activation of the crimping drive 180. Such an overlap between the end of the firing stroke of the firing member 165 and the beginning of the firing stroke of the cam actuator 181 can be created, in some circumstances, to apply at least some inward pressure on the clip 140 as it is moved into its fully-seated position within the receiving chamber 122 so as to reduce or eliminate relative movement between the clip 140 and the sidewalls of the receiving chamber 122, for example. In various circumstances, such an overlap can be created when the distal end 114 of the longitudinal slot 113 is positioned distally with respect to the proximal end 116 of the second longitudinal slot 115, for example.

Figure 17:
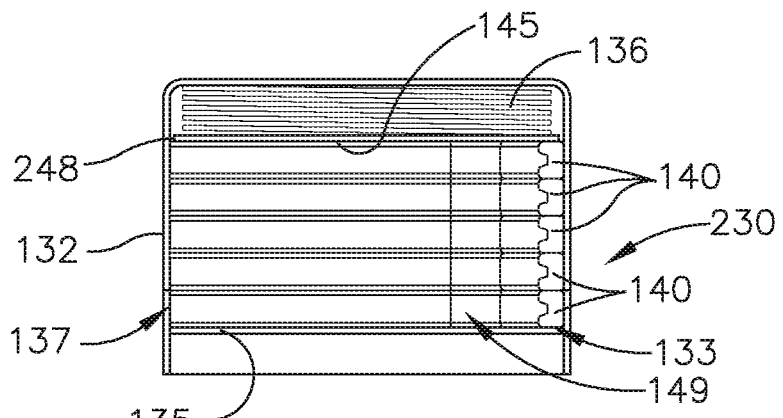
FIG. 17 is a side view of an alternative cartridge usable in connection with the clip applier of FIGS. 1-12 or any other suitable clip applier, wherein the cartridge is illustrated with portions removed to illustrate a biasing member and a pusher plate positioned intermediate the biasing member and the clips contained therein.

In the illustrated embodiment of FIG. 1 and/or any other suitable embodiment, turning now to FIG. 17, a clip cartridge, such as clip cartridge 230, for example, can comprise a pusher plate 248 positioned intermediate the biasing member 136 and the top-most clip 140 stacked within the clip cartridge 230. The pusher plate 248 can be rigid, or at least substantially rigid, and can comprise a first bearing surface against which the biasing member 136 can apply a biasing force. The pusher plate 248 can also comprise a second bearing surface which can transmit the biasing force to the top surface 145 of the top-most clip 140. The pusher plate 248 can be comprised of a sheet of stainless steel material, for example, although the pusher plate 248 can comprise any suitable shape and can be comprised of any suitable material. In certain instances, the pusher plate 248 may not be attached to the biasing member 136 while, in other instances, the pusher plate 248 can be affixed to the biasing member 136 such that the pusher plate 248 does not become dislodged from the cartridge housing 132. In various circumstances, the pusher plate 248 can be sized and configured such that it cannot pass through the proximal opening 133 and/or the distal opening 137 defined in the cartridge housing 132.

Figure 18:
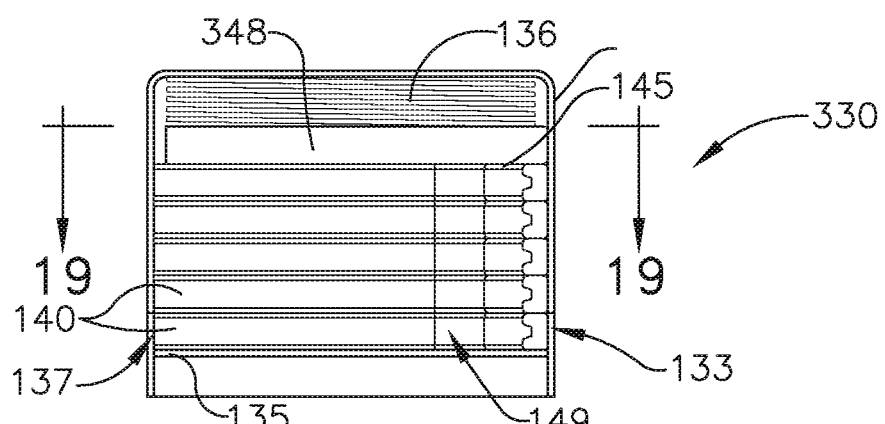
FIG. 18 is a side view of a cartridge in accordance with at least one alternative embodiment illustrated with portions removed to illustrate a biasing member and a lockout plate positioned intermediate the biasing member and the clips contained therein.
Figure 19:
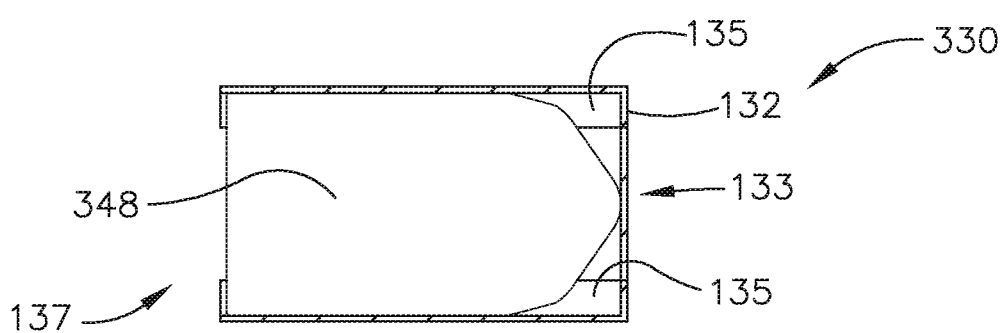
FIG. 19 is a cross-sectional plan view of the cartridge of FIG. 18 taken along line 19-19 in FIG. 18.

In the illustrated embodiment of FIG. 1 and/or any other suitable embodiment, turning now to FIGS. 18 and 19, a clip cartridge, such as clip cartridge 330, for example, can comprise a lockout member which can be positioned within the firing chamber 149 of the clip cartridge 330 after all of the clips 140 contained within the clip cartridge 330 have been ejected from the cartridge 330. The lockout member can comprise a lockout plate 348 which can be positioned intermediate the biasing member 136 and the top surface 145 of the top-most clip 140 contained within the clip cartridge 330. In use, further to the above, the clips 140 can be sequentially positioned in the firing chamber 149 of the clip cartridge 130 and then advanced distally out of the clip housing 132 wherein, after the last clip 140 has been advanced out of the clip housing 132 and the firing member 165 has been withdrawn from the clip cartridge 130, the biasing member 136 can bias the lockout plate 348 against the shelves 135. In such a position, the lockout plate 348 can be aligned with the proximal opening 133 and the distal opening 137 such that the firing member 165 cannot enter, or at least substantially enter, the clip cartridge 130. In such circumstances, the lockout plate 348 can block the firing member 165 from entering into and passing through the housing 132 and, as a result, prevent the inadvertent firing of the clip applier 100 after the clip cartridge 130 has run out of clips. In the event that the operator of the clip applier 100 were to actuate the firing drive 160 and attempt to advance the firing member 165 into the spent clip cartridge 130, the firing member 165 would contact and abut the lockout plate 348 wherein, in such circumstances, a compressive load can be created within the firing member 165. The clip applier 100 can further include a clutch which can be configured to slip and operably disconnect the motor from the drive screw 161 when the compressive load created within the firing member 165 exceeds a certain or predetermined amount. In addition to or in lieu of a clutch, the motor and/or motor controller of the clip applier 100 which operates the firing drive 160, for example, can comprise a load sensor configured to detect the load generated within the firing member 165 and, when the load created within the firing member 165 exceeds a certain or predetermined amount, the voltage and/or current supplied to the motor can be switched off and/or reduced. In any event, the lockout plate 348 can be sized and configured such that the lockout plate 348 cannot be dislodged through the distal opening 137 and/or the proximal opening 133 when the firing member 165 contacts the lockout plate 348. In order to use the clip applier 100 once again, the operator of the clip applier 100 can remove the spent cartridge 330 from the shaft 110 and insert a new clip cartridge 330, for example, into the shaft 110. At such point, a clip 140 may be positioned within the firing chamber 149 of the new clip cartridge 330 and the firing member 165 can be advanced distally into the new clip cartridge 330 to deploy the clip 140 as described above.

Figure 20:
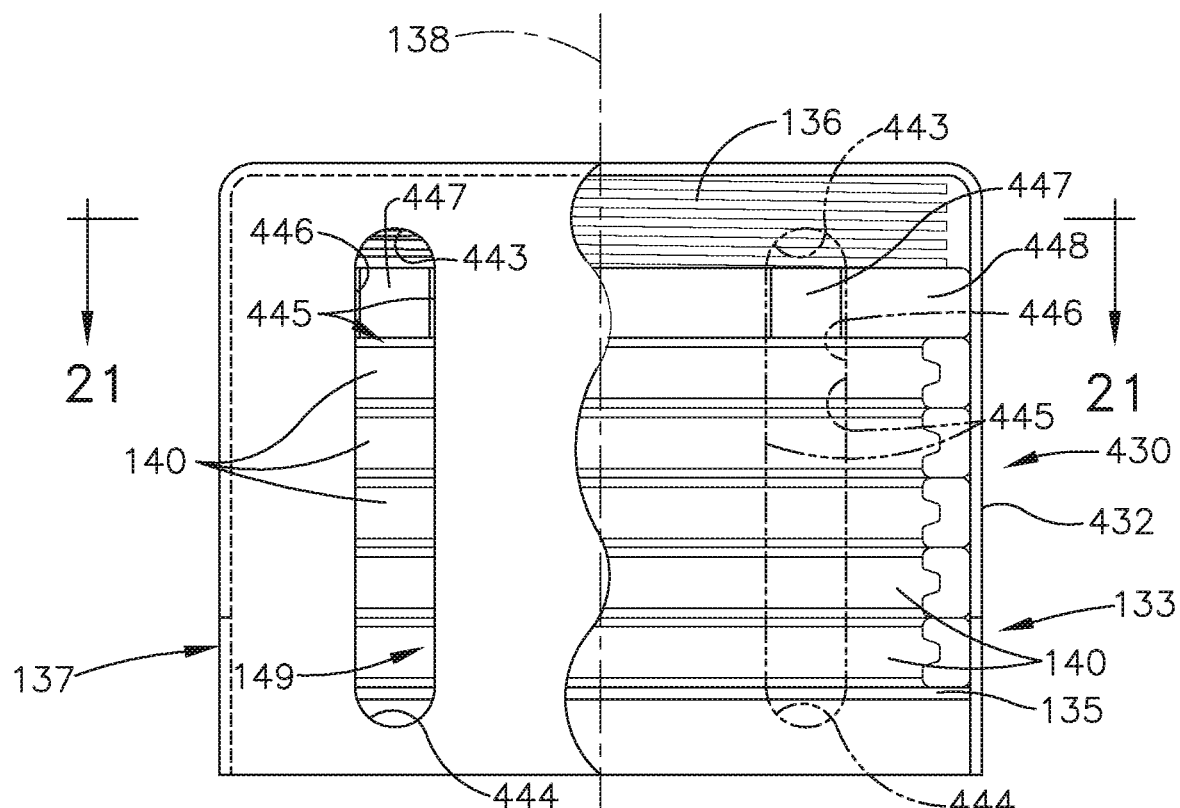
FIG. 20 is a side view of a further alternative cartridge usable in connection with the clip applier of FIGS. 1-12 or any other suitable clip applier, wherein the cartridge can comprise a housing illustrated with portions removed to illustrate a lockout plate comprising guides which are configured to co-operate with guides defined in the cartridge housing.
Figure 21:
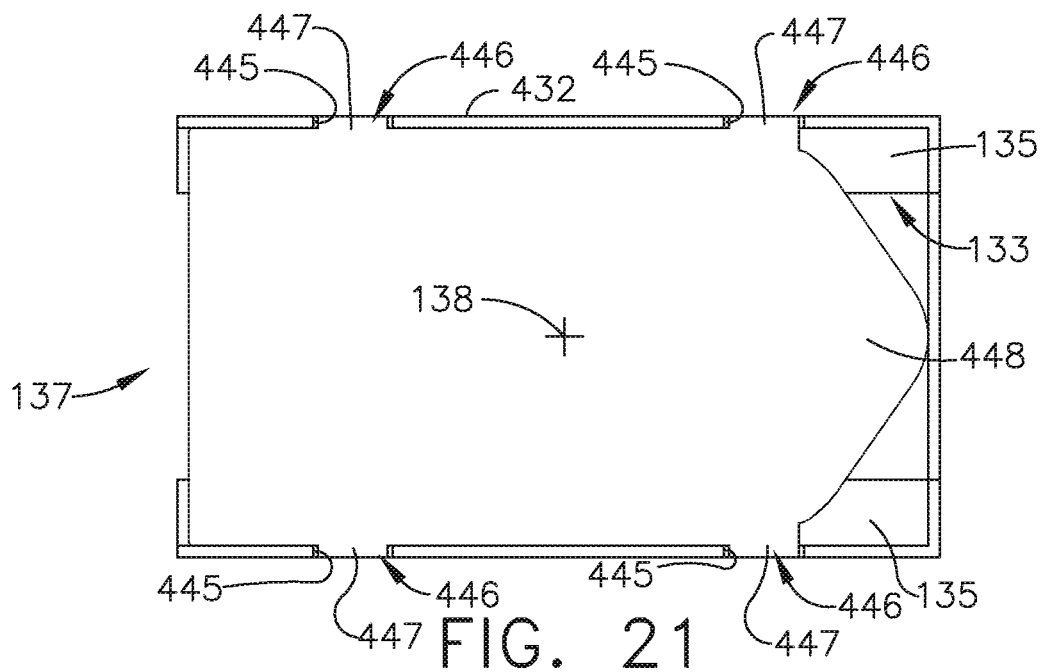
FIG. 21 is a cross-sectional plan view of the cartridge of FIG. 20 taken along line 21-21 in FIG. 20.

In the illustrated embodiment of FIG. 1 and/or any other suitable embodiment, referring now to FIGS. 20 and 21, a clip cartridge, such as clip cartridge 430, for example, can comprise guides which can be configured to limit or confine the movement of a lockout member within the clip cartridge 430. Similar to the above, the lockout member can comprise a lockout plate 448, for example, which can be positioned intermediate the biasing member 136 and the top surface 145 of the top-most clip 140 contained within the housing 432 of the clip cartridge 430. In use, similar to the above, the lockout plate 448 can be progressively pushed downwardly into the firing chamber 149 as the clips 140 are sequentially ejected from the clip cartridge 430. The lockout plate 448 can be sized and configured such that it is closely received within the cartridge housing 432 and such that relative lateral movement between the lockout plate 448 and the housing 432 can be limited in order to reduce, or prevent, the possibility of the lockout plate 448 becoming misaligned within the clip cartridge 430. In the event that the lockout plate 448 were to become misaligned within the clip cartridge 430, the lockout plate 448 may bind within the housing 432 and prevent the biasing member 136 from applying an appropriate biasing force to the stack of clips 140, for example. As illustrated in FIGS. 20 and 21, the lockout plate 438 can further comprise guide members 447 extending therefrom which can be received within guide slots 446 defined in the cartridge housing 432. The guide members 447 and the guide slots 446 can be sized and configured such that the guide members 447 are closely received within the guide slots 446 and such that relative lateral movement between the lockout plate 438 and the cartridge housing 432 can be limited. Each of the guide slots 446 can be defined by opposing sidewalls 445 which can define a distance therebetween which is equal to or slightly larger than the width of the guide member 447 positioned therein such that the guide member 447 can slide between the opposing sidewalls 445 between the top 443 and the bottom 444 of the guide slot 446. Thus, while the guide members 447 and the guide slots 446 can be configured to limit lateral movement therebetween, as outlined above, the guide members 447 and the guide slots 446 can be configured to permit relative movement between the lockout plate 438 and the cartridge housing 432 along a predetermined path parallel to or collinear with the supply axis 138, for example. When the lockout plate 438 is pushed into the firing chamber 149 by the biasing member 136, the lockout plate 438 can inhibit the advancement of the firing member 165 and the operation of the clip applier 100, as outlined above, until the spent clip cartridge 430 is replaced with another suitable clip cartridge.

Figure 22:
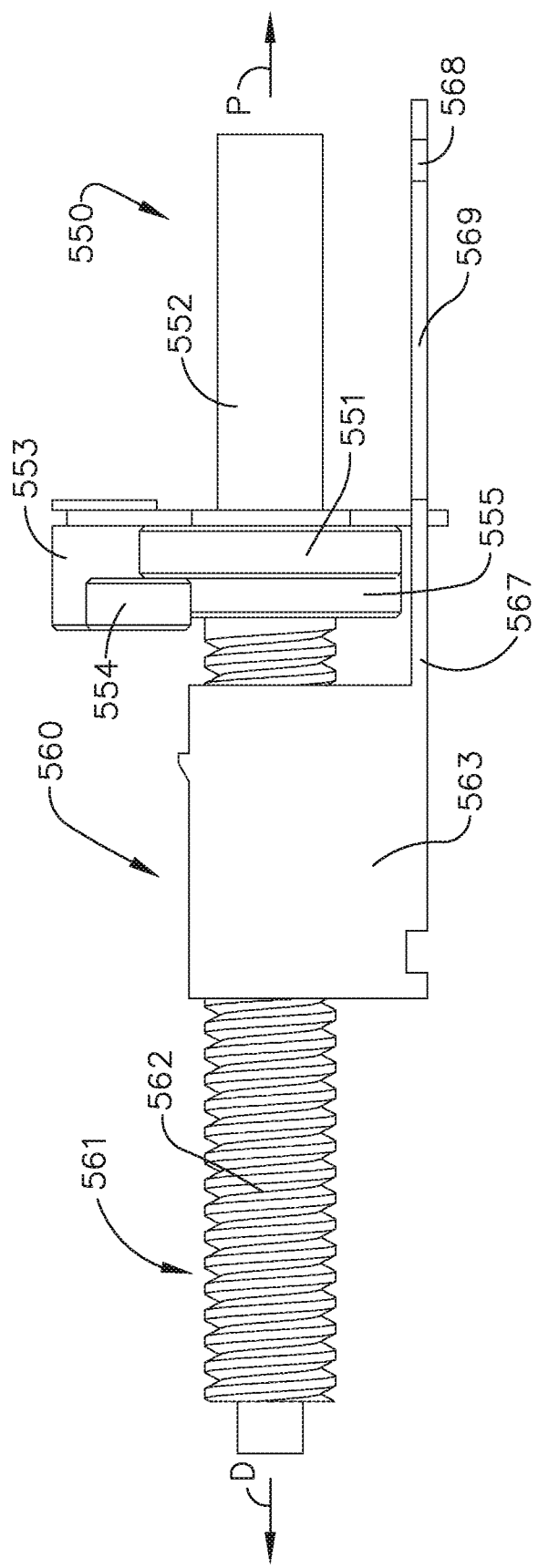
FIG. 22 is an elevational view of a firing drive comprising a rotary input, a rotary output, a firing nut engaged with the rotary output, and a transmission in a firing configuration in accordance with at least one embodiment.
Figure 23:
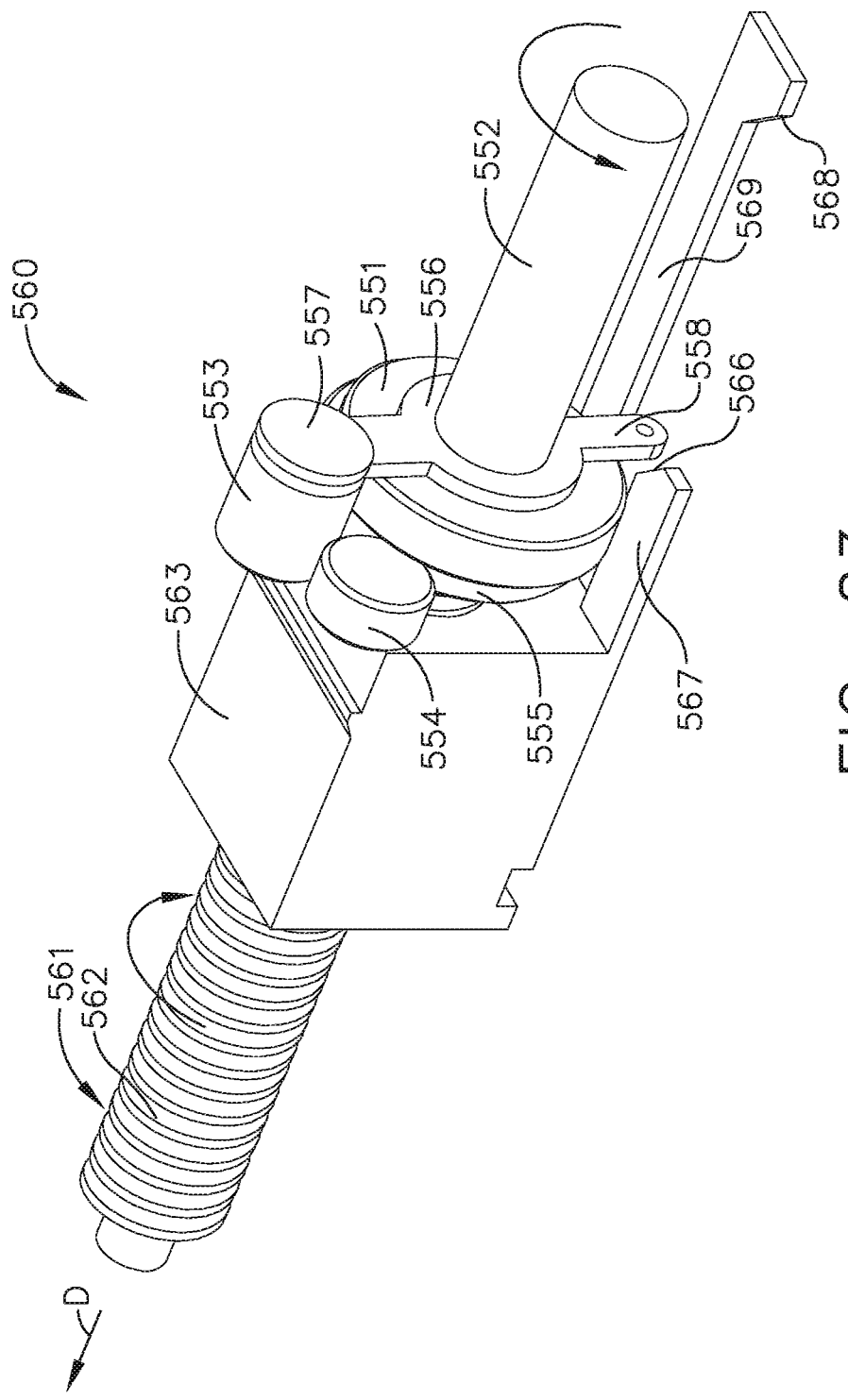
FIG. 23 is a perspective view of the firing drive of FIG. 22 illustrating the firing nut in an unfired position.
Figure 24:
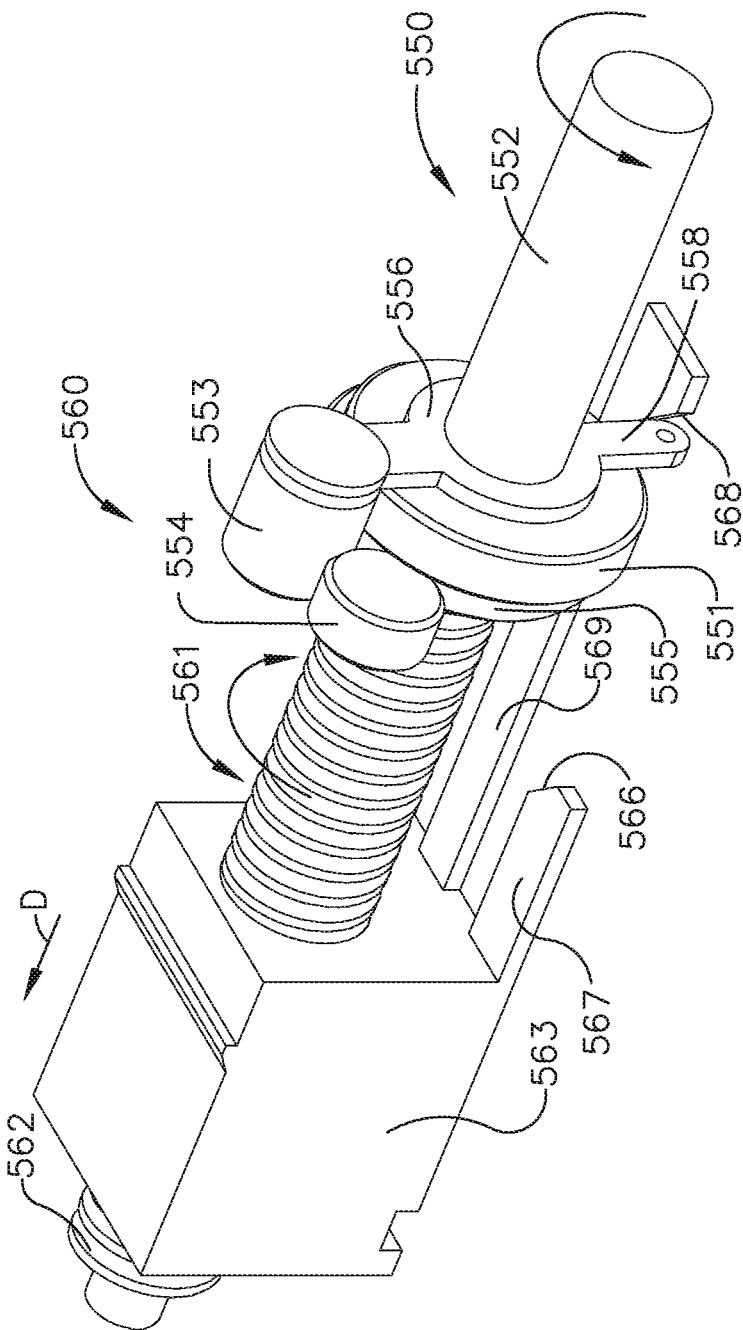
FIG. 24 is a perspective view of the firing drive of FIG. 22 illustrating the firing nut advanced along the rotary output and a cam extending from the firing nut.
Figure 25:
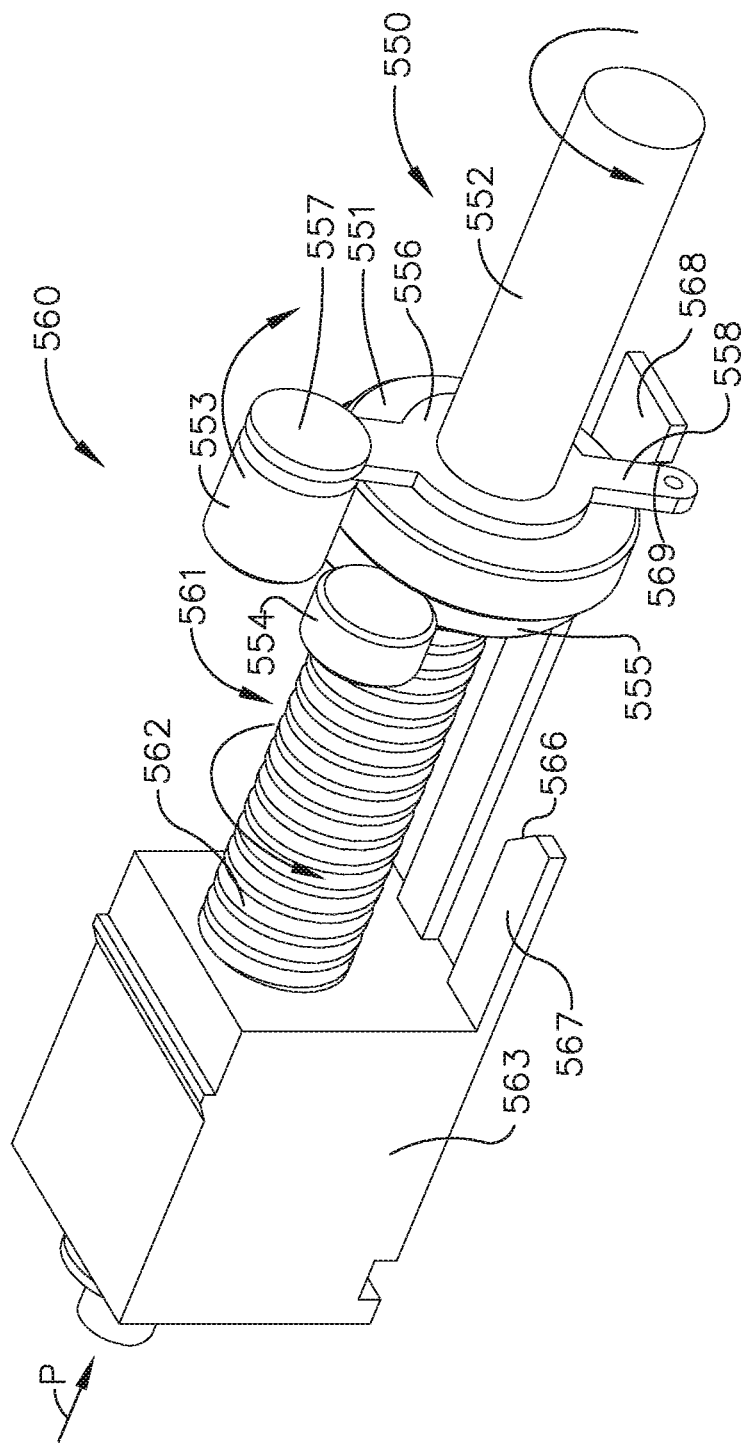
FIG. 25 is a perspective view of the firing drive of FIG. 22 illustrating the cam of the firing nut engaged with the transmission of the firing drive and the transmission in a reverse configuration.
Figure 26:
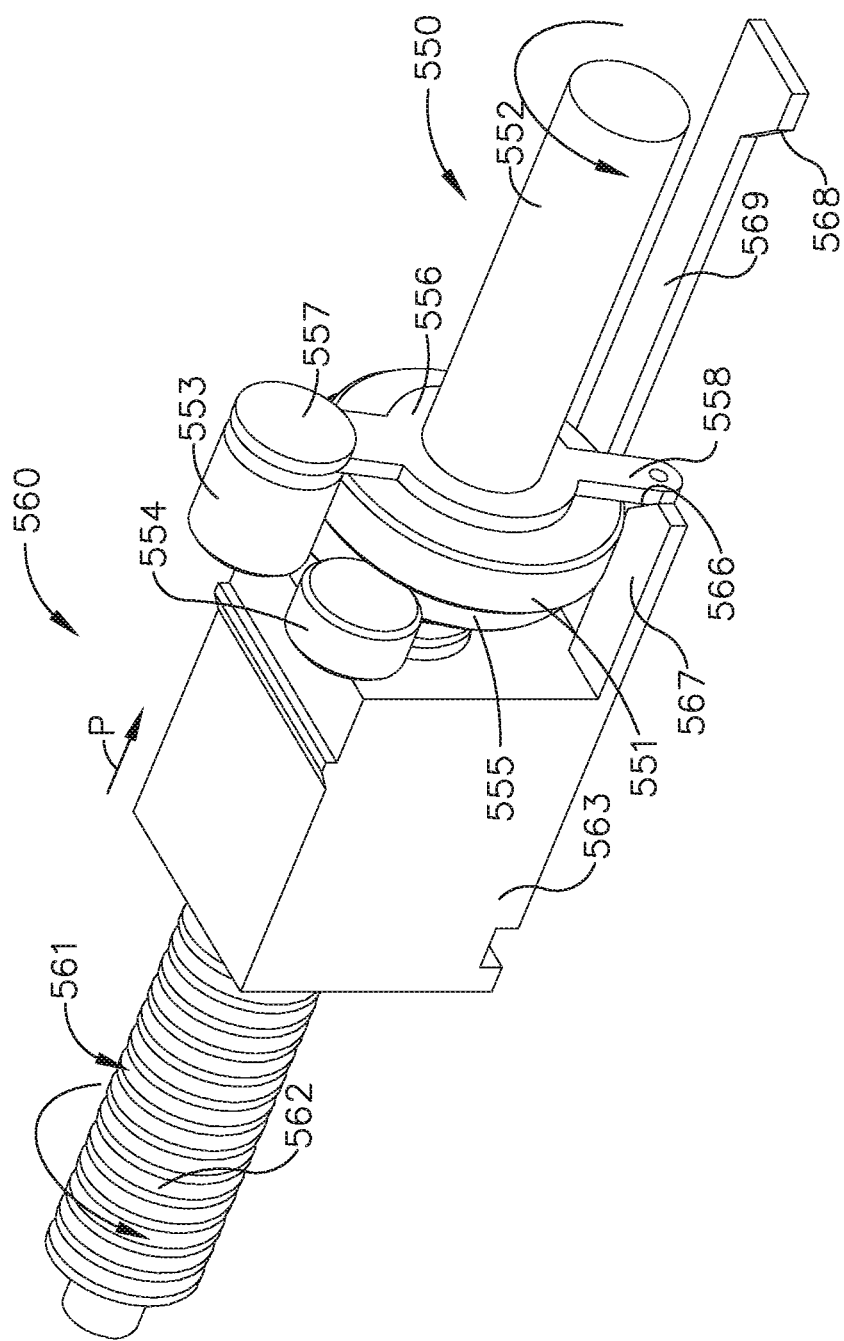
FIG. 26 is a perspective view of the firing drive of FIG. 22 illustrating firing nut in a retracted position and a second cam extending from the firing nut engaged with the transmission to shift the transmission from its reverse configuration to its firing configuration.

In the illustrated embodiment of FIG. 1 and/or any other suitable embodiment, as discussed above, the drive screw 161 can be rotated in a first direction to advance the firing nut 163 distally and rotated in a second, or reverse, direction to retract the firing nut 163 proximally. In order to rotate the drive screw 161 in the first and second directions, the electric motor operably coupled with the drive screw 161 can be operated in corresponding first and second directions. In the illustrated embodiment of FIG. 1 and/or any other suitable embodiment, a clip applier can utilize a motor which is operated in only a first direction wherein the rotation of the motor in such a single direction can be utilized to advance a firing nut distally and retract the firing nut proximally. Turning now to FIGS. 22-26, the output of an electric motor can be transmitted to a drive system 560 via a transmission system 550. The transmission system 550 can comprise an input shaft 552 which is operated in a single direction wherein the transmission system 550 can be switchable or shiftable between a first state, or configuration, in which the transmission system 550 rotates a drive screw 561 of the drive system 560 in a first direction and a second state, of configuration, in which the transmission system 550 rotates the drive screw 561 in a second, or opposite, direction. The first state of the transmission system 550 is depicted in FIGS. 22-24 and the second state of the transmission system 550 is depicted in FIGS. 25 and 26.

Referring again to FIGS. 22-24, the input shaft 552 can comprise an input gear 551 mounted thereto which is operably coupled, or meshingly engaged, with a shifter gear 553 such that the rotation of the input shaft 552 is transmitted to the shifter gear 553. With regard to all of the gears discussed herein, gears which are operably coupled or meshingly engaged with one another can comprise any suitable arrangement of teeth, for example, which can transmit the rotation of one gear to the other. When the input shaft 552 is rotated in the first direction, the shifter gear 553 is rotated in the second, or opposite, direction. In the first state of the transmission system, the shifter gear 553 is in a first position in which the shifter gear 553 is operably coupled with an intermediate gear 554 wherein, when the shifter gear 553 is rotated in the second direction by the input gear 551, as discussed above, the intermediate gear 554 is rotated in the first direction. Although not illustrated, the intermediate gear 554 can be rotatably supported within the shaft 110 of the clip applier 100, for example. The intermediate gear 554 can also be operably coupled with an output gear 555 mounted to the drive screw 561 such that the rotation of the intermediate gear 554 can be transmitted to the output gear 555. When the intermediate gear 554 is driven in the first direction by the shifter gear 553, as described above, the intermediate gear 554 can drive the output gear 555 and the drive screw 561 in the second direction. Similar to the above, the firing nut 563 can be operably coupled with the drive screw 561 and suitably constrained within the shaft 110 such that, when the drive screw 561 is rotated in the second direction, the firing nut 563 is advanced distally as indicated by the arrow D.

Similar to the above, the firing nut 563 can be advanced to its distal-most position, illustrated in FIG. 24, in order to advance a clip 140 from the clip cartridge 130 into the end effector 120 and crimp the clip 140 as described above. As illustrated in FIGS. 23 and 24, the firing nut 563 can further comprise a cam bar 569 extending therefrom which can be configured to shift the transmission system 550 from its first state to its second state. Upon comparing FIG. 24 and FIG. 25, the reader will note that the shifter gear 553 is movable between a first position in which the transmission system 550 is in its first state and a second position in which the transmission system 550 is in its second state. More particularly, the shifter gear 553 is mounted to a shifter 556 which is rotatable about the input shaft 552 such that the shifter gear 553 can be rotated from its first position in which the shifter gear 553 is operably engaged with the input gear 551 and the intermediate gear 554 and its second position in which the shifter gear 553 is operably disengaged from the intermediate gear 554. Although the shifter gear 553 is operably disengaged from the intermediate gear 554 when the shifter gear 553 is in its second position, the shifter gear 553 can be operably coupled with the input gear 551 and the output gear 555 in order to transmit rotary motion from the input shaft 552 to the drive screw 561. As illustrated in FIGS. 24 and 25, the shifter 556 can comprise a central aperture through which the input shaft 552 can extend; however, the shifter 556 may not be operably engaged with the input shaft 552 and, as a result, the rotation of the input shaft 552 may not rotate the shifter 556 and, likewise, the rotation of the shifter 556 may not rotate the input shaft 552. In any event, the shifter 556 can further comprise a cam follower 558 extending therefrom which can be engaged by a cam 568 defined on the cam bar 569 as the firing nut 563 is advanced distally. When the cam 568 engages the cam follower 558, the cam 568 can rotate the shifter 556 and the shifter gear 553 between its first position and its second position as described above.

When the shifter gear 553 is in its second position and the transmission system 550 is in its second state, as described above, the input shaft 552 and the drive screw 561 can both be rotated in the first direction. More particularly, the input shaft 552, when rotated in the first direction, can rotate the input gear 551 in the first direction and, as the shifter gear 553 is directly engaged with the input gear 551, the shifter gear 553 will be rotated in the second direction. The reader will note that the shifter gear 553 rotates in the second direction when the transmission system 550 is in its second state as compared to the first, or opposite, direction when the transmission system 550 is in its first state. Upon comparing FIGS. 24 and 25, further to the above, the reader will appreciate that the intermediate gear 554 is no longer operably positioned intermediate the input gear 551 and the shifter gear 553 when the transmission system 550 is in its second state thereby accounting for the different directions of rotation. As the shifter gear 553 is operably engaged with the input gear 551 and the output gear 555 when the shifter gear 553 is in its second position, the shifter gear 553 can rotate the output gear 555, and the drive screw 561 coupled to the output gear 555, in the first direction. When the drive screw 561 is rotated in the first direction, as illustrated in FIGS. 25 and 26, the firing nut 563 can be retracted proximally to permit the end effector 120 to be reopened and to retract the firing member 165. Referring primarily to FIG. 26, the firing nut 563 can further comprise a second cam bar 567 extending therefrom comprising a cam 566 which can be configured to contact the cam follower 558 of the shifter 556 as the firing nut 563 is retracted proximally into its fully-retracted position. In such circumstances, the cam 566 can push the shifter 556 back into its first position and into operative engagement with the intermediate gear 554 such that the transmission system 550 can be reset into its first state and the clip applier 100 can be actuated once again.

Figure 27:
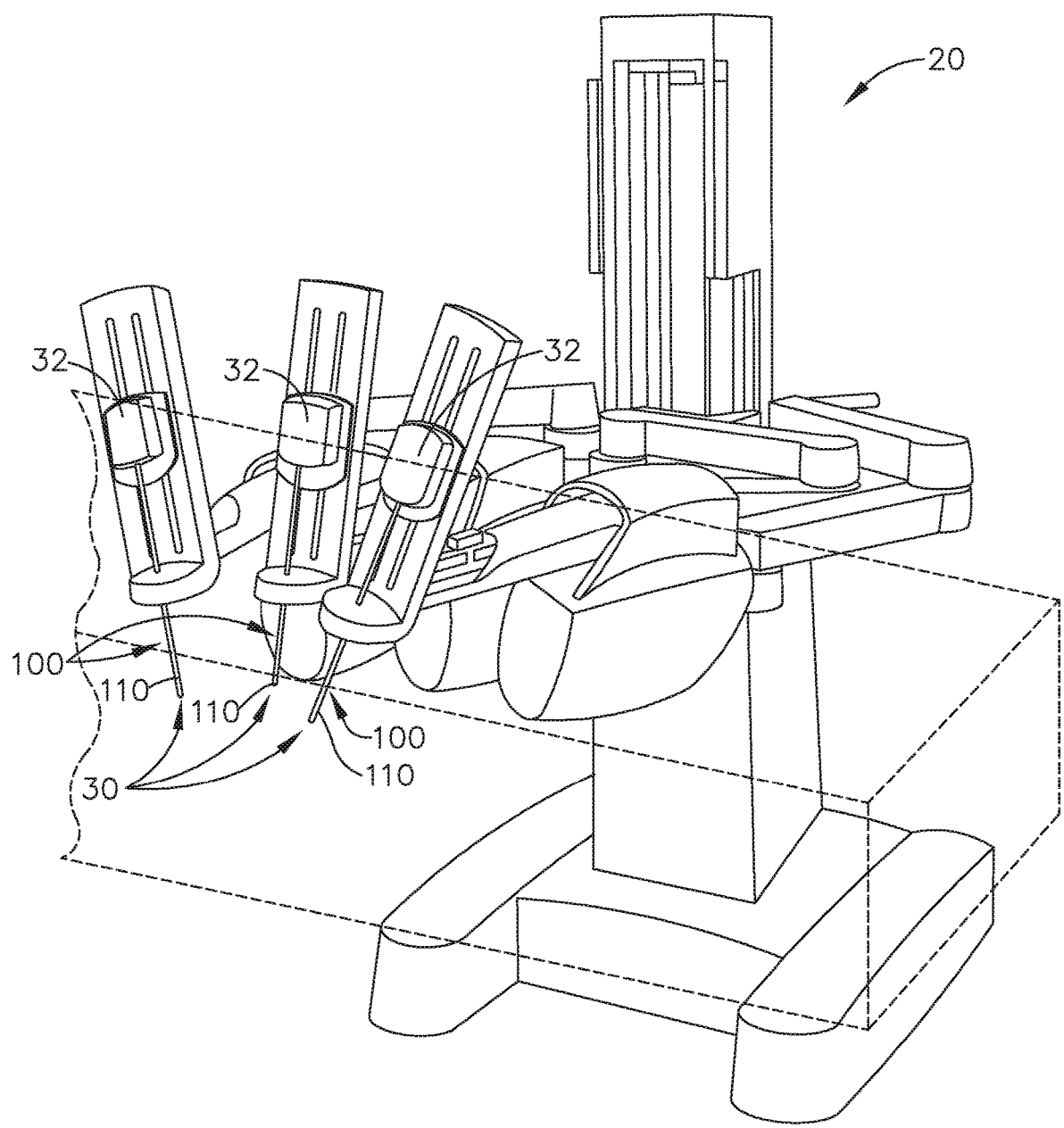
FIG. 27 is a perspective view of a robotic surgical instrument system operably supporting a plurality of surgical tools usable with the clip applier of FIGS. 2-12 or any other suitable clip applier.
Figure 28:
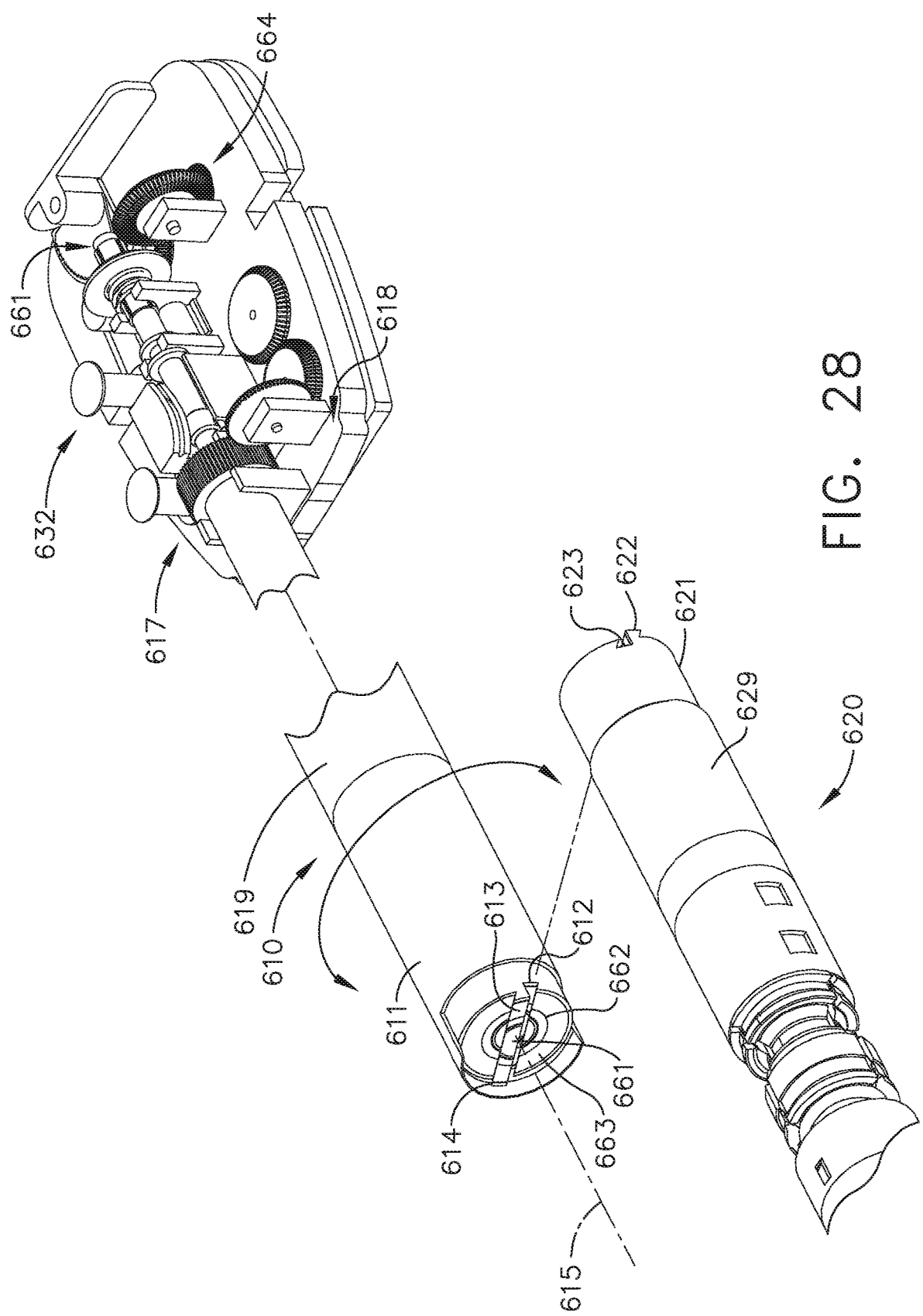
FIG. 28 is a perspective view of a surgical tool including an actuator module, a shaft extending from the actuator module, and a replaceable end effector.

As discussed above, the firing drive of the clip applier 100 can be operated by a surgical instrument system comprising an electric motor. A robotic surgical instrument system 20 is illustrated in FIG. 27 and can comprise a plurality of movable arms 30. Each arm 30 can comprise an actuator module 32 comprising an electric motor configured to supply the rotary motion to the shaft 110 of a clip applier 100, and/or any other suitable surgical instrument. Referring now to FIG. 28, an end effector 620 may be selectively engageable with and disengageable from an actuator shaft 610 of a clip applier wherein the end effector 620 can comprise a proximal end 621 which can be coupled to a distal end 611 of the shaft 610. The proximal end 621 of the end effector 620 can comprise an outer housing 629, a frame extending through the outer housing 629, an outer drive shaft extending through the frame, and an inner drive shaft extending through the outer drive shaft. Similarly, the distal end 611 of the shaft 610 can comprise an outer housing 619, a frame 663 extending through the outer housing 619, an outer drive shaft 662 extending through the frame 663, and an inner drive shaft 661 extending through the outer drive shaft 662. With regard to the distal end 611 of the shaft 610, the frame 663, the outer drive shaft 662, and the inner drive shaft 661 can each comprise a portion of a tongue connector 613 extending therefrom and a portion of a connector groove 612 defined therein, wherein the tongue connector 613 can be configured to be received within a tongue groove 623 defined in the proximal end 621 of the end effector 620, and wherein the tongue groove 612 can be configured to receive a tongue connector 622 extending from the proximal end 621 of the end effector 620. Similar to the tongue connector 613 which extends across the frame 663, the outer drive shaft 662, and the inner drive shaft 661 of the distal shaft end 611, the tongue connector 622 can extend across the frame, the outer drive shaft, and the inner drive shaft of the proximal end 621 of the end effector 620. Also, similar to the tongue groove 612 which extends across the frame 663, the outer drive shaft 662, and the inner drive shaft 661 of the distal shaft end 611, the tongue groove 623 can extend across the frame, the outer drive shaft, and the inner drive shaft of the proximal end 621 of the end effector 620. In the configuration depicted in FIG. 28, the tongue connector 622 of the end effector 620 can be slid laterally into the tongue groove 612 of the shaft 610 at the same time that the tongue connector 613 of the shaft 610 is slid laterally into the tongue groove 623 of the end effector 620. Owing to such assembly, the frame of the end effector 620 can be securely coupled to the frame 663 of the shaft 610, the outer drive shaft of the end effector 620 can be operably coupled to the outer drive shaft 662 of the shaft 110, and the inner drive shaft of the end effector 620 can be operable coupled to the inner drive shaft 661 of the shaft 110. The reader will note that the portions of the tongue connector 612 are aligned with one another, the portions of the tongue groove 613 are aligned with one another, the portions of the tongue groove 622 are aligned with one another, and the portions of the tongue connector 623 are aligned with one another when the end effector 620 is assembled to the shaft 610. Once assembled, the outer drive shaft 662 of the shaft 110 can rotate the outer drive shaft of the end effector 620, and the inner drive shaft 661 of the shaft 610 can rotate the inner drive shaft of the end effector 620. When the outer drive shaft 662 and/or the inner drive shaft 661 are rotated, the portions of the tongue connector 612, the portions of the tongue groove 613, the portions of the tongue groove 622, and the portions of the tongue connector 623 may no longer be aligned. In order to remove the end effector 620 from the shaft 610, the inner drive shaft 661 and/or the outer drive shaft 662 can be rotated into one or more positions in which the tongue connectors 612 and 623 and the tongue grooves 613 and 622 are sufficiently aligned.

Referring again to FIG. 28, the outer housing 619 of the shaft 610 can further comprise a stop 614 which can be configured to limit the lateral movement of the end effector 620 as the end effector 620 is being slid transversely onto the distal end 611 of the shaft 610. The stop 614 can provide a datum from which the inner drive shaft of the end effector 620 and the inner drive shaft 661 of the shaft 610 are aligned along longitudinal axis 615, the outer drive shaft of the end effector 620 and the other drive shaft 662 of the shaft 610 are aligned along longitudinal axis 615, and/or the frame of the end effector 620 and the frame 663 of the shaft 610 are aligned along the longitudinal axis 615. Further to the above, the inner drive shaft 661 can extend into an actuator module 632 which can comprise an electric motor and/or gear train 664 operably coupled with the inner drive shaft 661 configured to rotate the inner drive shaft 661. Furthermore, the actuator module 632 can comprise a second electric motor and gear train operably engaged with the second drive shaft 662 configured to drive the second drive shaft 662. As described in greater detail below, a second electric motor can be utilized to articulate the end effector 620. Also, further to the above, the outer housing 619 and/or the frame 663 of the shaft 610 can further comprise a gear 617 mounted thereto which is operably engaged with an electric motor and gear train 618 which can be configured to rotate the shaft 610 and the end effector 620 about the longitudinal axis 615. For instance, if the electric motor and gear train 618 are operated in a first direction, the shaft 610 and the end effector 620 can be rotated about the axis 615 in a clockwise direction while, if the electric motor and gear train 618 are operated in a second direction, the shaft 610 and the end effector 620 can be rotated about the axis 615 in a counter-clockwise direction in order to position and orient the end effector 620.

Figure 29:
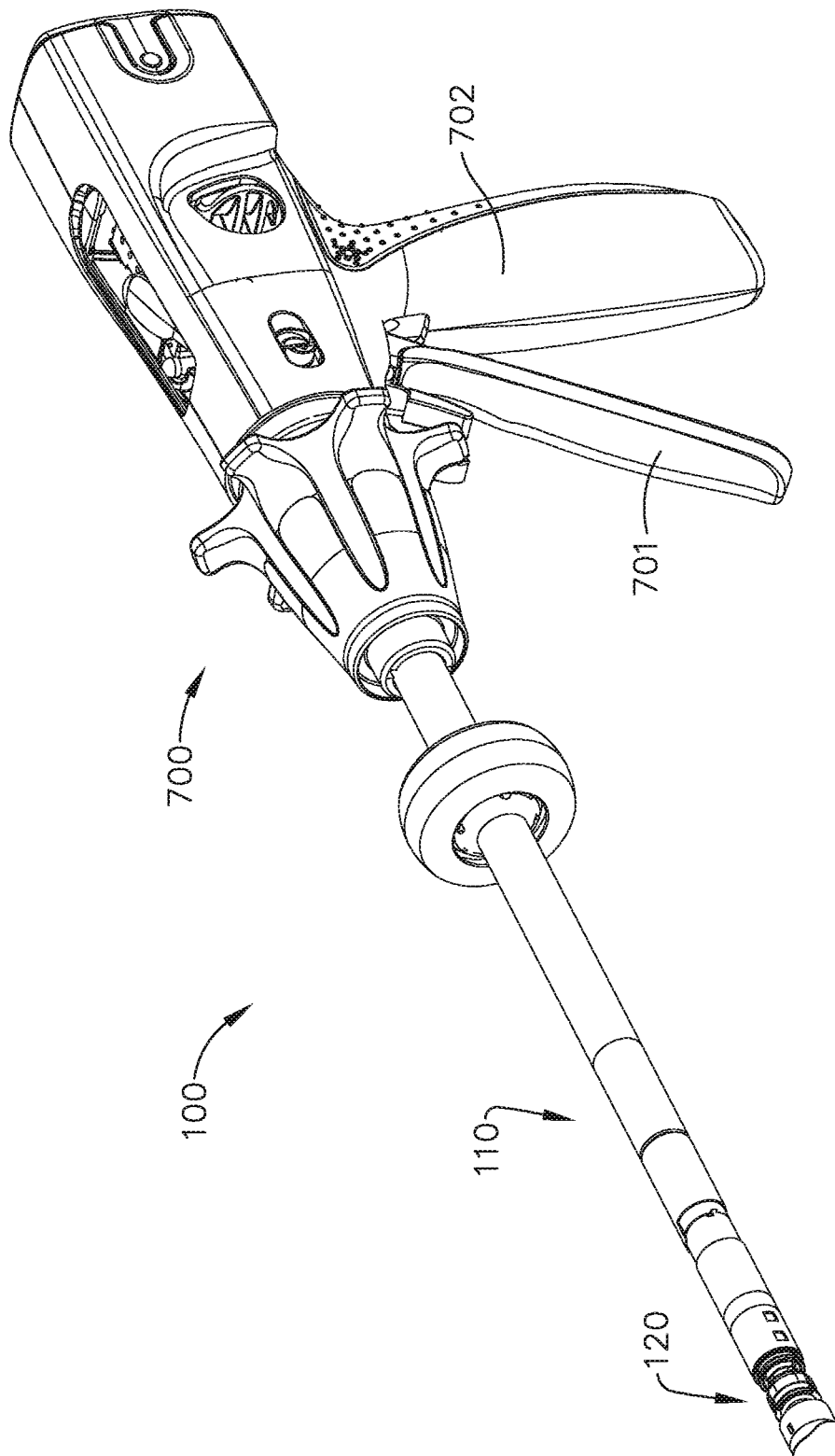
FIG. 29 is a perspective view of a handle actuator usable with the clip applier of FIGS. 2-12 or any other suitable clip applier.

As discussed above, the end effector 620 can be selectively attached to and detached from the shaft 610. The reader will note that the principles discussed in connection with the end effector 620 and shaft 610 can be equally applied to the end effector 120 and the shaft 110 of the embodiment disclosed in FIG. 1, among others. That said, referring again to FIG. 27, one of the robotic arms 30 can be selectively engaged with an end effector 120 of a clip applier or, alternatively, any other suitable end effector, such as the end effector of a surgical stapler, for example. In such circumstances, an end effector 120 can be selectively interchanged with another end effector and, as a result, a single robotic arm 30 can be utilized to perform more than one function. Stated another way, the clip applier 100 can comprise a replaceable loading unit which can be replaced by, or interchanged with, another clip applier loading unit and/or any other suitable replaceable loading unit. Turning now to FIG. 29, the end effector 120 and the shaft 110 of the clip applier 100 can be utilized with a surgical instrument system comprising a handle 700. The handle 700 can comprise an actuator 701 which can be operated, or squeezed toward grip 702, in order to apply a rotary motion to the drive screw 161 as described above. In some cases, the rotation of the actuator 701 can be mechanically transmitted to the drive screw 161 while, in other cases, the actuator 701 can operate a motor operably coupled to the drive screw 161.

Figure 30:
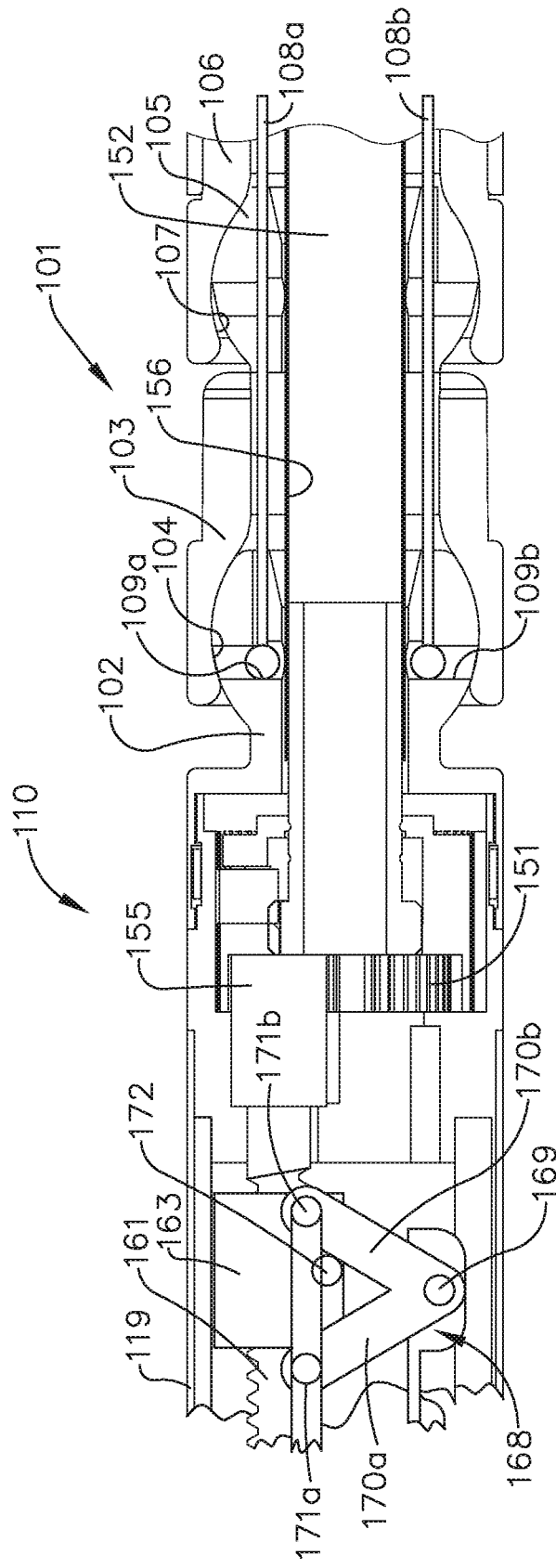
FIG. 30 is a cross-sectional view of the articulation joint illustrated in FIG. 2.

Further to the above, the end effector 120 and the shaft 110 of the clip applier 100 can be aligned along a longitudinal axis of the clip applier 100. Turning now to FIG. 30, the end effector 120 and/or the shaft 110 can further comprise an articulation joint 101 which can be configured to permit the end effector 120 to be articulated relative to the longitudinal axis of the clip applier 100. The shaft 110 can comprise an outer housing, or frame portion, 119 which can comprise a proximal end 102 and can comprise a distal portion of the articulation joint 101. The proximal end 102 can comprise a spherical, or an at least substantially spherical, end 102, for example, which can be received within a spherical, or an at least substantially spherical, cavity 104 defined in an articulation joint member 103. The articulation joint member 103 can also comprise a spherical, or at least substantially spherical, end 105, for example, which can be received within a spherical, or an at least substantially spherical, cavity 107 defined in a shaft frame portion 106. The proximal end 102 of the shaft 110 can be at least partially captured within the cavity 104 such that the proximal end 102 cannot be readily removed from the cavity 104. That said, the proximal end 102 and the cavity 104 can be sized and configured to permit the proximal end 102 to be rotated in any suitable direction within the cavity 104. As also illustrated in FIG. 30, the clip applier 100 can further comprise articulation controls 108a and 108b, for example, which can extend through the articulation joint 101 and can comprise distal ends mounted within mounting apertures 109a and 109b, respectively, defined within the proximal end 102 of the shaft housing 119. In use, the articulation controls 108a and 108b can be pushed and/or pulled in order to move the proximal end 102 within the cavity 104. Further to the above, the end 105 of the articulation joint member 103 can be at least partially captured within the cavity 107 defined in the shaft frame portion 106 such that the end 105 cannot be readily removed from the cavity 107. That said, the end 105 and the cavity 107 can be sized and configured to permit the end 105 to be rotated in any suitable direction within the cavity 107 when the shaft end 102 is pushed and/or pulled by the actuators 108a and 108b as described above.

Further to the above, referring again to FIG. 30, the drive screw 161 can be rotated by an input shaft, such as input shaft 152, for example. The input shaft 152 can extend through an aperture 156 defined within the shaft frame portion 106, the articulation joint member 103, and the proximal end 102 of the shaft housing 119. The input shaft 152 can comprise an input gear 151 mounted to the distal end thereof which can be operably coupled with an output gear 155 mounted to the proximal end of the drive screw 161. In use, the input shaft 152 can be rotated by the electric motor, described above, wherein the input shaft 152 can rotate the drive screw 161. As outlined above, the articulation joint 101 can be configured to permit the end effector 120 and at least a portion of the shaft 110 to be articulated relative to a longitudinal axis defined by the clip applier 100. In order to accommodate such movement, at least the portion of the input shaft 152 extending through the articulation joint 101 can be sufficiently flexible.

Figure 31:
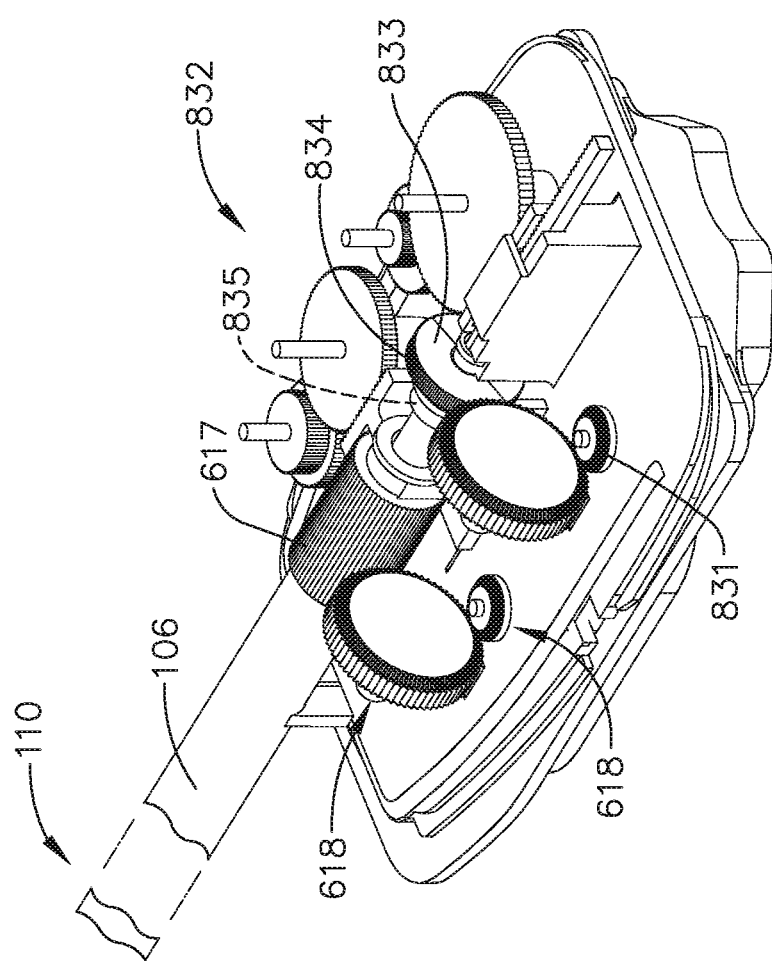
FIG. 31 is a rear perspective view of an alternative actuator module that may be used in place of the actuator module of FIG. 28 with at least a portion of its housing removed.
Figure 32:
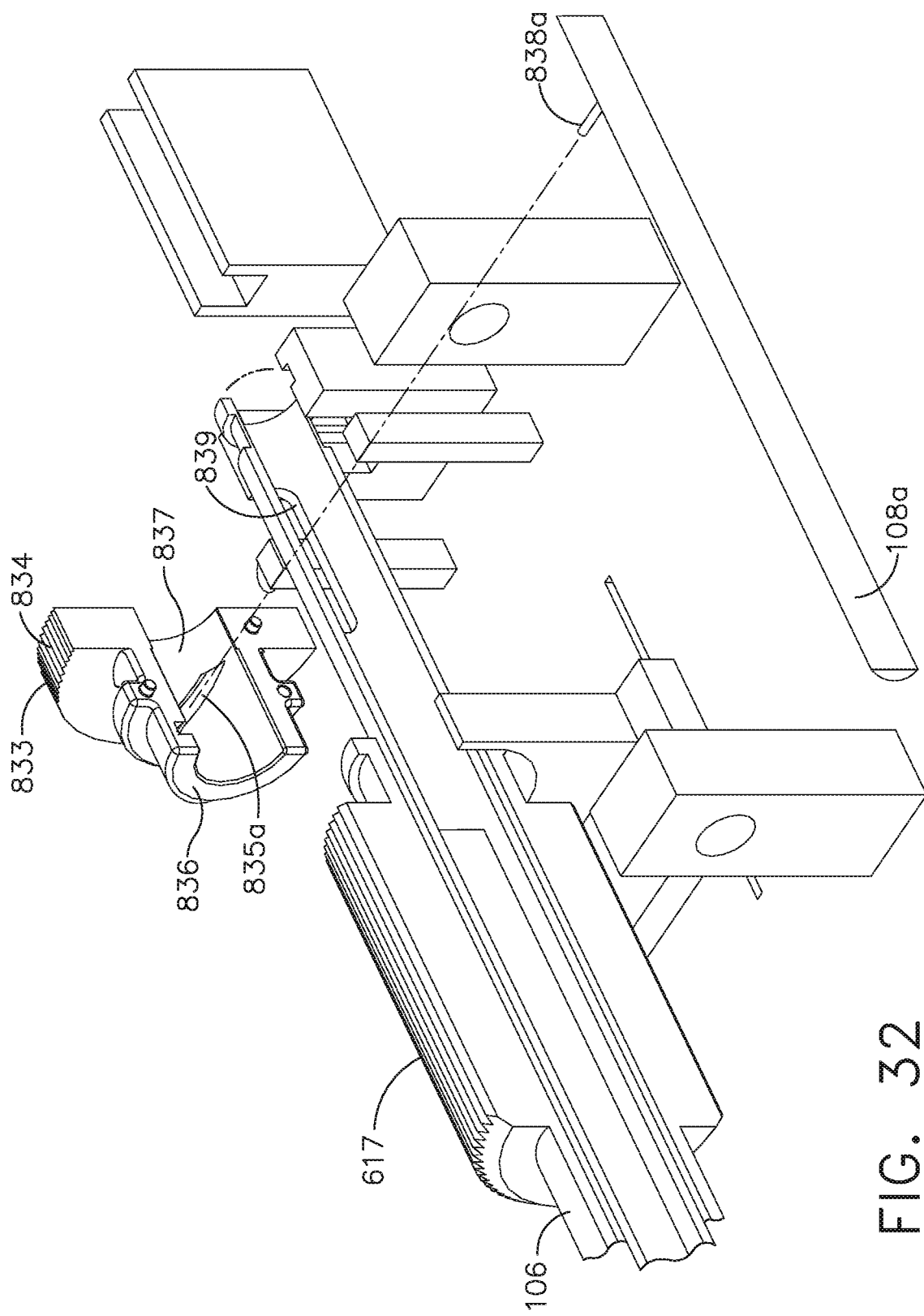
FIG. 32 is an exploded view of a portion of the actuator module of FIG. 31.
Figure 33:
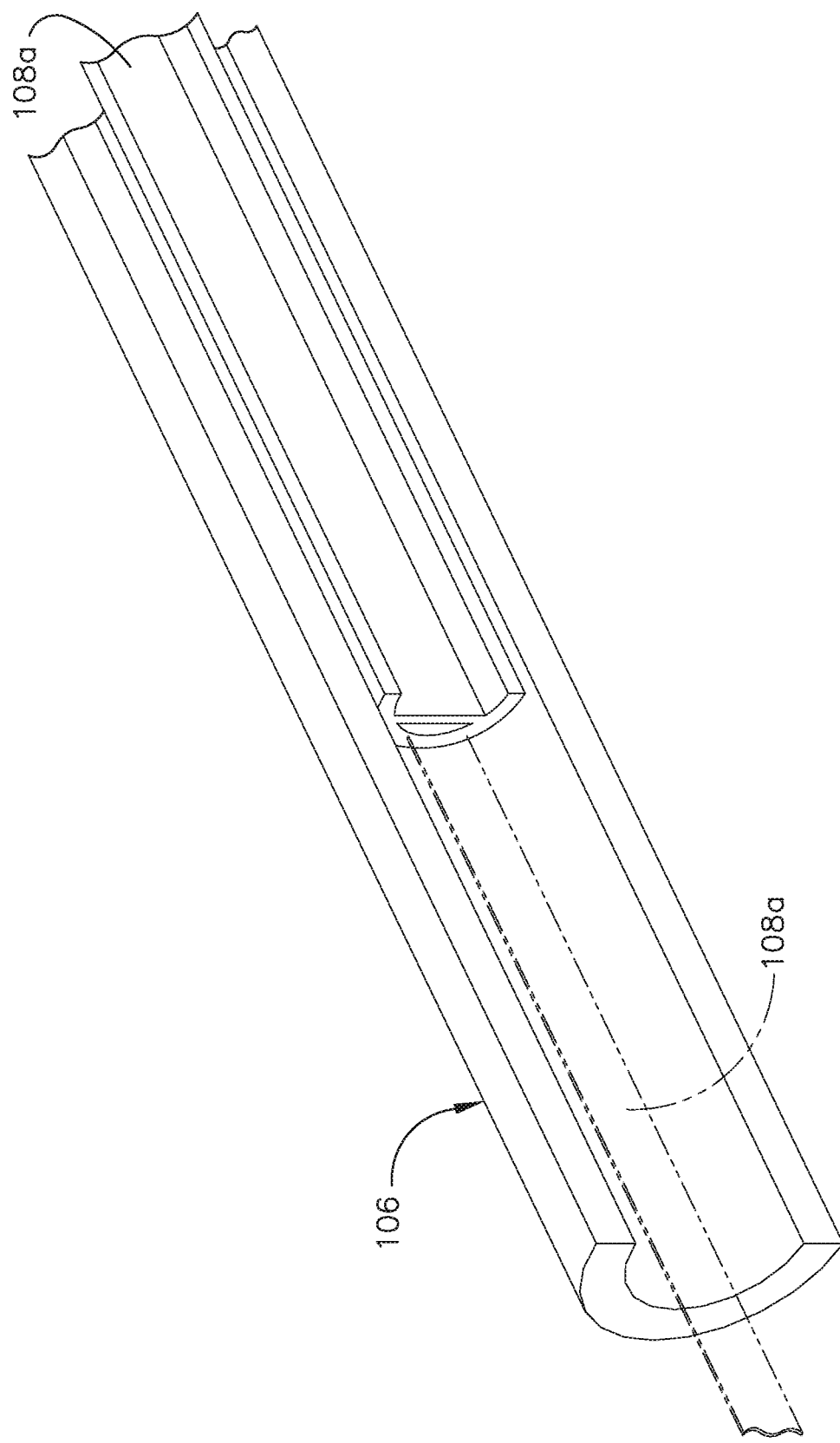
FIG. 33 is a partial sectional view of the actuator module of FIG. 31.
Figure 34:
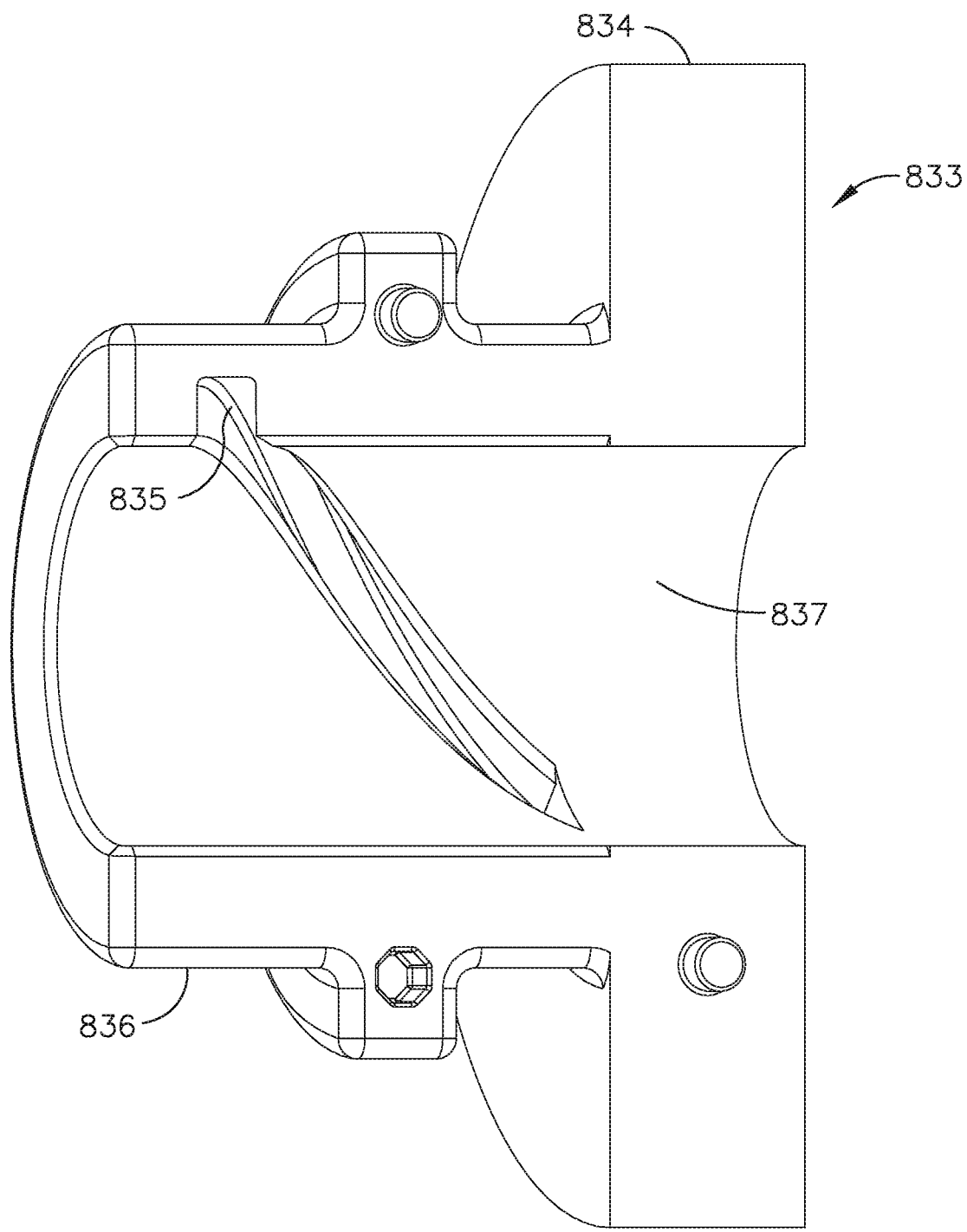
FIG. 34 is a cross-sectional view of an articulation actuator of the actuator module of FIG. 31.

Turning now to FIGS. 31-34, the articulation actuators 108a and 108b can be operated by an actuator module such as module 832, for example. Referring primarily to FIG. 31, the actuator module 832 can comprise a rotatable articulation driver 833 which can be configured to push and pull the articulation actuators 108a and 108b. The articulation driver 833 can comprise a cylindrical, or an at least substantially cylindrical, collar 835 including an aperture 837 which can be configured to receive at least a portion of the shaft frame 106 therein in order to rotatably support the collar 835. The articulation driver 833 can further comprise an input gear portion 834 which can be operably coupled with an electric motor and gear train 831 of the module 832 wherein, when the electric motor and gear train 831 are actuated, the articulation driver 833 can be rotated about the shaft frame 106. Referring primarily to FIGS. 32 and 34, the articulation driver 833 can further comprise two cam slots defined in the sidewall of the collar aperture 837, although the reader will note that only one cam slot 835a is illustrated in the provided views. The cam slot 835a is configured to receive a cam follower 838a extending from the articulation driver 108a wherein the cam follower 838a is configured to slide within the cam slot 835a. When the articulation driver 833 is rotated, the helical contour of the cam slot 835a, for example, can be configured to push the cam follower 838a distally or pull the cam follower 838a proximally, depending on the direction in which the articulation driver 833 is rotated. As a result of the proximal or distal movement of the cam follower 838a, the cam actuator 108a can be moved proximally or distally, respectively. While not illustrated, the articulation driver 108b can comprise a cam follower, similar to the cam follower 838a, which can be configured to slide within the other cam slot discussed above. The other cam slot can be configured such that, when the articulation actuator 108a is driven distally by the articulation driver 833 when the articulation driver 833 is rotated in a first direction, the articulation actuator 108b can be pulled proximally. Similarly, the other cam slot can be configured such that, when the articulation actuator 108a is pulled proximally by the articulation driver 833 when the articulation driver 833 is rotated in a second direction, the articulation actuator 108b can be driven distally. Referring primarily to FIG. 32, the shaft frame portion 106 can comprise clearance slots 839 defined therein through which the cam followers can extend. Although the above features have been discussed in connection with an actuator module 832, such features could be used in connection with the other actuator modules disclosed herein.

FIGS. 35A, 35B, and 35C depict a clip applier 70100 in accordance with at least one embodiment. The clip applier 70100 is similar to the clip applier 100 in many respects, most of which will not be repeated herein for the sake of brevity. Similar to the clip applier 100, the clip applier 70100 comprises an end effector 70120, a shaft, a clip cartridge, and a firing member 70165. The clip cartridge comprises a plurality of clips 70140 removably stored therein. The end effector 70120 comprise a first jaw 70123a and a second jaw 70123b wherein the first jaw 70123a and the second jaw 70123b at least partially define a receiving chamber 70122. Further, the first jaw 70123a and the second jaw 70123b are pivotally coupled to the shaft by a pin 70125 such that the first jaw 70123a and the second jaw 70123b are movable relative to each other between an open position (FIG. 35B) and a closed position (FIG. 35A). The first jaw 70123a and the second jaw 70123b are movable between the open position and the closed position by a crimping drive 70180 (see FIGS. 36-38). Other embodiments are envisioned where the first jaw 70123a and the second jaw 70123b are pivotally coupled to the shaft utilizing at least one pin similar to the first jaw 125a and second jaw 125b depicted in FIG. 1. The first jaw 70123a and the second jaw 70123b include pre-form features, such as protrusions 70126a and 70126b which are discussed in further detail below.

In use, the firing member 70165 advances a clip 70140 from the clip cartridge onto the protrusions 70126a and 70126b as depicted in FIG. 35A. In this position, the clip 70140 is in a pre-formed configuration. The width of the clip 70140 in the pre-formed configuration can be 0.080" preferably. When the first jaw 70123a and the second jaw 70123b are moved from the closed position to the open position, the protrusions 70126a and 70126b expand the clip 70140 to an expanded configuration as depicted in FIG. 35B. The width of the clip 70140 in the expanded configuration can be 0.210" preferably. During the transition of the clip 70140 from the pre-formed configuration to the expanded configuration, the firing member 70165 supports the backside of the clip 70140. More specifically, the firing member 70165 includes angled surfaces 70165a and 70165b which provide support for the backside of the clip 70140 as the clip 70140 expands. Further, as the clip 70140 is expanded, the firing member 70165 can be advanced to allow the angled surfaces 70165a and 70165b to continue to maintain contact against the backside of the clip 70140 as the clip 70140 expands. Once in the expanded configuration, the clip 70140 is advanced into the receiving chamber 70122 by the firing member 70165. The protrusions 70126a and 70126b include angled portions which allow the clip 70140 to slide over the protrusions 70126a and 70126b when the clip 70140 is advanced by the firing member 70165. After the clip 70140 has been advanced into the receiving chamber 70122, the firing member 70165 is retracted, and the crimping drive 70180 is actuated to transition the first jaw 70123a and the second jaw 70123b to the closed position depicted in FIG. 35A to crimp the clip 70140 positioned in the receiving chamber 70122. After the clip 70140 is crimped, another clip 70140 can be advanced onto the protrusions 70126a and 70126b by the firing member 70165. When the first jaw 70123a and the second jaw 70123b are moved from the closed position to the open position by the crimping drive 70180, the clip 70140 that has been crimped in the receiving chamber 70122 will be released from the receiving chamber 70122 and the clip 70140 that was advanced onto the protrusions 70126*a* and 70126*b* will be expanded into to the expanded configuration by the protrusions 70126*a* and 70126*b* of the first and second jaws 70123*a* and 70123*b*. Interaction between the crimping drive 70180 and the first and second jaws 70123*a* and 70123*b* is discussed in further detail below.

Figure 36:
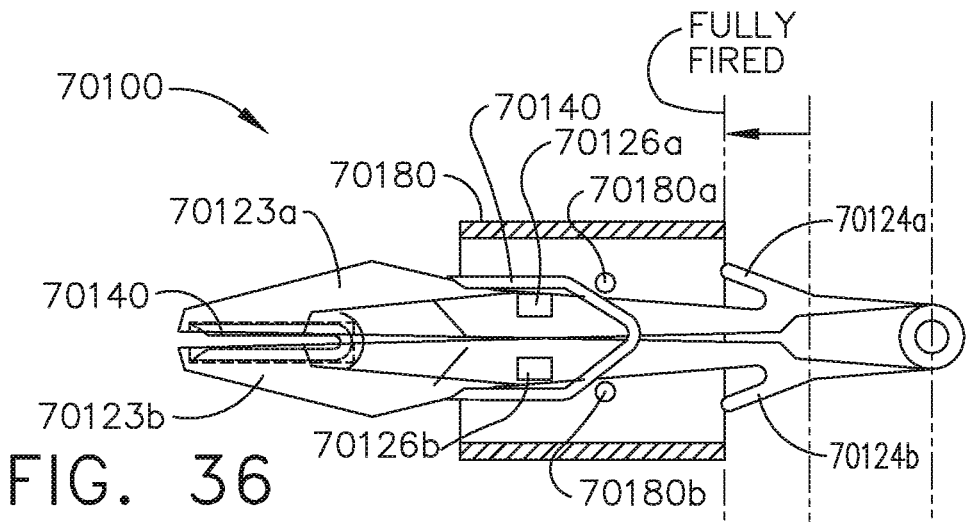
FIG. 36 is a partial cross-sectional view of the end effector of FIG. 35A illustrating the position of a stored clip when a crimping drive of the end effector is in a fully fired position.
Figure 37:
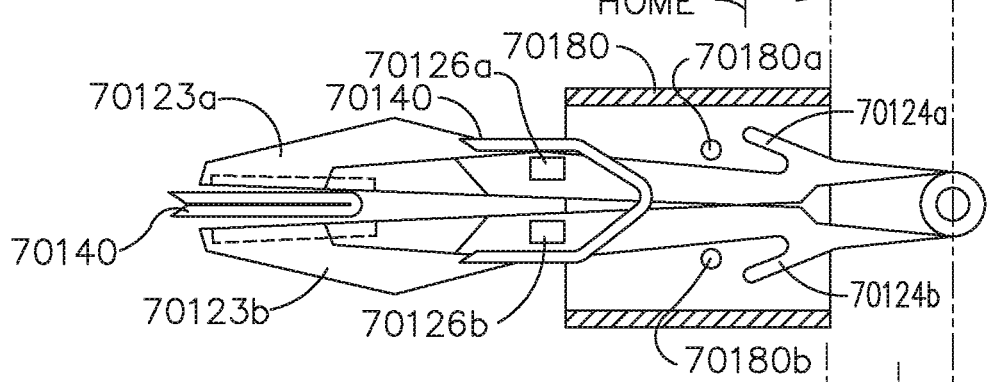
FIG. 37 is a partial cross-sectional view of the end effector of FIG. 35A illustrating the position of the stored clip when the crimping drive is in a home position.
Figure 38:
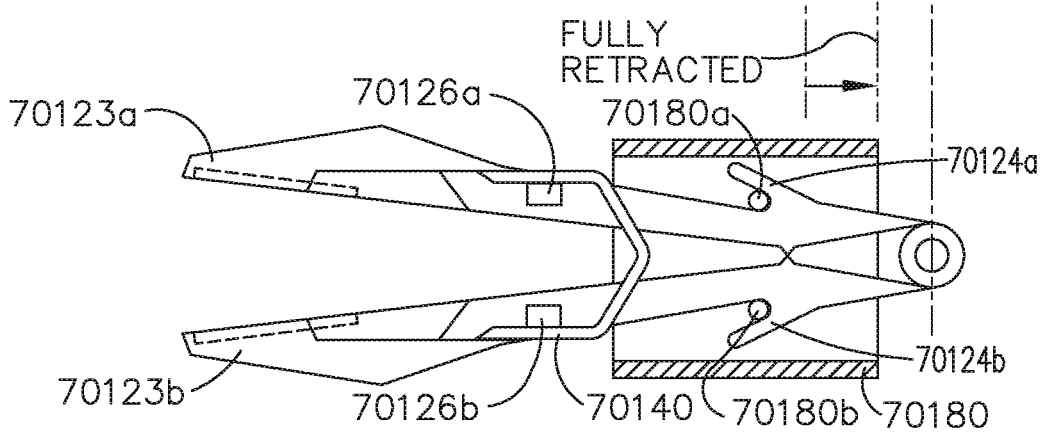
FIG. 38 is a partial cross-sectional view of the end effector of FIG. 35A illustrating the position of the stored clip when the crimping drive is in a fully retracted position.

FIGS. 36-38 depict the clip applier 70100 as described above. In addition, FIGS. 36-38 further depict the interaction between the crimping drive 70180 and the first and second jaws 70123*a* and 70123*b*. The crimping drive 70180 comprises a first crimping drive pin 70180*a* and a second crimping drive pin 70180*b* protruding therefrom. The first jaw 70123*a* comprises a first jaw cam 70124*a* extending therefrom and the second jaw 70123*b* comprises a second jaw cam 70124*b* extending therefrom. In use, the crimping drive 70180 is movable between a fully retracted position (FIG. 38), a home position (FIG. 37), and a fully-fired position (FIG. 36). The fully-fired position can preferably be 0.300" distal to the home position. The fully retracted position can preferably be 0.050" proximal to the home position. Other embodiments are envisioned with different distances between the home position, the fully retracted position, and the fully-fired position. The crimping drive 70180 cammingly engages outer surfaces of the first jaw 70123*a* and the second jaw 70123*b* to transition the first jaw 70123*a* and the second jaw 70123*b* to a closed position when the crimping drive 70180 is moved into the fully-fired position (FIG. 36)—similar to the interaction between the crimping drive 180 and the first and second jaws 123*a* and 123*b* described above. In the home position (FIG. 37), the first and second crimping drive pins 70180*a* and 70180*b* engage the first jaw cam 70124*a* and the second jaw cam 70124*b*, respectively, such that the first jaw 70123*a* and the second jaw 70123*b* are moved toward the open position to release a crimped clip 70140 from the first and second jaws 70123*a* and 70123*b*. When the crimping drive 70180 is in the home position, another clip 70140 can be advanced onto the protrusions 70126*a* and 70126*b* as discussed above. Further, as the crimping drive 70180 is moved from the home position (FIG. 37) to the fully retracted position (FIG. 38) the first crimping drive pin 70180*a* and the second crimping drive pin 70180*b* transition the first jaw 70123*a* and the second jaw 70123*b* towards the open position, and thus, the clip 70140 positioned around the protrusions 70126*a* and 70126*b* is expanded into the expanded configuration, as discussed above. Alternative embodiments are envisioned in which a crimped clip 70140 is released from the first and second jaws 70123*a* and 70123*b* and, at the same time, another clip 70140 positioned on the protrusions 70126*a* and 70126*b* is least partially expanded when the crimping drive is moved from the closed position to the home position.

Figure 39:
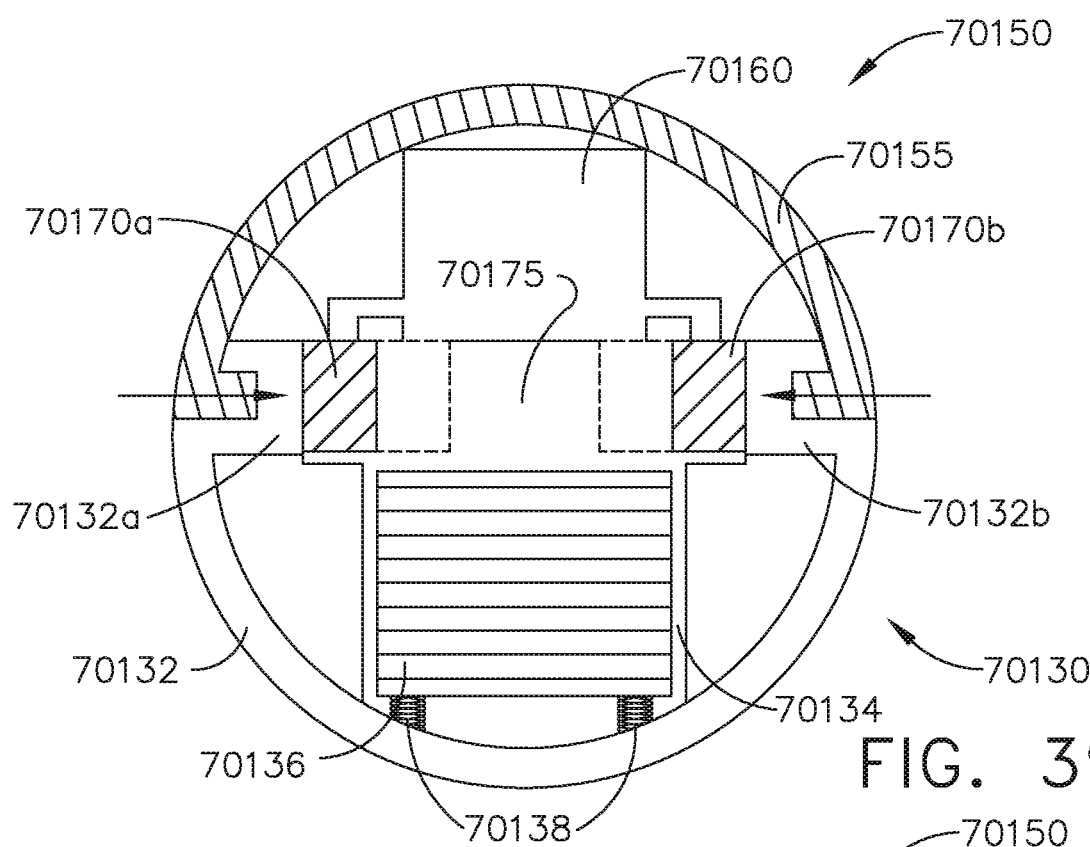
FIG. 39 is a partial cross-sectional view of a clip applier comprising a clip cartridge containing clips having a first size.
Figure 40:
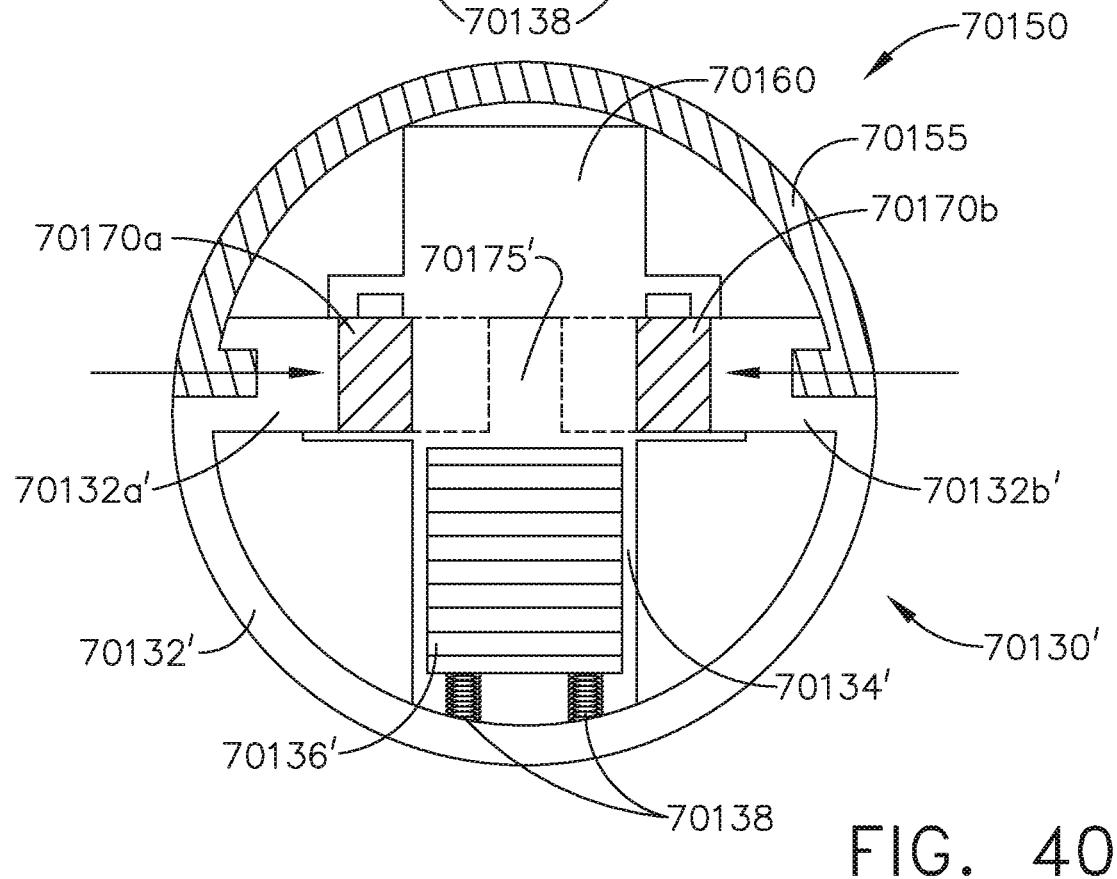
FIG. 40 is a partial cross-sectional view of the clip applier of FIG. 39 comprising a different clip cartridge containing clips having a second size.

FIGS. 39 and 40 depict a clip applier 70150 in accordance with at least one embodiment. The clip applier 70150 comprises a frame 70155, a firing member 70160, a first jaw 70170*a*, and a second jaw 70170*b*. The first jaw 70170*a* and the second jaw 70170*b* are pivotally coupled to the frame 70155 such that the first jaw 70170*a* and the second jaw 70170*b* are movable relative to each other. The clip applier 70150 is configured to receive various types of clip cartridges, such as clip cartridge 70130 depicted in FIG. 39, for example. The clip cartridge 70130 comprises a cartridge body 70132 including a first cartridge jaw 70132*a* and a second cartridge jaw 70132*b* that oppose each other. When the clip cartridge 70130 is attached to the frame 70155 of the clip applier 70150, the first cartridge jaw 70132*a* biases the first jaw 70170*a* towards the second jaw 70170*b*, and the second cartridge jaw 70132*b* biases the second jaw 70170*b* towards the first jaw 70170*a*. Thus, when the clip cartridge 70130 is attached to the clip applier 70150, the first and second jaws 70170*a* and 70170*b* are approximated to form a receiving chamber 70175. The clip cartridge 70130 further comprises a plurality of clips 70136 removably stored in a clip housing 70134. The clip cartridge 70130 further includes biasing members, such as springs 70138 for example, configured to bias the clips 70136 out of the clip housing 70134 into the receiving chamber 70175. Once in the receiving chamber 70175, a clip 70136 can be advanced by the firing member 70160 into a crimping chamber in the distal end of the first and second jaws 70170*a* and 70170*b*. A clip 70136 positioned in the crimping chamber can then be crimped when the first jaw 70170*a* and the second jaw 70170*b* are moved towards each other.

FIG. 40 depicts a different clip cartridge 70130' positioned in the clip applier 70150. The clip cartridge 70130' is similar to clip cartridge 70130 discussed above, except for the differences discussed below. The clip cartridge 70130' is configured to store clips 70136' which are smaller than clips 70136. Other embodiments are envisioned where the clip cartridge 70130' is configured to store clips that are larger than clips 70136. In any event, clip cartridge 70136' comprises, one, a clip housing 70134' which stores the clips 70136' and, two, biasing members, such as springs 70138' for example, which bias the stored clips 70136' into a receiving chamber 70175'. Further, the clip cartridge 70130' comprises a cartridge body 70132', a first cartridge jaw 70132*a*', and a second cartridge jaw 70132*b*' opposing the first cartridge jaw 70132*a*'. The first cartridge jaw 70132*a*' and the second cartridge jaw 70132*b*' extend further inward toward each other as compared to the first cartridge jaw 70132*a* and the second cartridge jaw 70132*b* of the clip cartridge 70130. Stated another way, the gap between the first cartridge jaw 70132*a*' and the second cartridge jaw 70132*b*' is smaller than the gap between the first cartridge jaw 70132*a* and the second cartridge jaw 70132*b*. When the clip cartridge 70130' is attached to the clip applier 70150, the receiving chamber 70175' defined between the first jaw 70170*a* and the second jaw 70170*b* will be smaller than the receiving chamber 70175. By changing the distance between the first cartridge jaw and the second cartridge jaw of the clip cartridges 70130 and 70130', various sizes of receiving chambers can be created. The clip cartridges 70130 and 70130' can therefore be modified to approximate the first jaw 70170*a* and the second jaw 70170*b* of the clip applier 70150 to receive any suitable clip size.

Figure 41:
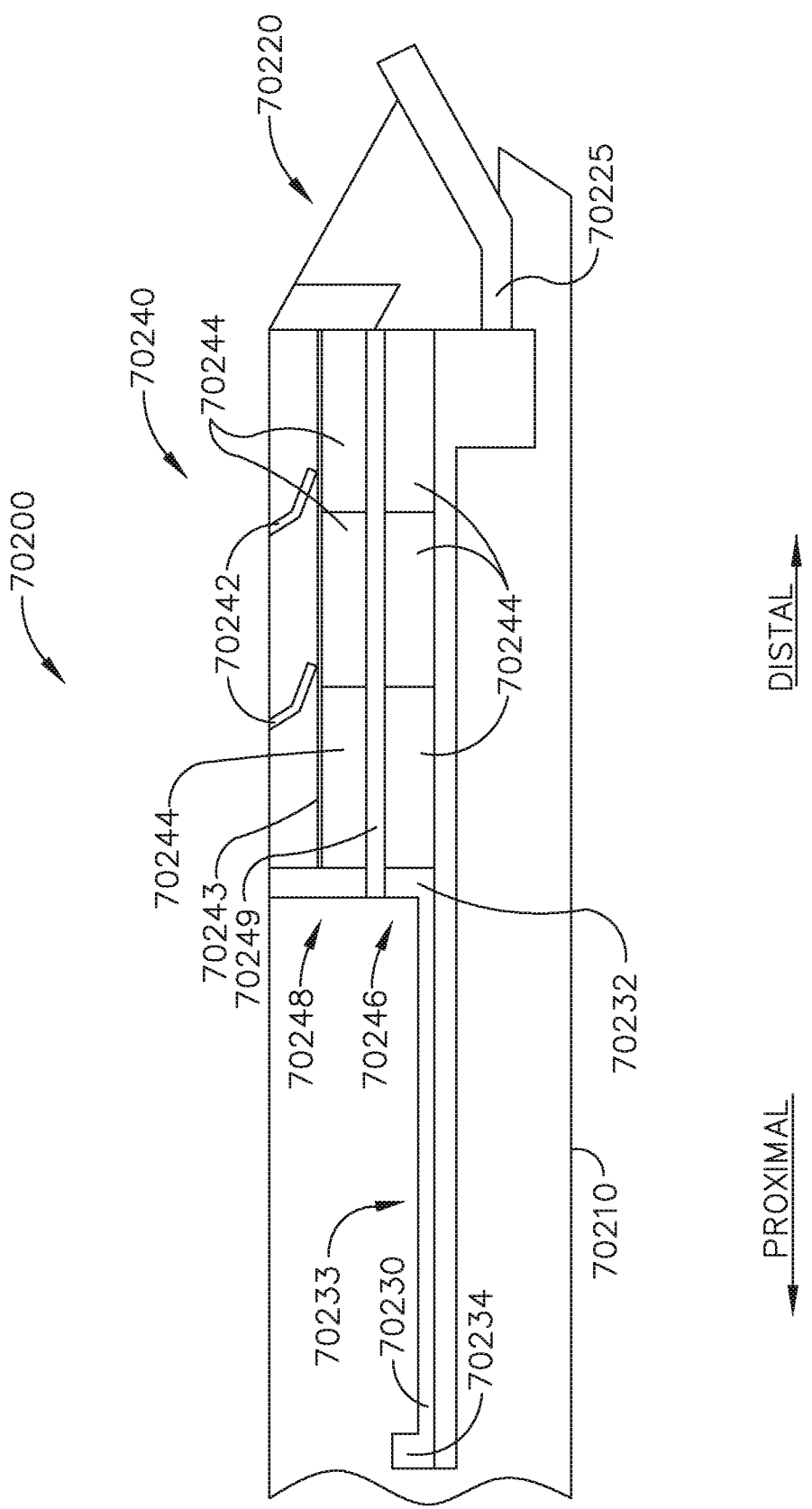
FIG. 41 is a partial cross-sectional view of a multi-level clip stack arrangement.

FIG. 41 depicts a clip applier 70200 in accordance with at least one embodiment. The clip applier comprises a shaft 70210 extending from a housing, an end effector 70220 extending from the shaft 70210, a feeder member 70230 configured to move through the clip applier 70200 in response to rotary motions generated in the housing, and a clip magazine 70240. The end effector comprises a pair of jaws 70225 configured to move relative to each other between open and closed positions. The clip magazine 70240 is not removable from the clip applier 70200; however, other embodiments are envisioned where the clip magazine 70240 is removable and/or replaceable. The clip magazine 70240 comprises a first layer 70246 of clips 70244 and a second layer 70248 of clips 70244 stored within the clip magazine 70240. The first layer 70246 of clips 70244 are in a feeding position from which they can be ejected from the clip magazine 70240. The second layer 70248 of clips 70244 are stored above the first layer 70246 of clips 70244 in a storage position from which they cannot be ejected from the clip magazine 70240. Each of the first layer 70246 and second layer 70248 comprises three clips 70244, however, other embodiments are envisioned with more or less than three clips. The first and second layers 70246 and 70248 are separated by a divider member, such as a divider plate 70249. The clip magazine 70240 further comprises a top plate 70243 and biasing members 70242. The top plate 70243 rests on top of the second layer 70248 of clips 70244. The biasing members 70242 bias the top plate 70243 toward the top of the second layer 70248 of clips 70244 and, thus, bias the second layer 70248 of clips 70244 toward the divider plate 70249. The divider plate 70249 rests on top of the first layer 70246 of clips 70244 and a distal protrusion 70232 of the feeder member 70230. The distal protrusion 70232 extends above the feeder member 70230. Operation of the clip applier 70200 is discussed in further detail below.

In use, the feeder member 70230 is translated distally to push the first layer 70246 of clips 70244 toward the end effector 70220 and out of the clip magazine 70240. As the first layer 70246 of clips 70244 is being advanced from the clip magazine 70240, the divider plate 70249 is supported by the distal protrusion 70232 of the feeder member 70230 and any of the clips 70244 which haven't been fully ejected from the clip magazine 70240. Once the feeder member 70230 has advance all of the clips 70244 in the first layer 70246 out of the clip magazine 70240, the divider plate 70249 is biased by the biasing members 70242 into a recess 70233 in the feeder member 70230. The recess 70233 is defined between the distal protrusion 70232 of the feeder member 70230 and a proximal protrusion 70234 of the feeder member 70230 extending upward from the proximal end of the feeder member 70230. Once the divider plate 70249 is seated in the recess 70233, the feeder member 70230 and divider plate 70249 can be retracted together proximally out of the clip magazine 70240. After the feeder member 70230 and divider plate 70249 are completely retracted out of the clip magazine 70240, the second layer 70248 of clips 70244 is biased by the biasing members 70242 into the feeding position (i.e., where the first layer 70246 of clips 70244 used to be). The feeder member 70230 and divider plate 70249 can be advanced together toward the end effector to eject the second layer 70248 of clips 70244 from the clip magazine 70240. The reader will appreciate that all of the clips 70244 in the first layer 70246 and/or second layer 70248 are not ejected at the same time, rather, they are ejected one at a time to allow each clip 70244 to be sequentially crimped by the pair of jaws 70255 of the end effector 70220. The above being said, other embodiments are envisioned in which more than one clip 70244 can be ejected at a time.

FIG. 42A depicts a clip applier 70250 in accordance with at least one embodiment. The clip applier 70250 comprises an elongate shaft 70260 extending from a housing, a clip cartridge 70270 extending from the elongate shaft 70260, and an end effector 70280 extending from the clip cartridge 70270. The elongate shaft 70260 and the clip cartridge 70270 define a shaft axis SA. The elongate shaft 70260 comprises a first inwardly extending detent 70264a and a second inwardly extending detent 70264b opposing the first inwardly extending detent 70264a. The first and second inwardly extending detents 70264a and 70264b extend inwardly toward the shaft axis SA and can flex outwardly away from the shaft axis SA when a force is applied thereto. The elongate shaft 70260 further comprises a top notch 70262a and a bottom notch 70262b opposing the top notch 70262a. The top notch 70262a and the bottom notch 70262b are located in the distal end of the elongate shaft 70260. The clip cartridge 70270 is releasably attachable to the distal end of the elongate shaft 70260 as discussed in further detail below.

The clip cartridge 70270 comprises a top protrusion 70272a and a bottom protrusion 70272b opposite the top protrusion 70272a. The top protrusion 70272a and the bottom protrusion 70272b extend from the clip cartridge 70270 away from the shaft axis SA. The clip cartridge 70270 further comprises a first slot and a second slot 70274b in the proximal end of the clip cartridge 70270. The first slot and the second slot 70274b oppose one another. The clip cartridge 70270 is configured to slide into the inner diameter of the elongate shaft 70260 such that the top protrusion 70272a slides into the top notch 70262a, the bottom protrusion 70272b slides into the bottom notch 70262b, the first inwardly extending detent 70264a engages the first slot of the clip cartridge 70270, and the second inwardly extending detent 70264b engages the second slot 70274b of the clip cartridge 70270 to attach the clip cartridge 70220 to the elongate shaft 70260. After the clip cartridge 70270 is attached to the elongate shaft 70260, the elongate shaft 70260 and clip cartridge 70270 are fixedly coupled such that they can rotate together about the shaft axis SA. Further, the clip cartridge 70270 can be detached from the elongate shaft 70260 by a clinician when the clinician applies a distal force to the clip cartridge 70270 to disengage the first and second inwardly extending detents 70264a and 70264b of the elongate shaft 70260 from the first slot and the second slot 70274b of the clip cartridge 70270.

Referring primarily to FIGS. 42A and 42B, the end effector 70280 comprises a first jaw 70280a and a second jaw 70280b configured to move relative to each other between an open position (FIG. 42A) and a closed position (FIG. 42B). To this end, the first jaw 70280a and the second jaw 70280b comprise openings at the proximal end thereof which are configured to receive a pin 70290. The pin 70290 is rotatably captured within an opening 70276 in the clip cartridge 70270. The pin 70290 defines a pin axis PA which is orthogonal to the shaft axis SA. The first jaw 70280a and the second jaw 70280b are rotatable relative to each other about the pin axis PA. When the first jaw 70280a and the second jaw 70280b are in the open position (FIG. 42A) a clip can be positioned between the first jaw 70280a and the second jaw 70280b. As the first jaw 70280a and the second jaw 70280b are moved towards the closed position (FIG. 42B) the clip is crimped between the first jaw 70280a and the second jaw 70280b. The first jaw 70280a and the second jaw 70280b are moved from the open position to the closed position by a closure tube which cammingly engages the outer surfaces of the first jaw 70280a and the second jaw 70280b as the closure tube moves distally. When the closure tube is retracted, the first jaw 70280a and the second jaw 70280b are returned to the open position by a biasing member, or spring, which biases the first jaw 70280a and the second jaw 70280b into the open position. Other embodiments are envisioned where the first jaw 70280a and the second jaw 70280b are movable from the closed position to the open position by jaw cams on the first jaw 70280a and the second jaw 70280b interacting with the closure tube, similar to jaw cams 70124a and 70124b depicted in FIGS. 36-38, for example.

Figure 43B:
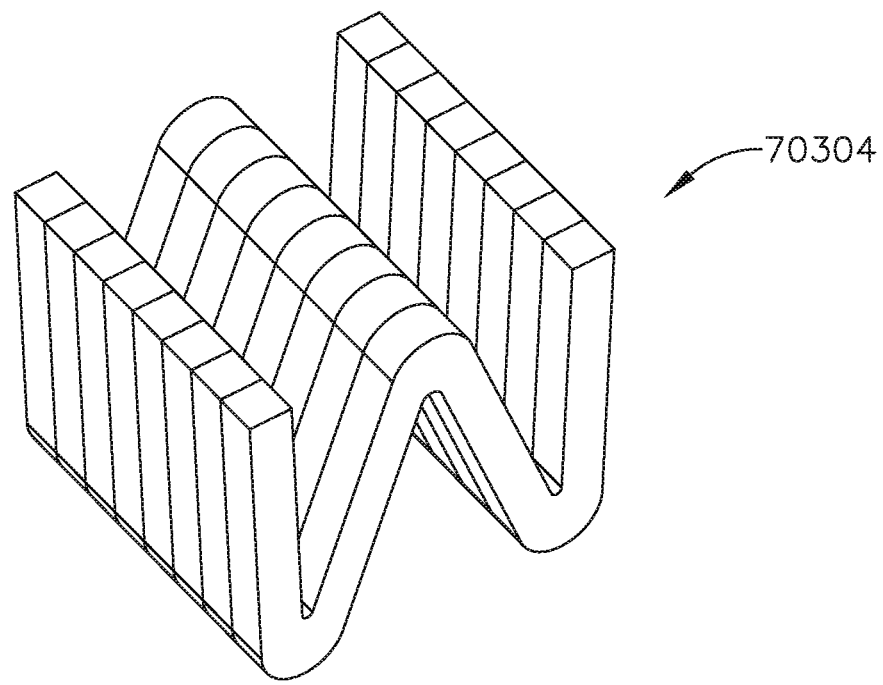
FIG. 43B is a perspective view of clips for use with the clip applier of FIG. 43A.
Figure 43A:
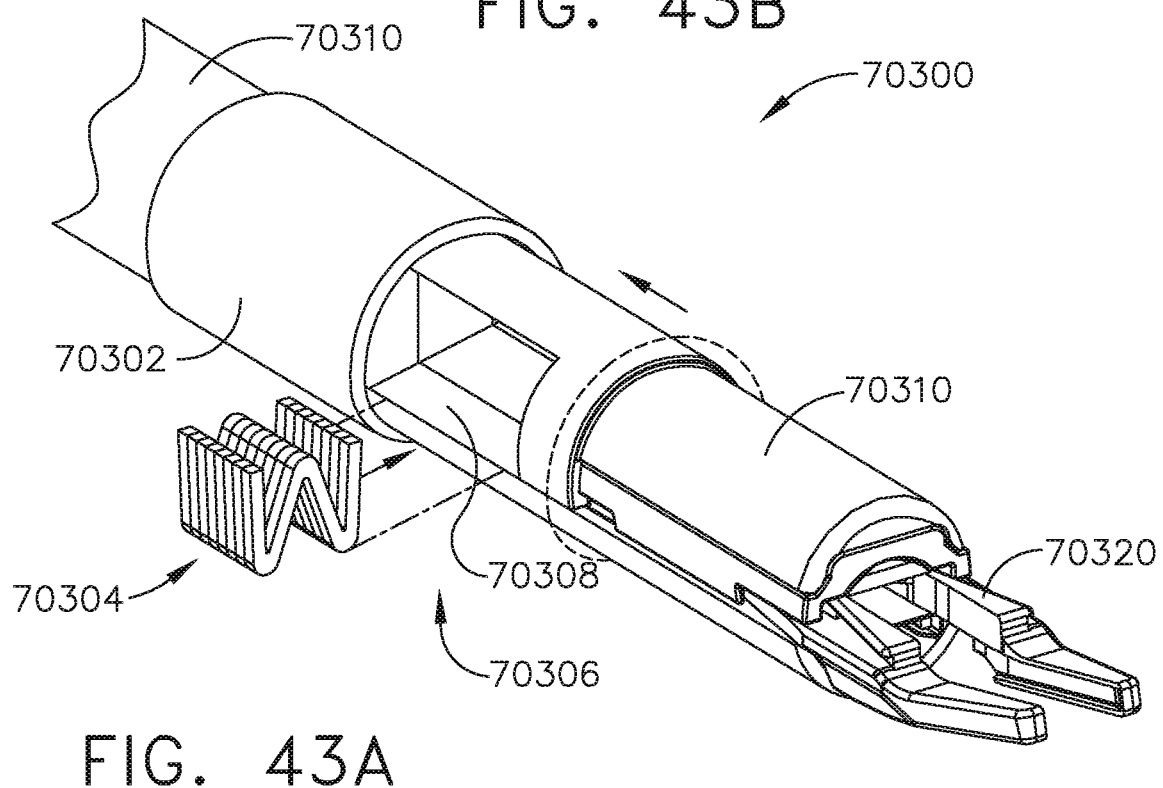
FIG. 43A is a perspective view of a clip applier comprising a clip magazine.

FIG. 43A depicts a clip applier 70300 in accordance with at least one embodiment. The clip applier 70300 comprises a shaft 70310, an end effector 70320 extending from the shaft 70310, a firing drive, and a clip magazine 70306. The clip magazine 70306 is built into the shaft 70310 of the clip applier 70300 as depicted in FIG. 43A. However, other embodiments are envisioned where the clip magazine 70306 is releasably attachable to the clip applier 70300. The shaft 70310 comprises openings 70308 on either side of the shaft 70310 which allow a user of the clip applier 70300 to access the clip magazine 70306. Other embodiments are envisioned with only one opening in the shaft 70310 of the clip applier. The clip applier 70300 further comprises an outer tube 70302 that is slidable along the shaft 70310 of the clip applier 70300. The outer tube 70302 is configured to slide along the shaft 70310 to cover the openings 70308 in the shaft 70310. The clip magazine 70306 is configured to store a plurality of clips, such as clips 70304 therein. The clips 70304 are insertable into the clip magazine 70306 through the openings 70308 when the outer tube 70302 is not obstructing the openings 70308, as depicted in FIG. 43A. Once positioned in the clip magazine 70306, the clips 70304 can be advanced out of the clip magazine 70306 into the end effector 70320 by the firing member. In at least one embodiment, the clips 70304 can be sequentially advanced out of the clip magazine 70306 into the end effector 70320. When the outer tube 70302 is covering the openings 70308, access to the clip magazine 70306 is prevented, and, if clips 70304 have already been inserted into the clip magazine 70306, the outer tube 70302 prevents the clips 70304 from exiting the clip magazine 70306 through the openings 70308. Once all of the clips 70304 inside the clip magazine 70306 have been advanced into the end effector 70320, the outer tube 70302 can be retracted to allow a new set of clips to be inserted into the clip magazine 70306. Further to the above, the outer tube 70302 can be operably engaged with the firing member of the clip applier 70300, such that, when the outer tube 70302 is retracted as depicted in FIG. 43A, or at least partially retracted, the firing member cannot be actuated.

Figure 44:
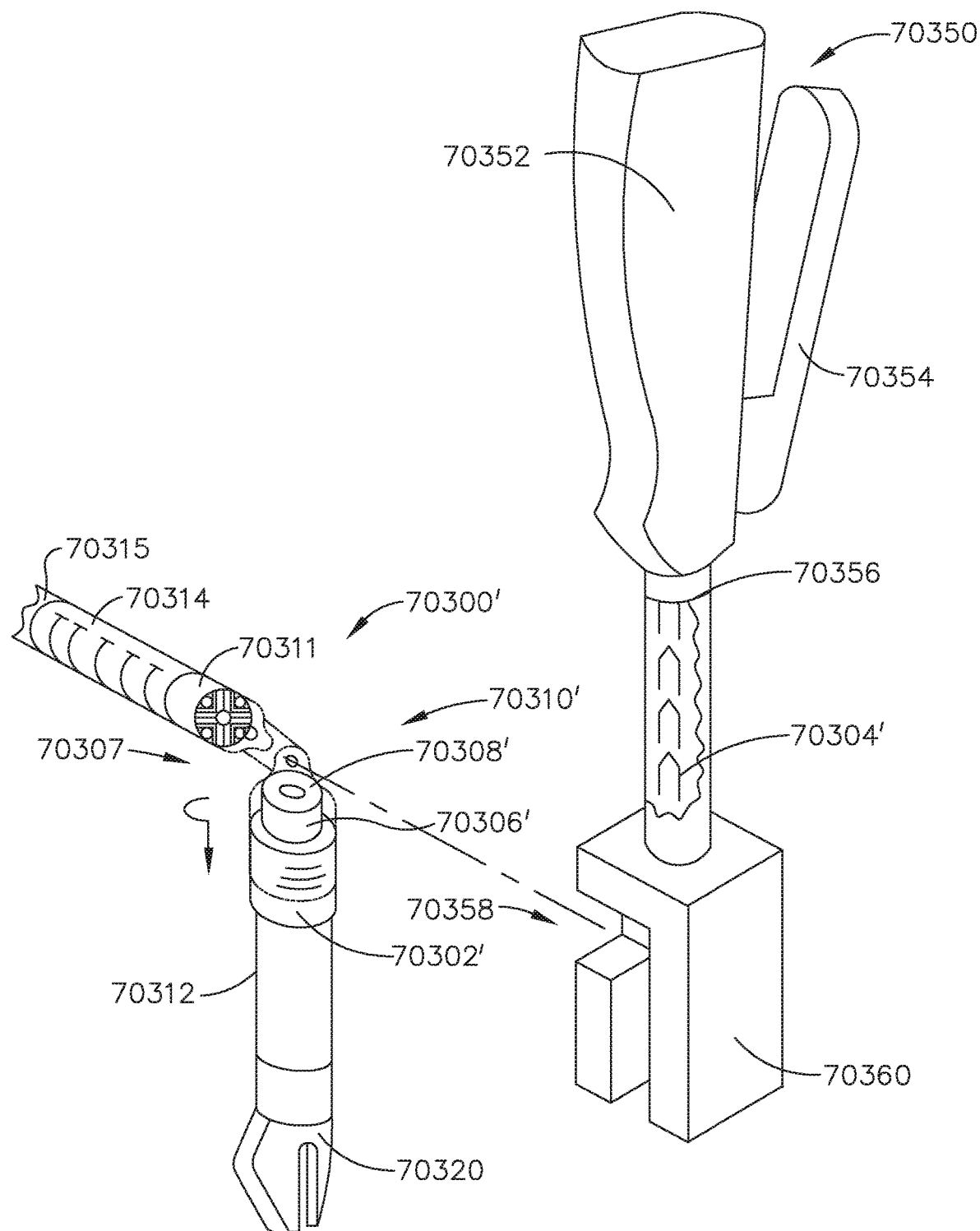
FIG. 44 is a perspective view of a clip reloader for use with a clip applier comprising a clip magazine.

FIG. 44 depicts a clip applier 70300'. Clip applier 70300' is similar to clip applier 70300 in many respects. The clip applier 70300' comprises an elongate shaft 70315 extending from a housing, an articulation joint 70314 extending from the elongate shaft 70315, a shaft assembly 70310' extending from the articulation joint 70314, an end effector 70320 extending from the shaft assembly 70310', and an outer tube 70302' positioned around the shaft assembly 70310'. The articulation joint 70314 connects the elongate shaft 70315 to the shaft assembly 70310' so that the shaft assembly 70310' can be articulated relative to the elongate shaft 70315. The shaft assembly 70310' comprises a proximal shaft portion 70311 extending from the articulation joint 70314, a distal shaft portion 70312 extending from the proximal shaft portion 70311, and a hinge 70307. The distal shaft portion 70312 further comprises a clip magazine 70306'. Other embodiments are envisioned where the proximal shaft portion 70311 comprises the clip magazine 70306'. The hinge 70307 allows the distal shaft portion 70312 to rotate away from the proximal shaft portion 70311. The outer tube 70302' is configured to slide along the shaft assembly 70310' between a locked position and an unlocked position when the proximal shaft portion 70311 and distal shaft portion 70312 are aligned. More specifically, when the proximal shaft portion 70311 and distal shaft portion 70312 are aligned and the outer tube 70302' is in the locked position, the distal shaft portion 70312 is prevented from rotating away from the proximal shaft portion 70311 about the hinge 70307. When the outer tube 70302' is in the unlocked position, the distal shaft portion 70312 is capable of rotating away from the proximal shaft portion 70311 about the hinge 70307. Further to the above, when the distal shaft portion 70312 is rotated away from the proximal shaft portion 70311, an opening 70308' in the clip magazine 70306' is exposed. The opening 70308' allows clips 70304' to be inserted into the clip magazine 70306'.

Further to the above, a clip reloader 70350 can be utilized to insert the clips 70304' into the clip applier 70300' as depicted in FIG. 44. The clip reloader comprises a housing 70352, a trigger 70354 movable relative to the housing 70352, a feeder bar operably engaged with the trigger 70354, an elongate shaft 70356 extending from the housing 70352, and a docking station 70360 extending from the elongate shaft 70356. A plurality of clips 70304' are removably stored in the elongate shaft 70356. In one embodiment, the elongate shaft 70356 stores 20 clips within a six inch span of the elongate shaft 70356. Other embodiments are envisioned with different numbers of clips and spans, for example. The clips 70304' are advanced from the elongate shaft 70356 into the docking station 70360 by the feeder bar when the trigger 70354 is moved towards the housing 70352. The docking station 70360 comprises a cavity 70358 configured to dock with the shaft assembly 70310' of the clip applier 70300' when the distal shaft portion 70312 is rotated away from the proximal shaft portion 70311. When the docking station 70360 is docked with the shaft assembly 70310' of the clip applier 70300', the clips 70304' can be advanced form the elongate shaft 70356 into the clip magazine 70306' of the clip applier.

Figure 45:
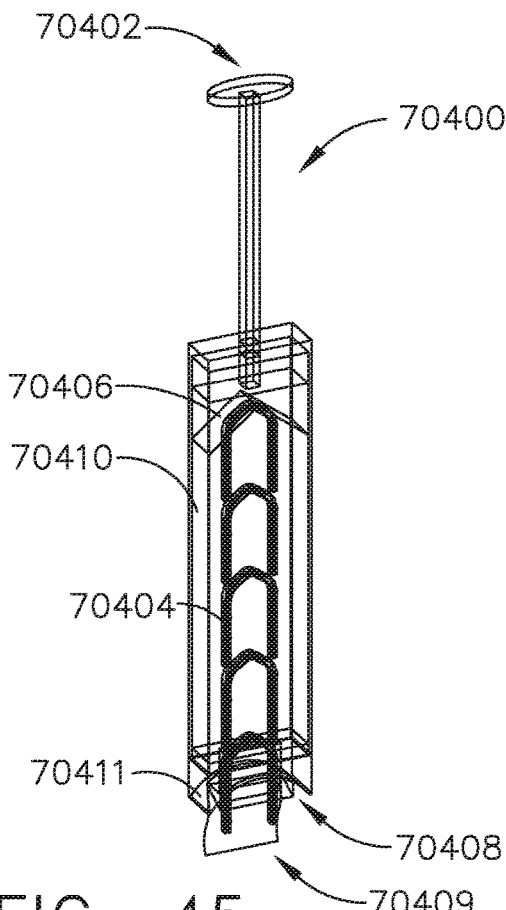
FIG. 45 is a perspective view of a clip reloader.
Figure 46:
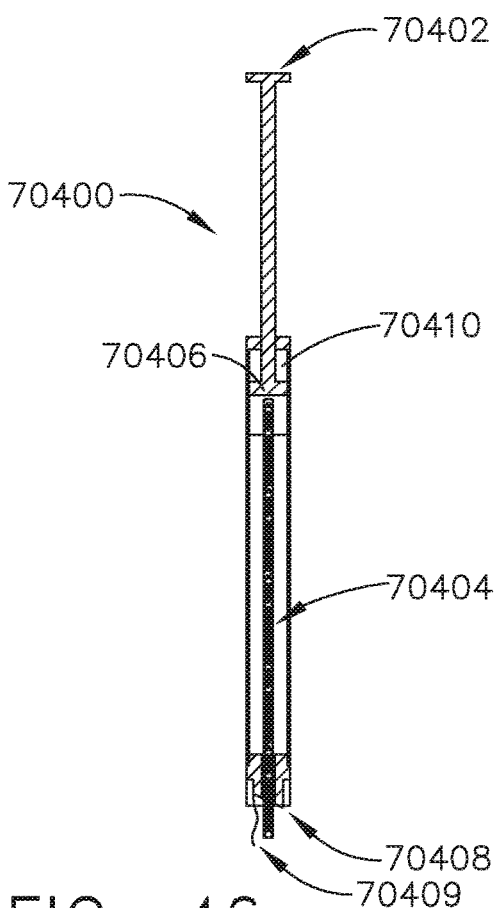
FIG. 46 is a cross-sectional view of the clip reloader of FIG. 45.
Figure 47:
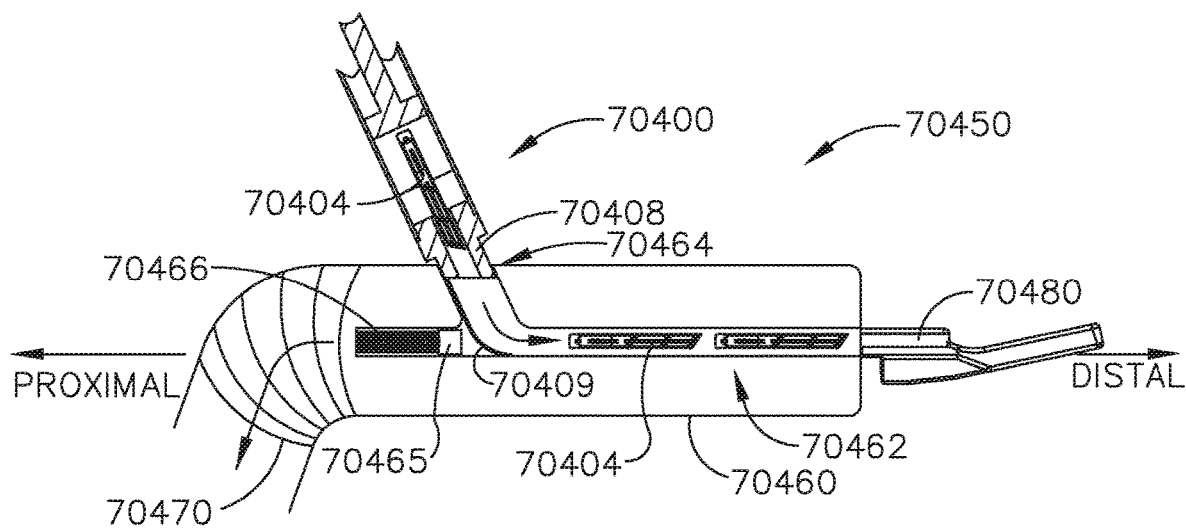
FIG. 47 is a cross-sectional view of the clip reloader of FIG. 45 and an end effector of a clip applier.

FIGS. 45-47 depict a different clip reloader 70400. The clip reloader 70400 is similar to the clip reloader 70350 in many respects. The clip reloader 70400 comprises a housing 70410, a plurality of clips 70404 stored inside the housing 70410, and a plunger 70402. The plunger 70402 extends into and is movable relative to the housing 70410. The clips 70404 are stacked vertically in the embodiment illustrated in FIGS. 45 and 46; however, other embodiments are envisioned where the clips are stacked horizontally. A feeder block 70406 extends from the plunger 70402 and is slidably engaged with the inside of the housing 70410. The feeder block 70406 comprises angled portions that support the backside of the top-most clip in the clip stack as depicted in FIG. 45. The housing 70410 comprises a boss 70408 extending from the bottom of the housing 70410, and a flexible ramp 70409 extending from the bottom of the boss 70408. The housing 70410 further comprises a cutout region 70411. Docking the clip reloader 70400 with a clip applier is discussed in further detail below.

In various circumstances, the clip reloader 70400 is configured to insert the clips 70404 into a clip applier, such as clip applier 70450, for example. The clip applier 70450 comprises a shaft 70460, an end effector 70480 extending distally from the shaft 70460, and an articulation joint 70470 extending proximally from the shaft 70460. To align the clip reloader 70400 with the clip applier 70450, the boss 70408 docks with an opening 70464 in the shaft 70460 of the clip applier 70450, the cutout region 70411 mates with the exterior of the shaft 70460, and the flexible ramp 70409 extends into a clip slot 70462 of the clip applier 70450 as depicted in FIG. 47. The opening 70464 leads to the clip slot 70462 which comprises an angled portion that receives the boss 70408 and flexible ramp 70409 of the clip reloader 70400. The clip slot 70462 further comprises a flat portion that facilitates the advancement of the clips 70404 into the end effector 70480 of the clip applier 70450. The operation of the clip reloader 70400 in conjunction with the clip applier 70450 is discussed in further detail below.

In use, after the clip reloader 70400 is docked with the clip applier 70450, the plunger 70402 is moved towards the clip applier 70450 to advance the clips 70404 from the housing 70410 into the angled portion of the clip slot 70462. The ramp 70409 supports and guides the clips 70404 from the angled portion of the clip slot 70462 into the flat portion of the clip slot 70462. As illustrated in FIG. 47, the housing 70410 of the clip reloader 70400 is positioned at an angle relative to the longitudinal axis of the clip applier 70450 when the clip reloader 70400 is docked with the clip applier 70450. Other embodiments are envisioned where the housing 70410 is orthogonal, or at least substantially orthogonal, to the clip applier 70450 when docked. Referring primarily to FIG. 47, the clip applier 70450 further comprises a flexible firing member 70465 positioned within a firing slot 70466 located proximal to the clip slot 70462. After the clip reloader 70400 is un-docked with the clip applier 70450, the flexible firing member 70465 can move from the firing slot 70466 into the clip slot 70462 to advance the clips 70404 into the end effector 70480. Once at least one, or all, of the clips 70404 have been advanced into the end effector 70480, the flexible firing member 70465 can be retracted from the clip slot 70462 into the firing slot 70466 and additional clips 70404 can be loaded into the clip slot 70462 by the clip reloader 70400.

Figure 48:
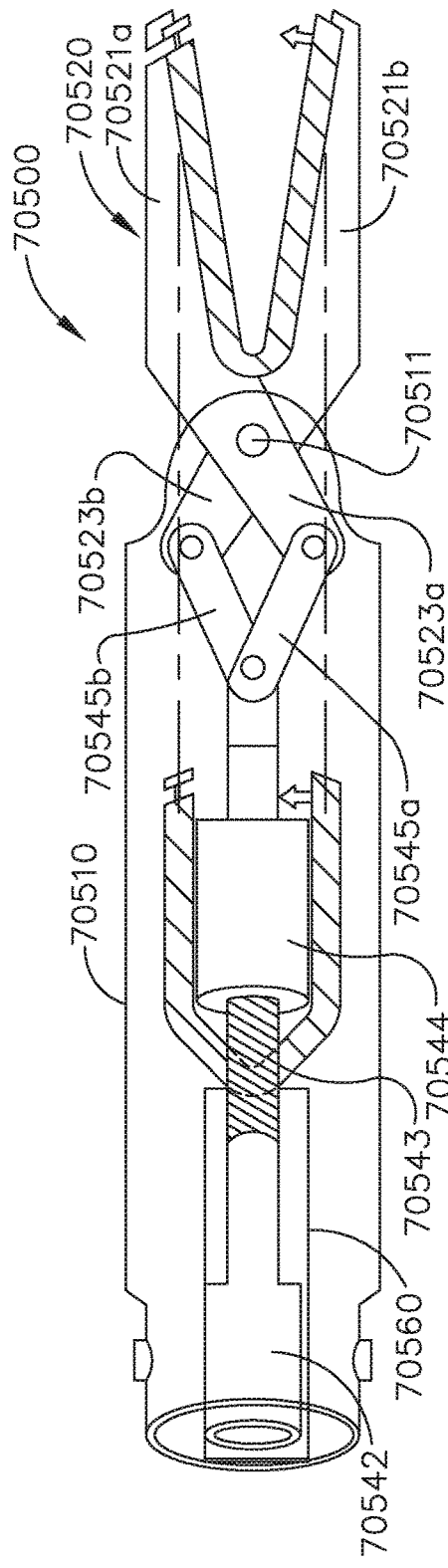
FIG. 48 is a partial cross-sectional plan view of a clip applier.
Figure 49:
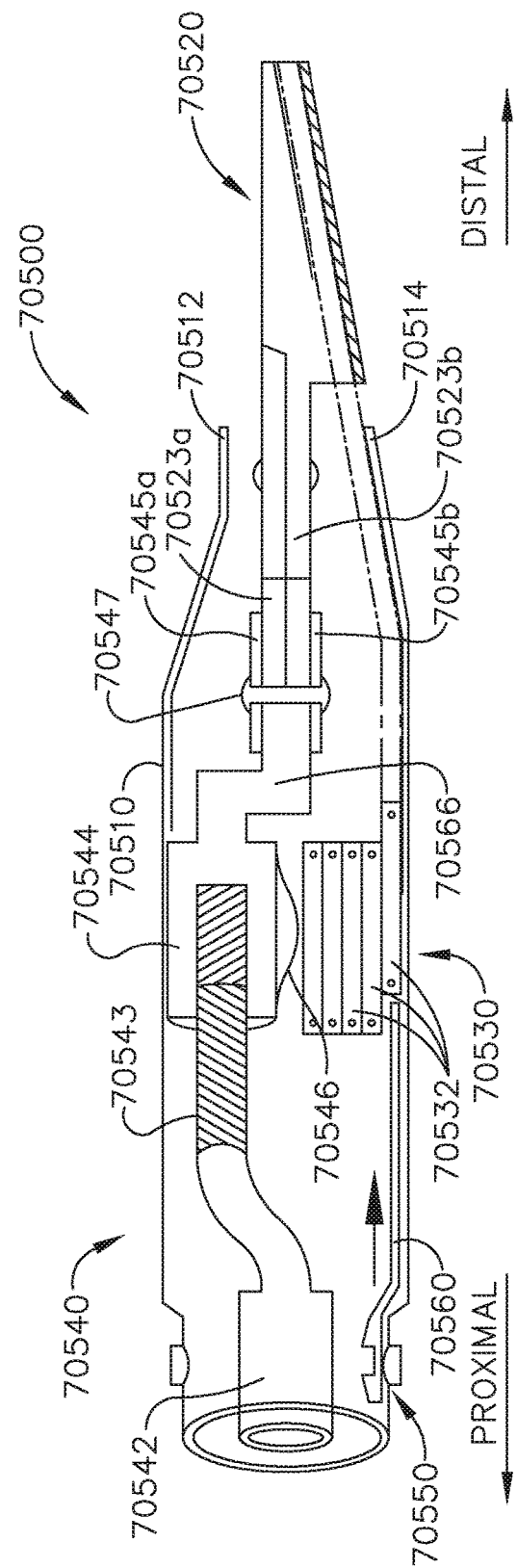
FIG. 49 is a partial cross-sectional side view of the clip applier of FIG. 48.
Figure 50:
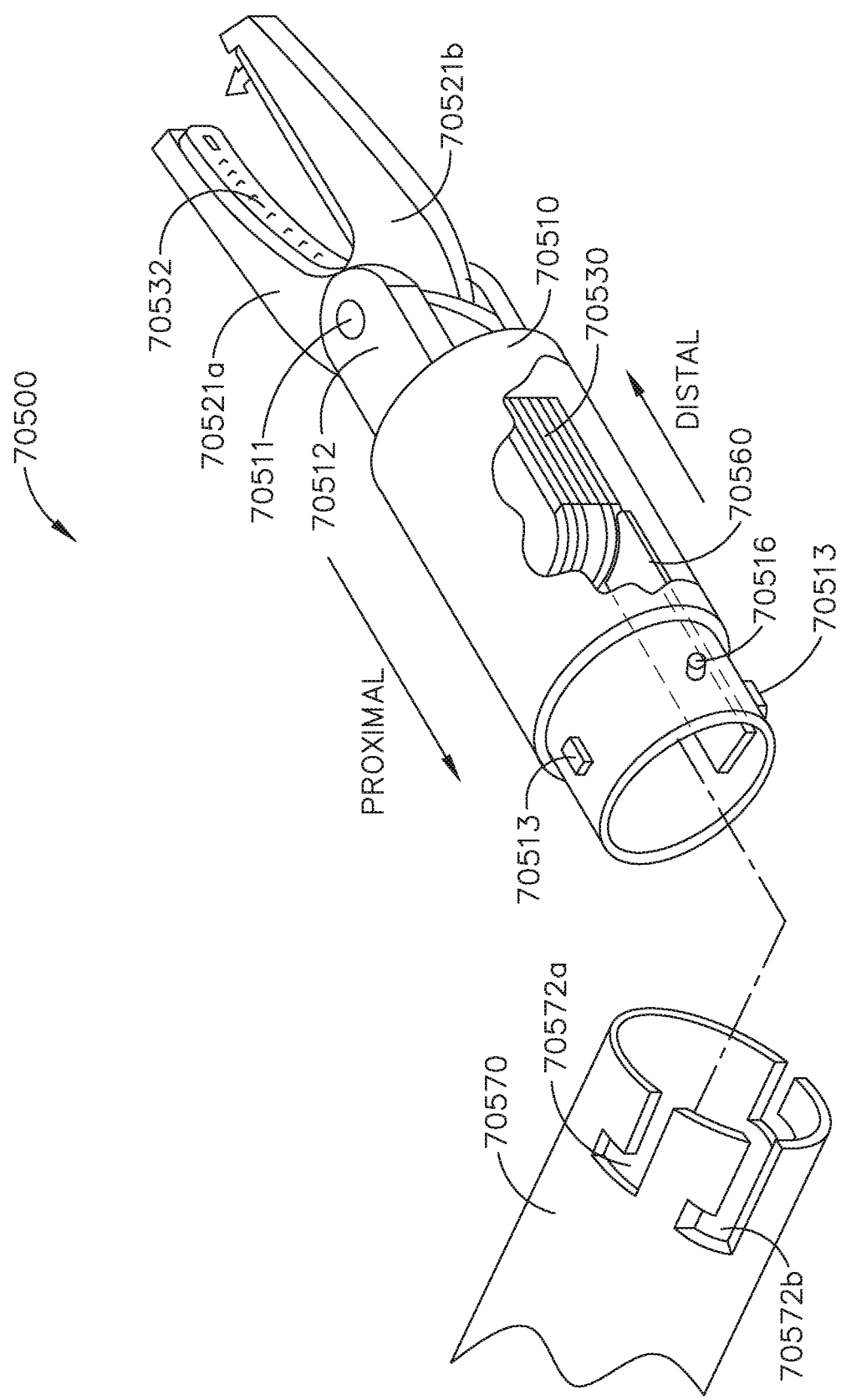
FIG. 50 is a perspective view of the clip applier of FIG. 48.

FIGS. 48-50 depict a clip applier 70500. The clip applier 70500 comprises an elongate shaft 70570 (see FIG. 50) extending from a housing, a shaft 70510 attachable to the elongate shaft 70570, an end effector 70520 extending from the shaft 70510, and a clip magazine 70530. The attachable shaft 70510 comprises an upper pivot link 70512 and a lower pivot link 70514 extending distally therefrom. The end effector 70520 comprises a first jaw 70521*a* and a second jaw 70521*b* movable relative to each other between an open position and a closed position about a pivot pin 70511. The pivot pin 70511 is constrained within openings in the upper pivot link 70512 and the lower pivot link 70514 of the shaft 70510. The clip magazine 70530 is removably positioned within the attachable shaft 70510 and comprises a plurality of clips 70532. The clip applier 70500 further comprises a closure system 70540 and a firing system 70550. The closure system 70540 and the firing system 70550 are discussed in greater detail below.

The closure system 70540 comprises a proximal closure driver 70542 comprising a threaded portion 70543, a distal closure driver 70566 comprising a closure nut 70544, an upper closure hinge 70545*a*, and a lower closure hinge 70545*b*. The proximal closure drive 70542 is configured to rotate in response to rotary motions generated inside the housing of the clip applier. The closure drive 70542 transmits rotational motion to the threaded portion 70543 which is threadably received in the closure nut 70544. The closure drive 70542 can comprise a flexible portion to facilitate the transfer of rotational motion to the closure nut 70544. The closure nut 70544 is rotatably constrained within the shaft 70510 such that rotation of the threaded portion 70543 in a first direction will result in translation of the nut 70544 distally, and rotation of the threaded portion 70543 in a second direction—opposite the first direction—will result in translation of the nut 70544 proximally. The distal closure driver 70566 extends from the closure nut 70544 and attaches to the upper closure hinge 70545*a* and the lower closure hinge 70545*b* via a closure pin 70547. The closure pin 70547 allows the upper and lower closure hinges 70545*a* and 70545*b* to translate distally and proximally with the distal closure driver 70566 while still being rotatable about the closure pin 70547. Further to the above, the upper closure hinge 70545*a* is rotatably engaged with a proximal portion 70523*a* of the first jaw 70521*a*, and the lower closure hinge 70545*b* is rotatably engaged with a proximal portion 70523*b* of the second jaw 70521*b*. As illustrated in FIG. 48, the first jaw 70521*a* and the second jaw 70521*b* cross over each other about the pivot pin 70511 in a scissor like formation. Such an arrangement allows the first jaw 70521*a* and the second jaw 70521*b* to move toward the open position when the upper and lower closure hinges 70545*a* and 70545*b* are translated distally by the closure system 70540, and allows the first jaw 70521*a* and the second jaw 70521*b* to move toward the closed position when the upper and lower closure hinges 70545*a* and 70545*b* are translated proximally by the closure system 70540.

The clip applier 70500 further comprises a firing system 70550 comprising a firing member 70560. The firing member 70560 is translatable through the end effector between an unfired position and a fired position in response to the rotary motions that drive the closure system 70540. Other embodiments are envisioned where the closure system 70540 and the firing system 70550 are operated by two separate motors within the housing of the clip applier, for instance. The firing member 70560 is configured to advance a clip 70532 from the clip magazine 70530 into the first and second jaws 70521*a* and 70521*b* of the clip applier 70500. As illustrated in FIG. 49, the clip magazine 70530 is at least partially supported by the closure system 70540. More specifically, a biasing member, such as leaf spring 70546, for example, biases the clips 70532 toward the firing member 70560 and holds the clip magazine 70530 in position. Other embodiments are envisioned where the closure system 70540 can align, and/or guide, and/or lock the clip magazine 70530 into place within the shaft 70510. The embodiment depicted in FIGS. 48 and 49 illustrates the closure system 70540 arranged around the clip magazine 70530 to allow a larger space inside the shaft 70510 for the clip magazine 70530 and clips 70532; however, a closure system can have any suitable arrangement. The closure system 70540 is discussed in further detail below.

The threaded portion 70543 and closure nut 70544 of the closure system 70540 allows for a more precise actuation of the first and second jaws 70521*a* and 70521*b* when moving between the open position and the closed position as compared to previous clip applier arrangements that utilize a translating closure tube or cam member. Rotary encoders and/or other sensors can be used in combination with the closure system 70540 to provide even greater accuracy in determining the position of the first and second jaws 70521*a* and 70521*b*.

Turning now to FIG. 50, the clip applier 70500 further comprise protrusions 70513 and 70516 extending from the proximal end of the shaft 70510. The protrusions 70513 and 70516 may be the same shape or different shapes. The protrusions 70513 and 70516 are configured to lockingly engage slots 70572*a* and 70572*b* in the elongate shaft 70570 of the clip applier 70500 to form a bayonet connection therebetween. The slots 70572*a* and 70572*b* comprise L-shaped portions that lock the protrusions 70513 and 70516 into place when the shaft 70510 is inserted into and then rotated relative to the elongate shaft 70570. FIG. 50 further depicts a clip 70532 located within the first jaw 70521*a* and the second jaw 70521*b*. The clip 70532 and other embodiments of clips for use with a clip applier, such as clip applier 70500, are discussed in further detail below.

Figure 51A:
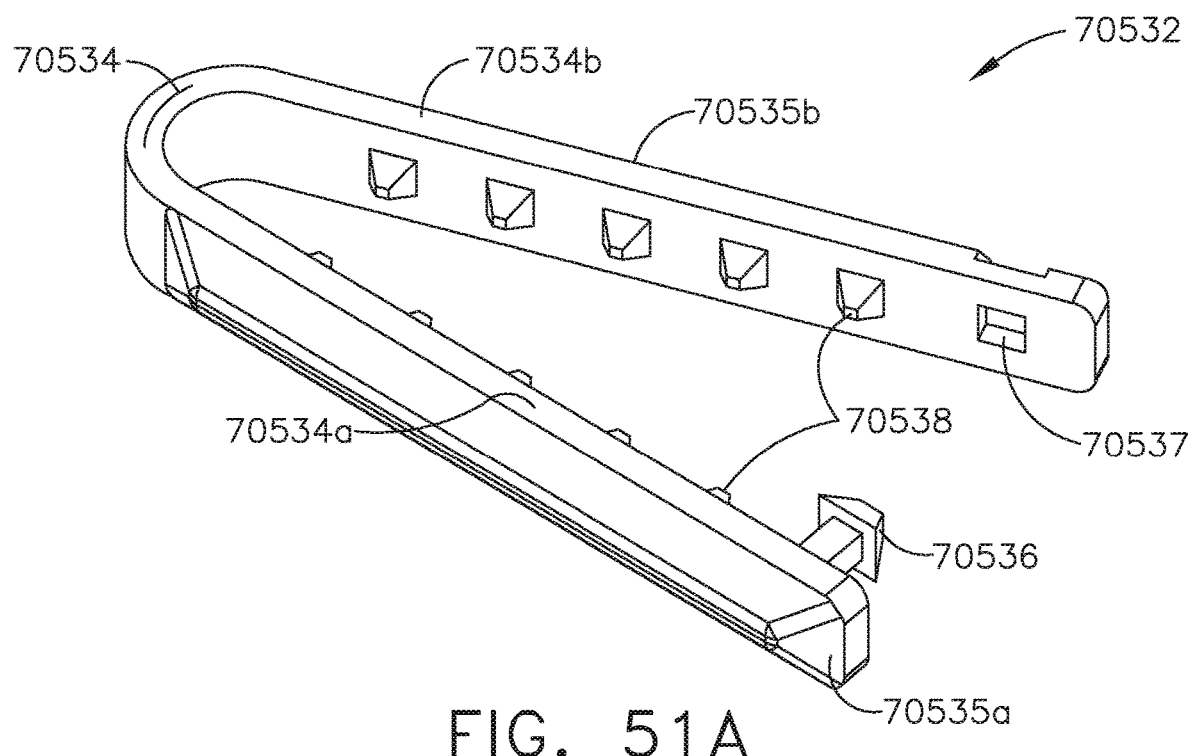
FIG. 51A is a perspective view of a clip including a flexible base.
Figure 51B:
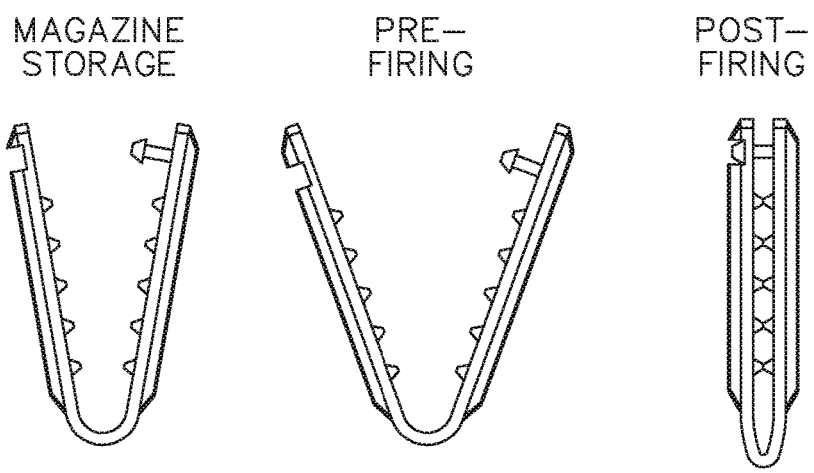
FIG. 51B is a side view of the clip of FIG. 51A in various configurations.
Figure 51C:
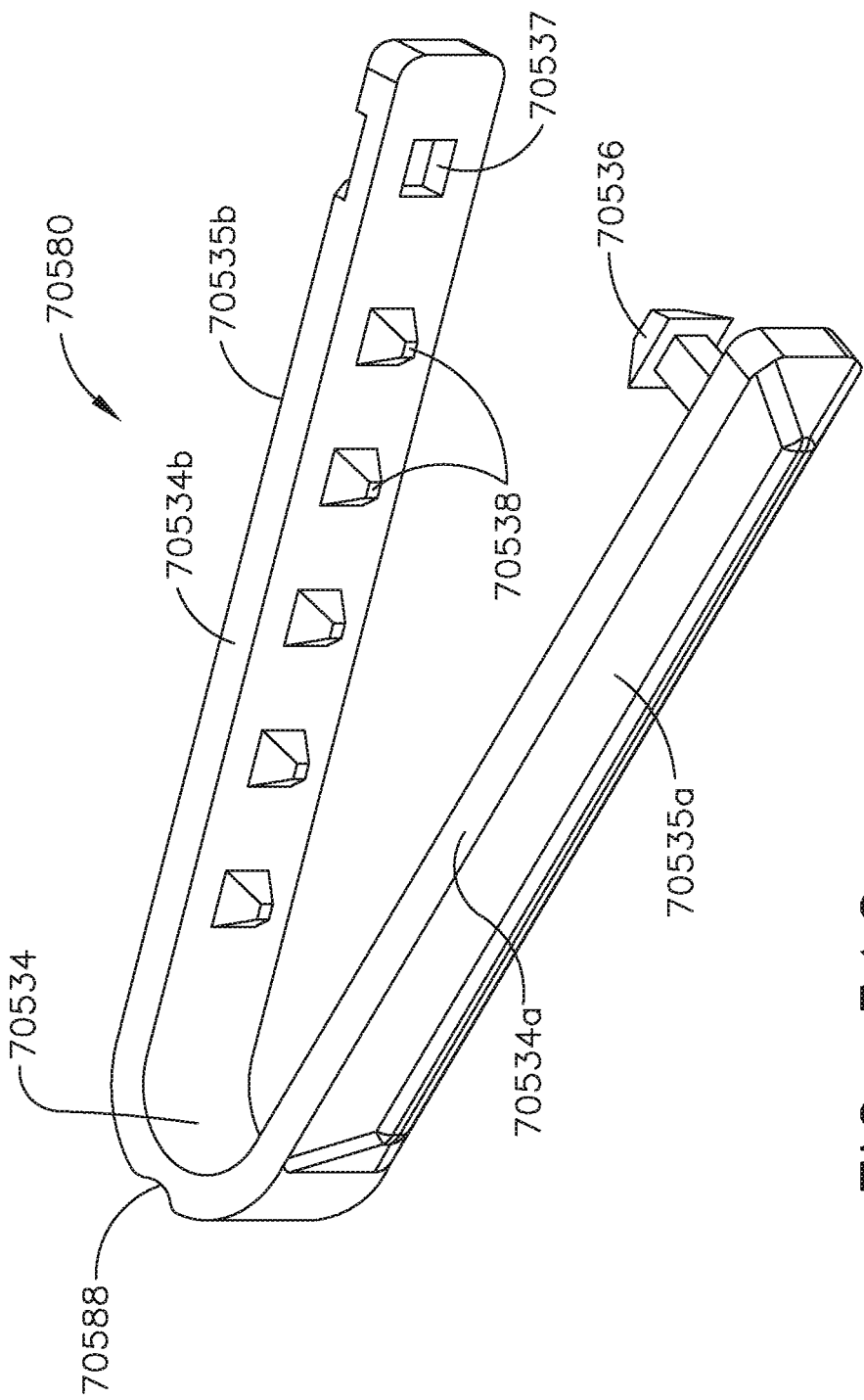
FIG. 51C is a perspective view of a clip for use with a clip applier.

Turning now to FIGS. 51A and 51B, the clip 70532 comprises a base portion 70534, a first leg 70534*a* extending from the base portion 70534, and a second leg 70534*b* extending from the base portion 70534 and opposing the first leg 70534*a*. The base portion 70534 can comprise a flexible material, such as plastic and/or any other suitable flexible material, to allow the clip 70532 to flex between multiple positions without breaking or becoming plastically deformed in an unsuitable manner. For example, the clip 70532 can be moved between a magazine storage configuration, a pre-firing configuration, and a post-firing configuration as depicted in FIG. 51B. The first leg 70534*a* comprises a reinforced region comprising a ridge 70535*a*, and the second leg 70534*b* comprises a reinforced region comprising a ridge 70535*b*. The ridges 70535*a* and 70535*b* extend along at least a portion of the first leg 70534*a* and the second leg 70534*b*, respectively. The ridges 70535*a* and 70535*b* act as a rigid backbone to prevent, or at least substantially reduce, the deformation of the first leg 70534*a* and the second leg 70534*b* during crimping. Other embodiments are envisioned where only one of the first leg 70534*a* and the second leg 70534*b* comprises a ridge. The ridges 70535*a* and/or 70535*b* may be comprised of a rigid material, such as a fiberglass-filled and/or particle-filled plastic, for example, to prevent, or at least reduce, deflection of the first leg 70534*a* and/or the second leg 70534*b* when the clip 70532 is crimped. The clip 70532 further comprises a locking portion, such as tooth 70536, for example, extending from a portion of the first leg 70534*a*. The tooth 70536 lockingly engages the edges of an opening, or window, 70537 in the second leg 70534*b* when the clip 70532 is crimped (see the post-firing configuration in FIG. 51B). Such an arrangement allows the clip 70532 to stay in a crimped state after the clip 70532 has been released from the jaws of a clip applier. Further, the clip 70532 includes grip features, such as protrusions 70538, extending from the inside surfaces of the first and second legs 70534*a* and 70534*b*. The protrusions 70538 engage tissue clamped between the first and second legs 70534*a* and 70534*b* when the clip 70532 is crimped. The protrusions 70538 prevent, or at least substantially reduce, the movement of the tissue relative to the clip 70532 after the clip 70532 is crimped around the tissue. The protrusions 70538 may be any number of shapes and sizes, such as pyramidal shapes, conical shapes, frustoconical shapes, for example, and/or any other suitable shape.

Turning now to FIGS. 51C-51F, a different clip 70580 for use with a clip applier is depicted. The clip 70580 is similar to clip 70532 in many respects. That said, the base 70534 of the clip 70580 comprises a stress relief notch 70588 on the side of the base 70534 opposite the first and second legs 70534*a* and 70534*b*. In use, the stress relief notch 70588 allows the first and second legs 70534*a* and 70534*b* to flex inwardly and then outwardly a number of times without being plastically deformed in an unsuitable manner. However, in various circumstances, the clip 70580 can be configured to yield, or deform plastically, when the clip 70580 is sufficiently compressed. Such designed or controlled yielding, in various instances, can help the clip 70580 fold into the desired shape.

Figure 52:
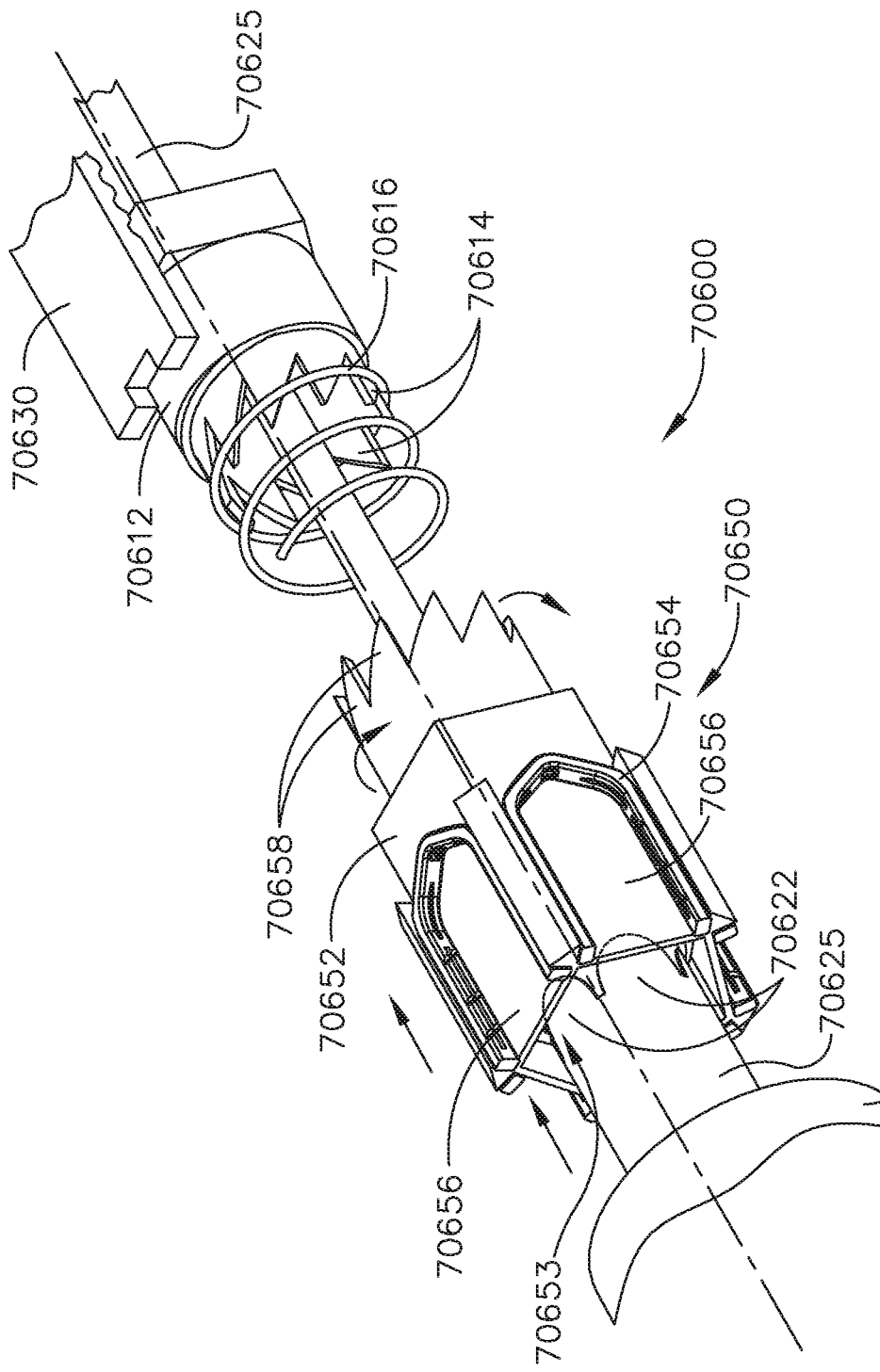
FIG. 52 is a perspective view of a clip applier including a rotatable clip magazine.
Figure 53:
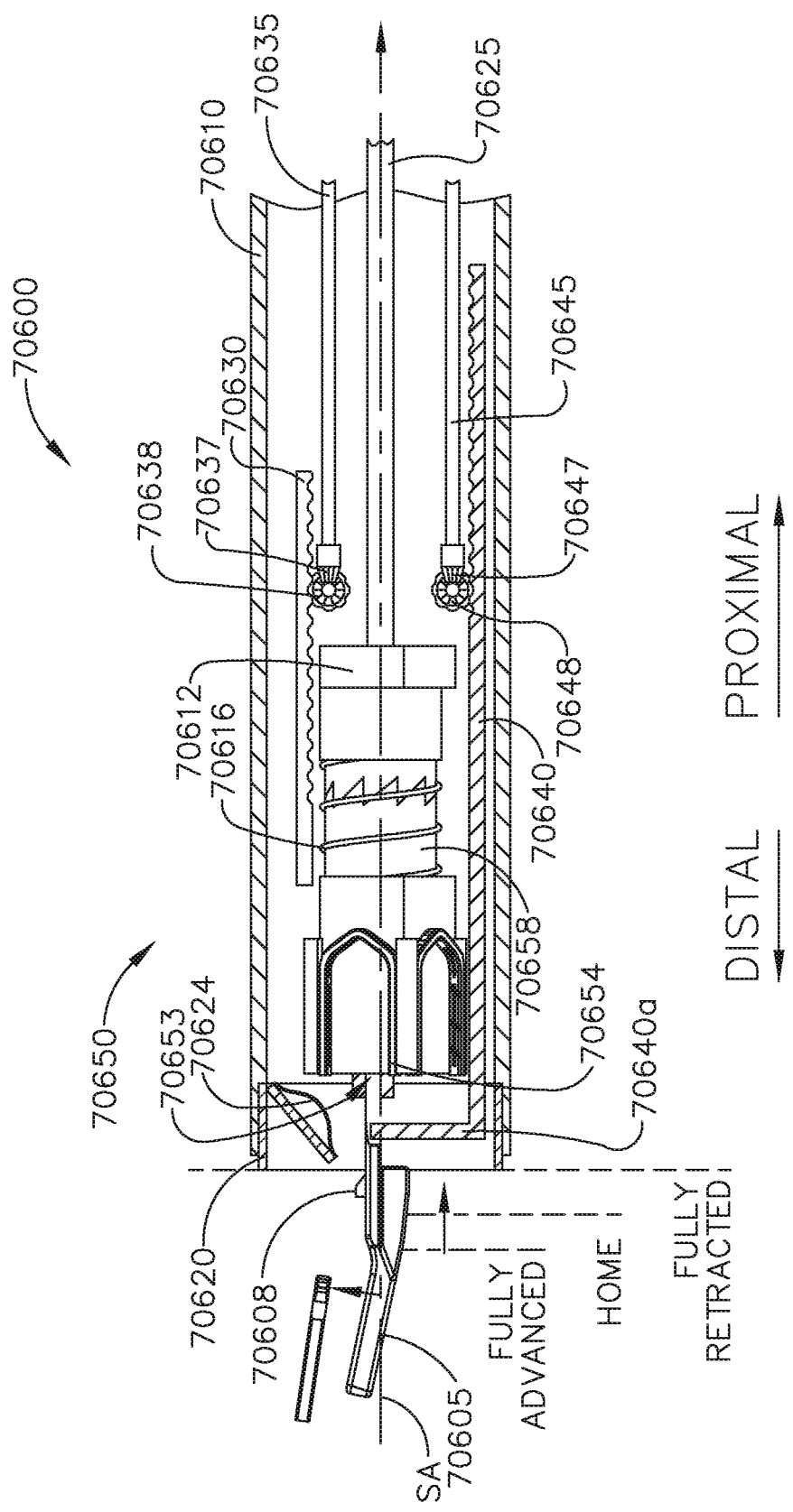
FIG. 53 is a partial cross-sectional view of the clip applier of FIG. 52 illustrating a closure tube of the clip applier in a fully retracted position.

FIGS. 52-60 depict a clip applier 70600. Turning now to FIG. 53, the clip applier 70600 comprises a shaft 70610 extending from a housing, an end effector 70605 extending from the shaft 70610, and a rotatable clip magazine 70650. The end effector 70605 comprises a first jaw and a second jaw that are movable relative to each other between an open position and a closed position, similar to the first jaw 70123*a* and the second jaw 70123*b* of the clip applier 70100 discussed above. The rotatable clip magazine 70650 is rotatably and slidably supported within the clip applier 70600. More specifically, the rotatable clip magazine 70650 is rotatable about shaft axis SA and translatable along shaft axis SA. The shaft axis SA is defined by the shaft 70610. Further detail regarding how the clip magazine 70650 is supported within the clip applier 70600 is provided below.

Referring to FIG. 52, the rotatable clip magazine 70650 comprises a body portion 70652 including five sides, each of which comprises a clip channel 70656 configured to removably store a clip 70654 therein. The body portion 70652 further comprises an opening 70653 that extends through the body portion 70652. In the illustrated embodiment, the body portion 70652 is pentagonal in shape, for example; however, other embodiments are envisioned in which the opening 70653 comprises different shapes to allow for more than or less than five clip channels 70656 and, therefore, more than or less than five clips 70654 stored in the rotatable clip magazine 70650. In at least one embodiment, the clips 70654 comprise a clip width of 0.080", a clip thickness of 0.03", and a clip length of 0.310" (for a LIGAMAX 5 Clip) or 0.315" (for an ER320 Clip), for example; however, clips having any suitable size can be used. Moreover, it is envisioned that the clips stored in the clip magazine 70650 will have the same, or at least substantially the same size; however, alternative embodiments are envisioned in which clips having different sizes may be stored in the same clip magazine. Further, in at least one embodiment, the overall diameter of the entire rotatable clip magazine 70650 is 0.996", for example; however, the clip magazine 70650 can have any suitable diameter—including diameters which can permit the clip magazine 70650 to be inserted through a trocar. The rotatable clip magazine 70650 further includes a clocking portion, such as teeth 70658, for example, extending proximally from the clip magazine 70650. The clip applier 70600 comprises several drives and drivers which define the motion and/or operating sequence of the clip applier 70600, as described in further detail below.

Referring again to FIG. 53, the clip applier 70600 further comprises a closure tube 70620, a feeder member 70630, and a firing member 70640. The closure tube 70620 comprises a closure drive 70625 extending proximally from the closure tube 70620. The closure drive 70625 extends through the opening 70653 in the clip magazine 70650 and is operably engaged with an actuator inside the housing of the clip applier 70600. The clip magazine 70650 is supported on at least a portion of the closure drive 70625. The closure tube 70620 is at least partially supported and aligned within a recess in the shaft 70610. The closure tube 70620 is movable between a plurality of positions, such as a fully retracted position, a home position, and a fully advanced position (see FIGS. 53 and 54A). Similar to the crimping drive 70180 of the clip applier 70100, the closure tube 70620 is configured to move the first jaw and the second jaw of the end effector 70605 toward and away from each other. When the closure tube 70620 moves distally, the closure tube 70620 cammingly engages the first and second jaws to move the first and second jaws to the closed position and, when the closure tube 70620 moves proximally, the closure tube 70620 engages jaw cams on each of the first and second jaws to move the first and second jaws to the open position. That said, any suitable jaw opening and closing arrangement could be used.

The feeder member 70630 is aligned with one of the clip channels 70656 of the rotatable clip cartridge 70650, and is configured to advance a clip 70654 out of the clip channel 70656 that is aligned with the feeder member 70630 toward the end effector 70605. The feeder member 70630 is translatable linearly through the clip applier 70600 by a feeder gear 70638 and a feeder drive 70635 which are operably engaged with a rack portion of the feeder member 70630. The feeder drive 70635 comprises a pinion gear 70637 at the distal end thereof which is operably engaged with the feeder gear 70638 such that, as the feeder drive 70635 is rotated, the feeder member 70630 is translated linearly through the clip applier 70600. The feeder drive 70635 is operably engaged with a first motor inside the housing of the clip applier 70600. The first motor transmits rotational motion to the feeder drive 70635. Similar to the operation of the feeder member 70630, the firing member 70640 is translatable linearly through the clip applier by a firing gear 70648 and a firing drive 70645 which are operably engaged with a rack portion of the firing member 70640. The firing drive 70645 comprises a pinion gear 70647 on the distal end thereof which is engaged with the firing gear 70648 such that, as the firing drive 70645 is rotated, the firing member 70640 is translated linearly through the clip applier 70600. Further, the firing drive 70645 is operably engaged with a second motor inside the housing of the clip applier 70600. The second motor transmits rotational motion to the firing drive 70645. Other embodiments are envisioned where the feeder drive 70635 and the firing drive 70645 are rotatable by the same motor utilizing a transmission. Further, other embodiments are envisioned, and are described further below, where the feeder member 70630 and the firing member 70640 translate together through the clip applier 70600. Operation of the feeder member 70630 and firing member 70640 are also described in greater detail below.

Referring primarily to FIG. 53, the firing member 70640 comprises a distal portion 70640a extending therefrom that is configured to advance a clip 70654 into the end effector. The shaft 70610 further includes a ground portion 70612 mounted to the shaft 70610 and aligned with the clip magazine 70650. The ground portion 70612 is mounted to the shaft 70610 such that the ground portion 70612 is not movable, translatable, and/or rotatable relative to the shaft 70610. The ground portion 70612 includes a clocking portion, such as teeth 70614, for example, extending distally therefrom as illustrated in FIG. 54B. The teeth 70614 of the ground portion 70612 are aligned, or at least substantially aligned, with the teeth 70658 of the rotatable clip magazine 70650. Further, the ground portion 70612 supports a biasing member, such as spring 70616, for example, thereon. The spring 70616 biases the clip magazine 70650 distally toward the closure tube 70620 and the end effector 70605, as illustrated in FIG. 54A. Other embodiments are envisioned where the spring comprises a leaf spring and the clip applier 70600 further comprises a track and the leaf spring can be configured to both index the clip magazine 70650 and prevent the clip magazine 70650 from counter rotation. In any event, the rotation of the clip magazine 70650 about the shaft axis SA and translation of the clip magazine 70650 along shaft axis SA is described in further detail below.

Referring primarily to FIG. 52, the closure tube 70620 includes clocking channels 70622 located radially around the closure drive 70625. The closure drive 70625 rotatably and slidably supports the rotatable clip magazine 70650 thereon as discussed above. The clocking channels 70622 are engaged with protrusions within the opening 70653 of the clip magazine 70650 to rotatingly lock the clip magazine 70650 into place relative to the closure tube 70620 when the closure tube is in the home position or the fully advanced position. When the closure tube 70620 is moved to the fully retracted position, as illustrated in FIG. 53, the spring 70616 moves/biases the clip magazine 70650 toward the closure tube 70620 resulting in the clocking channels 70622 becoming disengaged from the protrusions within the opening 70653 of the clip magazine 70650. As such, the clip magazine 70650 can rotate freely about shaft axis SA. Further, when the closure tube 70620 is moved to the fully retracted position, the teeth 70658 of the clip magazine 70650 engage the teeth 70614 of the ground portion 70612 to rotate (i.e., cycle) the clip magazine 70650. More specifically, the teeth 70658 and the teeth 70614 are structured to rotate the clip magazine 70650 about the shaft axis SA a predefined amount of degrees based on the spacing and angles of the teeth 70658 relative to the teeth 70614. The reader will appreciate that the spacing and angles of the teeth 70658 relative to the teeth 70614 can be designed to generate a suitable degree of rotation for the clip magazine 70650 about shaft axis SA. In the embodiment depicted in FIGS. 52-54A, the teeth 70658 and the teeth 70614 are spaced and aligned such that, when they are engaged, the clip magazine 70650 rotates 72 degrees to align an adjacent clip 70654 with the feeder member 70630. After the clip magazine 70650 is cycled, the closure tube 70620 can be moved distally from the fully retracted position to the home position (FIG. 54A) resulting in the clocking channels 70622 engaging the protrusions in the opening 70653 of the clip magazine 70650 to lock the rotation of the clip magazine 70650 as discussed above. Usage of the clip applier 70600 to advance, form, and fire a clip 70654 is describe in further detail below.

Figure 55:
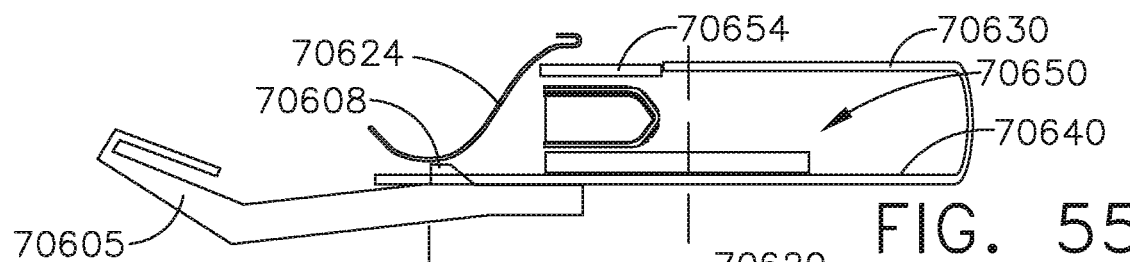
FIG. 55 is a partial cross-sectional view of the clip applier of FIG. 52 illustrating clips stored in the rotatable clip magazine prior to being advanced, illustrated with some components removed.
Figure 56:
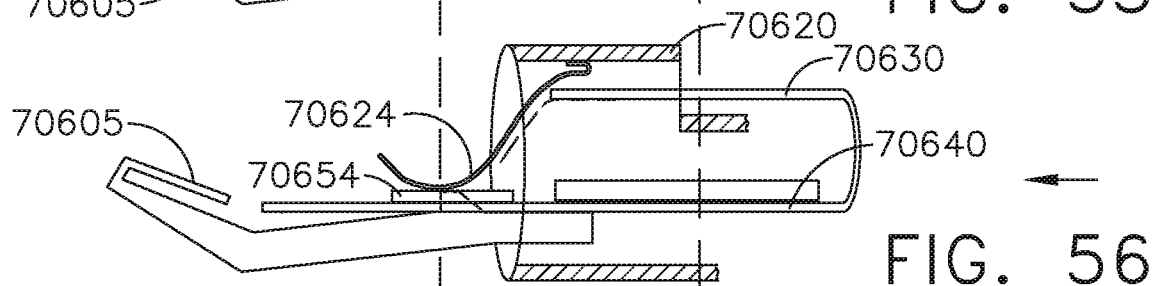
FIG. 56 is a partial cross-sectional view of the clip applier of FIG. 52 illustrating a clip being advanced from the rotatable clip magazine by a feeder member of the clip applier.
Figure 57:
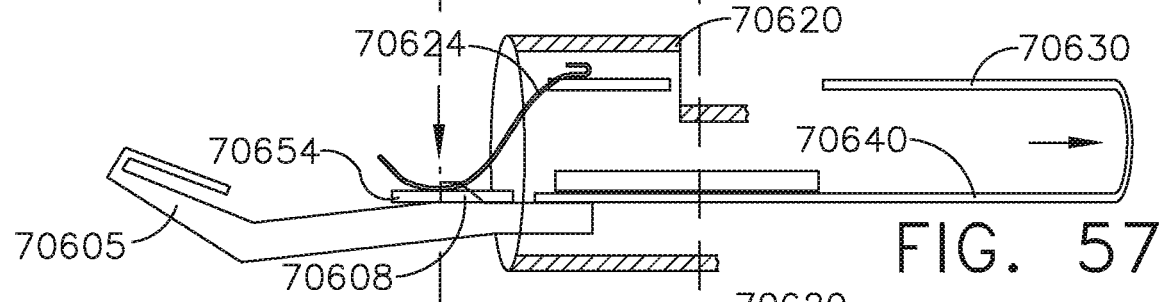
FIG. 57 is a partial cross-sectional view of the clip applier of FIG. 52 illustrating the feeder member retracted.

As mentioned above, the feeder member 70630 and firing member 70640 can be translatable together. For simplicity, FIGS. 55-60 illustrate the functions of clip applier 70600 where the feeder member 70630 and firing member 70640 move together to feed and fire a clip 70654 from the rotatable clip magazine 70650. Turning now to FIGS. 55 and 56, a clip 70654 is advanced from the rotatable clip magazine 70650 into engagement with a biasing member, such as a leaf spring 70624, for example, of the closure tube 70620 by the feeder member 70630. The leaf spring 70624 biases and guides the clip 70654 onto the top of the firing member 70640, as illustrated in FIG. 56. When the firing member 70640 and feeder member 70630 are retracted, the clip 70654 is moved further downward by the leaf spring 70624 and seated around pre-form features, such as protrusions 70608, for example, depicted in FIG. 57. Protrusions 70608 can be similar to protrusions 70126a and 70126b described above (See FIGS. 35A and 35B). One protrusion 70608 is located on one jaw of the end effector 70605, and another protrusion 70608 is located on another jaw of the end effector 70605.

Figure 58:
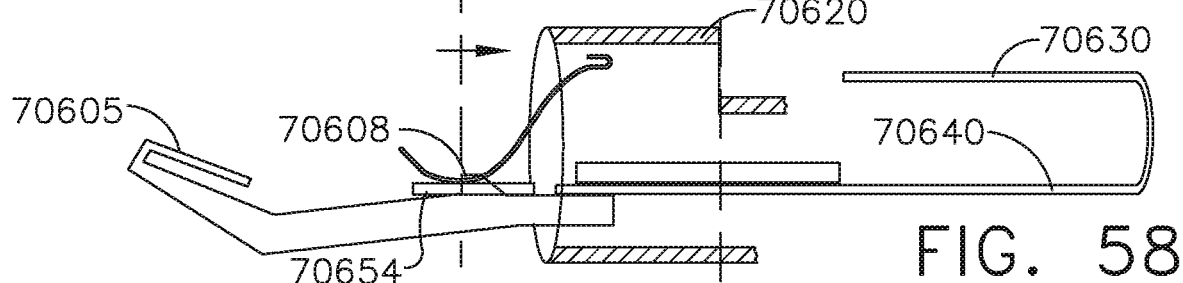
FIG. 58 is a partial cross-sectional view of the clip applier for FIG. 52 illustrating a closure tube of the clip applier in a fully retracted position.
Figure 59:
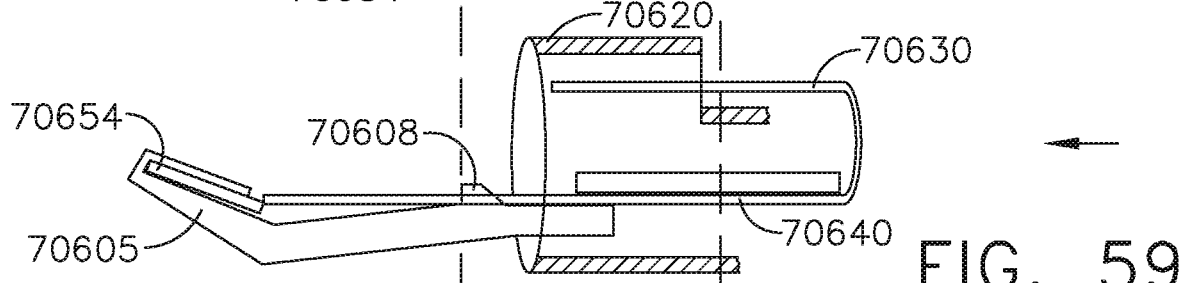
FIG. 59 is a partial cross-sectional view of the clip applier of FIG. 52 illustrating the closure tube in a home position and a firing member advancing a clip, illustrated with some components removed.
Figure 60:
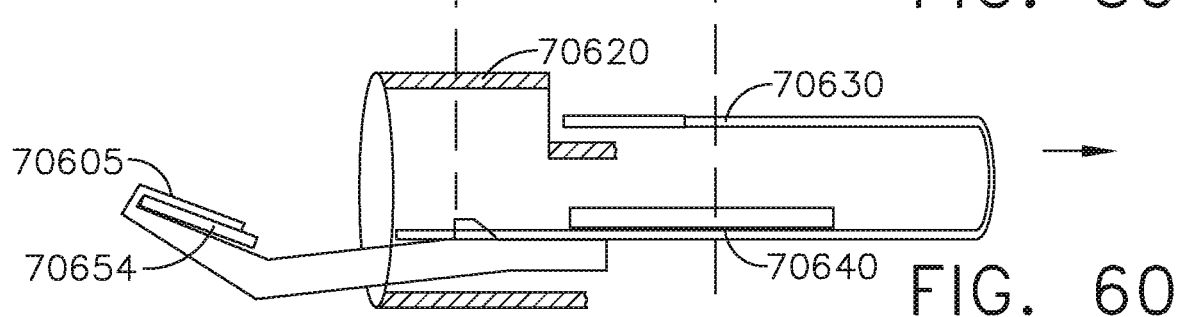
FIG. 60 is a partial cross-sectional view of the clip applier of FIG. 53 illustrating the firing member retracted and the closure tube in a fully advanced position, illustrated with some components removed.

When the closure tube 70620 is in the fully retracted position, referring to FIG. 58, the jaws of the clip applier 70600 are in the open position and the protrusions 70608 expand the clip 70654 from a storage configuration into a firing configuration—similar to the expansion of clip 70140 described above in connection with FIGS. 35A and 35B. When the closure tube 70620 is moved to the fully retracted position, as described above, the rotatable clip magazine 70650 is rotated (i.e., cycled) about the shaft axis SA to position another clip 70654 into alignment with the feeder member 70630. Turning to FIG. 59, the firing member 70640 can be moved toward the end effector 70605 to advance the clip 70654 over the protrusions 70608 and into the end effector 70605. As discussed above in connection with protrusions 70126a and 70126b, the protrusions 70608 can comprise angled portions that allow the clip 70654 to slide over the protrusions 70608 when advanced distally by the firing member 70640. Once the clip 70654 is positioned in the end effector 70605, the closure tube 70620 can be moved to the fully advanced position (FIG. 60) to move the jaws from the open position to the closed position to crimp the clip 70654 positioned between the jaws.

Because the feeder member 70630 and the firing member 70640 translate together, further to the above, the feeder member 70630 advances another clip 70654 (i.e., the clip that was rotated into position when the closure tube 70620 was fully retracted) from the clip cartridge 70650 down onto the firing member 70654 with the aid of the leaf spring 70624, as discussed above, when the firing member 70640 advances a clip 70654 into the end effector 70605. Again, the firing member 70640 and the feeder member 70630 can be retracted to allow the new clip 70654 to be biased downward by the leaf spring 70624 and seated around the protrusions 70608. The new clip 70654 can then be expanded to the firing configuration as clip magazine 70650 is cycled, and then the new clip 70654 can be advanced into the end effector 70605 for crimping as discussed above. The process discussed above can be repeated until the clip magazine 70650 has been spent. The reader will appreciate that the closure tube 70620 can be moved between the home position (FIGS. 56 and 57) and the fully advanced position (FIG. 60) to crimp and release a clip 70654 within the end effector 70605 without cycling the clip magazine 70650. This allows the jaws of the end effector 70605 to move between the open and closed positions without cycling the clip magazine 70650 and/or ejecting another clip from the clip magazine 70650.

Figure 61:
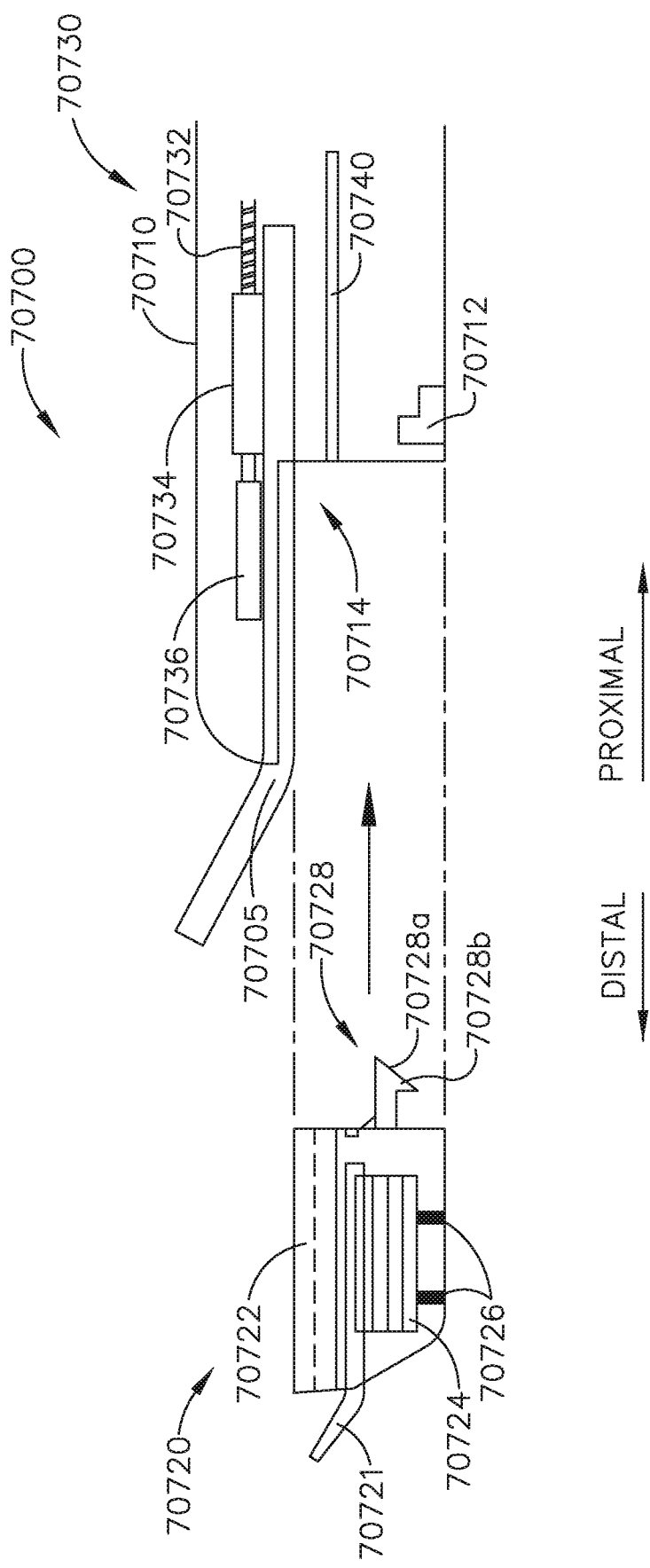
FIG. 61 is a partial cross-sectional view of a clip applier comprising a replaceable cartridge.

FIG. 61 depicts a clip applier 70700 in accordance with at least one embodiment. The clip applier 70700 comprises a shaft 70710 extending from a housing, an end effector 70705 extending from the shaft 70710, and a clip cartridge 70720 that is releasably attachable to the clip applier 70700. The end effector 70705 comprises a first jaw and a second jaw movable relative to each other, similar to the first and second jaws 70123*a* and 70123*b* discussed above. The clip applier 70700 further comprises a firing system 70730 that comprises a rotatable drive 70732 which is operably responsive to a motor inside the housing of the clip applier 70700. The rotatable drive 70732 comprises a threaded portion. The firing system 70730 further includes a firing member 70736 and a firing nut 70734. The firing nut 70734 is threadably received on the threaded portion of the rotatable drive 70732. The firing nut 70734 is rotatably constrained within the clip applier 70700 such that the rotation of the rotatable drive 70732 translates the firing nut 70734 through the clip applier 70700. The firing member 70736 is engaged with the firing nut 70734 and translates into the first and second jaws of the end effector 70705 in response to translation of the firing nut 70734 by the rotatable drive 70732. Attachment of the clip cartridge 70720 to the clip applier 70700 is described in greater detail below.

The clip applier 70700 further comprises a docking region, or recess 70714, in the distal end of the clip applier 70700, as illustrated in FIG. 61. The clip cartridge 70720 comprises a body portion 70722 that is slidably receivable in the recess 70714 of the clip applier 70700. A locking feature 70728 extends proximally from the clip cartridge 70720. The locking feature 70728 includes an angled surface 70728*a* at the proximal end thereof and a detent 70728*b* extending downwardly, although the locking feature 70728 can include any suitable arrangement. The locking feature 70728 engages a protrusion 70712 of the shaft 70710 when the clip cartridge 70720 is docked within the recess 70714. More specifically, the angled surface 70728*a* slides over the protrusion 70712 and the downwardly extending detent 70728*b* locks into place proximal to the protrusion 70712, thus locking the clip cartridge 70720 to the clip applier 70700. In such instances, the locking feature 70728 deflects as the angled surface 70728*a* slides over the protrusion 70712 and then resiliently returns to, or at least toward, its undeflected configuration, when the detent 70728*b* locks into place. A sufficient distal pulling motion can cause the locking feature 70728 to deflect and release the clip cartridge 70720 from the clip applier 70700. Operation of the clip applier 70700 is described in further detail below.

The clip cartridge 70720 further comprises a ramp portion 70721, a plurality of clips 70724 positioned in a stack, and biasing members, such as springs 70726, for example. The clips 70724 are biased toward the ramp portion 70721 by the springs 70726. In fact, the top clip 70724 in the stack of clips is biased into the ramp portion 70712 by the springs 70726. When the clip cartridge 70720 is docked with the clip applier 70700, as discussed above, the ramp portion 70721 aligns with a feeder drive 70740 of the clip applier 70700. The feeder drive 70740 is operably responsive to an actuator within the housing of the clip applier 70700. The feeder drive 70740 is configured to reciprocatingly actuate into the ramp portion 70721. To accommodate an angled portion within the ramp portion 70721 the feeder drive 70740 can be flexible. The feeder drive 70740 feeds the top clip 70724 in the stack of clips through the ramp portion 70721 and into the end effector 70720. Once in the end effector 70705, the clip 70724 can be advanced further distally into the first and second jaws of the end effector 70705 by translation of the firing member 70736, as discussed above. Once located in the first and second jaws, the clip 70724 can be crimped by a crimping drive. The feeder drive 70740 can be retracted, allowing another clip 70724 to be biased into the ramp portion 70721. The feeder drive 70740 can advance the new clip 70724 through the ramp portion 70721 and into the first and second jaws of the end effector 70705 as discussed above. The process discussed above can be repeated until all of the clips 70724 in the clip cartridge 70720 have been depleted, and/or until a suitable number of clips have been applied to the tissue.

Figure 62B:
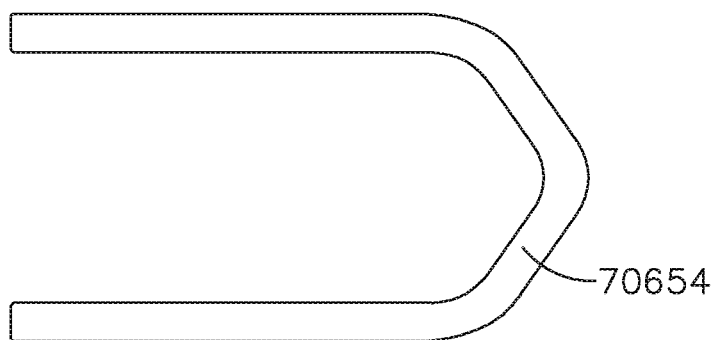
FIG. 62B is a plan view of a clip for use with the rotatable clip magazine of FIG. 62A.
Figure 62A:
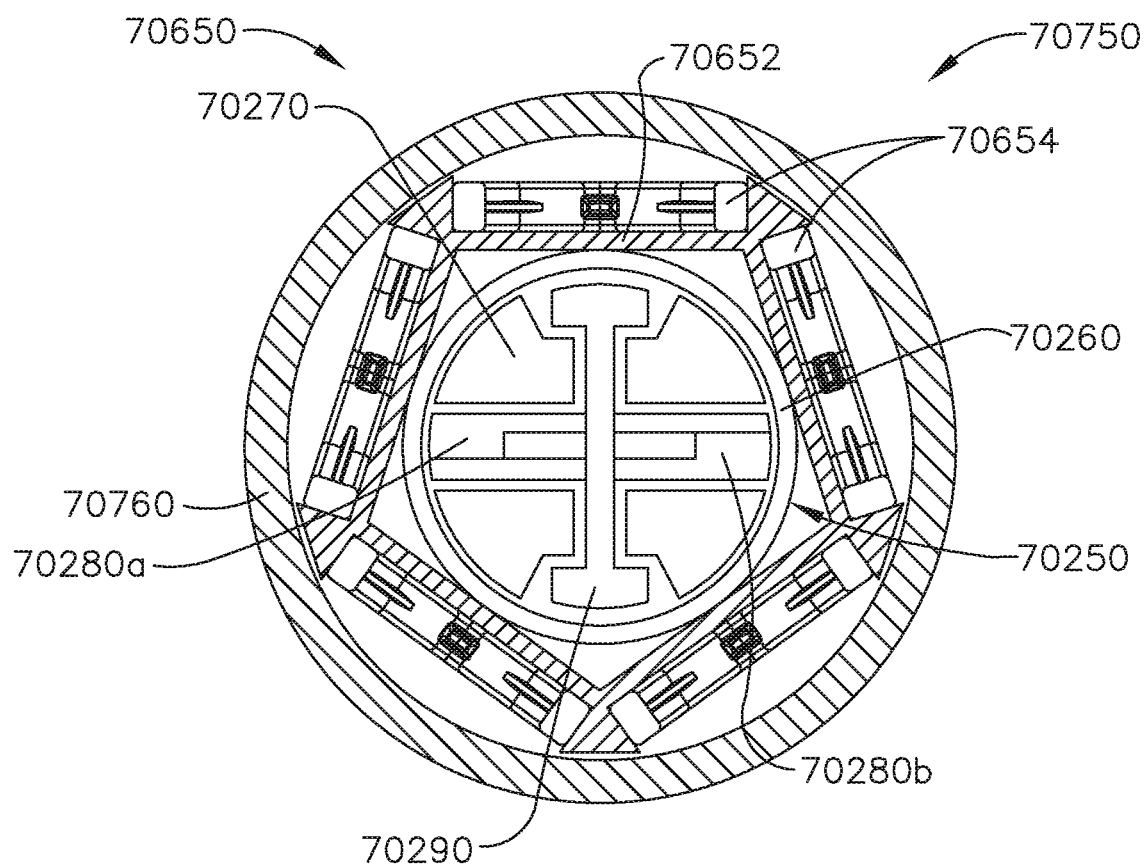
FIG. 62A is a cross-sectional end view of a rotatable clip magazine.

FIG. 62A depicts a clip applier system 70750 in accordance with at least one embodiment. The clip applier system 70750 comprises a shaft 70760 extending from a housing, the clip applier 70250 depicted in FIG. 42 positioned at least partially within the shaft 70760, and the rotatable clip magazine 70650 depicted in FIGS. 52-60 positioned within the shaft 70760. A feeder member is configured to advance the clips 70654 from the rotatable clip magazine 70650— one at a time—into the first and second jaws 70280*a* and 70280*b* of the clip applier 70250. Once located within the first and second jaws 70280*a* and 70280*b*, the clip 70654 can be crimped as discussed above in relation to FIGS. 42A and 42B. Once the clip 70654 is crimped, the rotatable clip magazine 70650 can be cycled (i.e., rotated) to position another clip 70654 for advancement into the first and second jaws 70280*a* and 70280*b* of the clip applier 70250 by the feeder member. This process can continue until all of the clips 70654 in the rotatable clip magazine 70650 have been spent. After all of the clips 70654 have been spent, the rotatable clip magazine 70650 can be replaced with another rotatable clip magazine 70650 containing a full complement of clips 70650. Other embodiments are envisioned where the spent rotatable clip magazine 70650 can be detached from the clip applier system 70750, reloaded with clips 70650, and then re-attached to the clip applier system 70750 for further use.

Turning now to FIGS. 63A and 63B, an articulation joint 70800 for use with a clip applier is illustrated. The articulation joint 70800 releasably couples a clip cartridge 70820 to a shaft 70810 of a clip applier. The shaft 70810 comprises an articulation pivot, or pivot pin 70814, extending from the inside of the shaft 70810. The pivot pin 70814 comprises a base portion 70817, a first leg 70814a extending from the base portion 70817, and a second leg 70814b extending from the base portion 70817 and opposing the first leg 70814a. The first and second legs 70814a and 70814b extend away from each other. The first leg 70814a comprises a first detent, or shoulder, 70816a extending outwardly from the first leg 70814a, and the second leg 70814b comprises a second detent, or shoulder, 70816b extending outwardly from the second leg 70814b. The clip cartridge 70820 comprises a first opening 70822 and, also, a second opening 70824 positioned adjacent and lateral to the first opening 70822. The first opening 70822 is centered in the clip cartridge 70820 and rotatably receives the pivot pin 70814 when the clip cartridge 70820 is attached to the shaft 70810. The first leg 70814a and the second leg 70814b flex towards each other when the first opening 70822 is slid onto the pivot pin 70814 due to angled surfaces at the end of each of the first leg 70814a and second leg 70814b (See FIG. 63B). As the first leg 70814a and second leg 70814b flex toward each other, the pivot pin 70814 can slide through the first opening 70822 until the first and second detents 70816a and 70816b clear the first opening 70822, as illustrated in FIG. 63B. Once the first and second detents 70816a and 70816b clear the first opening 70822, the first and second legs 70814a and 70814b can expand to lock the clip cartridge 70820 to the pivot pin 70814. More specifically, the bottom surfaces of the first and second detents 70816a and 70816b rest on an outer surface 70826 of the clip cartridge 70822 preventing the clip cartridge 70820 from being detached from the pivot pin 70814 unless a sufficient force is applied that exceeds a predetermined, or designed, force threshold. The reader will appreciate that, with force, a user of the clip applier can attach and detach the clip cartridge 70820 to the shaft 70810. Articulation of the clip cartridge about the pivot pin 70814 is described in further detail below.

The clip applier depicted in FIGS. 63A and 63B further comprises a rotatable output 70830 that is operably responsive to a motor located within the housing of the clip applier. The rotatable output 70830 is threadably engaged with a threaded portion 70834 of an articulation bar 70832. Rotation of the rotatably output 70830 in a first direction translates the articulation bar 70832 distally, and rotation of the rotatable output 70830 in a second, or opposite, direction translates the articulation bar 70832 proximally. The articulation bar 70832 comprises a downwardly extending protrusion 70836 that is slidably received in a slot 70812 defined in the shaft 70810. The protrusion 70836 and slot 70812 guide the articulation bar 70832 as the articulation bar 70832 translates and limit relative lateral motion between the articulation bar 70832 and the shaft 70810. The articulation bar 70832 further comprises an upwardly extending protrusion 70838 which is received in the second opening 70824 of the clip cartridge 70820 when the clip cartridge 70820 is attached to the shaft 70810. In use, the distal translation of the articulation bar 70832 will rotate the clip cartridge 70820 about the pivot pin 70814 in a first direction and the proximal translation of the articulation bar 70832 will rotate the clip cartridge 70820 about the pivot pin 70814 in a second, or opposite, direction. The articulation bar 70832 can be flexible to allow the articulation bar 70832 to flex as needed when the clip cartridge 70820 is articulated about the pivot pin 70814.

Figure 64:
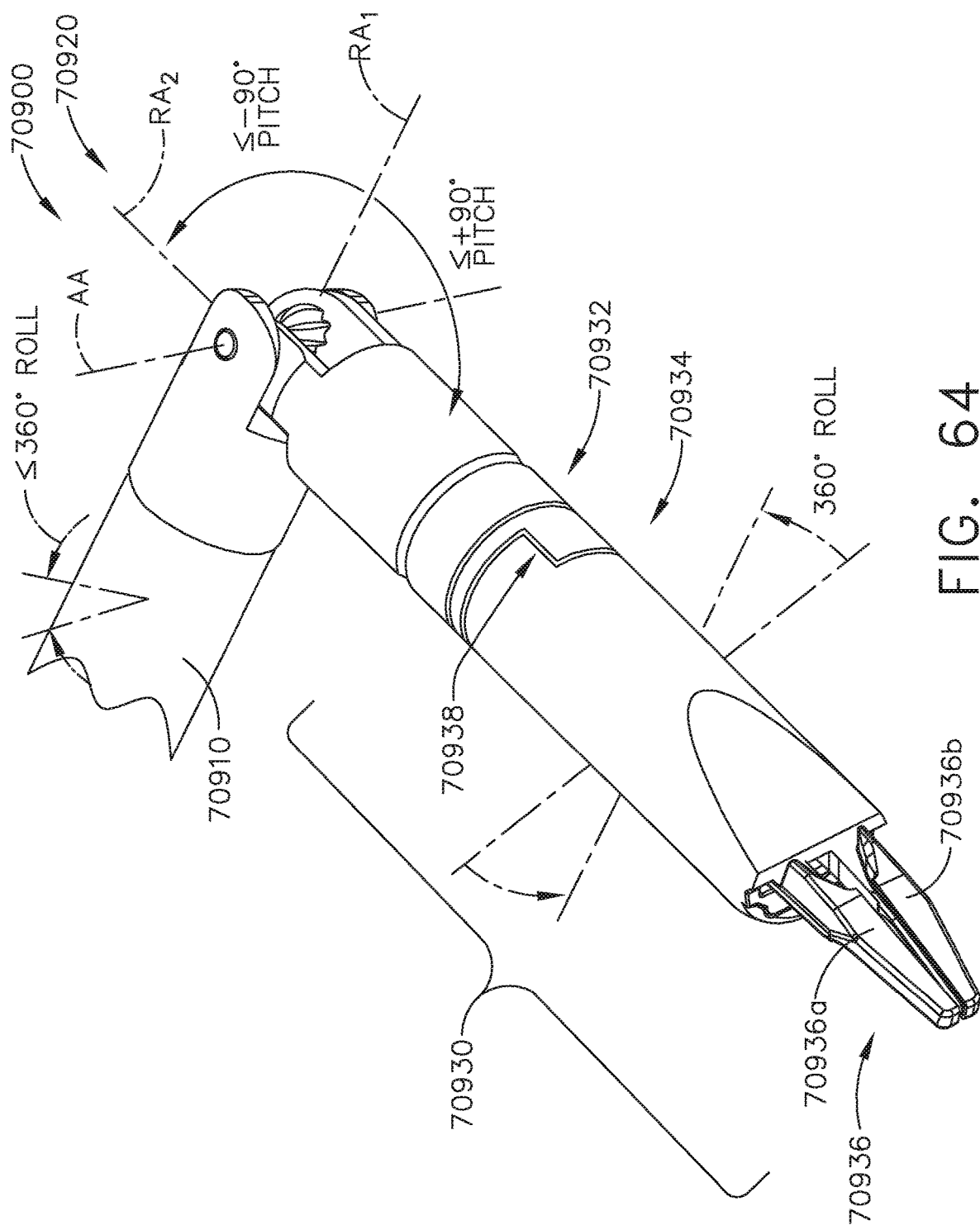
FIG. 64 is a perspective view of a clip applier including an articulation joint.

FIG. 64 depicts a clip applier 70900 in accordance with at least one embodiment. The clip applier 70900 comprises an elongate shaft 70910, an articulation joint 70920, and a distal head 70930. The articulation joint 70920 extends from the elongate shaft 70910 and the distal head 70930 extends from the articulation joint 70920. The distal head 70930 comprises a distal shaft 70932 attached to the articulation joint 70920, an end effector 70936 including a first jaw 70936a and a second jaw 70936b, and a clip cartridge 70934. The first jaw 70936a and second jaw 70936b are movable relative to each other between open and closed positions by any suitable drive system, such as the drive systems disclosed herein, for example. The clip cartridge 70934 stores a plurality of clips which can be advanced into the end effector 70936 and crimped by the first jaw 70936a and the second jaw 70936b. The clip cartridge 70934 is removably attachable to the distal shaft 70932 via a keying arrangement 70938. Other embodiments are envisioned where the clip cartridge 70934 is not removably attachable to the distal shaft 70932. The elongate shaft 70910 defines a first roll axis $RA_1$ and the distal head 70930 defines a second roll axis $RA_2$. The elongate shaft 70910 and the distal head 70930 are articulable relative to each other about articulation axis AA via the articulation joint 70920. The arrangement depicted in FIG. 64 is attachable—via the elongate shaft 70910—to a plurality of clip applier handle types, such as, a standard handle (i.e., a wand grip) and/or a pistol grip handle, for example. Depending on the type of handle that is attached to the elongate shaft 70910, different actuations of, or within, the handle may perform different actuations of the arrangement depicted in FIG. 64 about the first roll axis $RA_1$, the second roll axis $RA_2$, and the articulation axis AA. These actuations are described in further detail below.

If the elongate shaft 70910 is attached to a standard handle (i.e., a wand handle), referring still to FIG. 64, the elongate shaft 70910, the articulation joint 70920, and the distal head 70930 are all rotatable about the first roll axis $RA_1$ by the clinician rotating the wand handle. Further, a rotary knob on the wand handle is operably engaged with the elongate shaft 70910, through an electric motor and/or control system, for example, such that manually rotating the rotary knob will result in the distal head 70930 rotating about the second roll axis $RA_2$. Further, articulation of the distal head 70930 relative to the elongate shaft 70910 about articulation axis AA is driven by an articulation driver operably engaged with a motor housed within the wand handle, for example. If the elongate shaft 70910 is attached to a pistol grip handle, such as the handle 700 discussed above, for example, the elongate shaft 70910, the articulation joint 70920, and the distal head 70930 are all rotatable about the first roll axis $RA_1$ by a rotary knob, for example. Further, the distal head 70930 is rotated about the second roll axis $RA_2$ by a dedicated motor within the pistol grip handle. Further still, articulation of the distal head 70930 relative to the elongate shaft 70910 about articulation axis AA is induced by an articulation driver operably engaged with a motor housed within the pistol grip handle. The reader should appreciate that, depending on the type of handle attached to the arrangement depicted in FIG. 64, rotation of the elongate shaft 70910 about the first roll axis $RA_1$ can be accomplished by rotating the entire handle manually, rotation of a rotary knob engaged with the elongated shaft, and/or by a dedicated motor inside the handle. Further, the rotation of the distal head 70930 about the second roll axis $RA_2$ can be accomplished by rotation of a rotary knob engaged within the elongate shaft 70910 or by a dedicated motor inside the handle.

A clip applier jaw assembly 70950, or half of the jaw assembly 70950, and a clip leg 70954 of a clip are illustrated in FIG. 65. As can be seen in FIG. 65, the clip applier jaw assembly 70950 comprises a first jaw 70950*a* which includes a base 70952, a first leg 70952*a* extending from the base 70952, and a second leg 70952*b* extending from the base 70952. The first leg 70952*a* and second leg 70952*b* oppose one another and define a receiving area 70953 therebetween. The clip leg 70954 is received in the receiving area 70953 but, notably, part of the clip leg 70954 cross-section is not positioned within the receiving area 70953. Thus, only portions of the clip leg 70954 cross-section are supported by the first jaw 70950*a*. Other arrangements exist where the receiving area 70953 is substantially the same depth and width as the clip leg 70954 of the clip such that all, or at least substantially all, of the cross-section of the clip leg 70954 is positioned within the receiving area 70953 and supported by the first jaw 70950*a*.

A clip applier jaw assembly 70960 is depicted in FIG. 66A. The clip applier jaw assembly 70960 comprises a first jaw 70960*a* which includes a base 70962, a first leg 70962*a*, a second leg 70962*b*, and a receiving area 70963 which receives a first clip leg 70964 of a clip. The first leg 70962*a* of the first jaw 70960*a* extends from the base portion 70962 beyond the first clip leg 70964 when the first clip leg 70964 is seated in the receiving area 70963. The second leg 70962*b* of the first jaw 70960*a* extends from the base portion 70962 and terminates prior to the end of the first clip leg 70964 such that only a portion of the first clip leg 70964 is supported by the second leg 70962*b* of the first jaw 70960*a*.

The clip applier jaw assembly 70960 further comprises a second jaw 70960*b* positioned opposite, or opposing, the first jaw 70960*a*. The second jaw 70960*b* comprises a base 70962', a first leg 70962*a'*, a second leg 70962*b'*, and a receiving area 70963' which receives a second clip leg 70964' of the clip. The second jaw 70960*b* opposes the first jaw 70960*a* such that the first leg 70962*a* of the first jaw 70960*a* is aligned with the first leg 70962*a'* of the second jaw 70960*b*, and the second leg 70962*b* of the first jaw 70960*a* is aligned with the second leg 70962*b'* of the second jaw 70960*b*. The second leg 70962*b'* of the second jaw 70960*b* extends from the base portion 70962' beyond the second clip leg 70964' of the clip when the second clip leg 70964' is seated in the receiving area 70963'. Further, the first leg 70962*a'* of the second jaw 70960*b* extends from the base portion 70962' and terminates prior to the end of the second clip leg 70964' such that only a portion of the second clip leg 70964' is supported by the first leg 70962*a'* of the second jaw 70960*b*.

When the first jaw 70962*a* and the second jaw 70962*b* of the clip applier jaw assembly 70960 are in a closed configuration, as depicted in FIG. 66B, the first leg 70962*a* of the first jaw 70960*a* supports the entire first clip leg 70964 of the clip and, also, a portion of the second clip leg 70964' of the clip. Further, the second leg 70962*b'* of the second jaw 70960*b* supports the entire second clip leg 70964' of the clip and, also, a portion of the first clip leg 70964 of the clip. Because the first leg 70962*a* of the first jaw 70960*a* and the second leg 70962*b'* of the second jaw 70960*b* are opposite one another, the cross-sections of the first clip leg 70964 and the second clip leg 70964' are supported by both the first jaw 70960*a* and the second jaw 70960*b*—along at least a portion of the leg lengths. Such an arrangement prevents, or at least inhibits, the clip from twisting when the clip is crimped.

Referring to FIG. 67, the clip leg 70954 is seated within the first clip jaw 70950*a* of the clip applier jaw assembly 70950 but is not prevented from being slid longitudinally within the clip applier jaw assembly 70950. In accordance with at least one embodiment, such as the clip applier jaw assembly 70960, for example, the first jaw 70960*a* and/or the second jaw 70960*b* comprise a clip ejection prevention feature, such as distal stop 70966. The distal stop 70966 prevents the clip 70964 from sliding out of the distal end of the first jaw 70950*a* and/or the second jaw 70950*b* of the clip applier jaw assembly 70960. Other clip applier jaw shapes and guidance features configured to control the position of the clip, and/or prevent the unintentional dropping and/or ejection of the clip from the clip applier, are discussed in greater detail below.

As discussed above, the jaws of a clip applier, or "clip jaws", are used to deform the clips. As the reader should appreciate, the clip jaws themselves undergo stresses and strains and, in some instances, can be plastically deformed. Clip jaws designed to resist plastic deformation during use may comprise clip jaws which vary in thickness, width, and/or clip path depth along the clip jaw lengths in order to improve the stiffness in a lap clip applier, for example. Further, a proximal portion of one of the clip applier jaws can comprise a protruding bar (i.e., a tongue portion) and a proximal portion of the other clip applier jaw can comprise a recess (i.e., a groove portion) such that the protruding bar is seated in the recess when the clip applier jaws are closed. Such an arrangement provides for superior jaw resilience to vertical skewing and/or twisting of the clip applier jaws relative to each other during crimping of a clip. Improved clip retention structures are discussed in further detail below.

In at least one embodiment, the clip applier jaws may comprise a clip retention channel, or recess, to allow a clip to be advanced into the clip applier jaws via a feeder member from below. The feeder member includes a flexible drive plate that is retracted when the clip applier jaws are actuated (i.e., moved from an open position to a closed position) and is extended into the distal end of the clip applier jaws to hold the clip in a distal position until the clip applier jaws are actuated. Further, the feeding member prevents any further clips from inadvertently advancing into the clip applier jaws until the feeder member is retracted to retrieve and advance the next clip. Clip applier jaws including a distal retaining feature are discussed in greater detail below.

In at least one embodiment, the clip applier jaws each comprise a distal retaining feature, such as a ledge, for example, that extends above a guidance trough in the clip applier jaws. The guidance trough may comprise retention features, such as recesses, for example, on the distal end thereof which mate with protrusions on the clip to allow the clip to remain in a distal position within the clip applier jaws without needing to be held into place by a firing member and/or feeder member. The construction and manufacturing of certain clip applier jaws is discussed in greater detail below.

In various embodiments, the clip applier jaws are manufactured using a two part method where at least the distal portions of the clip applier jaws are metal injection molded (MIM) within an injection mold. In certain instances, the injection mold comprises two sides which are translatable toward and away from each other along a parting axis and the interface between the two mold halves is often planar, or at least substantially planar, and is often called a "parting plane". In at least one such instance, the parting plane is perpendicular to the axis of a clip trough of the clip applier jaws formed within the injection mold. Such an arrangement allows stiffening features, such as a rail, for example, to be designed onto the back side of the clip applier jaws, friction or holding features within the clip trough, and/or the distal holding features discussed above, for instance. Using a MIM process may often require the clip applier jaws to be machined, ground, and/or polished, for example, after being removed from the injection mold. The clip applier jaws are then either pivotally pined together and/or welded pivotally to the connection features of an end effector. By using MIM to produce certain portions of the jaws, the cost to produce the jaws can be reduced as inexpensive manufacturing methods can be utilized for the connection features, as opposed to using MIM to produce the entire clip applier jaws. Further, the clip applier jaws can be independently manufactured using MIM and then welded to a spring based interconnection clip. Moreover, independently manufactured clip applier jaws that are thereafter assembled together allows for the clip applier jaws to have a metallic clip guidance track to be built into the lateral inside facing portion of the clip applier jaws. The independently manufactured clip applier jaws using MIM may further comprise distal clip retention features, such as ledges, for example, which prevent the unintentional ejection of a clip from the distal end of the clip applier jaws. Such distal clip retention features can extend above the primary face of the clip applier jaws owing to these MIM processes.

As discussed above, and as described in greater detail below, certain clip appliers are configured to be inserted into a patient through a passage defined in a trocar. That said, the clip jaws of many clip appliers are wider than the trocar passage when they are in their open configuration. Described below are various systems that can be incorporated into a clip applier to facilitate the insertion of the clip applier through the trocar passage.

Figure 69:
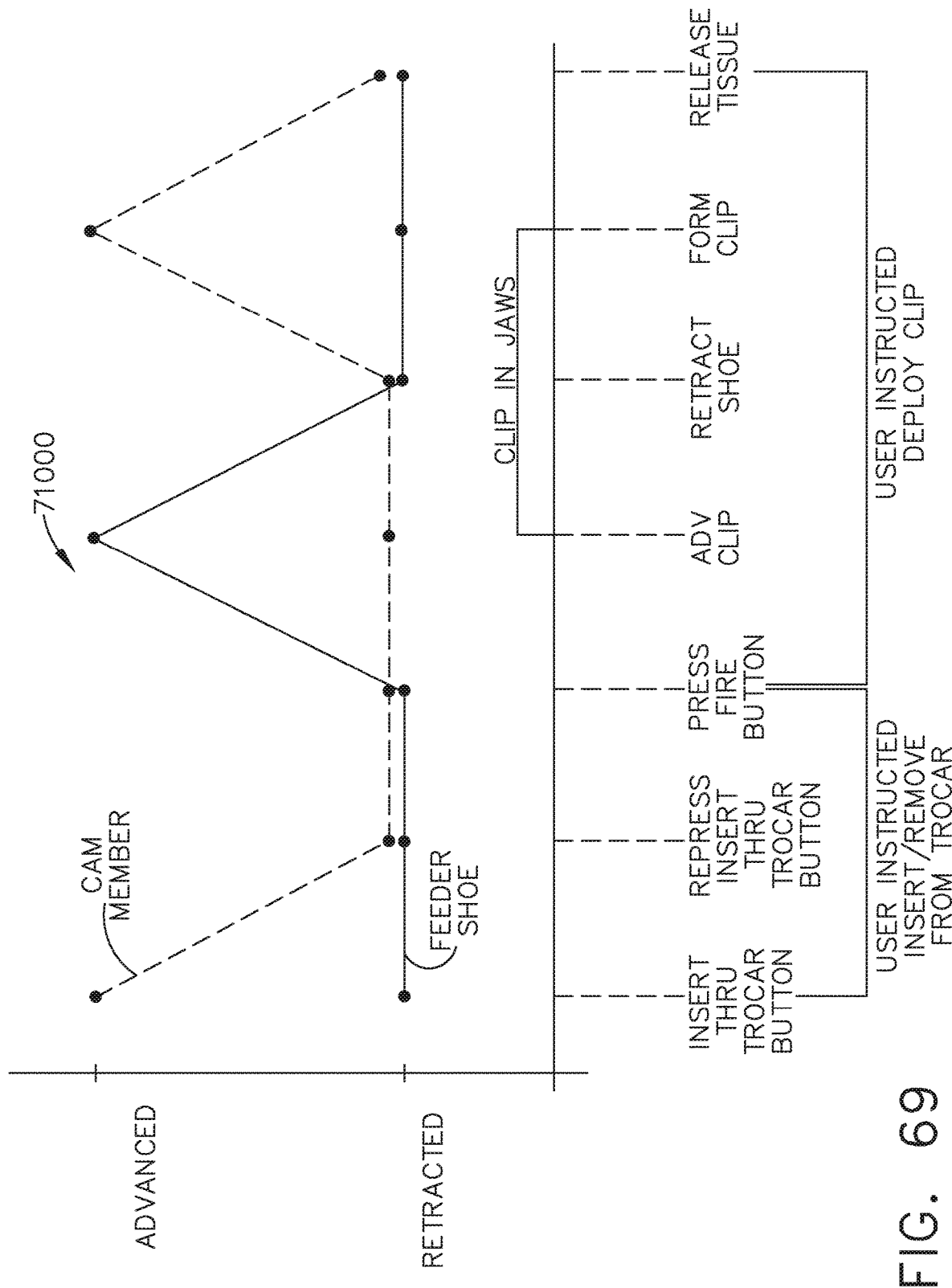
FIG. 69 is a graphical depiction of the movements of a cam member and a feeder shoe of a clip applier throughout the operation of the clip applier.

Referring to FIG. 69, a graph 71000 depicts the movements of a cam member and a feeder/firing member of a clip applier, such as the clip applier 70100, for example. The cam member is similar to cam member 70180 and the feeder shoe is similar to firing member 70165 illustrated in FIGS. 35A-38, for example. In order to configure the clip applier 70100 in a trocar-insertion configuration, the cam member is moved to a fully advanced position to close the jaws of the clip applier and the feeder shoe is moved to a fully retracted position. In various instances, the clip applier comprises a control system including a button which, when depressed, places the clip applier in its trocar-insertion configuration. In at least one instance, the control system operates the one or more electric motors of the clip applier to configure the drive systems as described above. At such point, the clip applier is ready to be inserted into the patient through the trocar. Once inserted into the patient, the button can be pressed again and, in response thereto, the control system will retract the cam member to a fully retracted position and open the jaws of the clip applier. This button can be pressed repeatedly to toggle the configuration of the clip applier as needed. Such an arrangement is also useful to remove the clip applier from the patient through the trocar. The reader should appreciate that the opening and closing of the jaws via the button will not affect the other functions of the clip applier such as advancing a clip, forming a clip, and/or ejecting a clip from the clip magazine.

Once the clip applier has been inserted through the trocar and the button has been actuated a second time (i.e., the jaws are open), further to the above, a firing button can be pressed resulting in the feeder shoe advancing to a fully advanced position. A clip will be advanced with the feeder shoe as described above in relation to clip applier 70100 (FIGS. 35A-38), for instance. The feeder shoe can then be retracted to a fully retracted position and the cam member can be advanced to the fully advanced position to form the clip around tissue of the patient, as also described above. The cam member can then be retracted to the fully retracted position to release the clip and the tissue. Once all of the clips have been applied, or at least a sufficient number of clips have been applied, the button could be actuated again to close the jaws to allow the clip applier to be removed through the trocar. Such an arrangement enables the user of the clip applier to close the jaws without releasing a loose clip into the patient.

Further to the above, embodiments are envisioned where a clip applier comprises a motor and a motor controller. The motor controller can be configured to control the motor via a processor and a memory. The motor controller can implement motor control algorithms to configure the jaws to open and close as well as advance a clip into the jaws. For example, a motor control algorithm can be implemented to allow the jaws to advance a clip into a crimping and/or forming position, as described above, after the jaws have been inserted through the trocar. By not feeding a clip into the jaws until after the clip applier has been introduced into the patient, the jaws can be moved into a very compact arrangement when being inserted through the trocar as discussed above.

Figure 70:
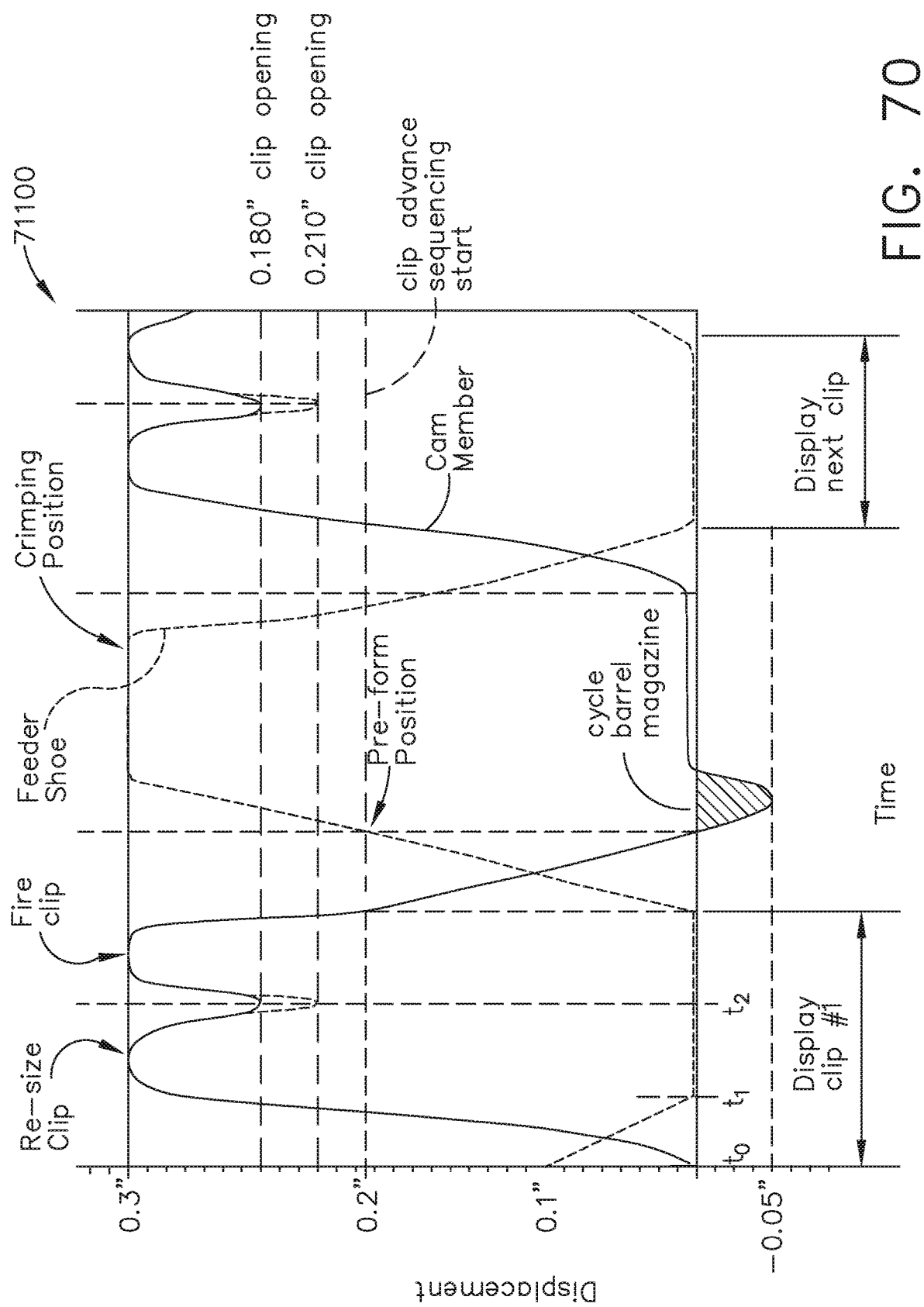
FIG. 70 is a graph depicting the displacement of a cam member and feeder shoe of the clip applier of FIG. 52 as a function of time.

Turning now to FIG. 70, a graph 71100 depicts the movements of a cam member and a feeder shoe of a clip applier comprising a rotating clip magazine (i.e., a barrel magazine), such as the clip applier 70600, for example. The operation of the clip applier depicted in FIG. 70 is similar to that of clip applier 70600 in many respects. For example, the cam member is similar to closure tube 70620, the feeder shoe is similar to feeder member 70630, and the barrel magazine is similar to rotatable clip magazine 70650 illustrated in FIGS. 52-60, for example. The clip applier is placed into the patient through a trocar with the jaws closed and a clip positioned in the jaws and another clip aligned with the feeder shoe for deployment out of the barrel magazine. With the feeder shoe in the home position (i.e., zero displacement) the cam member can be advanced to a fully advanced position from the home position to crimp the clip already placed within the jaws. In at least one instance, the distance between the home position and the fully advanced position is 0.3", for example. The cam member is then retracted to a partially advanced position just proximal to the fully advanced position to reduce the force applied to the clip by the jaws. The cam member is advanced again to the fully advanced position to crimp the clip again. By applying a force, reducing that force, and then applying the same, or another, force again, the elasticity within the clip can be reduced such that full plastic deformation can occur to properly crimp the clip onto the patient tissue. The partially advanced position is dependent on the type of clip being utilized with the clip applier. For example, the partially advanced position is preferably 0.2" distal from the home position for a clip with a clip opening of 0.210" and is preferably 0.23" distal from the home position for a clip with a clip opening of 0.180", for example. Suitable thresholds can be set by the user depending on the type of clips in the barrel magazine being utilized with the clip applier. Other embodiments are envisioned with different clip sizes and position arrangements for the partially retracted and fully advanced positions.

In any event, after the clip has been properly crimped, the cam member is then retracted proximally toward the home position as the feeder shoe distally advances a clip out of the barrel magazine toward the jaws of the clip applier into a pre-form position when the feeder shoe is 0.08" distal from the home position, for example. When the clip is in the pre-form position, the jaws can be partially opened by retracting the cam member slightly beyond the home position, i.e., the cam member interacts with the jaws of the clip applier to open the jaws when the cam member is retracted proximal to the home position, as discussed above. Such an arrangement allows the clip to be expanded by the pre-form features on each of the jaws (i.e., protrusions 70608) as discussed above. The feeder shoe then distally advances the clip further into a crimping position—0.3" distal to the home position, for example. Once the feeder shoe is advanced beyond the barrel magazine (i.e., to the pre-form position) the barrel magazine can be cycled (i.e., rotated) to position another clip for advancement into the jaws. The barrel magazine is cycled by retracting the cam member to a fully retracted position—0.05" proximal to the home position, for example. The cycled clip will be biased against the feeder shoe which prevents the clip from being completely ejected from the barrel magazine. Once the feeder shoe is retracted to the home position the cycled clip can be displayed (i.e., the biasing member in the barrel magazine can now position the cycled clip into alignment with the feeder shoe because the feeder shoe has been retracted and is no longer blocking such movement). At this point a clip that has been pre-formed is positioned in the jaws and another clip is aligned with the feeder shoe for deployment out of the barrel magazine into the clip applier jaws, just as when the clip applier was first inserted into the patient. The same operations discussed above can be performed until all of the clips in the barrel magazine are spent.

Figure 71:
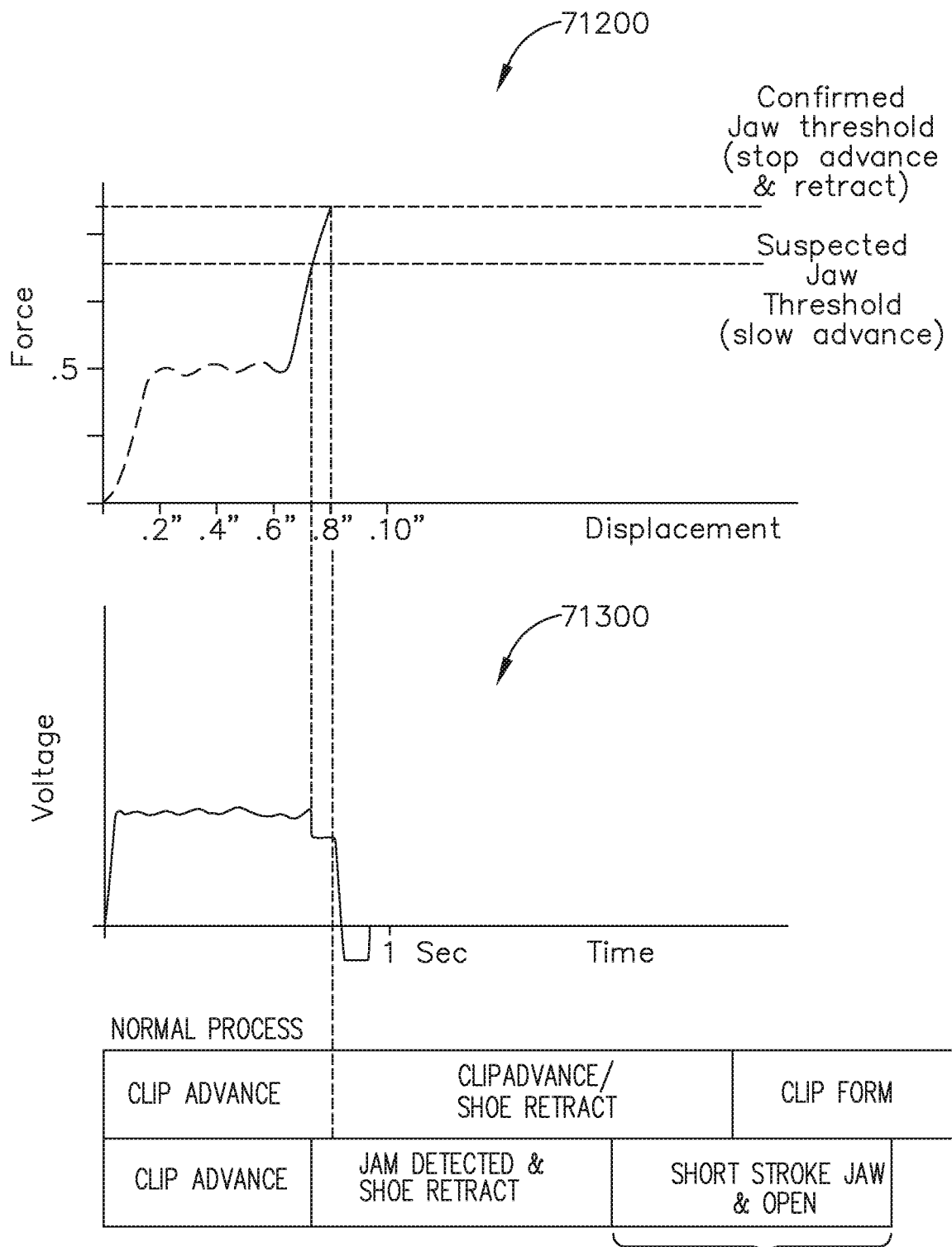
FIG. 71 depicts a first graph illustrating the force to advance a clip of a clip applier as a function of displacement and a second graph illustrating the voltage of a motor of the clip applier as a function of time.

A graph 71200 of a firing member of a clip applier, such as any of the clip appliers described herein, for example, is illustrated in FIG. 71. The graph 71200 shows the relationship between the force required to advance a clip within the clip applier (i.e., via the firing member) versus displacement. With further reference to FIG. 71, a graph 71300 of the same clip applier is illustrated showing the relationship between the voltage applied to the motor driving the firing member of the clip applier versus time. The motor controller of the clip applier can monitor the current being drawn by the motor and/or the force being applied to the firing member by the motor to detect a clip feed jam, or an irregular force within the clip applier, and then prevent further advancement of the firing member by implementing changes to the voltage applied to electric motor, as seen in graph 71300. In other words, if the monitored force exceeds a threshold value, and/or the monitored motor current exceeds a threshold value, during the clip feed step, the motor controller can, one, reduce the magnitude of the voltage potential being applied to the motor for a period of time and, two, further assess the force within the firing system and/or further assess the electrical current being drawn by the motor. If the force and/or motor current continue to increase with the continued application of voltage to the motor, the motor control system can stop the motor and/or reverse the direction of the motor shaft to retract the firing member through a short stroke distance to clear the jammed clip. Once the jammed clip is cleared, the clip applier can return to its normal operation and prepare the next clip to be advanced in accord with the normal operating sequence of the clip applier.

Other embodiments are envisioned where clearing the jammed clip is accomplished by interrupting the normal sequence of the end effector jaw operations. More specifically, once the clip jam is detected the control system of the clip applier (i.e., motor controller, processor, and memory) could request the clinician initiate a jam removal actuation. The jam removal actuation results in the jaws of the clip applier being opened further than normal prior to another attempt to re-advance the clip. During the attempt to re-advance the clip, the acceptable load threshold, i.e., the current threshold and/or the force threshold, could be elevated above the normal thresholds previously discussed to insure the clip is ejected from the jaws. Once the jammed clip has been ejected, the clip applier could return to its normal operation and prepare the next clip to be advanced in accord with the normal operating sequence of the clip applier.

As mentioned above, certain clip appliers can be loaded with clips having a first size and/or a second size. The relative size of the clips can be measured using any suitable dimension, such as the leg-to-leg width of the clips, for example. First clips having a first width can be wider than second clips having a second width. In various instances, the clip applier can be loaded with only first clips, only second clips, or both first and second clips at the same time. In any event, clips having different sizes may deform differently for a given closure stroke of the clip jaws. Thus, for instance, a first closure stroke of the clip jaws may be more preferable for the first clips while a second closure stroke of the clip jaws may be more preferable for the second clips. Many of the clip appliers disclosed herein are capable of selectively applying more than one closure stroke to the clip jaws; however, in order to apply the correct closure stroke to a clip, the clip applier needs to be able to assess which size of clip is positioned within the clip jaws. In certain instances, such information can be manually entered into the control system of the clip applier by the clinician. Such an arrangement is convenient when the clips in the clip applier all have the same size. In various instances, the clip cartridge attached to the clip applier comprises a marker, such as a microchip, for example, which can be evaluated by the control system and/or a sensor circuit in communication with the control system, for example. Such an arrangement is convenient when the clips in the clip cartridge all have the same size.

In various instances, further to the above, the clip applier can be configured to assess the clip positioned between the clip jaws of the clip applier to assess the size of the clip. Once a clip is loaded between the clip jaws, the control system can partially operate the jaw closure drive and observe the force within the jaw closure drive and/or the current drawn by the electric motor of the jaw closure drive. The control system is configured to compare the measured data to data stored in a memory device, for example, to assess whether the clip between the clip jaws is a first clip or a second clip, or any other clip. For instance, if the measured force and/or motor current follows a first profile, then the control system will determine that the clip is a first clip and then apply the first closure stroke. Similarly, the control system will apply the second closure stroke if the measured force and/or motor current follows a second profile for the second clip. As such, the control system can use the jaw closure drive to apply a short evaluation closure stroke to assess the clip size and then complete the full closure stroke as appropriate. In at least one instance, the control system can reset the jaw closure drive after performing the short evaluation closure stroke and then complete a full closure stroke as appropriate. In various instances, it is envisioned that the short evaluation closure stroke does not plastically deform, or at least substantially plastically deform, the clip.

Figure 72:
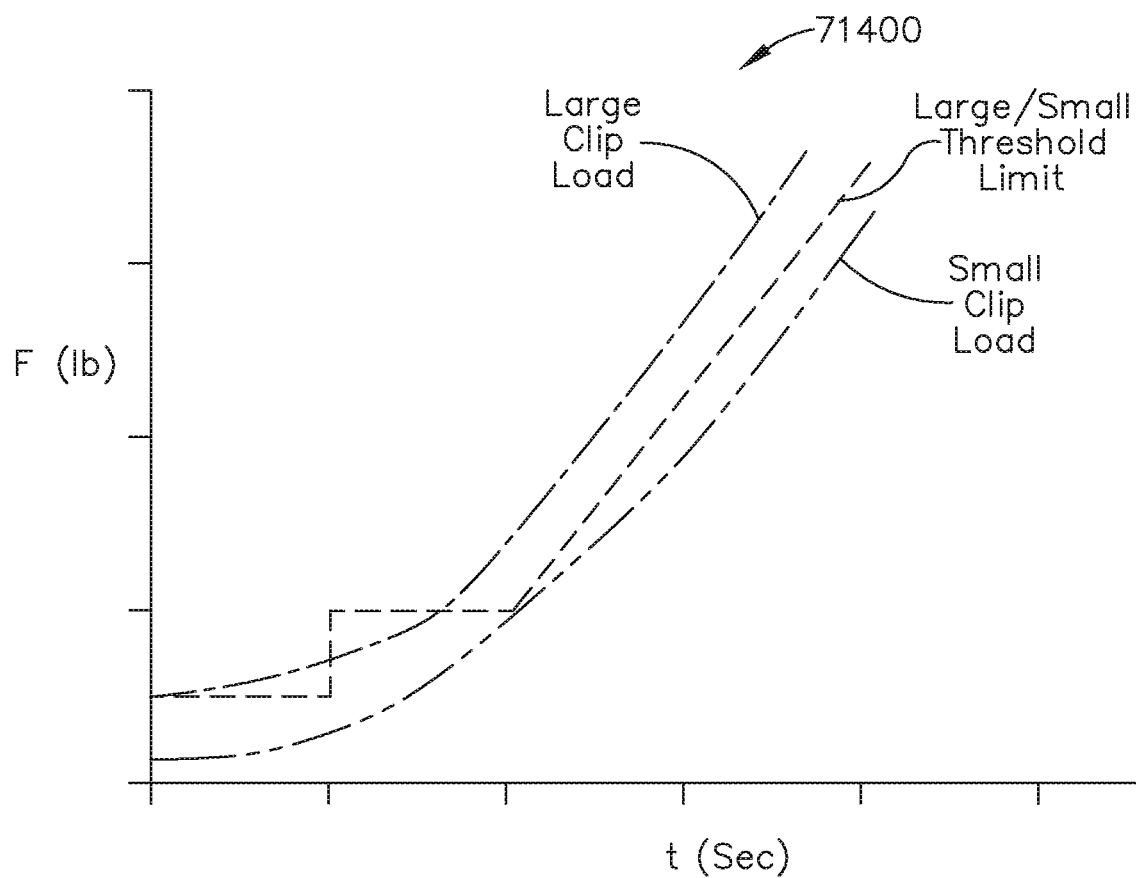
FIG. 72 depicts a graph of the force applied to a pair of jaws of a clip applier versus time.
Figure 73:
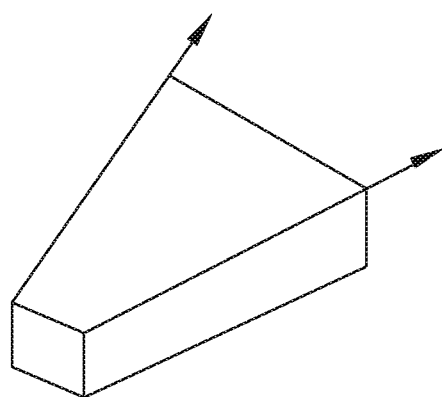
FIG. 73 is directed to an alternative embodiment.
Figure 74:
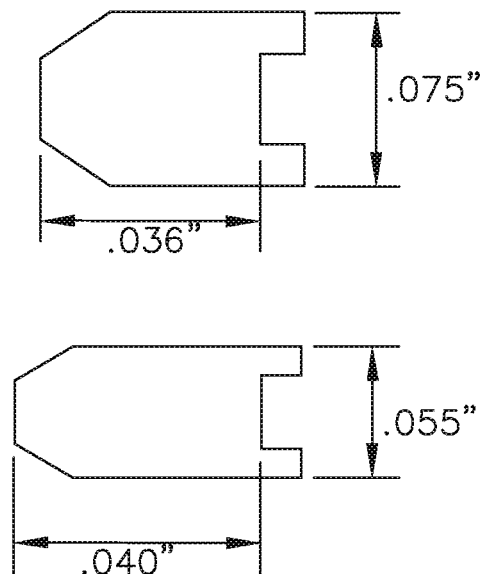
FIG. 74 is directed to an alternative embodiment.

Referring to FIG. 72, a graph 71400 of the force applied to a pair of jaws of a clip applier versus time is illustrated. The control system of the clip applier can monitor the force within the crimping drive and/or the electric current drawn by the motor to determine the amount of force needed to crimp a clip positioned within the jaws of the clip applier. This feedback force is initially dependent on the size and/or type of clip that is within the jaws for a first portion of the closure stroke of the jaws. Once the size/type of clip is determined, the force applied to the jaws of the clip applier can be adjusted for the remainder of the jaw closure stroke to crimp the clip with the proper amount of force. Such an arrangement is convenient when more than one size of clip has been loaded into the clip applier. Other embodiments are envisioned where an adaptive control program change is initiated by the cartridge identifying itself to the clip applier upon insertion into the clip applier. This allows the clip applier to update to the alternative control program and thresholds (i.e., the forces applied to the jaws) for the size/type of clip loaded into the clip applier. Further, an alternative to the identification of the cartridge could be the detection of the loads needed to accomplish the first job of the clip applier, which could be the advancement of a clip from the cartridge or pre-forming a clip within the jaws as discussed above. The first job of the clip applier may have a significantly higher load threshold needed to complete the operation and exceeding that threshold, or not, will then determine the subsequent operations the clip applier and the threshold limits of each operation.

Many of the clip appliers discussed herein have been discussed in the context that the clip jaws of the clip appliers are squeezed to crush a clip into its proper size. Other embodiments are envisioned in which a clip is elastically or resiliently stretched and then released once the targeted tissue has been positioned within the stretched clip. Such an arrangement can be particularly useful when clamping or clipping blood vessels, for example. In such instances, a clip can be released to resiliently return to, or at least toward, its unstretched position and clamp the blood vessel in an atraumatic, or a nearly atraumatic, manner. All of the clip appliers disclosed herein can be adapted to apply such stretch-and-release clips. Moreover, further to the above, the clip appliers disclosed herein can be configured to apply both the clamp-to-crush clips and the stretch-and-release clips. Similar to the above, the clip appliers would need to be able to identify the type of clips contained therein in order to apply them properly to the patient tissue. Identification chips in the clip cartridges could be used for such purposes, for example.

Figure 75:
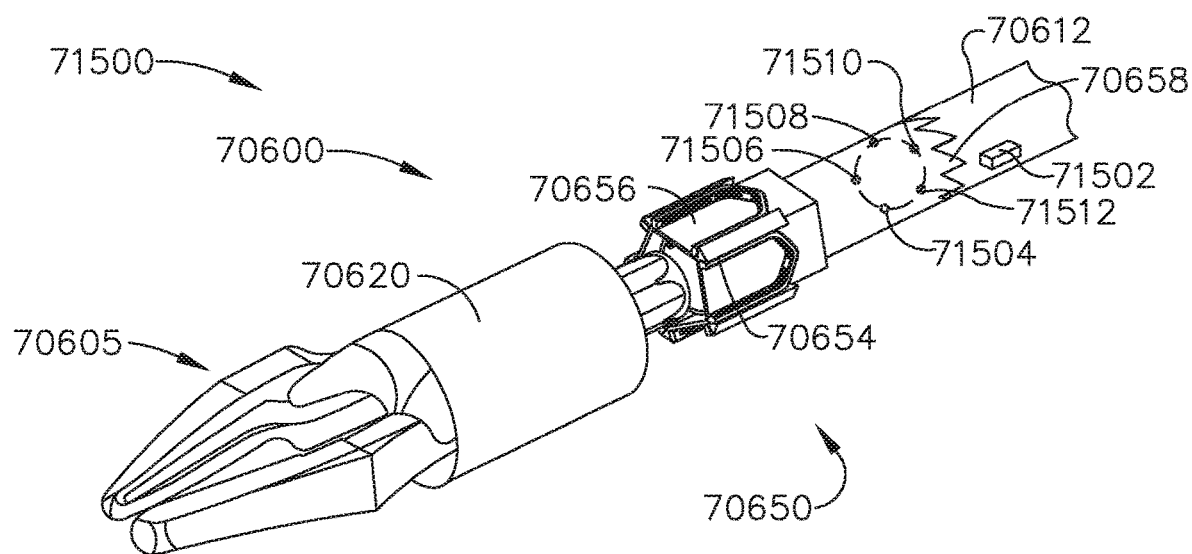
FIG. 75 is a perspective view of a clip applier including a rotating clip magazine, a magnet, and a Hall Effect sensor.
Figure 76:
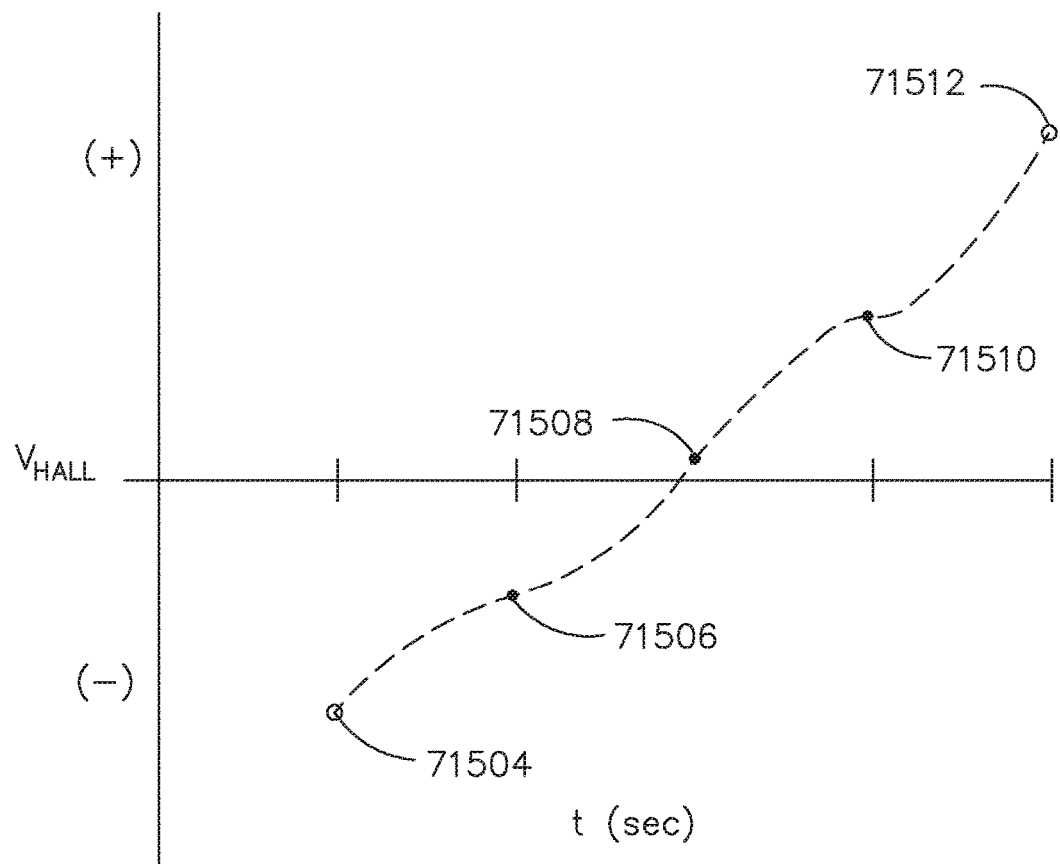
FIG. 76 is a graphical depiction of the clip applier of FIG. 75 illustrating the voltage of the Hall Effect sensor as a function of the position of the magnet over time.

FIG. 75 depicts a clip applier system 71500 in accordance with at least one embodiment. The clip applier system 71500 comprises the clip applier 70600 discussed above. The clip applier system 71500 further comprises a magnet aligned with one of the clips 70654 of the rotatable clip magazine 70650. The clip applier system 71500 further comprises a sensor, such as a Hall Effect sensor 71502, for example, fixedly positioned within the ground portion 70612 of the clip applier 70600. The magnet can be sensed by the Hall Effect sensor 71502 and, based on the voltage potential created by the Hall Effect sensor, the control system of the clip applier 71500 can determine the radial location and orientation of the magnet and, thus, the radial location and orientation of the clip magazine 70650. When the magnet is in a first position 71504, referring to FIG. 76, the rotatable clip magazine 70650 is loaded with a full compliment of clips 70654 and one of the clips 70654 can be advanced out of the rotatable clip magazine 70650 into the end effector 70605. The rotatable clip magazine 70650 can then be cycled (e.g., rotated) as discussed above, causing the magnet to move between the first position 71504 and a second position 71506. Another clip 70654 can be advanced out of the rotatable clip magazine 70650 and the rotatable clip magazine 70650 can be cycled again, causing the magnet to move to a third position 71508. Another clip 70654 can be advanced out of the rotatable clip magazine 70650 and the rotatable clip magazine 70650 can be cycled again, causing the magnet to move to a fourth position 71510. Further, another clip 70654 can be advanced out of the rotatable clip magazine 70650 and the rotatable clip magazine 70650 can be cycled again, causing the magnet to move to a fifth position 71512. In the fifth position 71512, the last clip 70654 in the rotatable clip magazine 70650 can be advanced out of the rotatable clip magazine 70650. Thus, the clip applier system 71500 can determine the status of the clip magazine 70650 (i.e., the number of clips remaining) depending on the position of the magnet relative to the Hall Effect sensor 71502. Further to the above, FIG. 76 depicts the voltage potential generated by the Hall Effect sensor 71502 depending on the position of the magnet.

In at least one alternative embodiment of the clip applier system 71500, the clip magazine 70650 further comprises an extension member, or bar, that extends proximally from the clip magazine 70650 once all of the clips 70654 have been ejected from the clip magazine 70650. The extension member is sensed by the Hall Effect sensor 71502 and/or another electrical sensor within the clip applier 70600. When the extension member is detected by the clip applier system 71500, the mechanical systems (i.e., the feeder member 70630, firing member 70640, and drive tube 70620) of the clip applier 70600 can be locked out to prevent further actuation.

Figure 77:
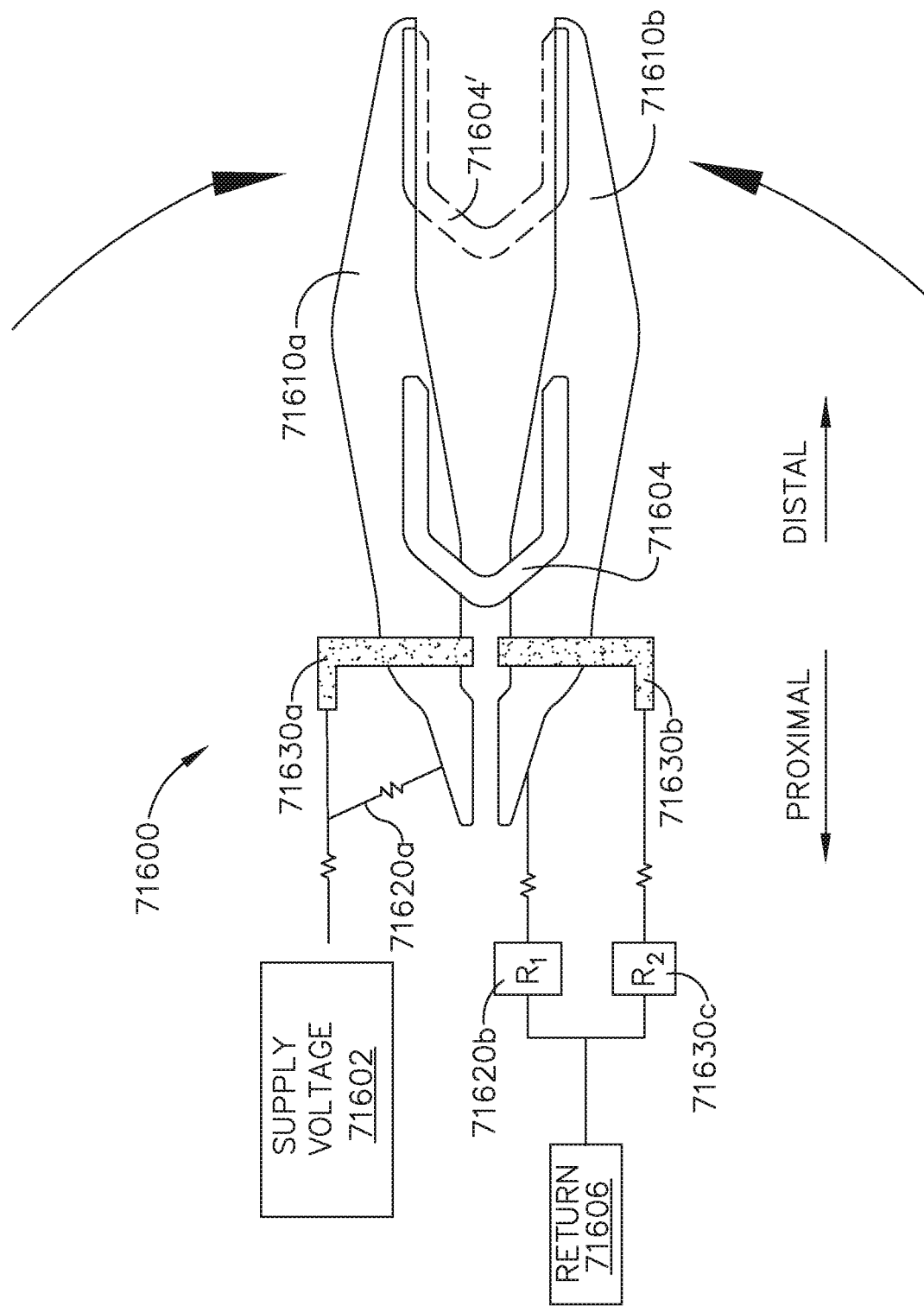
FIG. 77 is a partial cross-sectional view of a clip applier including resistive sensing circuits.

FIG. 77 depicts a clip applier 71600. The clip applier 71600 comprises a first jaw 71610a and a second jaw 71610b moveable relative to each other between open and closed positions. The clip applier 71600 is configured to receive a clip 71604 which is crimped by the first jaw 71610a and the second jaw 71610b when the first jaw 71610a and the second jaw 71610b are moved toward the closed position. The clip applier 71600 comprises a resistive sensing circuit configured to determine the position of the clip 71604 within the clip applier 71600. The resistive sensing circuit comprises a supply voltage source 71602 which supplies current through a first lead 71620a, the first jaw 71610a, the clip 71604, the second jaw 71610b, and a Resistor 71620b and back to a return 71606 where the current can be measured. When the clip 71604 is moved distally though the clip applier, such as to the position shown by clip 71604', for example, the path through which the current flows is larger (i.e., larger than the path for clip 71604) and the resistance within the path is greater and, as a result, the current measured at the return 71606 will be smaller. Thus, the current measured at the return 71606 is directly proportional to the position of the clip 71604 within the clip applier 71600. The control system of the clip applier is configured to use the magnitude of the current in this sensing circuit to assess the position of the clip 71604' within the jaws 71610a and 71610b. Higher current magnitudes indicate that the clip 71604' is more proximal and lower current magnitudes indicate that the clip 71604's is more distal, while intermediate current magnitudes indicate that the clip 71604' is positioned in the middle of the jaws 71610a and 71610b.

Referring still to FIG. 77, the clip applier 71600 further comprises a second resistive sensing circuit configured to determine when the first jaw 71610a and the second jaw 71610b are in the closed position. More specifically, the supply voltage supplies current which flows through a first lead 71630a connected to the first jaw 71610a. The first lead 71630a is insulated from the first jaw 71610a, i.e., it does not allow current to flow into the first jaw 71610*a*. When the first jaw 71610*a* and the second jaw 71610*b* are in the closed position, the first lead 71630*a* contacts a second lead 71630*b* connected to the second jaw 71610*b* which allows current to flow into a resistor 71630*c* and into the return 71606 where the current can be measured. The second lead 71630*b* is also insulated from the second jaw 71610*b*. Thus, when the first jaw 71610*a* and the second jaw 71610*b* are in the closed position, the control system, via the return, will sense a current determined by a second resistance through the resistor 71630*c* which indicates that the first and second jaws 71610*a*, 71610*b* are in the closed position. The control system may, at the same time, also sense the resistance through resistor 71620*b* which indicates the position of the clip 71604 within the clip applier 71600. Other embodiments are envisioned where only one of the resistive sensing circuits discussed above are utilized with the clip applier 71600.

Figure 78A:
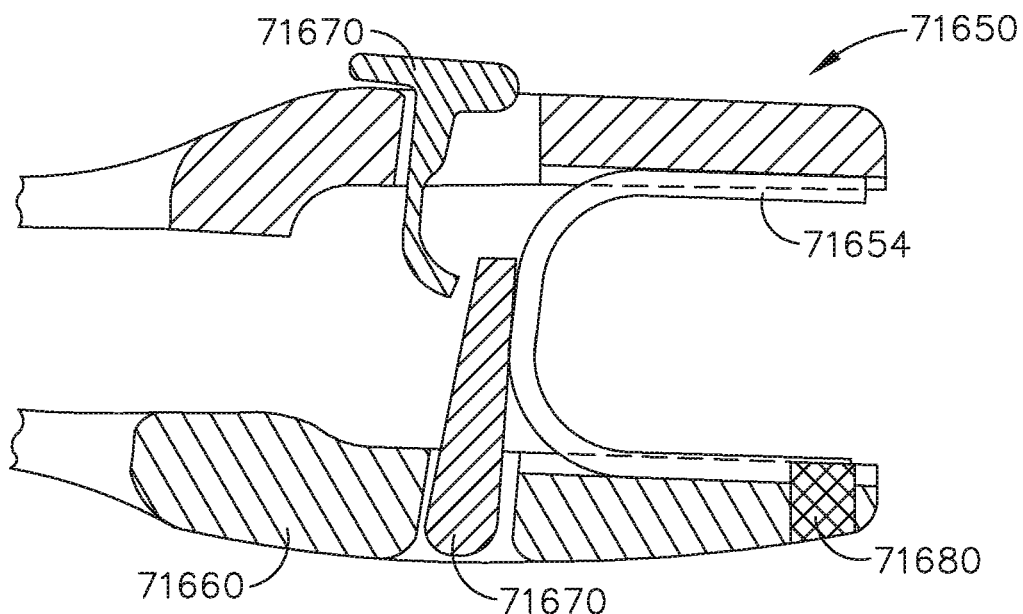
FIG. 78A is a partial cross-sectional view of a clip applier including a variable resistance meter.
Figure 78B:
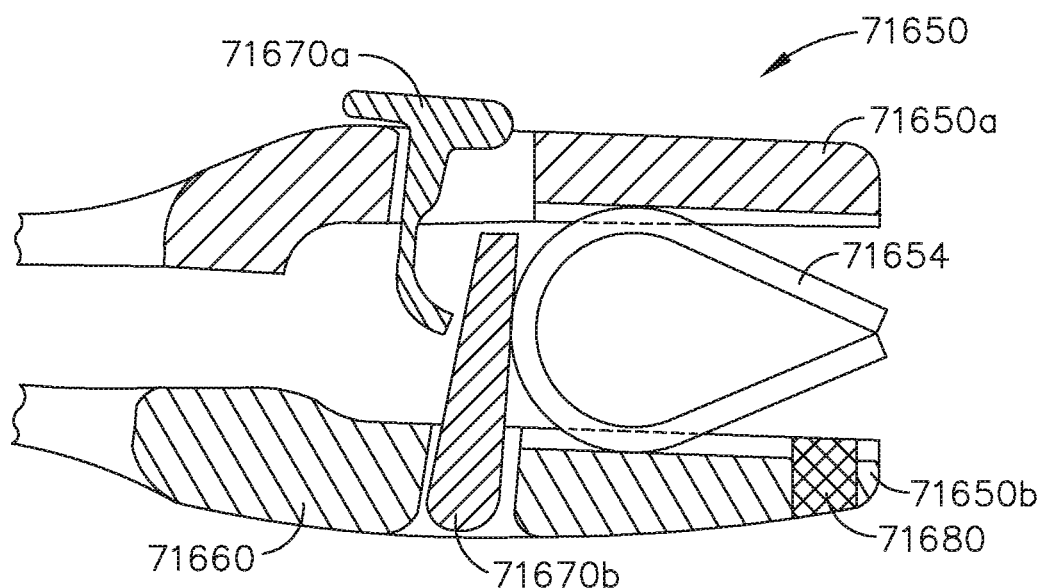
FIG. 78B is a partial cross-sectional view of the clip applier of FIG. 78A in a partially crimped configuration.

FIGS. 78A and 78B depict a variable resistance system for use with a clip applier 71650 configured to gather information (i.e., data) on the position of the clip jaws and the formation of the clip during a crimping stroke. The clip applier 71650 is similar to clip applier 71600, for example, in many respects. The clip applier 71650 comprises a first jaw 71650*a* and a second jaw 71650*b* moveable relative to each other between an open position (FIG. 78A), a partially closed position (FIG. 78B) and a closed position. The clip applier 71650 is configured to receive a clip 71654 which is crimped by the first and second jaws 71650*a*, 71650*b* when the first and second jaws 71650*a*, 71650*b* are moved toward the closed position. The legs of the clip 71654 positioned within the first and second jaws 71650*a*, 71650*b* extend outwardly into engagement with the first and second jaws 71650*a*, 71650*b* to ensure the clip 71654 is properly seated therebetween (i.e., so there is no slop or play between the clip 71654 and the first and second jaws 71650*a*, 71650*b*). In various instances, the legs of the clip are slightly deflected inwardly when the clip is fed into the first and second jaws 71650*a*, 71650*b*. The variable resistance system of the clip applier 71650 is described in further detail below.

The variable resistance system comprises three return paths through which an electrical current can flow and be sensed by the control system of the clip applier in order to determine the position of the first and second jaws 71650*a*, 71650*b* relative to each other, and to sense the formation of the clip 71654. The first return path 71660 comprises the second jaw 71650*b*. The second return path 71670 comprises a variable resistor configured to determine the position of the first jaw 71650*a* and the second jaw 71650*b* relative to each other. More specifically, as the first jaw 71650*a* and the second jaw 71650*b* are moved from the open position (FIG. 78A) toward the closed position the resistance in the variable resistor will change. The third return path 71680 comprises another variable resistor at the distal end of the second jaw 71650*b* which is insulated from the second jaw 71650*b*. When the first jaw 71650*a* and the second jaw 71650*b* are in the open position (FIG. 78A), the clip 71654 is in contact with the first return path 71660 and the third return path 71680. When the first jaw 71650*a* and the second jaw 71650*n* are in the partially closed position (FIG. 78B), the clip 71654 is only in contact with the first return path 71660. When the first jaw 71650*a* and the second jaw 71650*b* are in the closed position the clip 71654 has been fully crimped and is once again in contact with the first return path 71660 and the third path 71680. Throughout the movement of the first jaw 71650*a* and the second jaw 71650*b* between the open position, the partially closed position, and the closed position, the second return path 71670 determines the position of the first jaw 71650*a* relative to the second jaw 71650*b*. Thus, the variable resistance system can determine jaw position and sense clip formation throughout the clip formation process by determining the resistance through each of the three paths.

Figure 79:
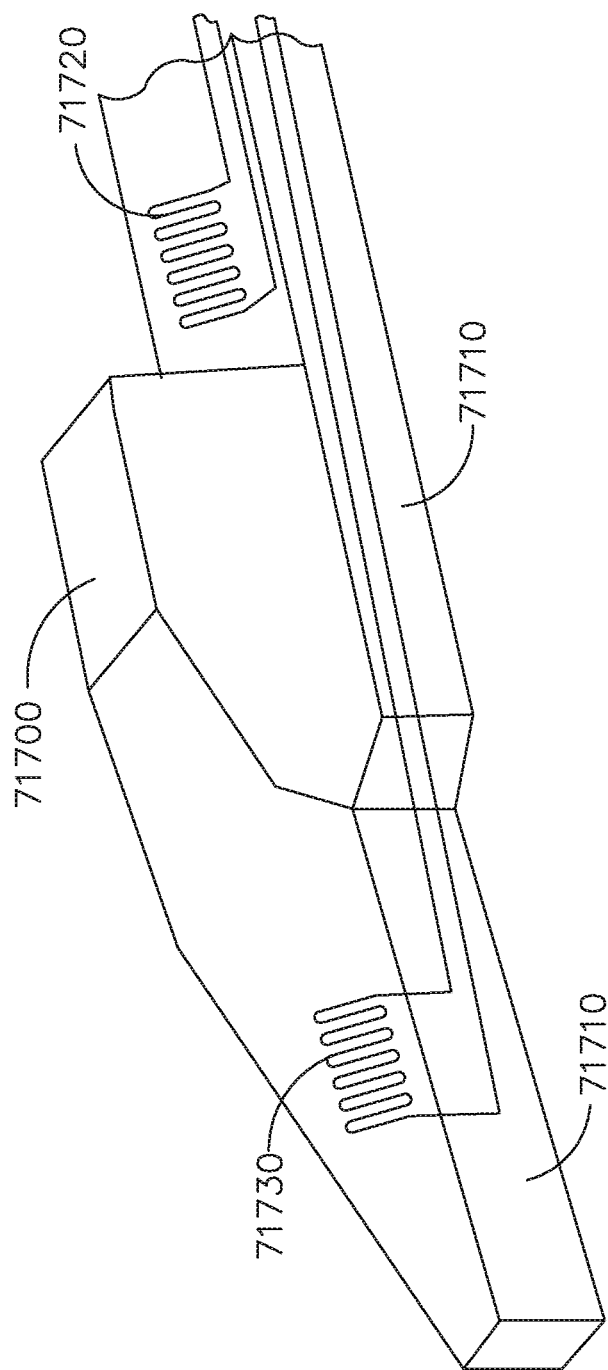
FIG. 79 is a perspective view of a clip applier jaw including strain gauges.

FIG. 79 depicts a clip applier jaw 71700 in accordance with at least one embodiment. The clip applier jaw 71700 is configured to move toward and away from another clip applier jaw and is further configured to crimp a clip as discussed above in relation to various embodiments disclosed herein. The clip applier comprises a proximal strain gauge 71720 and a distal strain gauge 71730, and/or any number of suitable strain gauges. The proximal strain gauge 71720 and the distal strain gauge 71730 are positioned on a face 71710 of the clip applier jaw 71700. Other embodiments are envisioned with more than two strain gauges spaced along any suitable face of the clip applier jaw 71700 and/or built into the clip applier jaw 71710 itself. The proximal strain gauge 71720 is part of a proximal strain gauge circuit and generates a voltage signal indicative of the strain within the clip applier jaw 71700 in a first location and the distal strain gauge 71730 is part of a distal strain gauge circuit and generates a voltage signal indicative of the strain within the clip applier jaw 71700 in a second location. The proximal and distal strain gauge circuits are in communication with the control system of the clip applier and, as a clip is formed between the clip applier jaw 71700 and another clip applier jaw, different levels of strain will be detected by the control system at the first location and the second location.

Figure 80:
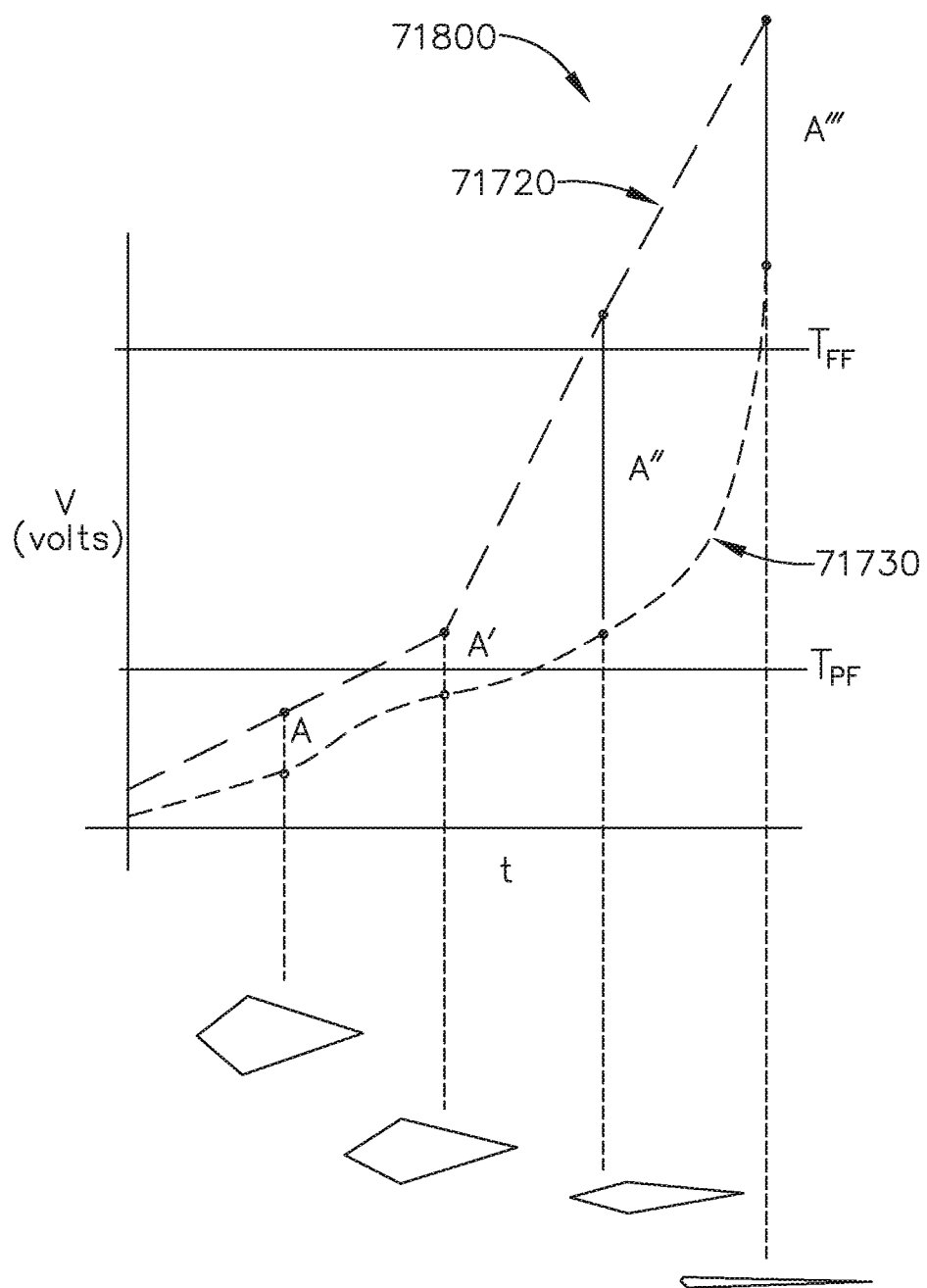
FIG. 80 is a graphical depiction of the clip applier jaw of FIG. 79 illustrating the voltage of the strain gauges as a function of time.

Referring to FIG. 80, a graph 71800 of the strain (measured in Volts, but could be more conveniently illustrated in mV) within the proximal strain gauge 71720 and the distal strain gauge 71730 at various stages of clip formation is depicted. Upon the initial placement of a clip between the clip applier jaws, the clip legs of certain clips are biased outwardly into engagement with the jaws, as discussed above. In such instances, a larger strain may be measured in the proximal strain gauge 71720 as compared to the distal strain gauge 71730. The difference in the voltages within the strain gauges 71720, 71730 at this stage is voltage A as depicted in FIG. 80. As the jaws of the clip applier begin to form the clip, the reading from the proximal strain gauge 71720 will exceed a pre-formed strain threshold $T_{PF}$ while the reading from the distal strain gauge 71730 remains below the pre-formed strain threshold $T_{PF}$. This can indicate that the clip has only been formed at or near the proximal strain gauge 71720. The difference in the voltages between the readings of the strain gauges 71720, 71730, at this stage, is measured to be A'. As the jaws of the clip applier form the clip further, the reading from the distal strain gauge 71730 will eventually exceed the pre-formed strain threshold $T_{PF}$ and the reading from the proximal strain gauge 71720 will eventually exceed a full-formed strain threshold $T_{FF}$. This can indicate that the clip has been fully formed at or near the proximal strain gauge 71720 and has begun to be deformed at or near the distal strain gauge 71730. When the readings from the proximal strain gauge 71720 and the distal strain gauge 71730 are both measured to be beyond the full-formed threshold $T_{FF}$ and the pre-formed threshold $T_{PF}$, respectively, the difference in the strain gauge readings is measured as A" as depicted in FIG. 80. Further, as the jaws of the clip applier form the clip further, the reading from the distal strain gauge 71730 will eventually exceed the full-formed strain threshold $T_{FF}$ and the reading from the proximal strain gauge 71720 will continue to increase above the full-formed strain threshold $T_{FF}$. When the reading from the proximal strain gauge 71720 and the distal strain gauge 71730 are measured to both be beyond the full-formed threshold $T_{FF}$, the difference in the strain gauge readings is measured as A''' as depicted in FIG. 80.

Further to the above, the state of the clip can be determined by measuring the differences between the readings of the proximal strain gauge 71720 and the distal strain gauge 71730 throughout the formation of a clip. More specifically, a difference in voltage measuring A indicates that the clip has yet to be deformed. A difference in voltage measuring A' indicates that only a proximal portion of the clip has been deformed. A difference in voltage measuring A" indicates that the proximal portion of the clip has been fully formed and the distal portion of the clip has begun to be deformed. And lastly, a difference in the voltage measuring A''' indicates that both the proximal and distal portions of the clip have been fully formed.

As discussed above, a clip applier is often inserted into a patient through a trocar. As a result, the diameter of the passageway through the trocar dictates a lot of the design considerations of the clip applier—especially of the portions of the clip applier that are inserted through and/or into the trocar passageway. That said, there is often motivation to make trocars as narrow as possible to reduce the size of the incisions in the patient, among other reasons. As such, narrow trocars, and narrow trocar passageways, present significant design constraints and often limit the widths of the clips that can be used. With this in mind, clip appliers are disclosed herein which are configured to store the clips in a small configuration and then enlarge the clips once they are on the other side of the trocar. Such an arrangement can allow clips to be used which, in their enlarged state, exceed the diameter of the trocar that they were inserted through.

FIGS. 81A and 81B depict a clip applier 71900 in accordance with at least one embodiment. The clip applier 71900 comprises a first jaw 71910*a* and a second jaw 71910*b* moveable relative to each other about a pivot pin 71912 between a closed position, a home position (FIG. 81A), and an open position (FIG. 81B). The clip applier 71900 further comprises a cam member 71920 configured to move the first jaw 71910*a* and the second jaw 71910*b* between the closed position, the home position, and the open position. More specifically, the first jaw 71910*a* and the second jaw 71910*b* are moved to the open position by the cam member 71920 when the cam member 71920 is moved to a fully retracted position (FIG. 81B) due to the cam member 71920 engaging a first jaw cam 71914*a* on the first jaw 71910*a* and a second jaw cam 71914*b* on the second jaw 71910*b*. Furthermore, the first jaw 71910*a* and the second jaw 71910*b* are moved to the home position by the cam member 71920 when the cam member 71920 is moved distally to a home position depicted in FIG. 81A (i.e., the cam member 71920 is no longer engaging the first jaw cam 71914*a* and the second jaw cam 71914*b* allowing the first jaw 71910*a* and the second jaw 71910*b* to assume the home position). Further still, the first jaw 71910*a* and the second jaw 71910*b* are moved to the closed position by the cam member 71920 when the cam member 71920 is moved distally to a fully advanced position due to the cam member 71920 cammingly engaging the outer surfaces of the first jaw 71910*a* and the second jaw 71910*b*. The first jaw 71910*a* and the second jaw 71910*b* are configured to receive a clip 71904 therein to be expanded during a pre-form operation and crimped during a crimping operation. FIG. 81A depicts the clip 71904 in a storage configuration when the first jaw 71910*a* and the second jaw 71910*b* are in the home position. The clip 71904 can be a 5 mm clip in the storage configuration, for example. Expansion of the clip 71904 during the pre-form operation and crimping of the clip 71904 during the crimping operation are described in further detail below.

The first jaw 71910*a* and the second jaw 71910*b* comprise pre-forming features, or protrusions 71930*a* and 71930*b*, similar to protrusions 70126*a* and 70126*b* discussed above. The protrusions 71930*a* and 71930*b* engage the inner surfaces of the clip 71904 and expand the clip 71904 from the storage configuration (FIG. 81A) to a firing configuration (FIG. 81B) when the first jaw 71910*a* and the second jaw 71910*b* are moved to the open position. For example, the clip 71904 is expanded from the storage configuration where the clip 71904 has an approximately 5 mm width to a firing configuration where the clip 71904 has an approximately 10 mm width. That said, a clip can have any suitable stored width and any suitable expanded width. After the clip 71904 has been expanded to the firing configuration, a firing member advances the clip over the protrusions 71930*a*, 71930*b* into a crimping position within the first jaw 71910*a* and the second jaw 71910*b*. The protrusions 71930*a* and 71930*b* comprise angled portions which allow the clip 71904 to slide over the protrusions 71930*a* and 71930*b* when advanced by the firing member. Once a clip is in the crimping position, the cam member 71920 is advanced distally to the fully advanced position during a crimping stroke to move the first jaw 71910*a* and the second jaw 71910*b* to the closed position, and, thus, crimp the clip 71904 within the crimping chamber.

Further to the above, the clip applier 71900 further comprises a sensor array 71940 that detects a magnet 71950 included in one of the first jaw 71910*a* and the second jaw 71910*b*. The sensor array 71940 detects the location of the magnet 71950 relative to the sensor array 71940 in order to determine the position of the first jaw 71910*a* and the second jaw 71910*b* relative to each other during the operation of the clip applier 71900.

As discussed herein, clip appliers are loaded with clips in a variety of manners. For instance, clips can be loaded into a clip applier by way of a clip cartridge. Such clip cartridges can comprise clips stacked along a longitudinal axis, for example. Such clip cartridges can also comprise clips stacked along an axis which is transverse to the longitudinal axis of the clip applier. Certain cartridges are stored in a circumferential configuration, as described above. That being said, some clip appliers may be configured to hold only one clip at a time. The teachings provided herein are adaptable to such clip appliers. In at least one instance, a one-clip clip applier, for example, can be used with a docking station comprising a plurality of clips stored therein. In such instances, the clinician can use the docking station to re-supply a clip to the one-clip clip applier after each use of the clip applier. In certain instances, the docking station can be positioned in the patient which prevents the need to remove the clip applier from the patient such that the clip applier can be reloaded. In at least one instance, as discussed below, the docking station can be attached to a trocar inserted into the patient, for example. The above being said, the idea of a docking station positioned within a patient can also be used with a multi-clip clip applier. In such instances, one or more clips from the docking station can be loaded into the multi-clip clip applier without having to remove the clip applier from the patient.

Figure 82:
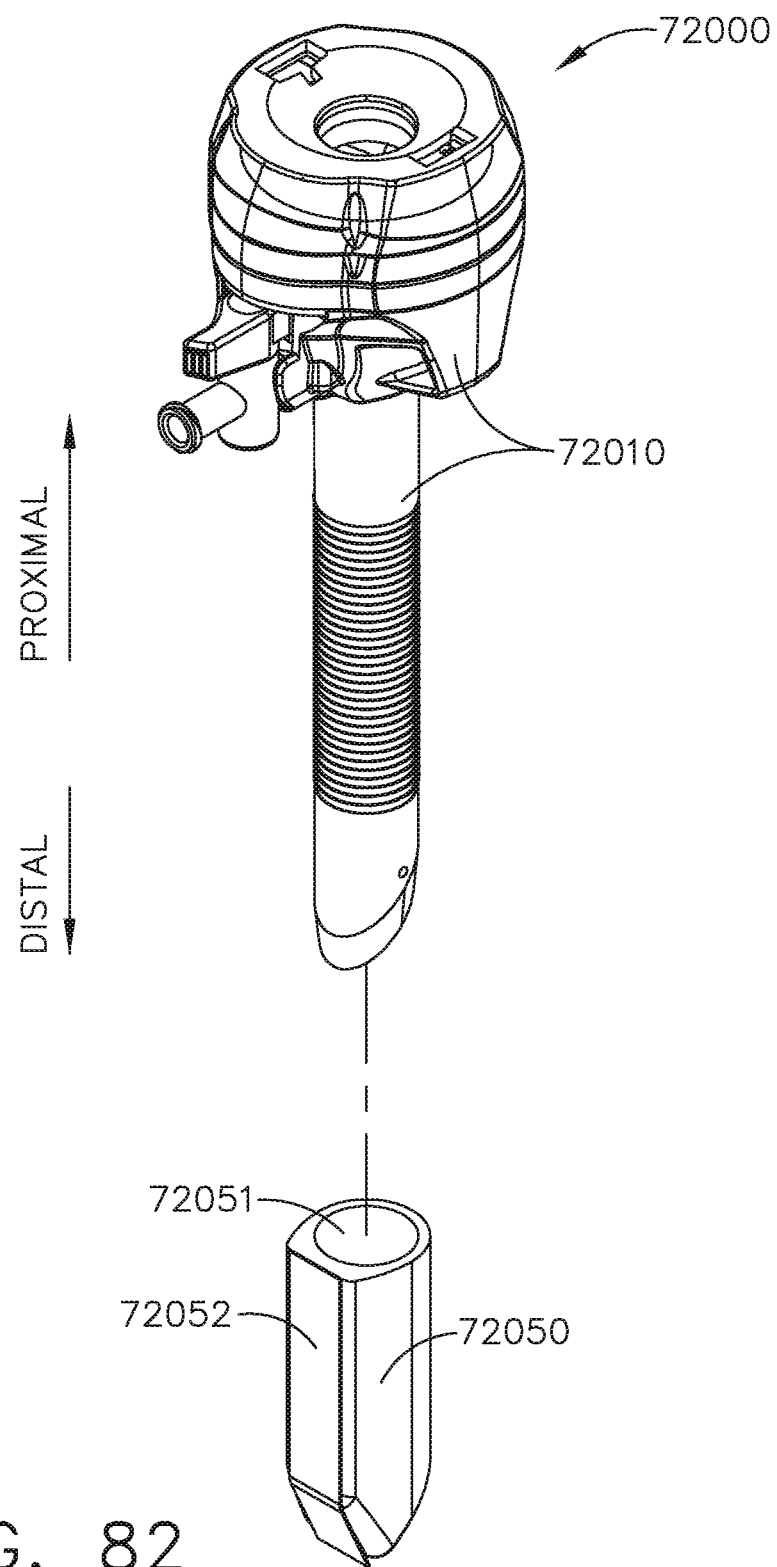
FIG. 82 is a perspective view of a clip applier system utilizing a trocar.
Figure 83:
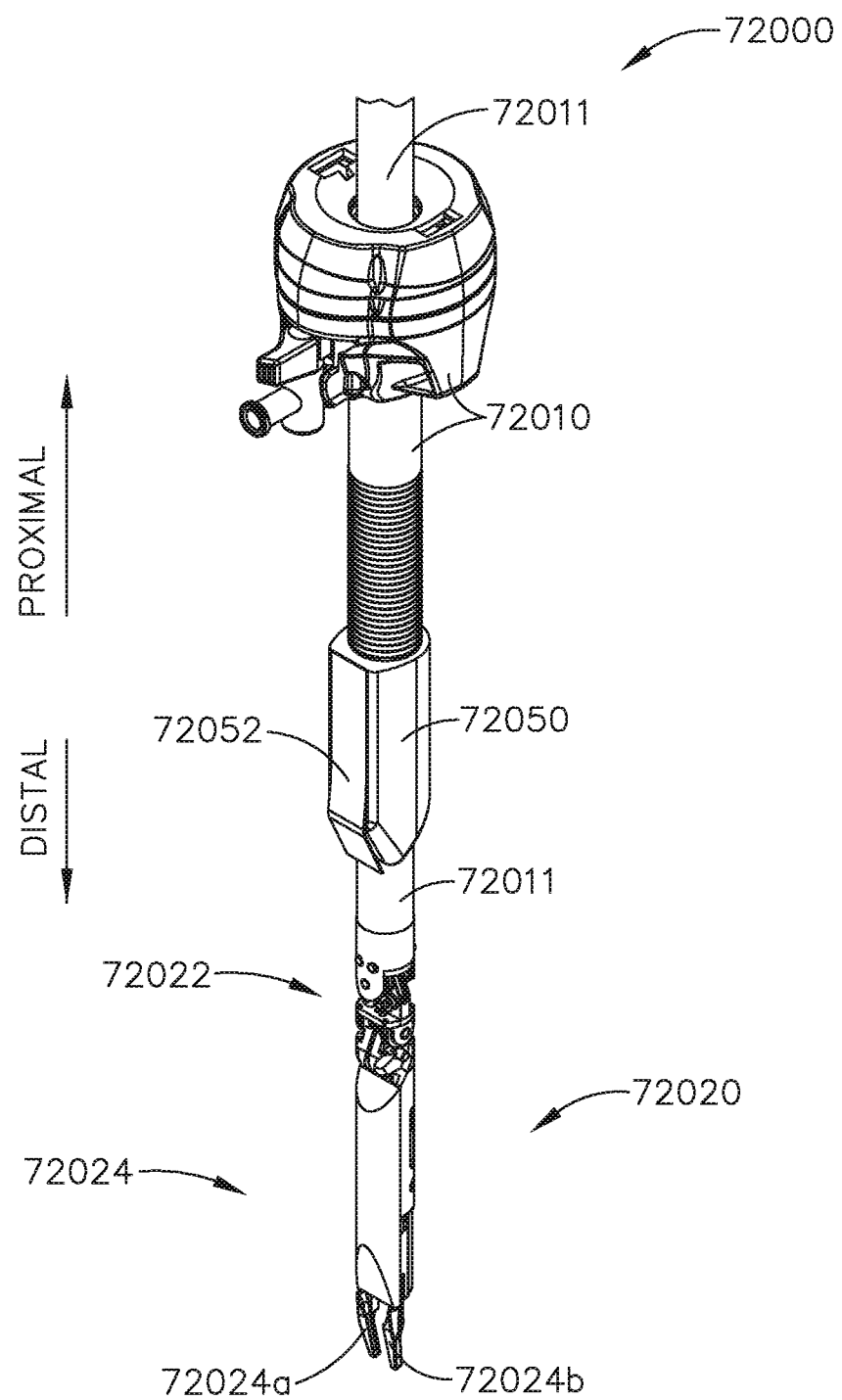
FIG. 83 is a perspective view of the clip applier system of FIG. 82.

Turning to FIGS. 82 and 83, a clip applier system 72000 is depicted. The clip applier system comprises a trocar 72010, a clip magazine 72050, and a clip applier 72020. The clip applier 72020 comprises an elongate shaft 72011 extending from a housing, an articulation joint 72022 extending from the elongate shaft 72011, and an end effector 72024 extending from the articulation joint 72022. The end effector 72024 comprises a first jaw 72024*a* and a second jaw 72024*b* moveable relative to each other between an open position and a closed position. The end effector 72024 is articulable relative to the elongate shaft 72011 about the articulation joint 72022. The clip magazine 72050 comprises an opening 72051 (see FIG. 82) through the clip magazine 72050. Prior to insertion of the clip applier 72020 through the trocar 72010, the clip magazine 72050 is positioned within the patient and attached to the distal end of the trocar 72010. The opening 72051 allows the clip magazine 72050 to be received and attached to the distal end of the trocar 72010 as depicted in FIG. 83. The clip magazine 72050 can be threadably attached to the distal end of the trocar 72010, for example. The clip applier 72020 is then inserted through the trocar 72010 and the opening 72051 of the clip magazine 72050 until the end effector 72024 of the clip applier 72020 is positioned distal to the clip magazine 72050. As the clip applier 72020 is retracted toward the clip magazine 72050, the clip applier 72020 engages the clip magazine 72050 to eject a clip from the clip magazine 72050 into the end effector of the clip applier 72020, as discussed in greater detail below.

Figure 85B:
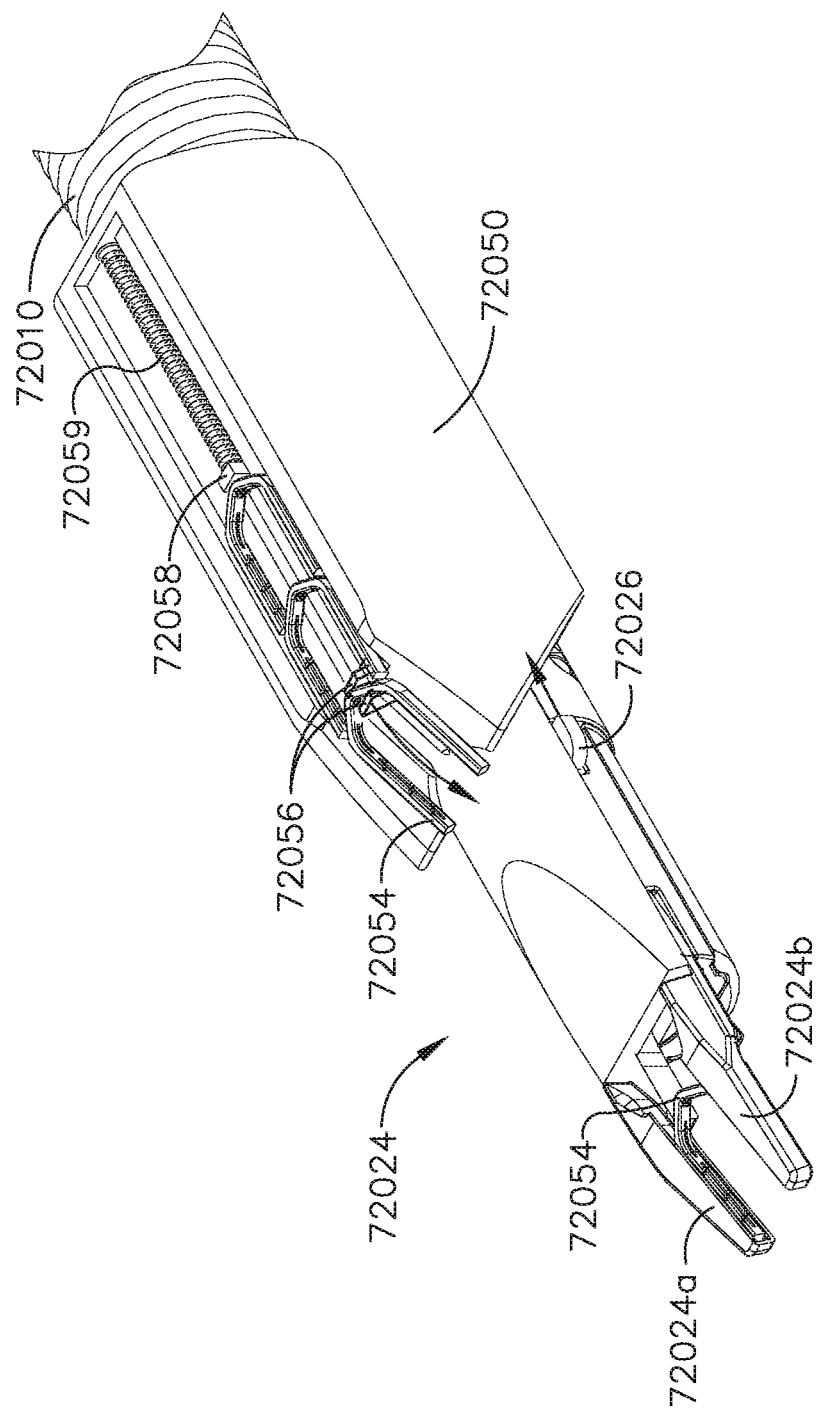
FIG. 85B is a cross-sectional perspective view of the clip applier system of FIG. 82.

Turning to FIGS. 85A and 85B, the clip magazine 72050 further comprises, a leaf spring 72052, a plurality of clips 72054 removably stored in the clip magazine 72050, a spring 72059, a sled 72058, and a loading arm 72056. The leaf spring 72052 prevents the clips 72054 from falling out of the clip magazine 72050 inadvertently. The spring 72059 biases the sled 72058 distally to bias the clips 72054 toward the loading arm 72056. The loading arm 72056 grasps and holds a clip 72054 in place until acted upon by the clip applier 72020. To this end, the loading arm 72056 engages a jaw wing 72026 of the clip applier 72020 as the clip applier 72020 is retracted towards the clip magazine 72050 (i.e., proximally). When the jaw wing 72026 is engaged by the loading arm 72056, the jaw wing 72026 moves proximally and the loading arm 72056 rotates toward the end effector 72024 to load a clip 72054 from the clip magazine 72050 into the end effector 72024 of the clip applier 72020. FIGS. 84A-84C depict the movements of the jaw wing 72024 and the loading arm 72056 as the clip applier 72020 is retracted towards the clip magazine 72050. After a clip 72054 has been loaded into the end effector 72024, the clip applier 72024 can be moved distally to a desired location within the patient to crimp the clip 72054 around patient tissue. After the clip 72054 is crimped and released, the clip applier 72020 can be retracted toward the clip magazine 72050 (i.e., proximally) to engage the jaw wing 72026 with the loading arm 72056 of the clip magazine 72050 to load another clip into the clip applier 72020. This process can be repeated until all of the clips 72054 have been depleted from the clip magazine 72050, and/or until a suitable number of clips have been applied.

Figure 86A:
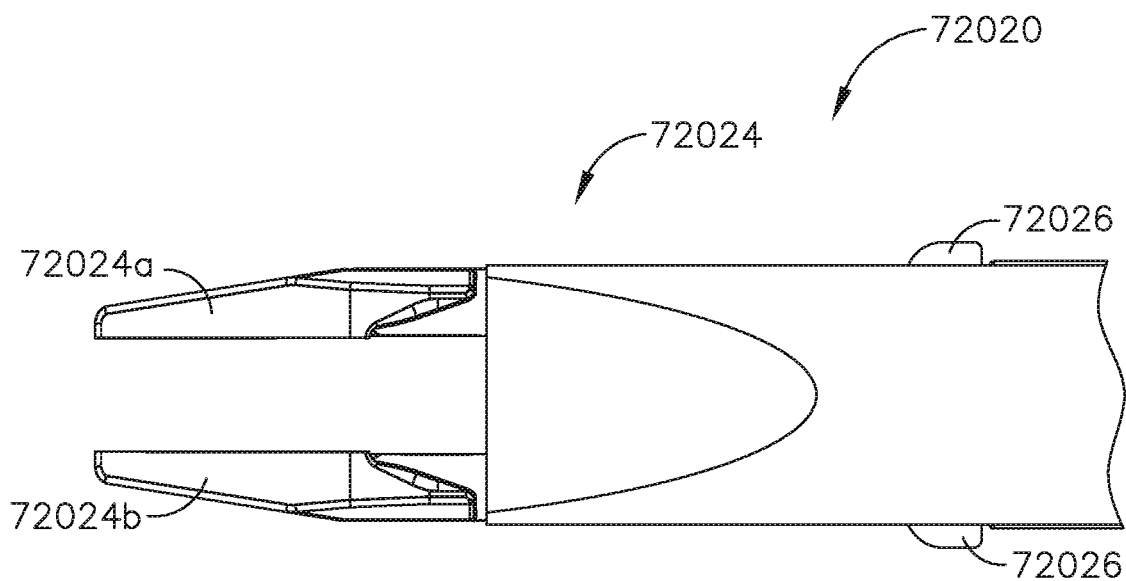
FIG. 86A is a plan view of the clip applier system of FIG. 82 depicting a jaw wing of the clip applier in an expanded configuration.
Figure 86B:
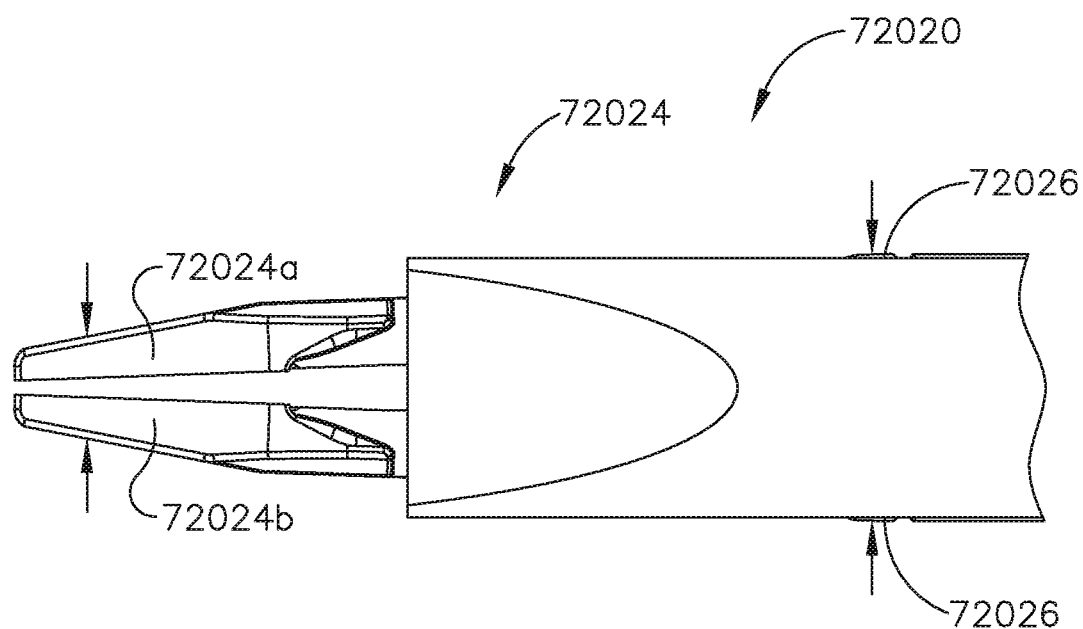
FIG. 86B is a plan view of the clip applier system of FIG. 82 depicting the jaw wing of the clip applier in a retracted configuration.

Turning now to FIGS. 86A and 86B, the relationship between the jaw wing 72026 and the first and second jaws 72024*a* and 72024*b* of the clip applier 72020 is depicted. The jaw wing 72026 is operably engaged with the first and second jaws 72024*a* and 72024*b* such that, when the first and second jaws 72024*a* and 72024*b* are in the closed position (FIG. 86B), the jaw wing 72026 is retracted. To this end, the clip applier 72020 can be inserted through the clip magazine 72050 without the jaw wing 72026 engaging the loading arm 72056 of the clip magazine 72050. Other embodiments are envisioned where the clip applier 72020 engages the clip magazine 72050 to load a clip 72054 into the end effector 72024 when the clip applier 72020 is moved from a proximal position behind the clip magazine 72050 to a distal position beyond the clip magazine 72050.

A clip applier 73000 is depicted in FIGS. 87A-87D. The clip applier 73000 comprises an elongate shaft 73010 extending from a housing, an articulation joint 73020 extending from the elongate shaft 73010, a magazine housing 73030 extending from the articulation joint 73020, and an end effector 73040 extending from the magazine housing 73030. The end effector 73040 comprises a first jaw 73040*a* and a second jaw 73040*b* moveable relative to each other between an open position and a closed position. The magazine housing 73030 comprises a bottom housing 73030*b* and a top housing 73030*a*. The top housing 73030*a* is movable relative to the bottom housing 73030*b* between an open position (FIG. 87A) and a closed position (FIG. 87C) about a pivot pin 73032 attached to the articulation joint 73020. The magazine housing 73030 can receive a clip magazine 73050 comprising a plurality of clips 73054 stored therein. The clips 73054 are loaded into the clip magazine 73030 and are locked in place by a biasing member, or leaf spring 73056. The leaf spring 73056 prevents the clips 73054 from being ejected form the clip magazine 73050 until the clip magazine 73050 is seated in the magazine housing 73030, as discussed in greater detail below.

Figure 87A:
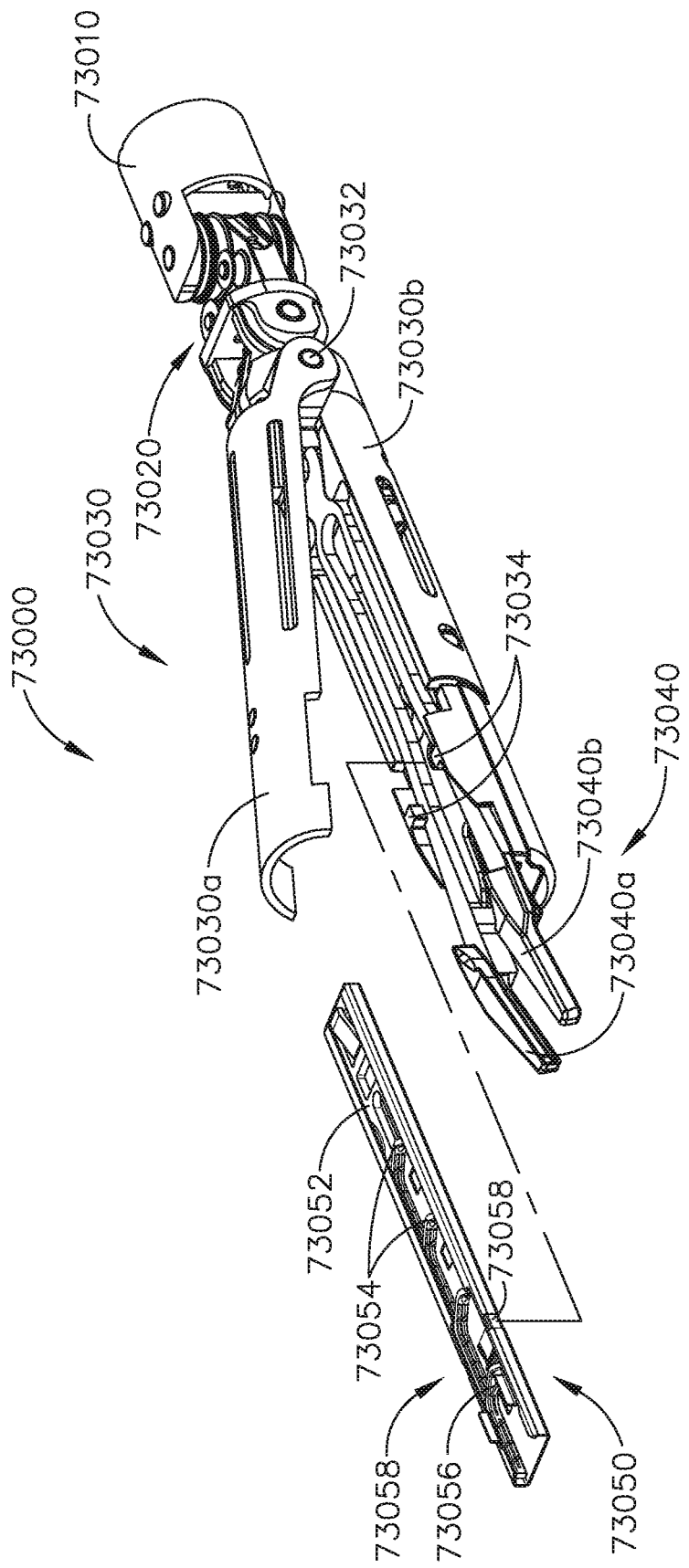
FIG. 87A is a perspective view of a clip applier and a clip magazine for use with the clip applier.
Figure 87B:
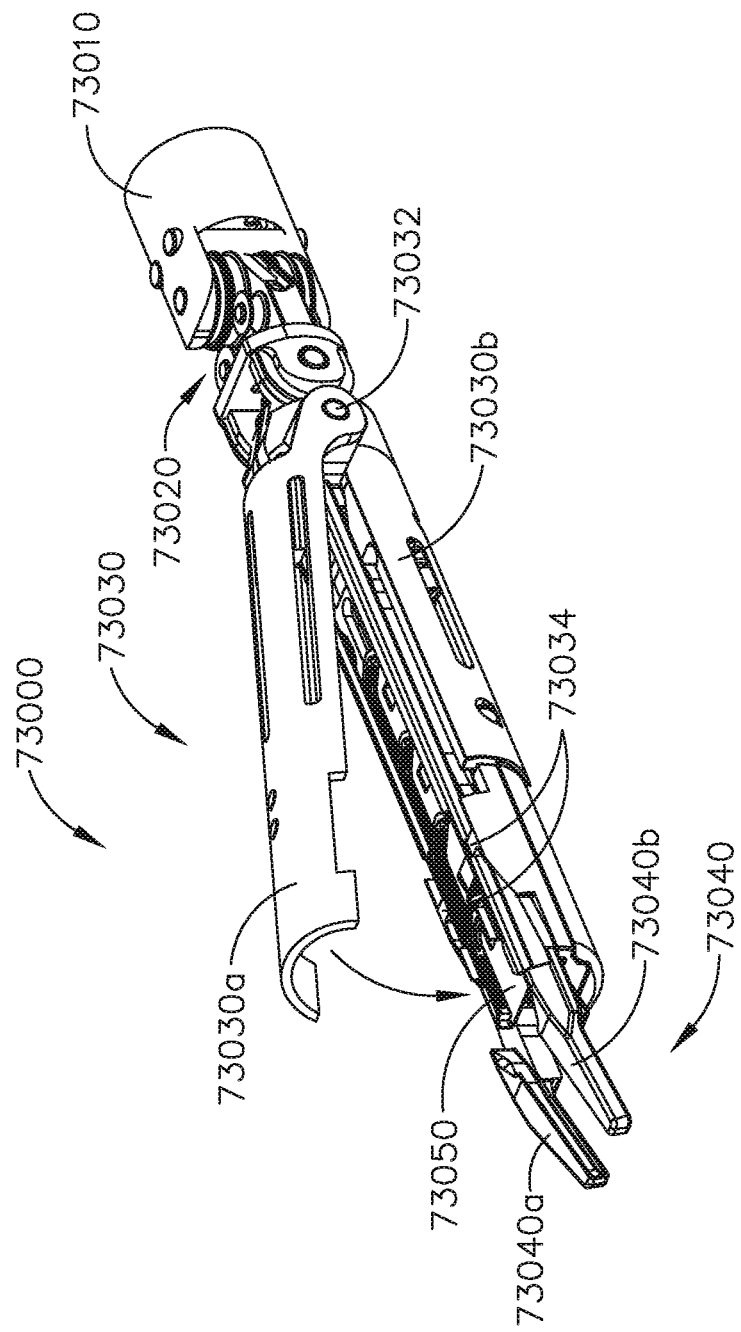
FIG. 87B is a perspective view of the clip magazine seated into the clip applier of FIG. 87A.
Figure 87C:
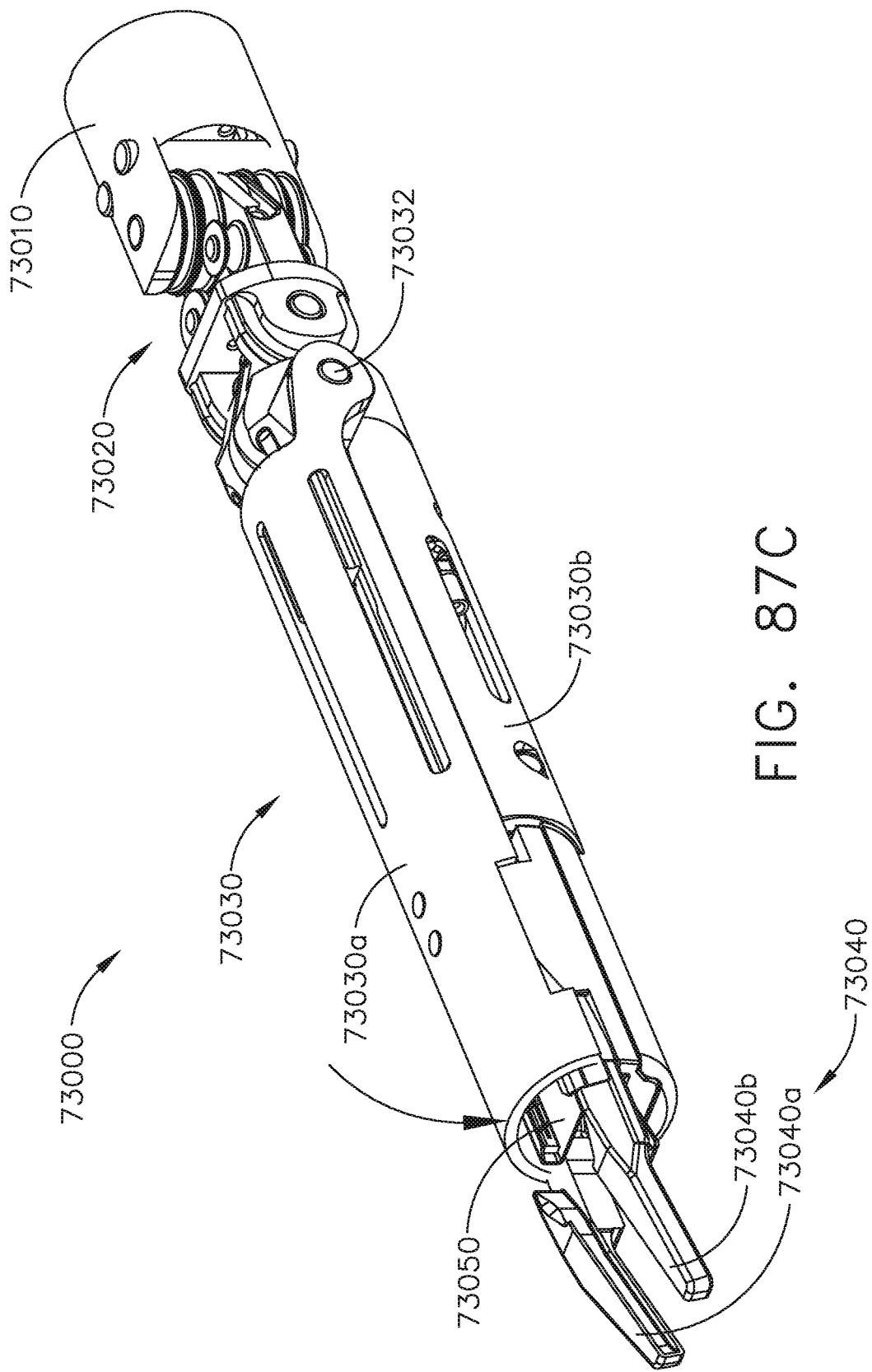
FIG. 87C is a perspective view of the clip applier and the clip magazine of FIG. 87A in a loaded configuration.
Figure 87D:
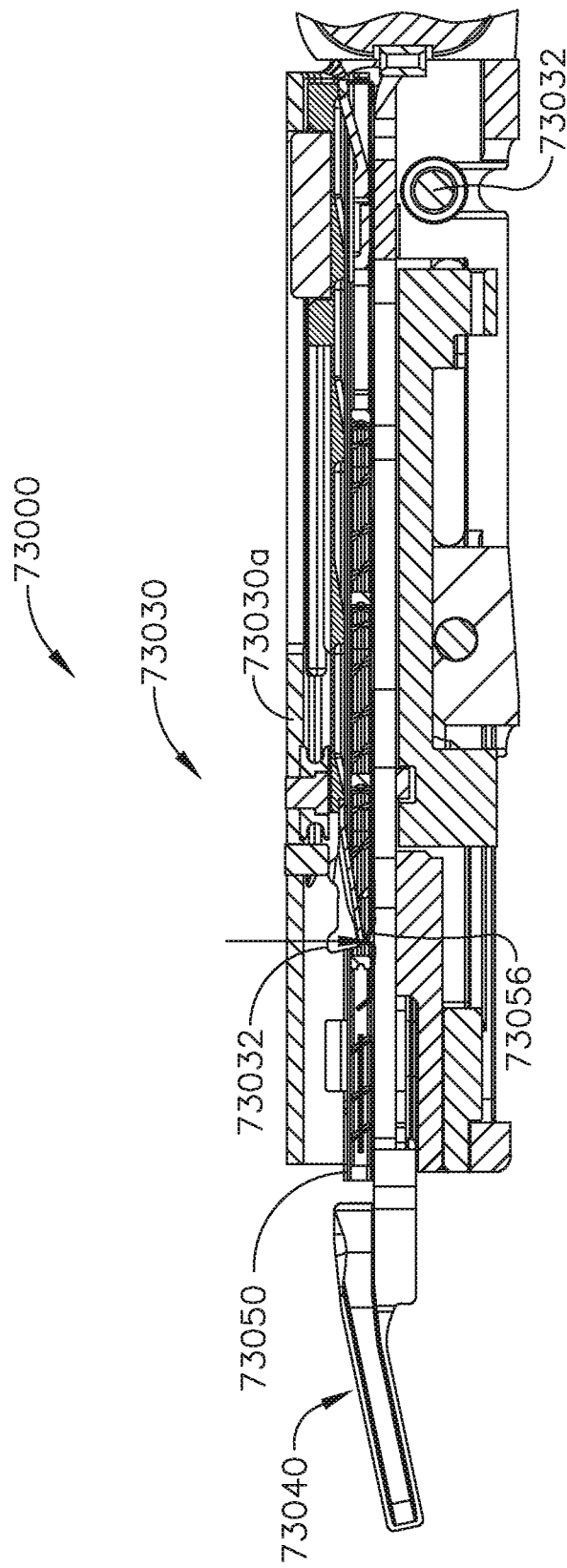
FIG. 87D is a cross-sectional view of the clip applier and the clip magazine of FIG. 87A in the loaded configuration of FIG. 87C.

The clip magazine 73050 further comprises notches 73058 on either side of the clip magazine 73050. To properly seat the clip magazine 73050 in the magazine housing 73030, the notches 73058 of the clip magazine 73050 are aligned with protrusions 73034 of the magazine housing 73030 to seat and align the clip magazine 73050 in the magazine housing 73030 as depicted in FIG. 87B. Once the clip magazine 73050 is installed into the magazine housing 73030, the top housing 73030*a* can be moved to the closed position as depicted in FIG. 87C. The top housing 73030*a* comprises a lockout release, or protrusion 73032, that engages the leaf spring 73056 of the clip magazine 73050 when the clip magazine 73050 is installed in the magazine housing 73030 and the top housing 73030*a* is in the closed position as depicted in FIG. 87D. When the leaf spring 73056 is depressed by the protrusion 73032, the clips 73054 are no longer locked into position within the clip magazine 73050 and can be ejected from the clip magazine 73050 into the end effector 73040 by a firing member.

Figure 88A:
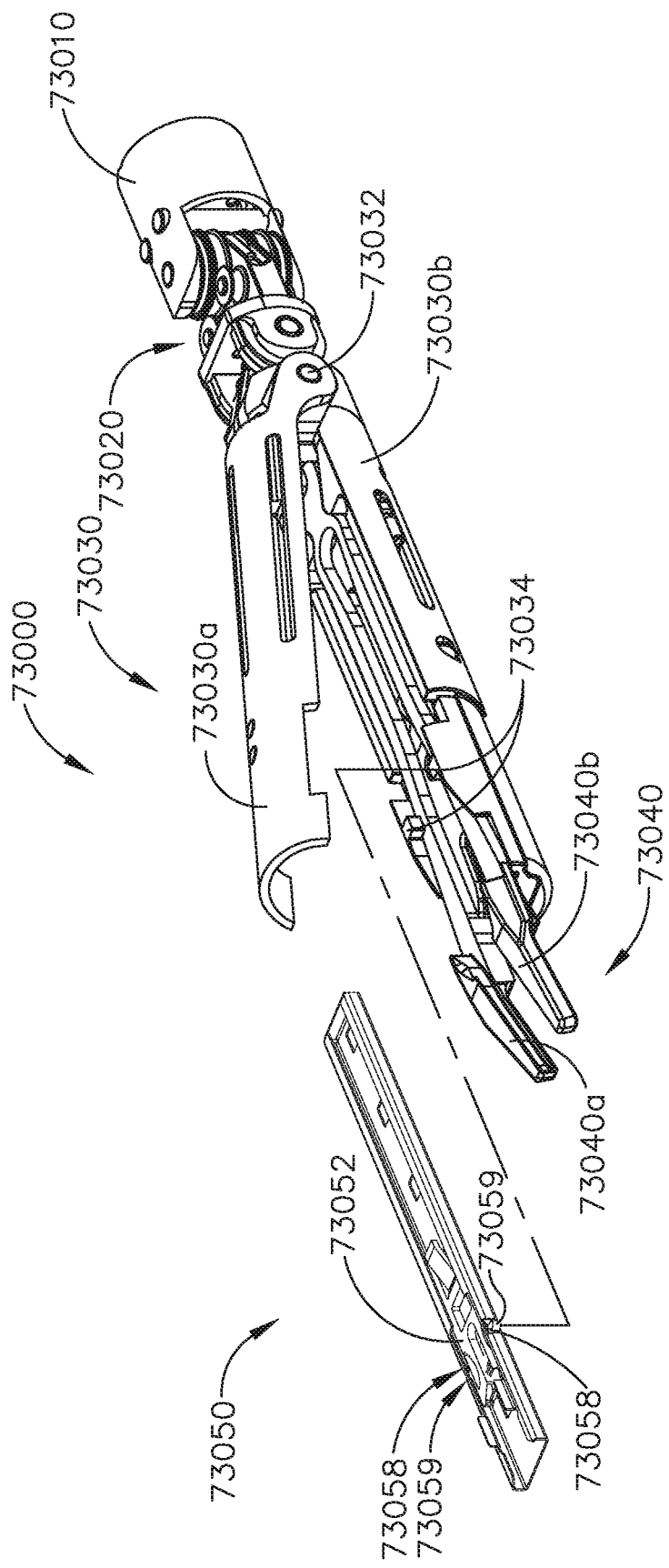
FIG. 88A is a perspective view the spent clip magazine removed from the clip applier of FIG. 87A.
Figure 88B:
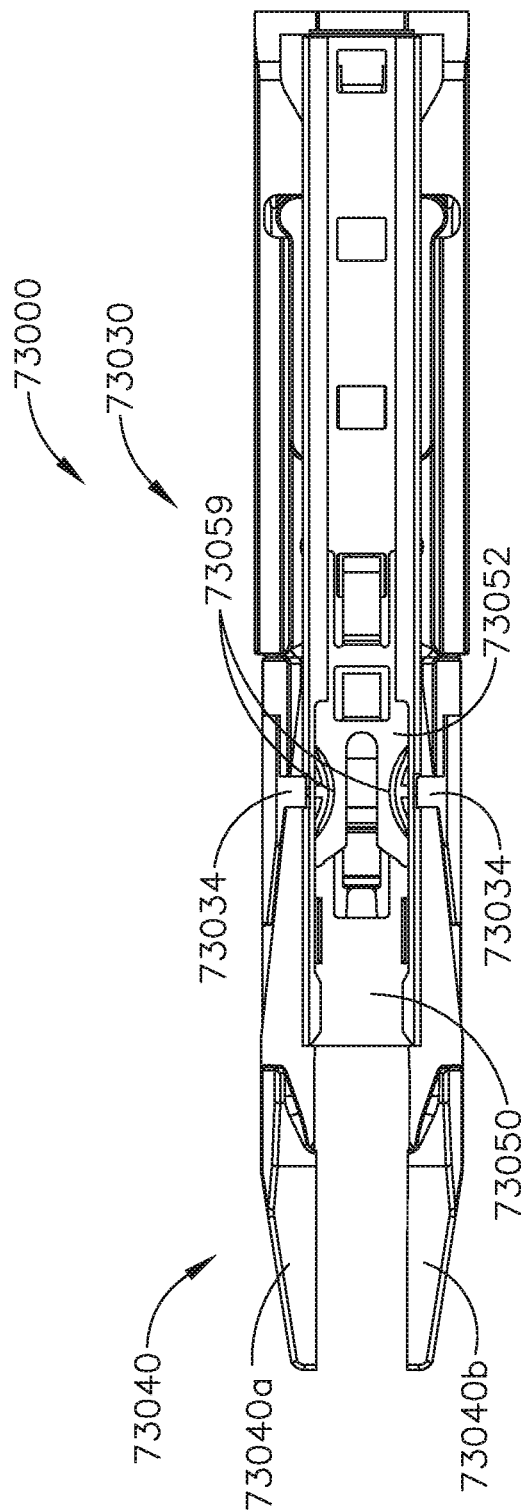
FIG. 88B is a plan view of the spent clip magazine seated into the clip applier of FIG. 87A.

Turning now to FIGS. 88A-88D, after all of the clips 73054 have been ejected from the clip magazine 73050, the clip magazine 73050 can be locked out when removed from the magazine housing 73030 to prevent the clip magazine 73050 from being re-installed into the magazine housing 73030 until reloaded with at least one new clip 73054. More specifically, the clip magazine 73030 comprises a sled 73052 that moves through the clip magazine 73030 as the clips 73054 are ejected. The sled 73052 comprises spring loaded detents 73059 which align with the notches 73058 in the clip magazine 73050 when the last clip 73054 has been ejected form the clip magazine 73050. When the clip magazine 73050 is installed in the magazine housing 73030 and the clip magazine 73050 has been spent, the spring loaded detents 73059 are biased against the protrusions 73034 as depicted in FIGS. 88B and 88D. After the clip magazine 73050 is removed from the magazine housing 73030, the spring loaded detents 73059 protrude through the notches 73058 to lock the sled 73052 into place as depicted in FIG. 88A. The spent clip magazine 73050 cannot be re-installed into the magazine housing 73030 unless at least one clip 73054 is loaded into the clip magazine 73050. More specifically, until the sled 73052 is retracted to disengage the spring loaded detents 73059 from the notches 73058 (i.e., at least one clip 73054 is installed) the clip magazine 73050 cannot be installed into the magazine housing 73030 because the spring loaded detents 73059 occupy the notches 73058 and will not allow the notches 73058 to properly align and seat with the protrusions 73034 of the magazine housing 73030.

Other embodiments are envisioned where a clip applier system comprises a clip applier, a trocar, and a sensing system. The clip applier of the clip applier system is similar to clip applier 72020 in many respects and the trocar is similar to the trocar 72010 in many respects. The trocar can comprise a sensor, such as a Hall Effect sensor, for example, attached to, or near, the distal end of the trocar. The clip applier further comprises a detectable element, such as a magnet, for example, positioned in the end effector of the clip applier. The magnet in the end effector of the clip applier and the Hall Effect sensor on the distal end of the trocar are included in the sensing system. The sensing system is in signal communication with the control system of the clip applier via a wireless signal transmitter in the trocar and a wireless signal receiver in the clip applier. The control system of the clip applier is configured to automatically control the opening and closing of the jaws of the end effector depending on the position of the magnet relative to the Hall Effect sensor. More specifically, when the magnet in the jaws is positioned a predetermined distance distal to the Hall Effect sensor of the trocar—which indicates that the jaws have passed through the trocar, the clip jaws are automatically moved to an open position by the control system of the clip applier. Moreover, the control system of the clip applier can also automatically load a clip into the open jaws. Such an arrangement reduces the time needed to load the clip applier after being inserted into a patient. Further, when the magnet in the jaws is approaching the Hall Effect sensor of the trocar from a distal position (i.e., the clip applier is being retracted proximally toward the trocar) the control system automatically moves the jaws to a closed position to allow the clip applier to be retracted through the trocar.

Figure 89:
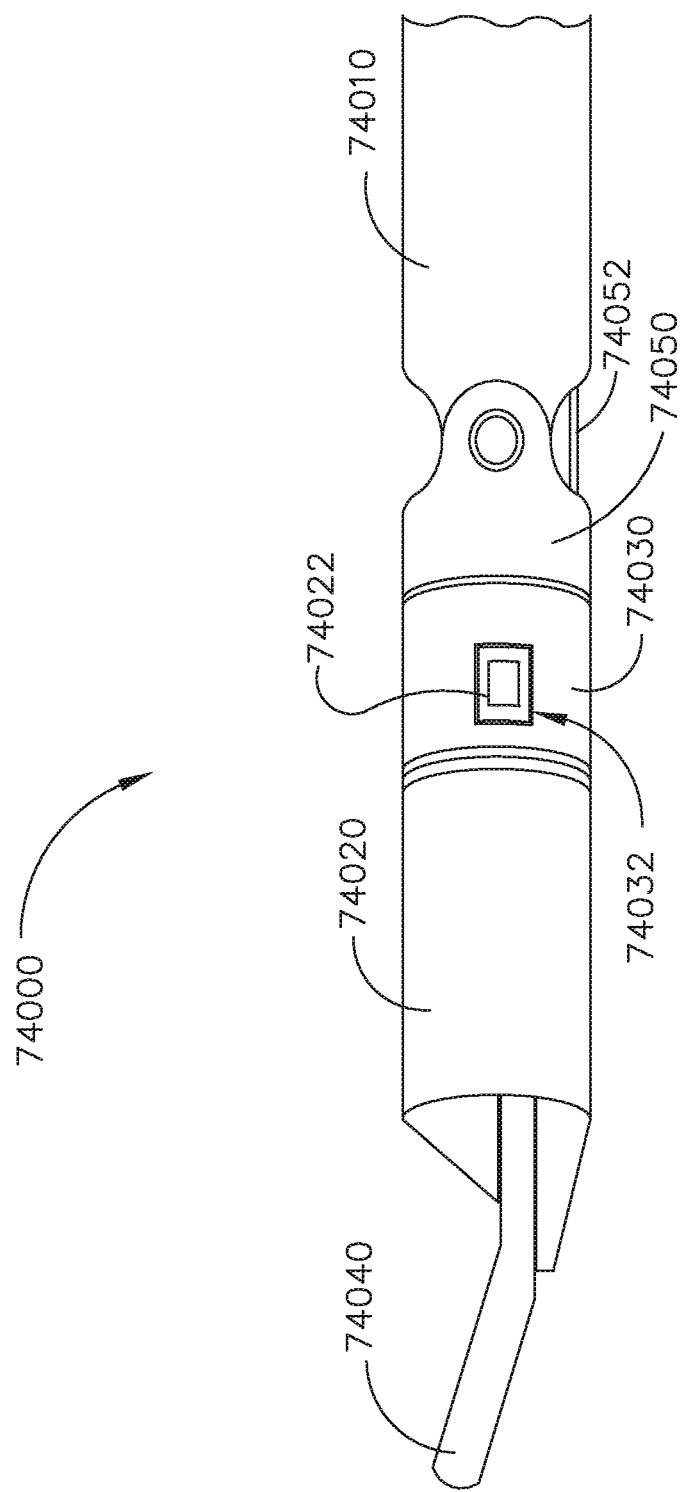
FIG. 89 is a side elevational view of a clip applier utilizing an interchangeable clip magazine.

FIG. 89 depicts a clip applier 74000 in accordance with at least one embodiment. The clip applier 74000 comprises an elongate shaft 74010 extending from a housing, a clip reload 74020 comprising a plurality of clips, a distal head 74030 rotatable relative to the housing, an end effector 74040 extending from the distal head 74030, and an articulation joint 74050 rotatably connecting the distal head 74030 and the elongate shaft 74010. The distal head 74030 is articulatable relative to the elongate shaft 74010 by an articulation bar 74052 that is operably responsive to a motor inside the housing of the clip applier 74000. Further, the clip reload 74020 is releasably attachable to the distal head 74030 by way of an opening 74032 in the distal head 74030 and a protrusion 74022 on the clip reload 74020. The protrusion 74022 extends outwardly and is captured by the opening 74032 to releasably attach the clip reload 74020 to the distal head 74030. The clip reload 74020 is interchangeable with other clip reloads, for instance, the clip reload 74020 can be interchanged with clip reloads containing clips that are smaller or larger than the clips of clip reload 74020. This arrangement allows for different size clip reloads to be attached to the same distal head, such as the distal head 74030, for example.

Figures 90A, 90B:
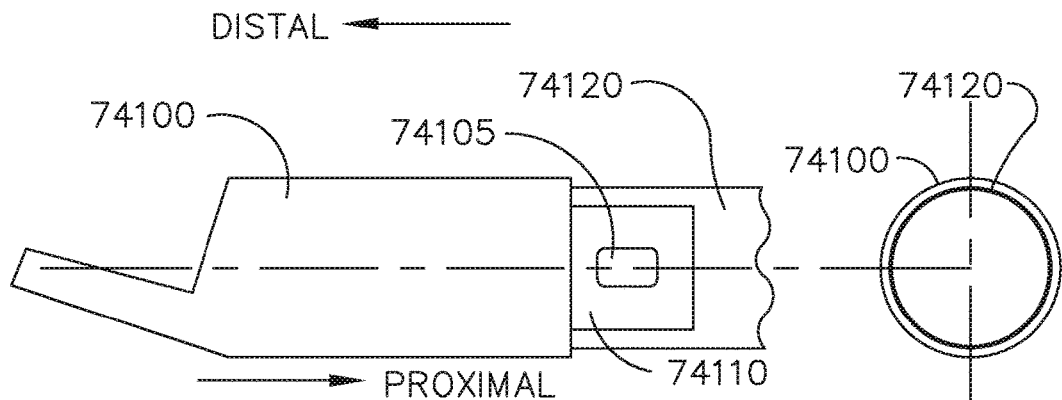
FIG. 90A is a side elevational view of a distal head releasably attached to a shaft of a clip applier.
FIG. 90B is a front elevational view of the distal head and shaft of FIG. 90A.

FIGS. 90A and 90B depict a distal head 74100 releasably attached to a shaft 74120 of a clip applier in accordance with at least one embodiment. The distal head 74100 has an eight millimeter diameter and is for use with LIGAMAX 5 clips from Ethicon Inc. and the shaft 74120 has an eight millimeter diameter shaft, for example. The distal head 74100 is releasably attachable to the shaft 74120 by a detent 74105. Other embodiments are envisioned with different attachment mechanisms. The distal head 74100 comprises a proximal portion 74110 which extends proximally from the distal head 74100 and comprises the detent 74105 thereon. The proximal portion 74110 is configured to fit inside and align with the shaft 74120 of the clip applier to facilitate proper attachment of the distal head 74100 to the shaft 74120.

Figures 91A, 91B:
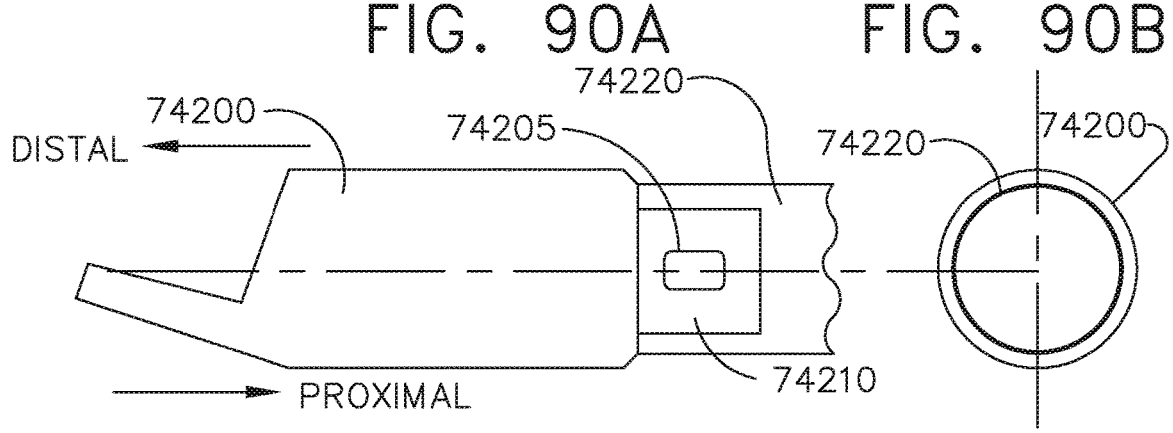
FIG. 91A is a side elevational view of a distal head releasably attached to a shaft of a clip applier.
FIG. 91B is a front elevational view of the distal head and shaft of FIG. 91A

FIGS. 91A and 91B depict a distal head 74200 releasably attached to a shaft 74220 of a clip applier in accordance with at least one embodiment. The distal head 74200 has a nine millimeter diameter and is for use with ER320 clips from Ethicon Inc. and the shaft 74220 has an eight millimeter shaft diameter. The distal head 74200 is releasably attachable to the shaft 74220 by a detent 74205. The distal head 74200 comprises a proximal portion 74210 which extends proximally from the distal head 74200 and comprises the detent 74205 thereon. The proximal portion 74210 is configured to fit inside and align with the shaft 74220 of the clip applier to facilitate proper attachment of the distal head 74200 to the shaft 74220.

Figures 92A, 92B:
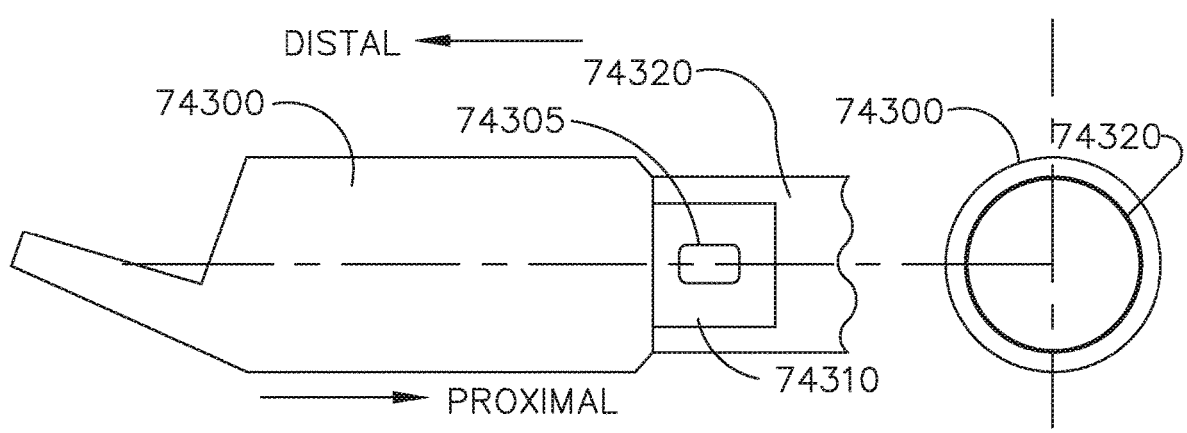
FIG. 92A is a side elevational view of a distal head releasably attached to a shaft of a clip applier.

FIGS. 92A and 92B depict a distal head 74300 releasably attached to a shaft 74320 of a clip applier in accordance with at least one embodiment. The distal head 74300 is an eleven millimeter distal clip applier head for use with ER420 clips and the shaft 74320 is an eight millimeter shaft, for example. The distal head 74300 is releasably attachable to the shaft 74320 by a detent 74305. The distal head 74300 comprises a proximal portion 74310 which extends proximally from the distal head 74300 and comprises the detent 74305 thereon. The proximal portion 74310 is configured to fit inside and align with the shaft 74320 of the clip applier to facilitate proper attachment of the distal head 74300 to the shaft 74320.

The distal heads 74100, 74200, and 74300 are of varying sizes as described above, however, the distal heads 74100, 74200, and 74300 are releasably attachable to the same size shaft (an eight millimeter shaft, for example).

FIG. 93A depicts a clip applier system 74400 in accordance with at least one embodiment. The clip applier system 74400 comprises a clip applier shaft 74410 extending from a housing of the clip applier system 74400. The clip applier shaft 74410 is configured to selectively receive various distal heads, such as distal head 74450, or in the alternative distal head 74460, for example. The clip applier shaft 74410 comprises a proximal shaft 74412 extending from the housing of the clip applier, a distal shaft 74420 comprising an opening 74422, and an articulation joint 74415 connecting the proximal shaft 74412 and the distal shaft 74420. The opening 74422 is configured to receiver protrusions 74452, 74462 of the distal heads 74450 and 74460, respectively, depending on which distal head is attached to the clip applier shaft 74410. In at least one embodiment, the distal heads 74450 and 74460 are different sizes (e.g., in diameter and/or length) and are configured to store different size clips, for example. Further, the distal head 74450 comprises an end effector 74454 extending therefrom and the distal head 74460 comprises end effector 74464 extending therefrom which have different sizes and can form clips to different sizes. As a result of the above, the clip applier system 74400 comprises a clip applier shaft 74410 configured to interchangeably connect different size distal heads with different size end effectors to the same size clip applier shaft 74410.

Figure 93D:
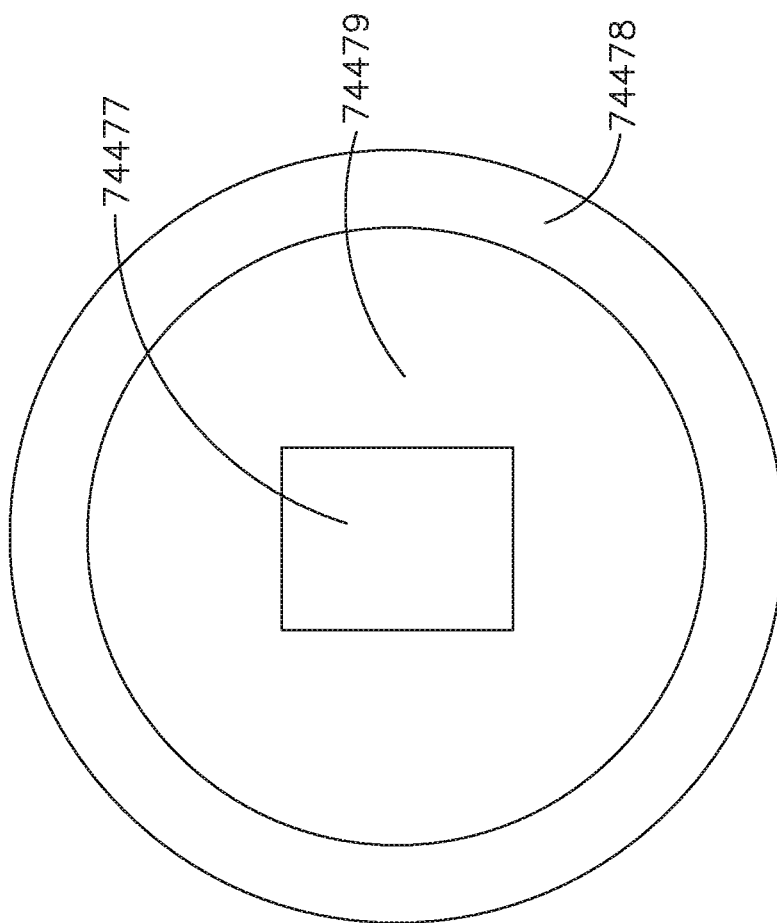

FIG. 93B depicts a clip applier system 74470 in accordance with at least one embodiment. The clip applier system 74470 comprises a distal head 74472 configured to releasably attach to a shaft 74478 comprising a rotary input 74479. The shaft 74478 extends from a housing of the clip applier system 74470 and is operably responsive to rotary motions generated by a motor within the housing. The distal head comprises a carriage 74474 and a drive screw 74477 threadably engaged with the carriage 74474. The carriage 74474 is configured to translate relative to the distal head 74472 when the distal head 74472 is attached to the shaft 74478. More specifically, the drive screw 74477 is threadably engaged with a collar 74476 of the carriage 74474 and the carriage 74474 is rotatably constrained within the distal head 74472 such that, as the drive screw 74477 is rotated, the carriage 74474 will translate through the distal head 74472. The rotary input 74479 is configured to connect to the drive screw 74477 via a quick disconnect 74475 on the distal end of the rotary input 74479 when the distal head 74472 and the shaft 74478 are brought together. Thus, the rotary input 74479 can rotate the drive screw 74477 when they are attached. In at least one embodiment, the proximal end of the drive screw 74477 comprises a square shape (see FIG. 93D) and the distal end of the rotary input 74479 comprises a square opening configured to receive the square shape of the drive screw 74477 to allow the transfer of rotational motions from the rotary input 74479 to the drive screw 74477. Other embodiments are envisioned with different mechanical connection types between the rotary input 74479 and drive screw 74477 to allow the distal head 74472 and shaft 74478 to releasably attach and rotate together.

Once the distal head 74472 is attached to the shaft 74478, the rotary input 74479 can be rotated to translate the carriage 74474 between a proximal position and a distal position within the distal head 74472. The thread pitch of the drive screw 74477 can be chosen to effectuate a translation of the carriage 74474 through a stroke of a predetermined length. The predetermined length can be based on the distal head function that the translation of the carriage 74474 is performing, such as feeding a clip through the distal head into an end effector or crimping a clip within the end effector, for example. Further, the predetermined length can be selected based on the size (e.g., diameter or length) of the distal head and/or the size of the clips to be advanced and/or formed.

FIG. 93C depicts a clip applier system 74480 in accordance with at least one embodiment. The clip applier system 74480 is similar to the clip applier system 74470 in many respects. The distal head 74482 comprises a carriage 74484 rotatably constrained within the distal head 74482, and the carriage 74484 comprises a collar 74486 configured to capture a drive screw 74487 of the distal head 74482. The drive screw 74487 is configured to releasably attach to the rotary input 74479 of the shaft 74478 of the clip applier system 74470, similar to the above. As illustrated in FIG. 93C, the distal head 74482 is larger than the distal head 74472; however, the carriage 74484 of the distal head 74482 is sized such that the drive screw 74487 and rotary input 74489 are aligned when the distal head 74482 is attached to the shaft 74478. Thus, the quick disconnect 74475 of the clip applier system 74470 is compatible with the drive screw 74487 of the clip applier system 74480. Similar to the drive screw 74477 of the clip applier system 74470, the thread pitch of the drive screw 74487 can be selected to effectuate a translation of the carriage 74484 through a stroke of a predetermined length. The predetermined length can be based on the distal head function that the translation of the carriage 74484 is performing, such as feeding a clip through the distal head 74482 into an end effector or crimping a clip within the end effector, for example. Further, the predetermined length can be selected based on the size (e.g., diameter and/or length) of the distal head and/or the size of the clips to be advanced or formed.

Figure 94:
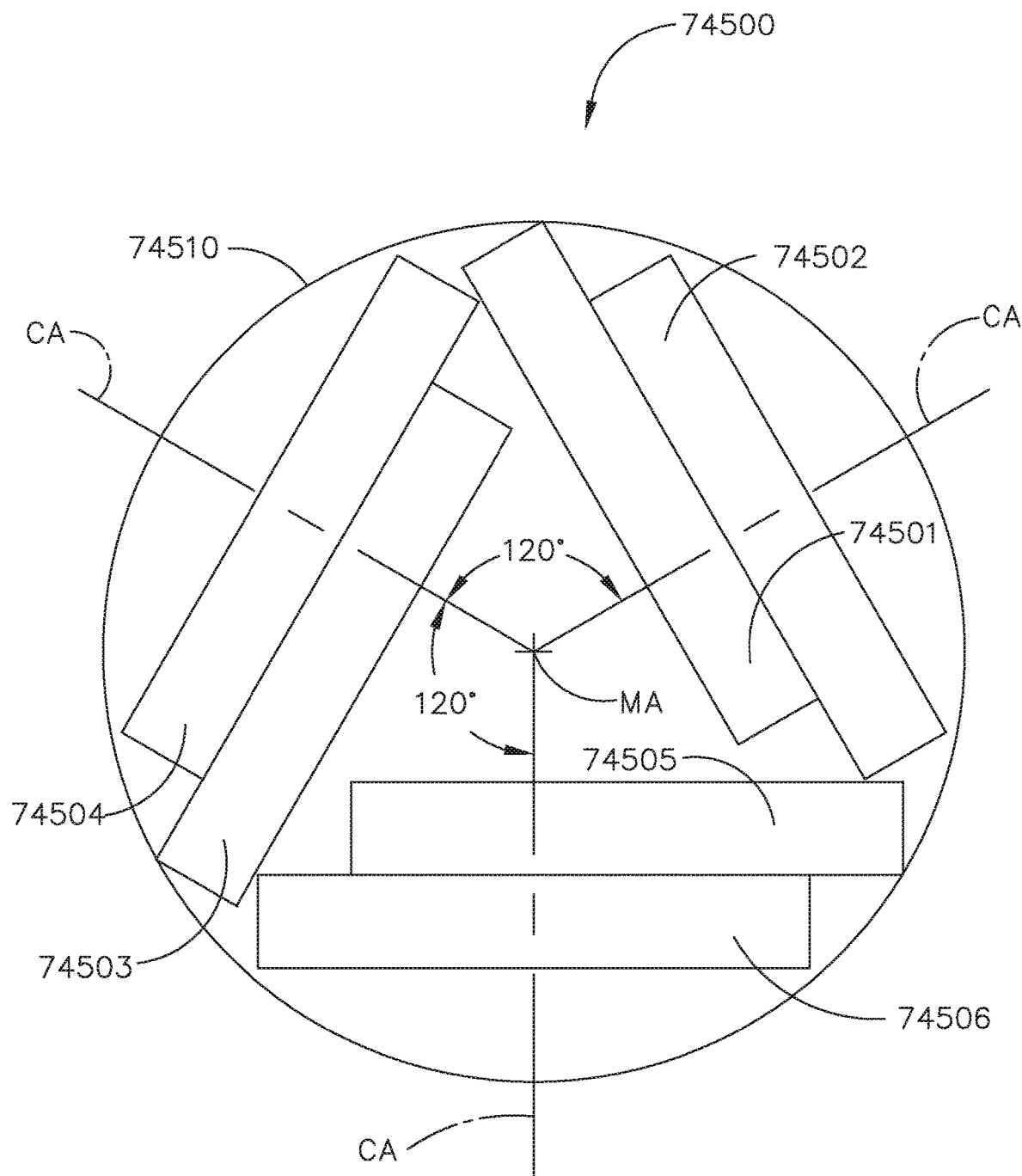

FIG. 94 depicts a clip magazine 74500 of a clip applier in accordance with at least one embodiment. The clip magazine 74500 is rotatable about a magazine axis MA. The clip magazine 74500 is configured to removable store a plurality of clips, such as inner clips 74501, 74503, 74505 and outer clips 74502, 74504, 74506, for example. The clip magazine 74500 comprises an outer housing 74510 with the plurality of clips removably stored therein. The clips are arranged in a radial array and spaced approximately 120 degrees apart around the magazine axis MA. Further, the outer clips 74502, 74504, and 74506 are closest to the outer housing 74510 and the inner clips 74501, 74503, 74505 are closest to the magazine axis MA. Each outer clip 74502, 74504, and 74506 is laterally offset from, and stacked on top of, a respective inner clip 74501, 74503, and 74505. Each outer clip 74502, 74504, 74506 is centered on a clip axis CA, the clip axes CA are approximately 120 degrees apart, and each inner clip 74501, 74503, 74505 is offset from its respective clip axis CA. For example, the outer clip 74502 is stacked on top of the inner clip 74501, and the edges of the outer clip 74502 are offset from the edges of the inner clip 74501 (the outer clip 7502 is centered on the clip axis CA and inner clip 74501 is not). When this arrangement is duplicated with the clip stacks at each 120 degree location, as illustrated in FIG. 94, the outer housing 74510 is smaller than a clip arrangement where the clip stacks are not offset, such as in FIG. 95A, for example. In other words, if the clips are stacked on top of one another with no lateral offset then the radial footprint of the clips will be larger, absent other considerations. Other embodiments of clip arrangements within a clip magazine are envisioned and described below.

FIG. 95A depicts a clip magazine 74550 in accordance with at least one embodiment. The clip magazine 74550 is configured to attach to and/or fit inside a clip applier shaft 74552 and is rotatable relative to the clip applier shaft 74552. The clip magazine 74550 comprises a plurality of clips 74554 arranged in stacks and stored in the clip magazine 74550 at storage locations 74556 that are radially spaced approximately 120 degrees apart, for example. The storage locations 74556 are sized to keep the edges of the clips 74554 aligned with one another. An opening 74558 in the clip magazine 74550 allows an internal drive to pass through the clip magazine 74550. The internal drive can advance a clip 74554 out of the clip magazine 74550 into an end effector of the clip applier and/or crimp a clip 74554 positioned in the end effector of the clip applier. Other embodiments are envisioned where more than one internal drive extends through the opening 74558, for example. The clips 74554 are the same size; however, in at least one alternative embodiment, the clips 74554 positioned at each storage location 74556 are different sizes, for example. Further, in at least one alternative embodiment, the clip size can vary between storage locations 74556, for example. The clip applier shaft 74552 comprises a loading slot 74559 configured to receive a clip 74554 when one of the storage locations 74556 is aligned with the loading slot 74559. In at least one embodiment, biasing members 74557 are configured to bias the clips 74554 from the clip magazine 74550 into the loading slot 74559.

FIG. 95B depicts a clip magazine 74560 in accordance with at least one embodiment. The clip magazine 74560 is configured to attach to and/or fit inside a clip applier shaft 74562 and is rotatable relative to the clip applier shaft 74562. The clip magazine 74560 comprises a plurality of clips 74564 arranged in stacks and stored in the clip magazine 74560 at storage locations 74566 that are radially spaced approximately 120 degrees apart. The storage locations 74566 are angled to offset the edges of the clips 74564 and each storage location 74566 stores multiple clips 74564. An opening 74568 in the clip magazine 74560 allows an internal drive of a clip applier to pass through the clip magazine 74560. The internal drive can advance a clip 74564 out of the clip magazine 74560 into an end effector of the clip applier and/or crimp a clip 74564 positioned in the end effector. Other embodiments are envisioned where more than one internal drive extends through the opening 74568. The clips 74564 are the same size; however, in at least one alternative embodiment, the clips 74564 positioned at each storage location 74566 are different sizes. In at least one alternative embodiment, the clip size can vary between storage locations 74566, for example. The clip applier shaft 74562 comprises a loading slot 74569 configured to receive a clip 74564 when one of the storage locations 74566 is aligned with the loading slot 74569. Biasing members 74567 are configured to bias the clips 74564 from the clip magazine 74560 into the loading slot 74569.

FIG. 95C depicts a clip magazine 74570 in accordance with at least one embodiment. The clip magazine 74570 is configured to attach to and/or fit inside a clip applier shaft 74572 and is rotatable relative to the clip applier shaft 74572 about a magazine axis MA. The clip applier shaft 74572 defines a shaft axis SA. Further, the clip magazine 74570 comprises a plurality of clips 74574 arranged in stacks and stored in the clip magazine 74570 at storage locations 74576 that are radially spaced approximately 120 degrees apart. The storage locations 74576 are sized to keep the edges of the clips 74574 aligned and each storage location 74576 stores multiple clips 74574. The magazine axis MA is offset from the shaft axis SA; thus, the diameter of the clip magazine 74570 is reduced (as compared to the clip magazine 74550) to provide ample storage for the clips 74574. Therefore, in at least one embodiment, the storage locations 74576 are closer together than storage locations 74556 of clip magazine 74550. The clip magazine 74570 works in conjunction with external drivers configured to advance the clips 74574 out of the clip magazine 74570 and/or crimp a clip 74574 positioned in an end effector of a clip applier. In at least one embodiment, the clips 74574 positioned at each storage location 74576 are different sizes. In at least one alternative embodiment, the clip size can vary between storage locations 74576. The clip applier shaft 74572 comprises a loading slot 74579 configured to receive a clip 74574 when one of the storage locations 74576 is aligned with the loading slot 74579. Biasing members 74577 are configured to bias the clips 74574 from the clip magazine 74570 into the loading slot 74579.

FIG. 95D depicts a clip magazine 74580 in accordance with at least one embodiment. The clip magazine 74580 is configured to attach to and/or fit inside a clip applier shaft 74582 and is rotatable relative to the clip applier shaft 74582 about a magazine axis MA. The clip applier shaft 74852 defines a shaft axis SA. The clip magazine 74580 comprises a plurality of clips 74584 arranged in stacks and stored in the clip magazine 74580 at storage locations 74586 that are radially spaced approximately 120 degrees apart. The storage locations 74586 are sized to keep the edges of the clips 74584 aligned and each storage location 74586 stores multiple clips 74584. The magazine axis MA is offset from the shaft axis SA; thus, the diameter of the clip magazine 74580 is reduced (as compared to the clip magazine 74550) to provide ample storage for the clips 74574. Therefore, in at least one embodiment, the storage locations 74586 are closer together than storage locations 74556 of clip magazine 74550, for example. The clip magazine 74580 works in conjunction with an external drive configured to advance a clip 74584 out of the clip magazine 74580. Further, the clip magazine 74580 is configured to protrude through an opening 74589 in the clip applier shaft 74582 which provides additional space for the clip magazine 74580 relative to the clip applier shaft 74582. In at least one embodiment, the clips 74584 positioned at each storage location 74586 are different sizes. In at least one alternative embodiment, the clip size can vary between storage locations 74586. The clip applier shaft 74582 comprises a loading slot 74581 configured to receive a clip 74584 when one of the storage locations 74586 is aligned with the loading slot 74581. Biasing members 74587 are configured to bias the clips 74584 from the clip magazine 74580 into the loading slot 74581.

FIG. 95E depicts a clip magazine 74590 in accordance with at least one embodiment. The clip magazine 74590 is configured to attach to and/or fit inside a clip applier shaft 74592 and is rotatable relative to the clip applier shaft 74592. The clip magazine 74590 comprises a plurality of clips 74594 arranged in stacks and stored in the clip magazine 74590 at storage locations 74596 that are radially spaced approximately 90 degrees apart. The storage locations 74596 are sized to keep the edges of the clips 74594 aligned and can store multiple clips in each location, for example. The clips 74594 are the same size; however, in at least one alternative embodiment, the clips 74594 positioned at each storage location 74596 are different sizes. In at least one alternative embodiment, the clip size can vary between storage locations 74596. The clip magazine 74590 is rotated using a gear and tooth arrangement 74591. More specifically, the clip magazine 74590 further comprises a circumferential rack of teeth 74593 that extends between the storage locations 74596. The circumferential rack of teeth 74593 is operably engaged with a rotatable drive shaft 74599 of a clip applier. The rotatable drive shaft 74599 comprises a gear 74598 fixed thereto which is engaged with the circumferential rack of teeth 74593. Thus, as the rotatable drive shaft 74599 rotates, the clip magazine 74590 rotates relative to the clip applier shaft 74592. The clip applier shaft 74592 comprises a loading slot 74595 configured to receive a clip 74594 when one of the storage locations 74596 is aligned with the loading slot 74595. Biasing members 74597 are configured to bias the clips 74594 from the clip magazine 74590 into the loading slot 74595.

FIG. 96 depicts a clip magazine 74600 in accordance with at least one embodiment. The clip magazine 74600 is configured for use with a clip applier and the clip magazine 74600 is configured to store a plurality of clips 74610. The clips 74610 are arranged in the clip magazine 74600 in a clip stack and are held in the clip magazine 74600 by a clip channel 74620 that is angled laterally relative to the radius of the clip magazine 74600. The clip channel 74620 partially mimics the shape of the clips 74610 in the clip stack in order to hold the clips 74610 into the clip magazine 74600. More specifically, the clip channel 74620 provides space for the clips 74610 to slide relative to the clip channel 74620 at discrete locations and at other discrete locations the clip channel 74620 releasably holds the clips 74610 in place. For example, the clip channel 74620 can comprises discrete holding locations 74630 and 74640 to hold the clips 74610 in place. The discrete holding locations 74630, 74640 provide for a tighter fit between the clips 74610 and the clip channel 74620 as compared to the rest of the clip channel 74620. The discrete holding locations 74630, 74640, along with the angled clip channel 74620, maintain the clips 74610 in the clip magazine 74600 until the clips 74610 are ejected.

FIGS. 97A and 97B depict a clip magazine 74700 in accordance with at least one embodiment. The clip magazine 74700 is configured to be attached to and/or fit inside a shaft 74720 of a clip applier, for example. The shaft 74720 defines a shaft axis SA. The clip magazine 74700 comprises a carriage 74710 comprising a plurality of clip holders 74712 configured to store a plurality of clips 74714. The clip holders 74712 extend from the driven portion of the carriage 74710 such that the plurality of clips 74714 are positioned distal to the carriage 74710. The clip magazine 74700 is configured to rotate relative to the shaft 74720 about the shaft axis SA between a plurality of clip firing positions (FIG. 97A) and a plurality of clip loading positions (FIG. 100). The clip magazine 74700 is rotatable via a rotary input 74726 which is operably responsive to a motor of a clip applier. As the clip magazine 74700 is rotated, the clips 74714 are configured to be biased into a clip track 74716 of the shaft 74720 when the clip magazine 74700 is in a loading position, as illustrated in FIG. 100. A clip 74714 positioned in the clip track 74716 is configured to be advanced into an end effector of the clip applier by a feeder shoe 74724 when the clip magazine 74700 is in a firing position, as illustrated in FIG. 97A. Other embodiments are envisioned where the clip track 74716 is part of the clip magazine 74700 and is aligned with another clip track in the shaft 74720 to facilitate the stripping and advancement of clips 74714 from the clip magazine 74700, for example.

Further to the above, each clip holder 74712 stores two clips 74714. Other embodiments are envisioned where each clip holder 74712 stores one clip or more than two clips 74714. Each clip holder 74712 comprises biasing members 74713 (see FIG. 101) configured to bias the clips 74714 away from the shaft axis SA. The clip track 74716 is configured to receive a clip 74714 when one of the clips 74714 is biased into the clip track 74716 (e.g., when the clip magazine 74700 is in a loading position, for example). Further, when the clip magazine 74700 is initially loaded into the clip applier one of the clips 74714 can already be loaded in the clip track 74716 as illustrated in FIG. 97A. The clip magazine 74700 further comprises a lockout, or lockout clip 74718, configured to prevent further rotation of the clip magazine 74700 after all of the clips 74714 have been spent. The lockout clip 74718 extends proximally further than the clips 74714, as illustrated in FIG. 97B, to allow the lockout clip 74718 to interfere with the carriage 74710 when the clip magazine 74700 is empty. Operation of the clip magazine 74700 is described in greater detail below.

In the orientation depicted in FIG. 97A, the clip magazine 74700 is in a firing position. After initially loading the clip magazine 74700 into the clip applier, a clip 74714 is already loaded into the clip track 74716 by the biasing members 74713, as discussed above. The initially loaded clip 74714 can be advanced into the end effector of the clip applier by a feeder shoe 74724 of the clip applier. The feeder shoe 74724 extends on a side of the carriage 74710 to engage the clip 74714 without interfering with the clip magazine 74700. Once the feeder shoe 74724 is retracted, the next clip 74714 is rotated into place as described in greater detail below.

Referring now to FIG. 98, after the initial clip 74714 is advanced by the feeder shoe 74724 and the feeder shoe 74724 is retracted, the clip magazine 74700 is rotated toward a loading position (see FIG. 100). As the clip magazine 74700 rotates toward a loading position, the leading edge of the next clip 74714 drops into a recessed portion 74719 of the clip track 74716 (see FIG. 98). As the clip magazine 74700 rotates further toward the loading position, the clip 74714 begins to seat in the clip track 74716 (see FIG. 99). Referring now to FIG. 100, the clip 74714 is biased completely into the clip track 74716 by the biasing members 74713 when the clip 74714 and the clip track 74716 are completely aligned. The clip 74714 is now in the loading position. Further operation of the clip magazine 74700 is discussed in greater detail below.

As the clip magazine 74700 rotates from the loading position depicted in FIG. 100 to another firing position, the remaining clips 74714 are held in their respective clip holders 74712. More specifically, referring to FIG. 100, another clip 74714 is sitting on top of the clip 74714 in the clip track 74716 when the clip magazine 74700 is in the loading position. This clip 74714 will continue to rotate with the carriage 74710 when the carriage 74710 is rotated as there is no room for the clip 74714 to move toward the clip track 74716 because the clip track 74716 is already occupied by a clip 74714. Once the clip magazine 74700 is rotated into the firing position, the clip 74714 positioned in the clip track 74716 is advanced into the end effector by the feeder shoe 74724, as discussed above. As the clip magazine 74700 is rotated toward another loading position, another clip 74714 is stripped (i.e., biased into the clip track 74716), as discussed above. This sequence continues until all of the clips 74714 are stripped from the clip magazine 74700 and advanced into the end effector. The outer clips 74714 (i.e., clips 2, 3, and 4) are stripped from the clip magazine 74700 first based on the arrangement described above. Once all of the outer clips 74714 are stripped the inner clips 74714 (i.e., clips 5, 6, and the lockout clip 74718) can be stripped from the clip magazine 74700. The lockout clip 74718 of the clip magazine 74700 is described in greater detail below.

Referring now to FIG. 101, after all of the clips 74714 have been stripped from the clip magazine 74700, the lockout clip 74718 is biased into the clip track 74716 when the clip magazine 74700 is rotated into a final loading position. As discussed above, the lockout clip 74718 extends further proximally toward the carriage 74710 than the clips 74714 (see FIG. 97B). Therefore, when the lockout clip 74718 is positioned in the clip track 74716 the lockout clip 74718 will interfere with the carriage 74710 as the clip magazine 74700 rotates from the loading position to the firing position. More specifically, the carriage 74710 of the clip magazine 74700 will engage the top of the lockout clip 74718 which prevents further rotation of the clip magazine 74700. The biasing members 74713 push the lockout clip 74718 into the clip track 74716 and hold the lockout clip 74718 in place. Alternatively, the biasing members 74713 in the last clip holder 74712 location can be configured to extend into the clip track 74716 to prevent further rotation of the clip magazine 74700 after all of the clips have been spent.

As a means to minimize rotational binding of the clips 74714 as the clip magazine 74700 rotates, the clip magazine 74700 can vary the amount of force the biasing members 74713 apply to the clips 74714 depending on the orientation of the clip magazine 74700, for example. In at least one embodiment, the clip magazine 74700 can decrease the amount of force the biasing members 74713 apply to the clips 74714 when the clip magazine 74700 is in a firing position. Alternatively, the clip magazine 74700 can increase the amount of force the biasing members 74713 apply to the clips 74714 in order to encourage the clip 74714 above the clip track 74716 into the clip track 74716 when the clip magazine 74700 is in a loading position. Other embodiments are envisioned where the clip magazine 74700 can relieve the spring bias of the biasing members 74713 just before a clip 74714 is aligned with the clip track 74716 (see FIGS. 98 and 99) and increase the spring bias when a clip 7471 is aligned with the clip track 74716 (see FIG. 100) in order to only encourage the clip 74714 to eject from the clip holder 74712 when the clip 74714 and the clip track 74716 are aligned. To reduce the spring bias in the non loading positions (i.e. the firing positions), the inside diameter 74722 of the clip magazine 74700 can be eccentric with respect to the travel path of the carriage 74710. In such instances, the inside diameter 74722 of the clip magazine 74700 can be shaped such that the biasing members 74713 are compressed when the clip magazine 74700 is in a loading position providing more force to the clips 74714. Further, the inside diameter 74722 can provided room for the biasing members 74713 to extend when the clip magazine 74700 is in a firing position and/or moving from a firing position to a loading position to provide less force to the dips 74714.

Further to the above, as another means to minimize rotational binding of the clips 74714 as the clip magazine 74700 rotates, the inside diameter 74722 of the clip magazine 74700 can be polished to reduce the friction between the carriage 74710 and the inside diameter 74722. Other embodiments are envisioned where the inside diameter 74722 is only polished in certain areas to reduce rotational friction when the carriage 74710 is rotated through certain radial positions, for example. In such instances, the high friction forces can hold the clip magazine 74700 in position when firing.

FIGS. 102-106 depict a clip applier 74800 in accordance with at least one embodiment. The clip applier 74800 comprises a clip magazine 74810 comprising a plurality of clips, a rotary input 74820, a shaft 74830 extending from a housing, a feeder shoe 74840, and a crimping drive 74850. The shaft 74830 defines a shaft axis SA and the clip magazine 74810 is translatable along and rotatable about the shaft axis SA. The plurality of clips comprise a first set of clips 74806 stored on a first side 74812 of the clip magazine 74810, a second set of clips 74807 stored on a second side 74814 of the clip magazine 74810, and a third set of clips 74808 stored on a third side 74816 of the clip magazine 74810. The first side 74812, the second side 74814, and the third side 74816 are positioned approximately 120 degrees apart about the shaft axis SA. Each of the first, second, and third sets of clips 74806, 74807, 74808 are biased radially outward relative to the clip magazine 74810 by biasing members 74809 (see FIG. 104). The first, second, and third sets of clips 74806, 74807, 74808 are stored in clip slots 74804 of the clip magazine 74810. The rotary input 74820 is configured to rotate in response to rotary motions generated by a motor positioned in the housing of the clip applier 74800. The rotary input 74820 is threadably engaged with the clip magazine 74810. Operation of the clip applier 74800 is discussed in greater detail below.

To strip the first set of clips 74806 from the clip magazine 74810, the clip magazine 74810 is translated distally by the rotary input 74820 until the first set of clips 74806 are aligned with a loading slot 74832 in the bottom of the shaft 74830 of the clip applier 74800. The first set of clips 74806 comprises a first clip 74806*a* and a second clip 74806*b* (see FIG. 106). The clip magazine 74810 is rotatably constrained within the shaft 74830 of the clip applier 74800 by the first set of clips 74806 and the biasing members 74809 such that when the rotary input 74820 is rotated in direction D1, the clip magazine 74810 is translated between a proximal position (FIG. 102) and a distal position (FIG. 103).

The clip magazine 74810 can then be retracted from the distal position (FIG. 103) to the proximal position (FIG. 102) to strip the first clip 74806*a* from the clip magazine 74810 by rotating the rotary input 74820 is an opposite direction D2. Notably, the second clip 74806*b* of the first set of clips 74806 is positioned on top of the first clip 74806*a* in the loading slot 74832 when the clip magazine 74810 is in the distal position, and therefore, the clip magazine 74810 is still rotatably constrained via the biasing members 74809. Thus, the clip magazine 74810 will translate proximally in response to a rotation of the rotary input 74820 in direction D2 (FIG. 102). Once the clip magazine 74810 is retracted to the proximal position, the first clip 74806*a* in the loading slot 74832 can be advanced into an end effector of the clip applier 74800 by the feeder shoe 74840. The clip magazine 74810 can then be translated from the proximal position to the distal position to place the second clip 74806*b* into the loading slot 74832. At this point, the clip magazine 74810 is still rotatably constrained by the biasing members 74809 which are still engaged with the second clip 74806*b* as it sits in the loading slot 74832. As such, rotation of the rotary input 74820 will translate the clip magazine 74810 proximally when the rotary input 74820 is rotated in the second direction D2. Further, when the biasing members 74809 are retracted proximally beyond the loading slot 74832, the biasing members 74809 still apply a force to the shaft 74830 of the clip applier 74800 and thus continue to rotatably constrain the clip magazine 74810. Once the clip magazine 74810 is in the proximal position, the second clip 74860*b* in the loading slot 74832 can be advanced into the end effector of the clip applier 74800 by the feeder shoe 74840. At this point, the clip magazine 74810 no longer has clips remaining on the first side 74812 of the clip magazine 74810. The clip magazine 74810 can then be translated from the proximal position (FIG. 102) to the distal position (FIG. 103) owing to the biasing members 74809 rotatably constraining the clip magazine 74810 against the shaft 74830, as discussed above. Once in the distal position (FIG. 103), the clip magazine 74810 will no longer be rotatably constrained as the biasing members 74809 no longer have a clip in the loading slot 74832 to press against; and, thus, the biasing members 74809 no longer rotatably constrain the clip magazine 74810. More specifically, the biasing members 74809 only extend downward far enough to engage the shaft 74830 of the clip applier 74800 and do not extend into the loading slot 74832. Thus, if a clip is not positioned in the loading slot 74832, the clip magazine 74810 will rotate in response to the rotation of the rotary input 74820. At this point, rotation of the rotary input 74820 rotates the clip magazine 74810.

Further to the above, when the loading slot 74832 is empty and the rotary input 74820 is rotated, the clip magazine 74810 will rotate until the second set of clips 74807 align with, and are biased toward, the loading slot 74832. The first clip of the second set of clips 74807 will occupy the loading slot 74832 and thus the clip magazine 74810 will again be rotatably constrained as discussed above. The clip magazine 74810 can now be translated between the distal position (FIG. 103) and the proximal position (FIG. 102) to strip the first clip and the second clip of the second set of clips 74807 from the clip magazine 74810. Once the first and second clip of the second set of clips 74807 are stripped and advanced, the clip magazine 74810 can be rotated to align the third set of clips 74808 with the loading slot 74832. The third set of clips 74808 can follow the same ejection and advancement sequence as the first set of clips 74806 and the second set of clips 74807. Other embodiments are envisioned where the clip magazine 74810 comprises more or less than three sides comprising clips, for example.

As the clip magazine 74810 translates from the proximal position (see FIG. 102) to the distal position (see FIG. 103), further to the above, the clip magazine 74810 engages a distal stop 74860 which extends downward from the shaft 74830 of the clip applier 74800. The distal stop 74860 prevents further distal translation of the clip magazine 74810 and properly aligns the clip magazine 74810 with the loading slot 74832. Further, the rotary input 74820 comprises a proximal stop 74862 which prevents further proximal translation of the clip magazine 74810. As mentioned above, the rotary input 74820 is threadably engaged with the clip magazine 74810. Other embodiments are envisioned with different rotary input to clip magazine connections, as discussed in greater detail below.

FIG. 107 depicts a rotary input 74920 and a clip magazine 74910 in accordance with at least one embodiment. The rotary input 74920 and clip magazine 74910 are similar to the rotary input 74820 and clip magazine 74810 of the clip applier 74800 in many respects (see FIGS. 102-106). For example, the rotary input 74920 is threadably engaged with the clip magazine 74910 and the rotary input 74820 is configured to advance, retract, and rotate the clip magazine 74910. The rotary input 74920 comprises protrusions 74922 extending from a distal end of the rotary input 74920. The protrusions 74922 are engaged with an internal thread 74912 of the clip magazine 74910. When the rotary input 74920 is rotated, and the clip magazine 74910 is rotatably constrained, the clip magazine 74910 will translate. In such instances, the protrusions 74922 of the rotary input 74920 engage the internal threads 74912 of the clip magazine 74910 to linearly advance and retract the clip magazine 74910. The rotary input 74920 is configured to rotate in a first direction to translate the clip magazine 74910 distally and, correspondingly, a second direction, opposite the first direction, to translate the clip magazine 74910 proximally. In use, the rotary input 74920 is rotated clock-wise and counter clock-wise to achieve the desired range of motion for the clip magazine 74910, such as translating the clip magazine 74910 back and forth between a proximal position and a distal position, for example.

FIGS. 108 and 109 depict a rotary input 74940 and a clip magazine 74930 in accordance with at least one embodiment. The rotary input 74940 and clip magazine 74930 are similar to the rotary input 74820 and clip magazine 74810 of the clip applier 74800 in many respects (see FIGS. 102-106). For example, the rotary input 74940 is threadably engaged with the clip magazine 74930 and the rotary input 74940 is configured to advance, retract, and rotate the clip magazine 74930. The clip magazine 74930 comprises a plurality of clips 74934 and a biasing member 74936 which acts to bias the clips 74934 out of the clip magazine 74930. The rotary input 74940 comprises external threads 74942 which are engaged with a collar 74932 in the clip magazine 74930. The collar 74932 engages the external threads 74942 at the base of the external threads 74942 and is configured to ride along the external threads 74942 of the rotary input 74940 to translate the clip magazine 74930 when the rotary input 74940 is rotated. The rotary input 74940 is a multi-direction rotary driver for the clip magazine 74930 that advances and retracts the clip magazine 74930 to strip clips from the clip magazine 74930. The rotary input 74940 is configured to rotate in a first direction to advance the clip magazine 74930 distally and, correspondingly, in a second direction, opposite the first direction, to advance the clip magazine 74930 proximally. In use, the rotary input 74940 is rotated clock-wise and counter clock-wise to achieve the desired range of motion for the clip magazine 74930, such as translating the clip magazine 74930 back and forth between a proximal position and a distal position, for example.

FIG. 110 depicts a rotary input 74960 and a clip magazine 74950 in accordance with at least one embodiment. The rotary input 74960 and clip magazine 74950 are similar to the rotary input 74820 and clip magazine 74810 of the clip applier 74800 in many respects (see FIGS. 102-106). For example, the rotary input 74960 is threadably engaged with the clip magazine 74950 and is configured to advance, retract, and rotate the clip magazine 74950. The rotary input 74960 comprises protrusions 74962 extending from the rotary input. The protrusions 74962 are engaged with an internal thread 74952 of the clip magazine 74950. The internal thread 74952 is a single-direction thread; thus, when the rotary input 74960 is rotated and the clip magazine 74950 is rotatably constrained, the clip magazine 74950 translates between a proximal position and a distal position. Once the clip magazine 74950 has reached the distal position, the protrusions 74962 move through a distal end 74954 of the internal thread 74952 which switches the direction the clip magazine 74950 is translated while the rotary input 74960 rotates in the same direction. The internal thread 74952 comprises a left-hand thread portion and a right-hand thread portion which are connected at their distal ends such that the left-hand threaded portion and the right-hand threaded portion comprise one continuous thread groove. Therefore, the rotary input 74960 need only be rotated in one direction to achieve the desired range of motion for the clip magazine 74950, i.e., translating the clip magazine 74950 back and forth between the proximal position and the distal position.

FIG. 111 depicts a rotary input 74980 and a clip magazine 74970 in accordance with at least one embodiment. The rotary input 74980 and clip magazine 74970 are similar to the rotary input 74820 and clip magazine 74810 in many respects. For example, the rotary input 74980 is threadably engaged with the clip magazine 74970 and the rotary input 74880 is configured to advance, retract, and rotate the clip magazine 74970. The rotary input 74980 comprises a thread groove 74982 defined on the outside of the rotary input 74980 which is engaged with a collar 74972 in the clip magazine 74970. The collar 74972 engages the thread groove 74982 at the base of the thread groove 74982. The thread groove 74982 is a single-direction thread, thus, when the rotary input 74980 is rotated and the clip magazine 74970 is rotatably constrained, the clip magazine 74970 translates back and forth between a proximal position and a distal position. Once the clip magazine 74970 has reached the distal position, the collar 74972 will move through a distal end 74984 of the thread groove 74982 which switches the direction the clip magazine 74970 is translated while the rotary input 74980 rotates in the same direction. The thread groove 74982 comprises a left-hand thread portion and a right-hand thread portion which are connected at their distal ends such that the left-hand threaded portion and the right-hand threaded portion comprise one continuous thread groove. Therefore, the rotary input 74980 need only be rotated in one direction to achieve the desired range of motion for the clip magazine 74970, i.e., translating the clip magazine 74970 back and forth between the proximal position and the distal position.

FIG. 112 depicts a rotary input 74990 and a clip magazine 74995 in accordance with at least one embodiment. The rotary input 74990 and the clip magazine 74995 are similar to the rotary input 74820 and clip magazine 74810 of the clip applier 74800 in many respects (see FIGS. 102-106). For example, the rotary input 74990 is threadably engaged with the clip magazine 74995 and the rotary input 74980 and the clip magazine 74995 are configured to advance, retract, and rotate the clip magazine 74995. The clip magazine 74995 comprises an upper portion 74995*a* and a lower portion 74995*b* which are assembled together using alignment pins 74999 and a coupling collar 74997. The clip magazine 74995 further comprises a cutout region 74996 configured to receive the coupling collar 74997 when the upper portion 74995*a* and the lower portion 74995*b* are positioned together. The coupling collar 74997 and alignment pins 74999 are configured to hold the upper portion 74995*a* and the lower portion 74995*b* together.

Further to the above, the clip magazine 74995 comprises an internal thread 74991 that can be molded and/or machined into the inside diameter of the clip magazine 74995. The upper portion 74995*a* and the lower portion 74995*b* can be assembled around the rotary input 74990 such that protrusions 74992 extending from the rotary input 74990 are engaged with the internal thread 74991. The internal threads 74991 can be molded and/or machined into any of the internal threads types described herein. The rotary input 74990 can be a single direction driver and/or a multi direction driver, as described herein, depending on the internal threads utilized. Further, a crimping drive 74993 can be placed through an opening in the rotary input 74990 such that the crimping drive 74993 and the rotary input 74990 are co-axial. The crimping drive 74993 is configured to actuate jaws of an end effector of the clip applier to crimp a clip positioned between the jaws.

A cross-sectional view of the clip magazine 74995 located inside a shaft 74994 of a clip applier, for example, is depicted in FIG. 113. In order to achieve the clam-shell construction described above (e.g., piecing together the upper portion 74995*a* and the lower portion 74995*b* of the clip magazine 74995) the clip magazine 74995 can be split so that only one clip storage location 74998 is cut in half. This allows for easy assembly and alignment of the upper portion 74995*a* and the lower portion 74995*b*.

FIG. 114 depicts a clip applier 76000 in accordance with at least one embodiment. The clip applier 76000 comprises a rotary input 76022, a magazine driver 76020 extending from the rotary input 76022, a clip magazine 76010, a firing drive 76030, and a biasing member 76040. The rotary input 76022 comprises a flexible rotary drive to flex and/or bend around an articulation joint of the clip applier. The magazine driver 76020 comprises a first cam surface 76024 comprising a notch 76026 at the distal end thereof. The clip magazine 76010 comprises a second cam surface 76014 comprising a protrusion 76016 extending from the proximal end thereof. The clip applier 76000 is shown in an exploded view in FIG. 114, with the clip magazine 76010 separated from the magazine driver 76020 in order to show the biasing member 76040.

Further to the above, the clip magazine 76010 is configured to translate between a proximal position (FIG. 115A) and distal position (FIG. 115B) relative to the magazine driver 76020 as the magazine driver 76020 rotates. The biasing member 76040 is configured to bias the clip magazine 76010 toward the proximal position and against the magazine driver 76020. The first cam surface 76024 and the second cam surface 76014 comprise complementary shapes and, when the clip magazine 76010 is in the proximal position (FIG. 115A), the first cam surface 76024 and the second cam surface 76014 are aligned. The second cam surface 76014 comprises a raised shoulder and the first cam surface 76024 is supported by a body 76003 of the clip magazine 76010 when the clip magazine 76010 and magazine driver 76020 are engaged. The clip magazine 76010 further comprises a first clip storage location 76001, a second clip storage location 76002, and a third clip storage location configured to store clips 76004 for clipping tissue. In the embodiment illustrated in FIG. 114, there are three clip storage locations, each of the clip storage locations are configured to store two clips 76004. Other embodiments are envisioned with more than or less than three clip storage locations with each clip storage location storing more or less than two clips 76004, for example. The rotary input 76022 is configured to rotate the magazine driver 76020 to both translate and rotate the clip magazine 76010 as described in greater detail below.

Referring now to FIG. 115A, the clip magazine 76010 is in its proximal position relative to the magazine driver 76020. As the rotary input 76022 is rotated in a first direction $D_1$, the first cam surface 76024 of the magazine driver 76020 engages the second cam surface 76014 of the clip magazine 76010 to translate the clip magazine 76010 to its distal position (FIG. 115B). In the distal position, the first clip storage location 76001 is located over a loading slot of the clip applier, similar to loading slot 74832 described in relation to clip applier 74800, for example. In at least one embodiment, a clip 76004 is ejected out of the first clip storage location 76001 by the biasing members 76006 into the loading slot when the first clip storage location 76001 is aligned with the loading slot. The rotary input 76022 is then rotated in a second direction $D_2$ to move the magazine driver 76020 from the distal position to the proximal position to strip the clip 76004 from the clip magazine 76010. Notably, the biasing member 76040 pulls the clip magazine 76010 toward the magazine driver 76020 such that the second cam surface 76014 and the first cam surface 76024 are continually engaged as the magazine driver 76020 is rotated in the second direction $D_2$. After the first clip in the first clip storage location 76001 has been stripped, the clip magazine 76010 can be advanced from the proximal position to the distal position, as discussed above, to align the second clip in the first clip storage location 76001 with the loading slot. To strip the second clip, the clip magazine 76010 is rotated to align the second clip storage location 76002 with the loading slot as discussed in greater detail below.

With the second clip of the first clip storage location 76001 located in the loading slot and the clip magazine 76010 positioned in its distal position, a further rotation of the magazine driver 76020 in the first direction $D_1$ will rotate the clip magazine 76010 to strip the second clip from the first clip storage location 76001. In such instances, the rotary input 76022 will rotate the magazine driver 76020 to engage the notch 76026 of the magazine driver 76020 with the protrusion 76016 of the clip magazine 76010. Once the notch 76026 and the protrusion 76016 are engaged, the clip magazine 76010 will rotate with the magazine driver 76020 as the rotary input 76022 rotates in direction $D_1$. The clip magazine 76010 rotates 120 degrees in the first direction $D_1$ to align the second clip storage location 76002 with the loading slot as illustrated in FIG. 115C. The first clip 76004 in the second clip storage location 76002 is stripped from the clip magazine 76010 by translating the clip magazine 76010 from its distal position to its proximal position via the magazine driver 76020 and biasing member 76040, as discussed above. After the first clip 76004 in the second clip storage location 76002 has been stripped, the clip magazine 76010 can be rotated by the magazine driver 76020 another 120 degrees in the first direction D₁ to strip the second clip in the second clip storage location 76002 and align the third clip storage location with the loading slot. The first clip in the third clip storage location can be stripped via the retraction of the clip magazine 76010 between its distal position and its proximal position, as discussed above. The second clip in the third clip storage location can also be stripped via the retraction of the clip magazine 76010 between its distal position and its proximal position, as discussed above. Further, the second clip in the third clip storage location can also be stripped via a rotation of the clip magazine 76010 in the first direction D₁ when the clip magazine is in its distal position, as discussed above.

Further to the above, alternative embodiments are envisioned where the clip magazine 76010 comprises a notch at the proximal end of the second cam surface 76014 and the magazine driver 76020 comprises a protrusion at the distal end of the first cam surface 76024. The notch and protrusion can perform the same functions as the notch 76026 and protrusion 76016 discussed above (i.e., engaging the magazine driver 76020 with the clip magazine 76010 in its distal position to rotate the clip magazine 76010, for example).

FIG. 116 is a graphical depiction of the rotary position of the magazine driver 76020 of the clip applier 76000 versus time. When the magazine driver 76020 is at position 76110, the clip magazine 76010 is in its proximal position illustrated in FIG. 115A. When the magazine driver 76020 is rotated to 90 degrees from zero, the clip magazine 76010 is moved to its distal position depicted in FIG. 115B and the first clip 76004 from the first clip storage location 76001 is biased into the loading slot. The magazine driver 76020 can then be rotated back to 0 degrees at position 76120 to strip the first clip 76004 from the first clip storage location 76001, as discussed above. The magazine driver 76020 can then be rotated 90 degrees from zero to place the second clip from the first clip storage location 76001 into the loading slot at position 76130. The second clip from the first clip storage location 76001 is then stripped when the magazine driver 76020 is rotated to 210 degrees from zero at position 76140. The second clip storage location 76002 is now aligned with the loading slot, and the first clip from the second clip storage location 76002 is biased into the loading slot at position 76140. The first clip from the second clip storage location 76002 is stripped when the magazine driver 76020 is rotated back to 90 degrees from zero at position 76150. As the magazine driver 76020 rotates to 210 degrees from zero the second clip from the second clip storage location 76002 is aligned with, and biased into, the loading slot at position 76160. The magazine driver is then rotated to 330 degrees from zero to strip the second clip from the second clip storage location 76002 and to align the first clip from the third clip storage location with the loading slot at position 76170. The first clip from the third clip storage location can be stripped when the magazine driver 76020 rotates back to 210 degrees from zero at position 76180. The second clip in the third clip storage location is then aligned with, and biased into, the loading slot when the magazine driver 76020 is rotated to 330 degrees from zero. The second clip in the third clip storage location can be stripped from the clip magazine 70610 either by rotating magazine driver 76020 back 90 degrees to 210 degrees from zero at position 76194 to retract the clip magazine 70610 to the proximal position, or by rotating the magazine driver 76020 an additional 120 degrees to 90 degrees from zero at position 76192 to rotate the clip magazine 70610 and strip the clip.

FIG. 117 depicts a clip applier 76200 in accordance with at least one embodiment. The clip applier 76200 comprises a distal head 76220 extending from an elongate shaft, a clip magazine 76210, an end effector 76230 extending through and from the distal head 76220, a clip carriage 76260, and a clip former 76242. The distal head 76220 is articulatable relative to the elongate shaft. The end effector 76230 comprises a pair of opposing jaws which are movable between an open position and closed position by a jaw cam 76232, as discussed herein. The jaw cam 76232 is operably engaged with a jaw cam driver 76250. As the jaw cam driver 76250 is rotated, the jaw cam 76232 is translated between a proximal position and a distal position to move the jaws of the end effector 72630 between the open position and the closed position. The jaw cam driver 76250 is rotatable in response to rotary motions generated by a motor in the housing of the clip applier 76200.

Further to the above, the jaw cam driver 76250 passes through an opening in the clip magazine 76210 and through an opening in a magazine driver 76202 extending proximally from the clip magazine 76210. The magazine driver 76202 is configured to rotate the clip magazine 76210 in response to rotary motions generated by the motor in the housing of the clip applier 76200. The magazine driver 76202 and the jaw cam driver 76250 are configured to rotate about the same axis (see FIG. 121). The clip magazine 76210 comprises a plurality of clips 76204 stored in a plurality of clip storage locations. Each clip storage location comprises a pair of clips 76204 stacked on top of one another, for example. The clips 76204 can be biased out of the clip storage locations by a biasing member, such as a leaf spring, for example, into a loading slot 76262 of the clip carriage 76260 as described in further detail below. Other embodiments are envisioned where the clip magazine 76210 stores one clip or more than two clips 76204 in each clip storage location.

The clip magazine 76210 is configured to rotate between a plurality of storage positions and a plurality of ejection positions. In the storage positions of the clip magazine 76210, the clips 76204 cannot be ejected from the clip magazine 76010. In the ejection positions of the clip magazine 76210, one of the clip storage locations is aligned with the loading slot 76262 of the clip carriage 76260, and one of the clips 76204 is biased from the clip magazine 76210 into the loading slot 76262. After a clip 76204 is positioned in the loading slot 76262, as illustrated in FIG. 118A, the clip 76204 can either be advanced distally to a staging position 76224 or retracted proximally to a forming position 76228 by the clip carriage 76260 as described in greater detail below.

The clip carriage 76260 is configured to translate proximally and distally in response to the rotation of a carriage driver 76264. The carriage driver 76264 is configured to rotate in response to rotary motions generated by the motor in the housing of the clip applier 76200. To advance a clip 76204 into the staging position 76224, the carriage driver 76264 is rotated in a first direction. After the clip carriage 76260 advances the clip 76204 to the staging position 76224 (see FIG. 118B), the clip carriage 76260 can be retracted proximally as a biasing member, or leaf spring 76226, engages the back side of the clip 76204 to keep the clip 76204 in the staging position 76224 (see FIG. 118C). The clip carriage 76260 is retracted via the carriage driver 76264 as the carriage driver 76264 rotates in a second direction opposite the first direction. After the clip 76204 is placed in the staging position 76224 and the clip carriage 76260 is retracted, the clip carriage 76260 can be advanced to engage a distal end 76266 of the clip carriage 72260 with the clip 76204 to advance the clip 76204 into the end effector (see FIGS. 118C and 118D).

Further to the above, after a clip 76204 is positioned in the loading slot 76262 from the clip magazine 76210, as illustrated in FIG. 118A, the clip carriage 76260 is retracted to a forming position 76228 by rotating the carriage driver 76264 in the second direction. Once in the forming position 76228 (see FIGS. 119A and 119B), the clip former or, anvil 76242, is lowered in between opposing legs 76204a and 76204b (see FIGS. 120A and 120B) of the clip 76204 by an anvil driver 76240. The anvil driver 76240 is configured to translate in response to rotary motions generated by the motor of the clip applier 76200, or another motor of the clip applier 76200, such that, as the anvil driver 76240 is translated, the anvil 76242 is configured to translate closer to and away from the loading slot 76262 of the clip carriage 76260—depending on the direction of translation of the anvil driver 76240.

Notably, the anvil driver 76240 comprises a pair of laterally extending pins 76244 which engage a pair of angled slots 76246 in the anvil 76242. When the anvil driver 76240 is translated distally, the anvil moves toward the loading slot 76262. When the anvil driver 76240 is translated proximally, the anvil 76242 moves away from the loading slot 76262. Forming of the clip 76204 positioned in the loading slot 76262 is described in further detail below.

After the anvil 76242 is lowered in between the legs 76204a and 76204b of the clip 76204, the clip carriage 76260 is advanced distally, as discussed above, such that the legs 76204a and 76204b of the clip 76204 are expanded away from each other by the anvil 76242 (see FIG. 120B). The clip 76204 comprises an angled portion 76206 connecting the legs 76204a and 76204b of the clip 76204 which is engaged by the anvil 76242 as the clip carriage 76260 is advanced such that the angled portion 76206 is deformed from a collapsed orientation (see FIG. 120A) to an expanded orientation (see FIG. 120B). After the clip 76204 has been expanded, the anvil 76242 can be moved away from the loading slot 76262 by the anvil driver 76240 such that the clip carriage 76260 can advance the clip 76204 into the staging position 76224, as described above. Once in the staging position 76224, the clip 76204 can be advanced into the end effector 76230 as discussed above.

Further to the above, the staging position 76224 is configured to store a single clip 76204. However, other embodiments are envisioned where the staging position 76224 is configured to store a plurality of clips 76204 in a clip stack, for example. The plurality of clips in the clip stack in the staging position 76224 can either be formed or unformed, as discussed above, and can be stacked in the staging position 76224 until they are sequentially advanced into the end effector by the clip carriage 76260 in the manner discussed above.

As discussed above, the jaw cam driver 76250, the magazine driver 76202, the carriage driver 76264, and the anvil driver 76240 are configured to rotate in response to rotary motions generated by the same motor of the clip applier 76200, or different motors of the clip applier 76200, in order to perform specific distal head functions. The motor of the clip applier 76200 further comprises a motor controller configured to control the jaw cam driver 76250, the magazine driver 76202, the carriage driver 76264, and the anvil driver 76240. The jaw cam driver 76250, the magazine driver 76202, the carriage driver 76264, and the anvil driver 76240 can be actuated by the motor controller to synchronize the drivers and/or interrupt one or more of the drivers in order to perform more distal head functions than there are dedicated drivers.

FIG. 122 depicts a clip applier 76300 in accordance with at least one embodiment. The clip applier 76300 comprises an outer tube 76305 extending from a housing, a clip magazine 76307 attachable to the outer tube 76305, and an end effector 76309. The outer tube 76305 comprises a proximal tube portion 76380, an articulation tube portion 76350 extending from the proximal tube portion 76380, and a distal tube portion 76340 extending from the articulation tube portion 76350. The end effector 76309 comprises a first jaw 76310 movable relative to a second jaw 76320 between an open position and a closed position. The second jaw 76320 extends from the distal tube portion 73640 and the first jaw 76310 is rotatable relative to the second jaw about a pivot pin 76315. The first jaw 76310 is actuatable between the open position and the closed position via a jaw driver 76360 which is configured to rotate relative to the outer tube 76305 in response to rotary motions generated within the housing of the clip applier 76300. Other embodiments are envisioned where the first jaw 76310 and the second jaw 76320 are both rotatable relative to each other between an open and a closed position, for example.

Further to the above, the clip magazine 76307 comprises a plurality of clips removable stored therein. Each of the clips is translatable into the end effector 76309 by a clip advancer of the clip applier 76300 which is operably responsive to a clip driver 76370. The clip driver 76370 is configured to rotate relative to the outer tube 76305 in response to rotary motions generated by the motor within the housing of the clip applier 76300. The clip driver 76370 is housed within an opening in the jaw driver 76360 such that the clip driver 76370 and the jaw driver 76360 are co-axial. In other words, the clip driver 76370 and jaw driver 76360 comprise a nested rotary drive train. Further, both the clip driver 76370 and the jaw driver 76360 are operable independently of one another via the motor of the clip applier 76300. The articulation tube portion 76350, the jaw driver 76360, and the clip driver 76370 are configured to bend and/or flex as the outer tube 76305 is articulated. The jaw driver 76360 and the clip driver 76370 may be comprised of dual woven cables which provide torsional force no matter the direction the jaw driver 76360 and clip driver 76370 are rotated, for example. In various instances, the jaw driver 76360 and the clip driver 76370 may provide equal torsional force no matter the direction they are rotated, for example.

FIG. 123 depicts a clip applier 76300' in accordance with at least one embodiment. The clip applier 76300' is similar in many respects to the clip applier 76300. For example, the clip applier 76300' comprises a jaw driver 76360' and a clip driver 76370' which perform the same end effector functions as the jaw driver 76360' and the clip driver 76370', respectively. However, the jaw driver 76360' and the clip driver 76370' may be comprised of wire tubing which provides a different torsional force depending on the direction the jaw driver 76360' and the clip driver 76370' are rotated, for example. Other embodiments are envisioned where the jaw drivers 76360 and 76360' and/or the clip drivers 76370 and 76370' are comprised of dual woven cables and/or wire tubing and combinations thereof. In other words, construction of the tubes or shafts (e.g., the jaw drivers 76360, 76360' or the clip drivers 76370, 76370') could be selected based on the amount of torque required to perform a specific end effector function such as feeding a clip or crimping a clip, for example. Notably, dual woven cables may be more compatible with higher loads in both directions, and wire tubing (i.e., wound springs, for example) may be better suited to transmit torsional loads in one direction better than another. More specifically, wire tubing is wound in a specific direction; thus, less force is required to rotate the wire tubing in the direction of the windings as compared to rotating the wire tubing in the direction opposite the windings. Further, dual woven cables may comprise windings woven together in opposite directions; thus, it will require the same amount of force to rotate the dual woven cable in either direction if the windings are balanced, for example.

FIG. 124 depicts a rotary input 76400 in accordance with at least one embodiment. The rotary input 76400 may be utilized to drive distal head functions of any of the clip appliers discussed herein. The rotary input 76400 comprises an outer hollow tube 76410 and an inner hollow tube 76420 which rotate together. The inner hollow tube 76420 is housed inside the outer hollow tube 76410. The outer hollow tube 76410 comprises a plurality of coiled springs 76412 wound in a first direction. The inner hollow tube 76420 comprises a plurality of coiled springs 76422 wound in a second direction opposite the first direction. The plurality of coiled springs 76412 are interlocked with the plurality of coiled springs 76422. More specifically, each of the coiled springs 76422 in the inner hollow tube 76420 are flanked by a pair of coiled springs 76412 of the outer hollow tube 76410 such that each of the coiled springs in the inner hollow tube 76420 are intermediate the pair of coiled springs 76412 of the outer hollow tube 76410 such that torque is transmitted therebetween.

In at least one alternative embodiment, a clip applier may comprise a rotary input comprising solid wall tubes that are laser cut to create an interlocking pattern. The interlocking pattern provides a preferred rotational direction for the rotary input. Further, such a rotary input is relatively flexible to facilitate articulation of the end effector about an articulation joint as described in further detail in U.S. patent application Ser. No. 13/536,232, filed on Jun. 28, 2012, which is incorporated by reference in its entirety.

FIG. 125 depicts a clip applier 77000 in accordance with at least one embodiment. The clip applier 77000 comprises a shaft 77010 extending from a housing, an end effector 77050 (see FIG. 141A) extending from the shaft 77010, a clip magazine 77020, and a clip advancer 77030. The clip magazine 77020 and the clip advancer 77030 are housed within the shaft 77010. The clip magazine 77020 is configured to translate and rotate relative to the shaft 77010 in response to a translating motion transmitted from the housing. The clip advancer 77030 is configured to translate relative to the shaft 77010 when the clip magazine 77020 is translated as the clip advancer 77030 is translatably coupled to the clip magazine 77020. The clip magazine 77020 is configured to store a plurality of clips 77004 in a plurality of clip slots 77022 positioned radially around the clip magazine 77020. Each clip slot 77022 comprises a clip spring 77025 configured to bias a clip 77004 out of the clip magazine 77020.

The clip advancer 77030 comprises a slot 77036, a proximal feeder spring 77032, and a distal feeder spring 77034. As discussed below, the proximal feeder spring 77032 and the distal feeder spring 77034 advance and hold clips in position as the clips are advanced into the end effector 77050. The shaft 77010 comprises a stationary spring 77018 extending into a loading slot 77015 of the shaft 77010. The loading slot 77015 is configured to temporarily store a clip 77004 before the clip is advanced into the end effector 77050 of the clip applier 77000. The shaft 77010 comprises a groove 77012 comprising a translation portion 77014 and a rotation portion 77016. The clip magazine 77020 comprises pins 77024 configured to ride within the groove 77012 in order to translate and rotate the clip magazine 77020, as described in greater detail below.

When the clip magazine 77020 is in a proximal position, referring again to FIG. 125, the pins 77024 of the clip magazine 77020 are located in a proximal portion of the translation portion 77014 of the groove 77012. As the clip magazine 77020 is translated distally to a distal position, as illustrated in FIG. 126, the clip magazine 77020 and the clip advancer 77030 translate together distally and the pins 77024 ride within the translation portion 77014 of the groove 77012. As the clip magazine 77020 translates to the distal position (FIG. 126), the clip slot 77022 of the clip magazine 77020 will align with the loading slot 77015 of the shaft 77010 and the clip spring 77025 will bias the clip 77004 into the loading slot 77015, as illustrated in FIG. 126. When the clip magazine 77020 is retracted from the distal position toward the proximal position, as illustrated in FIG. 127, the pins 77024 of the clip magazine 77020 are configured to ride within the rotation portion 77016 of the groove 77012 to rotate the clip magazine 77020 relative to the shaft 77010 and retract the clip magazine 77020 to the proximal position. As the clip magazine 77020 rotates and translates proximally, the clip 77004 in the loading slot 77015 is left behind in the loading slot 77015, as illustrated in FIG. 128. At such point, the clip 77004 can be advanced into the end effector 77050.

As the clip magazine 77020 and the clip advancer 77030 are translated distally from the proximal position to the distal position, the proximal feeder spring 77032 will engage the clip 77004 in the loading slot 77015 and translate the clip 77004 distally into a staging position 77017 within the shaft 77010 of the clip applier 77000, as illustrated in FIGS. 129-131. As the proximal feeder spring 77032 pushes the clip 77004 distally, referring to FIG. 132, the clip 77004 engages the stationary spring 77018 which biases the clip 77004 from the loading slot 77015 into the staging position 77017. As the clip advancer 77030 and the clip magazine 77020 are retracted, the clip 77004 will remain in the staging position 77017, as illustrated in FIG. 133. The staging position 77017 comprises a slot, or any suitable means of holding the clip 77004.

Referring now to FIGS. 134-136, after the clip 77004 is positioned in the staging position 77017, the clip magazine 77020 can be translated again to the distal position to advance the clip 77004 into a clip track 77052 (see FIG. 141A). More specifically, as the clip magazine 77020 is moved toward the distal position, the distal feeder spring 77034 of the clip advancer 77030 will engage the clip 77004 and advance the clip 77004 from the staging position 77017 (see FIG. 134) into the clip track 77052 (see FIG. 136).

As discussed above, the clip magazine 77020 is configured to hold a plurality of clips 77004. However, only one clip 77004 is shown in FIGS. 125-136 in order to show how the clip 77004 is advanced by the clip advancer 77030 and clip magazine 77020. Referring primarily to FIG. 137, with each retraction of the clip magazine 77020 from the distal position to the proximal position the clip magazine 77020 will rotate, as discussed above. Thus, when the clip 77004 is advanced into the loading slot 77015 and the clip advancer 77030 and clip magazine 77020 are retracted, the clip magazine 77020 will rotate relative to the clip advancer 77030 to align a second clip 77005 with the slot 77036 of the clip advancer 77030. Thereafter, the second clip 77005 is advanced by the clip advancer 77030 into the loading slot 77015 while the clip 77004 is advanced by the proximal feeder spring 77032 into the staging position 77017, as discussed above. The clip advancer 77030 and clip magazine 77020 can then be retracted again while leaving the clip 77004 in the staging position 77017 and leaving the second clip 77005 in the loading slot 77015. When the clip magazine 77020 is retracted, once again, it will rotate once again, and thus, a third clip 77006 can be aligned with the slot 77036 of the clip advancer 77030. The third clip 77006 can then be advanced by the clip advancer 77030 toward the loading slot 77015 when the clip magazine 77020 is moved toward the distal position.

Referring now to FIG. 138, as the third clip 77006 is advanced into the loading slot 77015, the proximal feeder spring 77032 of the clip advancer 77030 will advance the second clip 77005 from the loading slot 77015 into the staging position 77017. Further, the clip 77004 positioned in the staging position 77017 will be advanced by the distal feeder spring 77034 into the clip track 77052. Referring now to FIG. 139, when the clip magazine 77020 is then retracted to the proximal position, it will rotate and align a fourth clip 77007 with the slot 77036 of the clip advancer 77030. The fourth clip 77007 can then be advanced into the loading slot 77015 while the third clip 77006 in the loading slot 77015 is advanced into the staging position 77017 (see FIG. 140). Further, while the fourth clip 77007 is advanced toward the loading slot 77015 the clips 77004, 77005 are advanced distally by the distal feeder spring 77034 (see FIG. 140). More specifically, the distal feeder spring 77034 engages the second clip 77005 and advances the second clip 77005 from the staging position 77017 into the clip track 77052. The second clip 77005 engages the backside of the clip 77004 such that the second clip 77005 advances the clip 77004.

Further to the above, the clip magazine 77020 can be retracted to rotate the clip magazine once again, which will align a fifth clip 77008 (see FIG. 141A) with the slot 77036 of the clip advancer 77030. The fifth clip 77008 can then be advanced into the loading slot 77015 while the fourth clip 77007 is advanced into the staging position 77017 and the third clip 77006 is advanced into the clip track 77052. The third clip 77006 engages the backside of the second clip 77005 and thus advances the second clip 77005 and the first clip 77004 through the clip track 77052. The stroke of the clip advancer 77030 and clip magazine 77020 is such that the clips are advanced through the clip track 77052 one clip length at a time. Other embodiments are envisioned with different clip advancer 77030 and clip magazine 77020 strokes, among other things. Further operation of the clip applier 77000 is discussed in greater detail below.

Referring primarily to FIGS. 141A-141C, the clip applier 77000 further comprises a jaw cam 77060 configured to actuate the end effector 77050. The end effector 77050 comprises a first jaw 77054 and a second jaw 77056 which at least partially define a receiving chamber 77055 therein and are movable relative to each other between an open position and a closed position. The end effector 77050 further comprises a proximal portion 77058 extending proximally from the first jaw 77054 and the second jaw 77056. The proximal portion 77058 is attached to the shaft 77010 via a laterally extending pin fixed within the distal end of the shaft 77010 such that the end effector 77050 is mounted to the shaft 77010. The jaw cam 77060 is configured to translate along the proximal portion 77058 of the end effector 77050 between a proximal position (see FIG. 141A) and a distal position (see FIG. 141C). The jaw cam 77060 is threadably engaged with a rotary input, such that rotation of the rotary input will translate the jaw cam 77060. The rotary input is operably responsive to rotary motions generated within the housing of clip applier 77000. The jaw cam 77060 is rotatably constrained by the proximal portion 77058 of the end effector 77050, such that, when the rotary input is rotated, the jaw cam 77060 is translated. The first jaw 77054 and the second jaw 77056 remain in the open position when the jaw cam 77060 is moved between the proximal position and the distal position; however, the jaw cam 77060 can be moved beyond the distal position to cammingly engage the first jaw 77054 and the second jaw 77056 to move the first jaw 77054 and the second jaw 77056 toward the closed position as described in greater detail below.

The jaw cam 77060 is slidably coupled to a feeder shoe 77062 extending distally from the jaw cam 77060. The jaw cam 77060 and the feeder shoe 77062 are configured to advance a clip from the clip track 77052—if a clip is present in the clip track—into the receiving chamber 77055 of the end effector 77050. The jaw cam 77060 comprises a pin 77065 extending into a slot 77064 of the feeder shoe 77062 (see FIG. 142). The feeder shoe 77062 further comprises a biasing member, such as a spring 77061, for example, extending proximally from the distal end of the slot 77064 which is engaged with the pin 77065 of the jaw cam 77060 such that the feeder shoe 77062 is biased distally by the spring 77061. In other words, the spring 77061 acts to keep the pin 77065 positioned in the proximal end of the slot 77064.

Further to the above, when the jaw cam 77060 is moved from the proximal position to the distal position the feeder shoe 77062 advances a clip—if a clip is present in the clip track 77052—into the receiving chamber 77055 of the end effector 77050. More specifically, when the jaw cam 77060 translates distally, the distal end of the feeder shoe 77062 engages the backside of a clip in the clip track 77052 to advance the clip (see FIG. 143). The biasing force of the spring 77061 is not overcome by translating the clip into the end effector 77050; thus, the feeder shoe 77062 moves with the jaw cam 77060 as the jaw cam 77060 translates to the distal position. When the jaw cam 77060 is moved to the distal position, the feeder shoe 77062 is stopped from further advancement by a distal stop 77057 protruding from the clip track 77052. More specifically, the feeder shoe 77062 comprises a protrusion 77063 extending toward the clip track 77052 that engages the distal stop 77057 to prevent further distal translation of the feeder shoe 77062. The jaw cam 77060 can then be translated further, beyond the distal position, to cammingly engage the first jaw 77054 and the second jaw 77056 of the end effector 77050 to crimp the clip positioned in the receiving chamber 77055. In other words, the feeder shoe 77062 will not translate with the jaw cam 77060 when the jaw cam 77060 translates beyond the distal position. As the rotary input continues to drive the jaw cam 77060 distally, the biasing force of the spring 77061 is overcome and the pin 77065 of the jaw cam 77060 will translate distally through the slot 77064 of the feeder shoe 77062 as the feeder shoe 77062 is prevented from distally translating via the distal stop 77057. In such instances, the spring 77061 is compressed to allow the jaw cam 77060 to translate distally without further advancing the feeder shoe 77062.

Further to the above, as the jaw cam 77060 retracts from beyond the distal position to the distal position, the spring 77061 will bias the feeder shoe 77062 proximally such that the pin 77065 is once again positioned in the proximal end of the slot 77064. Also, the first jaw 77054 and the second jaw 77056 will be moved from the closed position to the open position to release the crimped clip from the end effector 77050. The pin 77065 will remain in the proximal end of the slot 77064 as the jaw cam 77060 is retracted from the distal position to the proximal position due to the biasing force of the spring 77061 as discussed above. Thus, the jaw cam 77060 and feeder shoe 77062 are retractable together to position the feeder shoe 77062 behind another clip in the clip track 77052. More specifically, the distal end of the feeder shoe 77062 comprises an angled portion 77067 which allows the feeder shoe 77062 to slide up and over the next clip positioned in the clip track 77052. Further, the clip track 77052 comprises a proximal stop 77053 at its proximal end that prevents further proximal translation of the feeder shoe 77062, i.e., via the protrusion 77063 on the feeder shoe 77062. The proximal stop 77053 ensures that the distal end of the feeder shoe 77062 is aligned with the backside of the next clip in the clip track 77052.

The clip advancer 77030 and the jaw cam 77060 can be independently sequenced, i.e., intermittently actuated by the motor, in order to move the first jaw 77054 and the second jaw 77056 between the open and closed positions without advancing a clip into the end effector 77050. In such instances, the clip advancer 77030 can be prevented from being actuated while the jaw cam 77060 is being actuated. Thus, the jaw cam 77060 can open and/or close the first jaw 77054 and the second jaw 77056 without a clip positioned in between the first jaw 77054 and the second jaw 77056 until the clip advancer 77030 has been actuated. In at least one instance, the jaw cam 77060 can be utilized to open and/or close the first jaw 77054 and the second jaw 77056 a predetermined number of times before the clip advancer 77030 is actuated to feed a clip. In certain instances, after advancing a clip (or several clips) into the end effector 77050 for crimping between the first jaw 77054 and the second jaw 77056, the sequence between the jaw cam 77060 and the clip advancer 77030 can be interrupted so as to not advance another clip into the clip track 77052. The jaw cam 77060 and feeder shoe 77062 can advance and crimp the clip or clips remaining in the clip track 77052 until the clip track 77052 is empty. With the clip track 77052 empty, the jaw cam 77060 can be moved between the proximal position and the distal position as needed without the feeder shoe 77062 engaging a clip. The clip advancer 77030 can then be actuated again to advance more clips into the clip track 77052 for engagement with the feeder shoe 77062. In other words, the clip applier 77000 is capable of intermittently advancing clips into the end effector 77050 such that the first jaw 77054 and the second jaw 77056 can be actuated with or without a clip present, even after a clip has already been advanced and crimped.

FIGS. 144A-144C depict a clip applier 77000' in accordance with at least one embodiment. The clip applier 77000' is similar in many respects to the clip applier 77000. More specifically, the clip applier 77000' comprises a jaw cam 77060' configured to move the first jaw 77054 and the second jaw 77056 of the end effector 77050 between the open position and the closed position, as discussed above. The jaw cam 77060' comprises a body portion 77062' configured to threadably engage a rotary input 77070' that is operably responsive to rotary motions generated inside the housing of the clip applier 77000'. As the rotary input 77070' is rotated, the jaw cam 77060' will translate to move the first jaw 77054 and the second jaw 77056 between the open position and the closed position.

Further to the above, the body portion 77062' comprises a protrusion 77066' extending laterally therefrom. The protrusion 77066' is configured to extend into a proximal opening 77069' of a clip advancer 77064' to releasably engage the body portion 77062' with the clip advancer 77064'. Other embodiments are envisioned where the clip advancer 77064' and the body portion 77062' are releasably attachable with a spring clip, or any other suitable means, for example. In any event, the clip advancer 77064' comprises a feeder shoe 77067' extending distally therefrom. The feeder shoe 77067' is configured to advance a clip (one of the clips 77004, 77005, 77006, 77007, 77008, for example) from the clip track 77052 into the receiving chamber 77055 of the end effector 77050 as the body portion 77062' moves from a proximal position (FIG. 144A) to a distal position (FIG. 144B). During the translation of the body portion 77062' between the proximal position and the distal position, the first and second jaws 77054, 77056 are not approximated (i.e., they remain open).

Further to the above, the body portion 77062' can advance beyond the distal position (FIG. 144B) to a closing position (see FIG. 144C) in response to further rotation of the rotary input 77070'. As the body portion 77062' moves toward the closing position, it will cammingly engage the outer surfaces of the first jaw 77054 and the second jaw 77056 to move the first jaw 77054 and the second jaw 77056 toward the closed position. Once the clip 77004 has been advanced into the receiving chamber 77055, the distal end of the feeder shoe 77067' of the clip advancer 77064' is abutted against the clip 77004 and the clip 77004 is abutted against a distal stop 77059 preventing further distal advancement of the clip advancer 77064'. The distal stops 77059 are positioned at the distal end of both the first jaw 77054 and the second jaw 77056 and prevent the clip 77004 from translating distally out of the end effector 77050. Therefore, as the body portion 77062' of the jaw cam 77060' is advanced beyond the distal position (FIG. 144B) to the closing position (FIG. 144C), the protrusion 77066' of the body portion 77062' moves from the proximal opening 77069' of the clip advancer 77064' into a distal opening 77068' of the clip advancer 77064' because the clip advancer 77064' is no longer translatable distally, as discussed above. In other words, the retention force between the proximal opening 77069' and the protrusion 77066' is overcome by the body portion 77062' when the body portion 77062' is advanced from the distal position (FIG. 144B) toward the closing position (FIG. 144C). Thus, the body portion 77062' and clip advancer 77064' are translatable together to advance a clip into the end effector 77050 and then the body portion 77062' can be advanced further distally to move the first jaw 77054 and the second jaw 77056 to the closed position without further advancement of the clip advancer 77064'.

FIGS. 145-150 depict a clip applier 77100 in accordance with at least one embodiment. The clip applier 77100 comprises a shaft 77120, a clip magazine 77110, a clip advancer 77130, and a feeder shoe 77140. The shaft 77120 extends from a housing of the clip applier 77100 and defines a shaft axis SA. The clip magazine 77110 is configured to translate relative to the shaft 77120 between a proximal position (see FIGS. 146 and 150) and a distal position (see FIG. 148) in response to the rotational output of a motor within the housing of the clip applier 77100. Similar to the above, the clip magazine 77110 is further configured to store a plurality of clips 77104 in a plurality of clip storage positions 77112. The clip magazine 77110 further comprises a boss 77114 extending from its distal end. The clip advancer 77130 is rotatably mounted on the boss 77114 of the clip magazine 77110 such that the clip advancer 77130 is rotatable relative to the clip magazine 77110 and translatable with the clip magazine 77110. The clip advancer 77130 is configured to translate a clip 77104 through a clip track 77106 in response to a translation of the clip magazine 77110 as described in greater detail below.

The shaft 77120 of the clip applier 77100 comprises an annular groove 77124 on the inside diameter 77122 of the shaft 77120. The annular groove 77124 is configured to slidably receive a protrusion 77138 extending from a camming member 77132 of the clip advancer 77130. The annular groove 77124 is defined in the inside diameter 77122 of the shaft 77120 to provide a spiral travel path for the protrusion 77138 of the camming member 77132. The spiral travel path of the annular groove 77124 is in a first direction. The camming member 77132 extends laterally relative to the shaft axis SA from a body portion 77131 of the clip advancer 77130. The camming member 77132 comprises an annular slot 77134 configured to slidably receive a protrusion 77141 extending from the proximal end of the feeder shoe 77140. The annular slot 77134 is formed into the camming member 77132 to provide a spiral travel path for the protrusion 77141 extending from the feeder shoe 77140. The spiral travel path of the annular groove 77124 of the shaft 77120 and the spiral travel path of the annular slot 77134 of the camming member 77132 are in opposite directions.

The clip advancer further comprises a recess 77136 between the camming member 77132 and the body portion 77131. The recess 77136 provides clearance for the feeder shoe 77140 to translate relative to the clip advancer 77130. More specifically, when the protrusion 77141 of the feeder shoe 77140 is captured in the annular slot 77134 of the camming member 77132, the feeder shoe 77140 is positioned within the recess 77136.

Further to the above, the feeder shoe 77140 comprises a dovetail portion 77144 extending from the distal end of the feeder shoe 77140. The dovetail portion 77144 is captured in a longitudinal groove 77126 defined in the inside diameter 77122 of the shaft 77120. The longitudinal groove 77123 comprises a complementary shape to the dovetail portion 77144 such that the dovetail portion 77144 is retained within and slidable along the longitudinal groove 77123. The feeder shoe 77140 further comprises a clip feeder 77146 extending downward from its proximal end. The clip feeder 77146 is configured to feed a clip 77104 through the clip track 77106 of the clip applier 77100 when the clip magazine 77110 is translated distally as discussed in greater detail below.

Referring again to FIGS. 146-150. The protrusion 77138 extending from the camming member 77132 is configured to travel through the annular groove 77124 of the shaft 77120 and the protrusion 77141 of the feeder shoe 77140 is configured to travel through the annular slot 77134 of the camming member 77132 when the clip magazine 77110 is translated between its proximal position and its distal position. Referring primarily to FIG. 146, the clip magazine 77110 is in the proximal position and a clip 77104 is abutted against the clip feeder 77146 of the feeder shoe 77140. As the clip magazine 77110 is translated distally (see FIG. 147), the clip advancer 77130 will rotate due to the protrusion 77138 being constrained within the annular groove 77124 of the shaft 77120. As discussed above, the feeder shoe 77140 is constrained to longitudinal movement by the longitudinal groove 77126 and dovetail portion 77144 of the feeder shoe 77140. Thus, as the clip advancer 77130 rotates, the clip advancer 77130 will translate the feeder shoe 77140 distally due to the sidewalls of the annular slot 77134 engaging the protrusion 77141 of the feeder shoe 77140 as the annular slot 77134 is rotated. As the feeder shoe 77140 translates distally, the feeder shoe 77140 will translate the clip 77104 distally via the clip feeder 77146. Further, when the clip magazine moves from the proximal position to the distal position, it moves through a stroke length $SL_1$ and the feeder shoe 77140 moves through a stroke length $SL_2$ (see FIGS. 151A and 151B). The stroke length $SL_2$ of the feeder shoe 77140 is twice the stroke length $SL_1$ of the clip magazine 77110. Other embodiments are envisioned where the stroke length $SL_2$ is more than or less than twice the stroke length $SL_1$, for example. In various instances, the pitches of the annular groove 77124 and the annular slot 77134 can be constructed to modify the stroke lengths $SL_1$ and $SL_2$, for example.

Further to the above, as the clip magazine 77110 translates into the distal position (FIG. 148), the above-described rotation of the clip advancer 77130 will continue until the protrusion 77138 of the clip advancer 77130 reaches the end of the annular groove 77124—thus preventing further rotation of the clip advancer 77130. Further, the distal translation of the feeder shoe 77140 will continue until the protrusion 77141 reaches the end of the annular slot 77134 of the clip advancer 77130—thus preventing further distal translation of the feeder shoe 77140. Correspondingly, the clip magazine 77110 can be translated proximally toward the proximal position (see FIG. 149) to partially retract the feeder shoe 77140. Further proximal translation of the clip magazine 77110 to the proximal position (see FIG. 150) will completely retract the feeder shoe 77140.

FIGS. 152 and 153 depict a clip applier 77200 in accordance with at least one embodiment. The clip applier 77200 comprises a shaft 77220 extending from a housing of the clip applier 77200, a clip magazine 77210 extending from the shaft 77220, a clip advancer 77230 extending from the clip magazine 77210, a firing drive 77250, and an end effector 77240. The clip magazine 77210 defines a magazine axis MA. The clip magazine 77210 is configured to rotate about the magazine axis MA. The firing drive 77250 is also aligned with, and is rotatable about, the magazine axis MA in response to rotary motions generated by a motor within the housing of the clip applier 77200. The clip magazine 77210 comprises clip holders 77212 circumferentially positioned approximately 120 degrees apart about the magazine axis MA. The clip holders 77212 are configured to store a plurality of clips for clipping tissue. Each of the clip holders 77212 is configured to align with a clip track 77232 of the clip advancer 77230 as the clip magazine 77210 rotates about the magazine axis MA between a plurality of ejection positions. For example, one of the ejection positions is illustrated in FIG. 153, i.e., a clip holder 77212 is aligned with the clip track 77232. When the clip magazine 77210 is in an ejection position, the clip magazine 77210 is configured to bias a clip from the clip magazine 77210 into the clip track 77232. Once a clip is positioned in the clip track 77232, it can be advanced into the end effector 77240 by a feeder shoe 77270. The feeder shoe 77270 is translatable through the clip track 77232 relative to the shaft 77220 in response to rotary motions generated within the housing of the clip applier 77200.

Further to the above, the end effector 77240 comprises a proximal portion 77245 configured to extend through a first opening 77234 in the clip advancer 77230 and a second opening 77216 in the clip magazine 77210. The proximal portion 77245 comprises a first arm 77246 and a second arm 77248 which extend through the first opening 77234 in the clip advancer 77230 and the second opening 77216 in the clip magazine 77210. The end effector 77240 further comprises a proximal anchor 77249 extending through the first opening 77234 in the clip advancer 77230 and through slots 77214 of the clip magazine 77210. The slots 77214 are radially disposed approximately 120 degrees apart within the clip magazine 77210 about the magazine axis MA. The slots 77214 extend away from the second opening 77216 to provide clearance for the proximal anchor 77249 of the end effector 77240. Further, the first arm 77246 and the second arm 77248 are chamfered to provide clearance for the firing drive 77250.

Further to the above, the end effector 77240 further comprises a first jaw 77242 extending distally from the first arm 77246 of the proximal portion 77245, and a second jaw 77244 extending distally from the second arm 77248 of the proximal portion 77245. The first arm 77246 and the second arm 77248 of the proximal portion 77245 are coupled together via a collar 77260. The first arm 77246 and the second arm 77248 extend away from each other, at least partially, due to their connection via the proximal anchor 77249. The collar 77260 is advanceable from a proximal position to a distal position to move the first arm 77246 and the second arm 77248 together, or toward one another. In such instances, the first jaw 77242 and the second jaw 77244 are movable between an open position (as illustrated in FIG. 152) and a closed position in response to the distal movement of the collar 77260. Further, the first jaw 77242 and the second jaw 77244 extend down from a center plane CP (see FIG. 155) of the proximal portion 77245 such that the firing drive 77250, the first arm 77246 and the second arm 77248 of the proximal portion 77245, and the first jaw 77242 and the second jaw 77244 are positioned on different planes of the clip applier 77200. The first jaw 77242 and the second jaw 77244 at least partially define a receiving chamber 77241 configured to receive a clip from the clip magazine 77210.

The above-described arrangement allows a clip to be fed into the jaws of the end effector 77240 along a plane that is offset from the magazine axis MA. The jaws of the end effector are angled toward the magazine axis MA at their distal end, as illustrated in FIG. 152, to allow a clip positioned therein to be crimped in a plane that is closer to the magazine axis MA than the plane by which the clip was fed into the end effector 77240. This allows a different input other than the feeder shoe, such as the firing drive 77250, to extend through the clip magazine 77210 while crimping the clips on a plane that is coincident, or close to coincident, with the magazine axis MA.

FIGS. 156 and 157 depict a clip applier 77300 in accordance with at least one embodiment. The clip applier comprises an elongate tube 77320 extending from a housing of the clip applier 77300, a clip magazine 77310 housed within the elongate tube 77320, and an end effector 77340. The clip magazine 77310 comprises a central opening 77316 that defines a magazine axis MA. The clip magazine 77310 is configured to translate along and rotate about the magazine axis MA. The clip magazine 77310 further comprises clip slots 77312 radially disposed approximately 120 degrees apart about the magazine axis MA. The clip slots 77312 are configured to store a plurality of clips which are biased out of the clip magazine 77310. The clips can be biased out of the clip magazine 77310 by any suitable biasing member, including the biasing members discussed herein, for example. The elongate tube 77320 further comprises an opening 77322 which provides clearance for a clip from the clip magazine 77310 to be biased from the clip magazine 77310 onto a clip track when one of the clip slots 77312 is aligned with the opening 77322. The clip can be advanced through the clip track into the end effector by a feeder shoe, as described herein.

Referring primarily to FIG. 156, the end effector 77340 comprises a first jaw 77342, a second jaw 77344, and a proximal portion 77345 extending proximally from the first jaw 77342 and the second jaw 77344. The first jaw 77342 and the second jaw 77344 at least partially define a receiver 77341 configured to receive a clip from the clip track when the clip is advanced by the feeder shoe, as discussed above. The proximal portion 77345 is configured to attach the end effector 77340 to the elongate tube 77320. The proximal portion 77345 comprises a first support 77346 extending proximally from the first jaw 77342 and the second jaw 77344. The first support 77346 is located below the magazine axis MA, as discussed in greater detail below.

The proximal portion 77345 further comprises a second support 77348 located between the magazine axis MA and the first support 77346. Other embodiments are envisioned where the second support 77348 is located at and/or above the magazine axis MA, for example. In any event, the proximal portion 77345 comprises a U-shaped portion connecting the first support 77346 and the second support 77348 at their proximal ends. The elongate tube 77320 further comprises a lateral bar 77324 positioned at the distal end of the elongate tube 77320 and spanning across the inside diameter 77326 of the elongate tube 77320. The U-shaped portion 77347 is configured to receive the lateral bar 77324 to connect the proximal portion 77345 of the end effector 77340 to the elongate tube 77320.

Further to the above, and with regard to FIGS. 158 and 159, the clip applier 77300 further comprises a collar 77360 mounted around the first support 77346 of the proximal portion 77345 of the end effector 77340. The collar 77360 is formed around the first support 77346 after the proximal portion 77345 of the end effector 77340 is attached to the elongate tube 77320, as discussed above. More specifically, the collar 77360 comprises a first bendable side 77364 and a second bendable side 77365. The first bendable side 77364 comprises a groove 77366 and the second bendable side 77365 comprises a protrusion 77367. The first and second bendable sides 77364, 77365 are bent around the first support 77346 and attached together below the first support 77346. More specifically, the protrusion 77367 engages the groove 77366 to slidably secure the collar 77360 to the proximal portion 77345 of the end effector 77340. In at least one alternative embodiment, the assembled collar 77360 is attached to the end effector 77340 prior to attaching the end effector 77340 to the elongate tube 77320. More specifically, the collar 77360, after being assembled in the above-described manner, is slid onto the proximal portion 77345 of the end effector 77340 prior to bending the second support 77348 relative to the first support 77346. Once the collar 77360 is attached to the proximal portion 77345, the second support 77348 can be bent relative to the first support 77346 to form the U-shaped portion 77347. The end effector 77340 is then attached to the elongate tube 77320 in the above-described manner. Operation of the collar 77360 is discussed in greater detail below.

The collar 77360 is configured to cammingly engage the first jaw 77342 and the second jaw 77344 as the collar 77360 moves from a proximal position to a distal position. In such instances, the first jaw 77342 and the second jaw 77344 are movable relative to each other between an open position and a closed position as the collar 77360 moves from the proximal position to the distal position. The collar 77360 comprises a protrusion 77362 extending toward the magazine axis MA. The protrusion 77362 comprises a threaded aperture 77343 (see FIG. 158) that is threadably engaged with a collar driver. The collar driver is configured to move the collar 77360 between the proximal position and the distal position in response to rotary motions generated within the housing of the clip applier 77300. The protrusion 77362 extends within an opening 77349 in the second support 77348. In fact, the opening 77349 extends into the U-shaped portion 77347 to provide clearance for the collar driver to extend proximally through the central opening 77316 of the clip magazine 77310. This arrangement allows the clip magazine 77310 to rotate about the magazine axis MA, while the collar 77360 is translated along an axis parallel to, but offset from, the magazine axis MA. As illustrated in FIG. 157, the jaws of the end effector 77340 are angled toward the magazine axis MA at their distal end to allow a clip positioned therein to be crimped in a plane that is closer to the magazine axis MA than the plane by which the clip was fed into the end effector 77340. This allows a different input other than the feeder shoe, such as the collar driver, to extend through the clip magazine 77310 while still allowing the clips to be crimped on a plane that is coincident, or substantially coincident, with the magazine axis MA.

Referring now to FIG. 160, an alternative end effector 77340' for use with the clip applier 77300 is depicted. The end effector 77340' is similar to the end effector 77340 in many respects. The end effector 77340' comprises a first protrusion 77342a extending from the first jaw 77342, and a second protrusion 77344b extending from the second jaw 77344. The first protrusion 77342a and the second protrusion 77344b are angled relative to one another such that their proximal ends are closer together than their distal ends. The end effector 77340' is configured for use with a cam member 77370 that comprises a first slot 77372 oriented transversely relative to the first protrusion 77342a and a second slot 77374 oriented transversely relative to the second protrusion 77344b. The cam member 77370 is movable between a proximal position and a distal position by a cam member driver in response to rotary motions generated within the housing of the clip applier 77300. More specifically, the cam member driver is threadably engaged with the cam member 77370 via a threaded aperture 77376 defined in the cam member 77370 such that, as the cam member driver rotates, the cam member 77370 translates. As the cam member 77370 moves from the proximal position to the distal position, the sidewalls of the first slot 77372 and the second slot 77374 will engage the protrusions 77342a, 77344b. Because the protrusions 77342a, 77344b are angled relative to the slots 77372, 77374, the cam member 77370 will bias the first jaw 77342 and the second jaw 77344 toward a closed position as the cam member 77370 moves from the proximal position to the distal position. Further, the cam member 77370 will bias the first jaw 77342 and the second jaw 77344 toward an open position as the cam member 77370 moves from the distal position to the proximal position.

FIGS. 161 and 162 depict a clip applier 77400 in accordance with at least one embodiment. The clip applier 77400 comprises a clip applier head, or end effector 77420, for example, extending from a shaft. The end effector 77420 comprises a top portion 77422, a bottom portion 77424, and an intermediate portion 77426 connecting the top portion 77422 and the bottom portion 77424. The top portion 77422 and the bottom portion 77424 are in two different parallel, or at least substantially parallel planes. The bottom portion 77424 comprises a pair of opposing jaws 77421 extending distally therefrom. The pair of opposing jaws 77421 at least partially define a receiving chamber 77428 therein. The opposing jaws 77421 are movable between an open position and a closed position by way of a camming member 77440 slidably attached to the bottom portion 77424 of the end effector 77420. The camming member 77440 is rotatably constrained by the bottom portion 77424 and is threadably engage with a drive screw 77430. The drive screw 77430 comprises a distal thread portion 77434, a proximal thread portion 77432, and an intermediate portion 77436 connecting the distal thread portion 77434 and the proximal thread portion 77432.

Further to the above, the intermediate portion 77436 of the drive screw 77430 is rotatably supported by, but not threadably engaged with, an opening in the intermediate portion 77426 of the end effector 77420. The distal thread portion 77434 is threadably engaged with the camming member 77440 such that rotation of drive screw 77430 in a first direction will translate the camming member 77440 distally. In addition, the proximal thread portion 77432 is threadably engaged with a feeder shoe 77450 such that rotation of the drive screw 77430 in the first direction will translate the feeder shoe 77450 proximally. In other words, the distal thread portion 77434 and the proximal thread portion 77432 are threaded in opposite directions. Moreover, the distal thread portion 77434 comprises a smaller thread pitch than the proximal thread portion 77432. As a result, for a given rotation of the drive screw 77430, the camming member 77440 will translate less than the feeder shoe 77450, for example. As the drive screw 77430 is rotated in the first direction, the camming member 77440 will translate from a proximal position (see FIG. 161) to a distal position (see FIG. 162) and the feeder shoe 77450 will translate from a distal position (see FIG. 161) to a proximal position (see FIG. 162). As the camming member 77440 is moved toward the distal position, it will cammingly engage the pair of opposing jaws 77421 and move the jaws 77421 to the closed position. Correspondingly, as the drive screw 77430 is rotated in a second direction, opposite the first direction, the camming member 77440 will translate from the distal position (see FIG. 162) to the proximal position (see FIG. 161) and the feeder shoe 77450 will translate from the proximal position (see FIG. 162) to the distal position (see FIG. 161). As the camming member 77440 is moved toward the proximal position, the pair of opposing jaws 77421 will move to the open position.

Further to the above, the clip applier 77400 further comprises a clip track 77410 configured to store a first clip 77404, a second clip 77405, and a third clip 77406. In at least one embodiment, the first clip 77404, the second clip 77405, and the third clip 77406 can be fed into the clip track 77410 by a clip magazine. The clips 77404, 77405, 77406 are biased distally by a feeder block 77412 and a feeder spring 77413. The feeder shoe 77450 further comprises a feeder bar 77452 extending distally therefrom. The feeder bar 77452 comprises a first clip notch 77454 located at the distal end thereof, and a second clip notch 77456 located proximal to the first clip notch 77454. Operation of the clip applier 77400 is described in greater detail below.

When the clip applier 77400 is initially loaded into a surgical site through a trocar or cannula, for example (referring primarily to FIG. 161), the opposing jaws 77421 can already have the first clip 77404 positioned therein. In such instances, the second clip 77405 and the third clip 77406 are located in the clip track 77410 and biased distally by the feeder spring 77413. The second clip 77405 and the third clip 77406 are held in place by the second clip notch 77456 of the feeder bar 77452. The biasing force in this position from the feeder spring 77413 is not enough to force the second clip 77405 out of the second clip notch 77456 as the spring is in an expanded position. As the drive screw 77430 is rotated in the first direction, the opposing jaws 77421 will move toward the closed position and the feeder shoe 77450 will move toward the proximal position, as discussed above. As the feeder shoe 77450 is moved toward the proximal position, the first clip 77404 will be crimped and the feeder shoe 77450 will retract the second clip 77405 and the third clip 77406 proximally while compressing the feeder spring 77413. The second and third clips 77405, 77406 will retract proximally until the biasing force from the feeder spring 77413 overcomes the retention force between the second clip 77405 and the second clip notch 77456. At this point, the second clip 77405 will slide by the second clip notch 77456. However, the first clip notch 77454 will catch the second clip 77405. Moreover, the third clip 77406 will follow the second clip 77405 by the second clip notch 77456 such that the feeder spring 77413 is pushing on the second clip 77405 via the third clip 77406.

After the first clip 77404 has been crimped it can be released from the receiving chamber 77428 by rotating the drive screw 77430 in the second direction. As discussed above, when the drive screw 77430 is rotated in the second direction, the opposing jaws 77421 of the end effector 77420 will move to the open position and the feeder shoe 77450 will move toward the distal position. As the feeder shoe 77450 moves toward the distal position the feeder bar 77452 will carry the second and third clips 77405, 77406 distally. The second and third clips 77405, 77406 will remain biased into the first clip notch 77454 by the feeder spring 77413 until the distal end of the feeder shoe 77450 approaches the receiving chamber 77428 of the end effector 77420. The distal end of the feeder shoe 77450 is configured to curve, or bend, upwardly as it approaches the receiving chamber 77428 of the end effector 77420 and, as a result, the second clip 77405 is released from the first clip notch 77454. Once the second clip 77405 is released, the feeder spring 77413 biases the second clip 77405 into the receiving chamber 77428 of the end effector 77420. At the same time, the third clip 77406 is biased distally by the feeder spring 77413 but cannot enter the receiving chamber 77428 because the receiver is occupied by the second clip 77405. In such instances, the third clip 77406 is staged for the next actuation of the clip applier as described below.

Further to the above, the drive screw 77430 can now be rotated in the first direction to crimp the second clip 77405 positioned in the receiving chamber 77428 and retract the feeder bar 77452 via the feeder shoe 77450, as discussed above. As the feeder bar 77452 is retracted, the first clip notch 77454 will engage the third clip 77406 and retract the third clip 77406 proximally (see FIG. 162). At this stage, the feeder shoe 77450 is in the proximal position once again, the cam member 77440 is in the distal position once again, the second clip 77405 has been crimped by the opposing jaws 77421, and the third clip 77406 has been retracted. The drive screw 77430 can now be rotated in the first direction to release the second clip 77405 from the opposing jaws 77421 of the end effector 77420 and to advance the third clip 77406 into the opposing jaws 77421 by way of the feeder bar 77452, in the manner discussed above in connection with the second clip 77405. The third clip 77406 can then be crimped by rotating the drive screw 77430 in the second direction and then the crimped third clip 77406 can be released from the opposing jaws 77421 by rotating the drive screw 77430 in the first direction.

The above-discussed embodiment of FIGS. 161 and 162 comprises a system for automatically loading a plurality of clips into an end effector after the first clip has been crimped and released. The clips loaded into the end effector are then sequentially crimped and released.

FIGS. 163 and 164 depict a clip applier 77500 in accordance with at least one embodiment. The clip applier comprises an end effector 77520, an actuator 77510, and a drive screw 77530 extending proximally from the actuator 77510. The actuator 77510 comprises a drive bar 77511 and a threaded nut 77514 at the proximal end of the drive bar 77511. The drive bar 77511 comprises internal threads 77512 configured to receive the external threads 77532 of the drive screw 77530. The actuator 77510 is rotatably constrained within a shaft of the clip applier 77500 by the threaded nut 77514 thus, the drive screw 77530 can be rotated to translate the actuator 77510 between a proximal position (FIG. 163) and a distal position (FIG. 164). The drive screw 77530 is rotatable about a drive axis DA in response to rotary motions generated by a motor of the clip applier 77500. The drive screw 77530 comprises a pair of laterally-extending pins 77516 which extend away from the drive bar 77511 of the actuator. The end effector 77520 comprise a first jaw 77522 and a second jaw 77524 movable relative to each other between an open position (FIG. 163) and a closed position (FIG. 164). The first jaw 77522 and the second jaw 77524 at least partially define a receiving chamber 77521 between an inner surface 77518 of the first jaw 77522 and an inner surface 77519 of the second jaw 77524. The first jaw 77522 and the second jaw 77524 are discussed in greater detail below.

The first jaw 77522 comprises a first cam member 77526. The second jaw 77524 comprises a second cam member 77528. The first cam member 77526 comprises a first pair of parallel slots 77527 that are angled transverse to the drive axis DA. The second cam member 77528 comprises a second pair of parallel slots 77529 that are angled transverse to the drive axis DA. The first pair of parallel slots 77527 are transverse to the second pair of parallel slots 77529. The laterally-extending pins 77516 of the actuator 77510 are received in the first pair of parallel slots 77527 and the second pair of parallel slots 77529. In addition, the first cam member 77526 comprises a lateral slot 77523 located at the proximal end of the first cam member 77526. The second cam member 77528 comprises a protrusion, or pin 77525, extending into the lateral slot 77523 of the first cam member 77526. Operation of the clip applier 77500 is discussed in greater detail below.

As discussed above, the rotation of the drive screw 77530 translates the actuator 77510. As the actuator 77510 translates from the proximal position to the distal position, the laterally-extending pins 77516 will engage the sidewalls of the first pair of slots 77527 and the second pair of slots 77529 to move the end effector from its open position to its closed position. Notably, the first jaw 77522 and the second jaw 77524 close in a parallel manner. Stated another way, the first jaw 77522 and the second jaw 77524 are translated closed, not rotated closed. This motion is controlled by the arrangement of the laterally-extending pins 77516 and the pin 77525.

FIGS. 165 and 166 depict a clip applier 77600 in accordance with at least one embodiment. The clip applier comprises a shaft 77640 extending from a housing of the clip applier 77600. The shaft 77640 defines a shaft axis SA. The clip applier 77600 further comprises an end effector 77620, an actuator 77650, and a drive screw 77660 extending proximally from the actuator 77650. The actuator 77650 comprises a boss 77658 at its proximal end. The boss 77658 comprises an internal thread configured to receive the drive screw 77660; thus, the drive screw 77660 is threadably engaged with the actuator 77650. The actuator 77650 is rotatably constrained within the shaft 77640, such that, the actuator 77650 is translated between a distal position (FIG. 165) and a proximal position (FIG. 166) when the drive screw 77660 is rotated. The drive screw 77660 is rotatable about the shaft axis SA in response to rotary motions generated by a motor of the clip applier 77600.

Further to the above, the end effector 77620 comprise a first jaw 77622 and a second jaw 77632 movable relative to each other between an open position (FIG. 165) and a closed position (FIG. 166). The first jaw 77622 and the second jaw 77632 at least partially define a receiving chamber 77621 between an inner surface 77623 of the first jaw 77622 and an inner surface 77633 of the second jaw 77632. The first jaw 77622 comprises a first cam member 77624 extending proximally from the first jaw 77622. The second jaw 77632 comprises a second cam member 77634 extending proximally from the second jaw 77632. The first cam member 77624 comprises a first slot 77626 that is angled transverse to the shaft axis SA. More specifically, the first slot 77626 comprises a distal portion extending in one direction and a proximal portion extending in another direction. The second cam member 77634 comprises a second slot 77636 that is transverse to the shaft axis SA. More specifically, the second slot 77636 comprises a distal portion extending in one direction and a proximal portion extending in another direction. The first slot and the second slot overlap to form an X-shape as illustrated in FIG. 165.

The actuator 77650 comprises a distal slot 77654, a proximal slot 77656, and a distal protrusion 77652. The distal slot 77654 is transverse to the shaft axis SA in a first direction, and the proximal slot 77656 is transverse to the shaft axis SA in a second direction, opposite the first direction. The distal protrusion 77652 of the actuator 77650 is configured to be slidably received in the first slot 77626 and the second slot 77636. Further, the first cam member 77624 comprises a first cam protrusion 77628 located at the proximal end of the first cam member 77624. The second cam member 77634 comprises a second cam protrusion 77638 located at the proximal end of the second cam member 77634. The first cam protrusion 77628 is located proximal to the second cam protrusion 77638. The first cam protrusion 77628 is configured to be slidably received in the proximal slot 77656 of the actuator 77650 and the second cam protrusion 77638 is configured to be slidably received in the distal slot 77654 of the actuator 77650. Operation of the clip applier 77600 is discussed in greater detail below.

As discussed above, the rotation of the drive screw 77660 results in translation of the actuator 77650. As the actuator 77650 translates from the distal position (FIG. 165) to the proximal position (FIG. 166), the distal protrusion 77652 of the actuator 77650 will move proximally a distance D1. As the distal protrusion 77652 moves proximally, the distal protrusion 77652 engages the sidewalls of the first slot 77626 and the second slot 77636 which are moved toward each other. Further, as the actuator 77650 moves proximally, the distal slot 77654 and the proximal slot 77656 will move proximally resulting in the second cam protrusion 77638 and the first cam protrusion 77628 moving transversely to the shaft axis SA in opposite directions. More specifically, the first cam protrusion 77628 will move distally along the shaft axis SA and transverse to the shaft axis SA in a first direction FD. Further, the second cam protrusion 77638 will move distally along the shaft axis SA and transverse to the shaft axis SA in a second direction SD. As the first cam protrusion 77628 moves in the first direction FD and the second cam protrusion 77638 moves in the second direction SD, the first jaw 77622 and the second jaw 77632 will move toward the closed position illustrated in FIG. 166. More specifically, the distal end of the inner surface 77623 of the first jaw 77622 and the distal end of the inner surface 77633 of the second jaw 77632 will move toward each other. Thus, the inner surface 77623 of the first jaw 77622 and the inner surface 77633 of the second jaw 77632 are not parallel when the first jaw 77622 and the second jaw 77632 are in the closed position. In other words, the end effector 77620 has tip-first closure of the jaws as compared to the end effector 77520 which has parallel closure of the jaws.

FIGS. 167A-167D depict a clip applier 77700 in accordance with at least one embodiment. The clip applier 77700 comprises an end effector 77720, a clip magazine 77710, a clip feeding system 77730, and a jaw cam assembly 77740. The end effector 77720 comprises a pair of opposing jaws 77721 configured to move between an open position and a closed position, as described herein. The clip magazine 77710 and the jaw cam assembly 77740 are actuatable via two separate rotary inputs. The clip magazine 77710 is similar to the clip magazine 76010 of the clip applier 76000 (see FIG. 114). The clip magazine 77710 comprises a plurality of clips 77714 stored in a plurality of clip holders 77718. The clip magazine 77710 is rotatable and translatable via a magazine driver 77716 that is operably responsive to a first rotary input 77712. The first rotary input 77712 is operably responsive to rotary motions generated within a housing of the clip applier 77700. In any event, the clip magazine 77710 is configured to be advanced and retracted to strip the clips 77714 from the clip magazine 77710 into a loading slot, such as loading slot 77722 of end effector 77720.

The jaw cam assembly 77740 comprises a jaw cam 77742 that is threadably engaged with a second rotary input 77744. The second rotary input 77744 is operably responsive to rotary motions generated within the housing of the clip applier 77700. The second rotary input 77744 is configured to translate the jaw cam 77742 between a fully-advanced position (FIG. 167D), a retracted position (FIG. 167B), and a fully-retracted position (FIG. 167C). The jaw cam 77742 is configured to interact with the opposing jaws 77721 of the end effector 77720 to move the opposing jaws 77721 between the open position and the closed position. More specifically, the jaw cam 77742 comprises a cam window 77743 (see FIG. 168) configured to be receive over a proximal portion 77723 of the opposing jaws 77721. The first rotary input 77712 and the second rotary input 77744 are operable independently of one another by a motor control system of the clip applier 77700.

When the jaw cam 77742 is in its fully-advanced position (FIG. 167D), the opposing jaws 77721 of the end effector 77720 are in their closed position. More specifically, as the jaw cam 77742 moves toward the fully-advanced position the cam window 77743 of the jaw cam 77742 will cammingly engage the exterior of the opposing jaws 77721 to move the opposing jaws 77721 to the closed position. When the jaw cam 77742 is in its retracted position (FIG. 167B) or the fully-retracted position (FIG. 167C), the opposing jaws 77721 are in their open position. The opposing jaws 77721 are biased away from each allowing the opposing jaws 77721 to move to the open position when the jaw cam 77742 is not holding the opposing jaws 77721 together. The opposing jaws 77721 can be moved between the open and closed position without performing clip feed or clip magazine functions.

The above being said, the jaw cam 77742 is also used to release the clip feeding system 77730 such that a clip is fed into the end effector 77720. As described below, the jaw cam 77742 is retracted from its retracted position to its fully-retracted position to release a feeder shoe 77732 which is pushed distally by a feeder spring 77734.

Referring now to FIGS. 168 and 169, the jaw cam 77742 further comprises a shoe release latch 77746 positioned thereon. The shoe release latch 77746 is biased toward the jaw cam 77742 by a biasing member 77748. The shoe release latch 77746 comprises a protrusion 77747 on its distal end that extends through a top opening 77745 in the jaw cam 77742 and down into the cam window 77743 of the jaw cam 77742. The protrusion 77747 comprises a chamfered portion 77747a on the distal end of the shoe release latch 77746. The shoe release latch 77746 further comprises a chamfered portion 77749 on its proximal end.

Further to the above, the clip feeding system 77730 comprises the feeder shoe 77732, a release latch 77731, and the feeder spring 77734. In its stored position, the feeder shoe 77732 is biased away from a proximal stop 77750 of the clip applier 77700 by the feeder spring 77734, but held in place by the release latch 77731 (see FIG. 167A).

When the clip applier 77700 is in an initial position (e.g., when the clip applier 77700 is placed into a surgical site), the opposing jaws 77721 of the end effector 77720 can be in the closed position (see FIG. 167A). In such instances, the feeder shoe 77732 is held in its stored, or ready-to-be-fired position, as described above.

When the jaw cam 77742 is retracted to the retracted position (FIG. 167B) to open the opposing jaws 77721, the loading slot 77722 can receive one of the clips 77714 from the clip magazine 77710. The jaw cam 77742 can then be retracted to the fully-retracted position (FIG. 167C) to release the feeder shoe 77732 and advance the clip 77714 into the opposing jaws 77721 of the end effector 77720. More specifically, as the jaw cam 77742 is retracted to the fully-retracted position (FIG. 167C), the jaw cam 77742 engages a front side 77738 of the release latch 77731 to rotate the release latch 77731 away from the feeder shoe 77732. Further, as the jaw cam 77742 is moved to the fully-retracted position, the shoe release latch 77746 engages the proximal stop 77750 which moves the shoe release latch 77746 in an upward direction UD (see FIG. 169) providing clearance for the feeder shoe 77732 to be advanced toward the end effector 77720.

After the clip 77714 has been advanced into the end effector 77720, the jaw cam 77742 is moved to its fully-advanced position (see FIG. 167D) to move the opposing jaws 77721 of the end effector 77720 to their closed position to crimp the clip 77714 positioned in the end effector 77720. Notably, the jaw cam 77742 carries the shoe release latch 77746 distally to engage the feeder shoe 77732 once again. More specifically, as the jaw cam 77742 moves toward the fully-advanced position, the chamfered portion 77747a on the distal end of the shoe release latch 77746 engages the proximal end of the feeder shoe 77732 such that the shoe release latch 77746 is biased in the upward direction UD. When the jaw cam 77742 is in the fully-advanced position, the shoe release latch 77746 moves downward toward the feeder shoe 77732 by the biasing member 77748. In other words, as the jaw cam 77742 is moved toward the fully-advanced position, the shoe release latch 77746 can move up and over the feeder shoe 77732 to engage a distal side of the feeder shoe 77732.

The jaw cam 77742 can now be used to retract the feeder shoe 77732. The feeder shoe 77732 is re-engaged with the release latch 77731 when the jaw cam 77742 reaches its retracted position (FIG. 167B).

When the feeder shoe 77732 is engaged with the release latch 77731, the jaw cam 77742 can translate freely between the retracted position FIG. 167A and the fully-advanced position (FIG. 167D) to actuate the opposing jaws 77721 of the end effector 77720, as discussed herein. The opposing jaws 77721 can be opened and closed without having to feed and/or crimp a clip. Such opening and closing is often needed to position the end effector of the clip applier within the patient. This is possible, in part, owing to the fact that the clip feeding system isn't triggered within the closing stroke of the jaw cam system. Rather, as described above, the clip feeding system is actuated only when the jaw cam is fully-retracted, i.e., retracted proximally behind the position of the jaw cam associated with the fully-open position of the opposing jaws. Once the jaw cam 77742 is moved to the retracted position (FIG. 167B), another clip 77714 can be positioned in the loading slot 77722 from the clip magazine 77710 and this clip 77714 can be advanced into the end effector 77720 by the feeder shoe 77732 and crimped by the opposing jaws 77721, as discussed above. This process can continue until all of the clips 77714 have been spent from the clip magazine 77710.

FIGS. 170-175 depict a clip applier 77800 in accordance with at least one embodiment. The clip applier 77800 comprises an end effector 77820, a clip track 77840, a cam member 77850, a clip advancer 77860, and a rotary input 77870. The rotary input 77870 defines a rotary axis RA and is rotatable about the rotary axis RA in response to rotary motions generated by a motor within a housing of the clip applier 77800. The rotary input 77870 comprises a proximal threaded portion 77872 and a distal threaded portion 77874 extending from the proximal threaded portion 77872. The proximal threaded portion 77872 comprises a larger thread pitch than the distal threaded portion 77874; however, any suitable thread pitches could be used.

The end effector 77820 extends distally from the clip track 77840 and is mounted to the clip track 77840 via a mounting member 77830. The mounting member 77830 extends above the clip track 77840 and in-between a first jaw 77822 and a second jaw 77824 of the end effector 77820. The first jaw 77822 and the second jaw 77824 are movable relative to each other between an open position (FIGS. 172 and 175) and a closed position (FIGS. 170 and 173). The first jaw 77822 and the second jaw 77824 at least partially define a receiving chamber 77826 there between. Further, the mounting member 77830 comprises a pair of laterally-extending pins 77832. Each of the first jaw 77822 and the second jaw 77824 comprises holes 77829 configured to slidably receive the pair of laterally-extending pins 77832 of the mounting member 77830. Thus, the first jaw 77822 and the second jaw 77824 are movable laterally relative to each other along the laterally-extending pins 77832.

The first jaw 77822 comprises a first pin 77827 extending upward intermediate the holes 77829 in the first jaw 77822. Further, the second jaw 77824 comprises a second pin 77828 extending upward intermediate the holes 77829 in the second jaw 77824. The first pin 77827 is slidably received in a first slot 77852 of the cam member 77850, and the second pin 77828 is slidably received in a second slot 77854 of the cam member 77850. The first slot 77852 comprises a longitudinal portion 77856 and a transverse portion 77857. The longitudinal portion 77856 is parallel to the rotary axis RA of the rotary input 77870 and the transverse portion 77857 is transverse to the rotary axis RA of the rotary input 77870. Similarly, the second slot 77854 comprises a longitudinal portion 77858 and a transverse portion 77859. The longitudinal portion 77858 is parallel to the rotary axis RA of the rotary input 77870 and the transverse portion 77859 is transverse to the rotary axis RA of the rotary input 77870.

The transverse portions 77857 and 77859 extend toward the rotary axis RA from the longitudinal portions 77856 and 77858.

Further to the above, the cam member 77850 further comprises a protrusion 77851 extending upward from its proximal end. The protrusion 77851 comprises an internal thread 77853 (see FIG. 175) that is threadably engaged with the distal thread portion 77874 of the rotary input 77870. Similarly, the clip advancer 77860 comprises a protrusion 77862 extending upward from its proximal end. The protrusion 77862 comprise an internal thread 77864 that is threadably engaged with the proximal threaded portion 77872 of the rotary input 77870. Both the protrusion 77851 of the cam member 77850 and the protrusion 77862 of the clip advancer 77860 are rotatably constrained within a slot 77882 of a top housing 77880 of the clip applier 77800. The slot 77882 allows for the cam member 77850 and the clip advancer 77860 to translate along the rotary axis RA as the rotary input 77870 is rotated about the rotary axis RA. As discussed above, the proximal thread portion 77872 of the rotary input 77870 comprises a larger thread pitch than the distal thread portion 77874 of the rotary input 77870. Thus, rotation of the rotary input 77870 will translate the clip advancer 77860 through a clip advancement stroke and will translate the cam member 77850 through a jaw closure stroke that is smaller than the clip advancement stroke. In other words, rotation of the rotary input 77870 will translate the clip advancer 77860 a greater distance than it will translate the cam member 77850. The clip advancer 77860 further comprises a feeder shoe 77866 extending downward from the clip advancer 77860. The feeder shoe 77866 is configured to translate through a loading slot 77842 of the clip track 77840 as the clip advancer 77860 is translated via the rotary input 77870. The loading slot 77842 is configured to store a plurality of clips 77804 in a longitudinal row for sequential advancement into the receiving chamber 77826 of the end effector 77820. The operation of the clip applier 77800 is discussed in greater detail below.

In an initial position, the first jaw 77822 and the second jaw 77824 are in the closed position without a clip 77804 placed between them, such instances can occur, when the clip applier 77800 is first loaded into a surgical site. Also in such instances, both the clip advancer 77860 and the cam member 77850 are in their proximal position (see FIGS. 170 and 173), for example. When the rotary input 77870 is rotated in a first direction FD, the clip advancer 77860 and cam member 77850 translate distally to intermediate positions to move the first jaw 77822 and the second jaw 77824 into the open position and to advance a clip 77804 through the clip track 77840 to a position just proximal to the receiving chamber 77826 of the end effector 77820. When the cam member 77850 is translated distally from its proximal position to this intermediate position (FIGS. 171 and 174), as described above, the transverse portions 77857 and 77859 of the first and second slots 77852 and 77854 of the cam member 77850 engage the first and second pins 77827 and 77828 of first and second jaws 77822,77824 and move the first and second pins 77827 and 77828 away from each other until the first and second pins 77827 and 77828 move into the longitudinal portions 77856 and 77858 of the first and second slots 77852,77854 (see FIG. 171).

As discussed above, the first and second pins 77827 and 77828 extend upward from the first and second jaws 77822 and 77824, and the first and second jaws 77822 and 77824 are slidable relative to each other along the pair of laterally-extending pins 77832 of the mounting member 77830. Thus, as the cam member 77850 is moved distally from its proximal position to this intermediate position, the first jaw 77822 and the second jaw 77824 are moved to their open position. Further, the first clip 77804 is advanced to a position just proximal to the receiving chamber 77826 by the feeder shoe 77866 of the clip advancer 77860 when the clip advancer 77860 is moved from its proximal position (FIG. 173) to this intermediate position (FIG. 174). In other words, the rotary input 77870 can be rotated in the first direction FD to move the first and second jaws 77822 and 77824 to the open position without advancing a clip 77804 into the end effector 77820.

When the clip advancer 77860 and cam member 77850 are in their intermediate positions (FIGS. 171 and 174), the rotary input 77870 can be rotated further in the first direction FD to translate the clip advancer 77860 and the cam member 77850 further distally to advance the first clip 77804 into the receiving chamber 77826 of the end effector 77820. More specifically, the cam member 77850 can be moved from the intermediate position (FIG. 171) to a distal position (FIG. 172) and the clip advancer 77860 can be moved from the intermediate position (FIG. 171) to a distal position (FIG. 172). As the cam member 77850 is moved toward the distal position, the first and second pins 77827 and 77828 of the first and second jaw 77822 and 77824 will move through the longitudinal portions 77856 and 77858 of the first and second slots 77852 and 77854 of the cam member 77850 and the first and second jaws 77822, 77824 are not driven laterally. As the clip advancer 77860 is moved toward the distal position, the feeder shoe 77866 of the clip advancer 77860 will advance the first clip 77804 into the receiving chamber 77826 defined between the first and second jaws 77822 and 77824. The feeder shoe 77866 is angled such that it will also advance the second clip 77804 distally to a position just proximal to the receiving chamber 77826.

Once the first clip 77804 has been advanced into the receiving chamber 77826, the rotary input 77870 can be rotated in the second direction to retract the clip advancer 77860 and cam member 77850 to their intermediate positions. When the clip advancer 77860 and cam member 77850 are moved into their intermediate positions, the first and second jaws 77822 and 77824 will remain in the open position and the feeder shoe 77866 of the clip advancer 77860 is retracted proximally beyond the receiving chamber 77826. Thus, the feeder shoe 77866 will not interfere with the crimping of the first clip 77804 positioned in the receiving chamber 77826.

Further to the above, the rotary input 77870 can be rotated further still in the second direction to retract the clip advancer 77860 and cam member 77850 from their intermediate positions to their proximal positions. When the clip advancer 77860 and cam member 77850 are moved toward their proximal positions, the first and second jaws 77822 and 77824 move to the closed position to crimp the first clip 77804 positioned therebetween. Further, the clip advancer 77860 moves proximally such that the feeder shoe 77866 moves proximally beyond the second clip 77804 positioned in the clip track 77840 just proximal to the receiving chamber 77826. The distal end of the feeder shoe 77866 is angled such that the feeder shoe 77866 can move up and over the second clip 77804 into position behind the second clip 77804. The first and second jaws 77822 and 77824 can then be moved to the open position to release the first clip 77804 from the first and second jaws 77822 and 77824 while the second clip 77804 is advanced into the receiving chamber 77826. The second clip 77804 can then be crimped and released while a third clip 77804 is advanced into the receiving chamber 77826, and so forth.

Referring to FIG. 176, a graph 78000 of the displacement of a crimping drive of a clip applier system at various set points over time is depicted. The crimping drive is configured to crimp a clip 78004 positioned in between the jaws of an end effector, as discussed herein. The crimping drive is operably responsive to a motor of the clip applier system configured to generate rotary motions. Further, the motor is controllable by a motor controller comprising a processor and a memory in signal communication with the processor. The motor controller is configured to detect the current draw of the motor, compare the detected current to pre-determined ranges of current stored in the memory of the motor controller, and then adjust the speed and/or force of the crimping drive based on the detected current. The pre-determined ranges of current stored in the memory can be based on the expected amount of current draw on the motor for various clip formations. This information can be programmed into the motor controller when it is manufactured and/or from a surgical hub, as described in greater detail below.

As the crimping drive is moved from distance $\delta_O$ to distance $\delta_A$, referring still to FIG. 176, the clip 78004 positioned in the end effector is configured to be crimped by the crimping drive such that the distal ends of the legs of the clip touch at set point 78010. This type of formation is called, tip first, however other types of formation can be used. As the crimping drive is moved from distance $\delta_A$ to distance $\delta_B$, the clip is further formed at set point 78020. As the crimping drive is moved from distance $\delta_B$ to distance $\delta_C$, the clip is completely formed at set point 78030. Each orientation of the clip 78004 at set points 78010, 78020, and 78030 can be detected by the motor controller based on the current draw of the motor and/or any other performance characteristic of the motor. With this data, the motor controller can adapt the operation of the motor to achieve a desired result. For instance, when the ends of the legs of the clip 78004 touch (e.g., at set point 78010), the motor controller will likely detect an increase in the current draw of the motor due to the force required to form the clip beyond the configuration shown at set point 78010. As the clip 78004 is further formed to the orientation depicted at set point 78020, the current draw will likely increase further as the force required to crimp the clip 78004 will increase further owing to the resistance of the tissue and the additional deformation of the clip 78004. As the clip 78004 is fully formed (e.g., at point 78030), the current draw of the motor will significantly increase as the clip 78004 cannot be formed further. The current draw on the motor at each of these set points 78010, 78020, 78030 can be compared to the pre-determined ranges of current stored in the memory of the motor controller to determine how the motor controller is to proceed, as described in greater detail below.

At set point 78010, further to the above, the motor controller can direct the motor to continue advancing the crimping drive from distance $\delta_A$ to $\delta_B$ or $\delta_C$ to further form the clip. Additionally, the motor controller can direct the motor to dwell for a set period of time at set point 78010 (e.g., from $t_A$ to $t_x$, for example) and then either retract the crimping drive from distance $\delta_A$ to distance $\delta_O$ to release the clip 78004 or advance the crimping drive from distance $\delta_A$ to distance $\delta_B$ or distance $\delta_C$ to further crimp the clip 78004. The motor controller can direct the motor to perform similar functions at each set point 78010, 78020, and 78030. For example, at set point 78020, the motor controller can direct the motor to continue to advance the crimping drive from distance $\delta_B$ to distance $\delta_c$ to further form the clip. Additionally, at set point 78020, the motor controller can direct the motor to dwell for a set period of time (e.g., from $t_b$ to $t_D$, for example) and then either retract the crimping drive from distance $\delta_B$ to distance $\delta_O$ to release the clip 78004 or advance the crimping drive from distance $\delta_B$ to distance $\delta_C$ to completely crimp the clip 78004, for example.

The current draws expected at each of the set points 78010, 78020, 78030 can be pre-programmed into the memory of the motor controller such that the motor controller will automatically stop the motor when the current draw on the motor is indicative of one of the set points 78010, 78020, 78030. The motor controller can then require a manual input from the user of the clip applier system in order to proceed. Thus, a user of the clip applier system can selectively determine how much to deform the clip 78004 and when to release the clip 78004 such that varying ranges of clip formation are possible depending on the pre-programmed set points 78010, 78020, 78030. Further, the motor controller can be configured to slow down the motor, pause the motor, or speed up the motor at each set point based on the manual input from the user. More specifically, once a set point 78010, 78020, 78030 is reached the motor will be paused and/or stopped, the user can then select a slow motion button (e.g., some form of actuator, for example) on the clip applier to direct the motor controller to slowly advance the crimping drive from one set point to another or the user can select a fast motion button, or actuator, to direct the motor controller to more quickly advance the crimping drive.

In previous devices, the opening and closing of the jaws of a clip applier resulted in a clip being automatically cycled, i.e., fed into the jaws and then crimped. In many instances, such an arrangement is suitable; however, many instances can arise where cycling a clip results in the clip being dropped into the patient, or otherwise wasted. For instance, when the jaws are closed to insert the clip applier through a trocar and then re-opened inside the patient, a clip is crimped and then dropped into the patient when the jaws are opened. In many embodiments described herein, the clip feeding system and the jaw drive system of a clip applier are operated by separate and distinct drive systems. In such embodiments, the clip feeding system can be deactivated while the jaw drive system is cycled. Such an arrangement allows the jaws of the clip applier to be opened and closed, as many times as needed, to position the clip applier in a patient without cycling a clip. Once the clip applier is suitably positioned in the patient, the clip feeding system can be re-activated such that the clip feeding system and the jaw drive system can be used to co-operatively apply clips to the patient tissue. In various embodiments, the clip applier includes an actuator and/or control in communication with the control system of the clip applier that deactivates the clip feeding system when actuated. In certain embodiments, the actuator is re-actuated to re-activate the clip feeding system or the clip applier comprises a separate actuator to re-activate the clip applier.

Further to the above, the jaws of a clip applier can be used to grasp and/or dissect the patient's tissue. In such instances, the jaws can be repeatedly opened and closed. Deactivating the clip feeding system, as described above, can facilitate an end effector being used in this manner. In addition to or in lieu of the above, a clip applier can have a grasping and/or dissecting mode. In such a mode, or modes, the controller of the clip applier can move the jaws outside of their normal closing and opening strokes. In a grasping mode, for instance, the jaws can be moved closer together than their fully-crimped, or fully-fired, position. In such a position, the jaws can be used to grasp very small objects, such as a suturing needle, for example. In a dissecting mode, for instance, the jaws can be moved further apart than their open, or ready-to-fire, position. In such a position, the jaws can be used to spread open an otomy in the patient tissue. Similar to the above, the clip applier can include one or more actuators and/or controls which can be used to place the clip applier in a grasping and/or dissecting mode, or modes by the clinician.

Notably, further to the above, the loads, or forces, experienced by the jaws of the clip applier, and/or patterns of forces experienced by the jaws of the clip applier, are detectably different by one or more strain gauges and/or load cells, for example. For instance, the jaws of the clip applier may experience very little loading throughout the closing stroke of the jaws, or at least until the end of the closing stroke, when a clip is not positioned between the jaws and the jaws are being used for grasping. The controller of the clip applier can identify such a force pattern and automatically enter into the grasping mode. A similar pattern can occur when the jaws of the clip applier are being used to dissect the tissue, except that the force suddenly increases as the jaws are being opened. The controller of the clip applier can identify such a force pattern and automatically enter into the dissecting mode. The clip applier can have an override feature which, when actuated by the clinician, can place the clip applier back into its clip firing mode.

As described above, the control system of the clip applier is pre-programmed, or programmed prior to being used by the clinician, to move the jaws of the clip applier to pre-determined positions. In various instances, the control system comprises an interface configured to permit the clinician to set, or program, positions for the jaws. Such an interface can include a control screen and/or actuators in communication with the clip applier control system, for example. The control system comprises a memory, such as a solid state memory, for example, configured to store these settings such that the jaws can be automatically moved to these positions when directed to do so by the clinician. In at least one instance, the clip applier comprises a first position control and a second position control, but could include any suitable number of position controls. For each position control, the clinician can program a specific position or configuration for the jaws when the position control is actuated. Such positions can include a less than fully-open position and a less than fully-closed position, for example.

Further to the above, the initial testing of a clip applier on a manufacturing line generates the expected load curve needed to fire a clip in that specific clip applier. The load curve can be used to form a set of thresholds that the device is expected to operate within, such as the set points discussed above, for example. The motor current is measured as an indicator of load while closing the jaws while the motor voltage is an indicator of motor speed. If, during use, the load on the motor exceeds the expected threshold (indicating higher loads and/or thicker tissue, for example), the closed loop nature of the system allows the control algorithm stored in the memory of the motor controller to adjust the current supplied to the motor. These changes, however, are on-the-fly changes. They do not evaluate the loads experienced during other firings in that instrument, or in other instruments. That said, such data can be used to adapt the control program of the clip applier. Such adjustments can comprise adjusting the motor voltage to slow down the advancement rate of the crimping drive and/or change the final stroke position of the crimping drive, for example.

Situational awareness can be used to adjust operations of the clip applier. Situational awareness is the ability of a surgical system to determine or infer information related to a surgical procedure from data received from databases and/or instruments. The information can include the type of procedure being undertaken, the type of tissue being operated on, or the body cavity that is the subject of the procedure. With the contextual information related to the surgical procedure, the surgical system can, for example, improve the manner in which it controls an instrument and provide suggestions to the surgeon during the course of the surgical procedure. In various instances, the control of the surgical instrument can be adjusted without requiring input from the user of the surgical instrument.

The clip appliers described herein, when used in conjunction with the surgical hub and situational awareness modules as described herein and/or incorporated by reference herein, can be utilized to detect diseased tissue and/or detect tissue quality. For example, the clip appliers disclosed herein can detect an atherosclerosis (e.g., hardening of the arteries) or aneurysms (e.g., weak artery walls), as well as detect the presence of another clip, staple, or artificial object captured between the jaws of the clip applier.

More specifically, a surgical hub or system, can detect the risk of a potential atherosclerosis (hardening of the arteries) by surveying contextual cues (e.g., pre-determined patient information and/or patient information gathered by the surgical system during the procedure, for example) stored in the surgical hub that are indicative of such a condition, such as, high blood pressure, high cholesterol (especially LDL cholesterol), and co-morbidities (e.g., obesity and diabetes, for example). If such conditions are detected, the surgical hub can direct the clip applier being used to respond in a specific manner. The first action to the contextual cues can include slowing down the jaw actuation rate, lowering the max torque and clamp load thresholds for non-firing operations (e.g., opening and closing the jaws of the clip applier without a clip present, for example) and/or decrease the max stroke of a cam member or crimping drive being used to form the clip, for example. Further contextual cues can be monitored by the surgical system and a second action can be taken by the surgical system in response to the monitored contextual cues, as discussed in greater detail below.

Further to the above, the surgical system can monitor a contextual cue such as the force required to crimp the clip. For example, the irregular force peaks outside of the anticipated forming events and associated slopes can be detected by the surgical system and the surgical system can direct the clip applier to perform a second action. More specifically, when irregular force peaks are detected, the motor can be stopped and the force on the jaws can be monitored to monitor the tissue creep. Further, if the tissue does not relax (e.g., the tissue creep is abnormal) then something irregular may be in between the jaws. The surgical system can then indicate a fault condition and request feedback from the user to open the jaws of the clip applier to prevent unintentionally clamping the unknown object. Further still, if tissue relaxation (e.g., tissue creep) is detected but is outside of the predefined anticipated range, the surgical system can adjust the advancement rate of the crimping/closure drive with additional set stop points for further monitoring and move the jaws at a slower crimping rate. In other words, the surgical system can pause the closing of the jaws to monitor the tissue creep and then determine how to proceed based on the tissue creep detected, for example.

Further to the above, the surgical system can monitor a contextual cue such as the load on the crimping drive shaft of the clip applier, for example. The crimping drive shaft can be outfitted with a strain gauge in order to determine the forces within the crimping drive shaft when the clip applier crimps a clip. Thus, the strain gauge can be used to determine the forces being applied to the tissue by the clip applier jaws. The clip applier can be used in conjunction with a surgical system, as discussed above, including a surgical grasper, for example. The surgical grasper is used to hold the target tissue and can stretch or relax the tissue depending on the load detected within the crimping drive shaft. For example, if the loading of the crimping drive shaft approaches a threshold value this indicates that the tissue being grasped or clipped is too thick for a clip to be crimped around the tissue, the grasper of the surgical system will automatically move in an attempt to relieve the forces on the crimping drive shaft. More specifically, the grasper can move to stretch the tissue to thin the tissue between the jaws of the clip applier so that the clip can be properly crimped around the tissue, for example. If automatic relief efforts do not relieve the load, the actuation of the jaws of the clip applier (e.g., via the crimping drive shaft, for example) can be slowed or stopped by the surgical system.

Further to the above, the surgical hub can detect an aneurysm (weak artery wall strength) by surveying contextual cues (e.g., pre-determined patient information and/or patient information gathered by the surgical system during the procedure, for example) stored in the surgical hub that are indicative of such a condition. For example, a vision system of the surgical system including one or more cameras can detect a bulge or change in artery thickness in a clamping location relative to adjacent areas. In addition to or in lieu of the above, the impedance of tissue can be monitored to determine if a fatty deposit within the artery wall exists, which may be a sign of a weak artery wall. Also, the clip applier jaw loading can be monitored to determine if there is a sudden compliance of the tissue indicative of a weak artery wall. In such instances, the force required to crimp a clip around the tissue is less than expected. A action to the contextual cues can be taken in response to the monitored parameters, which can include slowing down the jaw actuation rate, lowering the max torque and clamp load thresholds for non-firing operations, and/or decrease the max stroke of a cam member or crimping drive that drives clip formation, for example.

Further to the above, the surgical system can initiate an inquiry to the surgical hub databases for a list of known contributing factors for an aneurysm that the patient may exhibit prior to or during the surgical procedure. This information can be used by the surgical system to determine if the cause of the irregularity during tissue clamping requires a greater/different response. For example, the known contributing factors inquired by the surgical system may include high blood pressure, smoking, obesity, family history of atherosclerosis, bacterial activity, and/or polyarteritis *nodosa* (e.g., inflammation of the small and medium arteries)—which, if present, can cause the controller of the hub to assume that an aneurysm is present.

Further to the above, the surgical system can monitor the contextual cues to identify a potential issue such as a weakened artery wall, for example. If the surgeon pauses to inspect the surgical site after the detected weakness is presented to the user, the clip applier can automatically slow the crimping rate of the clip. In other words, the surgical system assumes that a hesitation by the surgeon indicates that the surgeon is being cautious due to the contextual cue presented; thus, the surgical system automatically responds by slowing down the crimping rate of the clip to prevent unintended tissue damage if there is in fact an artery wall weakness present.

Further to the above, the surgical hub can detect the presence of another clip, staple, or object within the jaws of the clip applier by surveying contextual cues stored in the surgical hub that are indicative of such a condition.

For instance, if a previous procedure used clips in the relevant body cavity, the controller can assume that high force stresses and/or strains are the result of a previous clip being captured in the end effector. The contextual cues to monitor to determine if an undesired object is between the jaws when clamping can include the forces on the clip during clip formation. If the forces depict a spike with high magnitude and very steep slope during clip formation, at a time after tip contact, or during leg forming, this can be indicative of an irregular object within the clip applier jaws. Further, visual cues from the vision system, described herein, can indicate to the use that an irregular object, such as a staple or clip already positioned in the surgical site may be in between the jaws of the clip applier. This information can be fed back to the surgical hub, and/or the clip applier directly, to direct the clip applier to perform specific actions in response to the detected information. For example, the clip applier jaws can be stopped and a visual alert can be provided to the clinician, the final stroke distance to form the clip can be shortened such that the final crimped clip is not fully crimped to avoid shearing the irregular object, and/or the jaws can be closed at a very slow rate to minimize the damage to the irregular object and surrounding tissue.

FIG. 177 is a logic diagram of a control system 75000 for use with any of the various clip appliers described herein. The control system 75000 comprises a control circuit. The control circuit includes a microcontroller 75040 comprising a processor 75020 and a memory 75030. One or more sensors, such as sensor 75080, sensor 75090, sensor 71502, and sensor array 71940, for example, provide real time feedback to the processor 75020. The control system 75000 further comprises a motor driver 75050 configured to control an electric motor 75010 and a tracking system 75060 configured to determine the position of one or more longitudinally movable components in the clip applier, such as firing member 70165 (FIG. 35A), crimping drive 70180 (FIG. 36), feeder member 70630 (FIG. 53), firing member 70640 (FIG. 53), and closure tube 70620 (FIG. 53), for example. The tracking system 75060 is also configured to determine the position of one or more rotational components in the clip applier, such as the rotatable clip magazine 70650 (FIG. 52), for example. The tracking system 75060 provides position information to the processor 75020, which can be programmed or configured to, among other things, determine the position of the rotatable clip magazine 70650 (FIG. 52), determine the position of the firing member, feeder member, closure tube and/or crimping drive, as well as determine the orientation of the jaws of the clip applier. The motor driver 75050 may be an A3941 available from Allegro Microsystems, Inc., for example; however, other motor drivers may be readily substituted for use in the tracking system 75060. A detailed description of an absolute positioning system is described in U.S. Patent Application Publication No. 2017/0296213, entitled SYSTEMS AND METHODS FOR CONTROLLING A SURGICAL STAPLING AND CUTTING INSTRUMENT, the entire disclosure of which is hereby incorporated herein by reference.

The microcontroller 75040 may be any single core or multicore processor such as those known under the trade name ARM Cortex by Texas Instruments, for example. In at least one instance, the microcontroller 75040 is a LM4F230H5QR ARM Cortex-M4F Processor Core, available from Texas Instruments, for example, comprising onchip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules and/or frequency modulation (FM) modules, one or more quadrature encoder inputs (QEI) analog, one or more 12-bit Analog-to-Digital Converters (ADC) with 12 analog input channels, for example, details of which are available from the product datasheet.

In various instances, the microcontroller 75040 comprises a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 75040 is programmed to perform various functions such as precisely controlling the speed and/or position of the firing member, feeder member, crimping drive or closure tube of any of the clip appliers disclosed herein, for example. The microcontroller 75040 is also programmed to precisely control the rotational speed and position of the end effector of the clip applier and the articulation speed and position of the end effector of the clip applier. In various instances, the microcontroller 75040 computes a response in the software of the microcontroller 75040. The computed response is compared to a measured response of the actual system to obtain an "observed" response, which is used for actual feedback decisions. The observed response is a favorable, tuned, value that balances the smooth, continuous nature of the simulated response with the measured response, which can detect outside influences on the system.

The motor 75010 is controlled by the motor driver 75050. In various forms, the motor 75010 is a DC brushed driving motor having a maximum rotational speed of approximately 25,000 RPM, for example. In other arrangements, the motor 75010 includes a brushless motor, a cordless motor, a synchronous motor, a stepper motor, or any other suitable electric motor. The motor driver 75050 may comprise an H-bridge driver comprising field-effect transistors (FETs), for example. The motor driver 75050 may be an A3941 available from Allegro Microsystems, Inc., for example. The A3941 motor driver 75050 is a full-bridge controller for use with external N-channel power metal oxide semiconductor field effect transistors (MOSFETs) specifically designed for inductive loads, such as brush DC motors. In various instances, the motor driver 75050 comprises a unique charge pump regulator provides full (>10 V) gate drive for battery voltages down to 7 V and allows the A3941 motor driver 75050 to operate with a reduced gate drive, down to 5.5 V. A bootstrap capacitor may be employed to provide the above-battery supply voltage required for N-channel MOSFETs. An internal charge pump for the high-side drive allows DC (100% duty cycle) operation. The full bridge can be driven in fast or slow decay modes using diode or synchronous rectification. In the slow decay mode, current recirculation can be through the high-side or the lowside FETs. The power FETs are protected from shoot-through by resistor adjustable dead time. Integrated diagnostics provide indication of undervoltage, overtemperature, and power bridge faults, and can be configured to protect the power MOSFETs under most short circuit conditions. Other motor drivers may be readily substituted.

The tracking system 75060 comprises a controlled motor drive circuit arrangement comprising one or more position sensors, such as the sensor 75080, sensor 75090, sensor 71502, and sensor array 71940, for example. The position sensors for an absolute positioning system provide a unique position signal corresponding to the location of a displacement member. As used herein, the term displacement member is used generically to refer to any movable member of any of the clip appliers disclosed herein. In various instances, the displacement member may be coupled to any position sensor suitable for measuring linear displacement or rotational displacement. Linear displacement sensors may include contact or non-contact displacement sensors. The displacement sensors may comprise linear variable differential transformers (LVDT), differential variable reluctance transducers (DVRT), a slide potentiometer, a magnetic sensing system comprising a movable magnet and a series of linearly arranged Hall Effect sensors similar to the arrangement illustrated in FIG. 75, a magnetic sensing system comprising a fixed magnet and a series of movable linearly arranged Hall Effect sensors similar to the arrangement illustrated in FIGS. 81A and 81B, an optical sensing system comprising a movable light source and a series of linearly arranged photo diodes or photo detectors, or an optical sensing system comprising a fixed light source and a series of movable linearly arranged photo diodes or photo detectors, or any combination thereof.

The position sensors 75080, 75090, 71502, and 71940 for example, may comprise any number of magnetic sensing elements, such as, for example, magnetic sensors classified according to whether they measure the total magnetic field or the vector components of the magnetic field. The techniques used to produce both types of magnetic sensors encompass many aspects of physics and electronics. The technologies used for magnetic field sensing include search coil, fluxgate, optically pumped, nuclear precession, SQUID, Hall-Effect, anisotropic magnetoresistance, giant magnetoresistance, magnetic tunnel junctions, giant magnetoimpedance, magnetostrictive/piezoelectric composites, magnetodiode, magnetotransistor, fiber optic, magnetooptic, and microelectromechanical systems-based magnetic sensors, among others.

In various instances, one or more of the position sensors of the tracking system 75060 comprise a magnetic rotary absolute positioning system. Such position sensors may be implemented as an AS5055EQFT single-chip magnetic rotary position sensor available from Austria Microsystems, AG and can be interfaced with the controller 75040 to provide an absolute positioning system. In certain instances, a position sensor comprises a low-voltage and low-power component and includes four Hall-Effect elements in an area of the position sensor that is located adjacent a magnet. A high resolution ADC and a smart power management controller are also provided on the chip. A CORDIC processor (for Coordinate Rotation Digital Computer), also known as the digit-by-digit method and Volder's algorithm, is provided to implement a simple and efficient algorithm to calculate hyperbolic and trigonometric functions that require only addition, subtraction, bitshift, and table lookup operations. The angle position, alarm bits, and magnetic field information are transmitted over a standard serial communication interface such as an SPI interface to the controller 75040. The position sensors can provide 12 or 14 bits of resolution, for example. The position sensors can be an AS5055 chip provided in a small QFN 16-pin 4×4×0.85 mm package, for example.

The tracking system 75060 may comprise and/or be programmed to implement a feedback controller, such as a PID, state feedback, and adaptive controller. A power source converts the signal from the feedback controller into a physical input to the system, in this case voltage. Other examples include pulse width modulation (PWM) and/or frequency modulation (FM) of the voltage, current, and force. Other sensor(s) may be provided to measure physical parameters of the physical system in addition to position. In various instances, the other sensor(s) can include sensor arrangements such as those described in U.S. Pat. No. 9,345,481, entitled STAPLE CARTRIDGE TISSUE THICKNESS SENSOR SYSTEM, which is hereby incorporated herein by reference in its entirety; U.S. Patent Application Publication No. 2014/0263552, entitled STAPLE CARTRIDGE TISSUE THICKNESS SENSOR SYSTEM, which is hereby incorporated herein by reference in its entirety; and U.S. patent application Ser. No. 15/628,175, entitled TECHNIQUES FOR ADAPTIVE CONTROL OF MOTOR VELOCITY OF A SURGICAL STAPLING AND CUTTING INSTRUMENT, which is hereby incorporated herein by reference in its entirety. In a digital signal processing system, absolute positioning system is coupled to a digital data acquisition system where the output of the absolute positioning system will have finite resolution and sampling frequency. The absolute positioning system may comprise a compare and combine circuit to combine a computed response with a measured response using algorithms such as weighted average and theoretical control loop that drives the computed response towards the measured response. The computed response of the physical system takes into account properties like mass, inertial, viscous friction, inductance resistance, etc., to predict what the states and outputs of the physical system will be by knowing the input.

The absolute positioning system provides an absolute position of the displacement member upon power up of the instrument without retracting or advancing the displacement member to a reset (zero or home) position as may be required with conventional rotary encoders that merely count the number of steps forwards or backwards that the motor 75010 has taken to infer the position of a device actuator, a firing member, a feeder drive, a crimping drive, a closure tube, and the like.

A sensor 75080 comprising a strain gauge or a microstrain gauge, for example, is configured to measure one or more parameters of the end effector of the clip applier, such as, for example, the strain experienced by the jaws during a crimping operation. In one embodiment, the sensor 75080 can comprise the strain gauges 71720 and 71730 (FIG. 79) discussed in greater detail above, for example. The measured strain is converted to a digital signal and provided to the processor 75020. In addition to or in lieu of the sensor 75080, a sensor 75090 comprising a load sensor, for example, can measure the closure force applied by the closure drive system to the jaws of the clip applier. In various instances, a current sensor 75070 can be employed to measure the current drawn by the motor 75010. The force required to clamp the first and second jaws to crimp a clip can correspond to the current drawn by the motor 75010, for example. The measured force is converted to a digital signal and provided to the processor 75020. A magnetic field sensor can be employed to measure the thickness of the captured tissue. The measurement of the magnetic field sensor can also be converted to a digital signal and provided to the processor 75020.

The measurements of the tissue compression, the tissue thickness, and/or the force required to close the end effector and crimp a clip around tissue as measured by the sensors can be used by the controller 75040 to characterize the position and/or speed of the movable member being tracked. In at least one instance, the memory 75030 may store a technique, an equation, and/or a look-up table which can be employed by the controller 75040 in the assessment. In various instances, the controller 75040 can provide the user of the clip applier with a choice as to the manner in which the clip applier should be operated. To this end, a display 75044 can display a variety of operating conditions of the clip applier and can include touch screen functionality for data input. Moreover, information displayed on the display 75044 may be overlaid with images acquired via the imaging modules of one or more endoscopes and/or one or more additional surgical instruments used during the surgical procedure.

As discussed above, the clip appliers disclosed herein may comprise control systems. Each of the control systems can comprise a circuit board having one or more processors and/or memory devices. Among other things, the control systems are configured to store sensor data, for example. They are also configured to store data which identifies the type of clip applier attached to a handle or housing, such as handle 700 (FIG. 29), for example. More specifically, the type of clip applier can be identified when attached to the handle or housing by the sensors and the sensor data can be stored in the control system. Moreover, they are also configured to store data including whether or not the clip applier has been previously used and/or how many clips have been ejected from the clip magazine or clip cartridge of the clip applier during operation. This information can be obtained by the control system to assess whether or not the clip applier is suitable for use and/or has been used less than a predetermined number of times, for example.

The surgical instrument systems described herein are motivated by an electric motor; however, the surgical instrument systems described herein can be motivated in any suitable manner. In certain instances, the motors disclosed herein may comprise a portion or portions of a robotically controlled system. U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535, for example, discloses several examples of a robotic surgical instrument system in greater detail, the entire disclosure of which is incorporated by reference herein.

EXAMPLES

Various aspects of the subject matter disclosed herein are set out in the following example sets.

Example Set 1

Example 1

A surgical device for clipping tissue. The surgical device comprises a housing, a shaft extending from the housing, and a first reload releasably attachable to the shaft. The first reload comprises a first end effector and a first clip magazine including a plurality of first clips. The surgical device further comprises a second reload releasably attachable to the shaft when the first reload is not attached to the shaft. The first reload and the second reload are different sizes. The second reload comprises a second end effector and a second clip magazine including a plurality of second clips.

Example 2

The surgical device of Example 1, wherein the first clips and the second clips are different sizes.

Example 3

The surgical device of Examples 1 or 2, wherein the shaft comprises a proximal portion and a distal portion, and wherein the surgical device further comprises an articulation joint connecting the proximal portion and the distal portion.

Example 4

The surgical device of Examples 1, 2, or 3, further comprising a motor configured to output rotary motions and a firing drive operably responsive to the rotary motions, wherein the firing drive is operably connected to a first driver of the first reload when the first reload is attached to the shaft, and wherein the firing drive is operably connected to a second driver of the second reload when the second reload is attached to the shaft.

Example 5

The surgical device of Example 4, wherein the first driver is configured to translate through a first driver stroke in response to a rotation of the firing drive when the first reload is attached to the shaft, wherein the second driver is configured to translate through a second driver stroke in response to the rotation of the firing drive when the second reload is attached to the shaft, and wherein the first driver stroke and the second driver stroke are different lengths.

Example 6

The surgical device of Example 5, wherein the first driver is configured to advance a first clip from the first clip magazine into the first end effector during the first driver stroke, and wherein the second driver is configured to advance a second clip from the second clip magazine into the second end effector during the second driver stroke.

Example 7

The surgical device of Example 5, wherein the first end effector comprises a first jaw and a second jaw movable relative to each other between an open position and a closed position, and wherein the second end effector comprises a first jaw and a second jaw movable relative to each other between an open position and a closed position.

Example 8

The surgical device of Example 7, wherein the first driver is configured to move the first jaw and the second jaw of the first end effector toward the closed position during the first driver stroke, and wherein the second driver is configured to move the first jaw and the second jaw of the second end effector toward the closed position during the second driver stroke.

Example 9

The surgical device of Example 5, wherein the first reload comprises a first drive screw threadably engaged with the first driver, wherein the first drive screw is operably connected to the firing drive when the first reload is attached to the shaft, wherein the second reload comprises a second drive screw threadably engaged with the second driver, wherein the second driver is operably connected to the firing drive when the second reload is attached to the shaft, wherein the first drive screw comprises a first thread pitch, and wherein the second drive screw comprises a second thread pitch that is different than the first thread pitch.

Example 10

A surgical device for clipping tissue. The surgical device comprises a housing, a shaft extending from the housing, and a first reload comprising a magazine of first clips. The first reload is releasably attachable to the shaft. The surgical device further comprises a second reload comprising a magazine of second clips. The second reload is releasably attachable to the shaft when the first reload is not attached to the shaft. The magazine of first clips and the magazine of second clips are different sizes. The surgical device further comprises an end effector extending from the shaft. The end effector comprises a first jaw and a second jaw. The first jaw and the second jaw are movable relative to each other between an open position and a closed position. The end effector further comprises a receiving portion at least partially defined between the first jaw and the second jaw.

Example 11

The surgical device of Example 10, wherein the magazine of second clips is larger than the magazine of first clips.

Example 12

The surgical device of Examples 10 or 11, wherein each first clip of the magazine of first clips and each second clip of the magazine of second clips are different sizes.

Example 13

The surgical device of Examples 10, 11, or 12, wherein the shaft comprises a proximal portion and a distal portion, wherein the end effector extends from the distal portion, and wherein the surgical device further comprises an articulation joint configured to connect the proximal portion and the distal portion.

Example 14

The surgical device of Examples 10, 11, 12, or 13, further comprising a motor configured to output rotary motions and a firing drive operably responsive to the rotary motions, wherein the firing drive is operably connected to a first driver of the first reload when the first reload is attached to the shaft, and wherein the firing drive is operably connected to a second driver of the second reload when the second reload is attached to the shaft.

Example 15

The surgical device of Example 14, wherein the first driver is configured to translate through a first driver stroke in response to a rotation of the firing drive when the first reload is attached to the shaft, wherein the second driver is configured to translate through a second driver stroke in response to the rotation of the firing drive when the second reload is attached to the shaft, and wherein the first driver stroke and the second driver stroke are different.

Example 16

The surgical device of Example 15, wherein a clip from the magazine of first clips is advanced into the receiving portion of the end effector during the first driver stroke, and wherein a clip from the magazine of second clips is advanced into the receiving portion of the end effector during the second driver stroke.

Example 17

The surgical device of Example 15, wherein the first jaw and the second jaw are moved toward the closed position during the first driver stroke, and wherein the first jaw and the second jaw are moved toward the closed position during the second driver stroke.

Example 18

A surgical device for clipping tissue. The surgical device comprises a housing, a shaft extending from the housing and defining a shaft axis, an end effector extending from the shaft. The end effector comprises a receiver. The surgical device further comprises a rotary clip magazine configured to rotate about the shaft axis between a plurality of feeding positions. The rotary clip magazine comprises a plurality of clip storage chambers corresponding to the plurality of feeding positions. Each clip storage chamber removably stores a first clip comprising a first central axis, and a second clip comprising a second central axis. The second clip is stacked on top of the first clip. The first central axis is radially and circumferentially offset from the second central axis.

Example 19

The surgical device of Example 18, wherein each clip storage chamber comprises an angled slot configured to hold the first clip and the second clip in the rotary clip magazine such that the first central axis of the first clip is radially and circumferentially offset from the second central axis of the second clip.

Example 20

The surgical device of Example 19, wherein each angled slot comprises a plurality of discrete holding locations configured to hold the first clip and the second clip.

Example 21

The surgical device of Examples 18, 19, or 20, wherein the rotary clip magazine further comprises an opening positioned between the plurality of clip storage chambers, and wherein the opening is configured to receive a rotary input extending from the housing.

Example Set 2

Example 1

A surgical device for clipping tissue. The surgical device comprises a housing, a shaft extending from the housing and defining a shaft axis, an end effector extending from the shaft, a motor, a rotary input configured to rotate in response to the motor, and a clip magazine comprising a plurality of clips. The clip magazine is operably connected to the rotary input. The clip magazine is movable in a first direction through a clip feed stroke in response to the rotation of the rotary input. The clip magazine is movable in a second direction in response to the rotation of the rotary input. The second direction is transverse to the first direction.

Example 2

The surgical device of Example 1, wherein the first direction is translation along the shaft axis, and wherein the second direction is rotation about the shaft axis.

Example 3

The surgical device of Examples 1 or 2, wherein the end effector comprises a loading portion configured to receive a clip from the clip magazine, a receiving portion, and a firing drive configured to advance a clip from the loading portion into the receiving portion.

Example 4

The surgical device of Example 3, wherein the plurality of clips are biased outward relative to the shaft axis, and wherein, as the clip magazine is rotated about the shaft axis, a dip is biased into the loading portion when the clip and the loading portion are aligned.

Example 5

The surgical device of Example 4, wherein, when the clip is positioned in the loading portion, the clip magazine is prevented from rotating.

Example 6

The surgical device of Example 5, wherein, after the clip in the loading portion is advanced into the receiving portion, the clip magazine is rotatable by the rotary input to align another clip with the loading portion to bias another clip into the loading portion.

Example 7

The surgical device of Examples 1, 2, 3, 4, 5, or 6, wherein the clip magazine comprises at least two storage locations for the plurality of clips, and wherein each storage location comprises at least two clips in a clip stack.

Example 8

The surgical device of Examples 1, 2, 3, 4, 5, 6, or 7, wherein a first amount of rotation of the rotary input moves the clip magazine in the first direction, and wherein a second amount of rotation of the rotary input moves the clip magazine in the second direction.

Example 9

A surgical device for clipping tissue. The surgical device comprises a housing and a shaft extending from the housing. The housing comprises a motor. The shaft defines a shaft axis and comprises a loading portion. The surgical device further comprises an end effector extending from the shaft, a rotary input, and a clip magazine. The rotary input is configured to rotate in response to the motor. The rotary input comprises a first cam lobe. The clip magazine comprises a plurality of clips and a second cam lobe. The first cam lobe is configured to engage the second cam lobe to translate the clip magazine from a fully-retracted position to a fully-advanced position in response to rotation of the rotary input in a first direction. A first clip from the clip magazine is aligned with the loading portion of the shaft when the clip magazine is in the fully-advanced position.

Example 10

The surgical device of Example 9, wherein the first clip is stripped from the clip magazine into the loading portion as the clip magazine is retracted from the fully-advanced position to the fully-retracted position in response to rotation of the rotary input in a second direction opposite the first direction.

Example 11

The surgical device of Example 10, wherein the clip magazine is biased toward the rotary input via a biasing member, and wherein the biasing member retracts the clip magazine toward the fully-retracted position when the rotary input is rotated in the second direction.

Example 12

The surgical device of Examples 9, 10, or 11, wherein the rotary input further comprises a notch at a distal end of the first cam lobe, wherein the clip magazine further comprises a protrusion extending proximally from the second cam lobe, and wherein the protrusion is configured to engage the notch when the clip magazine is in the fully-advanced position.

Example 13

The surgical device of Example 12, wherein the rotary input and the clip magazine rotate together when the protrusion of the clip magazine is engaged with the notch of the rotary input and the rotary input is rotated in the first direction.

Example 14

The surgical device of Examples 12 or 13, wherein the clip magazine is rotatable relative to the shaft axis to align another clip with the loading portion of the end effector when the protrusion of the clip magazine is engaged with the notch of the rotary input.

Example 15

The surgical device of Examples 9, 10, 11, 12, 13, or 14, wherein the clip magazine comprises at least two storage locations for the plurality of clips, and wherein each storage location comprises at least two clips stacked on top of each other.

Example 16

The surgical device of Examples 9, 10, 11, 12, 13, 14, or 15, further comprising an articulation joint configured to permit articulation of the end effector relative to the shaft.

Example 17

A surgical device for clipping tissue. The surgical device comprises a housing and a shaft extending from the housing. The housing comprises a motor configured to output rotary motions. The shaft defines a shaft axis. The surgical device further comprises an end effector extending from the shaft and a magazine comprising a plurality of clips. The magazine is movable in a first direction in response to the rotary motions. The magazine is movable in a second direction in response to the rotary motions. The second direction is transverse to the first direction.

Example 18

The surgical device of Example 17, wherein the first direction is translation along the shaft axis, and wherein the second direction is rotation about the shaft axis.

Example 19

The surgical device of Examples 17 or 18, further comprising a rotary input operably responsive to the rotary motions, wherein the rotary input is configured to transmit the rotary motions from the motor to the magazine to move the magazine in the first direction and the second direction.

Example 20

The surgical device of Example 19, wherein a first amount of rotation of the rotary input moves the magazine in the first direction, and wherein a second amount of rotation of the rotary input moves the magazine in the second direction.

Example Set 3

Example 1

A surgical device for clipping tissue. The surgical device comprises a housing, a shaft extending from the housing, an end effector extending from the shaft, a feeder drive, and a clip magazine. The shaft comprises a loading chamber and defines a shaft axis. The end effector comprises a receiver. The feeder drive is configured to translate relative to the shaft through a plurality of feeding strokes. The clip magazine is attachable to the shaft. The clip magazine comprises a plurality of clips stored therein. The clip magazine is configured to rotate about the shaft axis between a plurality of positions. The plurality of positions comprises a plurality of loading positions and a plurality of neutral positions. A clip is biased from the clip magazine into the loading chamber when the clip magazine is in a loading position. None of the plurality of clips can be biased from the clip magazine into the loading chamber when the clip magazine is in a neutral position. A clip positioned in the loading chamber can be advanced into the receiver of the end effector by the feeder drive during a feeding stroke. The feeding stroke can only be performed when the clip magazine is in a neutral position.

Example 2

The surgical device of Example 1, wherein the clip magazine further comprises biasing members, and wherein each clip in the clip magazine is biased away from the shaft axis by a biasing member.

Example 3

The surgical device of Example 2, wherein the amount of force applied by the biasing member to a clip when the clip magazine is in a loading position is greater than the amount of force applied by the biasing member to a clip when the clip magazine is in a neutral position.

Example 4

The surgical device of Examples 2 or 3, wherein a biasing member is configured to occupy the loading chamber after all of the clips in the clip magazine have been spent to prevent rotation of the clip magazine.

Example 5

The surgical device of Examples 1, 2, 3, or 4, wherein the clip magazine is configured to support the feeder drive during a feeding stroke when the clip magazine is in a neutral position.

Example 6

The surgical device of Examples 1, 2, 3, 4, or 5, further comprising a lockout configured to prevent rotation of the clip magazine after all of the clips in the clip magazine have been spent.

Example 7

The surgical device of Example 6, wherein the lockout comprises a lockout clip stored in the clip magazine, and wherein the lockout clip prevents rotation of the clip magazine when the lockout clip is biased into the loading chamber.

Example 8

A surgical device for clipping tissue. The surgical device comprises a housing, a shaft extending from the housing and defining a shaft axis, an end effector extending from the shaft, a feeder drive, and a clip magazine attachable to the shaft. The end effector comprises a receiver. The feeder drive is configured to translate relative to the surgical device through a plurality of feeding strokes. The clip magazine comprises an outer tube and a carriage contained within the outer tube. The outer tube comprises a loading chamber. The carriage comprises a plurality of clips stored therein. The carriage is configured to rotate relative to the outer tube about the shaft axis between a plurality of positions. The plurality of positions comprises a plurality of loading positions and a plurality of neutral positions. A clip is biased from the carriage into the loading chamber when the carriage is in a loading position. None of the plurality of clips can be biased from the carriage into the loading chamber when the carriage is in a neutral position. A clip positioned in the loading chamber can be advanced into the receiver of the end effector by the feeder drive during a feeding stroke.

Example 9

The surgical device of Example 8, wherein a feeding stroke can only be performed when the clip magazine is in a neutral position.

Example 10

The surgical device of Examples 8 or 9, wherein each loading position is located 120 degrees apart, wherein each neutral position is located 120 degrees apart, and wherein the loading positions and the neutral positions are located 60 degrees apart.

Example 11

The surgical device of Examples 8, 9, or 10, wherein the carriage is configured to support the feeder drive during a feeding stroke when the carriage is in a neutral position.

Example 12

The surgical device of Examples 8, 9, 10, or 11, wherein the clip magazine further comprises a plurality of biasing members, and wherein each clip in the carriage is biased away from the shaft axis by a biasing member.

Example 13

The surgical device of Example 12, wherein the amount of force applied by the biasing member to a clip when the carriage is in a loading position is greater than the amount of force applied by the biasing member to a clip when the carriage is in a neutral position.

Example 14

The surgical device of Examples 12 or 13, wherein a biasing member is configured to occupy the loading chamber after all of the clips in the carriage have been spent to prevent rotation of the carriage relative to the outer tube.

Example 15

The surgical device of Examples 8, 9, 10, or 11, wherein the carriage further comprises a lockout configured to occupy the loading chamber after all of the clips in the carriage have been spent, and wherein the lockout prevents rotation of the carriage relative to the outer tube when the lockout is positioned in the loading chamber.

Example 16

The surgical device of Example 15, wherein the lockout comprises a lockout clip stored in the carriage, and wherein the lockout clip is larger than the clips and prevents rotation of the carriage relative to the outer tube when the lockout clip is positioned in the loading chamber.

Example 17

A surgical device for clipping tissue. The surgical device comprises a housing, a shaft extending from the housing, an end effector extending from the shaft, a feeder drive, and a rotatable clip magazine attachable to the shaft. The shaft defines a shaft axis and comprises a loading chamber. The feeder drive is configured to translate relative to the surgical device. The rotatable clip magazine is configured to rotate about the shaft axis between a plurality of positions. The clip magazine comprises a plurality of clips stored therein. The plurality of positions comprises a loading position wherein a clip is biased from the clip magazine into the loading chamber when the clip magazine is in the loading position, and a neutral position, wherein none of the clips can be biased from the clip magazine into the loading chamber and a clip positioned in the loading chamber can be advanced into the end effector by the feeder drive when the clip magazine is in the neutral position.

Example 18

The surgical device of Example 17, wherein each clip in the clip magazine is biased away from the shaft axis by a biasing member.

Example 19

The surgical device of Example 18, wherein the amount of force applied by the biasing member to a clip when the clip magazine is in the loading position is greater than the amount of force applied by the biasing member to a clip when the clip magazine is in the neutral position.

Example 20

The surgical device of Examples 17, 18, or 19, wherein the clip magazine further comprises a lockout configured to prevent rotation of the clip magazine about the shaft axis after all of the clips in the clip magazine have been spent.

Example 21

A surgical device comprising a housing, a shaft extending from the housing and defining a shaft axis, an end effector extending from the shaft, a feeder drive, a rotatable clip magazine, and a rotary input. The shaft comprises a feeding chamber. The feeder drive is configured to move between a proximal position and a distal position relative to the shaft. The rotatable clip magazine is configured to rotate about the shaft axis. The rotary input is selectively engageable with the feeder drive and the rotatable clip magazine. The rotary input is configured to be engaged with the feeder drive and the rotatable clip magazine to consecutively feed a clip from and deliver a clip to the feeding chamber.

Example Set 4

Example 1

A surgical device for clipping tissue. The surgical device comprises a housing, a shaft extending from the housing and defining a shaft axis, and an end effector extending from the shaft. The end effector comprises a first jaw, a second jaw, and a receiver at least partially defined between the first jaw and the second jaw. The first jaw and the second jaw are movable relative to each other between an open position and a closed position. The surgical device further comprises a rotatable clip magazine, a first advancing system, and a second advancing system. The rotatable clip magazine is configured to rotate about the shaft axis. The clip magazine is configured to store at least two clips. The second advancing system is configured to operate sequentially with the first advancing system. The first advancing system and the second advancing system are configured to sequentially advance the clips into the receiver of the end effector.

Example 2

The surgical device of Example 1, wherein the first advancing system is configured to advance a clip from a feeding position adjacent the rotatable clip magazine into a firing position located distal to the feeding position, and wherein the second advancing system is configured to advance the clip in the firing position into the receiver of the end effector.

Example 3

The surgical device of Examples 1 or 2, wherein the first advancing system is driven by a first input and the second advancing system is driven by a second input.

Example 4

The surgical device of Examples 1, 2, or 3, wherein the first jaw and the second jaw are biased away from each other toward the open position, wherein the second advancing system comprises a cam member positioned around the first jaw and the second jaw, wherein the cam member is configured to translate relative to the end effector between a proximal position, an intermediate position, and a distal position, and wherein the intermediate position is located between the proximal position and the distal position.

Example 5

The surgical device of Example 4, wherein the first jaw and the second jaw are in the open position when the cam member is in the proximal position and the intermediate position, and wherein the first jaw and the second jaw are moved toward the closed position when the cam member moves from the intermediate position to the distal position.

Example 6

The surgical device of Examples 4 or 5, wherein the second advancing system further comprises a feeder bar extending distally from the cam member, and wherein the feeder bar is configured to move the clip in the firing position into the receiver of the end effector when the cam member is moved from the proximal position to the intermediate position.

Example 7

The surgical device of Example 6, wherein the clip positioned in the receiver is crimped by the first jaw and the second jaw when the cam member is moved from the intermediate position toward the distal position by the second advancing system.

Example 8

A surgical device for clipping tissue. The surgical device comprises a housing, a shaft extending from the housing and defining a shaft axis, and an end effector extending from the shaft. The end effector comprises a first jaw, a second jaw, and a receiving portion at least partially defined between the first jaw and the. The first jaw and the second jaw are movable relative to each other between an unclamped position and a clamped position. The surgical device further comprises a rotatable clip magazine, a first feeding system, and a second feeding system. The rotatable clip magazine is configured to rotate about the shaft axis between a number of ejection positions. The clip magazine comprises a plurality of clips removable stored therein and one or more biasing members configured to bias a clip into a feeding position when the clip magazine is in one of the number of ejection positions. The first feeding system comprises a first feeder member configured to translate relative to the end effector. The first feeder member can advance a clip in the feeding position into a firing position located distal to the feeding position. The second feeding system comprises a second feeder member configured to translate relative to the end effector. The second feeder member is configured to advance the clip in the firing position into the receiving portion of the end effector.

Example 9

The surgical device of Example 8, wherein the firing position is located in a clip track of the end effector.

Example 10

The surgical device of Examples 8 or 9, wherein the first feeding system is driven by a first input and the second feeding system is driven by a second input.

Example 11

The surgical device of Examples 8, 9, or 10, wherein the first jaw and the second jaw are biased away from each other toward the unclamped position, wherein the second feeding member comprises a cam member and a feeder bar extending distally from the cam member, wherein the cam member is positioned around the first jaw and the second jaw and is configured to translate relative to the end effector between a proximal position, an intermediate position, and a distal position, and wherein the intermediate position is located between the proximal position and the distal position.

Example 12

The surgical device of Example 11, wherein the first jaw and the second jaw are in the unclamped position when the cam member is in the proximal position and the intermediate position, and wherein the first jaw and the second jaw are moved toward the clamped position when the cam member moves from the intermediate position to the distal position.

Example 13

The surgical device of Examples 11 or 12, wherein the feeder bar of the second feeder member is configured to move the clip in the firing position into the receiving portion of the end effector when the cam member is moved from the proximal position to the intermediate position.

Example 14

The surgical device of Example 13, wherein the clip positioned in the receiving portion is crimped by the first jaw and the second jaw when the cam member is moved from the intermediate position toward the distal position.

Example 15

A surgical device for clipping tissue. The surgical device comprises a housing, a shaft extending from the housing, and an end effector extending from the shaft. The end effector comprises a first jaw, a second jaw, and a receiver at least partially defined between the first jaw and the second jaw. The first jaw and the second jaw are movable relative to each other between an open position and a closed position. The surgical device further comprises a clip track, a clip magazine configured to store a plurality of clips, a first clip advancer configured to advance a clip from the clip magazine into a firing position located in the clip track, and a second clip advancer configured to advance the clip from the firing position into the receiver of the end effector. The second clip advancer is further configured to move the first jaw and the second jaw toward the closed position.

Example 16

The surgical device of Example 15, wherein the first clip advancer is driven by a first input and the second clip advancer is driven by a second input.

Example 17

The surgical device of Examples 15 or 16, wherein the second clip advancer comprises a jaw cam configured to move between a proximal position, an intermediate position, and a distal position, and wherein the intermediate position is located between the proximal position and the distal position.

Example 18

The surgical device of Example 17, wherein the second clip advancer further comprises a feeder shoe extending from the jaw cam, and wherein feeder shoe is configured to move a clip from the firing position into the receiver of the end effector when the second clip advancer moves from the proximal position to the intermediate position.

Example 19

The surgical device of Example 18, wherein the jaw cam is configured to move the first jaw and the second jaw toward the closed position to crimp the clip positioned in the receiver of the end effector when the jaw cam moves from the intermediate position to the distal position.

Example 20

The surgical device of Examples 18 or 19, wherein, when the jaw cam moves from the intermediate position to the distal position, the feeder shoe does not move.

Example Set 5

Example 1

A surgical device for clipping tissue. The surgical device comprises a housing comprising an electric motor, a shaft extending from the housing, and defining a central shaft axis, a clip magazine attachable to the shaft, and a clip crimping system. The clip magazine comprises a plurality of clips removably stored therein. The clip crimping system comprises a first jaw, a second jaw, a distal portion, a proximal connection portion, and a clamp operably coupled with the electric motor. The distal portion comprises a clip receiving chamber defined between the first jaw and the second jaw. The distal portion is offset from the central shaft axis. The proximal connection portion connects the first jaw and the second jaw. The proximal connection portion is positioned along the central shaft axis. The clamp is movable distally by the electric motor to perform a crimping stroke and engage the first jaw and the second jaw.

Example 2

The surgical device of Example 1, wherein the first jaw comprises a first cantilever arm and the second jaw comprises a second cantilever arm.

Example 3

The surgical device of Example 2, wherein the proximal connection portion integrally connects the first cantilever arm and the second cantilever arm.

Example 4

The surgical device of Examples 1, 2, or 3, wherein the proximal connection portion is positioned proximally with respect to the clip magazine.

Example 5

The surgical device of Examples 2, 3, or 4, wherein the first cantilever arm and the second cantilever arm extend in a first plane proximal to the clip magazine and a second plane distal to the clip magazine, and wherein the second plane is offset from the first plane.

Example 6

The surgical device of Example 5, wherein the proximal-most portion of the proximal connection portion extends out of the second plane.

Example 7

A surgical device for clipping tissue. The surgical device comprises a housing comprising an electric motor, a shaft extending from the housing and defining a central shaft axis, a clip magazine attachable to the shaft, and a clip crimping system. The clip magazine comprises a plurality of clips removably stored therein. The clip crimping system comprises a first jaw arm, a second jaw arm, a clip receiving chamber, a proximal connection portion connecting the first jaw arm and the second jaw arm, and a clamp drive operably coupled with the electric motor. The clip receiving chamber is defined between a distal end of the first jaw arm and a distal end of the second jaw arm. The clip receiving chamber is offset from the central shaft axis. The proximal connection portion extends along the central shaft axis. The clamp drive is movable distally by the electric motor to perform a crimping stroke and engage the first jaw arm and the second jaw arm.

Example 8

The surgical device of Example 7, wherein the first jaw arm comprises a first cantilever arm and the second jaw arm comprises a second cantilever arm.

Example 9

The surgical device of Example 8, wherein the proximal connection portion integrally connects the first cantilever arm and the second cantilever arm.

Example 10

The surgical device of Examples 7, 8, or 9, wherein the proximal connection portion is positioned proximally with respect to the clip magazine.

Example 11

The surgical device of Example 8, wherein the first cantilever arm and the second cantilever arm extend in a first plane proximal to the clip magazine and a second plane distal to the clip magazine, and wherein the second plane is offset from the first plane.

Example 12

The surgical device of Example 11, wherein the proximal-most portion of the proximal connection portion extends out of the second plane.

Example 13

A surgical device for clipping tissue. The surgical device comprises a shaft comprising a longitudinal shaft axis, a clip magazine attached to the shaft, and a clip crimping system. The clip magazine comprises a plurality of clips removably stored therein. The clip crimping system comprises a first jaw arm, a second jaw arm, and a clip receiving chamber defined between a distal end of the first jaw arm and a distal end of the second jaw arm. The clip receiving chamber is offset from the central shaft axis. The clip crimping system further comprises a proximal connection portion connecting the first jaw arm and the second jaw arm. The proximal connection portion extends along the longitudinal shaft axis. The clip crimping system further comprises a clamp drive comprising a driver movable distally to engage the first jaw arm and the second jaw arm and move the first jaw arm and the second jaw arm toward one another.

Example 14

The surgical device of Example 13, wherein the first jaw arm comprises a first cantilever arm and the second jaw arm comprises a second cantilever arm.

Example 15

The surgical device of Example 14, wherein the proximal connection portion integrally connects the first cantilever arm and the second cantilever arm.

Example 16

The surgical device of Examples 13, 14, or 15, wherein the proximal connection portion is positioned proximally with respect to the clip magazine.

Example 17

The surgical device of Example 14, wherein the first cantilever arm and the second cantilever arm extend in a first plane proximal to the clip magazine and a second plane distal to the clip magazine, and wherein the second plane is offset from the first plane.

Example 18

The surgical device of Example 17, wherein the proximal-most portion of the proximal connection portion extends out of the second plane.

Example 19

The surgical device of Examples 17 or 18, wherein the proximal-most portion of the proximal connection is folded out of the second plane and back toward the clip receiving chamber.

Example Set 6

Example 1

A surgical device for clipping tissue. The surgical device comprises a housing comprising a motor configured to output rotary motions, a shaft extending from the housing, and a clip applier head extending from the shaft. The clip applier head comprises a clip magazine, an end effector, a jaw closure cam, and a clip advancing member. The clip magazine comprises a plurality of clips. The end effector comprises a first jaw and a second jaw movable relative to each other between an unclamped position and a clamped position. The jaw closure cam is configured to move the first jaw and the second jaw toward the clamped position. The clip advancing member is operably attachable to the jaw closure cam. The clip advancing member is configured to move a clip from the clip magazine into a firing position. The jaw closure cam and the clip advancing member are configured to move in opposite directions at the same time.

Example 2

The surgical device of Example 1, further comprising a rotary drive, wherein the rotary drive is operably responsive to the rotary motions of the motor, and wherein the jaw closure cam is operably coupled to the rotary drive.

Example 3

The surgical device of Example 2, wherein the jaw closure cam translates in a distal direction to move the first jaw and the second jaw toward the clamped position in response to the rotary drive rotating in a first direction.

Example 4

The surgical device of Example 3, wherein the clip advancing member translates in a proximal direction to move a clip toward the firing position in response to the rotary drive rotating in a second direction.

Example 5

The surgical device of Example 4, wherein the first direction is opposite the second direction.

Example 6

The surgical device of Examples 1, 2, 3, 4, or 5, wherein the clip advancing member comprises a biasing member configured to bias the clip advancing member in a distal direction.

Example 7

The surgical device of Examples 1, 2, 3, 4, 5, or 6, further comprising a latch operably attached to the jaw closure cam. The latch is configured to operably couple the jaw closure cam and the clip advancing member. The surgical device further comprises a latch release configured to operably decouple the clip advancing member from the jaw closure cam when the clip advancing member is moved into the firing position.

Example 8

The surgical device of Examples 1, 2, 3, 4, 5, 6, or 7, wherein the shaft defines a shaft axis, and wherein the clip magazine is configured to rotate about the shaft axis.

Example 9

A surgical device for clipping tissue. The surgical device comprises a housing comprising a motor configured to output rotary motions, a shaft extending from the housing, a clip track comprising a plurality of clips removably stored therein, and an end effector extending from the shaft. The end effector comprises a first jaw, a second jaw, and a receiving portion at least partially defined between the first jaw and the second jaw. The first jaw and the second jaw are movable relative to each other between an unclamped position and a clamped position. The surgical device further comprises a drive screw, a jaw cam member, and a clip advancing member. The drive screw is operably responsive to the rotary motions. The jaw cam member is operably engaged with the drive screw. The jaw cam member is configured to move the first jaw and the second jaw toward the unclamped position in response to a rotation of the drive screw in a first direction. The clip advancing member is operably engaged with the drive screw. The clip advancing member is configured to advance a clip from the clip track into the receiving portion of the end effector in response to the rotation of the drive screw in the first direction.

Example 10

The surgical device of Example 9, wherein the drive screw comprises a first thread pitch and a second thread pitch that is different than the first thread pitch, wherein the jaw cam member is threadably engaged with the first thread pitch, and wherein the clip advancing member is threadably engaged with the second thread pitch.

Example 11

The surgical device of Example 9, wherein the drive screw is configured to translate the jaw cam member at a first rate in response to the rotation of the drive screw, wherein the drive screw is further configured to translate the clip advancing member at a second rate in response to the rotation of the drive screw, and wherein the second rate and the first rate are different.

Example 12

The surgical device of Example 11, wherein the second rate is faster than the first rate.

Example 13

The surgical device of Examples 9, 10, 11, or 12, wherein the jaw cam member is configured to translate a first distance in response to the rotation of the drive screw, wherein the clip advancing member is configured to translate a second distance in response to the rotation of the drive screw, and wherein the first distance and the second distance are different.

Example 14

The surgical device of Example 13, wherein the second distance is longer than the first distance.

Example 15

The surgical device of Example 9, wherein the jaw cam member moves the first jaw and the second jaw toward the clamped position in response to a rotation of the drive screw in a second direction, wherein the clip advancing member moves toward a proximal position when the drive screw is rotated in the second direction, and wherein the second direction is opposite the first direction.

Example 16

The surgical device of Example 15, wherein the jaw cam member is configured to translate a first distance in response to the rotation of the drive screw in the second direction, wherein the clip advancing member is configured to translate a second distance in response to the rotation of the drive screw in the second direction, and wherein the first distance and the second distance are different.

Example 17

A surgical device for clipping tissue. The surgical device comprises a housing comprising a motor configured to output rotary motions, a shaft extending from the housing, a clip magazine comprising a plurality of clips, a clip applier head extending from the shaft, and a drive screw operably responsive to the rotary motions. The drive screw is configured to perform a first clip applier head action when the drive screw is rotated in a first direction, and perform a second clip applier head action when the drive screw is rotated in a second direction opposite the first direction.

Example 18

The surgical device of Example 17, wherein the clip applier head comprises an end effector and a clip advancer. The end effector comprises a first jaw and a second jaw movable relative to each other between an unclamped position and a clamped position. The clip advancer is movable between an unbiased position and a biased position.

Example 19

The surgical device of Example 18, wherein the first clip applier head action comprises moving the first jaw and the second jaw toward the clamped position.

Example 20

The surgical device of Examples 18 or 19, wherein the second clip applier head action comprises moving the clip advancer toward the biased position.

Example Set 7

Example 1

A surgical device for clipping tissue. The surgical device comprises a housing comprising a motor, a shaft extending from the housing, a jaw actuator operably responsive to the motor, a clip magazine comprising a plurality of clips, a reciprocating feeder drive operably responsive to the motor, an end effector extending from the shaft. The end effector comprises a first jaw and a second jaw movable relative to each other between a plurality of positions by way of the jaw actuator. The plurality of positions comprises a ready-to-fire position where the first jaw and the second jaw are in a fully-open configuration, a fully-deployed position where the first jaw and the second jaw are in a fully-closed configuration, and a manipulation position intermediate the ready-to-fire position and the fully-deployed position. The surgical device further comprises a motor controller. The motor controller is configured to control the reciprocating feeder drive independent of the jaw actuator, advance a clip from the clip magazine into the end effector by way of the feeder drive without actuating the jaw actuator, and actuate the jaw actuator without advancing a clip into the end effector.

Example 2

The surgical device of Example 1, wherein the motor controller is further configured to control the motor based on a user input supplied to the motor controller by the user of the surgical device.

Example 3

The surgical device of Example 2, wherein the user input comprises an actuator which, when actuated, moves the first jaw and the second jaw to the fully-closed configuration without advancing a clip into the end effector.

Example 4

The surgical device of Example 2, wherein the user input comprises an actuator which, when actuated, moves the first jaw and the second jaw to one of the plurality of positions without advancing a clip into the end effector.

Example 5

The surgical device of Examples 1, 2, 3, or 4, further comprising a processor and a memory, wherein the motor controller is configured to control the motor via the processor and the memory.

Example 6

The surgical device of Example 5, wherein the processor is configured to execute a motor control algorithm stored in the memory to actuate the jaw actuator to move the first jaw and the second jaw between the plurality of positions.

Example 7

The surgical device of Examples 5 or 6, wherein the processor is configured to execute a motor control algorithm stored in the memory to actuate the reciprocating feeder drive independent of the jaw actuator.

Example 8

The surgical device of Examples 1, 2, 3, 4, 5, 6, or 7, wherein the clip magazine is replaceable.

Example 9

A surgical device for clipping tissue. The surgical device comprises a housing comprising a motor, a shaft extending from the housing, and a jaw actuator operably responsive to the motor. The jaw actuator is configured to translate between a proximal position and a distal position. The surgical device further comprises a clip magazine comprising a plurality of clips, a reciprocating feeder drive operably responsive to the motor, and an end effector extending from the shaft. The end effector comprises a first jaw and a second jaw movable relative to each other between an open configuration and a closed configuration when the jaw actuator is moved between the proximal position and the distal position. The surgical device further comprises a motor controller. The motor controller is configured to advance a clip from the clip magazine into the end effector by way of the feeder drive while actuating the jaw actuator to move the first jaw and the second jaw toward the open configuration in response to a first user input in a firing operating mode. The motor controller is further configured to actuate the jaw actuator to move the first jaw and the second jaw toward the closed configuration without advancing a clip into the end effector in response to a second user input in a manipulation operating mode.

Example 10

The surgical device of Example 9, wherein the first user input and the second user input are different.

Example 11

The surgical device of Examples 9 or 10, wherein the first user input comprises an actuator which, when actuated by the user of the surgical device, moves the first jaw and the second jaw toward the open configuration without advancing a clip into the end effector.

Example 12

The surgical device of Examples 9, 10, or 11, wherein the second user input comprises an actuator which, when actuated by the user of the surgical device, moves the first jaw and the second jaw toward the closed configuration without advancing a clip into the end effector.

Example 13

The surgical device of Examples 9, 10, 11, or 12, further comprising a processor and a memory, wherein the motor controller is configured to control the motor via the processor and the memory.

Example 14

The surgical device of Example 13, wherein the processor is configured to execute a motor control algorithm stored in the memory to actuate the jaw actuator to move the first jaw and the second jaw between the open configuration and the closed configuration.

Example 15

The surgical device of Examples 13 or 14, wherein the processor is configured to execute a motor control algorithm stored in the memory to actuate the reciprocating feeder drive independent of the jaw actuator.

Example 16

The surgical device of Examples 9, 10, 11, 12, 13, 14, or 15, wherein the clip magazine is replaceable.

Example 17

A surgical device for clipping tissue. The surgical device comprises a clip magazine comprising a plurality of clips, an end effector movable between an open position and a closed position, and a jaw actuator operably responsive to a first rotatable input. The jaw actuator is configured to move the end effector between the open position and the closed position. The surgical device further comprises a reciprocating feeder drive and a controller. The reciprocating feeder drive is operably responsive to a second rotatable input. The controller is configured to advance a clip from the clip magazine into the end effector by way of the feeder drive when the end effector is in the open position. The controller is further configured to actuate the jaw actuator to move the end effector toward the closed position without advancing a clip into the end effector.

Example 18

The surgical device of Example 17, wherein the controller is further configured to control the first rotatable input and the second rotatable input based on a user input supplied to the controller by the user of the surgical device.

Example 19

The surgical device of Examples 17 or 18, wherein the clip magazine is replaceable.

Example Set 8

Example 1

A surgical system for use in a surgical theater. The surgical system comprises a surgical tool and a surgical hub. The surgical tool comprises a motor, a motor controller in signal communication with the motor, and an end effector configured to perform an end effector function. The end effector is operably responsive to the motor. The surgical hub is in signal communication with the motor controller. The surgical hub is configured to detect a contextual cue within the surgical theater. The motor controller is configured to adjust an operating parameter of the motor based on the contextual cue detected by the surgical hub.

Example 2

The surgical system of Example 1, wherein the contextual cue comprises patient tissue properties.

Example 3

The surgical system of Examples 1 or 2, wherein the contextual cue comprises pre-determined biometric data of a patient.

Example 4

The surgical system of Examples 1, 2, or 3, wherein the surgical tool further comprises a sensor configured to measure at least one operational parameter of the motor, wherein the sensor is in signal communication with the surgical hub.

Example 5

The surgical system of Examples 1, 2, 3, or 4, wherein the contextual cue comprises the at least one operational parameter measured by the sensor.

Example 6

The surgical system of Examples 3, 4, or 5, wherein the at least one operational parameter comprises the speed of the motor.

Example 7

The surgical system of Examples 3, 4, or 5, wherein the at least one operational parameter comprises the current draw of the motor.

Example 8

The surgical system of Examples 3, 4, or 5, wherein the at least one operational parameter comprises the torque output of the motor.

Example 9

The surgical system of Examples 1, 2, 3, 4, 5, 6, 7, or 8, wherein the surgical system is further configured to initiate an inquiry to a database of the surgical hub, wherein the contextual cue results from the inquiry into the database.

Example 10

The surgical system of Examples 1, 2, 3, 4, 5, 6, 7, 8, or 9, wherein the end effector function comprises grasping tissue between a first jaw and a second jaw of the end effector, wherein the motor controller is configured to detect a current spike in the motor when the first jaw and the second jaw grasp abnormal tissue, and wherein the contextual cue detected by the surgical hub comprises the current spike detected by the motor controller.

Example 11

The surgical system of Examples 1, 2, 3, 4, 5, 6, 7, 8, or 9, wherein the surgical tool comprises a clip applier, wherein the end effector function comprises crimping a clip between a first jaw and a second jaw of the clip applier, wherein the motor controller is configured to detect a current spike in the motor indicative of an improperly crimped clip, and wherein the contextual cue detected by the surgical hub comprises the current spike detected by the motor controller.

Example 12

A surgical system for use in a surgical theater. The surgical system comprises a clip applier and a surgical hub. The clip applier comprises a motor, a motor controller in signal communication with the motor, a crimping drive operably responsive to the motor, and an end effector. The end effector comprises a first jaw and a second jaw movable relative to each other from an open position toward a closed position in response to a translation of the crimping drive during a crimping stroke. The surgical hub is in signal communication with the motor controller. The surgical hub is configured to detect a contextual cue within the surgical theater. The motor controller is configured to adjust the crimping stroke of the crimping drive based on the contextual cue detected by the surgical hub.

Example 13

The surgical system of Example 12, wherein the contextual cue comprises patient tissue properties.

Example 14

The surgical system of Examples 12 or 13, wherein the contextual cue comprises pre-determined biometric data of a patient.

Example 15

The surgical system of Examples 12, 13, or 14, wherein the clip applier further comprises a sensor configured to measure at least one operational parameter of the motor, wherein the sensor is in signal communication with the surgical hub.

Example 16

The surgical system of Example 15, wherein the contextual cue comprises the at least one operational parameter measured by the sensor.

Example 17

The surgical system of Examples 15 or 16, wherein the at least one operational parameter comprises the speed of the motor.

Example 18

The surgical system of Examples 15 or 16, wherein the at least one operational parameter comprises the current draw of the motor.

Example 19

The surgical system of Examples 12, 13, 14, 15, 16, 17, or 18, wherein the surgical system is further configured to initiate an inquiry to a database of the surgical hub, wherein the contextual cue is the result of the inquiry.

Example 20

A surgical system for use in a surgical theater. The surgical system comprises a surgical tool and a surgical hub. The surgical tool comprises a motor configured to output a rotary motion, a motor controller configured to control the motor, and a distal head configured to execute a distal head function. The distal head function is executed in response to the rotary motion of the motor. The surgical hub is in signal communication with the motor controller. The surgical hub is configured to detect a contextual cue within the surgical theater. The motor controller is configured to adjust the rotary motion of the motor based on the detected contextual cue.

The devices, systems, and methods disclosed in the Subject application can be used with the devices, systems, and methods disclosed in U.S. Provisional Patent Application Ser. No. 62/659,900, entitled METHOD OF HUB COMMUNICATION, filed Apr. 19, 2018; U.S. Provisional Patent Application Ser. No. 62/611,341, entitled INTERACTIVE SURGICAL PLATFORM, filed Dec. 28, 2017; U.S. Provisional Patent Application Ser. No. 62/611,340, entitled CLOUD-BASED MEDICAL ANALYTICS, filed Dec. 28, 2017; and U.S. Provisional Patent Application Ser. No. 62/611,339, entitled ROBOT ASSISTED SURGICAL PLATFORM, filed Dec. 28, 2017.

The devices, systems, and methods disclosed in the Subject application can also be used with the devices, systems, and methods disclosed in U.S. patent application Ser. No. 15/908,021, entitled SURGICAL INSTRUMENT WITH REMOTE RELEASE, filed Feb. 28, 2018; U.S. patent application Ser. No. 15/908,012, entitled SURGICAL INSTRUMENT HAVING DUAL ROTATABLE MEMBERS TO EFFECT DIFFERENT TYPES OF END EFFECTOR MOVEMENT, filed Feb. 28, 2018; U.S. patent application Ser. No. 15/908,040, entitled SURGICAL INSTRUMENT WITH ROTARY DRIVE SELECTIVELY ACTUATING MULTIPLE END EFFECTOR FUNCTIONS, filed Feb. 28, 2018; U.S. patent application Ser. No. 15/908,057, entitled SURGICAL INSTRUMENT WITH ROTARY DRIVE SELECTIVELY ACTUATING MULTIPLE END EFFECTOR FUNCTIONS, filed Feb. 28, 2018; U.S. patent application Ser. No. 15/908,058, entitled SURGICAL INSTRUMENT WITH MODULAR POWER SOURCES, filed Feb. 28, 2018; and U.S. patent application Ser. No. 15/908,143, entitled SURGICAL INSTRUMENT WITH SENSOR AND/OR CONTROL SYSTEMS, filed Feb. 28, 2018.

The surgical instrument systems described herein can be used in connection with the deployment and deformation of staples. Various embodiments are envisioned which deploy fasteners other than staples, such as clamps or tacks, for example. Moreover, various embodiments are envisioned which utilize any suitable means for sealing tissue. For instance, an end effector in accordance with various embodiments can comprise electrodes configured to heat and seal the tissue. Also, for instance, an end effector in accordance with certain embodiments can apply vibrational energy to seal the tissue. In addition, various embodiments are envisioned which utilize a suitable cutting means to cut the tissue.

The entire disclosures of:

U.S. Pat. No. 8,075,571, entitled SURGICAL CLIP APPLIER METHODS, which issued on Dec. 13, 2011;

U.S. Pat. No. 8,038,686, entitled CLIP APPLIER CONFIGURED TO PREVENT CLIP FALLOUT, which issued on Oct. 18, 2011;

U.S. Pat. No. 7,699,860, entitled SURGICAL CLIP, which issued on Apr. 20, 2010;

U.S. patent application Ser. No. 11/013,924, entitled TROCAR SEAL ASSEMBLY, now U.S. Pat. No. 7,371,227;

U.S. patent application Ser. No. 11/162,991, entitled ELECTROACTIVE POLYMER-BASED ARTICULATION MECHANISM FOR GRASPER, now U.S. Pat. No. 7,862,579;

U.S. patent application Ser. No. 12/364,256, entitled SURGICAL DISSECTOR, now U.S. Patent Application Publication No. 2010/0198248;

U.S. patent application Ser. No. 13/536,386, entitled EMPTY CLIP CARTRIDGE LOCKOUT, now U.S. Pat. No. 9,282,974;

U.S. patent application Ser. No. 13/832,786, entitled CIRCULAR NEEDLE APPLIER WITH OFFSET NEEDLE AND CARRIER TRACKS, now U.S. Pat. No. 9,398,905;

U.S. patent application Ser. No. 12/592,174, entitled APPARATUS AND METHOD FOR MINIMALLY INVASIVE SUTURING, now U.S. Pat. No. 8,123,764;

U.S. patent application Ser. No. 12/482,049, entitled ENDOSCOPIC STITCHING DEVICES, now U.S. Pat. No. 8,628,545;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 14/200,111, entitled CONTROL SYSTEMS FOR SURGICAL INSTRUMENTS, now U.S. Pat. No. 9,629,629;

U.S. patent application Ser. No. 14/248,590, entitled MOTOR DRIVEN SURGICAL INSTRUMENTS WITH LOCKABLE DUAL DRIVE SHAFTS, now U.S. Pat. No. 9,826,976;

U.S. patent application Ser. No. 14/813,242, entitled SURGICAL INSTRUMENT COMPRISING SYSTEMS FOR ASSURING THE PROPER SEQUENTIAL OPERATION OF THE SURGICAL INSTRUMENT, now U.S. Patent Application Publication No. 2017/0027571;

U.S. patent application Ser. No. 14/248,587, entitled POWERED SURGICAL STAPLER, now U.S. Pat. No. 9,867,612;

U.S. patent application Ser. No. 12/945,748, entitled SURGICAL TOOL WITH A TWO DEGREE OF FREEDOM WRIST, now U.S. Pat. No. 8,852,174;

U.S. patent application Ser. No. 13/297,158, entitled METHOD FOR PASSIVELY DECOUPLING TORQUE APPLIED BY A REMOTE ACTUATOR INTO AN INDEPENDENTLY ROTATING MEMBER, now U.S. Pat. No. 9,095,362;

International Application No. PCT/US2015/023636, entitled SURGICAL INSTRUMENT WITH SHIFTABLE TRANSMISSION, now International Patent Publication No. WO 2015/153642 A1;

International Application No. PCT/US2015/051837, entitled HANDHELD ELECTROMECHANICAL SURGICAL SYSTEM, now International Patent Publication No. WO 2016/057225 A1;

U.S. patent application Ser. No. 14/657,876, entitled SURGICAL GENERATOR FOR ULTRASONIC AND ELECTROSURGICAL DEVICES, U.S. Patent Application Publication No. 2015/0182277;

U.S. patent application Ser. No. 15/382,515, entitled MODULAR BATTERY POWERED HANDHELD SURGICAL INSTRUMENT AND METHODS THEREFOR, U.S. Patent Application Publication No. 2017/0202605;

U.S. patent application Ser. No. 14/683,358, entitled SURGICAL GENERATOR SYSTEMS AND RELATED METHODS, U.S. Patent Application Publication No. 2016/0296271;

U.S. patent application Ser. No. 14/149,294, entitled HARVESTING ENERGY FROM A SURGICAL GENERATOR, U.S. Pat. No. 9,795,436;

U.S. patent application Ser. No. 15/265,293, entitled TECHNIQUES FOR CIRCUIT TOPOLOGIES FOR COMBINED GENERATOR, U.S. Patent Application Publication No. 2017/0086910; and U.S. patent application Ser. No. 15/265,279, entitled TECHNIQUES FOR OPERATING GENERATOR FOR DIGITALLY GENERATING ELECTRICAL SIGNAL WAVEFORMS AND SURGICAL INSTRUMENTS, U.S. Patent Application Publication No. 2017/0086914, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

Any patent, publication, or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical device for clipping tissue, comprising:
   a housing comprising a motor;
   a shaft extending from said housing;
   a jaw actuator operably responsive to said motor;
   a clip magazine comprising a plurality of clips;
   a reciprocating feeder drive operably responsive to said motor;
   an end effector extending from said shaft, comprising:
      a first jaw; and
      a second jaw, wherein said first jaw and said second jaw are movable relative to each other between a plurality of positions by way of said jaw actuator, and wherein said plurality of positions comprises:
         a ready-to-fire position where said first jaw and said second jaw are in a fully-open configuration;
         a fully-deployed position where said first jaw and said second jaw are in a fully-closed configuration; and
         a manipulation position intermediate said ready-to-fire position and said fully-deployed position; and
   a motor controller configured to:
      control said reciprocating feeder drive independent of said jaw actuator;
      advance a said clip from said clip magazine into said end effector by way of said reciprocating feeder drive without actuating said jaw actuator; and
      actuate said jaw actuator without advancing a said clip into said end effector.

2. The surgical device of claim 1, wherein said motor controller is further configured to control said motor based on a user input supplied to said motor controller by a user of the surgical device.

3. The surgical device of claim 2, wherein the user input comprises an actuator which, when actuated, moves said first jaw and said second jaw to said fully-closed configuration without advancing a said clip into said end effector.

4. The surgical device of claim 2, wherein the user input comprises an actuator which, when actuated, moves said first jaw and said second jaw to one of said plurality of positions without advancing a said clip into said end effector.

5. The surgical device of claim 1, further comprising a processor and a memory, wherein said motor controller is configured to control said motor via said processor and said memory.

6. The surgical device of claim 5, wherein said processor is configured to execute a motor control algorithm stored in said memory to actuate said jaw actuator to move said first jaw and said second jaw between said plurality of positions.

7. The surgical device of claim 5, wherein said processor is configured to execute a motor control algorithm stored in said memory to actuate said reciprocating feeder drive independent of said jaw actuator.

8. The surgical device of claim 1, wherein said clip magazine is replaceable.

9. A surgical device for clipping tissue, comprising
   a housing comprising a motor;
   a shaft extending from said housing;
   a jaw actuator operably responsive to said motor, wherein said jaw actuator is configured to translate between a proximal position and a distal position;
   a clip magazine comprising a plurality of clips;
   a reciprocating feeder drive operably responsive to said motor;

an end effector extending from said shaft, comprising:
  a first jaw; and
  a second jaw, wherein said first jaw and said second jaw are movable relative to each other between an open configuration and a closed configuration when said jaw actuator is moved between said proximal position and said distal position; and
a motor controller configured to:
  advance a said clip from said clip magazine into said end effector by way of said reciprocating feeder drive while actuating said jaw actuator to move said first jaw and said second jaw toward said open configuration in response to a first user input in a firing operating mode; and
  actuate said jaw actuator to move said first jaw and said second jaw toward said closed configuration without advancing a said clip into said end effector in response to a second user input in a manipulation operating mode.

10. The surgical device of claim 9, wherein the first user input and said second user input are different.

11. The surgical device of claim 10, wherein the first user input comprises an actuator which, when actuated by a user of the surgical device, moves said first jaw and said second jaw toward said open configuration without advancing a said clip into said end effector.

12. The surgical device of claim 11, wherein the second user input comprises an actuator which, when actuated by the user of the surgical device, moves said first jaw and said second jaw toward said closed configuration without advancing a said clip into said end effector.

13. The surgical device of claim 9, further comprising a processor and a memory, wherein said motor controller is configured to control said motor via said processor and said memory.

14. The surgical device of claim 13, wherein said processor is configured to execute a motor control algorithm stored in said memory to actuate said jaw actuator to move said first jaw and said second jaw between said open configuration and said closed configuration.

15. The surgical device of claim 14, wherein said processor is configured to execute a motor control algorithm stored in said memory to actuate said reciprocating feeder drive independent of said jaw actuator.

16. The surgical device of claim 9, wherein said clip magazine is replaceable.

17. A surgical device for clipping tissue, comprising
a clip magazine comprising a plurality of clips;
an end effector movable between an open position and a closed position;
a jaw actuator operably responsive to a first rotatable input, wherein said jaw actuator is configured to move said end effector between said open position and said closed position;
a reciprocating feeder drive operably responsive to a second rotatable input; and
a controller configured to:
  advance a said clip from said clip magazine into said end effector by way of said reciprocating feeder drive when said end effector is in said open position; and
  actuate said jaw actuator to move said end effector toward said closed position without advancing a said clip into said end effector.

18. The surgical device of claim 17, wherein said controller is further configured to control said first rotatable input and said second rotatable input based on a user input supplied to said controller by a user of the surgical device.

19. The surgical device of claim 17, wherein said clip magazine is replaceable.

20. A surgical device for clipping tissue, the surgical device comprising:
an end effector, comprising:
  a first jaw; and
  a second jaw, wherein said first jaw and said second jaw are configurable relative to each other in an open configuration and a closed configuration;
a jaw actuator operably responsive to a motorized system, wherein said jaw actuator is configured to transition said first jaw and said second jaw between said open configuration and said closed configuration;
a reciprocating feeder drive operably responsive to the motorized system; and
a motor controller, configured to:
  control said reciprocating feeder drive independent of said jaw actuator;
  advance a clip from a clip magazine into said end effector by way of said reciprocating feeder drive without actuating said jaw actuator; and
  actuate said jaw actuator without advancing a said clip into said end effector.

21. A surgical device usable for clipping tissue, the surgical device comprising:
an end effector, comprising:
  a first jaw; and
  a second jaw, wherein said first jaw and said second jaw are transitionable between an open configuration and a closed configuration;
a jaw actuator operably responsive to a motorized system, wherein said jaw actuator is configured to move between a proximal position and a distal position, and wherein said first jaw and said second jaw are configured to transition between said open configuration and said closed configuration based on movement of said jaw actuator;
a reciprocating feeder drive operably responsive to the motorized system; and
a motor controller, configured to:
  advance a clip from a clip magazine into said end effector by way of said reciprocating feeder drive while actuating said jaw actuator to move said first jaw and said second jaw toward said open configuration, based on a first user input in a firing operating mode; and
  actuate said jaw actuator to move said first jaw and said second jaw toward said closed configuration without advancing a clip from the clip magazine into said end effector, based on a second user input in a manipulation operating mode.

22. A surgical device for clipping tissue, comprising:
an end effector transitionable between an open position and a closed position;
a jaw actuator operably responsive to a first rotatable input, wherein said jaw actuator is configured to transition said end effector between said open position and said closed position;
a reciprocating feeder drive operably responsive to a second rotatable input; and
a controller configured to:
  advance a clip from a clip magazine into said end effector by way of said reciprocating feeder drive based on said end effector being in said open position; and actuate said jaw actuator to move said end effector toward said closed position without advancing a clip from the clip magazine into said end effector.

* * * * *